(12) United States Patent
Purandare et al.

(10) Patent No.: US 9,556,178 B2
(45) Date of Patent: *Jan. 31, 2017

(54) IMIDAZOTRIAZINECARBONITRILES USEFUL AS KINASE INHIBITORS

(71) Applicant: Bristol-Myers Squibb Company, Princeton, NJ (US)

(72) Inventors: Ashok Vinayak Purandare, Pennington, NJ (US); Brian E. Fink, Yardley, PA (US); Ashvinikumar V. Gavai, Princeton Junction, NJ (US); Walter Lewis Johnson, Waterbury, CT (US); Amy C. Hart, Ewing, NJ (US); Liqi He, Furlong, PA (US); Tram N. Huynh, Pennington, NJ (US); Jennifer Inghrim, Plainsboro, NJ (US); Harold Mastalerz, Guilford, CT (US); Xiaopeng Sang, Glastonbury, CT (US); Christine M. Tarby, Lawrenceville, NJ (US); Honghe Wan, Pennington, NJ (US); Wayne Vaccaro, Yardley, PA (US); Guifen Zhang, Wallingford, CT (US); Yufen Zhao, Pennington, NJ (US); Kurt Zimmermann, Durham, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/532,218

(22) Filed: Nov. 4, 2014

(65) Prior Publication Data

US 2015/0065465 A1 Mar. 5, 2015

Related U.S. Application Data

(62) Division of application No. 13/940,619, filed on Jul. 12, 2013, now Pat. No. 8,940,736.

(60) Provisional application No. 61/671,179, filed on Jul. 13, 2012, provisional application No. 61/790,511, filed on Mar. 15, 2013.

(51) Int. Cl.

| | | |
|---|---|---|
| C07D 487/04 | (2006.01) |
| C07D 487/22 | (2006.01) |
| C07D 403/04 | (2006.01) |
| A61K 31/53 | (2006.01) |
| A61K 31/5377 | (2006.01) |
| A61K 31/5383 | (2006.01) |
| A61K 31/551 | (2006.01) |
| A61K 31/675 | (2006.01) |
| A61K 45/06 | (2006.01) |
| C07D 471/10 | (2006.01) |
| C07D 487/10 | (2006.01) |
| C07D 498/04 | (2006.01) |
| C07F 9/6521 | (2006.01) |
| A61K 31/541 | (2006.01) |
| A61K 31/55 | (2006.01) |
| C07D 487/08 | (2006.01) |
| C07D 519/00 | (2006.01) |
| C07F 9/6561 | (2006.01) |
| C07F 7/18 | (2006.01) |

(52) U.S. Cl.
CPC .......... *C07D 487/04* (2013.01); *A61K 31/53* (2013.01); *A61K 31/5377* (2013.01); *A61K 31/5383* (2013.01); *A61K 31/541* (2013.01); *A61K 31/55* (2013.01); *A61K 31/551* (2013.01); *A61K 31/675* (2013.01); *A61K 45/06* (2013.01); *C07D 471/10* (2013.01); *C07D 487/08* (2013.01); *C07D 487/10* (2013.01); *C07D 498/04* (2013.01); *C07D 519/00* (2013.01); *C07F 7/1804* (2013.01); *C07F 9/6561* (2013.01); *C07F 9/65213* (2013.01); *C07F 9/65616* (2013.01); *C07D 487/22* (2013.01)

(58) Field of Classification Search
CPC .... C07D 403/04; C07D 487/04; C07D 487/22
See application file for complete search history.

(56) References Cited

U.S. PATENT DOCUMENTS

| | | | |
|---|---|---|---|
| 7,723,336 B2 | 5/2010 | Vaccaro et al. |
| 8,188,272 B2 | 5/2012 | Liu et al. |
| 8,252,795 B2 | 8/2012 | Fink et al. |
| 2014/0018319 A1 | 1/2014 | Purandare et al. |

FOREIGN PATENT DOCUMENTS

| | | |
|---|---|---|
| DE | 43 27 027 | 8/1994 |
| WO | WO 02/062800 | 8/2002 |
| WO | WO 2006/065755 | 6/2006 |
| WO | WO 2006/065788 | 6/2006 |
| WO | WO 2007/038314 | 4/2007 |
| WO | WO 2008/057402 | 5/2008 |
| WO | WO 2008/116064 | 9/2008 |
| WO | WO 2010/011837 | 1/2010 |
| WO | WO 2010/068810 | 6/2010 |
| WO | WO 2011/089400 | 7/2011 |
| WO | WO 2011/141713 | 11/2011 |

*Primary Examiner* — Samira Jean-Louis
(74) *Attorney, Agent, or Firm* — Elliott Korsen; Hong Liu

(57) ABSTRACT

The invention provides compounds of Formula (I)

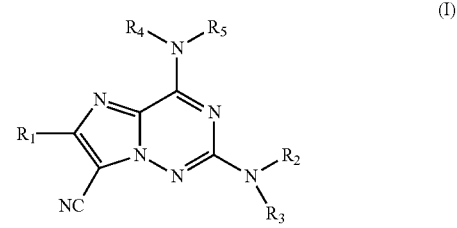

and pharmaceutically acceptable salts thereof. The Formula (I) imidazotriazines inhibit protein kinase activity thereby making them useful as anticancer agents.

7 Claims, No Drawings

IMIDAZOTRIAZINECARBONITRILES USEFUL AS KINASE INHIBITORS

CROSS REFERENCE TO RELATED APPLICATIONS

This Divisional application claims the benefit of U.S. Ser. No. 13/940,619 filed Jul. 12, 2013 which in turn claims the benefit of U.S. Provisional Application U.S. Ser. No. 61/671,179 filed Jul. 13, 2012 and U.S. Ser. No. 61/790,511 filed Mar. 15, 2013, hereby incorporated by reference in their entireties.

FIELD OF THE INVENTION

The invention relates to novel substituted imidazotriazine compounds useful as protein kinase inhibitors. The invention also relates to methods of using the compounds in the treatment of proliferative and other types of diseases and to pharmaceutical compositions containing the compounds.

BACKGROUND OF THE INVENTION

The invention relates to fused heterocyclic compounds which inhibit protein kinase enzymes, compositions which contain protein kinase inhibiting compounds and methods of using inhibitors of protein kinase enzymes to treat diseases which are characterized by an overexpression or upregulation of protein kinases. Protein kinases mediate intracellular signal transduction. They do this by effecting a phosphoryl transfer from a nucleoside triphosphate to a protein acceptor that is involved in a signaling pathway. There are a number of kinases and pathways through which extracellular and other stimuli cause a variety of cellular responses to occur inside the cell. An extracellular stimulus may effect one or more cellular responses related to cell growth, migration, differentiation, secretion of hormones, activation of transcription factors, muscle contraction, glucose metabolism, control of protein synthesis and regulation of cell cycle.

Many diseases are associated with abnormal cellular responses triggered by protein kinase-mediated events. These diseases include autoimmune diseases, inflammatory diseases, neurological and neurodegenerative diseases, cancer, cardiovascular diseases, allergies and asthma, Alzheimer's disease or hormone-related diseases. Accordingly, there has been a substantial effort in medicinal chemistry to find protein kinase inhibitors that are effective as therapeutic agents.

Serine/threonine kinases are a class of protein kinases that are among the most promising drug targets for future small molecule inhibitors. Inhibition of serine/threonine kinases is likely to have relevance to the treatment of cancer, diabetes and a variety of inflammatory disorders. The successful development of GLEEVEC® as a Bcr/Abl protein kinase inhibitor has provided further evidence that protein kinases including protein kinase CK2 are valid drug targets for potential cancer therapies.

Protein kinase CK2 (formerly known as casein kinase II) is a highly conserved serine/threonine kinase. Protein kinase CK2 is ubiquitously distributed and constitutively active in eukaryotes. In mammals, the enzyme exists in two isozymic forms due to variations in the catalytic subunits of the enzyme. The CK2 holoenzyme is a heterotetrameric complex composed of two catalytic α (CK2A1) subunits or α' (CK2A2) subunits and two regulatory β-subunits. The formation of CK2 complexes containing the catalytic subunits requires dimerization of the regulatory β-subunits. CK2 interacts with a variety of cellular proteins and has been implicated in cell replication such as cell proliferation and differentiation, cellular survival, and tumorigenesis. With respect to tumorigenesis, protein kinase CK2 has been implicated in kidney tumors (Stalter et al., "Asymmetric expression of protein kinase CK2 subunits in human kidney tumors", *Biochem. Biophys. Res. Commun.,* 202:141-147 (1994)), mammary gland tumors (Landesman-Bollag et al., "Protein kinase CK2 in mammary gland tumorigenesis", *Oncology,* 20:3247-3257 (2001)), lung carcinoma (Daya-Makin et al., "Activation of a tumor-associated protein kinase (p40TAK) and casein kinase II in human squamous cell carcinomas and adenocarcinomas of the lung", *Cancer Res.,* 54:2262-2268 (1994)), head and neck carcinoma (Faust et al., "Antisense oligonucleotides against protein kinase CK2-α inhibit growth of squamous cell carcinoma of the head and neck in vitro", *Head Neck,* 22:341-346 (2000)), and prostate cancer (Wang et al., "Role of protein kinase CK2 in the regulation of tumor necrosis factor-related apoptosis inducing ligand-induced apoptosis in prostate cancer cells", *Cancer Res.,* 66:2242-2249 (2006)).

Inhibitors of protein kinases are widely sought and small molecule compounds capable of modulating protein kinases have been reported. For example, pyrazolotriazines as CK2 kinase inhibitors were reported in Nie et al. (*Bioorganic & Medicinal Chemistry Letters,* 17:4191-4195 (2007); 18:619-623 (2008)). In addition, certain imidazotriazine compounds were disclosed in WO 2007/038314, published Apr. 5, 2007, US 2008/0045536, published Feb. 21, 2008, WO 2008/116064, published Sep. 25, 2008, all assigned to the present assignee. The present invention relates to a new class of imidazotriazine-carbonitriles found to be effective inhibitors of protein kinases, particularly the CK2 kinase. These novel compounds are provided to be useful as pharmaceuticals with desirable stability, bioavailability, therapeutic index and toxicity values that are important to their drugability.

SUMMARY OF THE INVENTION

The invention is directed to fused heterocyclic compounds of Formulae (I)-(VIII) or stereoisomers, tautomers, pharmaceutically acceptable salts, solvates or prodrugs thereof, which inhibit protein kinase enzymes, especially protein kinase CK2 for the treatment of cancer.

The present invention also provides processes and intermediates for making the compounds of the present invention or stereoisomers, tautomers, pharmaceutically acceptable salts, solvates, or prodrugs thereof.

The present invention also provides pharmaceutical compositions comprising a pharmaceutically acceptable carrier and at least one of the compounds of the present invention or stereoisomers, tautomers, pharmaceutically acceptable salts, solvates, or prodrugs thereof.

The present invention also provides methods for inhibiting the activity of protein kinase CK2 comprising administering to a host in need of such treatment a therapeutically effective amount of at least one of the compounds of the present invention or stereoisomers, tautomers, pharmaceutically acceptable salts, solvates, or prodrugs thereof.

The present invention also provides methods for inhibiting angiogenesis or treating cancers comprising administering to a host in need of such treatment a therapeutically effective amount of at least one of the compounds of the present invention or stereoisomers, tautomers, pharmaceutically acceptable salts, solvates, or prodrugs thereof.

The present invention also provides the compounds of the present invention or stereoisomers, tautomers, pharmaceutically acceptable salts, solvates, or prodrugs thereof, for use in therapy.

The present invention also provides the use of the compounds of the present invention or stereoisomers, tautomers, pharmaceutically acceptable salts, solvates, or prodrugs thereof, in preparing a medicament for the treatment of cancer in a human patient, particularly a cancer receptive to treatment via inhibition of the CK2 enzyme.

These and other features of the invention will be set forth in the expanded form as the disclosure continues.

DETAILED DESCRIPTION OF THE INVENTION

The invention provides for novel imidazotriazine compounds useful as therapeutic agents, pharmaceutical compositions employing such novel compounds and for methods of using such compounds.

In accordance with the invention, there are disclosed compounds of Formula (I) including enantiomers, diastereomers, tautomers, pharmaceutically-acceptable salts, prodrugs, hydrates, or solvates thereof,

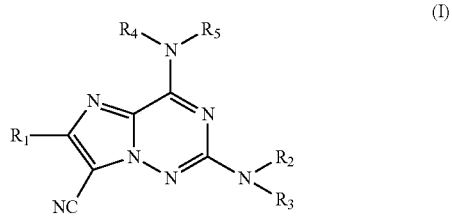

wherein
- $R_1$ is selected from the group consisting of H, F, Cl, Br, CN, and $C_{1-6}$alkyl;
- $R_2$ is selected from the group consisting of aryl substituted with 1-5 $R_6$ and heteroaryl substituted with 1-5 $R_6$;
- $R_3$ is selected from the group consisting of hydrogen and $C_{1-6}$alkyl substituted with 1-5 $R_e$;
- alternatively, $R_2$ and $R_3$ together with the nitrogen atom to which they are both attached form a heterocyclic ring substituted with 1-5 $R_6$;
- $R_4$ is selected from the group consisting of H, $C_{1-6}$alkyl substituted with 1-5 $R_e$, —(CH$_2$)$_r$OR$_b$, —(CH$_2$)$_r$S(O)$_p$R$_c$, —(CH$_2$)$_r$C(=O)R$_d$, —(CH$_2$)$_r$NR$_a$R$_a$, —(CH$_2$)$_r$C(=O)NR$_a$R$_a$, —(CH$_2$)$_r$NR$_a$C(=O)R$_d$, —(CH$_2$)$_r$NR$_a$C(=O)OR$_b$, —(CH$_2$)$_r$OC(=O)NR$_a$R$_a$, —(CH$_2$)$_r$NR$_a$C(=O)NR$_a$R$_a$, —(CH$_2$)$_r$C(=O)OR$_b$, —(CH$_2$)$_r$S(O)$_2$NR$_a$R$_a$, —(CH$_2$)$_r$NR$_a$S(O)$_2$NR$_a$R$_a$, —(CH$_2$)$_r$NR$_a$S(O)$_2$R$_c$, —(CH$_2$)$_r$—C$_{3-10}$carbocyclyl substituted with 1-5 $R_e$, —(CH$_2$)$_r$-heterocyclyl substituted with 1-5 $R_e$;
- $R_5$ is selected from the group consisting of H and $C_{1-6}$alkyl substituted with 1-5 $R_e$;
- $R_6$, at each occurrence, is independently selected from the group consisting of H, F, Cl, Br, CN, —NR$_2$R$_2$NO$_2$, —OR$_b$, —C(=O)NR$_2$R$_2$, —NR$_a$C(=O)R$_b$, —NR$_a$C(=O)OR$_b$, $C_{1-6}$ alkyl substituted with 1-5 $R_e$, $C_{3-6}$carbocyclyl substituted with 1-5 $R_8$, and heterocyclyl substituted with 1-5 $R_8$;
- $R_7$, at each occurrence, is independently selected from the group consisting of H, $C_{1-6}$ alkyl substituted with 1-5 $R_e$, —(CH$_2$)$_r$—C$_{3-10}$carbocyclyl substituted with 1-5 $R_e$, and —(CH$_2$)$_r$-heterocyclyl substituted with 1-5 $R_e$; or $R_7$ and $R_7$ together with the nitrogen atom to which they are both attached form a heterocyclic ring substituted with 1-5 $R_8$;
- $R_8$, at each occurrence, is independently selected from the group consisting of H, F, Cl, Br, $C_{1-6}$ alkyl substituted with 1-5 $R_e$, $C_{2-6}$ alkenyl substituted with 1-5 $R_e$, =O, —(CR$_g$R$_g$)$_r$OR$_b$, —(CR$_g$R$_g$)$_r$S(O)$_p$R$_c$, —(CR$_g$R$_g$)$_r$C(=O)(CR$_g$R$_g$)$_r$R$_d$, —(CR$_g$R$_g$)$_r$NR$_a$R$_a$, —(CR$_g$R$_g$)$_r$C(=O)NR$_a$R$_a$, —(CR$_g$R$_g$)$_r$NR$_a$C(=O)R$_d$, —(CR$_g$R$_g$)$_r$NR$_a$C(=O)OR$_b$, —(CR$_g$R$_g$)$_r$OC(=O)R$_d$, —(CR$_g$R$_g$)$_r$OC(=O)(CR$_g$R$_g$)$_r$NR$_a$R$_a$, —(CR$_g$R$_g$)$_r$NR$_a$C(=O)NR$_a$R$_a$, —(CR$_g$R$_g$)$_r$C(=O)(CH$_2$)$_r$OR$_b$, —(CR$_g$R$_g$)$_r$C(=O)(CR$_g$R$_g$)$_r$OC(=O)R$_b$—(CR$_g$R$_g$)$_r$S(O)$_2$NR$_a$R$_a$, —(CR$_g$R$_g$)$_r$NR$_a$S(O)$_2$NR$_a$R$_a$, —(CR$_g$R$_g$)$_r$NR$_a$S(O)$_2$R$_c$, —OPO$_3$H, —(CR$_g$R$_g$)$_r$NR$_a$C(=O)O(CR$_g$R$_g$)$_r$O(CR$_g$R$_g$)$_r$O(CR$_g$R$_g$)$_r$O(CR$_g$R$_g$)$_r$O(CR$_g$R$_g$)$_r$O(CR$_g$R$_g$)$_r$OC$_{1-4}$alkyl, —(CR$_g$R$_g$)$_r$—C$_{3-10}$carbocyclyl substituted with 1-5 $R_e$ and —(CR$_g$R$_g$)$_r$-heterocyclyl substituted with 1-5 $R_e$;
- $R_a$, at each occurrence, is independently selected from the group consisting of H, CN, $C_{1-6}$ alkyl substituted with 1-5 $R_e$, $C_{2-6}$ alkenyl substituted with 1-5 $R_e$, $C_{2-6}$ alkynyl substituted with 1-5 $R_e$, —(CH$_2$)$_r$—C$_{3-10}$carbocyclyl substituted with 1-5 $R_e$, and —(CH$_2$)$_r$-heterocyclyl substituted with 1-5 $R_e$; or $R_a$ and $R_a$ together with the nitrogen atom to which they are both attached form a heterocyclic ring substituted with 1-5 $R_e$;
- $R_b$, at each occurrence, is independently selected from the group consisting of H, $C_{1-6}$ alkyl substituted with 1-5 $R_e$, $C_{2-6}$ alkenyl substituted with 1-5 $R_e$, $C_{2-6}$ alkynyl substituted with 1-5 $R_e$, —(CH$_2$)$_r$—C$_{3-10}$carbocyclyl substituted with 1-5 $R_e$, and —(CH$_2$)$_r$-heterocyclyl substituted with 1-5 $R_e$;
- $R_c$, at each occurrence, is independently selected from the group consisting of $C_{1-6}$ alkyl substituted with 1-5 $R_e$, $C_{2-6}$alkenyl substituted with 1-5 $R_e$, $C_{2-6}$alkynyl substituted with 1-5 $R_e$, $C_{3-6}$carbocyclyl, and heterocyclyl;
- $R_d$, at each occurrence, is independently selected from the group consisting of H, OH, $C_{1-6}$ alkyl substituted with 1-5 $R_e$, $C_{2-6}$alkenyl substituted with 1-5 $R_e$, $C_{2-6}$alkynyl substituted with 1-5 $R_e$, —(CH$_2$)$_r$—C$_{3-10}$carbocyclyl substituted with 1-5 $R_e$, and —(CH$_2$)$_r$-heterocyclyl substituted with 1-5 $R_e$;
- $R_e$, at each occurrence, is independently selected from the group consisting of H, $C_{1-6}$alkyl substituted with 1-5 $R_f$, $C_{2-6}$alkenyl, $C_{2-6}$alkynyl, —(CH$_2$)$_r$—C$_{3-6}$cycloalkyl, —(CH$_2$)$_r$-heterocyclyl, F, Cl, Br, —(CH$_2$)$_r$CN, NO$_2$, =O, CO$_2$H, —OPO$_3$H, —OSi(C$_{1-4}$alkyl)$_3$, —(CH$_2$)$_r$OC$_{1-5}$ alkyl, —(CH$_2$)$_r$OH, —(CH$_2$)$_r$S(O)$_2$C$_{1-5}$alkyl, —(CH$_2$)$_r$S(O)$_2$-phenyl, —(CH$_2$)$_r$NHS(O)$_2$C$_{1-5}$alkyl, —S(O)$_2$NH$_2$, SH, —(CH$_2$)$_r$NR$_f$R$_f$, —(CH$_2$)$_r$NHC(=O)OR$_f$, —(CH$_2$)$_r$NHC(=O)R$_f$, and —(CH$_2$)$_r$C(=O)OR$_f$;
- $R_f$, at each occurrence, is independently selected from the group consisting of H, $C_{1-5}$alkyl, OH, OC$_{1-5}$alkyl, $C_{3-6}$cycloalkyl, and phenyl, heterocyclyl substituted with alkyl and CN, or $R_f$ and $R_f$ together with the nitrogen atom to which they are both attached form a heterocyclic ring optionally substituted with $C_{1-4}$alkyl;
- $R_g$, at each occurrence, is independently selected from the group consisting of H and $C_{1-5}$alkyl.
- p, at each occurrence, is independently selected from the group consisting of zero, 1, and 2; and
- r, at each occurrence, is independently selected from the group consisting of zero, 1, 2, 3, and 4.

In another aspect, there are disclosed compounds of Formula (I) including enantiomers, diastereomers, tautomers, pharmaceutically-acceptable salts, prodrugs, hydrates, or solvates thereof, wherein $R_1$ is selected from the group consisting of H, F, Cl, Br, CN, and $C_{1-6}$alkyl;

$R_2$ is selected from the group consisting of aryl substituted with 1-5 $R_6$ and heteroaryl substituted with 1-5 $R_6$;

$R_3$ is selected from the group consisting of hydrogen and $C_{1-6}$alkyl substituted with 1-5 $R_e$;

$R_4$ is selected from the group consisting of H, $C_{1-6}$alkyl substituted with 1-5 $R_e$, —$(CH_2)_rOR_b$, —$(CH_2)_rS(O)_pR_c$, —$(CH_2)_rC(=O)R_d$, —$(CH_2)_rNR_aR_a$, —$(CH_2)_rC(=O)NR_aR_a$, —$(CH_2)_rNR_aC(=O)R_d$, —$(CH_2)_rNR_aC(=O)OR_b$, —$(CH_2)_rOC(=O)NR_aR_a$, —$(CH_2)_rNR_aC(=O)NR_aR_a$, —$(CH_2)_rC(=O)OR_b$, —$(CH_2)_rS(O)_2NR_aR_a$, —$(CH_2)_rNR_aS(O)_2NR_aR_a$, —$(CH_2)_rNR_aS(O)_2R_c$, —$(CH_2)_r$—$C_{3-10}$carbocyclyl substituted with 1-5 $R_e$, —$(CH_2)_r$-heterocyclyl substituted with 1-5 $R_e$;

$R_5$ is selected from the group consisting of H and $C_{1-6}$alkyl substituted with 1-5 $R_e$;

$R_6$, at each occurrence, is independently selected from the group consisting of H, F, Cl, Br, CN, —$NR_2R_2NO_2$, —$OR_b$, —$C(=O)NR_2R_2$, —$NR_aC(=O)OR_b$, $C_{1-6}$ alkyl substituted with 1-5 $R_e$, $C_{3-6}$carbocyclyl substituted with 1-5 $R_8$, and heterocyclyl substituted with 1-5 $R_8$;

$R_7$, at each occurrence, is independently selected from the group consisting of H, $C_{1-6}$ alkyl substituted with 1-5 $R_e$, —$(CH_2)_r$—$C_{3-10}$carbocyclyl substituted with 1-5 $R_e$, and —$(CH_2)_r$-heterocyclyl substituted with 1-5 $R_e$; or $R_7$ and $R_7$ together with the nitrogen atom to which they are both attached form a heterocyclic ring substituted with 1-5 $R_8$;

$R_8$, at each occurrence, is independently selected from the group consisting of H, F, Cl, Br, $C_{1-6}$ alkyl substituted with 1-5 $R_e$, =O, —$(CH_2)_rOR_b$, —$(CH_2)_rS(O)_pR_c$, —$(CH_2)_rC(=O)R_d$, —$(CH_2)_rNR_aR_a$, —$(CH_2)_rC(=O)NR_aR_a$, —$(CH_2)_rNR_aC(=O)R_d$, —$(CH_2)_rNR_aC(=O)OR_b$, —$(CH_2)_rOC(=O)R_d$, —$(CH_2)_rOC(=O)(CH_2)_rNR_aR_a$, —$(CH_2)_rNR_aC(=O)NR_aR_a$, —$(CH_2)_rC(=O)OR_b$, —$(CH_2)_rS(O)_2NR_aR_a$, —$(CH_2)_rNR_aS(O)_2NR_aR_a$, —$(CH_2)_rNR_aS(O)_2R_c$, and —$(CH_2)_r$-heterocyclyl substituted with 1-5 $R_e$;

$R_a$, at each occurrence, is independently selected from the group consisting of H, CN, $C_{1-6}$ alkyl substituted with 1-5 $R_e$, $C_{2-6}$ alkenyl substituted with 1-5 $R_e$, $C_{2-6}$ alkynyl substituted with 1-5 $R_e$, —$(CH_2)_r$—$C_{3-10}$carbocyclyl substituted with 1-5 $R_e$, and —$(CH_2)_r$-heterocyclyl substituted with 1-5 $R_e$; or $R_a$ and $R_a$ together with the nitrogen atom to which they are both attached form a heterocyclic ring substituted with 1-5 $R_e$;

$R_b$, at each occurrence, is independently selected from the group consisting of H, $C_{1-6}$ alkyl substituted with 1-5 $R_e$, $C_{2-6}$ alkenyl substituted with 1-5 $R_e$, $C_{2-6}$ alkynyl substituted with 1-5 $R_e$, —$(CH_2)_r$—$C_{3-10}$carbocyclyl substituted with 1-5 $R_e$, and —$(CH_2)_r$-heterocyclyl substituted with 1-5 $R_e$;

$R_c$, at each occurrence, is independently selected from the group consisting of $C_{1-6}$ alkyl substituted with 1-5 $R_e$, $C_{2-6}$alkenyl substituted with 1-5 $R_e$, $C_{2-6}$alkynyl substituted with 1-5 $R_e$, $C_{3-6}$carbocyclyl, and heterocyclyl;

$R_d$, at each occurrence, is independently selected from the group consisting of H, OH, $C_{1-6}$ alkyl substituted with 1-5 $R_e$, $C_{2-6}$alkenyl substituted with 1-5 $R_e$, $C_{2-6}$alkynyl substituted with 1-5 $R_e$, —$(CH_2)_r$—$C_{3-10}$carbocyclyl substituted with 1-5 $R_e$, and —$(CH_2)_r$-heterocyclyl substituted with 1-5 $R_e$;

$R_e$, at each occurrence, is independently selected from the group consisting of H, $C_{1-6}$alkyl substituted with 1-5 $R_f$, $C_{2-6}$alkenyl, $C_{2-6}$alkynyl, —$(CH_2)_r$—$C_{3-6}$cycloalkyl, —$(CH_2)_r$-heterocyclyl, F, Cl, Br, CN, $NO_2$, =O, $CO_2H$, —$(CH_2)_rOC_{1-5}$ alkyl, —$(CH_2)_rOH$, SH, —$(CH_2)_rNR_fR_f$, —$(CH_2)_rNHC(=O)OR_f$, and —$(CH_2)_rC(=O)OR_f$;

$R_f$, at each occurrence, is independently selected from the group consisting of H, $C_{1-5}$alkyl, OH, $OC_{1-5}$alkyl, $C_{3-6}$cycloalkyl, and phenyl, or $R_f$ and $R_f$ together with the nitrogen atom to which they are both attached form a heterocyclic ring optionally substituted with $C_{1-4}$alkyl;

p, at each occurrence, is independently selected from the group consisting of zero, 1, and 2; and r, at each occurrence, is independently selected from the group consisting of zero, 1, 2, 3, and 4.

In another embodiment, $R_4$ is selected from the group consisting of —$(CH_2)OR_b$, —$(CH_2CH_2)OR_b$, —$(CH(CH_3)CH_2)OR_b$, —$(C(CH_3)_2CH_2)OR_b$, —$(CH_2CH(CH_3))OR_b$, —$(CH_2C(CH_3)_2)OR_b$, —$(CH_2)NR_aR_a$, —$(CH_2CH_2)NR_aR_a$, —$(CH(CH_3)CH_2)NR_aR_a$, —$(C(CH_3)_2CH_2)NR_aR_a$, —$(CH_2CH(CH_3))NR_aR_a$, and —$(CH_2C(CH_3)_2)NR_aR_a$, wherein $R_a$, at each occurrence, is independently selected from the group consisting of H and $C_{1-6}$ alkyl substituted with 1-3 $R_e$; or $R_a$ and $R_a$ together with the nitrogen atom to which they are attached form a heterocyclic ring selected from the group consisting of oxetanyl, imidazolidinyl, imidazolinyl, imidazolyl, indazolyl, indolinyl, indolizinyl, indolyl, isoquinolinyl, isoxazolyl, morpholinyl, oxadiazolyl, oxazolyl, pyrimidinyl, piperazinyl, pyrazinyl, pyrazolyl, pyridazinyl, pyridinyl, pyrimidinyl, pyrrolidinyl, pyrrolinyl, pyrrolyl, quinazolinyl, quinolinyl, tetrazolyl, thiazolyl, triazinyl, and triazolyl.

In another embodiment, $R_4$ is substituted with 1-3 $R_e$ and is selected from the group consisting of phenyl, naphthyl, biphenyl, cyclopropyl, cyclobutyl, cyclopentyl, cyclohexyl, and cycloheptyl.

In another embodiment, $R_4$ is —$(CH_2)_{0-2}$-heterocyclyl substituted with 1-3 $R_e$, wherein said heterocyclyl is selected from the group consisting of azetidinyl, oxetanyl, thiazolyl, oxazolyl, pyrazolyl, triazolyl, tetrazolyl, thiadiazolyl, isoxazolyl, imidazolyl, pyridyl, pyrimidinyl, pyrazinyl, pyridazinyl, indolyl, indazolyl, isoindolyl, indolinyl, isoindolinyl, benzimidazolyl, benzothiazolyl, benzotriazolyl, quinolinyl, isoquinolinyl, tetrahydroquinolinyl, and tetrahydroisoquinolinyl.

In another aspect, there are disclosed compounds of Formula (II) including enantiomers, diastereomers, tautomers, pharmaceutically-acceptable salts, prodrugs, hydrates, or solvates thereof,

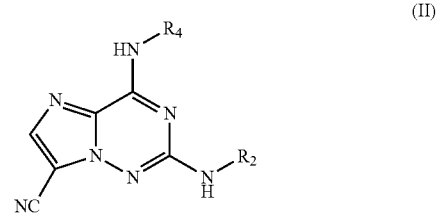

wherein $R_2$ is selected from the group consisting of aryl substituted with 1-4 $R_6$ and heteroaryl substituted with 1-4 $R_6$, wherein said heteroaryl comprises carbon atoms and 1-4 heteroatoms selected from the group consisting of N, $NR_{6a}$, O, and $S(O)_p$;

$R_4$ is selected from the group consisting of H, $C_{1-4}$alkyl substituted with 1-5 $R_e$, —$(CR_{4a}R_{4b})_rOR_b$, —$(CR_{4a}R_{4b})_rS(O)_pR_c$, —$(CR_{4a}R_{4b})_rC(\!\!=\!\!O)R_d$, —$(CR_{4a}R_{4b})_rNR_aR_a$, —$(CR_{4a}R_{4b})_rC(\!\!=\!\!O)NR_aR_a$, —$(CR_{4a}R_{4b})_rNR_aC(\!\!=\!\!O)R_d$, —$(CR_{4a}R_{4b})_rNR_aC(\!\!=\!\!O)OR_b$, —$(CR_{4a}R_{4b})_rOC(\!\!=\!\!O)NR_aR_a$, —$(CR_{4a}R_{4b})_rNR_aC(\!\!=\!\!O)NR_aR_a$, —$(CR_{4a}R_{4b})_rC(\!\!=\!\!O)OR_b$, —$(CR_{4a}R_{4b})_rNR_aS(O)_2R_c$, —$(CR_{4a}R_{4b})_r$—$C_{3-6}$carbocyclyl substituted with 1-4 $R_e$, —$(CR_{4a}R_{4b})_r$-heterocyclyl substituted with 1-4 $R_e$;

$R_{4a}$, at each occurrence, is independently selected from the group consisting of H and $C_{1-4}$alkyl;

$R_{4b}$, at each occurrence, is independently selected from the group consisting of H and $C_{1-4}$alkyl;

$R_6$, at each occurrence, is independently selected from the group consisting of H, F, Cl, Br, =O, CN, —$OR_b$, —$S(O)_pR_c$, —$C(\!\!=\!\!O)R_d$, —$NR_7R_7$, —$(CR_{2a}R_{2b})_rC(\!\!=\!\!O)NR_7R_7$, —$NR_aC(\!\!=\!\!O)R_d$, —$NR_aC(\!\!=\!\!O)OR_b$, —$OC(\!\!=\!\!O)NR_7R_7$, —$NR_aC(\!\!=\!\!O)NR_7R_7$, —$(CR_{2a}R_{2b})_rC(\!\!=\!\!O)OR_b$, —$S(O)_2NR_7R_7$, —$NR_aS(O)_2NR_7R_7$, —$NR_2S(O)_2R_c$, $C_{1-4}$ alkyl substituted with 1-3 $R_e$, —$(CR_{2a}R_{2b})_r$—$C_{3-6}$carbocyclyl substituted with 1-3 $R_e$, and —$(CR_{2a}R_{2b})_r$-heterocyclyl substituted with 1-3 $R_e$;

$R_{2a}$, at each occurrence, is independently selected from the group consisting of H and $C_{1-4}$alkyl;

$R_{2b}$, at each occurrence, is independently selected from the group consisting of H and $C_{1-4}$alkyl; and $R_7$, at each occurrence, is independently selected from the group consisting of H, $C_{1-6}$ alkyl substituted with 1-5 $R_e$, —$(CH_2)_r$—$C_{3-10}$carbocyclyl substituted with 1-5 $R_e$, and —$(CH_2)_r$-heterocyclyl substituted with 1-5 $R_e$; or $R_7$ and $R_7$ together with the nitrogen atom to which they are both attached form a heterocyclic ring substituted with 1-5 $R_8$;

$R_8$, at each occurrence, is independently selected from the group consisting of H, F, Cl, Br, $C_{1-6}$ alkyl substituted with 1-5 $R_e$, =O, —$(CH_2)_rOR_b$, —$(CH_2)_rS(O)_pR_c$, —$(CH_2)_rC(\!\!=\!\!O)R_d$, —$(CH_2)_rNR_aR_a$, —$(CH_2)_rC(\!\!=\!\!O)NR_aR_a$, —$(CH_2)_rNR_aC(\!\!=\!\!O)R_d$, —$(CH_2)_rNR_aC(\!\!=\!\!O)OR_b$, —$(CH_2)_rOC(\!\!=\!\!O)R_d$, —$(CH_2)_rOC(\!\!=\!\!O)NR_aR_a$, —$(CH_2)_rNR_aC(\!\!=\!\!O)NR_aR_a$, —$(CH_2)_rC(\!\!=\!\!O)OR_b$, —$(CH_2)_rS(O)_2NR_aR_a$, —$(CH_2)_rNR_aS(O)_2NR_aR_a$, —$(CH_2)_rNR_aS(O)_2R_c$, and —$(CH_2)_r$-heterocyclyl substituted with 1-5 $R_e$; and r, at each occurrence, is independently selected from the group consisting of zero, 1, 2, and 3.

In another embodiment, there are disclosed compounds of Formula (II) including enantiomers, diastereomers, tautomers, pharmaceutically-acceptable salts, prodrugs, hydrates, or solvates thereof, wherein $R_2$ is selected from the group consisting of aryl substituted with 1-4 $R_6$ and heteroaryl substituted with 1-4 $R_6$, wherein said heteroaryl comprises carbon atoms and 1-4 heteroatoms selected from the group consisting of N, $NR_{6a}$; O, and $S(O)_p$;

$R_4$ is selected from the group consisting of H, $C_{1-4}$alkyl substituted with 1-4 $R_e$, $C_{3-6}$cycloalkyl substituted with 1-4 $R_e$, aryl substituted with 1-4 $R_e$, and heterocyclyl substituted with 1-4 $R_e$;

$R_6$, at each occurrence, is independently selected from the group consisting of H, F, Cl, Br, CN, —$NR_7R_7$, —$C(\!\!=\!\!O)NR_7R_7$, —$NR_aC(\!\!=\!\!O)R_d$, —$NR_aC(\!\!=\!\!O)OR_b$, $C_{1-4}$alkyl substituted with 1-3 $R_e$, $C_{3-6}$carbocyclyl substituted with 1-3 $R_g$, and heterocyclyl substituted with 1-3 $R_8$;

$R_{6a}$ is selected from the group consisting of H and $C_{1-4}$alkyl substituted with 1-3 $R_e$;

$R_7$ and $R_7$ together with the nitrogen atom to which they are both attached form a heterocyclic ring comprising carbon atoms and 1-4 heteroatoms selected from the group consisting of N, $NR_{8a}$, O, and $S(O)_p$ and substituted with 1-5 $R_8$;

$R_8$, at each occurrence, is independently selected from the group consisting of H, F, Cl, Br, $C_{1-4}$alkyl substituted with 1-4 $R_e$, =O, —$OR_b$, —$S(O)_pR_c$, —$C(\!\!=\!\!O)R_d$; —$NR_aR_a$, —$C(\!\!=\!\!O)NR_aR_a$, —$NR_aC(\!\!=\!\!O)R_d$, —$NR_aC(\!\!=\!\!O)OR_b$, —$OC(\!\!=\!\!O)R_d$; —$OC(\!\!=\!\!O)(CH_2)_rNR_aR_a$, $NR_aC(\!\!=\!\!O)NR_aR_a$, —$C(\!\!=\!\!O)OR_b$, $S(O)_2NR_aR_a$, —$NR_aS(O)_2NR_aR_a$, —$NR_aS(O)_2R_c$, and heterocyclyl substituted with 1-4 $R_e$;

$R_{8a}$ is selected from the group consisting of H, $C_{1-4}$alkyl, $S(O)_pR_c$, and heterocyclyl substituted with 1-4 $R_e$;

p, at each occurrence, is independently selected from the group consisting of zero, 1, and 2.

In another embodiment, there are disclosed compounds of Formula (II) including enantiomers, diastereomers, tautomers, pharmaceutically-acceptable salts, prodrugs, hydrates, or solvates thereof, wherein $R_4$ is selected from the group consisting of H, $C_{1-4}$alkyl substituted with 1-5 $R_e$, —$(CH_2)_rOR_b$, —$(CH_2)_rNR_aR_a$, —$(CH_2)_r$—$C_{3-6}$cycloalkyl substituted with 1-3 $R_e$, —$(CH_2)_r$— aryl substituted with 1-3 $R_e$, and —$(CH_2)_r$-heterocyclyl substituted with 1-3 $R_e$.

In another embodiment, there are disclosed compounds of Formula (II) including enantiomers, diastereomers, tautomers, pharmaceutically-acceptable salts, prodrugs, hydrates, or solvates thereof, wherein $R_2$ is selected from the group consisting of phenyl substituted with 1-3 $R_6$ and heteroaryl substituted with 1-3 $R_6$;

$R_4$ is selected from the group consisting of H, $C_{1-6}$alkyl substituted with 1-3 $R_e$, —$(CH_2)_rOR_b$, —$C_{3-6}$cycloalkyl substituted with 1-3 $R_e$, aryl substituted with 1-3 $R_e$, —$(CH_2)_r$-4- to 6-membered saturated monocyclic heterocyclyl substituted with 1-3 $R_e$, and —$(CH_2)_r$-5- to 6-membered heteroaryl substituted with 1-3 $R_e$;

$R_6$, at each occurrence, is independently selected from the group consisting of H, F, Cl, Br, =O, CN, —$OR_b$, —$S(O)_2R_c$, —$C(\!\!=\!\!O)R_d$, —$NR_7R_7$, —$(CH_2)_rC(\!\!=\!\!O)NR_7R_7$, —$NHC(\!\!=\!\!O)R_d$, —$NHC(\!\!=\!\!O)OR_b$, —$NHC(\!\!=\!\!O)NR_2R_2$, —$(CH_2)_rC(\!\!=\!\!O)OR_b$, —$S(O)_2NR_2R_2$, —$NHS(O)_2NR_2R_2$, —$NHS(O)_2R_c$, $C_{1-4}$alkyl substituted with 1-3 $R_e$, non-aromatic heterocyclyl substituted with 1-3 $R_e$, and heteroaryl substituted with 1-3 $R_e$;

$R_7$, at each occurrence, is independently selected from the group consisting of H, $C_{1-6}$ alkyl substituted with 1-5 $R_e$, —$(CH_2)_r$—$C_{3-10}$carbocyclyl substituted with 1-5 $R_e$, and —$(CH_2)_r$-heterocyclyl substituted with 1-5 $R_e$; or $R_7$ and $R_7$ together with the nitrogen atom to which they are both attached form a heterocyclic ring substituted with 1-5 $R_8$;

$R_8$, at each occurrence, is independently selected from the group consisting of H, F, Cl, Br, $C_{1-6}$ alkyl substituted with 1-5 $R_e$, =O, —$(CH_2)_rOR_b$, —$(CH_2)_rS(O)_pR_c$, —$(CH_2)_rC(\!\!=\!\!O)R_d$, —$(CH_2)_rNR_aR_a$, —$(CH_2)_rC(\!\!=\!\!O)NR_aR_a$, —$(CH_2)_rNR_aC(\!\!=\!\!O)R_d$, —$(CH_2)_rNR_aC(\!\!=\!\!O)OR_b$, —$(CH_2)_rOC(\!\!=\!\!O)R_d$, —$(CH_2)_rOC(\!\!=\!\!O)$ —(CH$_2$)$_r$NR$_a$R$_a$, —(CH$_2$)$_r$NR$_a$C(=O)NR$_a$R$_a$, —(CH$_2$)$_r$C(=O)OR$_b$, —(CH$_2$)$_r$S(O)$_2$NR$_a$R$_a$, —(CH$_2$)$_r$NR$_a$S(O)$_2$NR$_a$R$_a$, —(CH$_2$)$_r$NR$_a$S(O)$_2$R$_c$, and —(CH$_2$)$_r$-heterocyclyl substituted with 1-5 R$_e$;

R$_a$, at each occurrence, is independently selected from the group consisting of H, CN, C$_{1-4}$ alkyl substituted with 1-5 R$_e$, —(CH$_2$)$_r$-heterocyclyl substituted with 1-3 R$_e$; or R$_a$ and R$_a$ together with the nitrogen atom to which they are both attached form a heterocyclic ring, having 1 to 3 heteroatoms selected from the group consisting of N, O, S, and substituted with 1-3 R$_e$;

R$_b$, at each occurrence, is independently selected from the group consisting of H, C$_{1-4}$ alkyl substituted with 1-3 R$_e$, and heterocyclyl;

R$_c$, at each occurrence, is independently C$_{1-4}$ alkyl substituted with 1-3 R$_e$;

R$_d$, at each occurrence, is independently selected from the group consisting of H and C$_{1-4}$ alkyl substituted with 1-3 R$_e$;

R$_e$, at each occurrence, is independently selected from the group consisting of H, C$_{1-4}$ alkyl substituted with 1-4 R$_f$, F, Cl, Br, =O, —(CH$_2$)$_r$OC$_{1-5}$ alkyl, —(CH$_2$)$_r$OH, and —(CH$_2$)$_r$NR$_f$R$_f$; and R$_f$, at each occurrence, is independently selected from the group consisting of H and C$_{1-3}$alkyl or R$_f$ and R$_f$ together with the nitrogen atom to which they are both attached form a heterocyclic ring;

r, at each occurrence, is independently selected from the group consisting of zero, 1, 2, and 3; and m, at each occurrence, is independently selected from the group consisting of zero, 1, 2, and 3.

In another embodiment, there are disclosed compounds of Formula (II) including enantiomers, diastereomers, tautomers, pharmaceutically-acceptable salts, prodrugs, hydrates, or solvates thereof, wherein R$_2$ is selected from the group consisting of 4- to 7-membered monocyclic or 8- to 12-membered bicyclic aryl substituted with 1-4 R$_6$ and 4- to 7-membered monocyclic or 7- to 12-membered bicyclic heteroaryl substituted with 1-4 R$_6$;

R$_4$ is selected from the group consisting of H, C$_{1-4}$alkyl substituted with 1-5 R$_e$, —(CH$_2$)$_r$OR$_b$, —(CH$_2$)$_r$S(O)$_p$R$_c$, —(CH$_2$)$_r$C(=O)R$_d$, —(CH$_2$)$_r$NR$_a$R$_a$, —(CH$_2$)$_r$C(=O)NR$_a$R$_a$, —(CH$_2$)$_r$NR$_a$C(=O)R$_d$, —(CH$_2$)$_r$NR$_a$C(=O)OR$_b$, —(CH$_{2c}$)$_r$OC(=O)NR$_a$R$_a$, —(CH$_2$)$_r$NR$_a$C(=O)NR$_a$R$_a$, —(CH$_2$)$_r$C(=O)OR$_b$, —(CH$_2$)$_r$NR$_a$S(O)$_2$R$_c$, —(CH$_2$)$_r$—C$_{3-6}$cycloalkyl substituted with 1-3 R$_e$, —(CH$_2$)$_r$-aryl substituted with 1-3 R$_e$, —(CH$_2$)$_r$— heterocyclyl substituted with 1-3 R$_e$;

R$_6$, at each occurrence, is independently selected from the group consisting of H, F, Cl, Br, =O, CN, —OR$_b$, —S(O)$_p$R$_c$, —C(=O)R$_d$, —NR$_7$R$_7$, —(CH$_2$)$_r$C(=O)NR$_7$R$_7$, —NHC(=O)R$_d$, —NHC(=O)OR$_b$, —OC(=O)NR$_2$R$_2$, —NHC(=O)NR$_2$R$_2$, —(CH$_2$)$_r$C(=O)OR$_b$, —S(O)$_2$NR$_7$R$_7$, —NHS(O)$_2$NR$_7$R$_7$, —NHS(O)$_2$R$_c$, or C$_{1-6}$ alkyl substituted with 1-3 R$_e$, —(CH$_2$)$_r$—C$_{3-6}$ carbocyclyl substituted with 1-3 R$_e$, and —(CH$_2$)$_r$-heterocyclyl substituted with 1-3 R$_e$;

R$_7$, at each occurrence, is independently selected from the group consisting of H, C$_{1-6}$ alkyl substituted with 1-5 R$_e$, —(CH$_2$)$_r$—C$_{3-10}$carbocyclyl substituted with 1-5 R$_e$, and —(CH$_2$)$_r$-heterocyclyl substituted with 1-5 R$_e$; or R$_7$ and R$_7$ together with the nitrogen atom to which they are both attached form a heterocyclic ring substituted with 1-5 R$_8$; and R$_8$, at each occurrence, is independently selected from the group consisting of H, F, Cl, Br, C$_{1-6}$ alkyl substituted with 1-5 R$_e$, =O, —(CH$_2$)$_r$OR$_b$, —(CH$_2$)$_r$S(O)$_p$R$_c$, —(CH$_2$)$_r$C(=O)R$_d$, —(CH$_2$)$_r$NR$_a$R$_a$, —(CH$_2$)$_r$C(=O)NR$_a$R$_a$, —(CH$_2$)$_r$NR$_a$C(=O)R$_d$, —(CH$_2$)$_r$NR$_a$C(=O)OR$_b$, —(CH$_2$)$_r$OC(=O)R$_d$, —(CH$_2$)$_r$OC(=O)(CH$_2$)$_r$NR$_a$R$_a$, —(CH$_2$)$_r$NR$_a$C(=O)NR$_a$R$_a$, —(CH$_2$)$_r$C(=O)OR$_b$, —(CH$_2$)$_r$S(O)$_2$NR$_a$R$_a$, —(CH$_2$)$_r$NR$_a$S(O)$_2$NR$_a$R$_a$, —(CH$_2$)$_r$NR$_a$S(O)$_2$R$_c$, and —(CH$_2$)$_r$-heterocyclyl substituted with 1-5 R$_e$.

In another embodiment, there are disclosed compounds of formula (II) including enantiomers, diastereomers, tautomers, pharmaceutically-acceptable salts, prodrugs, hydrates, or solvates thereof, wherein R$_2$ is selected from the group consisting of 4- to 7-membered monocyclic or 8- to 12-membered bicyclic aryl substituted with 1-4 R$_6$ and 4- to 7-membered monocyclic or 7- to 12-membered bicyclic heteroaryl comprising carbon atoms and 1-4 heteroatoms selected from the group consisting of N, NR$_{6a}$, and substituted with 1-4 R$_6$, R$_4$ is selected from the group consisting of C$_{1-4}$alkyl substituted with 1-3 R$_e$, C$_{3-6}$cycloalkyl, phenyl substituted with 1-3 R$_e$, and 4- to 6-membered heterocyclyl comprising carbon atoms and 1-4 heteroatoms selected from the group consisting of N, NH, NC$_{1-4}$alkyl, 0, and S(O)$_p$ and substituted with 1-3 R$_e$;

R$_6$, at each occurrence, is independently selected from the group consisting of H, F, Cl, Br, CN, —NR$_7$R$_7$, —C(=O)NR$_7$R$_7$, —NHC(=O)OR$_b$, C$_{1-4}$alkyl substituted with 1-3 R$_e$ and 5- to 6-membered heterocyclyl substituted with 1-3 R$_8$;

R$_7$ and R$_7$ together with the nitrogen atom to which they are both attached form a heterocyclic ring comprising carbon atoms and 1-4 heteroatoms selected from the group consisting of N, NR$_{8a}$, O, and S(O)$_p$ and substituted with 1-4 R$_8$; and R$_{8a}$ is selected from the group consisting of H and C$_{1-4}$alkyl, S(O)$_p$R$_c$, and heterocyclyl substituted with 1-4 R$_e$.

In another embodiment, there are disclosed compounds of Formula (II) including enantiomers, diastereomers, tautomers, pharmaceutically-acceptable salts, prodrugs, hydrates, or solvates thereof, wherein R$_2$ is selected from the group consisting of

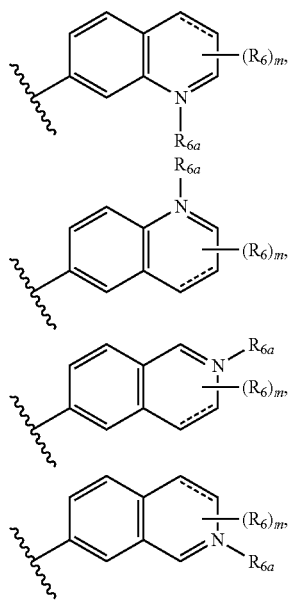

-continued

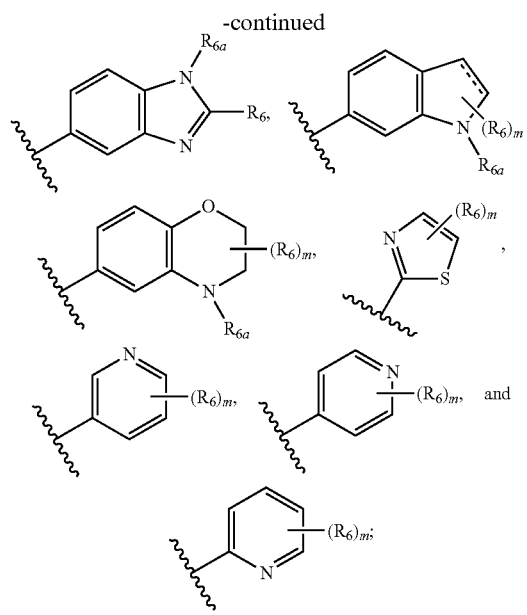

---- represents an optional bond;
R$_{6a}$, at each occurrence, is independently selected from the group consisting of H, C$_{1-4}$ alkyl substituted with 1-3 R$_e$, —S(O)$_p$R$_c$, —C(═O)R$_d$, C(═O)OR$_b$; and
m, at each occurrence, is independently selected from the group consisting of zero, 1, 2, 3, and 4.

In another embodiment, there are disclosed compounds of formula (II) including enantiomers, diastereomers, tautomers, pharmaceutically-acceptable salts, prodrugs, hydrates, or solvates thereof, wherein
R$_2$ is selected from the group consisting of

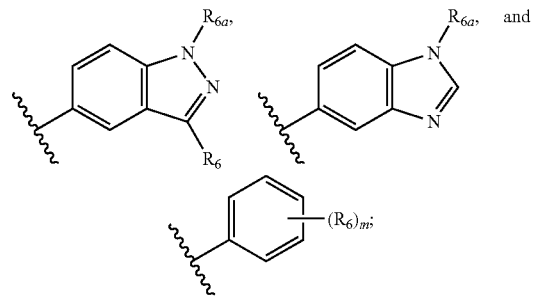

R$_{6a}$ is selected from the group consisting of H and C$_{1-4}$alkyl substituted with 1-2 R$_e$;
R$_6$, at each occurrence, is independently selected from the group consisting of H, F, Cl, Br, CN, —NR$_7$R$_7$, —C(═O)NR$_7$R$_7$, —NR$_a$C(═O)R$_d$, —NR$_a$C(═O)OR$_b$, C$_{1-4}$alkyl substituted with 1-3 R$_e$, and heterocyclyl substituted with 1-3 R$_8$;
R$_7$ and R$_7$ together with the nitrogen atom to which they are both attached form a heterocyclic ring comprising carbon atoms and 1-4 heteroatoms selected from the group consisting of N, NR$_{8a}$, O, and S(O)$_p$ and substituted with 1-4 R$_8$;
R$_e$, at each occurrence, is independently selected from the group consisting of C$_{1-6}$alkyl and OH; and
m, at each occurrence, is independently selected from the group consisting of zero, 1, 2, 3, and 4.

In another embodiment of the compounds of Formulae (I) and (II), R$_2$ is heteroaryl selected from the group consisting of pyridyl, pyrimidinyl, pyrazinyl, pyridazinyl, triazinyl, furyl, quinolinyl, dihydroquinolinyl, tetrahydroquinolinyl, isoquinolinyl, thienyl, imidazolyl, thiazolyl, indolyl, pyrrolyl, oxazolyl, benzofuryl, benzothienyl, benzthiazolyl, benzoxazinyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, and benzodioxane, each of which is substituted with 1-4 R$_6$.

In another embodiment, there are disclosed compounds of formula (III) or (IV) including enantiomers, diastereomers, tautomers, pharmaceutically-acceptable salts, prodrugs, hydrates, or solvates thereof,

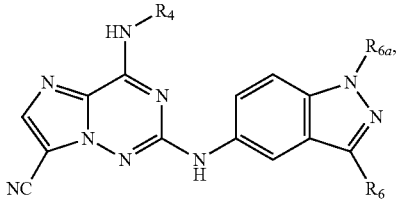

(III)

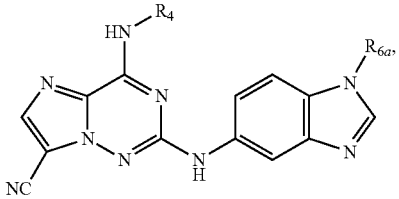

(IV)

wherein
R$_4$ is selected from the group consisting of C$_{1-4}$alkyl substituted with 1-3 R$_e$, C$_{3-6}$cycloalkyl substituted with 1-3 R$_e$, and 4- to 6-membered heterocyclyl comprising carbon atoms and 1-4 heteroatoms selected from the group consisting of N, NH, NC$_{1-4}$alkyl, O, and S(O)$_p$ and substituted with 1-3 R$_e$;
R$_{6a}$ is selected from the group consisting of H and C$_{1-4}$alkyl optionally substituted with OH; and
R$_6$ is selected from the group consisting of H, F, Cl, Br, CN, and C$_{1-4}$alkyl substituted with 1-2 R$_e$.

In another embodiment, there are disclosed compounds of formula (Va) including enantiomers, diastereomers, tautomers, pharmaceutically-acceptable salts, prodrugs, hydrates, or solvates thereof,

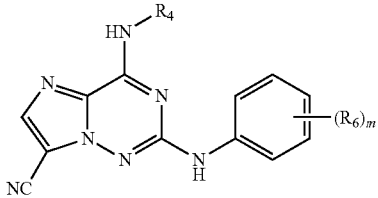

(Va)

wherein
R$_4$ is selected from the group consisting of H, C$_{1-6}$alkyl substituted with 1-5 R$_e$, —(CH$_2$)$_r$OR$_b$, —(CH$_2$)$_r$NR$_a$R$_a$, —(CH$_2$)$_r$—C$_{3-6}$cycloalkyl substituted with 1-3 R$_e$, —(CH$_2$)$_r$-aryl substituted with 1-3 R$_e$, and —(CH$_2$)$_r$-heterocyclyl substituted with 1-3 R$_e$;

R$_6$, at each occurrence, is independently selected from the group consisting of H, F, Cl, Br, =O, CN, —OR$_b$, —S(O)$_p$R$_c$, —C(=O)R$_d$, —NR$_7$R$_7$, —(CH$_2$)$_r$C(=O)NR$_7$R$_7$, —NHC(=O)R$_d$, —NHC(=O)OR$_b$, —OC(=O)NR$_7$R$_7$, —NHC(=O)NR$_7$R$_7$, —(CH$_2$)$_r$C(=O)OR$_b$, —S(O)$_2$NR$_7$R$_7$, —NHS(O)$_2$NR$_7$R$_7$, —NHS(O)$_2$R$_c$, or C$_{1-4}$ alkyl substituted with 1-3 R$_e$, —(CH$_2$)$_r$—C$_{3-6}$ carbocyclyl substituted with 1-3 R$_e$, and —(CH$_2$)$_r$-heterocyclyl substituted with 1-3 R$_e$;

R$_7$, at each occurrence, is independently selected from the group consisting of H, C$_{1-6}$ alkyl substituted with 1-5 R$_e$, —(CH$_2$)$_r$—C$_{3-10}$carbocyclyl substituted with 1-5 R$_e$, and —(CH$_2$)$_r$-heterocyclyl substituted with 1-5 R$_e$; or R$_7$ and R$_7$ together with the nitrogen atom to which they are both attached form a heterocyclic ring substituted with 1-5 R$_8$;

R$_8$, at each occurrence, is independently selected from the group consisting of H, F, Cl, Br, C$_{1-6}$ alkyl substituted with 1-5 R$_e$, =O, —(CH$_2$)$_r$OR$_b$, —(CH$_2$)$_r$S(O)$_p$R$_c$, —(CH$_2$)$_r$C(=O)R$_d$, —(CH$_2$)$_r$NR$_a$R$_a$, —(CH$_2$)$_r$C(=O)NR$_a$R$_a$, —(CH$_2$)$_r$NR$_a$C(=O)R$_d$, —(CH$_2$)$_r$NR$_a$C(=O)OR$_b$, —(CH$_2$)$_r$OC(=O)R$_d$, —(CH$_2$)$_r$OC(=O)(CH$_2$)$_r$NR$_a$R$_a$, —(CH$_2$)$_r$NR$_a$C(=O)NR$_a$R$_a$, —(CH$_2$)$_r$C(=O)OR$_b$, —(CH$_2$)$_r$S(O)$_2$NR$_a$R$_a$, —(CH$_2$)$_r$NR$_a$S(O)$_2$NR$_a$R$_a$, —(CH$_2$)$_r$NR$_a$S(O)$_2$R$_c$, and —(CH$_2$)$_r$-heterocyclyl substituted with 1-5 R$_e$;

R$_a$, at each occurrence, is independently selected from the group consisting of H, CN, C$_{1-6}$ alkyl substituted with 1-5 R$_e$, —(CH$_2$)$_r$—C$_{3-10}$carbocyclyl substituted with 1-5 R$_e$, and —(CH$_2$)$_r$-heterocyclyl substituted with 1-5 R$_e$; or R$_a$ and R$_a$ together with the nitrogen atom to which they are both attached form a heterocyclic ring substituted with 1-5 R$_e$;

R$_b$, at each occurrence, is independently selected from the group consisting of H, C$_{1-6}$ alkyl substituted with 1-5 R$_e$, —(CH$_2$)$_r$—C$_{3-10}$carbocyclyl substituted with 1-5 R$_e$, and —(CH$_2$)$_r$-heterocyclyl substituted with 1-5 R$_e$;

R$_c$, at each occurrence, is independently selected from the group consisting of C$_{1-6}$ alkyl substituted with 1-5 R$_e$, C$_{3-6}$carbocyclyl, and heterocyclyl;

R$_d$, at each occurrence, is independently selected from the group consisting of H, C$_{1-6}$ alkyl substituted with 1-5 R$_e$, —(CH$_2$)$_r$—C$_{3-10}$carbocyclyl substituted with 1-5 R$_e$, and —(CH$_2$)$_r$-heterocyclyl substituted with 1-5 R$_e$;

R$_e$, at each occurrence, is independently selected from the group consisting of H, C$_{1-6}$alkyl substituted with 1-5 R$_f$, C$_{2-6}$alkenyl, C$_{2-6}$alkynyl, —(CH$_2$)$_r$—C$_{3-6}$cycloalkyl, —(CH$_2$)$_r$-heterocyclyl, F, Cl, Br, CN, NO$_2$, =O, CO$_2$H, —(CH$_2$)$_r$OC$_{1-5}$ alkyl, —(CH$_2$)$_r$OH, SH, —(CH$_2$)$_r$NR$_f$R$_f$, —(CH$_2$)$_r$NHC(=O)OR$_f$, and —(CH$_2$)$_r$C(=O)OR$_f$;

R$_f$, at each occurrence, is independently selected from the group consisting of H, C$_{1-5}$ alkyl, and phenyl, or R$_f$ and R$_f$ together with the nitrogen atom to which they are both attached form a heterocyclic ring; and m, at each occurrence, is independently selected from the group consisting of zero, 1, 2, 3, and 4.

In another embodiment, there are disclosed compounds of Formula (Va) including enantiomers, diastereomers, tautomers, pharmaceutically-acceptable salts, prodrugs, hydrates, or solvates thereof, wherein R$_4$ is selected from the group consisting of H, C$_{1-6}$alkyl substituted with 1-3 R$_e$, —(CH$_2$)$_r$OR$_b$, —(CH$_2$)$_r$NR$_a$R$_a$, —C$_{3-6}$cycloalkyl substituted with 1-3 R$_e$, aryl substituted with 1-3 R$_e$, 4-, 5-, or 6-membered non-aromatic monocyclic heterocyclyl substituted with 1-3 R$_e$, and 5- or 6-membered heteroaryl substituted with 1-3 R$_e$;

R$_a$, at each occurrence, is independently selected from the group consisting of H, CN, C$_{1-4}$ alkyl substituted with 1-3 R$_e$, —(CH$_2$)$_r$-heterocyclyl substituted with 1-3 R$_e$; or R$_a$ and R$_a$ together with the nitrogen atom to which they are both attached form a monocyclic heterocyclic ring substituted with 1-3 R$_e$;

R$_b$, at each occurrence, is independently selected from the group consisting of H and C$_{1-4}$ alkyl substituted with 1-3 R$_e$, and heterocyclyl;

R$_c$, at each occurrence, is independently selected from the group consisting of C$_{1-4}$ alkyl substituted with 1-3 R$_e$ and heterocyclyl;

R$_d$, at each occurrence, is independently selected from the group consisting of H, C$_{1-4}$ alkyl substituted with 1-3 R$_e$, —(CH$_2$)$_r$—C$_{3-10}$carbocyclyl substituted with 1-3 R$_e$, and —(CH$_2$)$_r$-heterocyclyl substituted with 1-3 R$_e$;

R$_e$, at each occurrence, is independently selected from the group consisting of C$_{1-4}$ alkyl substituted with 1-4 R$_f$, F, Cl, Br, CN, NO$_2$, =O, CO$_2$H, —(CH$_2$)$_r$OC$_{1-5}$ alkyl, —(CH$_2$)$_r$OH, SH, and —(CH$_2$)$_r$NR$_f$R$_f$;

R$_f$, at each occurrence, is independently selected from the group consisting of H and C$_{1-4}$alkyl or R$_f$ and R$_f$ together with the nitrogen atom to which they are both attached form a heterocyclic ring.

In another embodiment, there are disclosed compounds of Formula (Va) including enantiomers, diastereomers, tautomers, pharmaceutically-acceptable salts, prodrugs, hydrates, or solvates thereof, wherein R$_6$, at each occurrence, is independently selected from the group consisting of H, F, Cl, Br, CN, =O, O—C$_{1-4}$alkyl substituted with 1-3 R$_e$, —O(CH$_2$)$_r$NR$_a$C$_{1-4}$alkyl —O—(CH$_2$)$_r$OC$_{1-4}$alkyl, —O(CH$_2$)$_r$-heterocyclyl, —S(O)$_2$C$_{1-4}$alkyl, —C(=O)C$_{1-4}$alkyl, —NH$_2$, —N(C$_{1-4}$alkyl)$_2$, —NHCN, —NR$_a$(CH$_2$)$_r$NR$_a$C$_{1-4}$ alkyl, —NR$_a$(CH$_2$)$_r$OC$_{1-4}$alkyl, —NH(CH$_2$)$_r$-heterocyclyl, —(CH$_2$)$_r$C(=O)NH$_2$, —C(=O)NH-heterocyclyl, —C(=O)NH(CH$_2$)$_r$N(C$_{1-4}$alkyl)$_2$, —C(=O)-heterocyclyl, —NHC(=O)C$_{1-4}$alkyl, —NHC(=O)OC$_{1-4}$alkyl, —NHC(=O)NHC$_{1-4}$alkyl, C(=O)OC$_{1-4}$alkyl, —(CH$_2$)$_r$C(=O)OH, —S(O)$_2$NH$_2$, —S(O)$_2$NH-heterocyclyl, —S(O)$_2$NHC$_{1-4}$alkyl, —S(O)$_2$-heterocyclyl substituted with 1-3 R$_e$, —NH$_2$S(O)$_2$NH$_2$, —NHS(O)$_2$C$_{1-4}$alkyl, C$_{1-4}$alkyl, CF$_3$, —(CH$_2$)$_r$OH, C$_{3-6}$carbocyclyl substituted with 1-3 R$_e$, non-aromatic heterocyclyl substituted with 1-3 R$_e$, and 5- or 6-membered heteroaryl substituted with 1-3 R$_e$.

In another embodiment, there are disclosed compounds of formula (V) including enantiomers, diastereomers, tautomers, pharmaceutically-acceptable salts, prodrugs, hydrates, or solvates thereof,

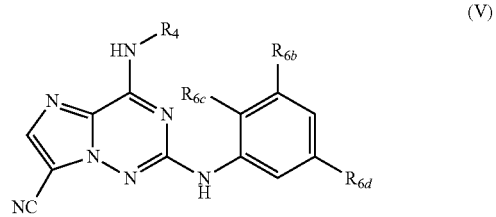

(V)

wherein
R$_4$ is selected from the group consisting of C$_{1-4}$alkyl substituted with 1-3 R$_e$, C$_{3-6}$cycloalkyl substituted with 1-3 R$_e$, aryl substituted with 1-3 R$_e$, and heterocyclyl substituted with 1-3 R$_e$;

$R_{6b}$ is selected from the group consisting of —$NR_7R_7$ and heterocyclyl substituted with 1-3 $R_8$ $R_{6c}$ is selected from the group consisting of F, Cl, and Br;

$R_{6d}$ is selected from the group consisting of CN, —NHC(=O)O($C_{1-4}$alkyl), and $CHF_2$;

$R_7$ and $R_7$ together with the nitrogen atom to which they are both attached form a heterocyclic ring comprising carbon atoms and 1-4 heteroatoms selected from the group consisting of N, $NR_{8a}$, O, and $S(O)_p$ and substituted with 1-4 $R_8$;

$R_8$ is independently selected from the group consisting of H, F, Cl, Br, $C_{1-4}$alkyl substituted with 1-4 $R_e$, =O, —$OR_b$, —$S(O)_pR_c$, —$C(=O)R_d$, —$NR_aR_a$, —$C(=O)NR_aR_a$, —$NR_aC(=O)R_d$, —$NR_aC(=O)OR_b$, —$OC(=O)R_d$, —$OC(=O)(CH_2)_rNR_aR_a$, $NR_aC(=O)NR_aR_a$, —$C(=O)OR_b$, $S(O)_2NR_aR_a$, —$NR_aS(O)_2NR_aR_a$, —$NR_aS(O)_2R_c$, and heterocyclyl substituted with 1-4 $R_e$;

$R_{8a}$ is selected from the group consisting of H, $C_{1-4}$alkyl, $S(O)_2R_c$, and 5- to 6-membered heterocyclyl substituted with 1-4 $R_e$;

$R_a$, at each occurrence, is independently selected from the group consisting of H, CN, $C_{1-6}$ alkyl substituted with 1-5 $R_e$, —$(CH_2)_r$—$C_{3-10}$carbocyclyl substituted with 1-5 $R_e$, and —$(CH_2)_r$-heterocyclyl substituted with 1-5 $R_e$; or $R_a$ and $R_a$ together with the nitrogen atom to which they are both attached form a heterocyclic ring substituted with 1-5 $R_e$;

$R_b$, at each occurrence, is independently selected from the group consisting of H, $C_{1-6}$ alkyl substituted with 1-5 $R_e$, —$(CH_2)_r$—$C_{3-10}$carbocyclyl substituted with 1-5 $R_e$, and —$(CH_2)_r$-heterocyclyl substituted with 1-5 $R_e$;

$R_c$, at each occurrence, is independently selected from the group consisting of $C_{1-6}$ alkyl substituted with 1-5 $R_e$, $C_{3-6}$carbocyclyl, and heterocyclyl;

$R_d$, at each occurrence, is independently selected from the group consisting of H, OH, $C_{1-6}$ alkyl substituted with 1-5 $R_e$, —$(CH_2)_r$—$C_{3-10}$carbocyclyl substituted with 1-5 $R_e$, and —$(CH_2)_r$-heterocyclyl substituted with 1-5 $R_e$;

$R_e$, at each occurrence, is independently selected from the group consisting of H, $C_{1-6}$alkyl substituted with 1-5 $R_f$, $C_{2-6}$alkenyl, $C_{2-6}$alkynyl, —$(CH_2)_r$—$C_{3-6}$cycloalkyl, —$(CH_2)_r$-heterocyclyl, F, Cl, Br, CN, $NO_2$, =O, $CO_2H$, —$(CH_2)_rOC_{1-5}$ alkyl, —$(CH_2)_rOH$, SH, —$(CH_2)_rNR_fR_f$ and —$(CH_2)_rNHC(=O)R_f$;

$R_f$, at each occurrence, is independently selected from the group consisting of H, $C_{1-5}$ alkyl, and phenyl, or $R_f$ and $R_f$ together with the nitrogen atom to which they are both attached form a heterocyclic ring.

In another embodiment, there are disclosed compounds of formula (V) including enantiomers, diastereomers, tautomers, pharmaceutically-acceptable salts, prodrugs, hydrates, or solvates thereof, wherein $R_{6b}$ is

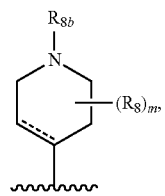

wherein

----- is an optional bond;

$R_{8b}$ is independently selected from the group consisting of H, $C_{1-6}$ alkyl substituted with 1-5 $R_e$, —$C(=O)NR_aR_a$, —$C(=O)(CR_gR_g)_rOR_b$, —$C(=O)(CR_gR_g)_rOC(=O)R_b$—$(CR_gR_g)_r$—$C_{3-10}$carbocyclyl substituted with 1-5 $R_e$ and —$(CR_gR_g)_r$-heterocyclyl substituted with 1-5 $R_e$;

$R_e$, at each occurrence, is independently selected from the group consisting of H, $C_{1-6}$alkyl substituted with 1-5 $R_f$, $C_{2-6}$alkenyl, $C_{2-6}$alkynyl, —$(CH_2)_r$—$C_{3-6}$cycloalkyl, —$(CH_2)_r$-heterocyclyl, F, Cl, Br, —$(CH_2)_rCN$, $NO_2$, =O, $CO_2H$, —$OPO_3H$, —$OSi(C_{1-4}alkyl)_3$, —$(CH_2)_rOC_{1-5}$ alkyl, —$(CH_2)_rOH$, —$(CH_2)_rS(O)_2C_{1-5}$alkyl, —$(CH_2)_rS(O)_2$-phenyl, —$(CH_2)_rNHS(O)_2C_{1-5}$alkyl, —$S(O)_2NH_2$, SH, —$(CH_2)_rNR_fR_f$, —$(CH_2)_rNHC(=O)OR_f$, —$(CH_2)_rNHC(=O)R_f$ and —$(CH_2)_rC(=O)OR_f$;

$R_f$, at each occurrence, is independently selected from the group consisting of H, $C_{1-5}$alkyl, OH, $OC_{1-5}$alkyl, $C_{3-6}$cycloalkyl, and phenyl, heterocyclyl substituted with alkyl and CN, or $R_f$ and $R_f$ together with the nitrogen atom to which they are both attached form a heterocyclic ring optionally substituted with $C_{1-4}$alkyl; and $R_g$, at each occurrence, is independently selected from the group consisting of H and $C_{1-5}$alkyl; other variables are as defined in Formula (V).

In another embodiment, there are disclosed compounds of formula (VI) including enantiomers, diastereomers, tautomers, pharmaceutically-acceptable salts, prodrugs, hydrates, or solvates thereof,

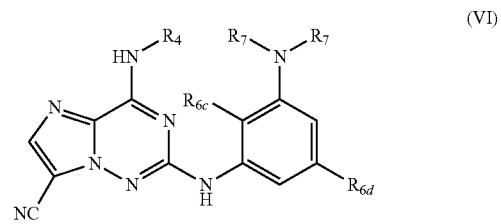

wherein $R_4$ is selected from the group consisting of $C_{1-4}$alkyl substituted with 1-3 $R_e$, $C_{3-6}$cycloalkyl and heterocyclyl substituted with 1-3 $R_e$;

$R_7$ and $R_7$ together with the nitrogen atom to which they are both attached form a 4- to 7-membered monocyclic or 7- to 12-membered bicyclic heterocycle containing carbon atoms and additional 1-3 heteroatoms selected from the group consisting of $NR_{8a}$, O, and $S(O)_2$ and substituted with 1-4 $R_8$; $R_8$ is independently selected from the group consisting of F, Cl, $C_{1-4}$alkyl substituted with 1-4 $R_e$, =O, —$OR_b$, —$S(O)_pR_c$, —$C(=O)R_d$, —$NR_aR_a$, —$C(=O)NR_aR_a$, —$NR_aC(=O)R_d$, —$NR_aC(=O)OR_b$, —$OC(=O)R_d$, —$OC(=O)(CH_2)_rNR_aR_a$, $NR_aC(=O)NR_aR_a$, —$C(=O)OR_b$, $S(O)_2NR_aR_a$, —$NR_aS(O)_2NR_aR_a$, —$NR_aS(O)_2R_c$, and heterocyclyl substituted with 1-4 $R_e$;

$R_{8a}$ is selected from the group consisting of H, $C_{1-4}$alkyl, $S(O)_2R_c$, and 5- to 6-membered heterocyclyl substituted with 1-4 $R_e$;

$R_a$, at each occurrence, is independently selected from the group consisting of H, CN, $C_{1-6}$ alkyl substituted with 1-5 $R_e$, —$(CH_2)_r$—$C_{3-10}$carbocyclyl substituted with 1-5 $R_e$, and —$(CH_2)_r$-heterocyclyl substituted with 1-5 $R_e$; or $R_a$ and $R_a$ together with the nitrogen atom to which they are both attached form a heterocyclic ring substituted with 1-5 $R_e$;

R$_b$, at each occurrence, is independently selected from the group consisting of H, C$_{1-6}$ alkyl substituted with 1-5 R$_e$, —(CH$_2$)$_r$-aryl substituted with 1-5 R$_e$, —(CH$_2$)$_r$—C$_{3-6}$cycloalkyl substituted with 1-5 R$_e$ and —(CH$_2$)$_r$-heterocyclyl substituted with 1-5 R$_e$;

R$_c$, at each occurrence, is independently selected from the group consisting of C$_{1-6}$ alkyl substituted with 1-5 R$_e$, aryl, C$_{3-6}$cycloalkyl, and heterocyclyl;

R$_d$, at each occurrence, is independently selected from the group consisting of H, OH, C$_{1-6}$ alkyl substituted with 1-5 R$_e$, —(CH$_2$)—C$_{3-10}$carbocyclyl substituted with 1-5 R$_e$, and —(CH$_2$)$_r$-heterocyclyl substituted with 1-5 R$_e$;

R$_e$, at each occurrence, is independently selected from the group consisting of H, C$_{1-6}$alkyl substituted with 1-5 R$_f$, —(CH$_2$)$_r$—C$_{3-6}$ cycloalkyl, —(CH$_2$)$_r$-heterocyclyl, F, Cl, Br, CN, NO$_2$, =O, CO$_2$H, —(CH$_2$)$_r$OC$_{1-5}$ alkyl, —(CH$_2$)$_r$OH, SH, —(CH$_2$)$_r$NR$_f$R$_f$ and —(CH$_2$)$_r$NHC(=O)OR$_f$; and R$_f$, at each occurrence, is independently selected from the group consisting of H, C$_{1-5}$ alkyl, and phenyl, or R$_f$ and R$_f$ together with the nitrogen atom to which they are both attached form a heterocyclic ring.

In another embodiment, there are disclosed compounds of formula (VI) including enantiomers, diastereomers, tautomers, pharmaceutically-acceptable salts, prodrugs, hydrates, or solvates thereof, wherein NR$_7$R$_7$ is selected from the group consisting of

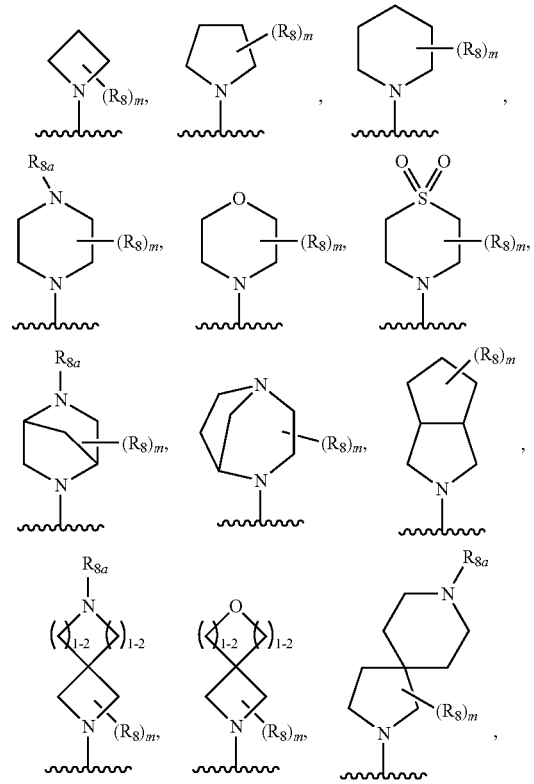

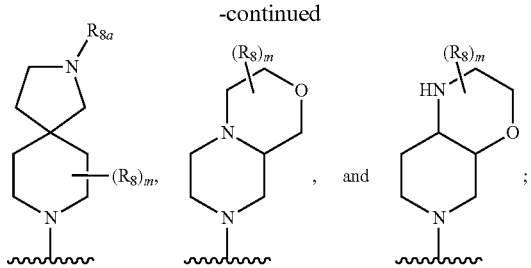

R$_8$ is selected from the group consisting of F, C$_{1-4}$alkyl substituted with 1-4 R$_e$, =O, —OH, —O(C$_{1-4}$alkyl), —NR$_a$R$_a$, —NR$_a$C(=O)R$_b$, —NR$_a$C(=O)OR$_b$, —OC(=O)(CH$_2$)$_r$NH$_2$, —NHC(=O)NR$_a$R$_a$, —NHS(O)$_2$(C$_{1-4}$alkyl);

R$_{8a}$ is selected from the group consisting of H, C$_{1-4}$alkyl, S(O)$_2$C$_{1-4}$alkyl, and 5- to 6-membered heterocyclyl substituted with 1-4 R$_e$;

R$_a$, at each occurrence, is independently selected from the group consisting of H, CN, C$_{1-6}$ alkyl substituted with 1-5 R$_e$, and —(CH$_2$)$_r$-heterocyclyl substituted with 1-5 R$_e$; or R$_a$ and R$_a$ together with the nitrogen atom to which they are both attached form a heterocyclic ring selected from the group consisting of

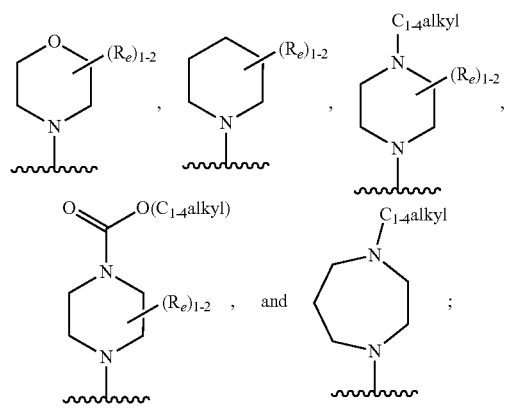

R$_b$, at each occurrence, is independently selected from the group consisting of H, C$_{1-6}$ alkyl substituted with 1-5 R$_e$, and —(CH$_2$)$_r$-heterocyclyl substituted with 1-5 R$_e$;

R$_e$, at each occurrence, is independently selected from the group consisting of C$_{1-6}$ alkyl substituted with 1-5 R$_f$, —(CH$_2$)$_r$-heterocyclyl, F, Cl, Br, CN, NO$_2$, =O, CO$_2$H, —(CH$_2$)$_r$OC$_{1-5}$alkyl, —(CH$_2$)$_r$OH, SH, NH, NH(C$_{1-5}$alkyl), N(C$_{1-5}$alkyl)$_2$, and —NHC(=O)OC$_{1-5}$alkyl;

m, at each occurrence, is independently selected from the group consisting of zero, 1, and 2; and r, at each occurrence, is independently selected from the group consisting of zero, 1, and 2; other variables are as defined in Formula (VI).

In another embodiment, there are disclosed compounds of formula (VI) including enantiomers, diastereomers, tautomers, pharmaceutically-acceptable salts, prodrugs, hydrates, or solvates thereof, wherein R$_4$ is selected from the group consisting of C$_{1-4}$alkyl, C$_{3-6}$cycloalkyl, and heterocyclyl, each substituted with 1-3 R$_e$;

R$_{6c}$ is selected from the group consisting of F and Cl; and

R$_{6d}$ is selected from the group consisting of CN, —NHC(=O)O(C$_{1-4}$alkyl), and CHF$_2$, other variables are as defined in Formula (VI).

In another embodiment, there are disclosed compounds of formula (VI) including enantiomers, diastereomers, tautomers, pharmaceutically-acceptable salts, prodrugs, hydrates, or solvates thereof, $R_4$ is selected from the group consisting of methyl, ethyl substituted with F and Cl, propyl, cyclopropyl, and

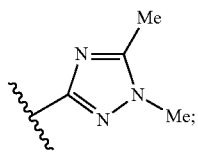 [SMILES: *c1nc(C)n(C)n1]

$R_{6c}$ is Cl;

$R_{6d}$ is selected from the group consisting of CN and $CHF_2$; other variables are as defined in Formula (VI).

In another embodiment, there are disclosed compounds of formula (II) including enantiomers, diastereomers, tautomers, pharmaceutically-acceptable salts, prodrugs, hydrates, or solvates thereof, wherein $R_1$ is H;

$R_2$ is selected from the group consisting of

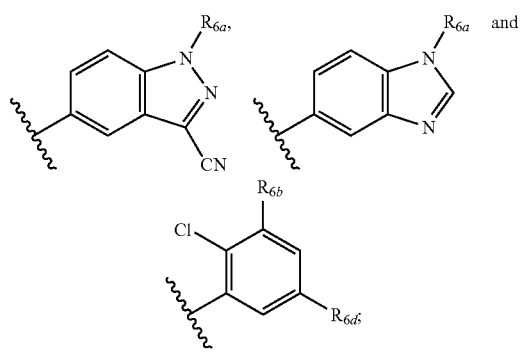

$R_4$ is selected from the group consisting of $CH_2CH_3$, $CH_2CF_3$, $CH_2CH_2CH_2OCH_3$,

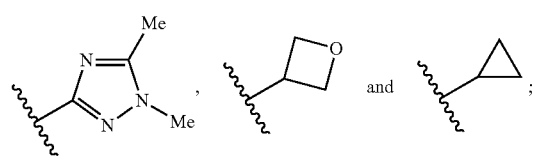

$R_{6a}$ is selected from the group consisting of H and $CH_3$, $CH_2CH_3$, and $CH_2CHOHCH_3$;

$R_{6b}$ is selected from the group consisting of —$NR_7R_7$ and

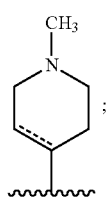

---- is an optional bond;

$R_{6d}$ is selected from the group consisting of CN, —NHC(=O)OCH$_3$, and CHF$_2$;

$R_7$ and $R_7$ together with the nitrogen atom to which they are both attached form a heterocyclic ring selected from the group consisting of

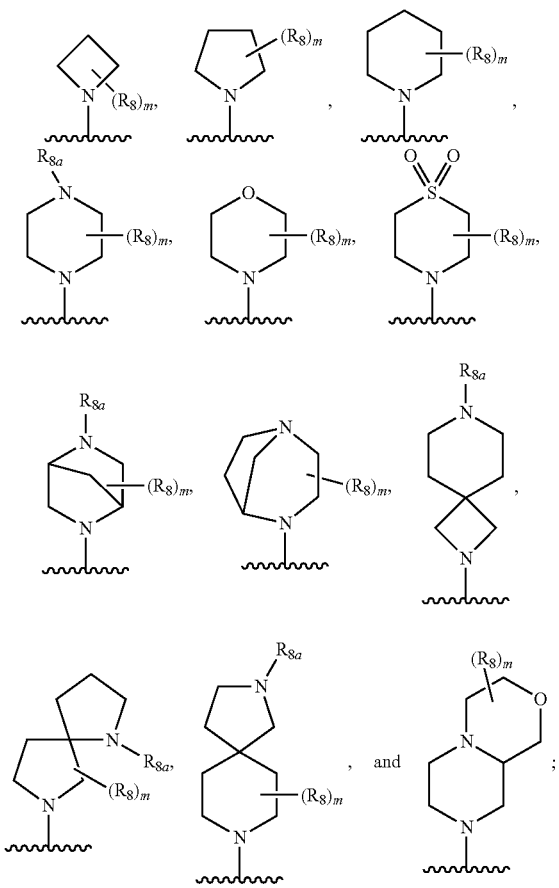

$R_8$ is selected from the group consisting of F, $C_{1-4}$alkyl substituted with 1-4 $R_e$, —OH, —O($C_{1-4}$alkyl), —$NR_aR_a$, —$NR_aC(=O)R_b$, —$NR_aC(=O)OR_b$, —OC(=O)(CH$_2$)$_r$NH$_2$, —NHC(=O)NR$_a$R$_a$, and —NHS(O)$_2$(C$_{1-4}$alkyl);

$R_{8a}$ is selected from the group consisting of H, $C_{1-4}$alkyl, S(O)$_2$C$_{1-4}$alkyl, and 5- to 6-membered heterocyclyl substituted with 1-4 $R_e$;

$R_a$, at each occurrence, is independently selected from the group consisting of H, $C_{1-6}$ alkyl substituted with 1-5 $R_e$, and —(CH$_2$)$_r$-heterocyclyl substituted with 1-5 $R_e$; or $R_a$ and $R_a$ together with the nitrogen atom to which they are both attached form a heterocyclic ring selected from the group consisting of

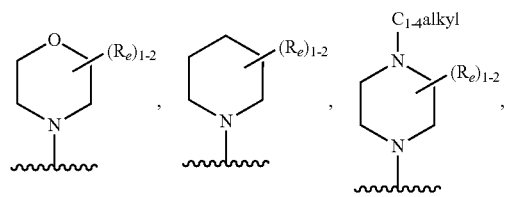

-continued

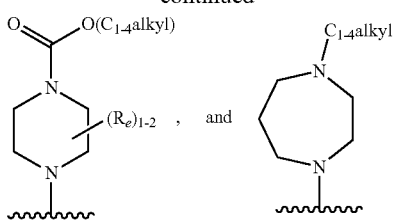

$R_b$, at each occurrence, is independently selected from the group consisting of H, $C_{1-6}$ alkyl substituted with 1-5 $R_e$, and —$(CH_2)_r$-heterocyclyl substituted with 1-5 $R_e$;

$R_e$, at each occurrence, is independently selected from the group consisting of F, Cl, Br, CN, $NO_2$, —$(CH_2)_r$-$OC_{1-5}$alkyl, —$(CH_2)_r$OH, $NH_2$, $NH(C_{1-5}$alkyl), $N(C_{1-5}$alkyl)$_2$, —NHC(=O)$OC_{1-5}$alkyl, —$(CH_2)_r$-heterocyclyl, and $C_{1-6}$ alkyl optionally substituted OH; and r, at each occurrence, is independently selected from the group consisting of zero, 1, and 2; other variables are as defined in Formula (II).

In another embodiment, there are disclosed compounds of formula (II) including enantiomers, diastereomers, tautomers, pharmaceutically-acceptable salts, prodrugs, hydrates, or solvates thereof, wherein $R_2$ is

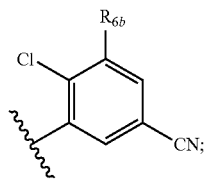

$R_4$ is selected from the group consisting of $CH_2CH_3$ and

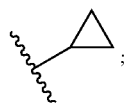 [SMILES: *C1CC1]

$R_{6b}$ is selected from the group consisting of —$NR_7R_7$ and

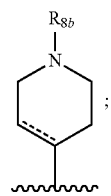

--- is an optional bond;

$R_7$ and $R_7$ together with the nitrogen atom to which they are both attached form a heterocyclic ring selected from the group consisting of

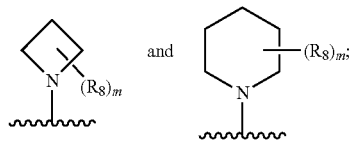

$R_8$ is selected from the group consisting of F, $C_{1-4}$alkyl substituted with 1-4 $R_e$, —OH, —$OC_{1-4}$alkyl, —NHC(=O)$OC_{1-4}$alkyl, and heterocyclyl substituted with 1-4 $R_e$;

$R_{8b}$ is independently selected from the group consisting of H, $C_{1-6}$ alkyl substituted with 1-5 $R_e$, and -heterocyclyl substituted with 1-5 $R_e$;

$R_e$, at each occurrence, is independently selected from the group consisting of H, $NH(C_{1-5}$alkyl), $N(C_{1-5}$alkyl)$_2$, —NHC(=O)$OC_{1-5}$alkyl, C(=O)$C_{1-4}$alkyl, and $C_{1-6}$ alkyl; other variables are as defined in Formula (II).

Further embodiments of the invention relate to compounds of Formulae (VII)-(VIII) below, wherein the variables, where they appear, can be selected from the group consisting of any of the embodiments as set forth above for compounds of Formula (I), (II), (III), (IV), (Va), (V), and/or (VI) (including as recited in any of the further embodiments).

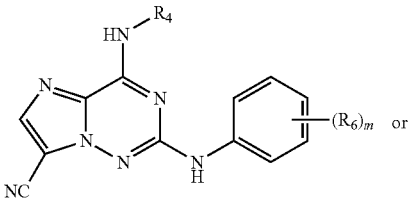

(VII)

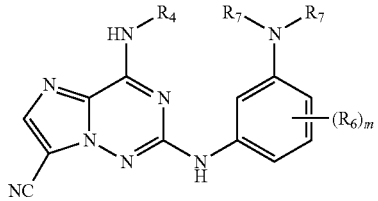

(VIII)

In another embodiment of the compounds of Formula (I), $R_6$, at each occurrence, is independently selected from the group consisting of H, F, Cl, Br, =O, CN, —$OR_b$, —$S(O)_pR_c$, —C(=O)$R_d$, —$NR_7R_7$, —$(CH_2)_rC$(=O)$NR_7R_7$, —$NR_aC$(=O)$R_d$, —$NR_aC$(=O)$OR_b$, —OC(=O)$NR_7R_7$, —$NR_aC$(=O)$NR_7R_7$, —$(CH_2)_rC$(=O)$OR_b$, —$S(O)_2NR_7R_7$, —$NR_aS(O)_2NR_7R_7$, —$NR_aS(O)_2R_c$, or $C_{1-6}$ alkyl substituted with 1-3 $R_e$, —$(CH_2)_r$-$C_{3-6}$carbocyclyl substituted with 1-3 Re, and —$(CH_2)_r$-heterocyclyl substituted with 1-3 $R_e$;

$R_a$, at each occurrence, is independently selected from the group consisting of H, CN, $C_{1-4}$ alkyl substituted with 1-3 $R_e$, —$(CH_2)_r$-heterocyclyl substituted with 1-3 $R_e$; or $R_a$ and $R_a$ together with the nitrogen atom to which they are both attached form a monocyclic heterocyclic ring substituted with 1-3 $R_e$;

$R_b$, at each occurrence, is independently selected from the group consisting of H and $C_{1-4}$ alkyl substituted with 1-3 $R_e$, and heterocyclyl;

$R_c$, at each occurrence, is independently selected from the group consisting of $C_{1-4}$ alkyl substituted with 1-3 $R_e$, $C_{2-4}$ alkenyl substituted with 1-3 $R_e$, and $C_{2-4}$ alkynyl substituted with 1-3 $R_e$;

$R_d$, at each occurrence, is independently selected from the group consisting of H, $C_{1-4}$ alkyl substituted with 1-3 $R_e$, —$(CH_2)_r$—$C_{3-10}$carbocyclyl substituted with 1-3 $R_e$, and —$(CH_2)_r$-heterocyclyl substituted with 1-3 $R_e$;

$R_e$, at each occurrence, is independently selected from the group consisting of H, $C_{1-6}$alkyl substituted with 1-5 $R_f$, $C_{2-6}$alkenyl, $C_{2-6}$alkynyl, —$(CH_2)_r$—$C_{3-6}$cycloalkyl, —$(CH_2)_r$-heterocyclyl, F, Cl, Br, CN, $NO_2$, =O, $CO_2H$, —$(CH_2)_rOC_{1-5}$ alkyl, —$(CH_2)_rOH$, SH, —$(CH_2)_rNR_fR_f$, —$(CH_2)_rNHC(=O)OR_f$, and —$(CH_2)_rC(=O)OR_f$;

$R_f$, at each occurrence, is independently selected from the group consisting of H and $C_{1-4}$alkyl or $R_f$ and $R_f$ together with the nitrogen atom to which they are both attached form a heterocyclic ring;

n, at each occurrence, is independently selected from the group consisting of zero, 1, 2, 3, and 4; and r, at each occurrence is independently selected from the group consisting of zero, 1, 2, and 3.

In another embodiment of the compounds of Formula (I), $R_6$, at each occurrence, is independently selected from the group consisting of H, F, Cl, Br, CN, O—$C_{1-4}$alkyl substituted with 1-3 $R_e$, —$O(CH_2)_rNR_aC_{1-4}$alkyl —O—$(CH_2)_rOC_{1-4}$alkyl, —$O(CH_2)_r$-heterocyclyl, —$S(O)_2C_{1-4}$ alkyl, —$C(=O)C_{1-4}$alkyl, —$NH_2$, —$N(C_{1-4}$alkyl$)_2$, —NHCN, —$NR_a(CH_2)_rNR_aC_{1-4}$alkyl, —$NR_a(CH_2)_rOC_{1-4}$alkyl, —$NH(CH_2)_r$-heterocyclyl, —$(CH_2)_rC(=O)NH_2$, —$C(=O)NH$-heterocyclyl, —$C(=O)NH(CH_2)_rN(C_{1-4}$alkyl$)_2$, —$C(=O)$-heterocyclyl, —$NHC(=O)C_{1-4}$ alkyl, —$NHC(=O)OC_{1-4}$alkyl, —$NHC(=O)NHC_{1-4}$alkyl, $C(=O)OC_{1-4}$alkyl, —$(CH_2)_rC(=O)OH$, —$S(O)_2NH_2$, —$S(O)_2NH$-heterocyclyl, —$S(O)_2NHC_{1-4}$alkyl, —$S(O)_2$-heterocyclyl substituted with 1-3 $R_e$, —$NH_2S(O)_2NH_2$, —$NHS(O)_2C_{1-4}$alkyl, $C_{1-4}$alkyl, $CF_3$, —$(CH_2)_rOH$, $C_{3-6}$carbocyclyl substituted with 1-3 $R_e$, non-aromatic heterocyclyl substituted with 1-3 $R_e$, and 5- or 6-membered heteroaryl substituted with 1-3 $R_e$.

In another embodiment of the compounds of Formula (I), $R_2$ is selected from the group consisting of phenyl substituted with 1-3 $R_6$ and

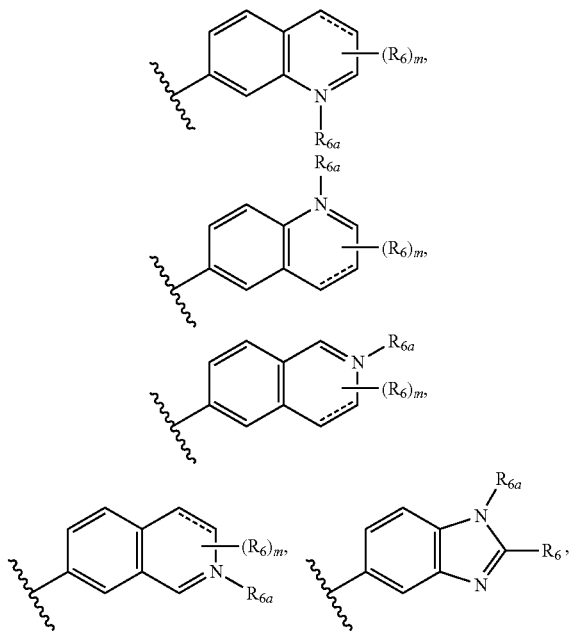

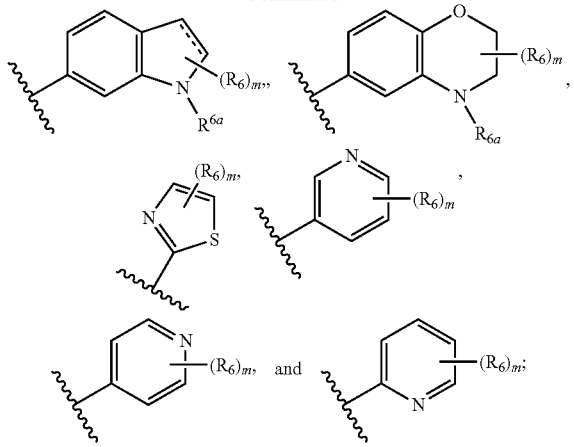

---- represents an optional bond;

$R_6$, at each occurrence, is independently selected from the group consisting of H, F, Cl, Br, =O, CN, —$OR_b$, —$S(O)_2R_c$, —$C(=O)R_d$, —$NR_7R_7$, —$(CH_2)_rC(=O)NR_7R_7$, —$NHC(=O)R_d$, —$NHC(=O)OR_b$, —$NHC(=O)NR_7R_7$, —$(CH_2)_rC(=O)OR_b$, —$S(O)_2NR_7R_7$, —$NHS(O)_2NR_7R_7$, —$NHS(O)_2R_c$, $C_{1-4}$alkyl substituted with 1-3 $R_e$, non-aromatic heterocyclyl substituted with 1-3 $R_e$, and heteroaryl substituted with 1-3 $R_e$;

$R_{6a}$, at each occurrence, is independently selected from the group consisting of H, $C_{1-4}$ alkyl substituted with 1-3 $R_e$, —$S(O)_pR_c$, —$C(=O)R_d$, $C(=O)OR_b$;

$R_4$ is selected from the group consisting of H, $C_{1-6}$alkyl substituted with 1-3 $R_e$, —$(CH_2)_rOR_b$, —$C_{3-6}$cycloalkyl substituted with 1-3 $R_e$, aryl substituted with 1-3 $R_e$, —$(CH_2)_r$-4- to 6-membered saturated monocyclic heterocyclyl substituted with 1-3 $R_e$, and —$(CH_2)_r$-5- to 6-membered heteroaryl substituted with 1-3 $R_e$;

$R_7$, at each occurrence, is independently selected from the group consisting of H, $C_{1-6}$ alkyl substituted with 1-5 $R_e$, —$(CH_2)_r$—$C_{3-10}$carbocyclyl substituted with 1-5 $R_e$, and —$(CH_2)_r$-heterocyclyl substituted with 1-5 $R_e$; or $R_7$ and $R_7$ together with the nitrogen atom to which they are both attached form a heterocyclic ring substituted with 1-5 $R_8$;

$R_8$, at each occurrence, is independently selected from the group consisting of H, F, Cl, Br, $C_{1-6}$ alkyl substituted with 1-5 $R_e$, =O, —$(CH_2)_rOR_b$, —$(CH_2)_rS(O)_pR_c$, —$(CH_2)_rC(=O)R_d$, —$(CH_2)_rNR_aR_a$, —$(CH_2)_rC(=O)NR_aR_a$, —$(CH_2)_rNR_aC(=O)R_d$, —$(CH_2)_rNR_aC(=O)OR_b$, —$(CH_2)_rOC(=O)R_d$, —$(CH_2)_rOC(=O)(CH_2)_rNR_aR_a$, —$(CH_2)_rNR_aC(=O)NR_aR_a$, —$(CH_2)_rC(=O)OR_b$, —$(CH_2)_rS(O)_2NR_aR_a$, —$(CH_2)_rNR_aS(O)_2NR_aR_a$, —$(CH_2)_rNR_aS(O)_2R_c$, and —$(CH_2)_r$-heterocyclyl substituted with 1-5 $R_e$;

$R_a$, at each occurrence, is independently selected from the group consisting of H, CN, $C_{1-4}$ alkyl substituted with 1-5 $R_e$, —$(CH_2)_r$-heterocyclyl substituted with 1-3 $R_e$; or $R_a$ and $R_a$ together with the nitrogen atom to which they are both attached form a heterocyclic ring, having 1 to 3 heteroatoms selected from the group consisting of N, O, S, and substituted with 1-3 $R_e$;

$R_b$, at each occurrence, is independently selected from the group consisting of H, $C_{1-4}$ alkyl substituted with 1-3 $R_e$, and heterocyclyl;

$R_c$, at each occurrence, is independently $C_{1-4}$ alkyl substituted with 1-3 $R_e$; $R_d$, at each occurrence, is independently selected from the group consisting of H and $C_{1-4}$ alkyl substituted with 1-3 $R_e$;

$R_e$, at each occurrence, is independently selected from the group consisting of H, $C_{1-6}$alkyl substituted with 1-5 $R_f$, $C_{2-6}$alkenyl, $C_{2-6}$alkynyl, —$(CH_2)_r$—$C_{3-6}$ cycloalkyl, —$(CH_2)_r$-heterocyclyl, F, Cl, Br, CN, $NO_2$, =O, $CO_2H$, —$(CH_2)_rOC_{1-5}$ alkyl, —$(CH_2)_rOH$, SH, —$(CH_2)_rNR_fR_f$, —$(CH_2)_rNHC(=O)OR_f$, and —$(CH_2)_rC(=O)OR_f$; and $R_f$, at each occurrence, is independently selected from the group consisting of H and $C_{1-3}$alkyl or $R_f$ and $R_f$ together with the nitrogen atom to which they are both attached form a heterocyclic ring;

r, at each occurrence, is independently selected from the group consisting of zero, 1, 2, and 3; and m, at each occurrence, is independently selected from the group consisting of zero, 1, 2, and 3.

In still another embodiment, $R_2$ is substituted with 1-5 $R_6$ and is selected from the group consisting of phenyl and naphthyl.

In another embodiment, $R_2$ is substituted with 1-5 $R_6$ and is heteroaryl selected from the group consisting of thiazolyl, oxazolyl, pyrazolyl, triazolyl, tetrazolyl, thiadiazolyl, isoxazolyl, imidazolyl, pyridyl, pyrimidinyl, pyrazinyl, pyridazinyl, indolyl, indazolyl, isoindolyl, indolinyl, isoindolinyl, benzimidazolyl, benzothiazolyl, benzotriazolyl, quinolinyl, isoquinolinyl, tetrahydroquinolinyl, and tetrahydroisoquinolinyl.

In another embodiment, $R_2$ is selected from the group consisting of

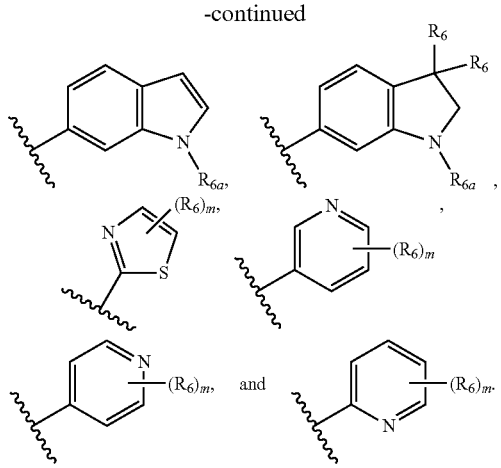

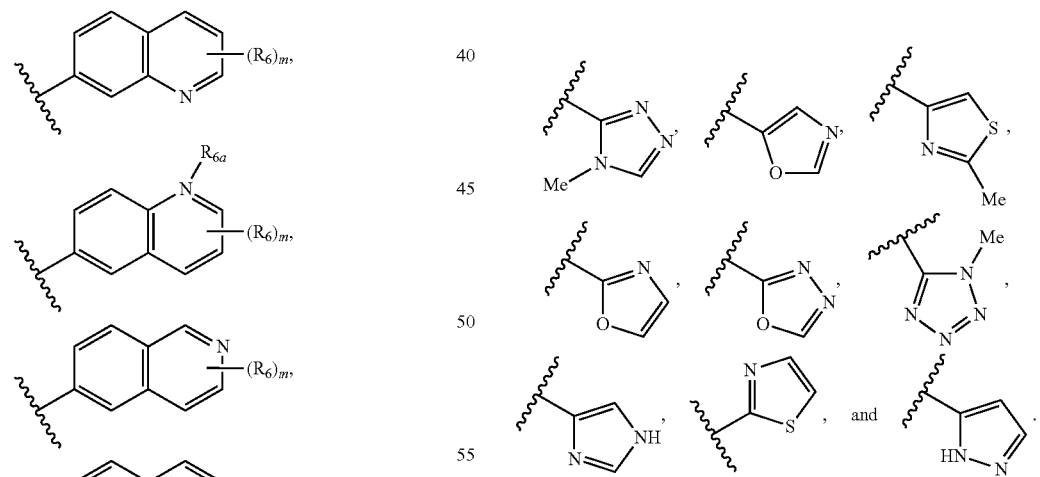

In another embodiment, $R_6$, at each occurrence, is independently selected from the group consisting of F, Cl, Br, —$OCF_3$, —$OCHF_2$, —$CF_3$, CN, $NO_2$, $CH_3$, —OH, —$OCH_3$, $NH_2$, —$N(CH_2CH_3)_2$, —$NHC(=O)CH_3$, —NHS$(O)_2CH_3$, —$NHC(=O)OCH_3$, —$NHC(=O)CH(CH_3)_2$, —$NHC(=O)CH_2CH_3$, —$C(=O)OH$, —$C(=O)OCH_3$, $C(=O)NH_2$, —$C(=O)NHCH_3$, —$S(O)_2CH_3$, —$S(O)_2NHCH_3$, —$N(CH_3)C(=O)CH_3$, —$NHS(O)_2NH_2$, —$C(=O)$-heterocyclyl substituted with 1-5 $R_e$, —$(CH_2)_r$-5- to 6-membered heterocyclyl comprising carbon atoms and 1-4 heteroatoms selected from the group consisting of N, O, and $S(O)_p$, wherein said heterocyclyl is substituted with 1-5 $R_e$. Non-limiting examples of the heterocyclyl include pyrrolidine, imidazole, pyrazole, oxazole, oxadiazole, thiazole, triazole, tetrazole, piperazine, piperidine, and morpholine.

In another embodiment, $R_6$ is substituted with 1-2 $R_e$ and is selected from the group consisting of:

In another aspect, the present invention provides a compound selected from any subset list of compounds exemplified in the present application.

All aspects of the compounds, including individual variable definitions, may be combined with other aspects to form additional compounds. For example, in one embodiment of Formula (I), $R_1$ is hydrogen and $R_2$ is aryl. In another embodiment, $R_1$ can be hydrogen and $R_2$ can be heteroaryl.

The compounds of Formulae (I)-(VIII) may form salts with alkali metals such as sodium, potassium and lithium, with alkaline earth metals such as calcium and magnesium, with organic bases such as dicyclohexylamine, tributylamine, pyridine and amino acids such as arginine, lysine and the like. Such salts can be formed as known to those skilled in the art.

The compounds for Formulae (I)-(VIII) may form salts with a variety of organic and inorganic acids. Such salts include those formed with hydrogen chloride, hydrogen bromide, methanesulfonic acid, sulfuric acid, acetic acid, trifluoroacetic acid, oxalic acid, maleic acid, benzenesulfonic acid, toluenesulfonic acid and various others (e.g., nitrates, phosphates, borates, tartrates, citrates, succinates, benzoates, ascorbates, salicylates and the like). Such salts can be formed as known to those skilled in the art.

In addition, zwitterions ("inner salts") may be formed.

The present invention is also intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

Compounds of the Formulae (I)-(VIII) may also have prodrug forms. Since prodrugs are known to enhance numerous desirable qualities of pharmaceuticals (e.g., solubility, bioavailability, manufacturing, etc.) the compounds of the present invention may be delivered in prodrug form. Thus, the present invention is intended to cover prodrugs of the presently claimed compounds, methods of delivering the same and compositions containing the same. "Prodrugs" are intended to include any covalently bonded carriers that release an active parent drug of the present invention in vivo when such prodrug is administered to a mammalian subject. Prodrugs of the present invention are prepared by modifying functional groups present in the compound in such a way that the modifications are cleaved, either in routine manipulation or in vivo, to the parent compound. Prodrugs include compounds of the present invention wherein a hydroxy, amino, or sulfhydryl group is bonded to any group that, when the prodrug of the present invention is administered to a mammalian subject, it cleaves to form a free hydroxyl, free amino, or free sulfhydryl group, respectively. Examples of prodrugs include, but are not limited to, acetate, formate, and benzoate derivatives of alcohol and amine functional groups in the compounds of the present invention.

Various forms of prodrugs are well known in the art. For examples of such prodrug derivatives, see:
a) *Design of Prodrugs*, H. Bundgaard, ed., Elsevier (1985), and *Methods in Enzymology*, 112:309-396, K. Widder et al., eds., Academic Press (1985);
b) Bundgaard, H., Chapter 5, "Design and Application of Prodrugs," *A Textbook of Drug Design and Development*, pp. 113-191, P. Krosgaard-Larsen et al., eds., Harwood Academic Publishers (1991); and
c) Bundgaard, H., *Adv. Drug Deliv. Rev.*, 8:1-38 (1992).

It should further be understood that solvates (e.g., hydrates) of the compounds of Formulae (I)-(VIII) are also within the scope of the invention. Methods of solvation are generally known in the art. The inventive compounds may either be in the free or hydrate form.

Compounds of this invention may have one or more asymmetric centers. Unless otherwise indicated, all chiral (enantiomeric and diastereomeric) and racemic forms of compounds of the present invention are included in the present invention. Many geometric isomers of olefins, C=N double bonds, and the like can also be present in the compounds, and all such stable isomers are contemplated in the present invention. Cis and trans geometric isomers of the compounds of the present invention are described and may be isolated as a mixture of isomers or as separated isomeric forms. The present compounds can be isolated in optically active or racemic forms. It is well known in the art how to prepare optically active forms, such as by resolution of racemic forms or by synthesis from optically active starting materials. All chiral, (enantiomeric and diastereomeric) and racemic forms and all geometric isomeric forms of a structure are intended, unless the specific stereochemistry or isomer form is specifically indicated. When no specific mention is made of the configuration (cis, trans or R or S) of a compound (or of an asymmetric carbon), then any one of the isomers or a mixture of more than one isomer is intended. The processes for preparation can use racemates, enantiomers, or diastereomers as starting materials. All processes used to prepare compounds of the present invention and intermediates made therein are considered to be part of the present invention. When enantiomeric or diastereomeric products are prepared, they can be separated by conventional methods, for example, by chromatography or fractional crystallization. Compounds of the present invention, and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

DEFINITIONS

The following are definitions of terms used in this specification and appended claims. The initial definition provided for a group or term herein applies to that group or term throughout the specification and claims, individually or as part of another group, unless otherwise indicated.

In accordance with a convention used in the art,

is used in structural formulas herein to depict the bond that is the point of attachment of the moiety or substituent to the core or backbone structure.

A dash "-" that is not between two letters or symbols is used to indicate a point of attachment for a substituent. For example, —$CONH_2$ is attached through the carbon atom.

As used herein, the term "alkyl" or "alkylene" is intended to include both branched and straight-chain saturated aliphatic hydrocarbon groups having the specified number of carbon atoms. For example, "$C_{1-10}$ alkyl" (or alkylene), is intended to include $C_1$, $C_2$, $C_3$, $C_4$, $C_5$, $C_6$, $C_7$, $C_8$, $C_9$, and $C_{10}$ alkyl groups. Additionally, for example, "$C_1$-$C_6$ alkyl" denotes alkyl having 1 to 6 carbon atoms.

Alkyl groups can be unsubstituted or substituted so that one or more of its hydrogens are replaced by another chemical group. Example alkyl groups include, but are not limited to, methyl(Me), ethyl(Et), propyl (e.g., n-propyl and isopropyl), butyl (e.g., n-butyl, isobutyl, t-butyl), pentyl (e.g., n-pentyl, isopentyl, neopentyl), and the like.

"Haloalkyl" is intended to include both branched and straight-chain saturated aliphatic hydrocarbon groups having the specified number of carbon atoms, substituted with 1 or more halogen. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" which is intended to include both branched and straight-chain saturated aliphatic hydrocarbon groups having the specified number of carbon atoms, substituted with 1 or more fluorine atoms.

The term "halogen" or "halo" refers to fluorine (F), chlorine (Cl), bromine (Br) and iodine.

"Haloalkoxy" or "haloalkyloxy" represents a haloalkyl group as defined above with the indicated number of carbon atoms attached through an oxygen bridge. For example, "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, pentafluorothoxy, and the like. Similarly, "haloalkylthio" or "thiohaloalkoxy" represents a haloalkyl group as defined above with the indicated number of carbon atoms attached through a sulphur bridge; for example trifluoromethyl-S—, pentafluoroethyl-S—, and the like.

As used herein, "carbocycle," "carbocyclic residue," or "carbocyclyl" is intended to mean any stable 3-, 4-, 5-, 6-, or 7-membered monocyclic or bicyclic or 7-, 8-, 9-, 10-, 11-, 12-, or 13-membered bicyclic or tricyclic hydrocarbon ring, any of which may be saturated, partially unsaturated, unsaturated or aromatic. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane, [2.2.2]bicyclooctane, fluorenyl, phenyl, naphthyl, indanyl, adamantyl, anthracenyl, and tetrahydronaphthyl(tetralin). As shown above, bridged rings are also included in the definition of carbocycle (e.g., [2.2.2]bicyclooctane). Preferred carbocycles, unless otherwise specified, are cyclopropyl, cyclobutyl, cyclopentyl, cyclohexyl, phenyl, and indanyl. When the term "carbocycle," "carbocyclic residue," or "carbocyclyl" is used, it is intended to include "aryl". A bridged ring occurs when one or more carbon atoms link two non-adjacent carbon atoms. Preferred bridges are one or two carbon atoms. It is noted that a bridge always converts a monocyclic ring into a tricyclic ring. When a ring is bridged, the substituents recited for the ring may also be present on the bridge.

The term "aryl" refers to monocyclic, bicyclic, tricyclic aromatic hydrocarbon groups having 6 to 15 carbon atoms in the ring portion, such as phenyl, naphthyl, biphenyl and diphenyl groups, each of which may be substituted. Aryl groups which are bicyclic or tricyclic must include at least one fully aromatic ring but the other fused ring or rings may be aromatic or non-aromatic. When an aryl is substituted with a further heterocyclic ring, said ring may be attached to the aryl through a carbon atom or a heteroatom and said ring in turn is optionally substituted with one to two substituents as valence allows.

The terms "aryloxy", "arylamino", "arylalkylamino", "arylthio", "arylalkanoylamino", "arylsulfonyl", "arylalkoxy", "arylsulfinyl", "arylheteroaryl", "arylalkylthio", "arylcarbonyl", "arylalkenyl", or "arylalkylsulfonyl" refer to an aryl or substituted aryl bonded to an oxygen; an amino; an alkylamino; a thio; an alkanoylamino; a sulfonyl; an alkoxy; a sulfinyl; a heteroaryl or substituted heteroaryl; an alkylthio; a carbonyl; an alkenyl; or an alkylsulfonyl; respectively.

The term "alkenyl" refers to straight or branched chain hydrocarbon groups of 2 to 20 carbon atoms, preferably 2 to 15 carbon atoms, and most preferably 2 to 8 carbon atoms, having one to four double bonds.

The term "alkynyl" refers to straight or branched chain hydrocarbon groups of 2 to 20 carbon atoms, preferably 2 to 15 carbon atoms, and most preferably 2 to 8 carbon atoms, having one to four triple bonds.

An "alkylidene" group refers to an alkylene group consisting of at least two carbon atoms and at least one carbon-carbon double bond. Substituents on this group include those in the definition of "substituted alkyl".

The term "cycloalkyl" refers to an optionally substituted, saturated cyclic hydrocarbon ring systems, preferably containing 1 to 3 rings and 3 to 7 carbons per ring. Exemplary groups include cyclopropyl, cyclobutyl, cyclopentyl, cyclohexyl, cycloheptyl, cyclooctyl, cyclodecyl, cyclododecyl, and adamantyl. Exemplary substituents include one or more alkyl groups as described above, or one or more groups described above as alkyl substituents.

As used herein, the term "heterocycle," "heterocyclyl," "heterocyclic ring" or "heterocyclic group" is intended to mean a stable 4-, 5-, 6-, or 7-membered monocyclic or bicyclic or 7-, 8-, 9-, 10-, 11-, 12-, 13-, or 14-membered bicyclic heterocyclic ring which is saturated, partially unsaturated or fully unsaturated or aromatic, and which consists of carbon atoms and 1, 2, 3 or 4 heteroatoms independently selected from the group consisting of N, O and S; and including any bicyclic group in which any of the above-defined heterocyclic rings is fused to a benzene ring. The nitrogen and sulfur heteroatoms may optionally be oxidized (i.e., N→O and $S(O)_p$). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. When the term "heterocycle," "heterocyclyl," "heterocyclic ring" or "heterocyclic group" is used, it is intended to include heteroaryl.

Examples of heterocycles include, but are not limited to, acridinyl, azocinyl, benzimidazolyl, benzofuranyl, benzothiofuranyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

Preferred 5- to 10-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl.

Preferred 5- to 6-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, and triazolyl. Also included are fused ring and spiro compounds containing, for example, the above heterocycles.

Bridged rings are also included in the definition of heterocycle. A bridged ring occurs when one or more atoms (i.e., C, O, N, or S) link two non-adjacent carbon or nitrogen atoms. Preferred bridges include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

The term "heteroaryl" refers to substituted and unsubstituted aromatic 5- or 6-membered monocyclic groups, 9- or 10-membered bicyclic groups, and 11- to 14-membered tricyclic groups which have at least one heteroatom (O, S or N) in at least one of the rings, said heteroatom-containing ring preferably having 1, 2, or 3 heteroatoms selected from the group consisting of O, S, and N. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. Heteroaryl groups can be substituted or unsubstituted. The nitrogen atom may be substituted or unsubstituted (i.e., N or NR wherein R is H or another substituent, if defined). The nitrogen and sulfur heteroatoms may optionally be oxidized (i.e., N→O and $S(O)_p$) and the nitrogen atoms may optionally be quaternized.

Heteroaryl groups which are bicyclic or tricyclic must include at least one fully aromatic ring but the other fused ring or rings may be aromatic or non-aromatic. The heteroaryl group may be attached at any available nitrogen or carbon atom of any ring. The heteroaryl ring system may contain zero, one, two or three substituents.

Exemplary monocyclic heteroaryl groups include pyrrolyl, pyrazolyl, pyrazolinyl, imidazolyl, oxazolyl, isoxazolyl, thiazolyl, thiadiazolyl, isothiazolyl, furanyl, thienyl, oxadiazolyl, pyridyl, pyrazinyl, pyrimidinyl, pyridazinyl, triazinyl and the like.

Exemplary bicyclic heteroaryl groups include indolyl, benzothiazolyl, benzodioxolyl, benzoxazolyl, benzothienyl, quinolinyl, dihydroisoquinolinyl, tetrahydroquinolinyl, isoquinolinyl, benzimidazolyl, benzopyranyl, benzoxazinyl, indolizinyl, benzofuranyl, chromonyl, coumarinyl, benzopyranyl, cinnolinyl, quinoxalinyl, indazolyl, pyrrolopyridyl, furopyridyl, dihydroisoindolyl, and the like.

Exemplary tricyclic heteroaryl groups include carbazolyl, benzidolyl, phenanthrollinyl, acridinyl, phenanthridinyl, xanthenyl and the like.

The term "heteroatoms" shall include oxygen, sulfur and nitrogen.

As referred to herein, the term "substituted" means that one or more hydrogen atoms is replaced with a non-hydrogen group, provided that normal valencies are maintained and that the substitution results in a stable compound. When a substituent is keto (i.e., =O), then 2 hydrogens on the atom are replaced. Keto substituents are not present on aromatic moieties. When a ring system (e.g., carbocyclic or heterocyclic) is said to be substituted with a carbonyl group or a double bond, it is intended that the carbonyl group or double bond be part (i.e., within) of the ring. Ring double bonds, as used herein, are double bonds that are formed between two adjacent ring atoms (e.g., C=C, C=N, or N=N).

When any variable occurs more than one time in any constituent or formula for a compound, its definition at each occurrence is independent of its definition at every other occurrence. Thus, for example, if a group is shown to be substituted with 1-3 $R_e$, then said group may optionally be substituted with up to three $R_e$ groups and $R_e$ at each occurrence is selected independently from the definition of $R_e$. Also, combinations of substituents and/or variables are permissible only if such combinations result in stable compounds.

Utility

The compounds of the invention may be used to modulate kinase activities.

Applicants have discovered that compounds of Formulae (I)-(VIII) have particular utility in treating proliferative conditions associated with the modulation of kinase activity, and particularly the inhibition of serine/threonine kinase activities. The compounds of the present invention can be used to treat proliferative disorders associated with abnormal kinase activity. As used herein, the terms "treating" and "treatment" encompass either or both responsive and prophylaxis measures, e.g., measures designed to inhibit or delay the onset of the disease or disorder, achieve a full or partial reduction of the symptoms or disease state, and/or to alleviate, ameliorate, lessen, or cure the disease or disorder and/or its symptoms.

Accordingly, one aspect of the invention is the use of a compound of the Formulae (I)-(VIII), or a pharmaceutically acceptable salt thereof in the manufacture of a medicament for use in the production of an antiproliferative effect in a warm-blooded animal such as a human being.

According to a further feature of the invention there is provided a method for producing an antiproliferative effect in a warm-blooded animal, such as a human being, in need of such treatment which comprises administering to said animal an effective amount of a compound of Formulae (I)-(VIII) or a pharmaceutically acceptable salt thereof as defined herein before.

The anti-proliferative treatment defined herein before may be applied as a sole therapy or may involve, in addition to a compound of the invention, one or more other substances and/or treatments. Such treatment may be achieved by way of the simultaneous, sequential or separate administration of the individual components of the treatment. The compounds of this invention may also be useful in combination with known anti-cancer and cytotoxic agents and treatments, including radiation. Compounds of Formulae (I)-(VIII) may be used sequentially with known anticancer or cytotoxic agents and treatment, including radiation when a combination formulation is inappropriate.

The term "anti-cancer" agent includes any known agent that is useful for the treatment of cancer including the following: 17α-ethinylestradiol, diethylstilbestrol, testosterone, prednisone, fluoxymesterone, dromostanolone propionate, testolactone, megestrolacetate, methylprednisolone, methyl-testosterone, prednisolone, triamcinolone, chlorotrianisene, hydroxyprogesterone, aminoglutethimide, estramustine, medroxyprogesteroneacetate, leuprolide, flutamide, toremifene, ZOLADEX®; matrix metalloproteinase inhibitors; VEGF inhibitors, such as anti-VEGF antibodies (AVASTIN®) and small molecules such as ZD6474 and SU6668; Vatalanib, BAY-43-9006, SU11248, CP-547632, and CEP-7055; HER 1 and HER 2 inhibitors including anti-HER2 antibodies (HERCEPTIN®); EGFR inhibitors including gefitinib, erlotinib, ABX-EGF, EMD72000, 11F8, and cetuximab; Eg5 inhibitors, such as SB-715992, SB-743921, and MKI-833; pan Her inhibitors, such as canertinib, EKB-569, CI-1033, AEE-788, XL-647, mAb 2C4, and GW-572016; Src inhibitors, e.g., GLEEVEC® and dasatinib; CASODEX® (bicalutamide, Astra Zeneca), Tamoxifen; MEK-1 kinase inhibitors, MAPK kinase inhibitors, PI3 kinase inhibitors; PDGF inhibitors, such as imatinib; anti-angiogenic and antivascular agents which, by interrupting blood flow to solid tumors, render cancer cells quiescent by depriving them of nutrition; castration, which renders androgen dependent carcinomas non-proliferative; inhibitors of non-receptor and receptor tyrosine kinases; inhibitors of integrin signaling; tubulin acting agents such as vinblastine, vincristine, vinorelbine, vinflunine, paclitaxel, docetaxel, 7-O-methylthiomethylpaclitaxel, 4-desacetyl-4-methylcarbonatepaclitaxel, 3'-tert-butyl-3'-N-tert-butyloxy-carbonyl-4-deacetyl-3'-dephenyl-3'-N-debenzoyl-4-O-methoxycarbonyl-paclitaxel, C-4 methyl carbonate paclitaxel, epothilone A, epothilone B, epothilone C, epothilone D, [1S-[1R*,3R*(E),7R*,10S*,11R*,12R*,16S*]]-7-11-dihydroxy-8,8,10,12,16-pentamethyl-3-[1-methyl-2-(2-methyl-4-thiazolyl)ethenyl]-4-aza-17 oxabicyclo[14.1.0] heptadecane-5,9-dione (ixabepilone), [1S-[1R*,3R*(E), 7R*,10S*,11R*,12R*,16S*]]-3-[2-[2-(aminomethyl)-4-thiazolyl]-1-methylethenyl]-7,11-dihydroxy-8,8,10,12,16-pentamethyl-4-17-dioxabicyclo[14.1.0]-heptadecane-5,9-dione, and derivatives thereof; other CDK inhibitors, antiproliferative cell cycle inhibitors, epidophyllotoxin, etoposide, VM-26; antineoplastic enzymes, e.g., topoisomerase I inhibitors, camptothecin, topotecan, SN-38; procarbazine; mitoxantrone; platinum coordination complexes such as cisplatin, carboplatin and oxaliplatin; biological response modifiers; growth inhibitors; antihormonal therapeutic agents; leucovorin; tegafur; antimetabolites such as purine antagonists (e.g., 6-thioguanine and 6-mercaptopurine; glutamine antagonists, e.g., DON (AT-125; d-oxonorleucine); ribonucleotide reductase inhibitors; mTOR inhibitors; and haematopoietic growth factors.

Additional cytotoxic agents include, cyclophosphamide, doxorubicin, daunorubicin, mitoxanthrone, melphalan, hexamethyl melamine, thiotepa, cytarabin, idatrexate, trimetrexate, dacarbazine, L-asparaginase, bicalutamide, leuprolide, pyridobenzoindole derivatives, interferons, and interleukins.

In the field of medical oncology it is normal practice to use a combination of different forms of treatment to treat each patient with cancer. In medical oncology the other component(s) of such treatment in addition to the antiproliferative treatment defined herein may be surgery, radiotherapy or chemotherapy. Such chemotherapy may cover three main categories of therapeutic agent:

(i) antiangiogenic agents that work by different mechanisms from those defined herein before (for example, linomide, inhibitors of integrin αvβ3 function, angiostatin, razoxane);

(ii) cytostatic agents such as antiestrogens (for example, tamoxifen, toremifene, raloxifene, droloxifene, iodoxifene), progestogens (for example, megestrol acetate), aromatase inhibitors (for example, anastrozole, letrozole, borazole, exemestane), antihormones, antiprogestogens, antiandrogens (for example, flutamide, nilutamide, bicalutamide, cyproterone acetate), LHRH agonists and antagonists (for example, gosereline acetate, leuprolide), inhibitors of testosterone 5α-dihydroreductase (for example, finasteride), farnesyltransferase inhibitors, anti-invasion agents (for example, metalloproteinase inhibitors such as marimastat and inhibitors of urokinase plasminogen activator receptor function) and inhibitors of growth factor function, (such growth factors include for example, EGF, FGF, platelet derived growth factor and hepatocyte growth factor, such inhibitors include growth factor antibodies, growth factor receptor antibodies such as AVASTIN® (bevacizumab) and ERBITUX® (cetuximab); tyrosine kinase inhibitors and serine/threonine kinase inhibitors); and (iii) antiproliferative/antineoplastic drugs and combinations thereof, as used in medical oncology, such as antimetabolites (for example, antifolates such as methotrexate, fluoropyrimidines such as 5-fluorouracil, purine and adenosine analogues, cytosine arabinoside); intercalating antitumour antibiotics (for example, anthracyclines such as doxorubicin, daunomycin, epirubicin and idarubicin, mitomycin-C, dactinomycin, mithramycin); platinum derivatives (for example, cisplatin, carboplatin); alkylating agents (for example, nitrogen mustard, melphalan, chlorambucil, busulphan, cyclophosphamide, ifosfamide, nitrosoureas, thiotepa; antimitotic agents (for example, vinca alkaloids like vincristine, vinorelbine, vinblastine and vinflunine) and taxoids such as TAXOL® (paclitaxel), Taxotere (docetaxel) and newer microbtubule agents such as epothilone analogs (ixabepilone), discodermolide analogs, and eleutherobin analogs; topoisomerase inhibitors (for example, epipodophyllotoxins such as etoposide and teniposide, amsacrine, topotecan, irinotecan); cell cycle inhibitors (for example, flavopyridols); biological response modifiers and proteasome inhibitors such as VELCADE® (bortezomib).

As stated above, the Formulae (I)-(VIII) compounds of the invention are of interest for their antiproliferative effects. Such compounds of the invention are expected to be useful in a wide range of disease states including cancer, psoriasis, and rheumatoid arthritis.

More specifically, the compounds of Formulae (I)-(VIII) are useful in the treatment of a variety of cancers, including (but not limited to) the following:

carcinoma, including that of the prostate, pancreatic ductal adenocarcinoma, breast, colon, lung, ovary, pancreas, and thyroid;

tumors of the central and peripheral nervous system, including neuroblastoma, glioblastoma, and medulloblastoma; and other tumors, including melanoma and multiple myeloma.

Due to the key role of kinases in the regulation of cellular proliferation in general, inhibitors could act as reversible cytostatic agents which may be useful in the treatment of any disease process which features abnormal cellular proliferation, e.g., benign prostate hyperplasia, familial adenomatosis polyposis, neurofibromatosis, pulmonary fibrosis, arthritis, psoriasis, glomerulonephritis, restenosis following angioplasty or vascular surgery, hypertrophic scar formation and inflammatory bowel disease.

The compounds of Formula (I)-(VIII) are especially useful in treatment of tumors having a high incidence of serine/threonine kinase activity, such as prostate, colon, brain, thyroid and pancreatic tumors. Additionally, the compounds of the invention may be useful in treatment of sarcomas and pediatric sarcomas. By the administration of a composition (or a combination) of the compounds of this invention, development of tumors in a mammalian host is reduced.

Compounds of Formula (I)-(VIII) may also be useful in the treatment of other cancerous diseases (such as acute myelogenous leukemia) that may be associated with signal transduction pathways operating through kinases such as DYRK1a, CDK, and GSK3β. The inventive compositions may contain other therapeutic agents as described above and may be formulated, for example, by employing conventional solid or liquid vehicles or diluents, as well as pharmaceutical additives of a type appropriate to the mode of desired administration (e.g., excipients, binders, preservatives, stabilizers, flavors, etc.) according to techniques such as those well known in the art of pharmaceutical formulation.

Accordingly, the present invention further includes compositions comprising one or more compounds of Formula (I)-(VIII) and a pharmaceutically acceptable carrier.

A "pharmaceutically acceptable carrier" refers to media generally accepted in the art for the delivery of biologically active agents to animals, in particular, mammals. Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and, the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences,* 17th ed. (1985), which is incorporated herein by reference in its entirety.

The pharmaceutical compositions of the invention containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil.

The pharmaceutical compositions may be in the form of sterile injectable aqueous solutions. Among the acceptable vehicles and solvents that may be employed are water, Ringer's solution and isotonic sodium chloride solution. The sterile injectable preparation may also be a sterile injectable oil-in-water microemulsion where the active ingredient is dissolved in the oily phase. For example, the active ingredient may be first dissolved in a mixture of soybean oil and lecithin. The oil solution then introduced into a water and glycerol mixture and processed to form a microemulation.

The injectable solutions or microemulsions may be introduced into a patient's blood-stream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CADD-PLUS® Model 5400 intravenous pump.

The pharmaceutical compositions may be in the form of a sterile injectable aqueous or oleagenous suspension for intramuscular and subcutaneous administration. This suspension may be formulated according to the known art using those suitable dispersing or wetting agents and suspending agents which have been mentioned above.

The compounds of Formulae (I)-(VIII) may be administered by any means suitable for the condition to be treated, which may depend on the need for site-specific treatment or quantity of drug to be delivered. Topical administration is generally preferred for skin-related diseases, and systematic treatment preferred for cancerous or pre-cancerous conditions, although other modes of delivery are contemplated. For example, the compounds may be delivered orally, such as in the form of tablets, capsules, granules, powders, or liquid formulations including syrups; topically, such as in the form of solutions, suspensions, gels or ointments; sublingually; bucally; parenterally, such as by subcutaneous, intravenous, intramuscular or intrasternal injection or infusion techniques (e.g., as sterile injectable aq. or non-aq. solutions or suspensions); nasally such as by inhalation spray; topically, such as in the form of a cream or ointment; rectally such as in the form of suppositories; or liposomally. Dosage unit formulations containing non-toxic, pharmaceutically acceptable vehicles or diluents may be administered.

The compounds may be administered in a form suitable for immediate release or extended release Immediate release or extended release may be achieved with suitable pharmaceutical compositions or, particularly in the case of extended release, with devices such as subcutaneous implants or osmotic pumps.

Exemplary compositions for topical administration include a topical carrier such as Plastibase (mineral oil gelled with polyethylene).

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The inventive compounds may also be orally delivered by sublingual and/or buccal administration, e.g., with molded, compressed, or freeze-dried tablets. Exemplary compositions may include fast-dissolving diluents such as mannitol, lactose, sucrose, and/or cyclodextrins. Also included in such formulations may be high molecular weight excipients such as celluloses (AVICEL®) or polyethylene glycols (PEG); an excipient to aid mucosal adhesion such as hydroxypropyl cellulose (HPC), hydroxypropyl methyl cellulose (HPMC), sodium carboxymethyl cellulose (SCMC), and/or maleic anhydride copolymer (e.g., Gantrez); and agents to control release such as polyacrylic copolymer (e.g., Carbopol 934). Lubricants, glidants, flavors, coloring agents and stabilizers may also be added for ease of fabrication and use.

Exemplary compositions for nasal aerosol or inhalation administration include solutions which may contain, for example, benzyl alcohol or other suitable preservatives, absorption promoters to enhance absorption and/or bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, suitable non-irritating excipients, such as cocoa butter, synthetic glyceride esters or polyethylene glycols, which are solid at ordinary temperatures but liquefy and/or dissolve in the rectal cavity to release the drug.

When a compound according to this invention is administered into a human subject, the daily dosage will normally be determined by the prescribing physician with the dosage generally varying according to the age, weight, sex and response of the individual patient, as well as the severity of the patient's symptoms. Exemplary dosage amounts for a mammal may include from about 0.05 to 1000 mg/kg; 1-1000 mg/kg; 1-50 mg/kg; 5-250 mg/kg; 250-1000 mg/kg of body weight of active compound per day, which may be administered in a single dose or in the form of individual divided doses, such as from 1 to 4 times per day. It will be understood that the specific dose level and frequency of dosage for any particular subject may be varied and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats, horses, and the like. Thus, when the term "patient" is used herein, this term is intended to include all subjects, most preferably mammalian species, that are affected by mediation of protein kinase enzyme levels.

If formulated as a fixed dose, a combination product can, for example, utilize a dosage of the compound of Formulae (I)-(III) within the dosage range described above and the dosage of another anti-cancer agent/treatment within the approved dosage range for such known anti-cancer agent/treatment. If a combination product is inappropriate, the compounds of Formulae (I)-(III) and the other anti-cancer agent/treatment can, for example, be administered simultaneously or sequentially. If administered sequentially, the present invention is not limited to any particular sequence of administration. For example, compounds of Formulas (I)-(III) can be administered either prior to, or after, administration of the known anti-cancer agent or treatment.

Biological Assays

A. CK2 Kinase Assay

The effectiveness of compounds of the present invention as inhibitors of protein kinases can be readily tested by assays known to those skilled in the art. For example, in vitro protein kinase assays may be conducted with a relevant purified protein kinase and an appropriate synthetic substrate to determine the inhibitory activity of the compounds. Assays for inhibition of CK2 by the instant compounds were performed in 384-well plates with reaction mixtures containing 10 µM of peptide substrate (RRRADDSDDDDD-NH2), [γ-$^{33}$P]ATP (10 µCi) at 25 µM (CK2A1) or 5 µM (CK2A2), 20 mM Hepes (pH 7.4), 100 mM NaCl, 10 mM MgCl$_2$, 0.25 mM dithiothreitol, Brij-35 at 0.015%, and recombinant CK2A1 (10 nM, Invitrogen) or CK2A2 (5 nM, Upstate Biotechnology). Reaction mixtures were incubated at 30° C. for 1 hour, and reaction products were captured by binding to phosphocellulose (P81) filter plates. Incorporation of radioactive phosphate into the peptide substrate was determined by liquid scintillation counting. The potency of compounds in inhibiting CK2 is expressed as IC$_{50}$, defined as the concentrations of compounds required to inhibit the enzymatic activity by 50%.

The inhibitory activity of the instant compounds may also be measured by recombinant CK2 holoenzyme kinase assays. The assays were performed in U-bottom 384-well plates. The final assay volume was 30 µl prepared from 15 µl additions of enzyme and substrates (fluoresceinated peptide FL-RRRADDSDDDDD-NH2 and ATP) and test compounds in assay buffer (20 mM HEPES pH 7.4, 10 mM MgCl$_2$, 100 mM NaCl, 0.015% Brij35 and 0.25 mM DTT). The reaction was initiated by the combination of bacterially expressed, CK2 α/β or CK2 α'/β holoenzyme with substrates and test compounds. The reaction was incubated at room temperature for 60 minutes and terminated by adding 30 µl of 35 mM EDTA to each sample. The reaction mixture was analyzed on the Caliper LABCHIP® 3000 (Caliper, Hopkinton, Mass.) by electrophoretic separation of the fluorescent substrate and phosphorylated product Inhibition data were calculated by comparison to no enzyme control reactions for 100% inhibition and vehicle-only reactions for 0% inhibition. The final concentration of reagents in the CK2 α/β assay was 25 µM ATP, 1.5 µM FL-RRRADDSDDDDD-NH2, 50 µM CK2 α/β holoenzyme, and 1.6% DMSO. The final concentration of reagents in the CK2 α'/β assay was 10 µM ATP, 1.5 µM FL-RRRADDSDDDDD-NH2, 100 µM CK2 α'/β holoenzyme, and 1.6% DMSO. Dose response curves were generated to determine the concentration required inhibiting 50% of kinase activity ($IC_{50}$). Compounds were dissolved at 10 mM in dimethylsulfoxide (DMSO) and evaluated at eleven concentrations. $IC_{50}$ values were derived by non-linear regression analysis.

B. Cell Proliferation Inhibition Assay

Compounds were evaluated for their ability to inhibit cell proliferation, using an assay that measures mitochondrial metabolic activity, that is directly correlated with cell numbers. Cells were plated at 2000 cells/well in 96-well plates and were cultured for 24 h in RPMI-1640 supplemented with 2% fetal bovine serum, before test compounds were added. Compounds were diluted in culture medium such that the final concentration of dimethyl sulfoxide never exceeded 1%. Following the addition of compounds, the cells were cultured for an additional 72 h before cell viability was determined by measuring the conversion of 3-(4,5-dimethylthiazol-2-yl)-2,5-diphenyltetrazolium bromide (MTT) dye using the CellTiter96 kit (Promega) or by measuring the conversion of [3-(4,5-dimethylthiazol-2-yl)-5-(3-carboxymethoxyphenyl)-2-(4-sulfophenyl)-2H-tetrazolium (MTS) dye using the CELLTITER 96® AQueous (Promega).

The following compounds were found to have the $IC_{50}$ described in Table A when measured in the CK2 kinase assays described above.

TABLE A

| Example No. | CK2A1 ($IC_{50}$, nM) | CK2A2 ($IC_{50}$, nM) |
| --- | --- | --- |
| 6 | 0.15 | 0.09 |
| 7 | 0.17 | 0.07 |
| 23 | 1.40 | 0.87 |
| 49 | 0.23 | 0.11 |
| 55 | 0.29 | 0.20 |
| 57 | 0.30 | 0.28 |
| 60 | 1.35 | 0.93 |
| 65 | 1.44 | 0.99 |
| 108 | 1.37 | 0.70 |
| 115 | 31.02 | 15.53 |
| 117 | 0.22 | 0.15 |
| 119 | 1.56 | 1.53 |
| 126 | 29.89 | 20.89 |
| 130 | 178.40 | 153.60 |
| 131 | 91.56 | 85.66 |
| 132 | 20.88 | 24.95 |
| 133 | 0.30 | 0.54 |
| 150 | 1.31 | 1.61 |
| 160 | 0.24 | 0.11 |
| 161 | 0.21 | 0.31 |
| 163 | 0.27 | 0.49 |
| 167 | 0.30 | 0.27 |
| 173 | 0.41 | 0.27 |
| 174 | 0.72 | 0.35 |

TABLE A-continued

| Example No. | CK2A1 ($IC_{50}$, nM) | CK2A2 ($IC_{50}$, nM) |
| --- | --- | --- |
| 176 | 1.53 | 0.49 |
| 179 | 1.36 | 0.26 |
| 184 | 1.37 | 0.64 |
| 189 | 220.10 | 61.21 |
| 207 | 0.31 | 0.23 |
| 218 | 8.54 | 8.18 |
| 221 | 1.34 | 0.76 |
| 224 | 5.87 | 2.05 |
| 229 | 0.21 | 0.16 |
| 238 | 1.35 | 0.27 |
| 252 | 3.83 | 1.17 |
| 253 | 1.50 | 0.47 |
| 263 | 9.61 | 5.96 |
| 267 | 6.16 | 4.72 |
| 268 | 15.25 | 3.21 |
| 269 | 13.86 | 3.16 |
| 274 | 1.42 | 0.75 |
| 276 | 6.04 | 3.01 |
| 281 | 0.27 | 0.09 |
| 285 | 0.14 | 0.45 |
| 313 | 0.29 | 0.21 |
| 314 | 1.40 | 1.32 |
| 319 | 0.28 | 0.25 |
| 327 | 4.71 | 2.95 |
| 328 | 0.52 | 0.13 |
| 347 | 173.50 | 81.62 |
| 348 | 1.42 | 0.76 |
| 364 | 1.33 | 0.61 |
| 374 | 1.37 | 0.52 |
| 382 | 0.39 | 0.61 |
| 390 | 8.00 | 4.53 |
| 391 | 0.13 | 0.03 |
| 392 | 7.54 | 2.47 |
| 394 | 0.27 | 0.27 |
| 395 | 0.22 | 0.21 |
| 396 | 1.44 | 0.94 |
| 399 | 0.23 | 0.16 |
| 402 | 0.16 | 0.11 |
| 408 | 1.39 | 0.23 |
| 409 | 1.32 | 0.82 |
| 415 | 25.51 | 19.71 |
| 418 | 13.06 | 16.04 |
| 419 | 8.62 | 1.43 |
| 420 | 60.08 | 46.59 |
| 423 | 9.80 | 2.75 |
| 428 | 1.39 | 0.74 |
| 433 | 23.09 | 5.10 |

Compounds of the present invention exhibit enhanced CK2 inhibitory activity over the compounds disclosed in WO 2007/038314 and US 2008/0045536. Comparing the data in Table A and Table B, compounds of the invention herein, e.g., compounds of Formula (I) (including Formulae (II), (III), (IV), (Va), (V), (VI), (VII), (VIII)), are surprisingly advantageous for their CK2 enzyme inhibition activity and/or other drugability properties.

TABLE B

| Example No. | Structure | CK2A1 $IC_{50}$ (μM) | CK2A2 $IC_{50}$ (μM) |
| --- | --- | --- | --- |
| XIII (WO 2007/038314, pages 80-81) XIII(1) (US 2008/0045536 Page 54) | [chemical structure] | 1.8 | 0.331 |

Methods of Preparation

The compounds of the present invention may be prepared by methods such as those illustrated in the following schemes. Solvents, temperatures, pressures, and other reaction conditions may readily be selected by one of ordinary skill in the art. Starting materials are commercially available or readily prepared by one of ordinary skill in the art. These schemes are illustrative and are not meant to limit the possible techniques one skilled in the art may use to manufacture compounds disclosed herein. Different methods may be evident to those skilled in the art. Additionally, the various steps in the synthesis may be performed in an alternate sequence or order to give the desired compound(s). All documents cited herein are incorporated herein by reference in their entirety.

In general, the time taken to complete a reaction procedure will be judged by the person performing the procedure, preferably with the aid of information obtained by monitoring the reaction by methods such as HPLC or TLC. A reaction does not have to go to completion to be useful to this invention. The methods for the preparation of various heterocycles used to this invention can be found in standard organic reference books, for example, Katritzky, A. R. et al., eds., *Comprehensive Heterocyclic Chemistry, The Structure, Reactions, Synthesis and Uses, of Heterocyclic Compounds*, First Edition, Pergamon Press, New York (1984), and Katritzky, A. R. et al., eds., *Comprehensive Heterocyclic Chemistry II, A Review of the Literature 1982-1995: The Structure, Reactions, Synthesis and Uses, of Heterocyclic Compounds*, Pergamon Press, New York (1996).

Unless otherwise specified, the various substituents of the compounds are defined in the same manner as the Formula (I) compound of the invention.

Compounds of general formula (I) may be prepared by as described in Scheme A

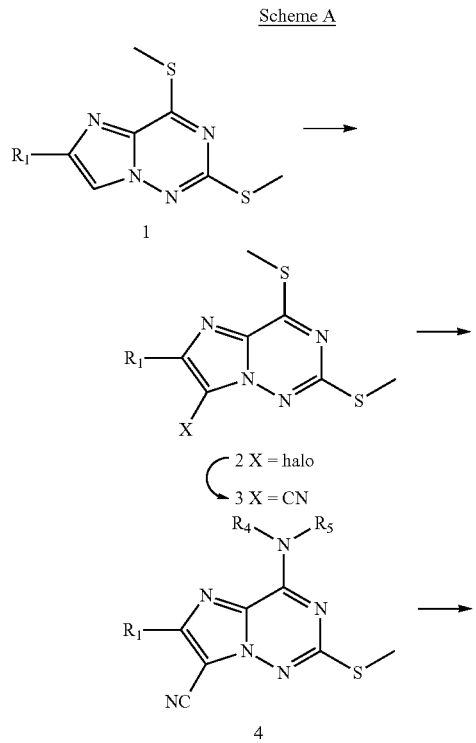

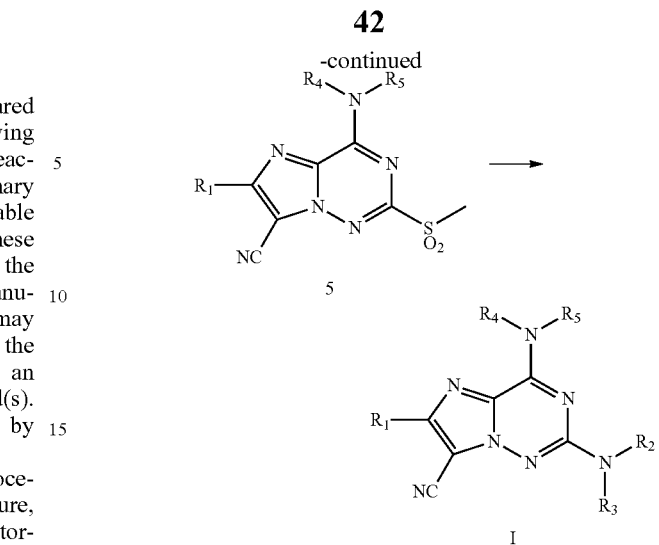

Halogenation of imidazotriazine 1 with electrophilic reagent such as N-bromosuccinamide in suitable solvent provides haloimidazotriazine 2. Treatment of 2 with nucleophilic metal cynide reagent (such as zinc or copper cyanide) with or without transition metal catalyst would give cyanoimidazotriazine 3. Nucleophiles (such as amines) add under neat or in appropriate solvent to provide imidazotriazine 4. See e.g. *Journal of The Chemical Society, Perkins Transactions I*, Vol. 20 (1999) at pp. 2929. Treatment of imidazotriazine 4 with a suitable oxidizing agent (such as MCPBA) in a suitable solvent (such as DMF) provides imidazotriazine 5. Treatment of imidazotriazine 5 with a nucleophile (such as an amine) under neat conditions provides imidazotriazine (I).

Similarly, compounds of general formula (II) could be prepared in analogus manner using readily cleavable R5 (such as 4-methoxybenzyl or t-butyloxycaronyl) and unmasking it at the end using suitable conditions.

Alternatively the compounds of general formula (I) could also be prepared according to Scheme B. Ester of imidazole-2-carboxylic acid 1 could be electrophilically aminated, condensed with ethyl chloroformate and cyclized with ammonia to afford imidazotiazine diaone 4. Halogenation followed by treatment with POCl3 would afford dichloro compound 6. Displacement of 4-Cl with suitable amine followed by cyanation and then subsequent displacement of Cl atom would yield desired imidazotriazine I.

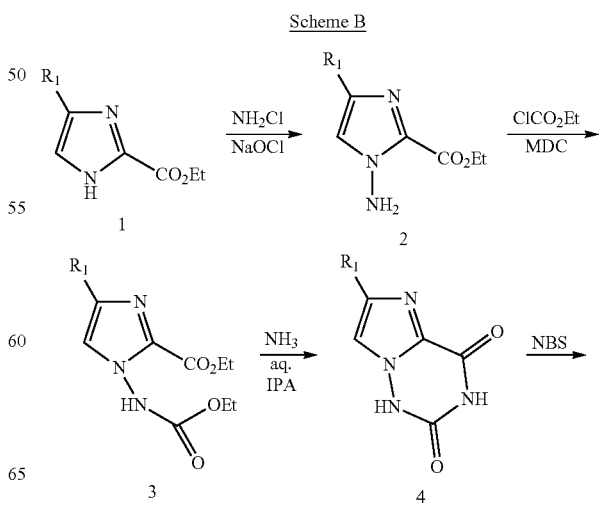

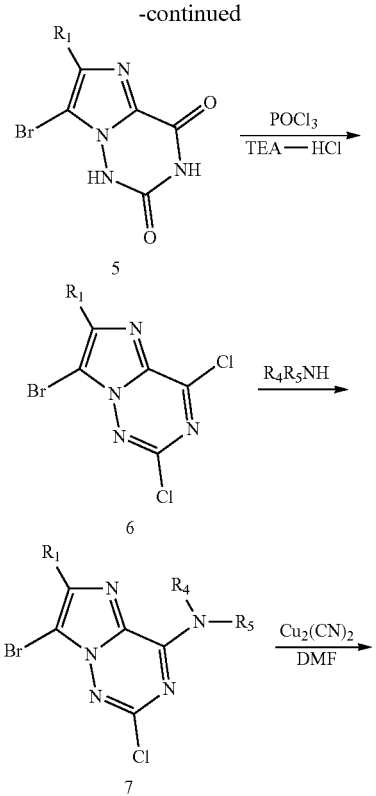

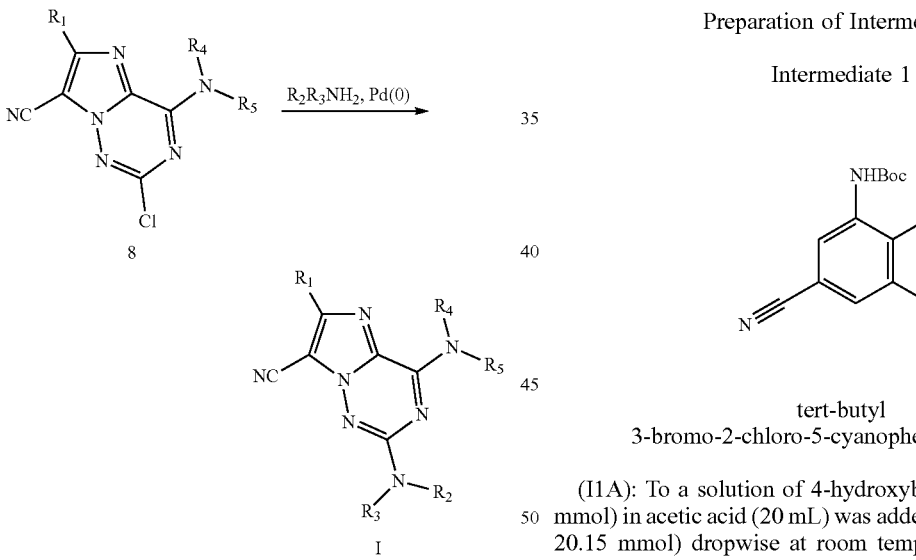

EXAMPLES

The following Examples illustrate embodiments of the inventive compounds and starting materials, and are not intended to limit the scope of the claims. For ease of reference, the following abbreviations are used herein:
BOC32 tert-butoxycarbonyl
bp=boiling point
Bu=butyl
DMAP=4-dimethylaminopyridine
DIPEA or DIEA=N,N-diisopropylethylamine
DME=1,2-dimethoxyethane
DMF=dimethyl formamide
EDCI=1-3-dimethylaminopropyl)-3-ethylcarbodiimide
Et=ethyl
$Et_2O$=diethyl ether
HOBT=1-hydroxybenzotriazole
EtOAc=ethyl acetate
EtOH=ethanol
g=gram(s)
H=hydrogen
l=liter
mCPBA=meta chloro perbenzoic acid
Me=methyl
MeCN=acetonitrile
MeOH=methanol
NMP=1-methyl-2-pyrrolidinone
Ph=phenyl
Pr=propyl
PS=polystyrene
TEA=triethylamine
TFA=trifluoroacetic acid
mg=milligram(s)
ml or mL=milliliter
μl=microliter
mmol=millimole
μmol=micromole
mol=mole
mp=melting point
RT=room temperature
HPLC=high pressure liquid chromatography
LC/MS=liquid chromatography/mass spectrometry Preparation of Intermediates Intermediate 1 tert-butyl
3-bromo-2-chloro-5-cyanophenylcarbamate (I1A): To a solution of 4-hydroxybenzonitrile (1 g, 8.39 mmol) in acetic acid (20 mL) was added bromine (1.038 mL, 20.15 mmol) dropwise at room temperature. The mixture was stirred for 30 minutes. The mixture was poured onto ice, the solid was collected by filtration, rinsed with water and dried to give 2.25 g of 3,5-dibromo-4-hydroxybenzonitrile as white solid product.

MS (ESI) m/z 277.

1H NMR (400 MHz, CHLOROFORM-d) δ ppm 7.77 (2H, s), 6.37 (1H, br. s.)

(I1B): To a suspension of 3,5-dibromo-4-hydroxybenzonitrile (2.11 g, 7.62 mmol) in acetic acid (70 mL) was added sodium nitrite (2.63 g, 38.1 mmol) in small portion, evolving bubbles and bromine were observed. After addition, the mixture was stirred at 50° C. overnight. Reaction was cooled to room temperature; water (250 mL) was added and extracted with EtOAc for two times. The combined extracts were washed with water and brine, dried over MgSO filtered and the filtrate was concentrated to give yellow orange solid.

The solid was treated with small amount of MeOH, collected by filtration, rinsed with MeOH, dried to afford 1.56 g of 3-bromo-4-hydroxy-5-nitrobenzonitrile as yellow solid.

1H NMR (400 MHz, CHLOROFORM-d) δ ppm 7.26 (2H, s), 8.11 (1H, d, J=1.72 Hz), 8.44 (1H, d, J=1.94 Hz)

(I1C): DMF (2 mL) was cooled to −20° C. and treated gradually in dropwise manner with oxalyl chloride (0.216 mL, 2.469 mmol). After 10 min, a solution of 3-bromo-4-hydroxy-5-nitrobenzonitrile (200 mg, 0.823 mmol) in DMF (2 mL) was added slowly via syringe while maintaining internal temperature below −10° C. After addition, the mixture was allowed to warmed to room temperature and then heated at 100° C. for 1.5 h. The reaction mixture was cooled and poured into ice-water, the solid was collected by filtration, rinsed with water and dried to give 172 mg of 3-bromo-4-chloro-5-nitrobenzonitrile as tan solid.

1H NMR (400 MHz, CHLOROFORM-d) δ ppm 8.13 (1H, d, J=1.76 Hz), 8.02 (1H, d, J=1.98 Hz)

(I1D): A mixture of 3-bromo-4-chloro-5-nitrobenzonitrile (0.99 g, 3.79 mmol), iron (1.057 g, 18.93 mmol) and ammonium chloride (2.025 g, 37.9 mmol) in THF, MeOH and water (60 ml, 1:1:1) was heated to reflux for 1 h. More iron (0.5 g) and NH$_4$Cl (2 g) added, heated for another 2 h and then cooled to RT. Filtered off solid, the filtrate was concentrated to remove the organic solvent. The residue was diluted with water, extracted with EtOAc twice, dried and concentrated to dryness. The resulting solid was triturard with EtOAc, solid was filtered off through celite pad and the filtrate was concentrated to give 0.88 g of 3-amino-5-bromo-4-chlorobenzonitrile as yellow solid which was used as such in the next reaction.

Intermediate 1: To a solution of 3-amino-5-bromo-4-chlorobenzonitrile (0.88 g, 3.80 mmol) in DCM (25 mL) was added TEA (1.590 mL, 11.41 mmol), BOC$_2$O (1.059 mL, 4.56 mmol) and DMAP (0.464 g, 3.80 mmol). The mixture was stirred at RT for 16 h. The reaction mixture was concentrated, the crude product was purified using ISCO silica gel column (24 g, EtOAc/hexane=0-30%) to give 0.667 g of tert-butyl 3-bromo-2-chloro-5-cyanophenylcarbamate as white solid MS (ESI) m/z 331.

1H NMR (400 MHz, CHLOROFORM-d) δ ppm 8.62 (1H, d, J=1.76 Hz), 7.59 (1H, d, J=1.98 Hz), 7.21 (1H, br. s.), 1.57 (9H, s)

Intermediate 2

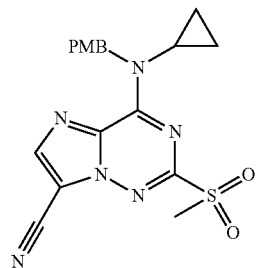

4-(cyclopropyl(4-methoxybenzyl)amino)-2-(methylsulfonyl)imidazo[2,1-f][1,2,4]triazine-7-carbonitrile (I2A): A mixture of 7-bromo-2,4-bis(methylthio)imidazo[2,1-f][1,2,4]triazine (6 g, 20.61 mmol), zinc cyanide (1.694 g, 14.42 mmol) and zinc powder (0.270 g, 4.12 mmol) in DMA (150 mL) in a 350 mL round bottom pressure flask was degassed by evacuating with vacuum and back filling with nitrogen three times. bis(tri-t-butylphosphine)palladium (O) (1.053 g, 2.061 mmol) was added and the above process was repeated three times. The reaction mixture was heated at 100° C. for 4 hours. LCMS showed completion of reaction with small amount of de-bromination byproduct and mostly product. The reaction mixture was filtered through a plug of Celite and the filtrate was concentrated in vacuo. The crude product was purified by flash chromatography on silica gel using an automated ISCO system (330 g column, eluting with 0-10% ethyl acetate/dichloromethane). 2,4-bis(methylthio)imidazo[2,1-f][1,2,4]triazine-7-carbonitrile (3.35 g) was obtained as a light yellow solid.

MS (ESI) m/z 238.0.

1H NMR (500 MHz, CDCl3) δ: 8.05 (s, 1H), 2.73 (s, 3H), 2.66 (s, 3H).

(I2B): Cyclopropanamine (2.69 mL, 42.4 mmol) was added to a suspension of 2,4-bis(methylthio)imidazo[2,1-f][1,2,4]triazine-7-carbonitrile (3.35 g, 14.12 mmol) in THF (30 mL) and the resulting mixture was heated at 50° C. overnight. Solvent was evaporated and the crude product was purified by flash chromatography on silica gel using an automated ISCO system (120 g column, eluting with 5-30% ethyl acetate/hexanes). 4-(cyclopropylamino)-2-(methylthio)imidazo[2,1-f][1,2,4]triazine-7-carbonitrile (3.39 g) was obtained as light yellow solid.

MS (ESI) m/z 247.1.

(I2C): Sodium hydride (60% in mineral oil, 0.890 g, 22.02 mmol) was added to a solution of 4-(cyclopropylamino)-2-(methylthio)imidazo[2,1-f][1,2,4]triazine-7-carbonitrile (3.39 g, 13.76 mmol) in DMF (110 mL) at room temperature and the resulting mixture was stirred for 30 min. 1-(chloromethyl)-4-methoxybenzene (3.05 mL, 22.02 mmol) was added and the reaction mixture was heated at 80° C. for 2 h. The reaction solution was quenched with ethyl acetate/sodium bicarbonate saturated solution. The organic phase was separated, washed with 10% lithium chloride solution, dried and concentrated. The crude product was purified by flash chromatography on silica gel using an automated ISCO system (220 g column, eluting with 5-20% ethyl acetate/hexanes). 4-(cyclopropyl(4-methoxybenzyl)amino)-2-(methylthio)imidazo[2,1-f][1,2,4]triazine-7-carbonitrile (4.59 g) was obtained as an off-white solid.

MS (ESI) m/z 367.1.

$^1$H NMR (400 MHz, chloroform-d) δ 7.94 (s, 1H), 7.21 (d, J=5.1 Hz, 2H), 6.86 (d, J=8.6 Hz, 2H), 3.81 (s, 3H), 2.59 (s, 3H), 1.05 (d, J=5.5 Hz, 2H), 0.86 (br. s., 2H).

Intermediate 2: mCPBA (7.02 g, 31.3 mmol) was added to a solution of 4-(cyclopropyl(4-methoxybenzyl)amino)-2-(methylthio)imidazo[2,1-f][1,2,4]triazine-7-carbonitrile (4.59 g, 12.53 mmol) in dichloromethane (120 mL) at room temperature and the reaction mixture was stirred at room temperature for 2 h. The reaction mixture was diluted with dichloromethane and washed with 20% sodium thiosulfate and saturated sodium bicarbonate. The organic layer was dried over magnesium sulfate, filtered and concentrated in vacuo, the crude product was purified by flash chromatography on silica gel using an automated ISCO system (220 g column, eluting with 0-10% ethyl acetate/dichloromethane). 4-(cyclopropyl(4-methoxybenzyl)amino)-2-(methylsulfonyl)imidazo[2,1-f][1,2,4]triazine-7-carbonitrile (4.74 g) was obtained as a white foaming solid.

MS (ESI) m/z 399.1.

1H NMR shows a mixture of two rotomers in the ration of 1.2 to 1 (500 MHz, chloroform-d) δ 8.14 (s, 1H), 7.36 (d, J=8.3 Hz, 1H), 7.20 (d, J=8.3 Hz, 1H), 6.91-6.83 (m, 2H), 5.72 (s, 1H), 5.09 (s, 1H), 3.80 (s, 3H), 3.61-3.53 (m, 0.55H), 3.42 (s, 1.36H), 3.35 (s, 1.64H), 3.07-2.99 (m, 0.45H), 1.24-1.17 (m, 1.1H), 1.16-1.11 (m, 0.9H), 1.03-0.96 (m, 1.1H), 0.96-0.90 (m, 0.9H).

Intermediate 3

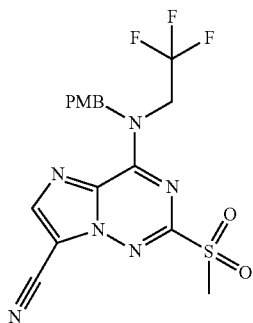

4-((4-methoxybenzyl)(2,2,2-trifluoroethyl)amino)-2-(methylsulfonyl)imidazo[2,1-f][1,2,4]triazine-7-carbonitrile (I3A): 2,2,2-trifluoroethanamine (1252 mg, 12.64 mmol) was added to a solution of 2,4-bis(methylthio)imidazo[2,1-f][1,2,4]triazine-7-carbonitrile (I2A), 300 mg, 1.264 mmol) in NMP (3 mL) and the resulting mixture was heated at 120° C. for 5 h. The reaction mixture was diluted with ethyl acetate and washed with saturated sodium bicarbonate. The organic layer was dried over magnesium sulfate, filtered and concentrated in vacuo, the crude product was purified by flash chromatography on silica gel using an automated ISCO system (40 g column, eluting with 0-40% ethyl acetate/dichloromethane). 2-(methylthio)-4-((2,2,2-trifluoroethyl)amino)imidazo[2,1-f][1,2,4]triazine-7-carbonitrile (363 mg) was obtained as a white solid.

MS (ESI) m/z 289.0

(I3B): The compound was prepared from 2-(methylthio)-4-(2,2,2-trifluoroethyl)amino)imidazo[2,1-f][1,2,4]triazine-7-carbonitrile using a method analogous to that used to prepare intermediate I2C. 4-((4-methoxybenzyl)(2,2,2-trifluoroethyl)amino)-2-(methylthio)imidazo[2,1-f][1,2,4]triazine-7-carbonitrile (405 mg) was obtained as a white solid.

MS (ESI) m/z 409.1

Intermediate 3: The compound was prepared from 4-((4-methoxybenzyl)(2,2,2-trifluoroethyl)amino)-2-(methylthio)imidazo[2,1-f][1,2,4]triazine-7-carbonitrile (405 mg, 0.992 mmol) using a method analogous to that used to prepare intermediate 2. 4-((4-methoxybenzyl)(2,2,2-trifluoroethyl)amino)-2-(methylsulfonyl)imidazo[2,1-f][1,2,4]triazine-7-carbonitrile (395 mg) was obtained as a white solid.

MS (ESI) m/z 441.1

Intermediate 4

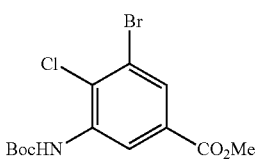

methyl 3-bromo-5-(tert-butoxycarbonylamino)-4-chlorobenzoate (I4A): Methyl 4-hydroxy-3-nitrobenzoate (15 g, 76 mmol) was suspended in acetic acid (152 ml) and then treated with NBS (20.31 g, 114 mmol). The mixture became a homogeneous yellow solution which was stirred for 2 h. The mixture was quenched with water and the suspension was filtered. Methyl 3-bromo-4-hydroxy-5-nitrobenzoate (20 g) was obtained as a yellow solid.

MS (ESI) m/z 276, 278. (M, M+2)

1H NMR (400 MHz, CHLOROFORM-d) δ ppm 11.48 (1H, s), 8.80 (1H, d, J=1.98 Hz), 8.53 (1H, d, J=1.98 Hz), 3.95-3.99 (3H, m).

(I4B): Anhydrous DMF (242 ml) was cooled to −20° C. in a dry ice/acetone bath and the internal temperature was monitored carefully and maintained at or below this temperature. Neat oxalyl chloride (9.51 ml, 109 mmol) was then slowly added dropwise via addition funnel and the vessel was properly vented to allow the escape of gases generated. Following the addition, the cloudy-white suspension was stirred at −20° C. for 30 min. A solution containing methyl 3-bromo-4-hydroxy-5-nitrobenzoate (10 g, 36.2 mmol) in DMF (121 ml) was then added slowly, not allowing the internal temp to exceed −10° C. Following the addition, the suspension was warmed to rt and then heated to 100° C. for 2 h. The reaction was cooled to rt and stirred over weekend. The dark brown solution was poured into ice water and diluted with EtOAc. The aqueous phase was extracted twice with EtOAc. The combined organics were washed with water and brine, then dried over anhydrous sodium sulfate. Filtration and concentration afforded methyl 3-bromo-4-chloro-5-nitrobenzoate (10 g) as a yellow solid that was dried in vacuo overnight.

MS (ESI) m/z 294. (M+H)

1H NMR (400 MHz, CHLOROFORM-d) δ ppm 8.50 (1H, d, J=1.98 Hz), 8.35 (1H, d, J=1.98 Hz), 3.95-4.00 (3H, s)

(I4C): Fe powder (2.84 g, 50.9 mmol) was added to a solution of methyl 3-bromo-4-chloro-5-nitrobenzoate (5 g, 16.98 mmol) in AcOH (29.3 ml). The suspension was heated to 60° C. 1 h. The vessel was cooled to rt and then AcOH was removed via rotovap. The residue was placed in a 1 L beaker and was carefully neutralized with saturated sodium bicarbonate. The precipitate was removed via filtration through Celite and the filtrate was extracted with EtOAc. The organics were combined, washed with water and brine, then dried over sodium sulfate. Filtration and concentration afforded methyl 3-amino-5-bromo-4-chlorobenzoate (4.19 g)) as a yellow solid.

MS (ESI), m/z 264

1H NMR (400 MHz, CHLOROFORM-d) δ ppm 7.67 (1H, d, J=1.76 Hz), 7.38 (1H, d, J=1.76 Hz), 4.33 (2H, br. s.), 3.90 (3H, s)

(I4D): Methyl 3-amino-5-bromo-4-chlorobenzoate (2.16 g, 8.17 mmol), BOC2O (3.79 ml, 16.33 mmol) and DMAP (0.100 g, 0.817 mmol) were dissolved in THF (40.8 ml) at rt. TEA (2.85 ml, 20.42 mmol) was added and the reaction was stirred at rt for 5 h. After 5 h, still about 30% starting material in the reaction. Added another 1.8 g of BOC$_2$O (3.79 ml, 16.33 mmol) to the reaction mixture and let stir overnight. The reaction mixture was concentrated and the residue was partitioned between EtOAc and H2O. The organic layer was washed twice with water and once with brine, then concentrated and purified by flash column chromatography, eluting with 0-50% EtOAc/Hex. Methyl 3-(bis(tert-butoxycarbonyl)amino)-5-bromo-4-chlorobenzoate (3.06 g).

MS (ESI), m/z 350 (M-C6H12O2), loss of Boc and ester hydrolysis.

1H NMR (400 MHz, DMSO-d6) δ ppm 8.25 (1H, d, J=1.98 Hz), 7.99 (1H, d, J=1.98 Hz), 3.90 (3H, s), 1.39 (18H, s)

Intermediate 4: Methyl 3-(bis(tert-butoxycarbonyl)amino)-5-bromo-4-chlorobenzoate (3.06 g, 6.58 mmol) was dissolved in a solution of TFA (1.015 ml, 13.17 mmol) in CH$_2$Cl$_2$ (32.9 ml). The reaction was stirred at rt for 45 min, and then sat. NaHCO$_3$ solution was added. The reaction mixture was diluted with a little more CH$_2$Cl$_2$ and washed 2× with sat. NaHCO3 to remove any residual TFA. The organic layer was dried over Na$_2$SO$_4$, filtered, and concentrated to provide methyl 3-bromo-5-(tert-butoxycarbonylamino)-4-chlorobenzoate (2.33 g) as a cream solid.

MS (ESI), m/z 350 (M-CH3, ester hydrolysis product).

1H NMR (400 MHz, CHLOROFORM-d) δ ppm 8.83 (1H, d, J=1.98 Hz), 8.02 (1H, d, J=1.76 Hz), 7.15 (1H, s), 3.96 (3H, s), 1.58 (9H, s).

Intermediate 5

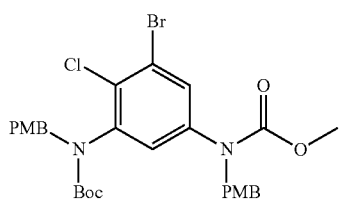

tert-butyl methyl(5-bromo-4-chloro-1,3-phenylene)bis(4-methoxybenzylcarbamate)

(I5A): A stirred solution of methyl 3-bromo-5-((tert-butoxycarbonyl)amino)-4-chlorobenzoate (1 g, 2.74 mmol, Intermediate 4) in THF (15 mL), MeOH (3.75 mL) and water (3.75 mL) was treated with LiOH (0.263 g, 10.97 mmol). The reaction was stirred at rt for 2 h. The reaction mixture was concentrated and the white residue was suspended in water, then neutralized with AcOH to pH ~6-7. The suspension was stirred for 30 min, then the white solid was collected by filtration and dried in air to yield 3-bromo-5-((tert-butoxycarbonyl)amino)-4-chlorobenzoic acid (0.95 g).

1H NMR (400 MHz, DMSO-d6) δ ppm 8.85 (s., 1H), 8.04 (d, J=1.54 Hz, 1H), 7.91 (d, J=1.76, 1H), 5.74 (s, 1H), 1.46 (s, 9H)

(I5B): A stirred mixture of 3-bromo-5-((tert-butoxycarbonyl)amino)-4-chlorobenzoic acid (6 g, 17.11 mmol) in dioxane (342 mL) was treated with TEA (7.16 mL, 51.3 mmol), followed by DPPA (9.18 mL, 42.8 mmol). The reaction was heated at 70° C. under N2 for 1.5 h, then methanol (15 mL, 17.11 mmol) was added, and the reaction heated at 70° C. overnight. The reaction was quenched with water, then extracted (3×) with EtOAc. The combined organic extracts were dried over Mg2SO4, filtered and concentrated. The crude material was purified by flash column chromatography, eluting with 0-17% EtOAc/Hex, to yield tert-butyl methyl(5-bromo-4-chloro-1,3-phenylene)dicarbamate (2.2 g)

1H NMR (400 MHz, CHLOROFORM-d) δ ppm 8.06 (d, J=2.4 Hz, 1H), 7.75 (br. s, 1H), 7.11 (br. s, 1H), 6.63 (br. s., 1H), 3.78 (s, 3H), 1.54 (s, 9H Intermediate 5: A stirred solution of tert-butyl methyl(5-bromo-4-chloro-1,3-phenylene)dicarbamate (710 mg, 1.870 mmol) in DMF (10 mL) was treated with NaHMDS (3.93 mL, 3.93 mmol) at 0° C. dropwise. The reaction mixture was stirred for 15 min, and 1-(chloromethyl)-4-methoxybenzene (0.533 mL, 3.93 mmol) was added. The reaction was stirred for 45 min, then heated at 75° C. for 1.5 h. The reaction was quenched with half saturated NH4Cl solution and extracted with EtOAc 3×. The organic layers were combined, dried over Mg2SO4, filtered and concentrated. The crude material was purified by flash column chromatography, eluting with 0%-40% EtOAc/Hex. The desired fractions were concentrated to yield tert-butyl methyl(5-bromo-4-chloro-1,3-phenylene)bis(4-methoxybenzylcarbamate) (953.4 mg).

1H NMR (400 MHz, CHLOROFORM-d) δ ppm 7.30 (br. s, 1H), 7.07 (d, J=8.36 Hz, 2H), 7.00 (d, J=8.58 Hz, 2H), 6.84-6.75 (m, 4H), 3.79 (s, 3H), 3.78 (s, 2H), 3.66 (s, 3H), 1.59-1.52 (m, 3H), 1.34 (br. s, 6H) Intermediate 6

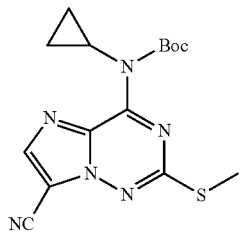 [SMILES: CSc1nc(N(C(=O)OC(C)(C)C)C2CC2)c2ncc(C#N)n2n1]

Tert-butyl(7-cyano-2-(methylsulfonyl)imidazo[2,1-f][1,2,4]triazin-4-yl)(cyclopropyl)carbamate (I6A): 4-(cyclopropylamino)-2-(methylthio)imidazo[2,1-f][1,2,4]triazine-7-carbonitrile (200 mg, 0.812 mmol, Intermediate 2) and Boc2O (0.283 mL, 1.218 mmol) were taken up in THF (4 mL) and cooled to 0° C. LiHMDS (1.218 mL, 1.218 mmol) was added dropwise, and the reaction was brought to rt. The reaction mixture was stirred for 6 h. An additional 0.5 eq each of Boc$_2$O and LiHMDS was added and the reaction was stirred at rt for 1 h. The reaction was quenched with water and extracted with EtOAc. The organic layer was dried over Na$_2$SO$_4$, filtered, and concentrated. The material was purified by flash column chromatography, eluting with 0-50% EtOAc/Hex. The fractions were combined to give tert-butyl(7-cyano-2-(methylthio)imidazo[2,1-f][1,2,4]triazin-4-yl)(cyclopropyl)carbamate (180 mg) as a colorless foam.

MS (ESI) m/z 369 (M+Na)

1H NMR (400 MHz, CHLOROFORM-d) δ 8.08 (s, 1H), 3.24-3.12 (m, 1H), 2.66 (s, 3H), 1.47 (s, 9H), 1.08-0.97 (m, 2H), 0.81-0.68 (m, 2H)

(I6B): Tert-butyl(7-cyano-2-(methylthio)imidazo[2,1-f][1,2,4]triazin-4-yl)(cyclopropyl)carbamate (180 mg, 0.520 mmol) was taken up in DCM (5 mL) and mCPBA (291 mg, 1.299 mmol) was added. The reaction was stirred at rt for 2 h. The reaction mixture was diluted with DCM and washed with 20% Na$_2$S2O$_3$ and saturated sodium bicarbonate. The organic layer was dried over Na2SO4, filtered, and concentrated. The remaining white solid was purified by flash column chromatography, eluting with 0-50% EtOAc/Hex. Tert-butyl(7-cyano-2-(methylsulfonyl)imidazo[2,1-f][1,2,4]triazin-4-yl)(cyclopropyl)carbamate (163 mg) was obtained as a white solid.

MS (ESI) m/z 401 (M+Na)

1H NMR (400 MHz, DMSO-d6) δ 8.77 (s, 1H), 3.46 (s, 3H), 3.26-3.19 (m, 1H), 1.45 (s, 9H), 1.06-0.94 (m, 2H), 0.88-0.73 (m, 2H)

(I6C): 4-(cyclopropylamino)-2-(methylthio)imidazo[2,1-f][1,2,4]triazine-7-carbonitrile (200 mg, 0.812 mmol) and Boc$_2$O (0.283 mL, 1.218 mmol) were taken up in THF (4 mL) and cooled to 0° C. LiHMDS (1.218 mL, 1.218 mmol) was added dropwise, and the reaction was brought to rt. The reaction mixture was stirred for 6 h. An additional 0.5 eq each of Boc2O and LiHMDS was added and the reaction was stirred at rt for 1 h. The reaction was quenched with water and extracted with EtOAc. The organic layer was dried over Na$_2$SO$_4$, filtered, and concentrated. The material was purified by flash column chromatography, eluting with 0-50% EtOAc/Hex. The fractions were combined to give tert-butyl(7-cyano-2-(methylthio)imidazo[2,1-f][1,2,4]triazin-4-yl)(cyclopropyl)carbamate (180 mg) as a colorless foam.

MS (ESI) m/z 369 (M+Na)

1H NMR (400 MHz, CHLOROFORM-d) δ 8.08 (s, 1H), 3.24-3.12 (m, 1H), 2.66 (s, 3H), 1.47 (s, 9H), 1.08-0.97 (m, 2H), 0.81-0.68 (m, 2H)

Intermediate 6: Tert-butyl(7-cyano-2-(methylthio)imidazo[2,1-f][1,2,4]triazin-4-yl)(cyclopropyl)carbamate (180 mg, 0.520 mmol) was taken up in DCM (5 mL) and mCPBA (291 mg, 1.299 mmol) was added. The reaction was stirred at rt for 2 h. The reaction mixture was diluted with DCM and washed with 20% Na$_2$S$_2$O$_3$ and saturated sodium bicarbonate. The organic layer was dried over Na$_2$SO$_4$, filtered, and concentrated. The remaining white solid was purified by flash column chromatography, eluting with 0-50% EtOAc/Hex. Tert-butyl(7-cyano-2-(methylsulfonyl)imidazo[2,1-f][1,2,4]triazin-4-yl)(cyclopropyl)carbamate (163 mg) was obtained as a white solid.

MS (ESI) m/z 401 (M+Na)

1H NMR (400 MHz, DMSO-d6)™ 8.77 (s, 1H), 3.46 (s, 3H), 3.26-3.19 (m, 1H), 1.45 (s, 9H), 1.06-0.94 (m, 2H), 0.88-0.73 (m, 2H)

Intermediate 7

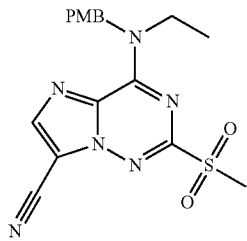

4-(ethyl(4-methoxybenzyl)amino)-2-(methylsulfonyl)imidazo[1,2-f][1,2,4]triazine-7-carbonitrile (I7A): A mixture of 2,4-bis(methylthio)imidazo[2,1-f][1,2,4]triazine-7-carbonitrile (70 mg, 0.295 mmol) and N-(4-methoxybenzyl)ethanamine (180 mg, 1.089 mmol) in dry THF (2 mL) (Aldrich, Sure seal) was treated with DIEA (0.35 mL, 2.004 mmol). The mixture was heated in microwave at 115° C. for 8 hrs. The reaction mixture was concentrated. The residue was triturated with cold MeOH. The solid was collected by filtration, washed with cold MeOH and water (4×10 mL), dried under vacuum to give 98 mg of desired product, which was used as such in the next step.

(I7B): mCPBA (343 mg, 1.531 mmol) was added to a solution of 4-(ethyl(4-methoxybenzyl)amino)-2-(methylthio)imidazo[2,1-f][1,2,4]triazine-7-carbonitrile (217 mg, 0.612 mmol) in DCM (5 mL) at rt and the reaction mixture was stirred at rt for 2 h. LCMS showed completion of reaction. The reaction mixture was diluted with DCM and washed with 20% Na$_2$S$_2$O$_3$ and saturated sodium bicarbonate. The organic layer was dried over magnesium sulfate, filtered and concentrated in vacuo. The crude product was purified by flash chromatography on silica gel using an automated biotage system (40 g column, eluting with 0-10% ethyl acetate in dichloromethane) to give 235 mg of desired product.

MS (ESI) m/z 387.3 (M+1).

1H NMR (400 MHz, CHLOROFORM-d)™ 8.11 (d, J=0.8 Hz, 1H), 7.40 (d, J=8.8 Hz, 1H), 7.22 (d, J=8.5 Hz, 1H), 6.97-6.79 (m, 2H), 5.72 (s, 1H), 5.06 (s, 1H), 4.44 (q, J=7.0 Hz, 1H), 4.00-3.83 (m, 1H), 3.82 (d, J=3.5 Hz, 3H), 3.39 (d, J=15.1 Hz, 3H), 1.42-1.23 (m, 3H)

Intermediate 8

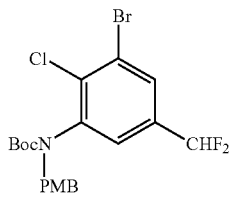

tert-butyl(3-bromo-2-chloro-5-(difluoromethyl)phenyl)(4-methoxybenzyl)carbamate (I8A): Methyl 3-bromo-5-((tert-butoxycarbonyl)amino)-4-chlorobenzoate (5 g, 13.71 mmol, Intermediate 4) was dissolved in THF (91 mL) at 0° C. under N$_2$. Lithium aluminum hydride solution (10 ml, 10.00 mmol, 1 M in THF) was added dropwise. The reaction mixture was stirred for 2 hours at which point reaction appeared complete by LC/MS. Water (1.4 mL) was added slowly and resulted in a vigorous quench. 1 M aq. NaOH soln (1.4 mL) was added dropwise, followed by a final addition of H$_2$O (4.2 mL). The mixture was stirred vigorously for 15 minutes and then several scoops of MgSO$_4$ were added. The reaction was diluted with Et$_2$O, stirred for 1 hour and then filtered through celite. Concentrated afforded tert-butyl(3-bromo-2-chloro-5-(hydroxymethyl)phenyl)carbamate (4.08 g).

1H NMR (400 MHz, CHLOROFORM-d)™ 8.19 (d, J=2.0 Hz, 1H), 7.39 (d, J=2.0 Hz, 1H), 7.14 (br. s., 1H), 4.69 (s, 2H), 1.57 (s, 9H). (I8B): tert-Butyl(3-bromo-2-chloro-5-(hydroxymethyl)phenyl)carbamate (4.08 g, 12.12 mmol) was dissolved in CH$_2$Cl$_2$ (60.6 mL) at rt. Dess-Martin Periodinane (5.14 g, 12.12 mmol) was added and the reaction was stirred at rt overnight. The reaction was complete by TLC, and was diluted with water and filtered through celite. The aqueous layer was extracted with CH$_2$Cl$_2$ (3×) and the combined organics were dried over Na$_2$SO4 and concentrated. Column chromatography (220 g SiO2, 0 to 10% EtOAc-hexane, gradient elution) afforded the expected product tert-butyl(3-bromo-2-chloro-5-formylphenyl)carbamate (2.45 g).

$^1$H NMR (400 MHz, CHLOROFORM-d)™ 10.00 (s, 1H), 8.75 (dd, J=1.3, 0.4 Hz, 1H), 7.76-7.44 (m, 2H), 7.13 (br. s., 1H), 1.58 (s, 9H). (I8C): tert-Butyl(3-bromo-2-chloro-5-formylphenyl)carbamate (2.45 g, 7.32 mmol) was dissolved in CH$_2$Cl$_2$ (36.6 ml) at rt. DAST (1.451 ml, 10.98 mmol) was added and the reaction was stirred at rt overnight. The reaction was not complete by TLC and an add'l 700 μL of DAST was added. After 5 hours, a trace of starting material still remained. Another 350 μL of DAST was added and the reaction stirred overnight. Sat. aq. NaHCO$_3$ solution was added and the reaction was stirred vigorously for 30 minutes. The reaction was filtered through celite and the aqueous layer was extracted with CH$_2$Cl$_2$ (3×). The combined organics were dried over Na$_2$SO$_4$ and concentrated. Column chromatography (220 g SiO$_2$, 0 to 10% EtOAc-hexane, gradient elution) afforded the expected product tert-butyl(3-bromo-2-chloro-5-(difluoromethyl)phenyl)carbamate (1.82 g).

$^1$H NMR (400 MHz, CHLOROFORM-d)™ 8.47-8.34 (m, 1H), 7.55-7.42 (m, 1H), 7.20 (br. s., 1H), 6.78-6.41 (m, 1H), 1.57 (s, 9H). Intermediate 8: tert-Butyl(3-bromo-2-chloro-5-(difluoromethyl)phenyl)carbamate (1.82 g, 5.10 mmol) was dissolved in DMF (11.1 .mL) at room temperature. NaHMDS (6.12 mL, 6.12 mmol) was added dropwise and the reaction was stirred for 30 minutes before the addition of 4-methoxybenzyl chloride (0.904 mL, 6.64 mmol) and stirring overnight. The reaction mixture was diluted with EtOAc causing a ppt to form. 10% aq. LiCl solution was added and the two layers became clear with stirring. The mixture was poured into a separatory funnel and the organic layer was washed with an extra equivalent of 10% aq. LiCl solution. The organic layer was dried over Na$_2$SO$_4$ and concentrated. Column chromatography (220 g SiO$_2$, 0 to 8% EtOAc-hexane, gradient elution) afforded the expected product tert-butyl(3-bromo-2-chloro-5-(difluoromethyl)phenyl)(4-methoxybenzyl)carbamate (2.29 g).

Intermediate 9

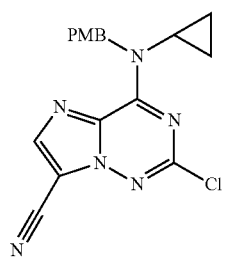

2-chloro-4-(cyclopropyl(4-methoxybenzyl)amino) imidazo[1,2-f][1,2,4]triazine-7-carbonitrile (I9A): Ammonium chloride (121 g, 2355 mmol) and MTBE (4.5 lit) were charged into 20 lit. RBF at RT, IT was cooled to −20° C. and then ammonium hydroxide saturated solution 2 lit. was added at −20° C. and Sodium hypochlorite was added at −20° C. for 1 hr. After addition it was stirred for 30 min at −20° C. MTBE layer was separated and washed with 200 ml of brine, separated MTBE layer dried with sodium sulphate. 15° C. and used as such in next reaction (I9B): NaH (34.2 g, 856 mmol) charged into 20 lit. round bottom flask at room temperature under N2 atmosphere. It was cooled to 0° C. and DMF added slowly for 15 min at 0° C. under N2 atmosphere. After addition the suspension was stirred for 5 min and then ethyl 1H-imidazole-2-carboxylate (100 g, 714 mmol) dissolved in 1 lit. of DMF was added slowly for 30 min at 0° C. After addition the reaction mixture was stirred for 2 hrs at room temperature. Chloramine solution in MTBE (I9A) layer charged at −20° C. After addition it was bring to 15° C. the mixture was stirred for 2 hrs at 15° C. under/N2 atmosphere. The reaction mixture was cooled 0° C. and quenched with 1.5 Lit of 10% Na2S2O3, separated the organic layer and then aq layer was back extracted with ethyl acetate (3 lit×4). Combined organic layer was washed with 2×300 ml of brine, separated the organic layer and dried with Anhydrous sodium sulfate, IT was concentrated to remove the MTBE and ethyl acetate, Crude
was taken as such along with DMF for next step.

MS (ESI) m/z: 146

(I9C): In 10 lit. round bottom flask charged ethyl 1-amino-1H-imidazole-2-carboxylate (70 g, 451 mmol) along with DMF and DCM (1200 ml) was added and cooled to 10-15° C. Then pyridine was added (35 ml) at single lot. Followed by slow addition of ethyl chloroformate (30 ml) and stirred at same temperature for 1.5 hrs. After 1.5 hrs additional pyridine (25 ml) and ethyl chloroformate (20 ml) was added. The reaction mixture was stirred for additional 30 minutes. The reaction mixture was concentrated under high vacuum and the crude residue was diluted with ethyl acetate and given saturated aqueous citric acid (250 ml) washing. The organic layer was separated. The citric acid layer was extracted with EtoAc (3×500 ml). All organic layer combined and washed with brine (2×150 ml), dried with sodium sulphate and concentrated to get the syrapy gel. The syrapy gel was triturated with ether-hexane mixture to give 65 g of ethyl 1-((ethoxycarbonyl)amino)-1H-imidazole-2-carboxylate as pale yellow solid.

MS (ESI) m/z: 228

(I9D): ethyl 1-((ethoxycarbonyl)amino)-1H-imidazole-2-carboxylate (120 g, 528 mmol) was dissolved in 800 ml of 2-propanol purged the ammonia gas for 1 hr. to increase the volume up to three times approximately at −50° C. Then reaction mixture was charged into an autoclave with 2 kg of ice. It was heated at 120° C. for 20 hrs while maintaining 8-10 kg pressure. The reaction mixture was cooled and concentrated under high vacuum to remove the water and 2-propanol. The crude solid was suspended in minimum amount of methanol and stirred for 5 min and filtered to give 59 g of imidazo[2,1f][1,2,4]triazine-2,4(1H,3H)-dione as off white solid.

(I9E): In a 3 liter 4-necked round bottom flask was taken imidazo[2,1-f][1,2,4]triazine-2,4(1H,3H)-dione (30 g, 197 mmol) and water (50 mL). The mixture was cooled to 10 to 15° C. N-bromosuccinimide (24.57 g, 138 mmol) was added portionwise while maintaining the temperature. After completion of addition, mixture was stirred at room temperature for 1 hr. Solid was filtered and washed with water (100 ml). The filtrate was extracted with dichloromethane (2×150 ml). The aqueous layer was concentrated to dryness. Compound was taken in 800 ml Solid was taken in 800 ml of methanol and filtered. 35 g of the solid was taken in 700 ml of water and heated to 80° C. for 1 hour and filtered in hot condition using sintered funnel Allowed to bring to rt slowly. Precipitated solid was filtered to afford f][1,2,4]triazine-2,4(1H,3H)-dione.

MS (ESI) m/z: 231

(I9F): Phosphoryl trichloride (200 mL, 2178 mmol) was added to a mixture of 7-bromoimidazo[2,1-f][1,2,4]triazine-2,4(1H,3H)-dione (20 g, 87 mmol) and triethylamine Hydrochloride (24 g, 174 mmol) in 500 ml pressure tube. The reaction was heated to 110° C. for 24 hrs. The reaction mixture was cooled to room temperature and concentrated using high vacuum pump. The residue was suspended in toluene and azeotroped with toluene (3×250 ml). The residue was taken in a cooled mixture of 1000 ml of ethylacetate and 500 ml of saturated sodium bicarbonate solution. The organic layer was separated.

Aqueous layer was extracted with ethylacetate (3×300 ml). Combined organic layer was washed with aqueous sodium bicarbonate solution (2×150 ml) and 100 ml of brine solution. The organic layer was dried over sodium sulphate and concentrated to give 51 g of 7-bromo-2,4-dichloroimidazo[2,1-f][1,2,4]triazine.

$^1$H NMR (400 MHz, CHLOROFORM-d)™ 7.99 (s, 1H)

Intermediate 9: The title intermediate was prepared in similar manner as Intermediate 10 from I9F.

Intermediate 10

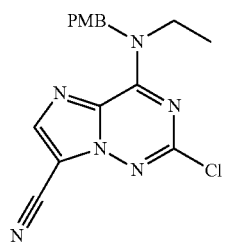

2-chloro-4-(ethyl(4-methoxybenzyl)amino)imidazo [2,1-f][1,2,4]triazine-7-carbonitrile (I10A): A solution of 7-bromo-2,4-dichloroimidazo[2,1-f][1,2,4]triazine (Intermediate I9F)(10 g, 37.3 mmol) in anhydrous THF (300 ml) was treated with N-(4-methoxybenzyl)ethanamine (8.01 ml, 46.7 mmol), resulting in the immediate precipitation of a solid. The reaction was stirred for 1 hour; the mixture was concentrated in vacuo. To the residue was added EtOAc (100 ml) and the mixture stirred 10 min. The salts were filtered off and the filtrate was washed with 0.5M citric acid, sat. NaHCO$_3$, water and brine. The solution was dried over Na$_2$SO$_4$ and solvents removed to afford 7-bromo-2-chloro-N-ethyl-N-(4-methoxybenzyl) imidazo[2,1-f][1,2,4]triazin-4-amine (15.8 g).

MS (ESI): m/z 398

$^1$H NMR (500 MHz, DMSO-d$_6$) δ 7.80 (d, J=17.5 Hz, 1H), 7.37-7.31 (m, 1H), 7.28 (d, J=8.7 Hz, 1H), 6.90 (dd, J=12.3, 8.8 Hz, 2H), 5.67 (s, 1H), 4.93 (s, 1H), 4.39-4.22 (m, 1H), 3.74 (d, J=4.3 Hz, 3H), 3.67-3.54 (m, 1H), 1.27-1.09 (m, 3H)

(I10B): To an oven dried 500 ml round bottom flask was added 7-bromo-2-chloro-N-ethyl-N-(4-methoxybenzyl)imidazo[2,1-f][1,2,4]triazin-4-amine (12.5 g, 31.5 mmol) and copper(i) cyanide (9.0 g, 100 mmol). The flask was capped under nitrogen and NMP (250 mL) was added. The mixture stirred 5 min at 25° C. and the flask was evacuated and back-filled with nitrogen 3×. The reaction stirred at 135° C. (oil bath) 21 hr. The reaction cooled to 25° C., diluted with ethyl acetate (500 ml) and filter through celit bed. The bed was washed with EtOAc 3×100 ml and the filtrate washed with water 1×300 ml and brine 3×150 ml. The organics dried with sodium sulphate and remove solvent. The material was crystallized from IPA and filtered to afford 2-chloro-4-(ethyl (4-methoxybenzyl)amino)imidazo[2,1-f][1,2,4]triazine-7-carbonitrile (11 g).

MS (ESI): m/z 343

$^1$H NMR (500 MHz, DMSO-d$_6$) δ 8.41 (d, J=16.2 Hz, 1H), 7.42-7.27 (m, 2H), 6.97-6.85 (m, 2H), 5.66 (s, 1H), 4.95 (s, 1H), 4.33-4.23 (m, 1H), 3.74 (d, J=3.5 Hz, 3H), 3.62 (d, J=7.0 Hz, 1H), 1.30-1.10 (m, 3H)

Intermediate 11

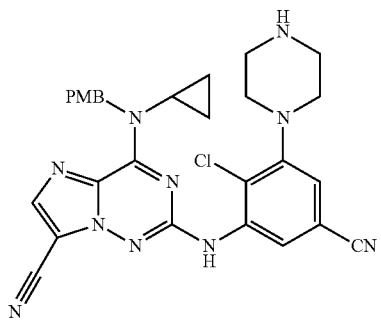

2-((2-chloro-5-cyano-3-(piperazin-1-yl)phenyl) amino)-4-(cyclopropyl(4-methoxybenzyl)amino) imidazo[2,1-f][1,2,4]triazine-7-carbonitrile (I11A): Tert-butyl(3-bromo-2-chloro-5-cyanophenyl) carbamate (Intermediate 1)(4.5 g, 13.57 mmol), Pd$_2$dba$_3$ (0.746 g, 0.814 mmol), BINAP (0.676 g, 1.086 mmol) and Cs$_2$CO$_3$ (8.84 g, 27.1 mmol) were suspended in toluene (12.0 mL) at room temperature. Tert-butyl piperazine-1-carboxylate (3.29 g, 17.64 mmol) was added and the reaction was degassed and purged with Argon, degassed for 6 times. The reaction mixture was heated at 105° C. for overnight. On completion of the reaction, the reaction mixture was cooled to room temperature, diluted with ethyl acetate, filtered through celite and concentrated. The Crude material was purified by column chromatography (ISCO), using 0-10% ethyl acetate-hexane as eluent. Pure fractions were concentrated to obtain tert-butyl 4-(3-((tert-butoxycarbonyl)amino)-2-chloro-5-cyanophenyl) piperazine-1-carboxylate (3.0 g) as an off-white solid.

MS (ESI) m/z 437.2

(I11B): To the stirred solution of tert-butyl 4-(3-((tert-butoxycarbonyl)amino)-2-chloro-5-cyanophenyl)piperazine-1-carboxylate (2.0 g, 4.58 mmol) in dichloromethane (40 mL) was added trifluoroacetic acid (8.89 mL, 115 mmol) slowly drop wise at room temperature, stirred it for 3 hours at room temperature. On completion of the reaction, the reaction mixture was diluted with methylene chloride (300 mL), cooled it to 0° C., basified with ammonia solution and extracted twice, the organic layer was washed with brine, dried over anhydrous sodium sulfate and concentrated. The crude material was washed with diethyl ether several times and dried under vacuum to get 3-amino-4-chloro-5-(piperazin-1-yl)benzonitrile (1.0 g) as a brown color solid. MS (ESI) m/z 237.5

(I11C): To the stirred solution of 3-amino-4-chloro-5-(piperazin-1-yl)benzonitrile (1.0 g, 4.22 mmol) in dichloromethane (10 mL) was added BOC$_2$O (0.981 mL, 4.22 mmol) at 0° C., drop wise over a period of 10 minutes followed by triethylamine (0.883 mL, 6.34 mmol). The reaction mixture was allowed to warm to room temperature, stirred it for 1 hour. The reaction mixture was diluted with methylene chloride (100 mL), washed with brine (30 mL), dried over Na$_2$SO$_4$ and concentrated at 45° C. to get tert-butyl 4-(3-amino-2-chloro-5-cyanophenyl)piperazine-1-carboxylate (1.4 g) as a brown solid. The crude material was washed with diethyl ether four times and dried under vacuum to get tert-butyl 4-(3-amino-2-chloro-5-cyanophenyl)piperazine-1-carboxylate (1.4 g) as an off-white solid.

MS (ESI) m/z 335.1

(I11D): To the stirred solution of tert-butyl 4-(3-amino-2-chloro-5-cyanophenyl)piperazine-1-carboxylate (1.0 g, 2.97 mmol), 2-chloro-4-(cyclopropyl(4-methoxybenzyl)

amino)imidazo[2,1-f][1,2,4]triazine-7-carbonitrile (Intermediate 9)(1.16 g, 3.27 mmol), in dry Dioxane (35 mL), added $Cs_2CO_3$ (1.64 g, 5.03 mmol) and degassed for 10 minutes. added 1,1'-Bis(diphenylphosphino)ferrocene (115 mg, 0.205 mmol), and 9,9-dimethyl-4,5-bis(diphenylphosphino)xanthene (172 mg, 0.297 mmol) followed by addition of Pd(OAc)2 (220 mg, 0.980 mmol), reaction mixture degassed and purged with argon for 10 minutes, reaction placed on pre-heated oil bath at 100° C. for 4 hour. On completion of the reaction, the reaction mixture was cooled to room temperature, filtered through celite washed with ethyl acetate (20 mL), organic layer concentrated to get dark brown semi solid. The solid was purified by Combiflash using 12 g Redisep column, using 0-10% methanol-chloroform as eluent. Pure fractions were concentrated to get off-white solid (1.3 g). This solid was dissolved in tetrahydrofuran (25 mL) added methanol for crystallization to get off-white solid, filtered the solid and dried under vacuum to get tert-butyl 4-(2-chloro-5-cyano-3-((7-cyano-4-(cyclopropyl(4-methoxybenzyl)amino)imidazo[2,1-f][1,2,4]triazin-2-yl)amino)phenyl)piperazine-1-carboxylate (900 mg) as an off-white solid.

MS (ESI) m/z 655.2

Intermediate 11: To the stirred solution of tert-butyl 4-(2-chloro-5-cyano-3-((7-cyano-4-(cyclopropyl(4-methoxybenzyl)amino)imidazo[2,1-f][1,2,4]triazin-2-yl)amino)phenyl)piperazine-1-carboxylate (3.5 g, 5.34 mmol) in dry dichloromethane (60 mL) was added 2,6-lutidine (1.867 mL, 16.03 mmol), followed by addition of trimethylsilyl triflate (2.90 mL, 16.03 mmol) at room temperature. The reaction mixture stirred at room temperature for 1 hour. On completion of the reaction, the reaction mixture was diluted with dichloromethane and washed with saturated sodium bicarbonate. The organic layer was separated and aqueous layer was extracted with dichloromethane twice, dried over sodium sulfate, concentrated under reduced pressure to get (4.5 g) off-white solid. This solid was washed with n-Hexane and diethyl ether twice (50 mL) to remove 2,6-lutidine to get 2-((2-chloro-5-cyano-3-(piperazin-1-yl)phenyl)amino)-4-(cyclopropyl(4-methoxybenzyl)amino)imidazo[2,1-f][1,2,4]triazine-7-carbonitrile (2.9 g) as off-white solid.

MS (ESI) m/z 555.2

Intermediate 12

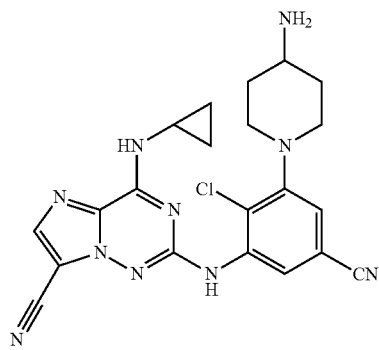 [SMILES: N#Cc1cc(Nc2nc(NC3CC3)c3ncc(C#N)n3n2)c(Cl)c(N2CCC(N)CC2)c1]

2-((3-(4-Aminopiperidin-1-yl)-2-chloro-5-cyanophenyl)amino)-4-(cyclopropylamino)imidazo[2,1-f][1,2,4]triazine-7-carbonitrile (I12A): A round bottom flask was charged with tert-butyl (3-bromo-2-chloro-5-cyanophenyl)carbamate (5.79 g, 17.48 mmol), tert-butyl piperidin-4-ylcarbamate (3.5 g, 17.48 mmol), cesium carbonate (11.4 g, 35 mmol), Pd2(dba)3 (1.600 g, 1.748 mmol) and BINAP (1.088 g, 1.748 mmol) in toluene (58.3 ml). The flask was evacuated and purged with nitrogen (4×) and heated at 100° C. ON. The reaction mixture was cooled to rt, diluted with methanol and vacuum filtered through a pad of Celite. The filtrate was concentrated in vacuo. The crude residue was purified by column chromatography on the Isco system (120 g, 0-100% EtOAc/$CH_2Cl_2$) to provide 112A (4.316 g) as a yellow solid.

MS (ESI) m/z 451.1

(I12B): To a round bottom flask charged with 112A (4.36 g, 9.67 mmol) in dichloromethane (51.6 ml) was added TFA (12.89 ml). The reaction mixture was stirred at rt 4 h. The reaction mixture was concentrated in vacuo. Toluene was added to the crude material and it was concentrated in vacuo (3×). The product was left on the vacuum ON and used as is in the next reaction. To a round bottom flask charged with 3-amino-5-(4-aminopiperidin-1-yl)-4-chlorobenzonitrile (2.425 g, 9.67 mmol) in dichloromethane (97 ml) was added triethylamine (6.74 ml, 48.4 mmol) and $Boc_2O$ (3.37 ml, 14.51 mmol). The reaction mixture was stirred at rt for 2 h. The reaction mixture was diluted with dichloromethane and poured into a separatory funnel containing saturated aqueous sodium bicarbonate. The aqueous layer was extracted with dichloromethane. The combined organics were washed with brine, dried over anhydrous sodium sulfate, filtered and concentrated in vacuo. Material was taken up in a minimal amount of dichloromethane and ether. After sitting for 1 h, the solid was isolated by filtration. The filtrate contained additional product and was purified by column chromatography on the Isco system (80 g, 0-20% EtOAc/$CH_2Cl_2$). tert-Butyl(1-(3-amino-2-chloro-5-cyanophenyl)piperidin-4-yl)carbamate (2.82 g).

MS (ESI) m/z 351.1

$^1$H NMR (400 MHz, CHLOROFORM-d) δ 6.74 (d, J=1.8 Hz, 1H), 6.69 (d, J=1.8 Hz, 1H), 4.29 (s, 2H), 3.64 (br. s., 1H), 3.29 (d, J=12.3 Hz, 2H), 2.75 (t, J=10.8 Hz, 2H), 2.14-2.02 (m, 2H), 1.69-1.57 (m, 2H), 1.47 (s, 9H)

(I12C): 2-Chloro-4-(cyclopropyl(4-methoxybenzyl)amino)imidazo[2,1-f][1,2,4]triazine-7-carbonitrile (Intermediate 9, 0.912 g, 2.57 mmol), tert-butyl(1-(3-amino-2-chloro-5-cyanophenyl)piperidin-4-yl)carbamate (0.902 g, 2.57 mmol), $Pd(OAc)_2$ (0.173 g, 0.771 mmol), dppf (0.143 g, 0.257 mmol), Xantphos (0.149 g, 0.257 mmol), and cesium carbonate (1.675 g, 5.14 mmol) were combined in a round bottom flask and dioxane (17.14 ml) was added. The flask was evacuated and backfilled with nitrogen (3×), then heated at 100° C. for 1 h. The reaction mixture was filtered through Celite, rinsing with EtOAc. The organic layer was concentrated and the material was purified by column chromatography on the ISCO Companion (80 g, 0-100% EtOAc/Hex). tert-Butyl(1-(2-chloro-5-cyano-3-((7-cyano-4-(cyclopropyl(4-methoxybenzyl)amino)imidazo[2,1-f][1,2,4]triazin-2-yl)amino)phenyl)piperidin-4-yl)carbamate (I12C) (1.14 g) was obtained as a yellow foam.

MS (ESI) m/z 669.1 (M+H)

$^1$H NMR (400 MHz, CHLOROFORM-d) δ 7.94 (s, 1H), 7.19 (d, J=8.6 Hz, 2H), 6.97 (d, J=1.8 Hz, 1H), 6.85 (d, J=8.6 Hz, 2H), 4.51 (br. s., 1H), 3.79 (s, 3H), 3.71 (s, 2H), 3.66 (br. s., 1H), 3.29 (d, J=11.4 Hz, 2H), 2.80 (t, J=10.7 Hz, 2H), 2.10 (d, J=11.0 Hz, 2H), 1.71-1.59 (m, 3H), 1.48 (s, 9H), 1.14 (br. s., 2H), 0.95-0.86 (m, 2H)

Intermediate 12: To a round bottom flask charged with tert-butyl(1-(2-chloro-5-cyano-3-((7-cyano-4-(cyclopropyl(4-methoxybenzyl)amino)imidazo[2,1-f][1,2,4]triazin-2-yl)amino)phenyl)piperidin-4-yl)carbamate (I12C) (0.517 g, 0.773 mmol) in dichloromethane (5.15 ml) was added anisole (1.688 ml, 15.45 mmol), followed by the slow addition of trifluoroacetic acid (2.381 ml, 30.9 mmol). The reaction mixture was stirred at rt 2 d. The reaction mixture was warmed to 45° C. for 1 h. The reaction mixture was cooled to rt and concentrated in vacuo. After cooling to rt, 25 mL 2 N ammonia/methanol was added and a white solid crashed out of solution. The slurry was stirred for 30 min and the solid was isolated by vacuum filtration washing with cold methanol. 2-((3-(4-Aminopiperidin-1-yl)-2-chloro-5-cyanophenyl)amino)-4-(cyclopropylamino)imidazo[2,1-f][1,2,4]triazine-7-carbonitrile (0.1563 g) was isolated as a white solid. Material used as is in subsequent transformations.

MS (ESI) m/z 449.1

Intermediate 13

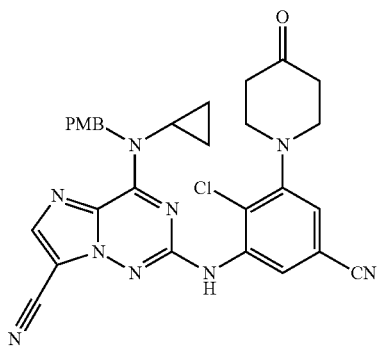

2-((2-Chloro-5-cyano-3-(4-oxopiperidin-1-yl)phenyl)amino)-4-(cyclopropyl(4-methoxybenzyl)amino)imidazo[2,1-f][1,2,4]triazine-7-carbonitrile (I13A): A round bottom flask was charged with tert-butyl (3-bromo-2-chloro-5-cyanophenyl)carbamate (Intermediate 1)(5.39 g, 16.25 mmol), 4-((tert-butyldimethylsilyl)oxy)piperidine (3.5 g, 16.25 mmol), cesium carbonate (10.5 g, 32.5 mmol), $Pd_2(dba)_3$ (1.488 g, 1.625 mmol) and BINAP (1.012 g, 1.625 mmol) in toluene (54.2 ml). The flask was evacuated and purged with nitrogen (4×) and heated at 100° C. 2 d. After cooling to rt, the reaction mixture was diluted with ethyl acetate and vacuum filtered through a pad of Celite. The filtrate was concentrated in vacuo. The crude residue was purified by column chromatography on the Isco system (330 g, 60-95% $CH_2Cl_2$/Hex) to provide tert-butyl(3-(4-((tert-butyldimethylsilyl)oxy)piperidin-1-yl)-2-chloro-5-cyanophenyl)carbamate (I13A) (3.27 g) as a yellow solid.

MS (ESI) m/z 466.1

$^1$H NMR (400 MHz, CHLOROFORM-d) δ 8.27 (d, J=1.5 Hz, 1H), 7.00 (d, J=1.8 Hz, 1H), 3.92 (dt, J=7.0, 3.7 Hz, 1H), 3.24-3.14 (m, 2H), 2.83 (ddd, J=11.3, 7.9, 3.1 Hz, 2H), 1.98-1.88 (m, 2H), 1.80-1.68 (m, 2H), 1.55 (s, 9H), 0.93 (s, 9H), 0.09 (s, 6H)

(I13B): To a round bottom flask charged with tert-butyl (3-(4-((tert-butyldimethylsilyl)oxy)piperidin-1-yl)-2-chloro-5-cyanophenyl)carbamate (I13A) (3.27 g, 7.02 mmol) in dichloromethane (35.1 ml) and cooled to 0° C. was added 2,6-lutidine (2.451 ml, 21.05 mmol). Trimethylsilyl trifluoromethanesulfonate (3.80 ml, 21.05 mmol) was added dropwise over 5 min. After 1 h, the reaction mixture was quenched by the addition of saturated aqueous sodium bicarbonate and dichloromethane. The mixture was transferred to a separatory funnel and the aqueous layer was extracted with dichloromethane (3×). The combined organics were washed with brine, dried over anhydrous sodium sulfate, filtered and concentrated in vacuo. The crude residue was purified by column chromatography on the Isco system (120 g, 0-50% EtOAc/$CH_2Cl_2$). 3-amino-5-(4-((tert-butyldimethylsilyl)oxy)piperidin-1-yl)-4-chlorobenzonitrile (I13B) (1.892 g) was isolated as a sticky yellow oil.

MS (ESI) m/z 366.1

$^1$H NMR (400 MHz, CHLOROFORM-d) δ 6.72 (s, 2H), 4.28 (s, 2H), 3.95-3.85 (m, 1H), 3.20 (ddd, J=11.2, 7.5, 3.3 Hz, 2H), 2.83 (ddd, J=11.3, 7.9, 3.2 Hz, 2H), 1.98-1.86 (m, 2H), 1.80-1.68 (m, 2H), 0.92 (s, 9H), 0.09 (s, 6H)

(I13C): 2-Chloro-4-(cyclopropyl(4-methoxybenzyl)amino)imidazo[2,1-f][1,2,4]triazine-7-carbonitrile (Intermediate 1) (0.646 g, 1.820 mmol), 3-amino-5-(4-((tert-butyldimethylsilyl)oxy)piperidin-1-yl)-4-chlorobenzonitrile (I13B) (0.666 g, 1.820 mmol), $Pd(OAc)_2$ (0.123 g, 0.546 mmol), dppf (0.101 g, 0.182 mmol), Xantphos (0.105 g, 0.182 mmol), and cesium carbonate (1.186 g, 3.64 mmol) were combined in a round bottom flask and dioxane (12.13 ml) was added. The flask was evacuated and backfilled with nitrogen (3×), then heated at 100° C. 10 h. The reaction mixture was diluted with ethyl acetate and vacuum filtered through a pad of Celite. The filtrate was concentrated in vacuo and the crude material purified by column chromatography on the Isco system (40 g, 0-100% EtOAc/Hex). 2-((3-(4-((tert-Butyldimethylsilyl)oxy)piperidin-1-yl)-2-chloro-5-cyanophenyl)amino)-4-(cyclopropyl(4-methoxybenzyl)amino)imidazo[2,1-f][1,2,4]triazine-7-carbonitrile (I13C) (0.9309 g) was isolated as a dark yellow solid.

MS (ESI) m/z 684.1

$^1$H NMR (400 MHz, CHLOROFORM-d) δ 7.93 (s, 1H), 7.19 (d, J=8.1 Hz, 2H), 6.99 (d, J=2.0 Hz, 1H), 6.85 (d, J=8.6 Hz, 2H), 3.93 (br. s., 1H), 3.79 (s, 3H), 3.71 (s, 2H), 3.21 (d, J=7.5 Hz, 2H), 2.88 (d, J=8.1 Hz, 2H), 2.00-1.89 (m, 2H), 1.77 (br. s., 2H), 1.14 (br. s., 2H), 0.98-0.86 (m, 11H), 0.10 (s, 6H)

(I13D): To a round bottom flask charged with 2-((3-(4-((tert-butyldimethylsilyl)oxy)piperidin-1-yl)-2-chloro-5-cyanophenyl)amino)-4-(cyclopropyl(4-methoxybenzyl)amino)imidazo[2,1-f][1,2,4]triazine-7-carbonitrile (I13C) (1.446 g, 2.113 mmol) in tetrahydrofuran (21.13 ml) and cooled to 0° C. was added TBAF (4.23 ml, 4.23 mmol). The reaction mixture was stirred at rt 2 d. The reaction mixture was poured into a separatory funnel containing saturated aqueous sodium bicarbonate and ethyl acetate. The aqueous layer was extracted with ethyl acetate (3×). The combined organics were washed with brine, dried over anhydrous sodium sulfate, filtered and concentrated in vacuo. The crude residue was taken up in dichloromethane. A white precipitate was isolated by filtration. The filtrate was purified by column chromatography on the Isco system (40 g, 0-50% EtOAc/CH2Cl2). The precipitate was combined with the column isolate to provide 2-((2-chloro-5-cyano-3-(4-hydroxypiperidin-1-yl)phenyl)amino)-4-(cyclopropyl(4-methoxybenzyl)amino)imidazo[2,1-f][1,2,4]triazine-7-carbonitrile (I13D) (0.816 g) as a white solid.

MS (ESI) m/z 570.0

Intermediate 13: To a round bottom flask charged with 2-((2-chloro-5-cyano-3-(4-hydroxypiperidin-1-yl)phenyl)amino)-4-(cyclopropyl(4-methoxybenzyl)amino)imidazo[2,1-f][1,2,4]triazine-7-carbonitrile (0.27 g, 0.474 mmol) in wet dichloromethane (3.16 ml) was added Dess-Martin periodinane (0.402 g, 0.947 mmol). The reaction mixture was stirred at rt 2.5 h. The reaction mixture was diluted with dichloromethane and quenched by the addition of sodium thiosulfate doped saturated aqueous sodium bicarbonate (25 g/100 mL). The mixture was stirred until 2 clear layers were visible. The mixture was transferred to a separatory funnel and the aqueous layer was extracted with dichloromethane (3×). The combined organics were washed with brine, dried over anhydrous sodium sulfate, filtered and concentrated in vacuo. 2-((2-Chloro-5-cyano-3-(4-oxopiperidin-1-yl)phenyl)amino)-4-(cyclopropyl(4-methoxybenzyl)amino)imidazo[2,1-f][1,2,4]triazine-7-carbonitrile (0.2465 g) was isolated as a yellow solid.

MS (ESI) m/z 568.1

Intermediate 14

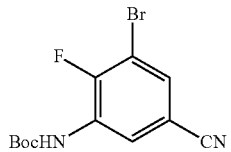 [SMILES: CC(C)(C)OC(=O)Nc1cc(C#N)cc(Br)c1F]

tert-butyl(3-bromo-5-cyano-2-fluorophenyl)carbamate (I14A): 4-fluorobenzonitrile (4.35 g, 35.9 mmol) was dissolved in sulfuric acid (40 ml, 750 mmol). The solution was cooled to 0° C. NBS (13.56 g, 75 mmol) was added. The reaction mixture was allowed to slowly warm to room temperature, then stirred for 3 days at room temperature. The reaction mixture was poured onto ice. The slurry was diluted with ice cold water to a total volume of ~500 ml. The colorless precipitate was collected by filtration. Solids were washed with water, then aq. NaHCO3 solution until the run-off was pH neutral, then washed with water again, then dried in an air stream over the weekend (2.5 days). 3,5-dibromo-4-fluorobenzamide (9.85 g) was obtained. Estimated purity ~60%. The crude product contains some tribromo-byproduct and a regioisomeric dibromo-compound and was used in the next reaction without further purification.

MS (ESI) m/z 294/296/298 (with 2 Br isotope pattern),
$^1$H NMR (400 MHz, DMSO-d$_6$) δ 8.21 (d, $J_{HF}$=6 Hz, 2H), 8.18 (bs, 1H), 7.70 (bs, 1H).
$^{19}$F NMR (376 MHz, DMSO-d$_6$) δ −97.6 (t, $J_{HF}$=6 Hz).

(I14B): Phosphoryl trichloride (8.0 ml, 86 mmol) was added to a suspension of 3,5-dibromo-4-fluorobenzamide (11.27 g, crude, ~22.7 mmol) in acetonitrile (400 ml) at room temperature. The reaction mixture was heated to reflux for 30 minutes. Additional Phosphoryl trichloride (8.0 ml, 86 mmol) was added and the mixture heated to reflux for an additional hour, then stirred at room temperature overnight. A precipitate had formed and was removed by filtration. (The product is well soluble in acetonitrile) The reaction mixture was evaporated to dryness, then partitioned between EtOAc and aq. NaHCO3 solution. The organic layer was washed one more time with aq. NaHCO3 solution, once with brine, then dried over MgSO4, filtered and evaporated to dryness. Purification by column chromatography on silica (gradient 100% hexanes to 25% DCM in hexanes). 3,5-dibromo-4-fluorobenzonitrile (7.5 g) was obtained. The material is (by 1H NMR and 19F NMR) a 76:17:7 mixture of 3,5-dibromo-4-fluorobenzonitrile (desired product), 2,3,5-tribromo-4-fluorobenzonitrile (over-bromination) and 2,5-dibromo-4-fluorobenzonitrile (wrong regio-isomere). The material was used without further purification in the next reaction.

$^1$H NMR (500 MHz, DMSO-d$_6$) δ 8.41 (d, $J_{HF}$=6 Hz, 2H).
$^{19}$F NMR (400 MHz, DMSO-d$_6$) δ −91.7 (t, $J_{HF}$=6 Hz).

Intermediate 14: A 500 ml round bottom flask vial was loaded with 3,5-dibromo-4-fluorobenzonitrile (5.7 g, 15.53 mmol) (76% pure, rest di-bromo-regioisomer and tribromo-analog), tert-butyl carbamate (2.63 g, 22.45 mmol) palladium(ii) acetate (177 mg, 0.788 mmol), XANTPHOS (1.14 g, 1.970 mmol) and cesium carbonate (19.3 g, 59.2 mmol). The flask was evacuated and back-filled with nitrogen 2 times. 1,4-Dioxane (200 ml) was added and the flask evacuated and back-filled with nitrogen 2 times. The reaction mixture was heated (with vigorous stirring) to 90° C. for 15 hours in an oil bath. The reaction mixture was cooled to room temperature, filtered through a layer of Celite, evaporated and purified by column chromatography on silica. (750 g cartridge, gradient from 100% hexanes to 20% EtOAc in hexanes, product elutes at ~17 to 21 column volumes). tert-butyl(3-bromo-5-cyano-2-fluorophenyl)carbamate (2.93 g) was isolated.

MS (ESI) m/Z 315/317
$^1$H NMR (500 MHz, DMSO-d$_6$) δ 9.65 (bs, 1H), 8.16 (dd, J=6.6, 1.6 Hz, 1H), 8.03 (dd, J=6.0, 2.0 Hz, 1H), 1.49 (s, 9H).

Example 1

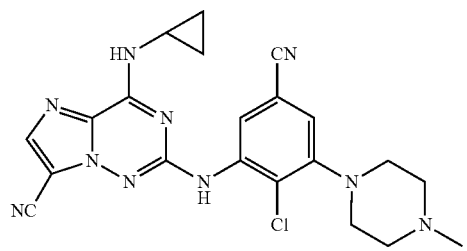 [SMILES: CN1CCN(c2cc(C#N)cc(Nc3nc(NC4CC4)c4ncc(C#N)n4n3)c2Cl)CC1]

2-((2-chloro-5-cyano-3-(4-methyl-1-piperazinyl)phenyl)amino)-4-(cyclopropylamino)imidazo[2,1-f][1,2,4]triazine-7-carbonitrile (1A): A mixture of tert-butyl 3-bromo-2-chloro-5-cyanophenylcarbamate (Intermediate (300 mg, 0.905 mmol), 1-methylpiperazine (0.110 mL, 0.995 mmol), PdOAc2 (20.31 mg, 0.090 mmol), racemic BINAP (56.3 mg, 0.090 mmol) and Cs2CO3 (590 mg, 1.809 mmol) in Toluene (Volume: 5 mL) was purged with bubbling N2 for 2 min. The mixture was then heated at 110° C. for overnight. Reaction mixture was cooled to room temperature, diluted with EtOAc, washed with water and brine, dried over MgSO4 and concentrated. The crude was purified by ISCO (24 g, MeOH/DCM=0-4.5%) to give 136 mg of -chloro-5-cyano-3-(4-methylpiperazin-1-yl)phenylcarbamate as yellow oil.

MS (ESI) m/z 351.

1H NMR (400 MHz, CHLOROFORM-d) δ ppm 8.32 (1H, d, J=1.76 Hz), 7.20 (1H, s), 6.98-7.08 (1H, m), 3.07 (4H, t, J=4.40 Hz), 2.63 (4H, br. s.), 2.39 (3H, s), 1.57 (9H, s)

(1B): To a solution of tert-butyl 2-chloro-5-cyano-3-(4-methylpiperazin-1-yl)phenylcarbamate (135 mg, 0.385 mmol) in DCM (1.4 mL) was added TFA (0.6 mL, 3.89 mmol). The mixture was stirred at reaction mixture. The solvent was evaporated under vacuum, the residue was dissolved in EtOAc, washed with small amount of sat NaHCO3, and brine, dried over MgSO4, filtered, concentrated, and the residue was purified by ISCO (12 g, EtOAc/DCM=0-60%) to give 82 mg of 3-amino-4-chloro-5-(4-methylpiperazin-1-yl)benzonitrile MS (ESI) m/z 251.

1H NMR (400 MHz, DMSO-d6) δ ppm 6.85 (1H, d, J=1.98 Hz), 6.70 (1H, d, J=1.98 Hz), 5.80 (2H, s), 3.31 (3H, s), 2.90-2.99 (4H, m), 2.23-2.30 (4H, m) (1C): A mixture of 2,4-bis(methylthio)imidazo[2,1-f][1,2,4]triazine (5.27 g, 24.82 mmol) and 1-bromopyrrolidine-2,5-dione (6.19 g, 34.8 mmol) in DMF (15 mL) was stirred at RT for 2 hours. The reaction was diluted with water, and the product extracted with dichloromethane (3×50 mL). The organic layer was washed with brine, dried and concentrated. The crude product mixture was purified via ISCO (0-50% of ethyl acetate/dichloromethane in 10 minutes, 80 g silica column) to give the pure product 7-bromo-2,4-bis(methylthio)imidazo[2,1-f][1,2,4]triazine (4.61 g, 15.83 mmol, 63.8% yield).

MS (ESI) m/z 290.

1H NMR (400 MHz, CHLOROFORM-d) δ 7.60 (s, 1H), 2.69 (s, 3H), 2.64 (s, 3H). (1D): To a 25 mL flask was added a mixture of 7-bromo-2,4-bis(methylthio)imidazo[2,1-f][1,2,4]triazine (2.0 g, 6.87 mmol), N-(4-methoxybenzyl)cyclopropanamine (1.34 g, 7.56 mmol) in anhydrous THF (20 mL). The reaction solution was cooled to −78° C. and treated dropwise with 1.0 M lithium bis(trimethylsilyl)amide in THF solution (20.61 mL, 20.61 mmol, 3 eq, 1M solution in THF). The reaction was stirred at −78° C. for 1 hour, then allowed to come to room temperature and stirred for 3 hours. The reaction was quenched with saturated ammonium chloride. The product was extracted with ethyl acetate, the organic layer was dried with sodium sulfate and concentrated in vacuo. The crude product mixture was purified via ISCO (0-100% of ethyl acetate/heptane in 10 minutes, 24 g silica column) to give the pure product 7-bromo-N-cyclopropyl-N-(4-methoxybenzyl)-2-(methylthio)imidazo[2,1-f][1,2,4]triazin-4-amine (2.1 g)

MS (ESI) m/z 420

(1E): A solution of 7-bromo-N-cyclopropyl-N-(4-methoxybenzyl)-2-(methylthio)imidazo[2,1-f][1,2,4]triazin-4-amine (2.3 g, 5.47 mmol) in dichloromethane (10 mL) was treated with m-CPBA (3.07 g, 13.68 mmol) at room temperature. The reaction mixture was stirred for 2 hours. The reaction solution was washed with 5% Na2S2O3 (2×10 mL), 1 N Na2CO3 (2×10 mL) and brine. The organic layer was dried (Na2SO4), filtered and concentrated to dryness to afford the crude product mixture. The crude product mixture was purified via ISCO (0-50% of ethyl acetate/dichloromethane in 10 minutes, 80 g silica column) to give the pure product 7-bromo-N-cyclopropyl-N-(4-methoxybenzyl)-2-(methylthio)imidazo[2,1-f][1,2,4]triazin-4-amine (2.1 g, 5.00 mmol, 72.7% yield).

MS (ESI) m/z 451.84

(1F): In a round-bottom flask, a mixture of 7-bromo-N-cyclopropyl-N-(4-methoxybenzyl)-2-(methylsulfonyl)imidazo[2,1-f][1,2,4]triazin-4-amine (0.115 g, 0.254 mmol), zinc cyanide (0.021 g, 0.178 mmol), and zinc powder (4.99 mg, 0.076 mmol) in DMA (30 mL) was degassed by evacuating with vacuum and back filling with nitrogen. The mixture was treated with bis(tri-t-butylphosphine)palladium (O) (0.026 g, 0.051 mmol), degassed again as described above, and the reaction was heated at 100° C. for 4 hours. The reaction mixture was filtered and the filtrate diluted with ethyl acetate, washed with water, brine, dried with sodium sulfate and concentrated in vacuo. The crude product mixture was purified via ISCO (0-15% of methanol/dichloromethane in 20 minutes, 40 g silica column) to give the the pure product 4-(cyclopropyl(4-methoxybenzyl)amino)-2-(methylsulfonyl)imidazo[2,1-f][1,2,4]triazine-7-carbonitrile (75 mg).

MS (ESI) m/z 398.97

(1G): To a vial was charged 3-amino-4-chloro-5-(4-methylpiperazin-1-yl)benzonitrile (56.6 mg, 0.226 mmol) and tetrahydrofuran (3 mL). To the reaction solution was added sodium hydride (9.03 mg, 0.226 mmol). The solution was stirred at room temperature for 1 hour, then a solution of 4-(cyclopropyl(4-methoxybenzyl)amino)-2-(methylsulfonyl)imidazo[1,2-f][1,2,4]triazine-7-carbonitrile (60 mg, 0.151 mmol) in tetrahydrofuran (Volume: 3 mL) was added. The solution was then stirred at RT for 3 hours and then heated to 80° C. for 3 hours. The reaction solution was diluted with ethyl acetate, and the organic layer washed with NaHCO3 solution, and brine, dried with sodium sulfate and concentrated in vacuo to give the crude product mixture. The crude product mixture was purified via ISCO (0-15% of methanol/dichloromethane in 15 minutes, 24 g silica column) to give 2-((2-chloro-5-cyano-3-(4-methylpiperazin-1-yl)phenyl)amino)-4-(cyclopropyl(4-methoxybenzyl)amino) imidazo[2,1-f][1,2,4]triazine-7-carbonitrile MS (ESI) m/z 568.96

Example 1

In a vial was added 2-((2-chloro-5-cyano-3-(4-methylpiperazin-1-yl)phenyl)amino)-4-(cyclopropyl(4-methoxybenzyl)amino)imidazo[2,1-f][1,2,4]triazine-7-carbonitrile, dichloromethane (2 mL), anisole (0.1 mL) and TFA (0.2 mL). The reaction solution was stirred at 80° C. for 1 hour. The solution was concentrated and purified by PREP HPLC to give 2-(2-chloro-5-cyano-3-(4-methylpiperazin-1-yl)phenylamino)-4-(cyclopropylamino)imidazo[1,2-f][1,2,4]triazine-7-carbonitrile, 2 TFA (11.1 mg)

MS (ESI) m/z 448.96

1H NMR (400 MHz, METHANOL-d4) δ 8.70 (d, J=1.8 Hz, 1H), 8.00 (s, 1H), 7.28 (d, J=1.5 Hz, 1H), 3.80-3.53 (m, 4H), 3.41 (br. s., 2H), 3.19 (br. s., 2H), 3.10-2.93 (m, 4H), 1.06-0.91 (m, 2H), 0.82 (dd, J=3.6, 2.1 Hz, 2H).

The compounds listed below were prepared by the similar synthetic procedure used for Examples 1

TABLE 1

| Example No. | Structure | Name | [M + H]+ | HPLC Retention Time (min.) |
|---|---|---|---|---|
| 2 | 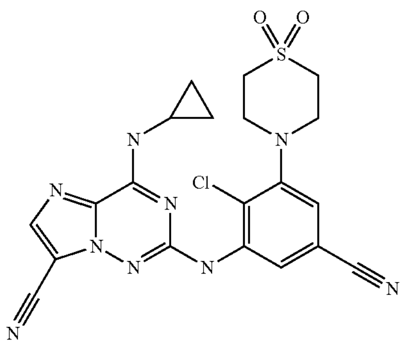 [SMILES: N#Cc1cc(Nc2nc(NC3CC3)c3ncc(C#N)n3n2)c(Cl)c(N2CCS(=O)(=O)CC2)c1] | 2-((2-chloro-5-cyano-3-(4-methyl-1-piperazinyl)phenyl)amino)-4-(cyclopropylamino)imidazo[2,1-f][1,2,4]triazine-7-carbonitrile | 484.94 | 1.57 |
| 3 | 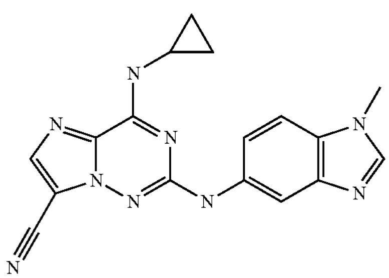 [SMILES: Cn1cnc2cc(Nc3nc(NC4CC4)c4ncc(C#N)n4n3)ccc21] | 4-(cyclopropylamino)-2-((1-methyl-1H-benzimidazol-5-yl)amino)imidazo[2,1-f][1,2,4]triazine-7-carbonitrile | 345.37 | 1.78 |
| 4 | 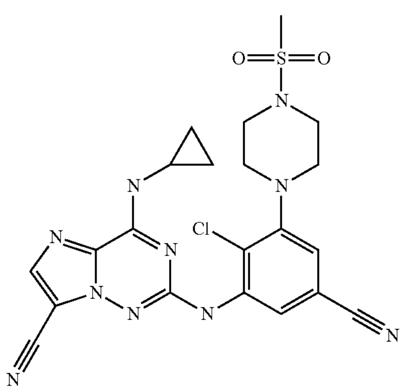 [SMILES: CS(=O)(=O)N1CCN(c2cc(C#N)cc(Nc3nc(NC4CC4)c4ncc(C#N)n4n3)c2Cl)CC1] | 2-((2-chloro-5-cyano-3-(4-(methylsulfonyl)-1-piperazinyl)phenyl)amino)-4-(cyclopropylamino)imidazo[2,1-f][1,2,4]triazine-7-carbonitrile | 512.98 | 1.80 |
| 5 | 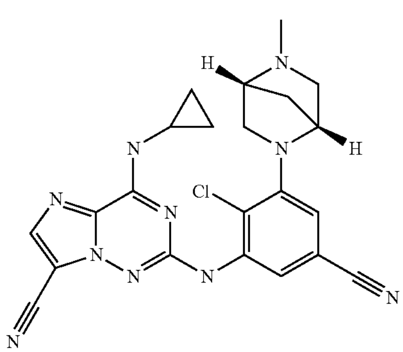 [SMILES: CN1C[C@H]2C[C@@H]1CN2c1cc(C#N)cc(Nc2nc(NC3CC3)c3ncc(C#N)n3n2)c1Cl] | 2-((2-chloro-5-cyano-3-((1R,4R)-5-methyl-2,5-diazabicyclo[2.2.1]hept-2-yl)phenyl)amino)-4-(cyclopropylamino)imidazo[2,1-f][1,2,4]triazine-7-carbonitrile | 460.93 | 1.7 |

TABLE 1-continued

| Example No. | Structure | Name | [M + H]⁺ | HPLC Retention Time (min.) |
|---|---|---|---|---|
| 6 | 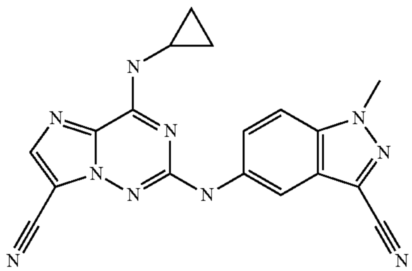 [SMILES: Cn1nc(C#N)c2cc(Nc3nc(NC4CC4)c4ncc(C#N)n4n3)ccc21] | 2-((3-cyano-1-methyl-1H-indazol-5-yl)amino)-4-(cyclopropylamino)imidazo[2,1-f][1,2,4]triazine-7-carbonitrile | 370.38 | 1.72 |
| 7 | 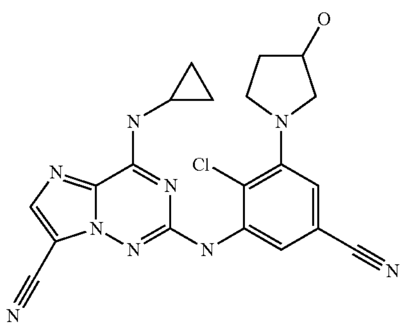 [SMILES: N#Cc1cc(Nc2nc(NC3CC3)c3ncc(C#N)n3n2)c(Cl)c(N2CCC(O)C2)c1] | (+/−) 2-((2-chloro-5-cyano-3-(3-hydroxy-1-pyrrolidinyl)phenyl)amino)-4-(cyclopropylamino)imidazo[2,1-f][1,2,4]triazine-7-carbonitrile | 436.88 | 1.79 |
| 8 | 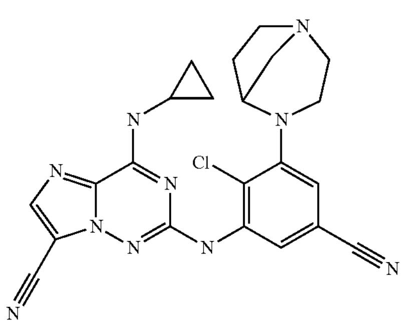 [SMILES: N#Cc1cc(Nc2nc(NC3CC3)c3ncc(C#N)n3n2)c(Cl)c(N2CCN3CCC2C3)c1] | 2(2-chloro-5-cyano-3(1,4-diazabicyclo[3.2.1]oct-4-yl)phenyl)amino)-4-(cyclopropylamino)imidazo[2,1-f][1,2,4]triazine-7-carbonitrile | 461.93 | 1.63 |
| 9 | 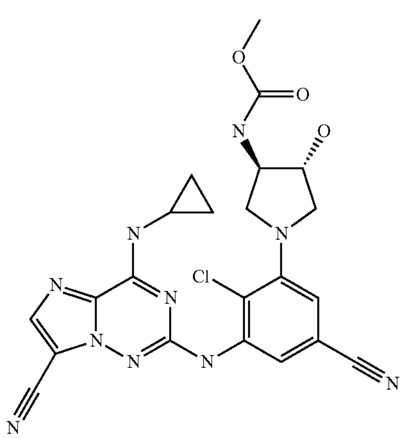 [SMILES: COC(=O)N[C@@H]1CN(c2cc(C#N)cc(Nc3nc(NC4CC4)c4ncc(C#N)n4n3)c2Cl)C[C@H]1O] | (+/−) methyl ((3R,4R)-1-(2-chloro-5-cyano-3-((7-cyano-4-(cyclopropylamino)imidazo[2,1-f][1,2,4]triazin-2-yl)amino)phenyl)-4-hydroxy-3-pyrrolidinyl)carbamate | 509.93 | 1.81 |

TABLE 1-continued

| Example No. | Structure | Name | [M + H]+ | HPLC Retention Time (min.) |
|---|---|---|---|---|
| 10 | 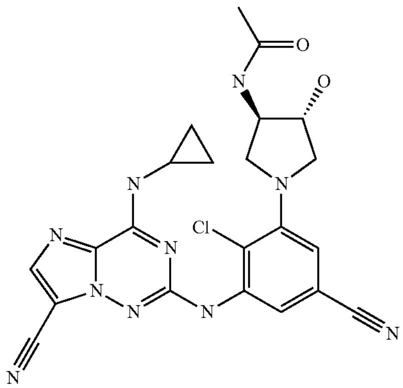 [SMILES: CC(=O)N[C@@H]1CN(c2cc(C#N)cc(Nc3nc(NC4CC4)c4ncc(C#N)n4n3)c2Cl)C[C@H]1O] | (+/−) N-((3R,4R)-1-(2-chloro-5-cyano-3-((7-cyano-4-(cyclopropylamino)imidazo[2,1-f][1,2,4]triazin-2-yl)amino)phenyl)-4-hydroxy-3-pyrrolidinyl)acetamide | 493.93 | 1.83 |
| 11 | 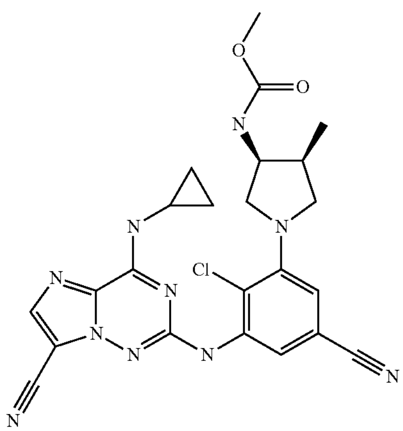 [SMILES: COC(=O)N[C@@H]1CN(c2cc(C#N)cc(Nc3nc(NC4CC4)c4ncc(C#N)n4n3)c2Cl)C[C@@H]1C] | (+/−) methyl ((3S,4S)-1-(2-chloro-5-cyano-3-((7-cyano-4-(cyclopropylamino)imidazo[2,1-f][1,2,4]triazin-2-yl)amino)phenyl)-4-methyl-3-pyrrolidinyl)carbamate | 506.96 | 2.93 |
| 12 | 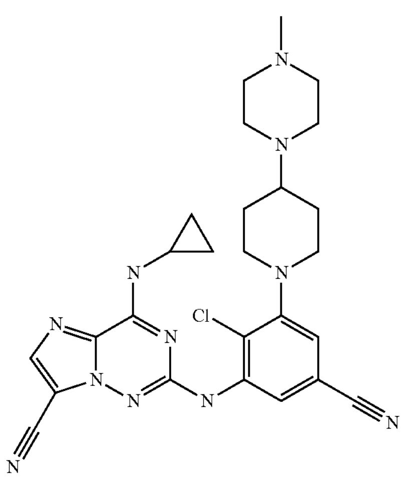 [SMILES: CN1CCN(C2CCN(c3cc(C#N)cc(Nc4nc(NC5CC5)c5ncc(C#N)n5n4)c3Cl)CC2)CC1] | 2-((2-chloro-5-cyano-3-(4-(4-methyl-1-piperazinyl)-1-piperidinyl)phenyl)amino)-4-(cyclopropylamino)imidazo[2,1-f][1,2,4]triazine-7-carbonitrile | 533.05 | 2.83 |

TABLE 1-continued

| Example No. | Structure | Name | [M + H]+ | HPLC Retention Time (min.) |
|---|---|---|---|---|
| 13 | Chiral | (+/−) methyl ((3aR,5r,6aS)-2-(2-chloro-5-cyano-3-((7-cyano-4-(cyclopropylamino)imidazo[2,1-f][1,2,4]triazin-2-yl)amino)phenyl)octahydrocyclopenta[c]pyrrol-5-yl)carbamate | 532.99 | 2.69 |
| 14 | Chiral | methyl ((3S,4R)-1-(2-chloro-5-cyano-3-((7-cyano-4-(cyclopropylamino)imidazo[2,1-f][1,2,4]triazin-2-yl)amino)phenyl)-4-methoxy-3-pyrrolidinyl)carbamate | 522.96 | 2.7 |
| 15 | 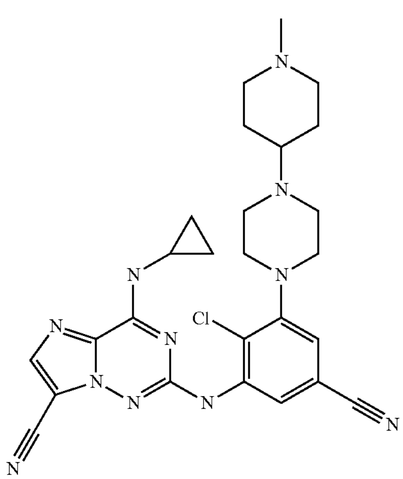 [SMILES: CN1CCC(N2CCN(c3cc(C#N)cc(Nc4nc(NC5CC5)c5ncc(C#N)n5n4)c3Cl)CC2)CC1] | 2-((2-chloro-5-cyano-3-(4-(1-methyl-4-piperidinyl)-1-piperazinyl)phenyl)amino)-4-(cyclopropylamino)imidazo[2,1-f][1,2,4]triazine-7-carbonitrile | 532.05 | 2.86 |

TABLE 1-continued

| Example No. | Structure | Name | [M + H]+ | HPLC Retention Time (min.) |
|---|---|---|---|---|
| 16 | 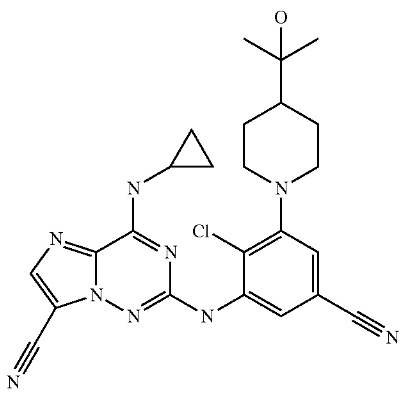 [SMILES: CC(C)(O)C1CCN(c2cc(C#N)cc(Nc3nc(NC4CC4)c4ncc(C#N)n4n3)c2Cl)CC1] | 2-((2-chloro-5-cyano-3-(4-(1-hydroxy-1-methylethyl)-1-piperidinyl)phenyl)amino)-4-(cyclopropylamino)imidazo[2,1-f][1,2,4]triazine-7-carbonitrile | 491.98 | 2.76 |
| 17 | 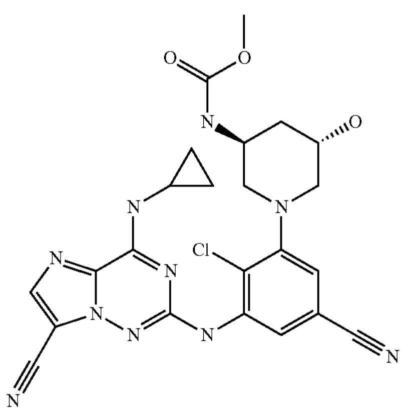 [SMILES: COC(=O)N[C@H]1C[C@H](O)CN(c2cc(C#N)cc(Nc3nc(NC4CC4)c4ncc(C#N)n4n3)c2Cl)C1] | (+/−) methyl ((3S,5S)-1-(2-chloro-5-cyano-3-((7-cyano-4-(cyclopropylamino)imidazo[2,1-f][1,2,4]triazin-2-yl)amino)phenyl)-5-hydroxy-3-piperidinyl)carbamate | 522.96 | 2.76 |
| 18 | 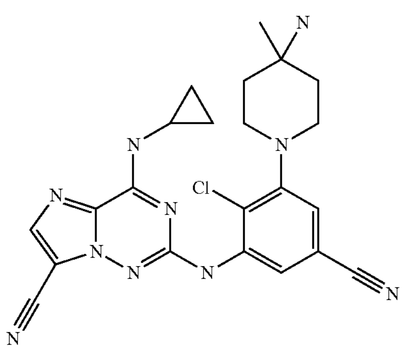 [SMILES: CC1(N)CCN(c2cc(C#N)cc(Nc3nc(NC4CC4)c4ncc(C#N)n4n3)c2Cl)CC1] | 2-((3-(4-amino-4-methyl-1-piperidinyl)-2-chloro-5-cyanophenyl)amino)-4-(cyclopropylamino)imidazo[2,1-f][1,2,4]triazine-7-carbonitrile | 462.95 | 2.97 |
| 19 | 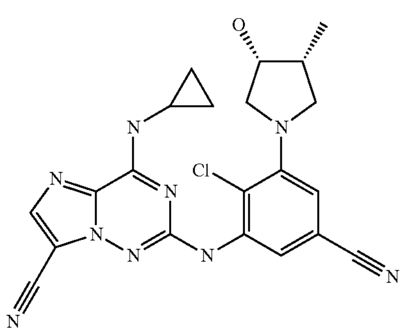 [SMILES: C[C@@H]1CN(c2cc(C#N)cc(Nc3nc(NC4CC4)c4ncc(C#N)n4n3)c2Cl)C[C@@H]1O] | (+/−) 2-((2-chloro-5-cyano-3-((3R,4R)-3-hydroxy-4-methyl-1-pyrrolidinyl)phenyl)amino)-4-(cyclopropylamino)imidazo[2,1-f][1,2,4]triazine-7-carbonitrile | 449.90 | 2.93 |

TABLE 1-continued

| Example No. | Name | [M + H]+ | HPLC Retention Time (min.) |
|---|---|---|---|
| 20 | (+/−) 2-((2-chloro-5-cyano-3-((3S,4R)-3-hydroxy-4-methyl-1-pyrrolidinyl)phenyl)amino)-4-(cyclopropylamino)imidazo[2,1-f][1,2,4]triazine-7-carbonitrile | 449.90 | 2.86 |
| 21 | (+/−) methyl ((3S,4R)-1-(2-chloro-5-cyano-3-((7-cyano-4-(cyclopropylamino)imidazo[2,1-f][1,2,4]triazin-2-yl)amino)phenyl)-4-methyl-3-pyrrolidinyl)carbamate | 506.96 | 2.5 |
| 22 | 2-((2-chloro-5-cyano-3-(7-methyl-2,7-diazaspiro[3.5]non-2-yl)phenyl)amino)-4-(cyclopropylamino)imidazo[2,1-f][1,2,4]triazine-7-carbonitrile | 488.99 | 3.62 |
| 23 | 2-((2-chloro-5-cyano-3-(6-methyl-2,6-diazaspiro[3.3]hept-2-yl)phenyl)amino)-4-(cyclopropylamino)imidazo[2,1-f][1,2,4]triazine-7-carbonitrile | 460.93 | 3.85 |

TABLE 1-continued

| Example No. | Structure | Name | [M + H]+ | HPLC Retention Time (min.) |
|---|---|---|---|---|
| 24 | 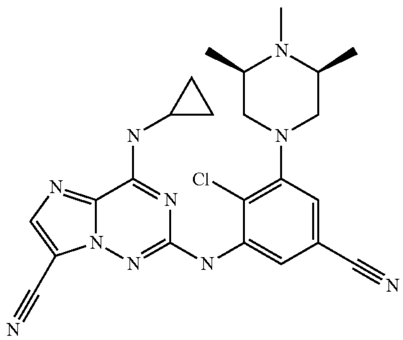 [SMILES: C[C@@H]1CN(c2cc(C#N)cc(Nc3nc(NC4CC4)c4ncc(C#N)n4n3)c2Cl)C[C@H](C)N1C] | (+/−) 2-((2-chloro-5-cyano-3-((3R,5S)-3,4,5-trimethyl-1-piperazinyl)phenyl)amino)-4-(cyclopropylamino)imidazo[2,1-f][1,2,4]triazine-7-carbonitrile | 476.97 | 3.31 |
| 25 | 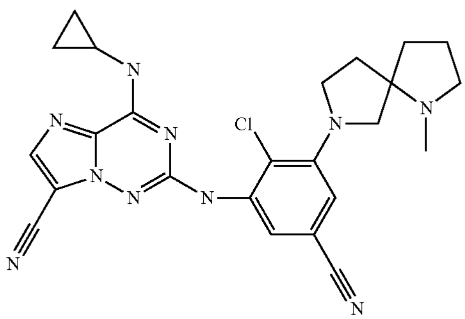 | (+/−) 2-((2-chloro-5-cyano-3-(1-methyl-1,7-diazaspiro[4.4]non-7-yl)phenyl)amino)-4-(cyclopropylamino)imidazo[2,1-f][1,2,4]triazine-7-carbonitrile | 488.99 | 3.11 |
| 26 | 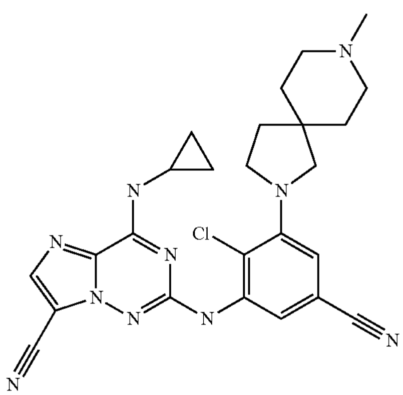 [SMILES: CN1CCC2(CC1)CCN(c1cc(C#N)cc(Nc3nc(NC4CC4)c4ncc(C#N)n4n3)c1Cl)C2] | (+/−) 2-((2-chloro-5-cyano-3-(8-methyl-2,8-diazaspiro[4.5]dec-2-yl)phenyl)amino)-4-(cyclopropylamino)imidazo[2,1-f][1,2,4]triazine-7-carbonitrile | 503.01 | 3.18 |
| 27 | 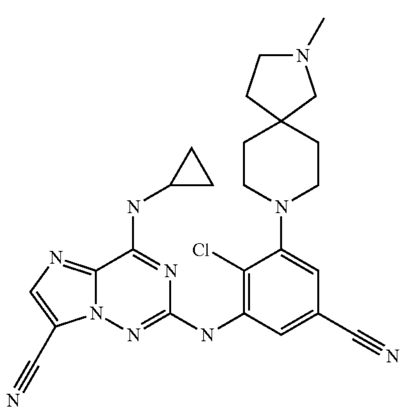 [SMILES: CN1CCC2(CCN(c3cc(C#N)cc(Nc4nc(NC5CC5)c5ncc(C#N)n5n4)c3Cl)CC2)C1] | (+/−) 2-((2-chloro-5-cyano-3-(2-methyl-2,8-diazaspiro[4.5]dec-8-yl)phenyl)amino)-4-(cyclopropylamino)imidazo[2,1-f][1,2,4]triazine-7-carbonitrile | 503.01 | 4.18 |

TABLE 1-continued

| Example No. | Structure | Name | [M + H]+ | HPLC Retention Time (min.) |
|---|---|---|---|---|
| 28 | 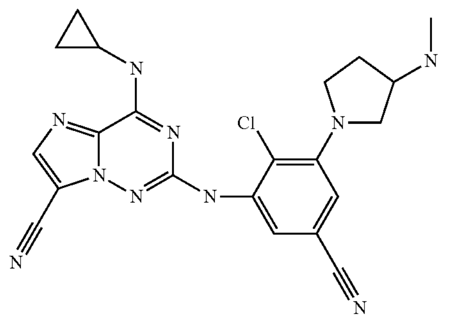 [SMILES: CNC1CCN(c2cc(C#N)cc(Nc3nc(NC4CC4)c4ncc(C#N)n4n3)c2Cl)C1] | (+/−) 2-((2-chloro-5-cyano-3-(3-(methylamino)-1-pyrrolidinyl)phenyl)amino)-4-(cyclopropylamino)imidazo[2,1-f][1,2,4]triazine-7-carbonitrile | 448.92 | 3.81 |
| 29 | 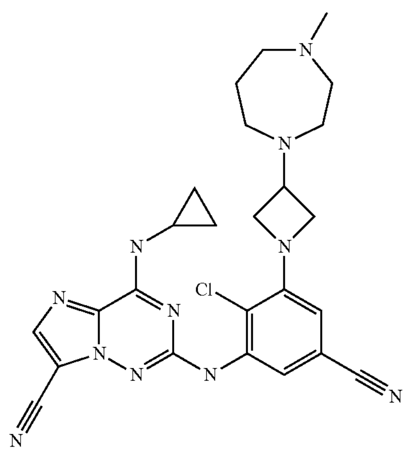 [SMILES: CN1CCCN(C2CN(c3cc(C#N)cc(Nc4nc(NC5CC5)c5ncc(C#N)n5n4)c3Cl)C2)CC1] | 2-((2-chloro-5-cyano-3-(3-(4-methyl-1,4-diazepan-1-yl)-1-azetidinyl)phenyl)amino)-4-(cyclopropylamino)imidazo[2,1-f][1,2,4]triazine-7-carbonitrile | 518.03 | 4.41 |
| 30 | Chiral | 2-((3-((3S,4R)-3-amino-4-methoxy-1-pyrrolidinyl)-2-chloro-5-cyanophenyl)amino)-4-(cyclopropylamino)imidazo[2,1-f][1,2,4]triazine-7-carbonitrile | 464.92 | 3.71 |
| 31 | 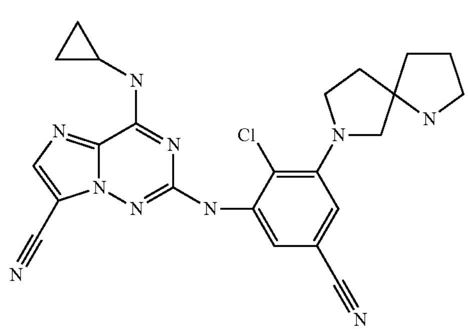 [SMILES: N#Cc1cc(Nc2nc(NC3CC3)c3ncc(C#N)n3n2)c(Cl)c(N2CCC3(CCCN3)C2)c1] | (+/−)2-((2-chloro-5-cyano-3-(1,7-diazaspiro[4.4]non-7-yl)phenyl)amino)-4-(cyclopropylamino)imidazo[2,1-f][1,2,4]triazine-7-carbonitrile | 474.96 | 3.99 |

TABLE 1-continued

| Example No. | Structure | Name | [M + H]+ | HPLC Retention Time (min.) |
|---|---|---|---|---|
| 32 | Chiral | (+/−) 1-((3S,4R)-1-(2-chloro-5-cyano-3-((7-cyano-4-(cyclopropylamino)imidazo[2,1-f][1,2,4]triazin-2-yl)amino)phenyl)-4-methoxy-3-pyrrolidinyl)-3-ethylurea | 536.00 | 3.34 |
| 33 | 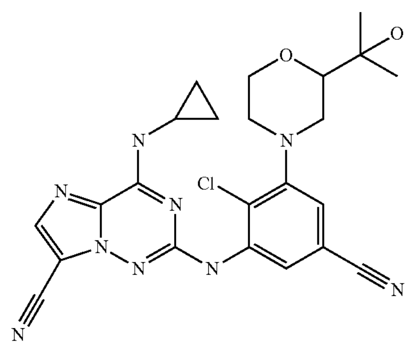 [SMILES: CC(C)(O)C1CN(c2cc(C#N)cc(Nc3nc(NC4CC4)c4ncc(C#N)n4n3)c2Cl)CCO1] | (+/−) 2-((2-chloro-5-cyano-3-(2-(1-hydroxy-1-methylethyl)-4-morpholinyl)phenyl)amino)-4-(cyclopropylamino)imidazo[2,1-f][1,2,4]triazine-7-carbonitrile | 493.96 | 3.28 |
| 34 | 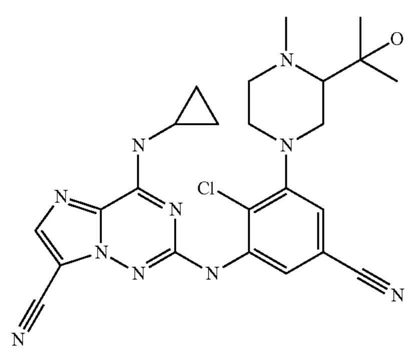 [SMILES: CN1CCN(c2cc(C#N)cc(Nc3nc(NC4CC4)c4ncc(C#N)n4n3)c2Cl)CC1C(C)(C)O] | (+/−) 2-((2-chloro-5-cyano-3-(3-(1-hydroxy-1-methylethyl)-4-methyl-1-piperazinyl)phenyl)amino)-4-(cyclopropylamino)imidazo[2,1-f][1,2,4]triazine-7-carbonitrile | 507.00 | 3.97 |
| 35 | 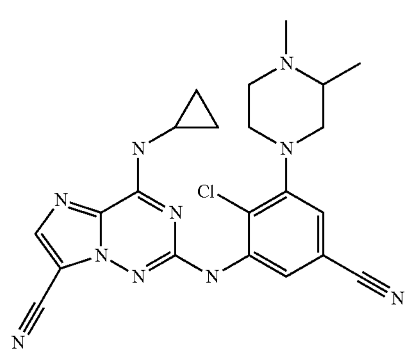 [SMILES: CC1CN(c2cc(C#N)cc(Nc3nc(NC4CC4)c4ncc(C#N)n4n3)c2Cl)CCN1C] | (+/−) 2-((2-chloro-5-cyano-3-(3,4-dimethyl-1-piperazinyl)phenyl)amino)-4-(cyclopropylamino)imidazo[2,1-f][1,2,4]triazine-7-carbonitrile | 462.95 | 2.98 |

TABLE 1-continued

| Example No. | Structure | Name | [M + H]+ | HPLC Retention Time (min.) |
|---|---|---|---|---|
| 36 | 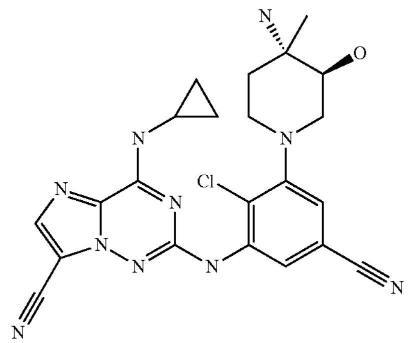 [SMILES: C[C@]1(N)CCN(c2cc(C#N)cc(Nc3nc(NC4CC4)c4ncc(C#N)n4n3)c2Cl)C[C@@H]1O] | 2-((3-((3S,4S)-4-amino-3-hydroxy-4-methyl-1-piperidinyl)-2-chloro-5-cyanophenyl)amino)-4-(cyclopropylamino)imidazo[2,1-f][1,2,4]triazine-7-carbonitrile | 478.95 | 3.91 |
| 37 | Chiral | 2-((2-chloro-5-cyano-3-((2S)-2-(1-hydroxy-1-methylethyl)-4-morpholinyl)phenyl)amino)-4-(cyclopropylamino)imidazo[2,1-f][1,2,4]triazine-7-carbonitrile | 493.96 | 2.43 |
| 38 | Chiral | 2-((2-chloro-5-cyano-3-((2R)-2-(1-hydroxy-1-methylethyl)-4-morpholinyl)phenyl)amino)-4-(cyclopropylamino)imidazo[2,1-f][1,2,4]triazine-7-carbonitrile | 493.96 | 2.67 |
| 39 | 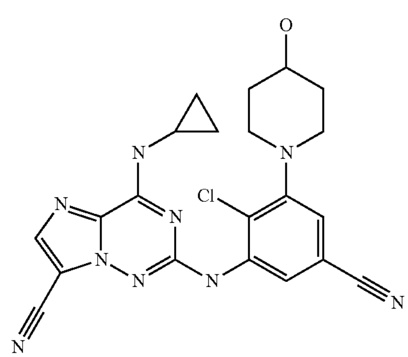 [SMILES: N#Cc1cc(Nc2nc(NC3CC3)c3ncc(C#N)n3n2)c(Cl)c(N2CCC(O)CC2)c1] | 2-((2-chloro-5-cyano-3-(4-hydroxy-1-piperidinyl)phenyl)amino)-4-(cyclopropylamino)imidazo[2,1-f][1,2,4]triazine-7-carbonitrile | 449.90 | 3.26 |

TABLE 1-continued

| Example No. | Structure | Name | [M + H]+ | HPLC Retention Time (min.) |
|---|---|---|---|---|
| 40 | 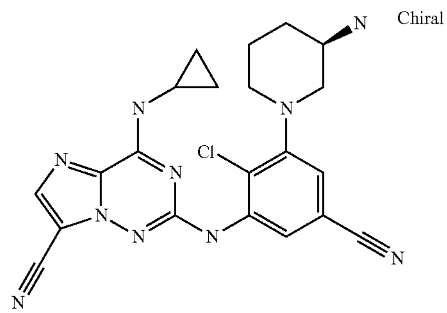 [SMILES: N#Cc1cc(Nc2nc(NC3CC3)c3ncc(C#N)n3n2)c(Cl)c(N2CCC[C@@H](N)C2)c1] | (R)-2-(3-(3-aminopiperidin-1-yl)-2-chloro-5-cyanophenylamino)-4-(cyclopropylamino)imidazo[1,2-f][1,2,4]triazine-7-carbonitrile | 448.92 | 1.69 |
| 41 | 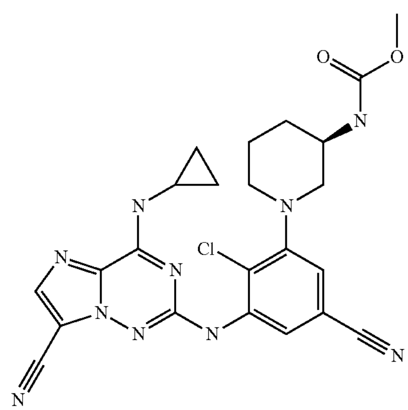 | methyl ((3R)-1-(2-chloro-5-cyano-3-((7-cyano-4-(cyclopropylamino)imidazo[2,1-f][1,2,4]triazin-2-yl)amino)phenyl)-3-piperidinyl)carbamate | 506.96 | 2.67 |
| 42 | 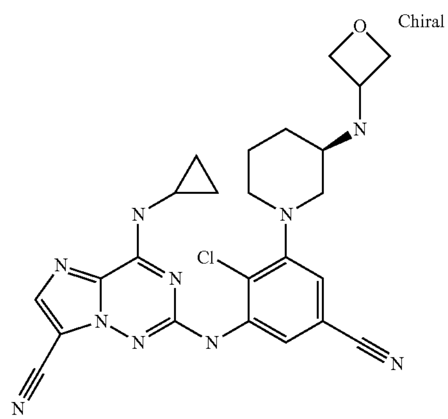 [SMILES: N#Cc1cc(Nc2nc(NC3CC3)c3ncc(C#N)n3n2)c(Cl)c(N2CCC[C@@H](NC3COC3)C2)c1] | 2-((2-chloro-5-cyano-3-((3R)-3-(3-oxetanylamino)-1-piperidinyl)phenyl)amino)-4-(cyclopropylamino)imidazo[2,1-f][1,2,4]triazine-7-carbonitrile | 504.98 | 3.96 |

TABLE 1-continued

| Example No. | Structure | Name | [M + H]+ | HPLC Retention Time (min.) |
|---|---|---|---|---|
| 43 | Chiral | 2-((2-chloro-5-cyano-3-((3R)-3-((2-hydroxy-2-methylpropyl)amino)-1-piperidinyl)phenyl)amino)-4-(cyclopropylamino)imidazo[2,1-f][1,2,4]triazine-7-carbonitrile | 521.03 | 3.59 |
| 44 | Chiral | 2-((2-chloro-5-cyano-3-((3R)-3-(3-oxetanylamino)-1-pyrrolidinyl)phenyl)amino)-4-(cyclopropylamino)imidazo[2,1-f][1,2,4]triazine-7-carbonitrile | 490.96 | 2.82 |
| 45 | Chiral | 2-((2-chloro-5-cyano-3-((3R)-3-(3-hydroxy-3-methyl-1-azetidinyl)-1-piperidinyl)phenyl)amino)-4-(cyclopropylamino)imidazo[2,1-f][1,2,4]triazine-7-carbonitrile | 519.01 | 3.48 |
| 46 | Chiral | (R)-2-(3-(3-aminopyrrolidin-1-yl)-2-chloro-5-cyanophenylamino)-4-(cyclopropylamino)imidazo[1,2-f][1,2,4]triazine-7-carbonitrile | 434.89 | 3.13 |

TABLE 1-continued

| Example No. | Structure | Name | [M + H]⁺ | HPLC Retention Time (min.) |
|---|---|---|---|---|
| 47 | 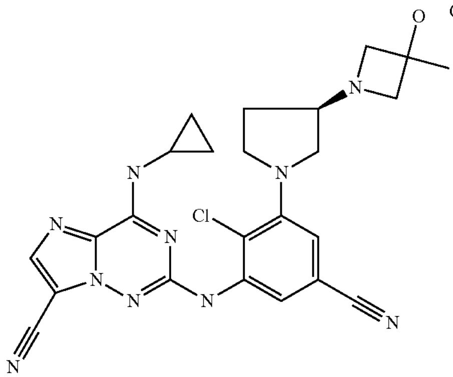 | (R)-2-(2-chloro-5-cyano-3-(3-(3-hydroxy-3-methylazetidin-1-yl)pyrrolidin-1-yl)phenylamino)-4-(cyclopropylamino)imidazo[1,2-f][1,2,4]triazine-7-carbonitrile | 504.98 | 3.78 |
| 48 | 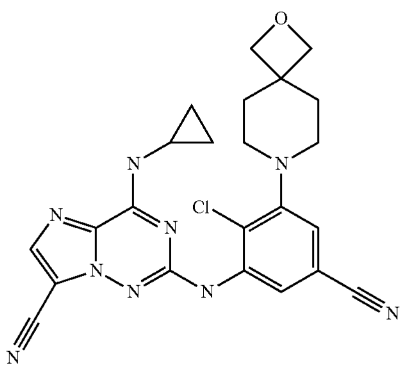 [SMILES: N#Cc1cc(Nc2nc(NC3CC3)c3ncc(C#N)n3n2)c(Cl)c(N2CCC3(CC2)COC3)c1] | 2-((2-chloro-5-cyano-3-(2-oxa-7-azaspiro[3.5]non-7-yl)phenyl)amino)-4-(cyclopropylamino)imidazo[2,1-f][1,2,4]triazine-7-carbonitrile | 475.94 | 3.93 |
| 49 | 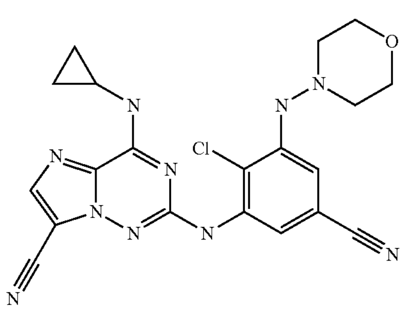 [SMILES: N#Cc1cc(Nc2nc(NC3CC3)c3ncc(C#N)n3n2)c(Cl)c(NN2CCOCC2)c1] | 2-((2-chloro-5-cyano-3-(4-morpholinylamino)phenyl)amino)-4-(cyclopropylamino)imidazo[2,1-f][1,2,4]triazine-7-carbonitrile | 450.89 | 3.76 |
| 50 | 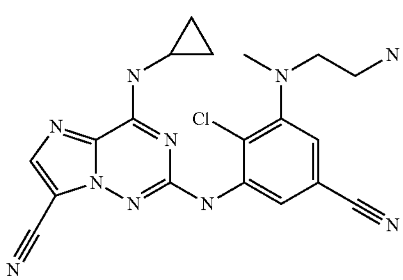 [SMILES: CN(CCN)c1cc(C#N)cc(Nc2nc(NC3CC3)c3ncc(C#N)n3n2)c1Cl] | 2-((3((2-aminoethyl)(methyl)amino)-2-chloro-5-cyanophenyl)amino)-4-(cyclopropylamino)imidazo[2,1-f][1,2,4]triazine-7-carbonitrile | 422.88 | 3.86 |

TABLE 1-continued

| Example No. | Structure | Name | [M + H]+ | HPLC Retention Time (min.) |
|---|---|---|---|---|
| 51 | 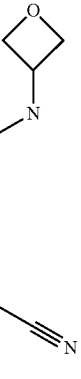 | 2-((2-chloro-5-cyano-3-(methyl(2-(3-oxetanylamino)ethyl)amino)phenyl)amino)-4-(cyclopropylamino)imidazo[2,1-f][1,2,4]triazine-7-carbonitrile | 478.95 | 3.769 [a] |

[a] = HPLC conditions
YMC S5 ODS 4.6 × 50 mm,10-90% aqueous methanol containing 0.2% $H_3PO_4$, 5 min. gradient, monitored at 220 nm

Example 52

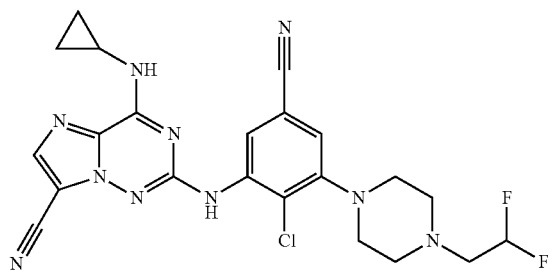 [SMILES: N#Cc1cc(Nc2nc(NC3CC3)c3ncc(C#N)n3n2)c(Cl)c(N2CCN(CC(F)F)CC2)c1]

2-((2-chloro-5-cyano-3-(4-(2,2-difluoroethyl)-1-piperazinyl)phenyl)amino)-4-(cyclopropylamino)imidazo[2,1-f][1,2,4]triazine-7-carbonitrile (52A): To the stirred solution of 2-((2-chloro-5-cyano-3-(piperazin-1-yl)phenyl)amino)-4-(cyclopropyl(4-methoxybenzyl)amino)imidazo[2,1-f][1,2,4]triazine-7-carbonitrile (Intermediate 11) (0.100 g, 0.180 mmol) in DMF (2.0 mL) and N,N-diisopropylethylamine, (63 µL, 0.361 mmol) was added 2,2-difluoroethyl trifluoromethanesulfonate (0.046 g, 0.216 mmol) at room temperature. The reaction mixture was stirred at room temperature for overnight. On completion of the reaction, the reaction mixture was diluted with ethyl acetate and washed with water. The organic layer was separated and aqueous layer was extracted with ethyl acetate twice. The combined organic layers were dried over sodium sulfate, filtered and concentrated in vacuum to give off-white solid, which was purified by flash chromatography on silica gel using an automated ISCO system (12 g Redisep column, eluting with 0-5% methanol/chloroform) to get 2-((2-chloro-5-cyano-3-(4-(2,2-difluoroethyl)piperazin-1-yl)phenyl)amino)-4-(cyclopropyl(4-methoxybenzyl)amino)imidazo[2,1-f][1,2,4]triazine-7-carbonitrile (100 mg) as an off-white solid.

MS (ESI) m/z 617.2

(52B): To the stirred solution of 2-((2-chloro-5-cyano-3-(4-(2,2-difluoroethyl)-piperazin-1-yl)phenyl)amino)-4-(cyclopropyl(4-methoxybenzyl)amino)imidazo[2,1-f][1,2,4]triazine-7-carbonitrile (120 mg, 0.194 mmol) in dry dichloromethane (2.0 mL) was added anisole (0.1 mL, 0.915 mmol) and trifluoroacetic acid (0.3 mL, 3.87 mmol) at room temperature. The reaction mixture stirred at room temperature for overnight. On completion of the reaction, the reaction mixture was diluted with dichloromethane and washed with saturated sodium bicarbonate. The organic layer was separated and aqueous layer was extracted with dichloromethane twice. The combined organic layers were dried over sodium sulfate, filtered and concentrated in vacuo to give off-white solid. This was purified by preparative HPLC to afford 2-((2-chloro-5-cyano-3-(4-(2,2-difluoroethyl)piperazin-1-yl)phenyl)amino)-4-(cyclopropylamino)imidazo[2,1-f][1,2,4]triazine-7-carbonitrile (50 mg, 0.098 mmol, 50.5% yield) as an off-white solid MS (ESI) m/z 499.2

Example 52

To the stirred solution of ((2-chloro-5-cyano-3-(4-(2,2-difluoroethyl)piperazin-1-yl)phenyl)amino)-4-(cyclopropylamino)imidazo[2,1-f][1,2,4]triazine-7-carbonitrile (0.045 g, 0.090 mmol) in dry acetonitrile (2.0 mL), water (4.0 mL) was added 1N HCl (90 µL, 0.090 mmol) at room temperature. The reaction mixture stirred at room temperature for 10 minutes. The reaction mixture converted in to clear solution. This mixture was freeze dried and lyophilized to afford 2-((2-chloro-5-cyano-3-(4-(2,2-difluoroethyl)piperazin-1-yl)phenyl)amino)-4-(cyclopropylamino)imidazo[2,1-f][1,2,4]triazine-7-carbonitrile, hydrochloride (48.0 mg) as an off-white solid.

MS (ESI) m/z 499.2

$^1$H NMR (400 MHz, DMSO-$d_6$): δ 9.35-9.34 (d, J=4.4 Hz, 1H), 8.91 (s, 1H), 8.21 (s, 1H), 8.15 (d, J=1.5 Hz, 1H), 7.41 (s, 1H), 6.50 (m, 1H), 3.32-3.15 (m, 8H), 3.04-2.92 (m, 2H), 0.79-0.78 (m, 4H).

The compounds listed below were prepared by the similar synthetic procedure used for Examples 52

TABLE 2

| Example No. | Structure | Name | [M + H]⁺ | HPLC Retention Time (min.) |
|---|---|---|---|---|
| 53 | 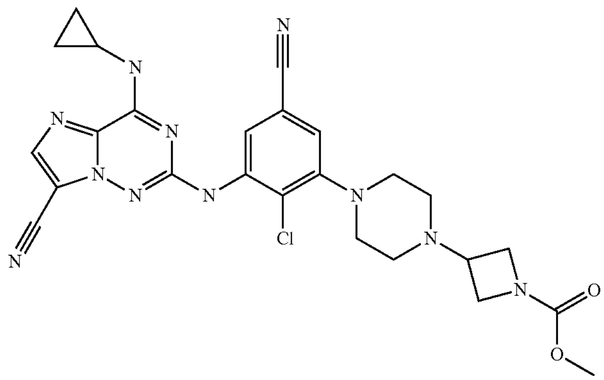 [SMILES: COC(=O)N1CC(N2CCN(c3cc(C#N)cc(Nc4nc(NC5CC5)c5ncc(C#N)n5n4)c3Cl)CC2)C1] | methyl 3-(4-(2-chloro-5-cyano-3-((7-cyano-4-(cyclopropylamino)imidazo[2,1-f][1,2,4]triazin-2-yl)amino)phenyl)-1-piperazinyl)-1-azetidinecarboxylate | 548.01 | 3.57 |
| 54 | 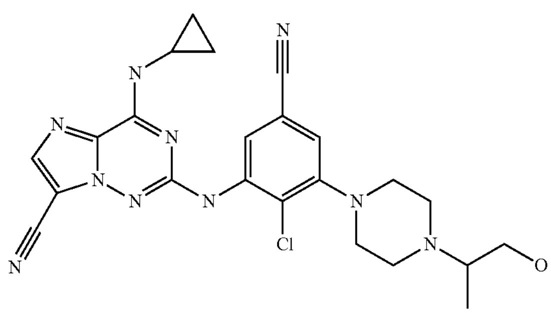 [SMILES: CC(CO)N1CCN(c2cc(C#N)cc(Nc3nc(NC4CC4)c4ncc(C#N)n4n3)c2Cl)CC1] | (+/−) 2-((2-chloro-5-cyano-3-(4-(2-hydroxy-1-methylethyl)-1-piperazinyl)phenyl)amino)-4-(cyclopropylamino)imidazo[2,1-f][1,2,4]triazine-7-carbonitrile | 492.97 | 3.78 |
| 55 | 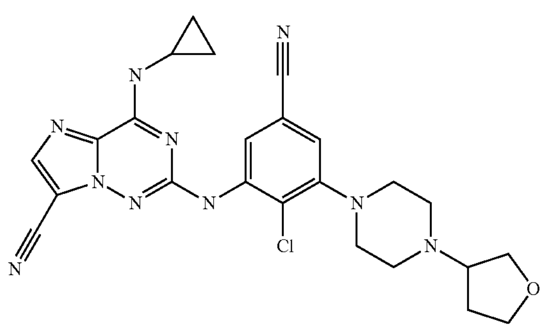 [SMILES: N#Cc1cc(Nc2nc(NC3CC3)c3ncc(C#N)n3n2)c(Cl)c(N2CCN(C3CCOC3)CC2)c1] | (+/−) 2-((2-chloro-5-cyano-3-(4-(tetrahydro-3-furanyl)-1-piperazinyl)phenyl)amino)-4-(cyclopropylamino)imidazo[2,1-f][1,2,4]triazine-7-carbonitrile | 504.98 | 3.80 |
| 56 | 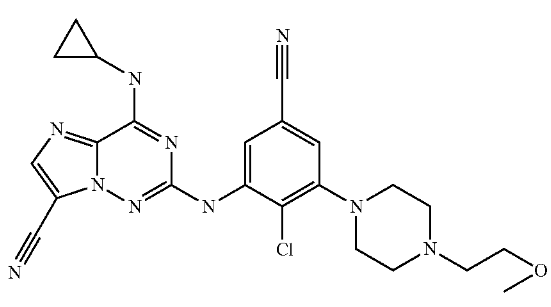 [SMILES: COCCN1CCN(c2cc(C#N)cc(Nc3nc(NC4CC4)c4ncc(C#N)n4n3)c2Cl)CC1] | 2-((2-chloro-5-cyano-3-(4-(2-methoxyethyl)-1-piperazinyl)phenyl)amino)-4-(cyclopropylamino)imidazo[2,1-f][1,2,4]triazine-7-carbonitrile | 492.97 | 3.72 |

TABLE 2-continued

| Example No. | Structure | | Name | [M + H]+ | HPLC Retention Time (min.) |
|---|---|---|---|---|---|
| 57 | 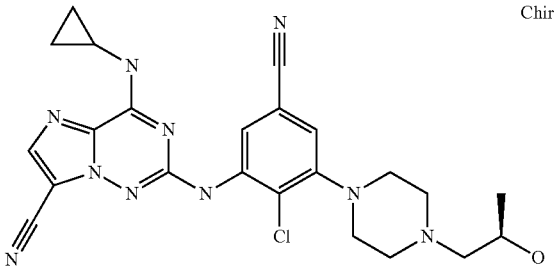 | Chiral | 2-((2-chloro-5-cyano-3-(4-((2R)-2-hydroxypropyl)-1-piperazinyl)phenyl)amino)-4-(cyclopropylamino)imidazo[2,1-f][1,2,4]triazine-7-carbonitrile | 492.97 | 3.72 |
| 58 | 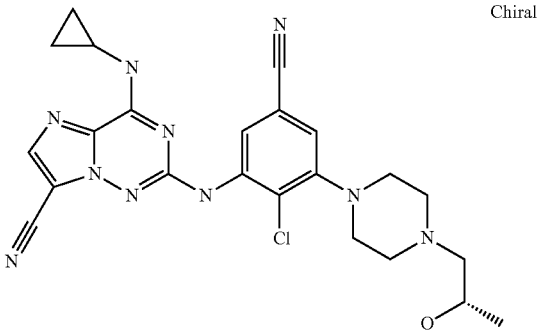 [SMILES: C[C@H](O)CN1CCN(c2cc(C#N)cc(Nc3nc(NC4CC4)c4ncc(C#N)n4n3)c2Cl)CC1] | Chiral | 2-((2-chloro-5-cyano-3-(4-((2S)-2-hydroxypropyl)-1-piperazinyl)phenyl)amino)-4-(cyclopropylamino)imidazo[2,1-f][1,2,4]triazine-7-carbonitrile | 492.97 | 3.79 |
| 59 | 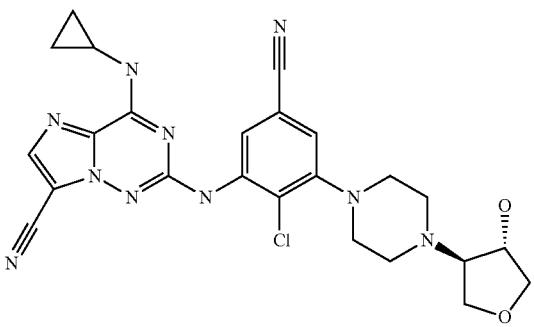 [SMILES: N#Cc1cc(Nc2nc(NC3CC3)c3ncc(C#N)n3n2)c(Cl)c(N2CCN([C@@H]3COC[C@H]3O)CC2)c1] | | (+/−) 2-((2-chloro-5-cyano-3-(4-((3R,4S)-4-hydroxytetrahydro-3-furanyl)-1-piperazinyl)phenyl)amino)-4-(cyclopropylamino)imidazo[2,1-f][1,2,4]triazine-7-carbonitrile | 520.98 | 3.63 |
| 60 | 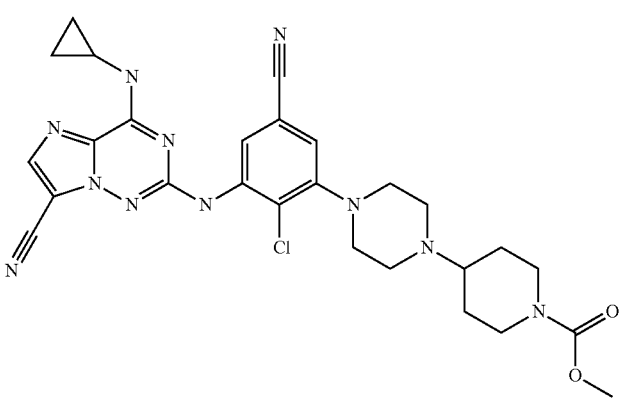 [SMILES: COC(=O)N1CCC(N2CCN(c3cc(C#N)cc(Nc4nc(NC5CC5)c5ncc(C#N)n5n4)c3Cl)CC2)CC1] | | methyl 4-(4-(2-chloro-5-cyano-3-((7-cyano-4-(cyclopropylamino)imidazo[2,1-f][1,2,4]triazin-2-yl)amino)phenyl)-1-piperazinyl)-1-piperidinecarboxylate | 576.06 | 3.81 |

| Example No. | Structure | Name | [M + H]+ | HPLC Retention Time (min.) |
|---|---|---|---|---|
| 61 | 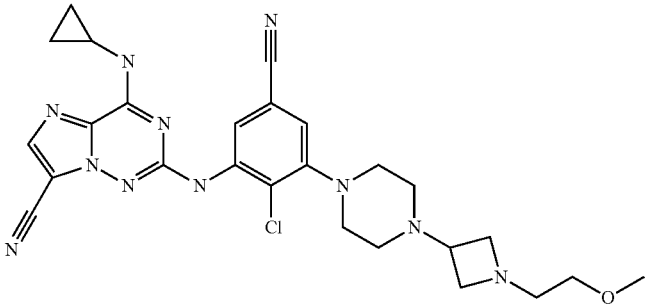 [SMILES: COCCN1CC(N2CCN(c3cc(C#N)cc(Nc4nc(NC5CC5)c5ncc(C#N)n5n4)c3Cl)CC2)C1] | 2-((2-chloro-5-cyano-3-(4-(1-(2-methoxyethyl)-3-azetidinyl)-1-piperazinyl)phenyl)amino)-4-(cyclopropylamino)imidazo[2,1-f][1,2,4]triazine-7-carbonitrile | 548.05 | 3.83 |
| 62 | 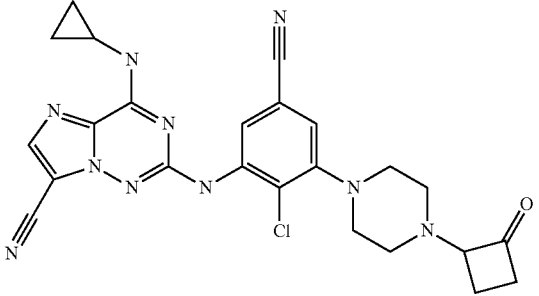 [SMILES: N#Cc1cc(Nc2nc(NC3CC3)c3ncc(C#N)n3n2)c(Cl)c(N2CCN(C3CCC3=O)CC2)c1] | 2-((2-chloro-5-cyano-3-(4-(2-oxocyclobutyl)piperazin-1-yl)phenyl)amino)-4-(cyclopropylamino)imidazo[2,1-f][1,2,4]triazine-7-carbonitrile | 502.97 | 3.93 |
| 63 | 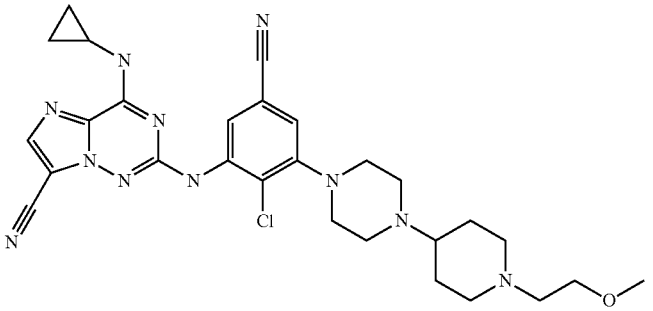 [SMILES: COCCN1CCC(N2CCN(c3cc(C#N)cc(Nc4nc(NC5CC5)c5ncc(C#N)n5n4)c3Cl)CC2)CC1] | 2-((2-chloro-5-cyano-3-(4-(1-(2-methoxyethyl)-4-piperidinyl)-1-piperazinyl)phenyl)amino)-4-(cyclopropylamino)imidazo[2,1-f][1,2,4]triazine-7-carbonitrile | 576.11 | 2.83 |
| 64 | 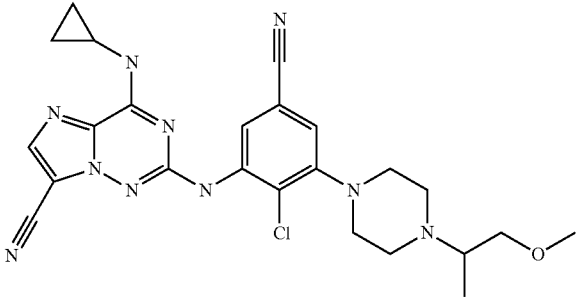 [SMILES: COCC(C)N1CCN(c2cc(C#N)cc(Nc3nc(NC4CC4)c4ncc(C#N)n4n3)c2Cl)CC1] | (+/−) 2-((2-chloro-5-cyano-3-(4-(2-methoxy-1-methylethyl)-1-piperazinyl)phenyl)amino)-4-(cyclopropylamino)imidazo[2,1-f][1,2,4]triazine-7-carbonitrile | 507.00 | 3.69 |
| 65 | 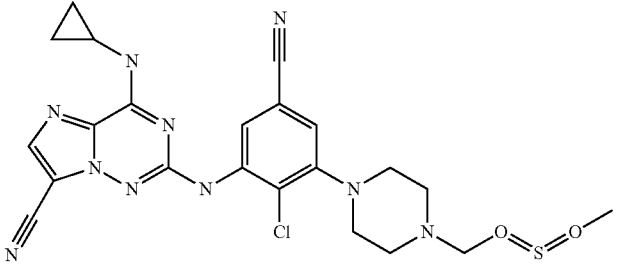 | 2-((2-chloro-5-cyano-3-(4-(2-(methylsulfonyl)ethyl)-1-piperazinyl)phenyl)amino)-4-(cyclopropylamino)imidazo[2,1-f][1,2,4]triazine-7-carbonitrile | 541.04 | 2.7 |

TABLE 2-continued

| Example No. | Structure | Name | [M + H]+ | HPLC Retention Time (min.) |
|---|---|---|---|---|
| 66 | 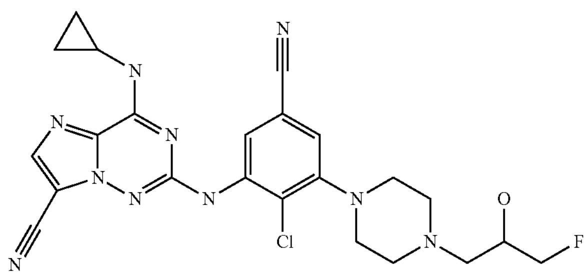 [SMILES: N#Cc1cc(Nc2nc(NC3CC3)c3ncc(C#N)n3n2)c(Cl)c(N2CCN(CC(O)CF)CC2)c1] | (+/−) 2-((2-chloro-5-cyano-3-(4-(3-fluoro-2-hydroxypropyl)-1-piperazinyl)phenyl)amino)-4-(cyclopropylamino)imidazo[2,1-f][1,2,4]triazine-7-carbonitrile | 510.96 | 3.86 |
| 67 | 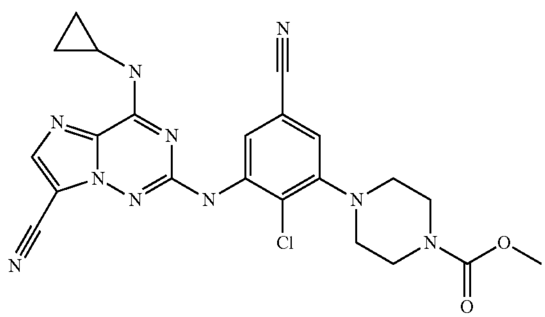 [SMILES: COC(=O)N1CCN(c2cc(C#N)cc(Nc3nc(NC4CC4)c4ncc(C#N)n4n3)c2Cl)CC1] | methyl 4-(2-chloro-5-cyano-3-((7-cyano-4-(cyclopropylamino)imidazo[2,1-f][1,2,4]triazin-2-yl)amino)phenyl)-1-piperazinecarboxylate | 492.93 | 3.76 |
| 68 | 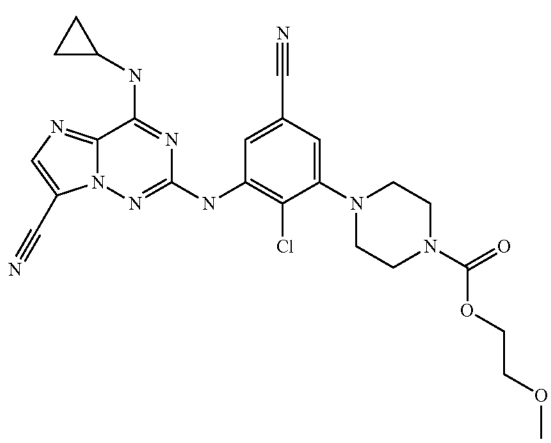 | 2-methoxyethyl 4-(2-chloro-5-cyano-3-((7-cyano-4-(cyclopropylamino)imidazo[2,1-f][1,2,4]triazin-2-yl)amino)phenyl)-1-piperazinecarboxylate | 536.98 | 3.76 |
| 69 Chiral | | N-((1S)-2-(4-(2-chloro-5-cyano-3-((7-cyano-4-(cyclopropylamino)imidazo[2,1-f][1,2,4]triazin-2-yl)amino)phenyl)-1-piperazinyl)-1-methylethyl)methanesulfonamide | 570.08 | 3.97 |

TABLE 2-continued

| Example No. | Structure | Name | [M + H]+ | HPLC Retention Time (min.) |
|---|---|---|---|---|
| 70 | 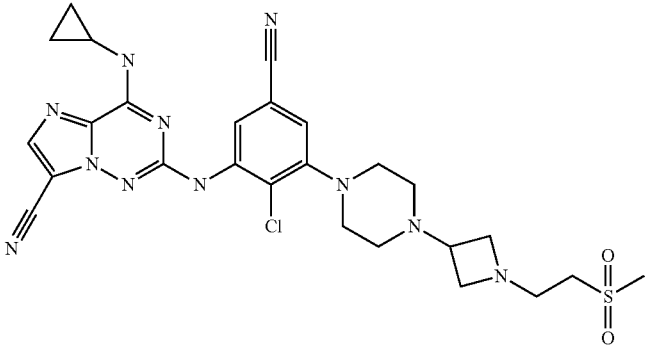 [SMILES: CS(=O)(=O)CCN1CC(N2CCN(c3cc(C#N)cc(Nc4nc(NC5CC5)c5ncc(C#N)n5n4)c3Cl)CC2)C1] | 2-((2-chloro-5-cyano-3-(4-(1-(2-(methylsulfonyl)ethyl)-3-azetidinyl)-1-piperazinyl)phenyl)amino)-4-(cyclopropylamino)imidazo[2,1-f][1,2,4]triazine-7-carbonitrile | 596.12 | 2.93 |
| 71 | 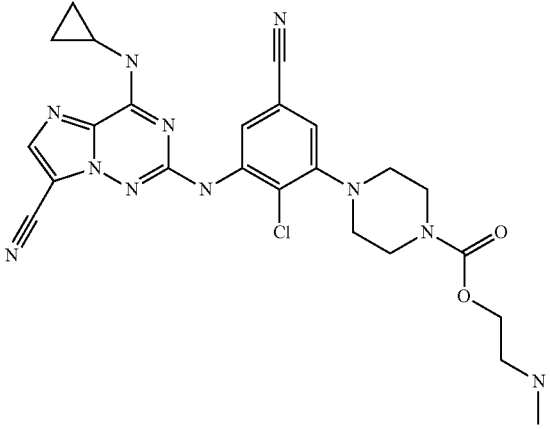 [SMILES: CNCCOC(=O)N1CCN(c2cc(C#N)cc(Nc3nc(NC4CC4)c4ncc(C#N)n4n3)c2Cl)CC1] | 2-(methylamino)ethyl 4-(2-chloro-5-cyano-3-((7-cyano-4-(cyclopropylamino)imidazo[2,1-f][1,2,4]triazin-2-yl)amino)phenyl)-1-piperazinecarboxylate | 536.00 | 2.86 |
| 72 | 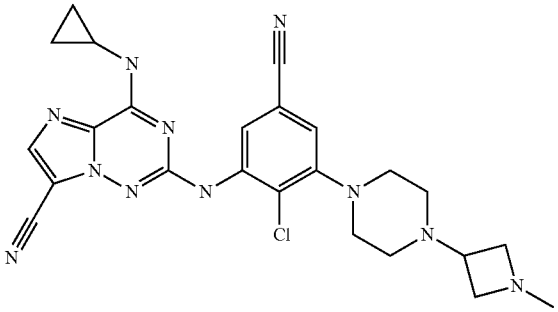 [SMILES: CN1CC(N2CCN(c3cc(C#N)cc(Nc4nc(NC5CC5)c5ncc(C#N)n5n4)c3Cl)CC2)C1] | 2-((2-chloro-5-cyano-3-(4-(1-methyl-3-azetidinyl)-1-piperazinyl)phenyl)amino)-4-(cyclopropylamino)imidazo[2,1-f][1,2,4]triazine-7-carbonitrile | 504.00 | 2.52 |
| 73 | 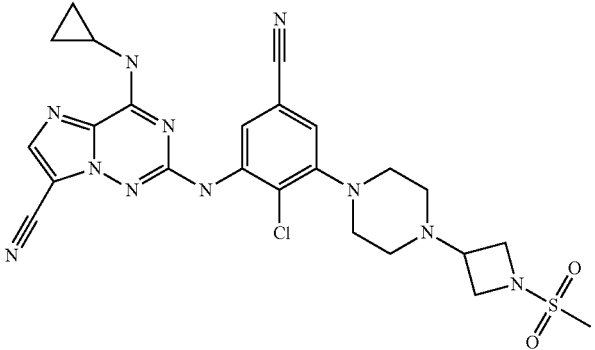 [SMILES: CS(=O)(=O)N1CC(N2CCN(c3cc(C#N)cc(Nc4nc(NC5CC5)c5ncc(C#N)n5n4)c3Cl)CC2)C1] | 2-((2-chloro-5-cyano-3-(4-(1-(methylsulfonyl)-3-azetidinyl)-1-piperazinyl)phenyl)amino)-4-(cyclopropylamino)imidazo[2,1-f][1,2,4]triazine-7-carbonitrile | 568.06 | 3.62 |

TABLE 2-continued

| Example No. | Name | [M + H]+ | HPLC Retention Time (min.) |
|---|---|---|---|
| 74 | 2-((2-chloro-5-cyano-3-(4-(cyclopropylcarbonyl)-1-piperazinyl)phenyl)amino)-4-(cyclopropylamino)imidazo[2,1-f][1,2,4]triazine-7-carbonitrile | 502.97 | 3.85 |
| 75 | 2-(2-chloro-5-cyano-3-(4-(2,2-difluoroacetyl)piperazin-1-yl)phenylamino)-4-(cyclopropylamino)imidazo[1,2-f][1,2,4]triazine-7-carbonitrile | 512.91 | 3.61 |
| 76 | N-(2-(4-(2-chloro-5-cyano-3-((7-cyano-4-(cyclopropylamino)imidazo[2,1-f][1,2,4]triazin-2-yl)amino)phenyl)-1-piperazinyl)-2-oxoethyl)acetamide | 533.98 | 3.76 |
| 77 | 2-((2-chloro-5-cyano-3-(4-(methoxyacetyl)-1-piperazinyl)phenyl)amino)-4-(cyclopropylamino)imidazo[2,1-f][1,2,4]triazine-7-carbonitrile | 506.96 | 3.83[a] |

TABLE 2-continued

| Example No. | Structure | Name | [M + H]+ | HPLC Retention Time (min.) |
|---|---|---|---|---|
| 78 | 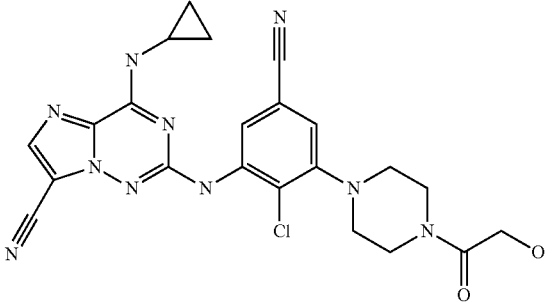 [SMILES: N#Cc1cc(Nc2nc(NC3CC3)c3ncc(C#N)n3n2)c(Cl)c(N2CCN(C(=O)CO)CC2)c1] | 2-(2-chloro-5-cyano-3-(4-(2-hydroxyacetyl)piperazin-1-yl)phenylamino)-4-(cyclopropylamino)imidazo[1,2-f][1,2,4]triazine-7-carbonitrile | 492.93 | 4.185 |
| 79 | 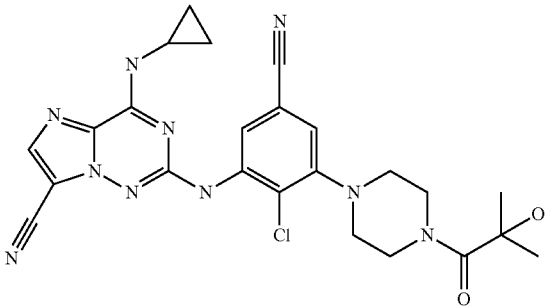 [SMILES: CC(C)(O)C(=O)N1CCN(c2cc(C#N)cc(Nc3nc(NC4CC4)c4ncc(C#N)n4n3)c2Cl)CC1] | 2-((2-chloro-5-cyano-3-(4-(2-hydroxy-2-methylpropanoyl)-1-piperazinyl)phenyl)amino)-4-(cyclopropylamino)imidazo[2,1-f][1,2,4]triazine-7-carbonitrile | 520.98 | 3.81 |
| 80 | 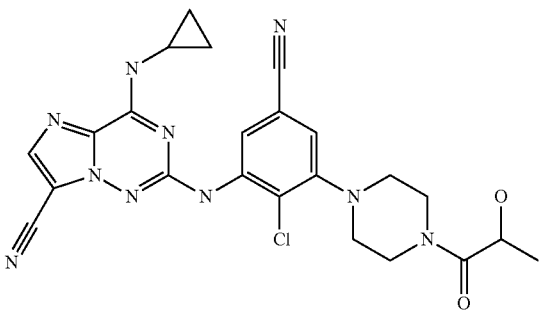 [SMILES: CC(O)C(=O)N1CCN(c2cc(C#N)cc(Nc3nc(NC4CC4)c4ncc(C#N)n4n3)c2Cl)CC1] | (+/−) 2-((2-chloro-5-cyano-3-(4-lactoyl-1-piperazinyl)phenyl)amino)-4-(cyclopropylamino)imidazo[2,1-f][1,2,4]triazine-7-carbonitrile | 506.96 | 4.41 |
| 81 | 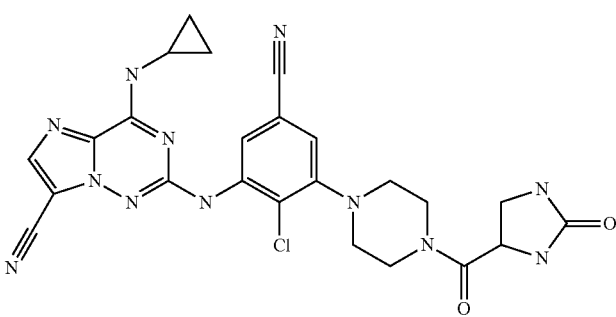 [SMILES: N#Cc1cc(Nc2nc(NC3CC3)c3ncc(C#N)n3n2)c(Cl)c(N2CCN(C(=O)C3CNC(=O)N3)CC2)c1] | (+/−) 2-((2-chloro-5-cyano-3-(4-((2-oxo-4-imidazolidinyl)carbonyl)-1-piperazinyl)phenyl)amino)-4-(cyclopropylamino)imidazo[2,1-f][1,2,4]triazine-7-carbonitrile | 546.98 | 3.71 |

TABLE 2-continued

| Example No. | Structure | | Name | [M + H]+ | HPLC Retention Time (min.) |
|---|---|---|---|---|---|
| 82 | 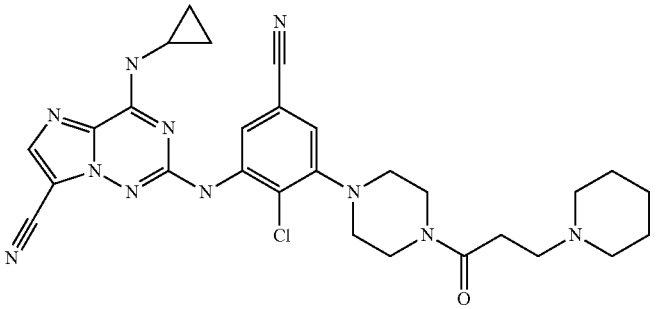 [SMILES: N#Cc1cc(Nc2nc(NC3CC3)c3ncc(C#N)n3n2)c(Cl)c(N2CCN(C(=O)CCN3CCCCC3)CC2)c1] | | 2-((2-chloro-5-cyano-3-(4-(3-(1-piperidinyl)propanoyl)-1-piperazinyl)phenyl)amino)-4-(cyclopropylamino)imidazo[2,1-f][1,2,4]triazine-7-carbonitrile | 574.09 | 3.99 |
| 83 | 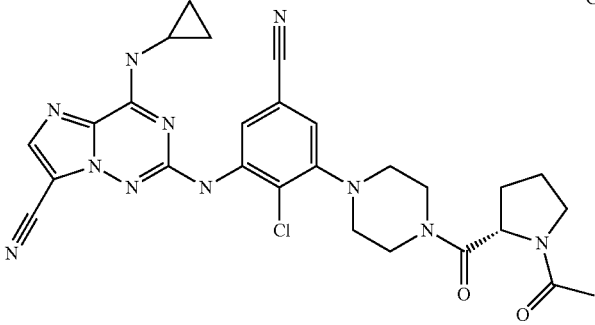 | Chiral | 2-((3-(4-(1-acetyl-L-prolyl)-1-piperazinyl)-2-chloro-5-cyanophenyl)amino)-4-(cyclopropylamino)imidazo[2,1-f][1,2,4]triazine-7-carbonitrile | 574.05 | 3.34 |
| 84 | 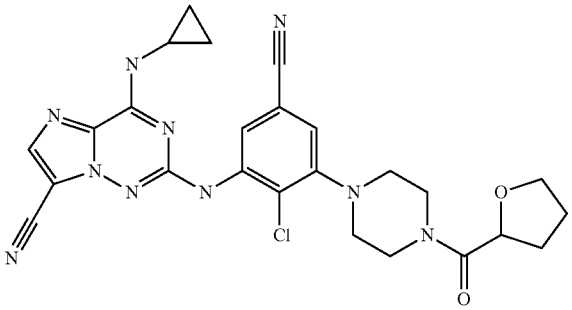 [SMILES: N#Cc1cc(Nc2nc(NC3CC3)c3ncc(C#N)n3n2)c(Cl)c(N2CCN(C(=O)C3CCCO3)CC2)c1] | | (+/−) 2-((2-chloro-5-cyano-3-(4-(tetrahydro-2-furanylcarbonyl)-1-piperazinyl)phenyl)amino)-4-(cyclopropylamino)imidazo[2,1-f][1,2,4]triazine-7-carbonitrile | 532.99 | 3.28 |
| 85 | 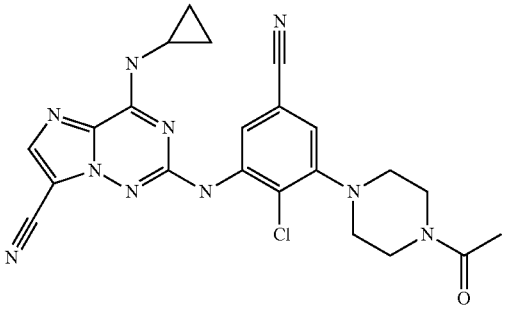 [SMILES: CC(=O)N1CCN(c2cc(C#N)cc(Nc3nc(NC4CC4)c4ncc(C#N)n4n3)c2Cl)CC1] | | 2-((3-(4-acetyl-1-piperazinyl)-2-chloro-5-cyanophenyl)amino)-4-(cyclopropylamino)imidazo[2,1-f][1,2,4]triazine-7-carbonitrile | 476.93 | 3.97 |

TABLE 2-continued

| Example No. | Structure | Name | [M + H]+ | HPLC Retention Time (min.) |
|---|---|---|---|---|
| 86 | 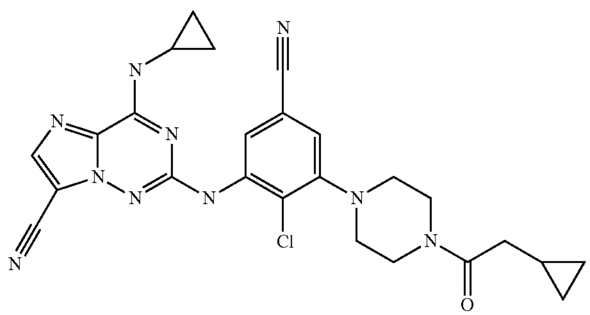 [SMILES: N#Cc1cc(Nc2nc(NC3CC3)c3ncc(C#N)n3n2)c(Cl)c(N2CCN(C(=O)CC3CC3)CC2)c1] | 2-((2-chloro-5-cyano-3-(4-(cyclopropylacetyl)-1-piperazinyl)phenyl)amino)-4-(cyclopropylamino)imidazo[2,1-f][1,2,4]triazine-7-carbonitrile | 517.00 | 2.98 |
| 87 | 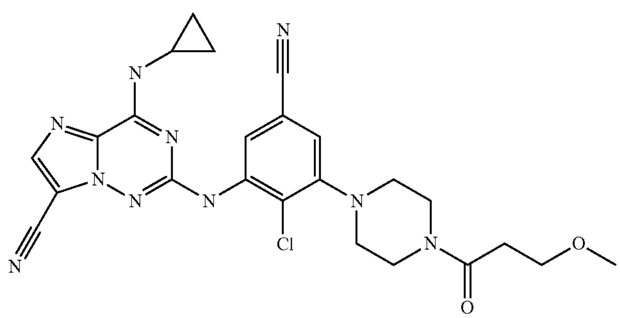 [SMILES: COCCC(=O)N1CCN(c2cc(C#N)cc(Nc3nc(NC4CC4)c4ncc(C#N)n4n3)c2Cl)CC1] | 2-((2-chloro-5-cyano-3-(4-(3-methoxypropanoyl)-1-piperazinyl)phenyl)amino)-4-(cyclopropylamino)imidazo[2,1-f][1,2,4]triazine-7-carbonitrile | 520.98 | 3.91 |
| 88 | 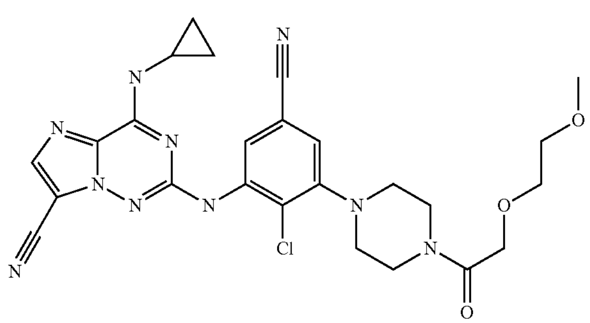 [SMILES: COCCOCC(=O)N1CCN(c2cc(C#N)cc(Nc3nc(NC4CC4)c4ncc(C#N)n4n3)c2Cl)CC1] | 2-((2-chloro-5-cyano-3-(4-((2-methoxyethoxy)acetyl)-1-piperazinyl)phenyl)amino)-4-(cyclopropylamino)imidazo[2,1-f][1,2,4]triazine-7-carbonitrile | 551.01 | 4.43 |
| 89 | 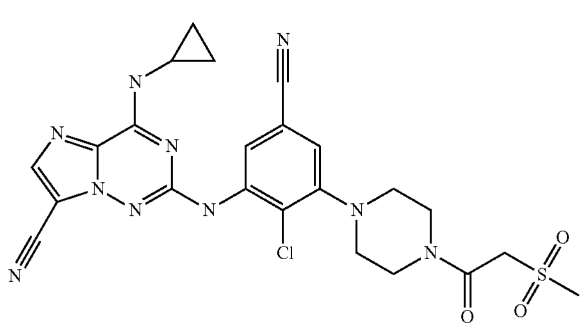 [SMILES: CS(=O)(=O)CC(=O)N1CCN(c2cc(C#N)cc(Nc3nc(NC4CC4)c4ncc(C#N)n4n3)c2Cl)CC1] | 2-((2-chloro-5-cyano-3-(4-((methylsulfonyl)acetyl)-1-piperazinyl)phenyl)amino)-4-(cyclopropylamino)imidazo[2,1-f][1,2,4]triazine-7-carbonitrile | 555.02 | 4.67 |

TABLE 2-continued

| Example No. | Structure | Name | [M + H]+ | HPLC Retention Time (min.) |
|---|---|---|---|---|
| 90 | 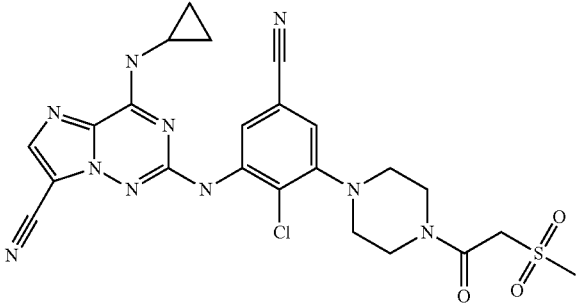 | 2-(2-chloro-5-cyano-3-(4-(3-hydroxypropanoyl)piperazin-1-yl)phenylamino)-4-(cyclopropylamino)imidazo[1,2-f][1,2,4]triazine-7-carbonitrile | 506.96 | 3.26 |
| 91 | 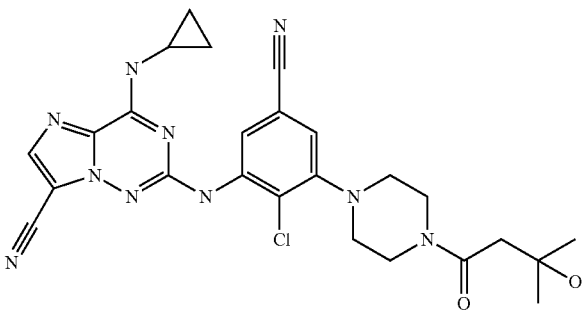 [SMILES: CC(C)(O)CC(=O)N1CCN(c2cc(C#N)cc(Nc3nc(NC4CC4)c4ncc(C#N)n4n3)c2Cl)CC1] | 2-((2-chloro-5-cyano-3-(4-(3-hydroxy-3-methylbutanoyl)-1-piperazinyl)phenyl)amino)-4-(cyclopropylamino)imidazo[2,1-f][1,2,4]triazine-7-carbonitrile | 535.01 | 3.69 |
| 92 | 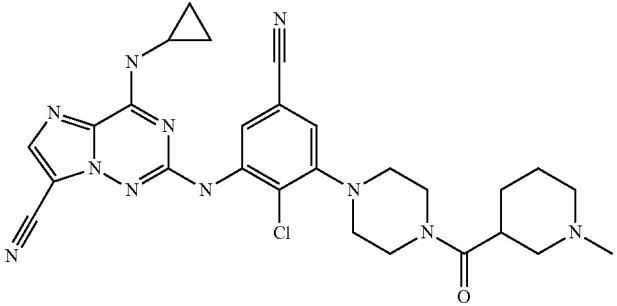 [SMILES: CN1CCCC(C(=O)N2CCN(c3cc(C#N)cc(Nc4nc(NC5CC5)c5ncc(C#N)n5n4)c3Cl)CC2)C1] | (+/−) 2-((2-chloro-5-cyano-3-(4-((1-methyl-3-piperidinyl)carbonyl)-1-piperazinyl)phenyl)amino)-4-(cyclopropylamino)imidazo[2,1-f][1,2,4]triazine-7-carbonitrile | 560.06 | 2.67 |
| 93 | 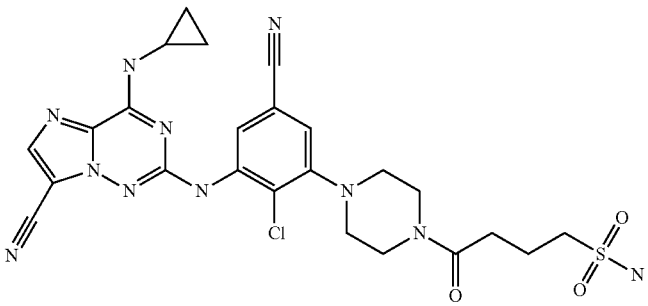 [SMILES: N#Cc1cc(Nc2nc(NC3CC3)c3ncc(C#N)n3n2)c(Cl)c(N2CCN(C(=O)CCCS(N)(=O)=O)CC2)c1] | 4-(4-(2-chloro-5-cyano-3-((7-cyano-4-(cyclopropylamino)imidazo[2,1-f][1,2,4]triazin-2-yl)amino)phenyl)-1-piperazinyl)-4-oxo-1-butanesulfonamide | 584.06 | 3.96 |

TABLE 2-continued

| Example No. | Structure | Name | [M + H]⁺ | HPLC Retention Time (min.) |
|---|---|---|---|---|
| 94 | 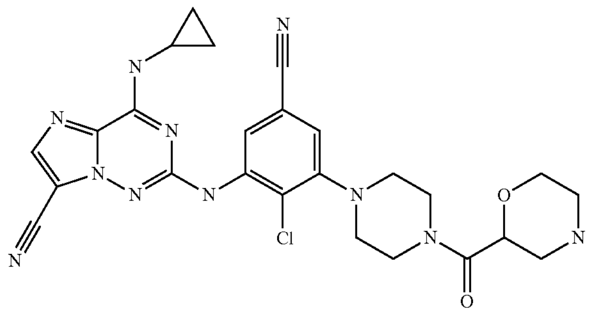 [SMILES: N#Cc1cc(Nc2nc(NC3CC3)c3ncc(C#N)n3n2)c(Cl)c(N2CCN(C(=O)C3CNCCO3)CC2)c1] | (+/−) 2-(2-chloro-5-cyano-3-(4-(morpholine-2-carbonyl)piperazin-1-yl)phenylamino)-4-(cyclopropylamino)imidazo[1,2-f][1,2,4]triazine-7-carbonitrile | 548.01 | 3.59 |
| 95 | 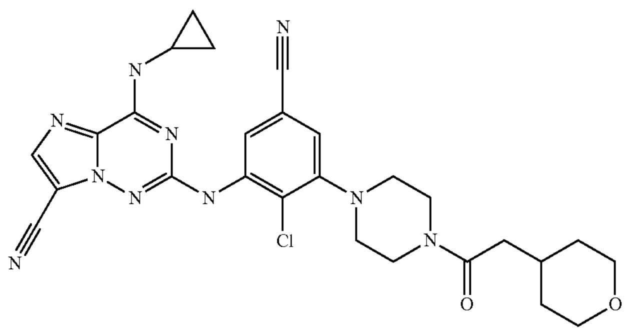 [SMILES: N#Cc1cc(Nc2nc(NC3CC3)c3ncc(C#N)n3n2)c(Cl)c(N2CCN(C(=O)CC3CCOCC3)CC2)c1] | 2-((2-chloro-5-cyano-3-(4-(tetrahydro-2H-pyran-4-ylacetyl)-1-piperazinyl)phenyl)amino)-4-(cyclopropylamino)imidazo[2,1-f][1,2,4]triazine-7-carbonitrile | 561.05 | 2.82 |
| 96 | 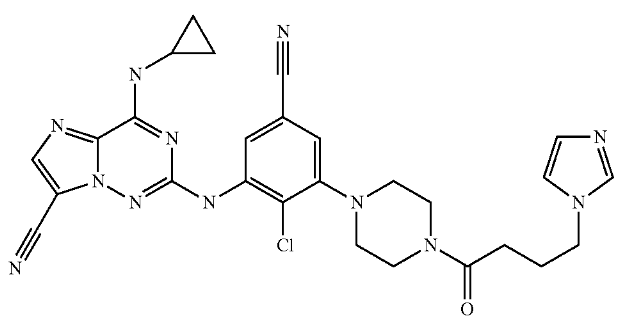 [SMILES: N#Cc1cc(Nc2nc(NC3CC3)c3ncc(C#N)n3n2)c(Cl)c(N2CCN(C(=O)CCCn3ccnc3)CC2)c1] | 2-((2-chloro-5-cyano-3-(4-(4-(1H-imidazol-1-yl)butanoyl)-1-piperazinyl)phenyl)amino)-4-(cyclopropylamino)imidazo[2,1-f][1,2,4]triazine-7-carbonitrile | 571.05 | 3.48 |
| 97 | 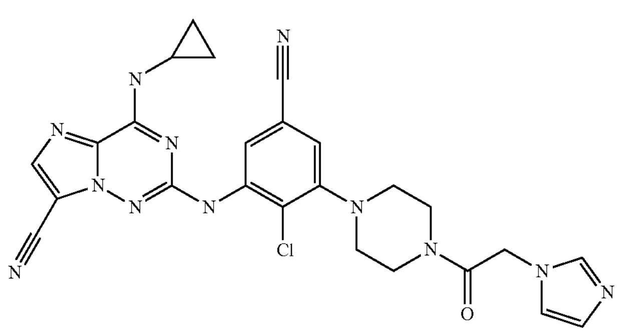 [SMILES: N#Cc1cc(Nc2nc(NC3CC3)c3ncc(C#N)n3n2)c(Cl)c(N2CCN(C(=O)Cn3ccnc3)CC2)c1] | 2-((2-chloro-5-cyano-3-(4-(1H-imidazol-1-ylacetyl)-1-piperazinyl)phenyl)amino)-4-(cyclopropylamino)imidazo[2,1-f][1,2,4]triazine-7-carbonitrile | 542.99 | 3.13 |

TABLE 2-continued

| Example No. | Structure | Name | [M + H]+ | HPLC Retention Time (min.) |
|---|---|---|---|---|
| 98 | 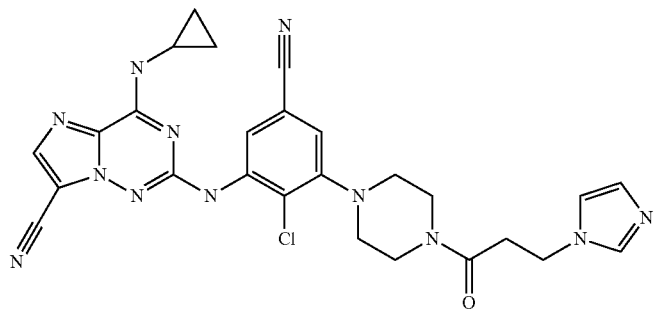 [SMILES: N#Cc1cc(Nc2nc(NC3CC3)c3ncc(C#N)n3n2)c(Cl)c(N2CCN(C(=O)CCn3ccnc3)CC2)c1] | | 557.02 | 3.78 |
| 99 | 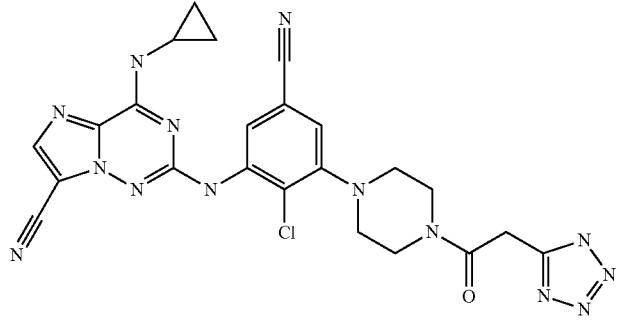 [SMILES: N#Cc1cc(Nc2nc(NC3CC3)c3ncc(C#N)n3n2)c(Cl)c(N2CCN(C(=O)Cc3nnn[nH]3)CC2)c1] | 2-((2-chloro-5-cyano-3-(4-(1H-tetrazol-5-ylacetyl)-1-piperazinyl)phenyl)amino)-4-(cyclopropylamino)imidazo[2,1-f][1,2,4]triazine-7-carbonitrile | 544.97 | 3.93 |
| 100 | 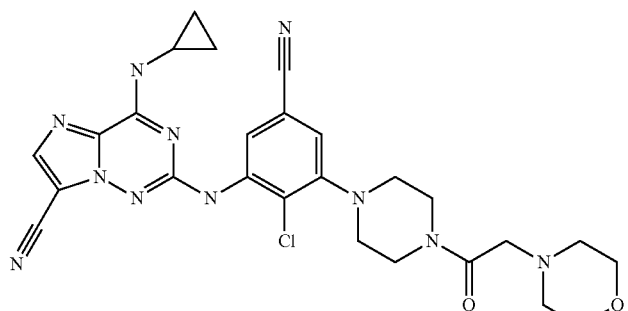 | 2-((2-chloro-5-cyano-3-(4-(4-morpholinylacetyl)-1-piperazinyl)phenyl)amino)-4-(cyclopropylamino)imidazo[2,1-f][1,2,4]triazine-7-carbonitrile | 562.04 | 3.76 |
| 101 | 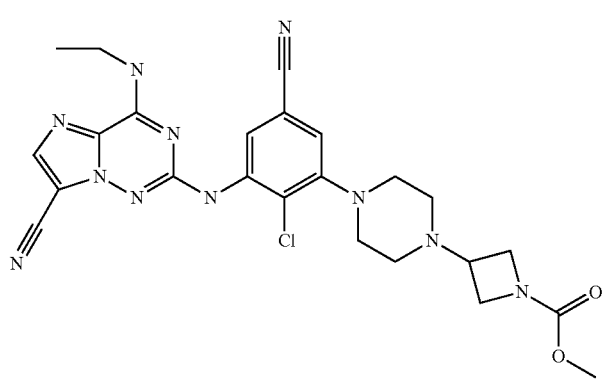 [SMILES: CCNc1nc(Nc2cc(C#N)cc(N3CCN(C4CN(C(=O)OC)C4)CC3)c2Cl)nn2c(C#N)cnc12] | methyl 3-(4-(2-chloro-5-cyano-3-((7-cyano-4-(ethylamino)imidazo[2,1-f][1,2,4]triazin-2-yl)amino)phenyl)-1-piperazinyl)-1-azetidinecarboxylate | 536.00 | 3.86 |

TABLE 2-continued

| Example No. | Structure | Name | [M + H]+ | HPLC Retention Time (min.) |
|---|---|---|---|---|
| 102 | Chiral | (+/−) 2-((2-chloro-5-cyano-3-(4-(trans-3-hydroxycyclobutyl)-1-piperazinyl)phenyl)amino)-4-(cyclopropylamino)imidazo[2,1-f][1,2,4]triazine-7-carbonitrile | 504.98 | 3.76 |
| 103 | 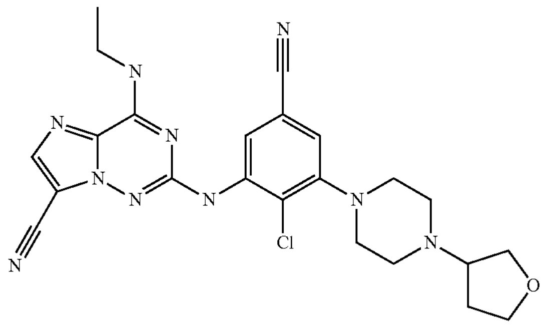 [SMILES: CCNc1nc(Nc2cc(C#N)cc(N3CCN(C4CCOC4)CC3)c2Cl)nn2c(C#N)cnc12] | (+/−) 2-((2-chloro-5-cyano-3-(4-(tetrahydro-3-furanyl)-1-piperazinyl)phenyl)amino)-4-(ethylamino)imidazo[2,1-f][1,2,4]triazine-7-carbonitrile | 492.97 | 3.82 |
| 104 | 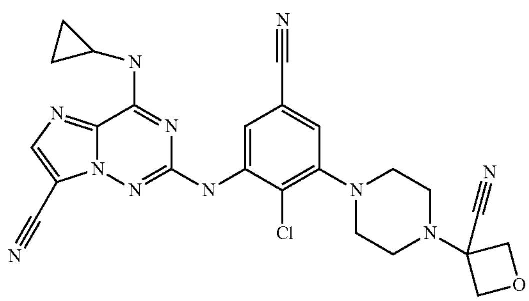 [SMILES: N#Cc1cc(Nc2nc(NC3CC3)c3ncc(C#N)n3n2)c(Cl)c(N2CCN(C3(C#N)COC3)CC2)c1] | 2-((2-chloro-5-cyano-3-(4-(3-cyano-3-oxetanyl)-1-piperazinyl)phenyl)amino)-4-(cyclopropylamino)imidazo[2,1-f][1,2,4]triazine-7-carbonitrile | 515.97 | 3.91 |
| 105 | 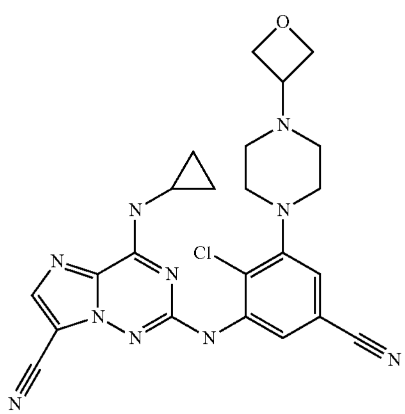 [SMILES: N#Cc1cc(Nc2nc(NC3CC3)c3ncc(C#N)n3n2)c(Cl)c(N2CCN(C3COC3)CC2)c1] | 2-(2-chloro-5-cyano-3-(4-(oxetan-3-yl)piperazin-1-yl)phenylamino)-4-(cyclopropylamino)imidazo[1,2-f][1,2,4]triazine-7-carbonitrile | 490.96 | 3.88 |

TABLE 2-continued

| Example No. | Structure | Name | [M + H]+ | HPLC Retention Time (min.) |
|---|---|---|---|---|
| 106 | 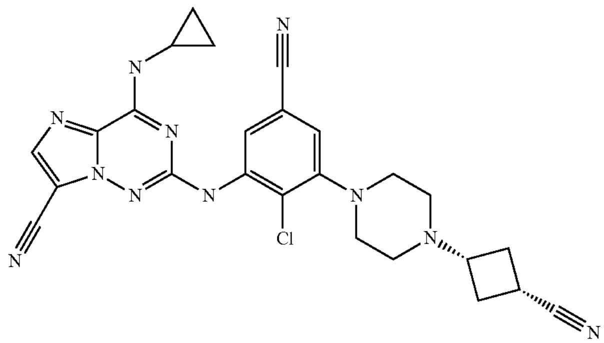 [SMILES: N#Cc1cc(Nc2nc(NC3CC3)c3ncc(C#N)n3n2)c(Cl)c(N2CCN([C@H]3C[C@@H](C#N)C3)CC2)c1] | (+/−) 2-((2-chloro-5-cyano-3-(4-(cis-3-cyanocyclobutyl)-1-piperazinyl)phenyl)amino)-4-(cyclopropylamino)imidazo[2,1-f][1,2,4]triazine-7-carbonitrile | 514.00 | 3.96 |
| 107 | 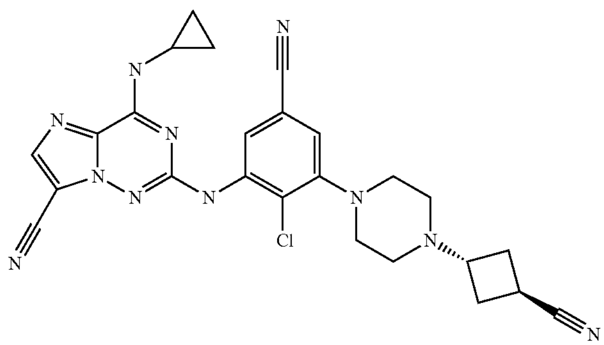 [SMILES: N#Cc1cc(Nc2nc(NC3CC3)c3ncc(C#N)n3n2)c(Cl)c(N2CCN([C@H]3C[C@H](C#N)C3)CC2)c1] | 2-((2-chloro-5-cyano-3-(4-(trans-3-cyanocyclobutyl)-1-piperazinyl)phenyl)amino)-4-(cyclopropylamino)imidazo[2,1-f][1,2,4]triazine-7-carbonitrile | 514.00 | 3.98 |

* = HPLC conditions
YMC S5 ODS 4.6 × 50 mm, 10-90% aqueous methanol containing 0.2% $H_3PO_4$, 5 min. gradient, monitored at 220 nm

Example 108

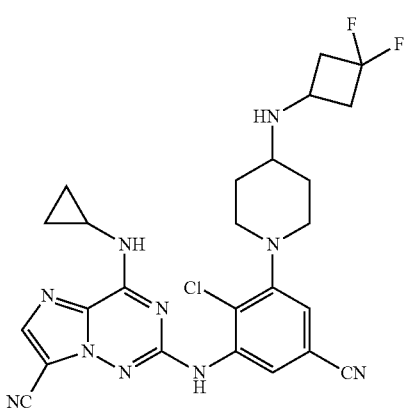 [SMILES: N#Cc1cc(Nc2nc(NC3CC3)c3ncc(C#N)n3n2)c(Cl)c(N2CCC(NC3CC(F)(F)C3)CC2)c1]

(108A): To a vial charged with 2-((2-chloro-5-cyano-3-(4-oxopiperidin-1-yl)phenyl)amino)-4-(cyclopropyl(4-methoxybenzyl)amino)imidazo[2,1-f][1,2,4]triazine-7-carbonitrile (Intermediate 13) (30 mg, 0.053 mmol) and 3,3-difluorocyclobutanamine (6.79 mg, 0.063 mmol) in methanol (132 µl) and tetrahydrofuran (132 µl) was added trimethyl orthoformate (58.4 µl, 0.528 mmol). The reaction mixture was stirred at room temperature. Sodium cyanoborohydride (6.64 mg, 0.106 mmol) was added and the reaction mixture was stirred at rt 6 h. The reaction mixture was diluted with water and methanol and filtered. The solid was taken up in DMF and partitioned between water and ethyl acetate. The aqueous layer was washed with ethyl acetate (3×). The combined organics were washed with 10% lithium chloride solution, dried over anhydrous sodium sulfate, filtered and concentrated in vacuo. The crude material was taken forward as is.

MS (ESI) m/z 659.5

Example 108

To a round bottom flask charged with 2-((2-chloro-5-cyano-3-(4-((3,3-difluorocyclobutyl)amino)piperidin-1-yl)phenyl)amino)-4-(cyclopropyl(4-methoxybenzyl)amino)imidazo[2,1-f][1,2,4]triazine-7-carbonitrile (34.9 mg, 0.053 mmol) in dichloromethane (530 µl) was added anisole (116 µl, 1.060 mmol), followed by the slow addition of trifluoroacetic acid (408 µl, 5.30 mmol). The reaction mixture was stirred at rt 2 d. Excess TFA was removed in vacuo. The crude residue was taken up in MeOH and free based using a Phenomenex Strata 1 g SCX column. The crude solid was purified via preparative LC/MS and provided 2-((2-chloro-5-cyano-3-(4-((3,3-difluorocyclobutyl)amino)piperidin-1-yl)phenyl)amino)-4-(cyclopropylamino)imidazo[2,1-f][1,2,4]triazine-7-carbonitrile (3.4 mg).

MS (ESI) m/z 539.1

$^1$H NMR (500 MHz, DMSO-$d_6$) δ 9.33 (d, J=4.0 Hz, 1H), 8.83 (s, 1H), 8.19 (s, 1H), 8.07 (d, J=1.3 Hz, 1H), 7.28 (d, J=1.3 Hz, 1H), 3.26 (d, J=11.8 Hz, 1H), 3.03-2.92 (m, 1H), 2.84-2.66 (m, 4H), 2.59 (br. s., 1H), 2.35 (d, J=11.4 Hz, 2H), 1.87 (d, J=11.1 Hz, 2H), 1.51-1.36 (m, 2H), 0.78 (d, J=5.4 Hz, 4H)

The compounds listed below were prepared by the similar synthetic procedure used for Examples 108

TABLE 3

| Example No. | Structure | Name | [M + H]+ | HPLC Retention Time (min.)* |
|---|---|---|---|---|
| 109 | 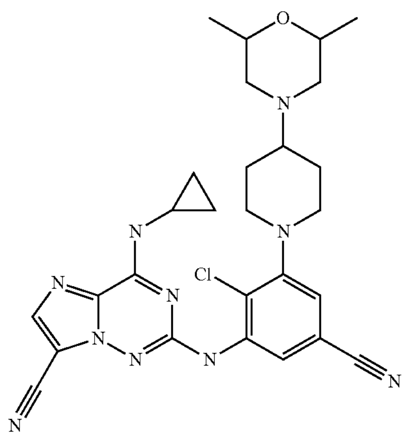 [SMILES: CC1CN(C2CCN(c3cc(C#N)cc(Nc4nc(NC5CC5)c5ncc(C#N)n5n4)c3Cl)CC2)CC(C)O1] | (+/−) 2-((2-chloro-5-cyano-3-(4-(2,6-dimethyl-4-morpholinyl)-1-piperidinyl)phenyl)amino)-4-(cyclopropylamino)imidazo[2,1-f][1,2,4]triazine-7-carbonitrile | 547.06 | 3.57 |
| 110 | 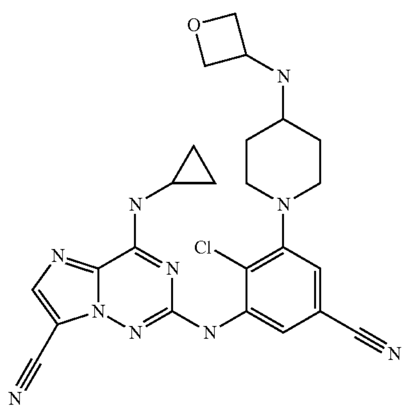 [SMILES: N#Cc1cc(Nc2nc(NC3CC3)c3ncc(C#N)n3n2)c(Cl)c(N2CCC(NC3COC3)CC2)c1] | 2-((2-chloro-5-cyano-3-(4-(3-oxetanylamino)-1-piperidinyl)phenyl)amino)-4-(cyclopropylamino)imidazo[2,1-f][1,2,4]triazine-7-carbonitrile | 504.98 | 3.78 |
| 111 | 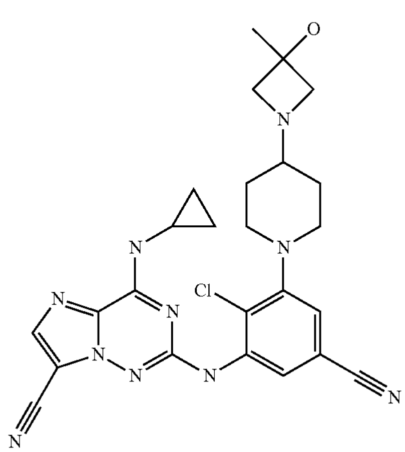 [SMILES: CC1(O)CN(C2CCN(c3cc(C#N)cc(Nc4nc(NC5CC5)c5ncc(C#N)n5n4)c3Cl)CC2)C1] | 2-(2-chloro-5-cyano-3-(4-(3-hydroxy-3-methylazetidin-1-yl)piperidin-1-yl)phenylamino)-4-(cyclopropylamino)imidazo[1,2-f][1,2,4]triazine-7-carbonitrile | 519.01 | 3.88 |

TABLE 3-continued

| Example No. | Structure | Name | [M + H]+ | HPLC Retention Time (min.)* |
|---|---|---|---|---|
| 112 | 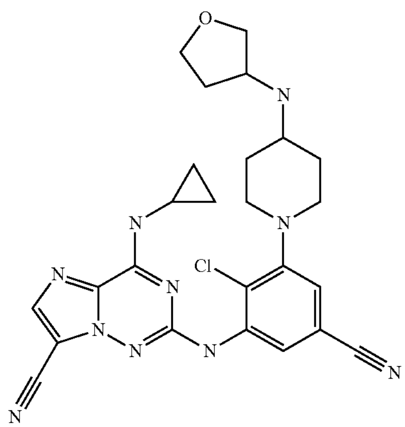 [SMILES: N#Cc1cc(Nc2nc(NC3CC3)c3ncc(C#N)n3n2)c(Cl)c(N2CCC(NC3CCOC3)CC2)c1] | (+/−) 2-((2-chloro-5-cyano-3-(4-(tetrahydro-3-furanylamino)-1-piperidinyl)phenyl)amino)-4-(cyclopropylamino)imidazo[2,1-f][1,2,4]triazine-7-carbonitrile | 519.01 | 1.7 |
| 113 | 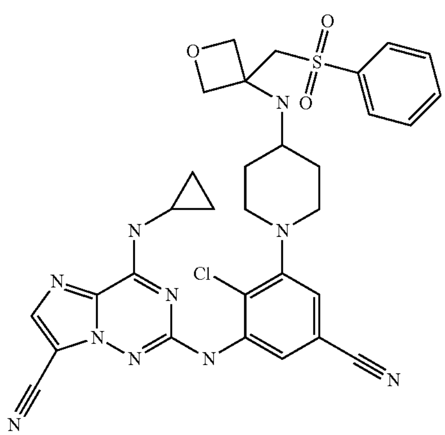 [SMILES: N#Cc1cc(Nc2nc(NC3CC3)c3ncc(C#N)n3n2)c(Cl)c(N2CCC(NC3(CS(=O)(=O)c4ccccc4)COC3)CC2)c1] | (+/−) 2-((2-chloro-5-cyano-3-(4-((3-((phenylsulfonyl)methyl)-3-oxetanyl)amino)-1-piperidinyl)phenyl)amino)-4-(cyclopropylamino)imidazo[2,1-f][1,2,4]triazine-7-carbonitrile | 659.17 | 4.72 |
| 114 | 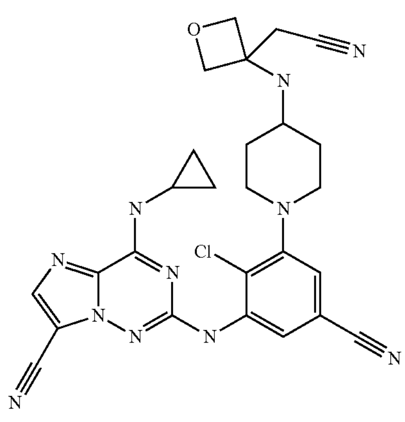 [SMILES: N#CCC1(NC2CCN(c3cc(C#N)cc(Nc4nc(NC5CC5)c5ncc(C#N)n5n4)c3Cl)CC2)COC1] | (+/−) 2-((2-chloro-5-cyano-3-(4-((3-(cyanomethyl)-3-oxetanyl)amino)-1-piperidinyl)phenyl)amino)-4-(cyclopropylamino)imidazo[2,1-f][1,2,4]triazine-7-carbonitrile | 544.02 | 3.79 |

TABLE 3-continued

| Example No. | Name | [M + H]+ | HPLC Retention Time (min.)* |
|---|---|---|---|
| 115 | 2-((2-chloro-5-cyano-3-(4-(isopropylamino)-1-piperidinyl)phenyl)amino)-4-(cyclopropylamino)imidazo[2,1-f][1,2,4]triazine-7-carbonitrile | 491.00 | 3.93 |
| 116 | (+/−) 2-((2-chloro-5-cyano-3-(4-((1-methyl-5-oxo-3-pyrrolidinyl)amino)-1-piperidinyl)phenyl)amino)-4-(cyclopropylamino)imidazo[2,1-f][1,2,4]triazine-7-carbonitrile | 546.04 | 3.81 |
| 117 | (+/−) 2-((2-chloro-5-cyano-3-(4-((1,1-dioxidotetrahydro-3-thiophenyl)amino)-1-piperidinyl)phenyl)amino)-4-(cyclopropylamino)imidazo[2,1-f][1,2,4]triazine-7-carbonitrile | 567.08 | 3.83 |
| 118 | ethyl 4-((1-(2-chloro-5-cyano-3-((7-cyano-4-(cyclopropylamino)imidazo[2,1-f][1,2,4]triazin-2-yl)amino)phenyl)-4-piperidinyl)amino)-1-piperidinecarboxylate | 604.12 | 4.13 |

TABLE 3-continued

| Example No. | Structure | Name | [M + H]+ | HPLC Retention Time (min.)* |
|---|---|---|---|---|
| 119 | 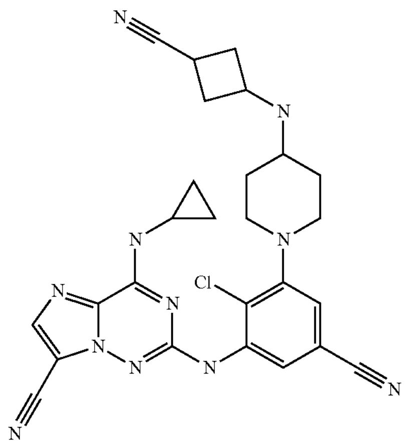 [SMILES: N#Cc1cc(Nc2nc(NC3CC3)c3ncc(C#N)n3n2)c(Cl)c(N2CCC(NC3CC(C#N)C3)CC2)c1] | (+/−) 2-((2-chloro-5-cyano-3-(4-((3-cyanocyclobutyl)amino)-1-piperidinyl)phenyl)amino)-4-(cyclopropylamino)imidazo[2,1-f][1,2,4]triazine-7-carbonitrile | 528.02 | 3.83 |
| 120 | 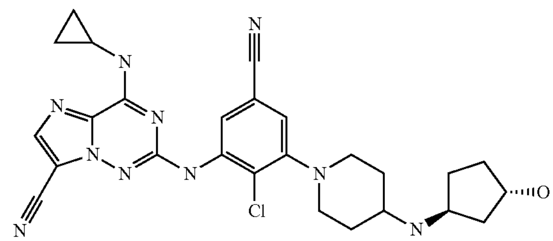 [SMILES: N#Cc1cc(Nc2nc(NC3CC3)c3ncc(C#N)n3n2)c(Cl)c(N2CCC(N[C@H]3CC[C@H](O)C3)CC2)c1] | (+/−) 2-((2-chloro-5-cyano-3-(4-(((1S,3S)-3-hydroxycyclopentyl)amino)-1-piperidinyl)phenyl)amino)-4-(cyclopropylamino)imidazo[2,1-f][1,2,4]triazine-7-carbonitrile | 533.04 | 3.69 |
| 121 | 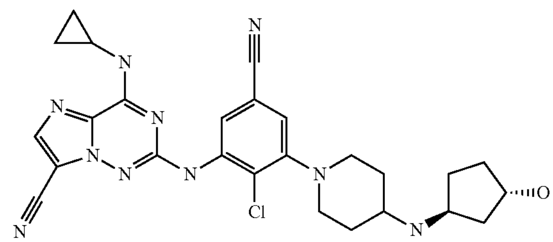 [SMILES: N#Cc1cc(Nc2nc(NC3CC3)c3ncc(C#N)n3n2)c(Cl)c(N2CCC(N[C@H]3CC[C@H](O)C3)CC2)c1] | (+/−) 2-((2-chloro-5-cyano-3-(4-(((1R,3S)-3-hydroxycyclopentyl)amino)-1-piperidinyl)phenyl)amino)-4-(cyclopropylamino)imidazo[2,1-f][1,2,4]triazine-7-carbonitrile | 533.04 | 3.71 |
| 122 | 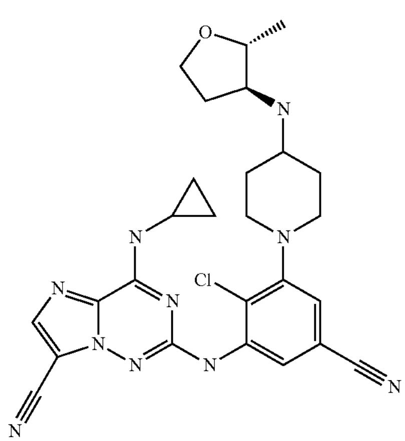 [SMILES: C[C@H]1OCC[C@@H]1NC1CCN(c2cc(C#N)cc(Nc3nc(NC4CC4)c4ncc(C#N)n4n3)c2Cl)CC1] | (+/−) 2-((2-chloro-5-cyano-3-(4-(((2R,3S)-2-methyltetrahydro-3-furanyl)amino)-1-piperidinyl)phenyl)amino)-4-(cyclopropylamino)imidazo[2,1-f][1,2,4]triazine-7-carbonitrile | 533.04 | 3.86 |

TABLE 3-continued

| Example No. | Name | [M + H]+ | HPLC Retention Time (min.)* |
|---|---|---|---|
| 123 | (+/−) 2-((2-chloro-5-cyano-3-(4-(((2S,3S)-2-methyltetrahydro-3-furanyl)amino)-1-piperidinyl)phenyl)amino)-4-(cyclopropylamino)imidazo[2,1-f][1,2,4]triazine-7-carbonitrile | 533.04 | 3.88 |
| 124 | 2-((2-chloro-5-cyano-3-(4-((1,2,2,6,6-pentamethyl-4-piperidinyl)amino)-1-piperidinyl)phenyl)amino)-4-(cyclopropylamino)imidazo[2,1-f][1,2,4]triazine-7-carbonitrile | 602.19 | 3.76 |
| 125 | 2-((2-chloro-5-cyano-3-(4-(tetrahydro-2H-pyran-4-ylamino)-1-piperidinyl)phenyl)amino)-4-(cyclopropylamino)imidazo[2,1-f][1,2,4]triazine-7-carbonitrile | 533.04 | 3.97 |
| 126 | 2-((2-chloro-5-cyano-3-(4-((2,2,2-trifluoroethyl)amino)-1-piperidinyl)phenyl)amino)-4-(cyclopropylamino)imidazo[2,1-f][1,2,4]triazine-7-carbonitrile | 530.94 | 3.93 |

TABLE 3-continued

| Example No. | Structure | Name | [M + H]+ | HPLC Retention Time (min.)* |
|---|---|---|---|---|
| 127 | 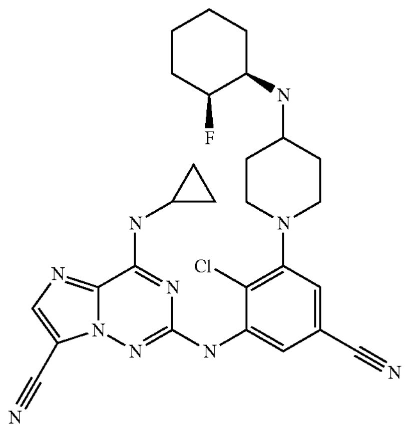 [SMILES: N#Cc1cc(Nc2nc(NC3CC3)c3ncc(C#N)n3n2)c(Cl)c(N2CCC(N[C@@H]3CCCC[C@@H]3F)CC2)c1] | (+/−) 2-(2-chloro-5-cyano-3-(4-((1R,2R)-2-fluorocyclohexylamino)piperidin-1-yl)phenylamino)-4-(cyclopropylamino)imidazo[1,2-f][1,2,4]triazine-7-carbonitrile | 549.06 | 3.86 |
| 128 | 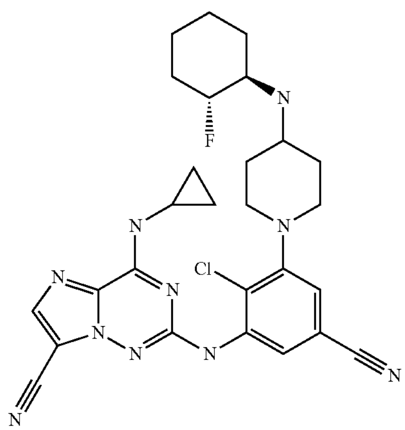 [SMILES: N#Cc1cc(Nc2nc(NC3CC3)c3ncc(C#N)n3n2)c(Cl)c(N2CCC(N[C@@H]3CCCC[C@H]3F)CC2)c1] | (+/−) 2-(2-chloro-5-cyano-3-(4-((1R,2S)-2-fluorocyclohexylamino)piperidin-1-yl)phenylamino)-4-(cyclopropylamino)imidazo[1,2-f][1,2,4]triazine-7-carbonitrile | 549.06 | 3.75 |
| 129 | 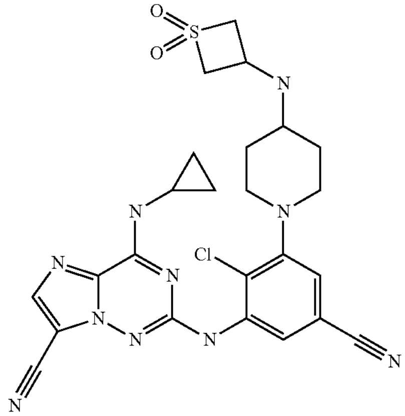 [SMILES: N#Cc1cc(Nc2nc(NC3CC3)c3ncc(C#N)n3n2)c(Cl)c(N2CCC(NC3CS(=O)(=O)C3)CC2)c1] | 2-((2-chloro-5-cyano-3-(4-((1,1-dioxido-3-thietanyl)amino)-1-piperidinyl)phenyl)amino)-4-(cyclopropylamino)imidazo[2,1-f][1,2,4]triazine-7-carbonitrile | 553.05 | 3.62 |

TABLE 3-continued

| Example No. | Structure | Name | [M + H]+ | HPLC Retention Time (min.)* |
|---|---|---|---|---|
| 130 | 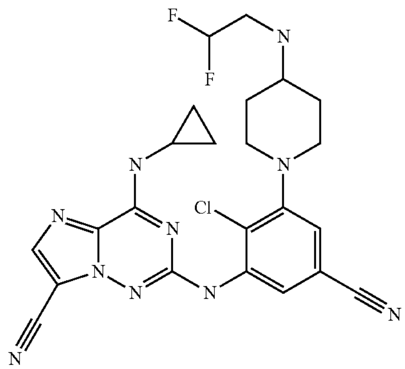 [SMILES: N#Cc1cc(Nc2nc(NC3CC3)c3ncc(C#N)n3n2)c(Cl)c(N2CCC(NCC(F)F)CC2)c1] | 2-((2-chloro-5-cyano-3-(4-((2,2-difluoroethyl)amino)-1-piperidinyl)phenyl)amino)-4-(cyclopropylamino)imidazo[2,1-f][1,2,4]triazine-7-carbonitrile | 512.95 | 3.85 |
| 131 | 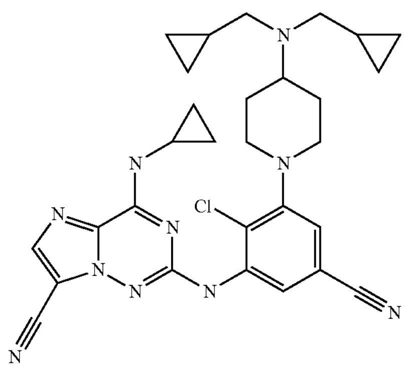 [SMILES: N#Cc1cc(Nc2nc(NC3CC3)c3ncc(C#N)n3n2)c(Cl)c(N2CCC(N(CC3CC3)CC3CC3)CC2)c1] | 2-((3-(4-(bis(cyclopropylmethyl)amino)-1-piperidinyl)-2-chloro-5-cyanophenyl)amino)-4-(cyclopropylamino)imidazo[2,1-f][1,2,4]triazine-7-carbonitrile | 557.10 | 3.31 |
| 132 | 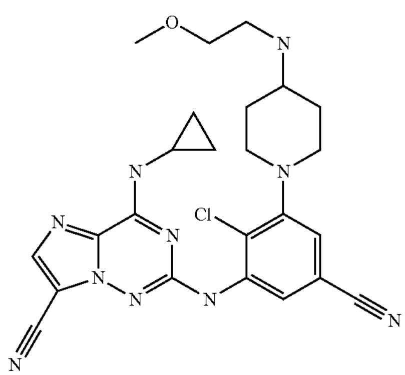 [SMILES: COCCNC1CCN(c2cc(C#N)cc(Nc3nc(NC4CC4)c4ncc(C#N)n4n3)c2Cl)CC1] | 2-((2-chloro-5-cyano-3-(4-((2-methoxyethyl)amino)-1-piperidinyl)phenyl)amino)-4-(cyclopropylamino)imidazo[2,1-f][1,2,4]triazine-7-carbonitrile | 507.00 | 3.11 |
| 133 | 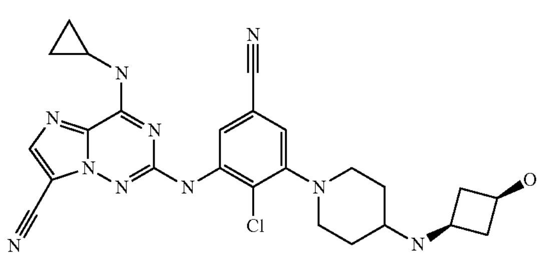 [SMILES: N#Cc1cc(Nc2nc(NC3CC3)c3ncc(C#N)n3n2)c(Cl)c(N2CCC(N[C@H]3C[C@@H](O)C3)CC2)c1] | (+/−) 2-((2-chloro-5-cyano-3-(4-((cis-3-hydroxycyclobutyl)amino)-1-piperidinyl)phenyl)amino)-4-(cyclopropylamino)imidazo[2,1-f][1,2,4]triazine-7-carbonitrile | 519.01 | 3.18 |

TABLE 3-continued

| Example No. | Structure | Name | [M + H]+ | HPLC Retention Time (min.)* |
|---|---|---|---|---|
| 134 | 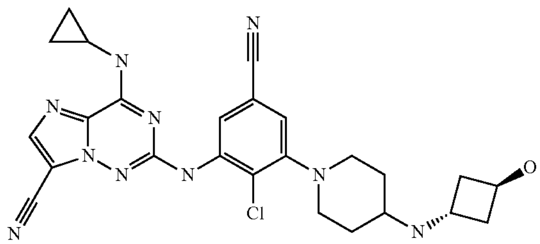 [SMILES: N#Cc1cc(Nc2nc(NC3CC3)c3ncc(C#N)n3n2)c(Cl)c(N2CCC(N[C@H]3C[C@H](O)C3)CC2)c1] | (+/−) 2-((2-chloro-5-cyano-3-(4-((trans-3-hydroxycyclobutyl)amino)-1-piperidinyl)phenyl)amino)-4-(cyclopropylamino)imidazo[2,1-f][1,2,4]triazine-7-carbonitrile | 519.01 | 4.18 |
| 135 | 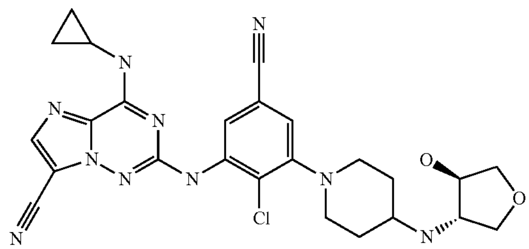 [SMILES: N#Cc1cc(Nc2nc(NC3CC3)c3ncc(C#N)n3n2)c(Cl)c(N2CCC(N[C@H]3COC[C@@H]3O)CC2)c1] | (+/−) 2-((2-chloro-5-cyano-3-(4-(((3S,4R)-4-hydroxytetrahydro-3-furanyl)amino)-1-piperidinyl)phenyl)amino)-4-(cyclopropylamino)imidazo[2,1-f][1,2,4]triazine-7-carbonitrile | 535.01 | 3.81 |
| 136 | 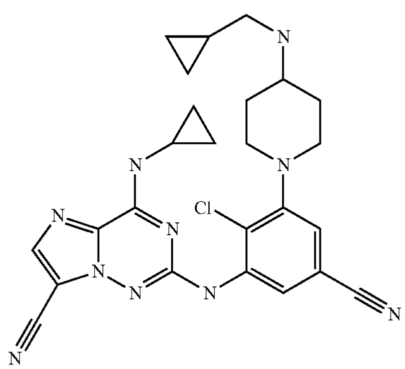 [SMILES: N#Cc1cc(Nc2nc(NC3CC3)c3ncc(C#N)n3n2)c(Cl)c(N2CCC(NCC3CC3)CC2)c1] | 2-((2-chloro-5-cyano-3-(4-((cyclopropylmethyl)amino)-1-piperidinyl)phenyl)amino)-4-(cyclopropylamino)imidazo[2,1-f][1,2,4]triazine-7-carbonitrile | 503.01 | 4.41 |
| 137 | Chiral | 2-((2-chloro-5-cyano-3-(4-(((2R)-2-fluoro-3-hydroxy-3-methylbutyl)amino)-1-piperidinyl)phenyl)amino)-4-(cyclopropylamino)imidazo[2,1-f][1,2,4]triazine-7-carbonitrile | 553.04 | 3.71 |
| 138 | 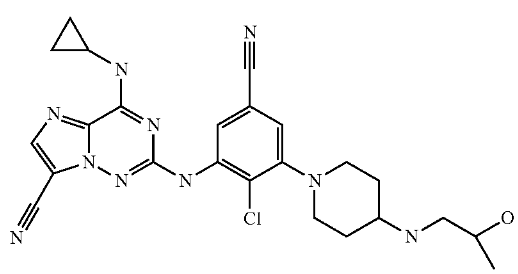 [SMILES: CC(O)CNC1CCN(c2cc(C#N)cc(Nc3nc(NC4CC4)c4ncc(C#N)n4n3)c2Cl)CC1] | (+/−). 2-(2-chloro-5-cyano-3-(4-(2-hydroxypropylamino)piperidin-1-yl)phenylamino)-4-(cyclopropylamino)imidazo[2,1-f][1,2,4]triazine-7-carbonitrile | 507.00 | 3.99 |

TABLE 3-continued

| Example No. | Structure | Name | [M + H]+ | HPLC Retention Time (min.)* |
|---|---|---|---|---|
| 139 | 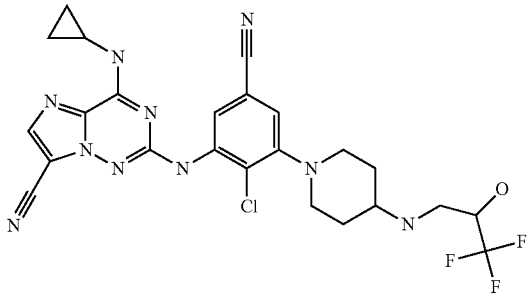 [SMILES: N#Cc1cc(Nc2nc(NC3CC3)c3ncc(C#N)n3n2)c(Cl)c(N2CCC(NCC(O)C(F)(F)F)CC2)c1] | (+/−) 2-((2-chloro-5-cyano-3-(4-((3,3,3-trifluoro-2-hydroxypropyl)amino)-1-piperidinyl)phenyl)amino)-4-(cyclopropylamino)imidazo[2,1-f][1,2,4]triazine-7-carbonitrile | 560.97 | 3.34 |
| 140 | 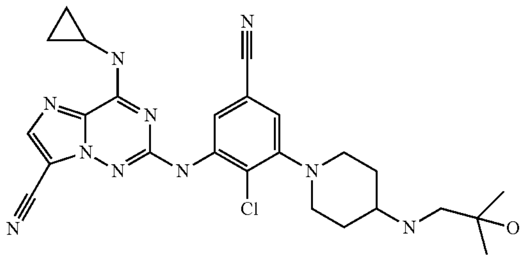 [SMILES: CC(C)(O)CNC1CCN(c2cc(C#N)cc(Nc3nc(NC4CC4)c4ncc(C#N)n4n3)c2Cl)CC1] | 2-((2-chloro-5-cyano-3-(4-((2-hydroxy-2-methylpropyl)amino)-1-piperidinyl)phenyl)amino)-4-(cyclopropylamino)imidazo[2,1-f][1,2,4]triazine-7-carbonitrile | 521.03 | 3.28 |
| 141 | 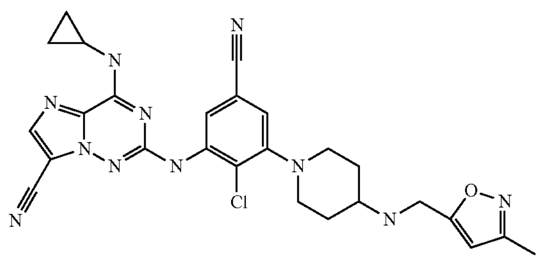 [SMILES: Cc1cc(CNC2CCN(c3cc(C#N)cc(Nc4nc(NC5CC5)c5ncc(C#N)n5n4)c3Cl)CC2)on1] | 2-(2-chloro-5-cyano-3-(4-((3-methylisoxazol-5-yl)methylamino)piperidin-1-yl)phenylamino)-4-(cyclopropylamino)imidazo[1,2-f][1,2,4]triazine-7-carbonitrile | 544.02 | 3.97 |
| 142 | 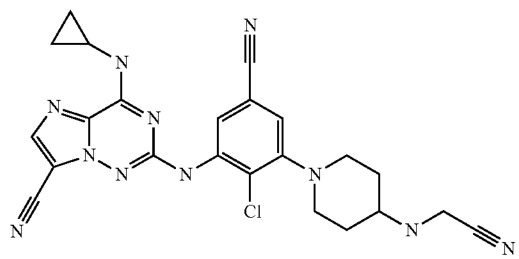 [SMILES: N#CCNC1CCN(c2cc(C#N)cc(Nc3nc(NC4CC4)c4ncc(C#N)n4n3)c2Cl)CC1] | 2-((2-chloro-5-cyano-3-(4-((cyanomethyl)amino)-1-piperidinyl)phenyl)amino)-4-(cyclopropylamino)imidazo[2,1-f][1,2,4]triazine-7-carbonitrile | 487.96 | 2.98 |
| 143 | 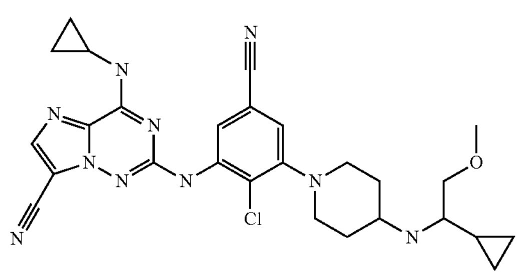 [SMILES: COCC(NC1CCN(c2cc(C#N)cc(Nc3nc(NC4CC4)c4ncc(C#N)n4n3)c2Cl)CC1)C1CC1] | (+/−) 2-((2-chloro-5-cyano-3-(4-((1-cyclopropyl-2-methoxyethyl)amino)-1-piperidinyl)phenyl)amino)-4-(cyclopropylamino)imidazo[2,1-f][1,2,4]triazine-7-carbonitrile | 547.06 | 3.91 |

TABLE 3-continued

| Example No. | Structure | Name | [M + H]+ | HPLC Retention Time (min.)* |
|---|---|---|---|---|
| 144 | 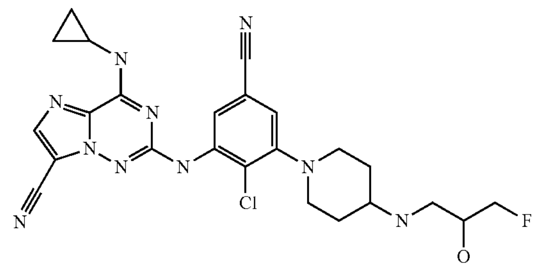 [SMILES: N#Cc1cc(Nc2nc(NC3CC3)c3ncc(C#N)n3n2)c(Cl)c(N2CCC(NCC(O)CF)CC2)c1] | (+/−) 2-((2-chloro-5-cyano-3-(4-((3-fluoro-2-hydroxypropyl)amino)-1-piperidinyl)phenyl)amino)-4-(cyclopropylamino)imidazo[2,1-f][1,2,4]triazine-7-carbonitrile | 524.99 | 3.43 |
| 145 | 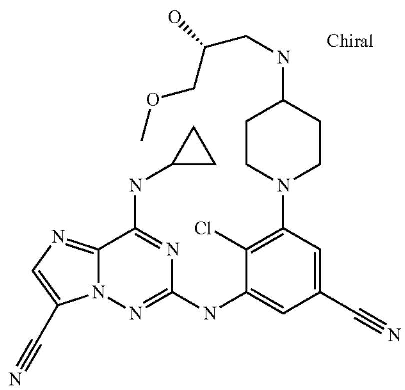 [SMILES: COC[C@H](O)CNC1CCN(c2cc(C#N)cc(Nc3nc(NC4CC4)c4ncc(C#N)n4n3)c2Cl)CC1] | 2-((2-chloro-5-cyano-3-(4-(((2R)-2-hydroxy-3-methoxypropyl)amino)-1-piperidinyl)phenyl)amino)-4-(cyclopropylamino)imidazo[2,1-f][1,2,4]triazine-7-carbonitrile | 537.03 | 2.67 |
| 146 | 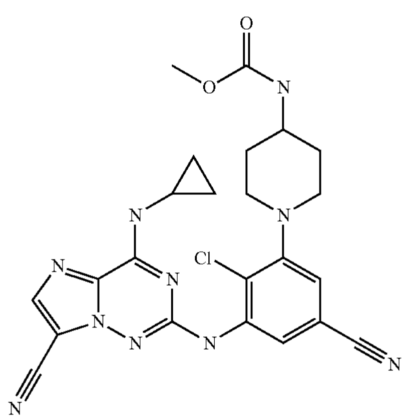 [SMILES: COC(=O)NC1CCN(c2cc(C#N)cc(Nc3nc(NC4CC4)c4ncc(C#N)n4n3)c2Cl)CC1] | methyl (1-(2-chloro-5-cyano-3-((7-cyano-4-(cyclopropylamino)imidazo[2,1-f][1,2,4]triazin-2-yl)amino)phenyl)-4-piperidinyl)carbamate | 506.96 | 3.26 |
| 147 | 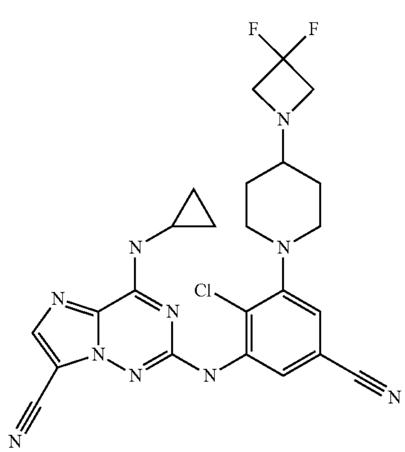 [SMILES: N#Cc1cc(Nc2nc(NC3CC3)c3ncc(C#N)n3n2)c(Cl)c(N2CCC(N3CC(F)(F)C3)CC2)c1] | 2-((2-chloro-5-cyano-3-(4-(3,3-difluoro-1-azetidinyl)-1-piperidinyl)phenyl)amino)-4-(cyclopropylamino)imidazo[2,1-f][1,2,4]triazine-7-carbonitrile | 524.97 | 3.69 |

TABLE 3-continued

| Example No. | Structure | Name | [M + H]+ | HPLC Retention Time (min.)* |
|---|---|---|---|---|
| 148 | 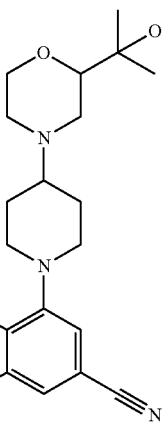 | (+/−) 2-((2-chloro-5-cyano-3-(4-(2-(1-hydroxy-1-methylethyl)-4-morpholinyl)-1-piperidinyl)phenyl)amino)-4-(cyclopropylamino)imidazo[2,1-f][1,2,4]triazine-7-carbonitrile | 577.09 | 3.67 |
| 149 | 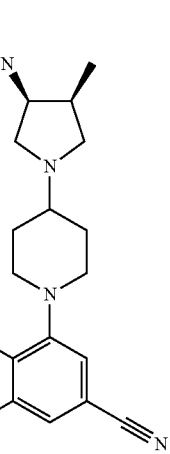 | (+/−) methyl ((3S,4S)-1-(1-(2-chloro-5-cyano-3-((7-cyano-4-(cyclopropylamino)imidazo[2,1-f][1,2,4]triazin-2-yl)amino)phenyl)-4-piperidinyl)-4-methyl-3-pyrrolidinyl)carbamate | 590.09 | 3.96 |
| 150 | 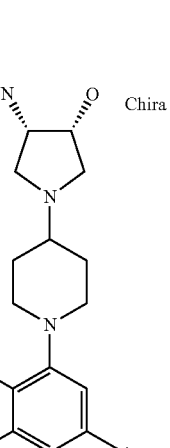 | methyl ((3S,4R)-1-(1-(2-chloro-5-cyano-3-((7-cyano-4-(cyclopropylamino)imidazo[2,1-f][1,2,4]triazin-2-yl)amino)phenyl)-4-piperidinyl)-4-methoxy-3-pyrrolidinyl)carbamate | 606.09 | 3.59 |

* = HPLC conditions
YMC S5 ODS 4.6 × 50 mm, 10-90% aqueous methanol containing 0.2% H₃PO₄, 5 min. gradient,

Example 151

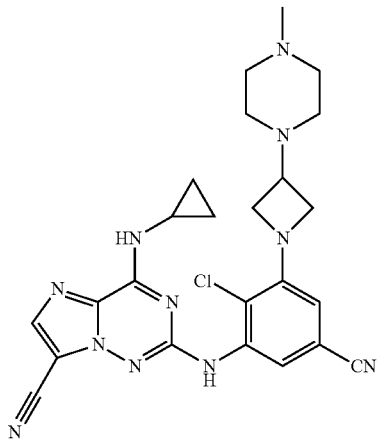 [SMILES: CN1CCN(C2CN(c3cc(C#N)cc(Nc4nc(NC5CC5)c5ncc(C#N)n5n4)c3Cl)C2)CC1]

2-((2-chloro-5-cyano-3-(3-(4-methylpiperazin-1-yl)azetidin-1-yl)phenyl)amino)-4-(cyclopropylamino)imidazo[2,1-f][1,2,4]triazine-7-carbonitrile (151A): A mixture of benzyl 3-oxoazetidine-1-carboxylate (1.026 g, 5 mmol), 1-methylpiperazine (0.833 mL, 7.50 mmol) and acetic acid (0.429 mL, 7.50 mmol) in 1,2-dichloroethane (5 mL) was stirred at room temperature for 3 h. sodium triacetoxyborohydride (2.119 g, 10.00 mmol) was added and the reaction mixture was stirred at room temperature overnight. A small amount of water was added to the reaction mixture and the reaction mixture was directly loaded onto a 120 g ISCO column and eluted with 1-12% 2N ammonia in methanol/dichloromethane). benzyl 3-(4-methylpiperazin-1-yl)azetidine-1-carboxylate (1.45 g) was obtained as a brown oil.

MS (ESI) m/z 290.2

$^1$H NMR (400 MHz, chloroform-d) δ 7.39-7.28 (m, 5H), 5.09 (s, 2H), 4.05-3.97 (m, 2H), 3.89 (dd, J=9.0, 5.3 Hz, 2H), 3.20-3.10 (m, 1H), 2.66-2.35 (m, 13H), 2.32 (s, 3H), 2.01 (s, 1H).

(151B): A mixture of benzyl 3-(4-methylpiperazin-1-yl)azetidine-1-carboxylate (1.45 g, 5.01 mmol) and Pd/C (0.320 g, 0.150 mmol) in methanol (30 mL) was hydrogenated at 30 psi over the weekend. The reaction mixture was filtered through celite and the filtrate was concentrated. The crude product 1-(azetidin-3-yl)-4-methylpiperazine (0.78 g, 5.02 mmol, 100% yield) was obtained as a colorless oil and used without purification.

MS (ESI) m/z 156.1

(151C): The title compound 3-amino-4-chloro-5-(3-(4-methylpiperazin-1-yl)azetidin-1-yl)benzonitrile was prepared starting from 1-(azetidin-3-yl)-4-methylpiperazine using a method analogous to that used to prepare Example 1A-B.

MS (ESI) m/z 306.2

Example 151

The title compound was prepared from 3-amino-4-chloro-5-(3-(4-methylpiperazin-1-yl)azetidin-1-yl)benzonitrile using a method analogous to that used to prepare Example 1.

MS (ESI) m/z 504.4

$^1$H NMR (500 MHz, chloroform-d) δ 8.50 (d, J=1.7 Hz, 1H), 7.87 (s, 1H), 7.51 (s, 1H), 6.72 (d, J=1.7 Hz, 1H), 6.48 (d, J=1.7 Hz, 1H), 4.28 (t, J=7.4 Hz, 2H), 3.94 (dd, J=7.6, 6.0 Hz, 2H), 3.30 (quin, J=6.3 Hz, 1H), 3.06 (tq, J=7.1, 3.5 Hz, 1H), 2.51 (br. s., 8H), 2.34 (s, 3H), 1.69 (s, 2H), 1.15-1.08 (m, 2H), 0.85-0.79 (m, 2H).

The compounds listed below were prepared by the similar synthetic procedure used for Examples 151

TABLE 4

| Example No. | Structure | Name | [M + H]⁺ | HPLC Retention Time (min.)* |
|---|---|---|---|---|
| 152 | 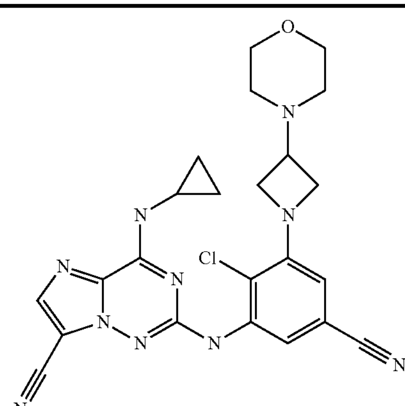 | 2-((2-chloro-5-cyano-3-(3-(4-morpholinyl)-1-azetidinyl)phenyl)amino)-4-(cyclopropylamino)imidazo[2,1-f][1,2,4]triazine-7-carbonitrile | 490.96 | 3.67 |

TABLE 4-continued

| Example No. | Structure | Name | [M + H]+ | HPLC Retention Time (min.)* |
|---|---|---|---|---|
| 153 | 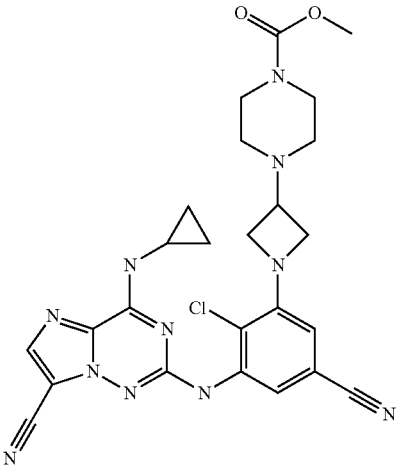 [SMILES: COC(=O)N1CCN(C2CN(c3cc(C#N)cc(Nc4nc(NC5CC5)c5ncc(C#N)n5n4)c3Cl)C2)CC1] | methyl 4-(1-(2-chloro-5-cyano-3-((7-cyano-4-(cyclopropylamino)imidazo[2,1-f][1,2,4]triazin-2-yl)amino)phenyl)-3-azetidinyl)-1-piperazinecarboxylate | 548.01 | 3.82 |
| 154 | 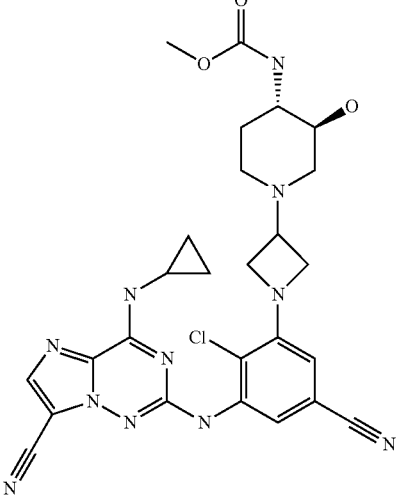 | (+/−) methyl ((3S,4S)-1-(1-(2-chloro-5-cyano-3-((7-cyano-4-(cyclopropylamino)imidazo[2,1-f][1,2,4]triazin-2-yl)amino)phenyl)-3-azetidinyl)-3-hydroxy-4-piperidinyl)carbamate | 578.03 | 4.31 |
| 155 | 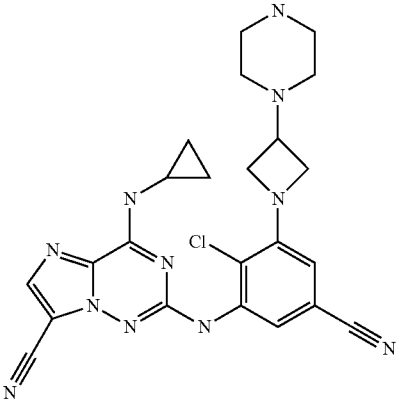 [SMILES: N#Cc1cc(Nc2nc(NC3CC3)c3ncc(C#N)n3n2)c(Cl)c(N2CC(N3CCNCC3)C2)c1] | 2-((2-chloro-5-cyano-3-(3-(1-piperazinyl)-1-azetidinyl)phenyl)amino)-4-(cyclopropylamino)imidazo[2,1-f][1,2,4]triazine-7-carbonitrile | 489.97 | 3.12 |

TABLE 4-continued

| Example No. | Structure | Name | [M + H]⁺ | HPLC Retention Time (min.)* |
|---|---|---|---|---|
| 156 | 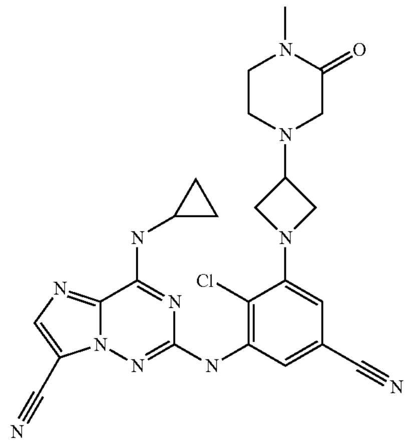 [SMILES: CN1CCN(C2CN(c3cc(C#N)cc(Nc4nc(NC5CC5)c5ncc(C#N)n5n4)c3Cl)C2)CC1=O] | 2-((2-chloro-5-cyano-3-(3-(4-methyl-3-oxo-1-piperazinyl)-1-azetidinyl)phenyl)amino)-4-(cyclopropylamino)imidazo[2,1-f][1,2,4]triazine-7-carbonitrile | 517.98 | 3.72 |
| 157 | 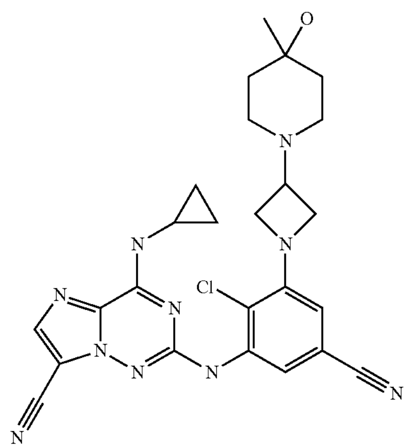 [SMILES: CC1(O)CCN(C2CN(c3cc(C#N)cc(Nc4nc(NC5CC5)c5ncc(C#N)n5n4)c3Cl)C2)CC1] | 2-((2-chloro-5-cyano-3-(3-(4-hydroxy-4-methyl-1-piperidinyl)-1-azetidinyl)phenyl)amino)-4-(cyclopropylamino)imidazo[2,1-f][1,2,4]triazine-7-carbonitrile | 519.01 | 4.19 |
| 158 | 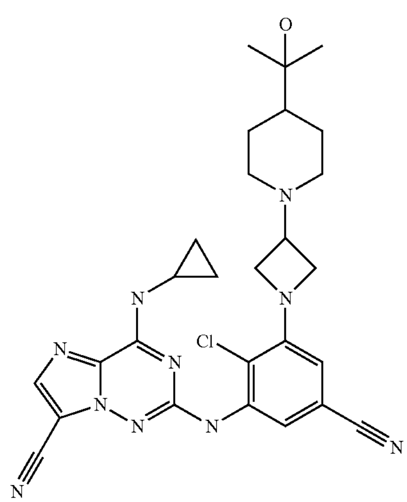 [SMILES: CC(C)(O)C1CCN(C2CN(c3cc(C#N)cc(Nc4nc(NC5CC5)c5ncc(C#N)n5n4)c3Cl)C2)CC1] | 2-(2-chloro-5-cyano-3-(3-(4-(2-hydroxypropan-2-yl)piperidin-1-yl)azetidin-1-yl)phenylamino)-4-(cyclopropylamino)imidazo[1,2-f][1,2,4]triazine-7-carbonitrile | 547.06 | 3.63 |

TABLE 4-continued

| Example No. | Structure | Name | [M + H]+ | HPLC Retention Time (min.)* |
|---|---|---|---|---|
| 159 | 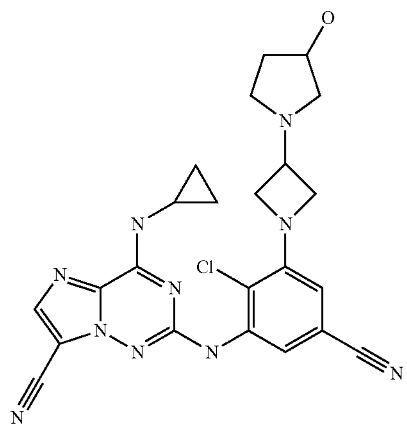 [SMILES: N#Cc1cc(Nc2nc(NC3CC3)c3ncc(C#N)n3n2)c(Cl)c(N2CC(N3CCC(O)C3)C2)c1] | (+/−) 2-((2-chloro-5-cyano-3-(3-(3-hydroxy-1-pyrrolidinyl)-1-azetidinyl)phenyl)amino)-4-(cyclopropylamino)imidazo[2,1-f][1,2,4]triazine-7-carbonitrile | 490.96 | 3.81 |
| 160 | 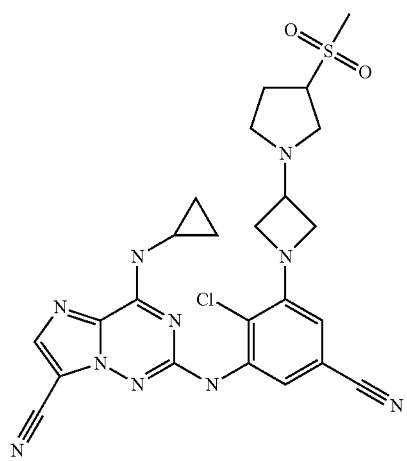 [SMILES: CS(=O)(=O)C1CCN(C2CN(c3cc(C#N)cc(Nc4nc(NC5CC5)c5ncc(C#N)n5n4)c3Cl)C2)C1] | (+/−) 2-((2-chloro-5-cyano-3-(3-(3-(methylsulfonyl)-1-pyrrolidinyl)-1-azetidinyl)phenyl)amino)-4-(cyclopropylamino)imidazo[2,1-f][1,2,4]triazine-7-carbonitrile | 553.05 | 4.13 |
| 161 | 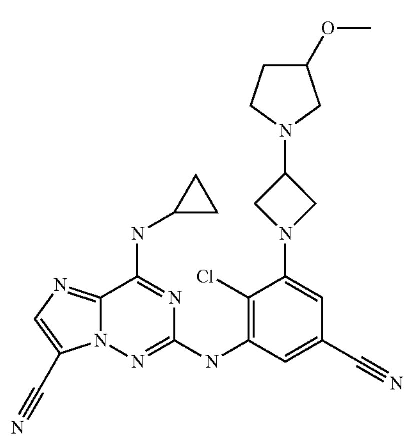 [SMILES: COC1CCN(C2CN(c3cc(C#N)cc(Nc4nc(NC5CC5)c5ncc(C#N)n5n4)c3Cl)C2)C1] | (+/−) 2-((2-chloro-5-cyano-3-(3-(3-methoxy-1-pyrrolidinyl)-1-azetidinyl)phenyl)amino)-4-(cyclopropylamino)imidazo[2,1-f][1,2,4]triazine-7-carbonitrile | 504.98 | 3.93 |

TABLE 4-continued

| Example No. | Structure | Name | [M + H]⁺ | HPLC Retention Time (min.)* |
|---|---|---|---|---|
| 162 | 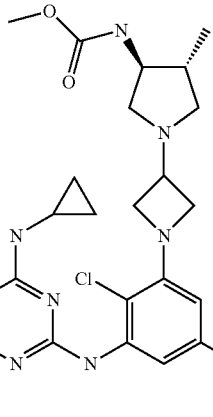 | (+/−) methyl ((3S,4R)-1-(1-(2-chloro-5-cyano-3-((7-cyano-4-(cyclopropylamino)imidazo[2,1-f][1,2,4]triazin-2-yl)amino)phenyl)-3-azetidinyl)-4-methyl-3-pyrrolidinyl)carbamate | 562.04 | 3.83$^c$ |
| 163 | 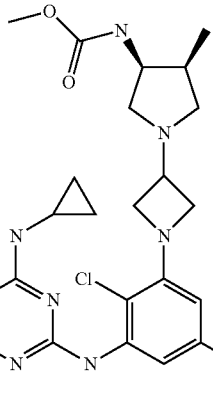 | (+/−) methyl ((3S,4S)-1-(1-(2-chloro-5-cyano-3-((7-cyano-4-(cyclopropylamino)imidazo[2,1-f][1,2,4]triazin-2-yl)amino)phenyl)-3-azetidinyl)-4-methyl-3-pyrrolidinyl)carbamate | 562.04 | 3.69 |
| 164 | 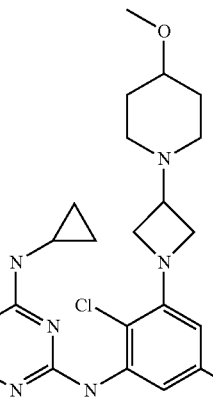 | 2-((2-chloro-5-cyano-3-(3-(4-methoxy-1-piperidinyl)-1-azetidinyl)phenyl)amino)-4-(cyclopropylamino)imidazo[2,1-f][1,2,4]triazine-7-carbonitrile | 519.01 | 4.27 |

TABLE 4-continued

| Example No. | Structure | Name | [M + H]+ | HPLC Retention Time (min.)* |
|---|---|---|---|---|
| 165 | 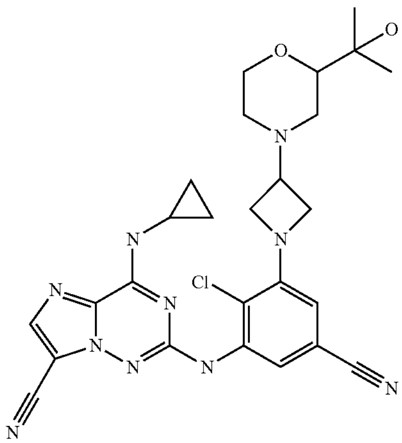 [SMILES: CC(C)(O)C1CN(C2CN(c3cc(C#N)cc(Nc4nc(NC5CC5)c5ncc(C#N)n5n4)c3Cl)C2)CCO1] | (+/−)2-(2-chloro-5-cyano-3-(3-(2-(2-hydroxypropan-2-yl)morpholino)azetidin-1-yl)phenylamino)-4-(cyclopropylamino)imidazo[1,2-f][1,2,4]triazine-7-carbonitrile | 549.04 | 3.86 |
| 166 | 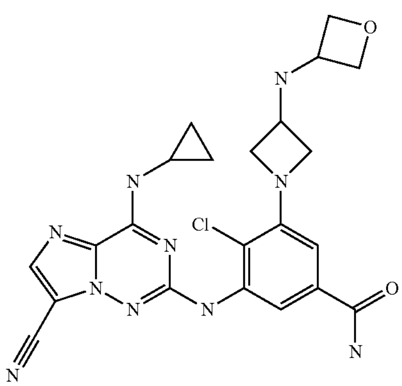 [SMILES: N#Cc1cnc2c(NC3CC3)nc(Nc3cc(C(N)=O)cc(N4CC(NC5COC5)C4)c3Cl)nn12] | 4-chloro-3-((7-cyano-4-(cyclopropylamino)imidazo[2,1-f][1,2,4]triazin-2-yl)amino)-5-(3-(3-oxetanylamino)-1-azetidinyl)benzamide | 494.95 | 3.76 |
| 167 | 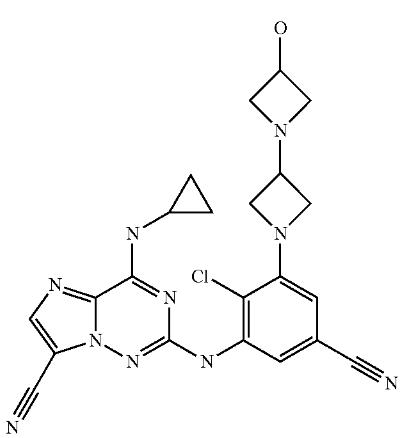 [SMILES: N#Cc1cc(Nc2nc(NC3CC3)c3ncc(C#N)n3n2)c(Cl)c(N2CC(N3CC(O)C3)C2)c1] | 2-((2-chloro-5-cyano-3-(3-hydroxy-1,3'-biazetidin-1'-yl)phenyl)amino)-4-(cyclopropylamino)imidazo[2,1-f][1,2,4]triazine-7-carbonitrile | 476.93 | 4.26 |

TABLE 4-continued

| Example No. | Structure | Name | [M + H]+ | HPLC Retention Time (min.)* |
|---|---|---|---|---|
| 168 | 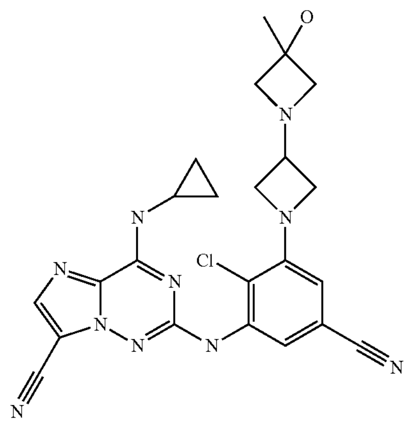 [SMILES: CC1(O)CN(C2CN(c3cc(C#N)cc(Nc4nc(NC5CC5)c5ncc(C#N)n5n4)c3Cl)C2)C1] | 2-((2-chloro-5-cyano-3-(3-hydroxy-3-methyl-1,3'-biazetidin-1'-yl)phenyl)amino)-4-(cyclopropylamino)imidazo[2,1-f][1,2,4]triazine-7-carbonitrile | 490.96 | 3.97 |
| 169 | 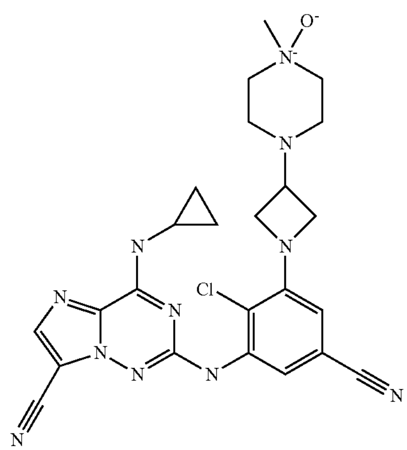 | 2-((2-chloro-5-cyano-3-(3-(4-methyl-4-oxido-1-piperazinyl)-1-azetidinyl)phenyl)amino)-4-(cyclopropylamino)imidazo[2,1-f][1,2,4]triazine-7-carbonitrile | 520.00 | 3.93 |
| 170 | 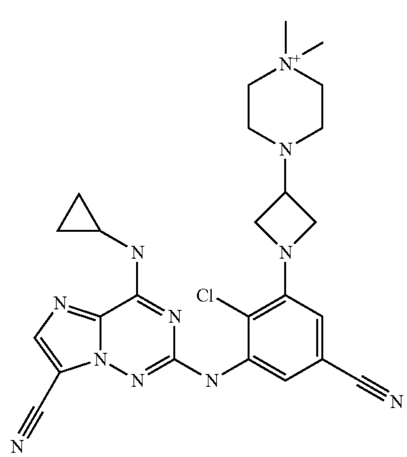 [SMILES: C[N+]1(C)CCN(C2CN(c3cc(C#N)cc(Nc4nc(NC5CC5)c5ncc(C#N)n5n4)c3Cl)C2)CC1] | 4-(1-(2-chloro-5-cyano-3-((7-cyano-4-(cyclopropylamino)imidazo[2,1-f][1,2,4]triazin-2-yl)amino)phenyl)-3-azetidinyl)-1,1-dimethylpiperazin-1-ium | 519.03 | 3.76 |

*= HPLC conditions
YMC S5 ODS 4.6 × 50 mm, 10-90% aqueous methanol containing 0.2% $H_3PO_4$, 5 min. gradient, monitored at 220 nm

Example 171

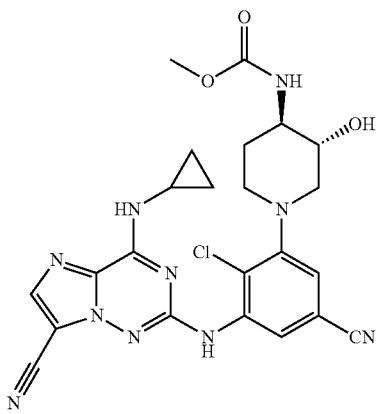 [SMILES: COC(=O)N[C@@H]1CCN(c2cc(C#N)cc(Nc3nc(NC4CC4)c4ncc(C#N)n4n3)c2Cl)C[C@H]1O]

(+/−)-methyl((3R,4R)-1-(2-chloro-5-cyano-3-((7-cyano-4-(cyclopropylamino)imidazo[2,1-f][1,2,4]triazin-2-yl)amino)phenyl)-3-hydroxypiperidin-4-yl)carbamate (171A): tert-butyldimethylchlorosilane (6.51 g, 43.2 mmol) was added to a solution of (+/−)(3R,4R)-benzyl 4-((tert-butoxycarbonyl)amino)-3-hydroxypiperidine-1-carboxylate (prepared according to a published literature procedure: Fink, Brian, et al., WO 2005/066176, 10.1 g, 28.8 mmol) and imidazole (3.92 g, 57.6 mmol) in DMF (60 mL). The mixture was stirred at room temperature overnight. Ice water was added and the reaction mixture was extracted with ether twice, the combined extracts were washed with brine, dried over magnesium sulfate, filtered and concentrated in vacuo, the crude product was purified by flash chromatography on silica gel using an automated ISCO system (330 g column, eluting with 5-20% ethyl acetate/dichloromethane) to give (+/−)-(3R,4R)-benzyl 4-((tert-butoxycarbonyl)amino)-3-((tert-butyldimethylsilyl)oxy)piperidine-1-carboxylate (13.3 g) as a white solid.

MS (ESI) m/z 465.4

1H NMR (500 MHz, DMSO-d6) δ 7.42-7.29 (m, 5H), 6.69 (d, J=7.2 Hz, 1H), 5.17-4.95 (m, 2H), 3.99-3.67 (m, 2H), 3.43-3.35 (m, 2H), 3.05-2.68 (m, 2H), 1.69 (d, J=11.1 Hz, 1H), 1.38 (s, 10H), 0.83 (br. s., 9H), 0.03 (br. s., 6H).

(171B): A mixture of (+/−)-(3R,4R)-benzyl 4-((tert-butoxycarbonyl)amino)-3-((tert-butyldimethylsilyl)oxy)piperidine-1-carboxylate (13 g, 28.0 mmol) and Pd/C (5% on carbon, 1.786 g, 0.839 mmol) in methanol (250 mL) was hydrogenated at 30 psi overnight. The mixture was filtered through Celite and the filtrate was concentrated in vacuo and further dried under high vacuum at 40° C. overnight. The crude product was used without purification. (+/−)-tert-butyl ((3R,4R)-3-((tert-butyldimethylsilyl)oxy)piperidin-4-yl)carbamate (8.8 g, 26.6 mmol, 95% yield) was obtained as a white solid.

MS (ESI) m/z 331.2

(171C): The compound was prepared starting from tert-butyl((3R,4R)-3-((tert-butyldimethylsilyl)oxy)piperidin-4-yl)carbamate (4.5 g, 13.61 mmol) using procedure for Example 1A. After flash chromatography on silica gel using an automated ISCO system (330 g column, eluting with 0-10% ethyl acetate/dichloromethane), 3.8 g of (+/−)-3-N-Boc-amino-5-((3R,4R)-4-N-Boc-amino-3-((tert-butyldimethylsilyl)oxy)piperidin-1-yl)-4-chlorobenzonitrile was obtained as an off-white solid.

MS (ESI) m/z 581.3

1H NMR (400 MHz, chloroform-d) δ 8.32 (d, J=1.8 Hz, 1H), 7.19 (s, 1H), 6.99 (d, J=1.8 Hz, 1H), 4.42 (br. s., 1H), 3.67 (td, J=9.4, 4.6 Hz, 1H), 3.49 (d, J=7.9 Hz, 1H), 3.38 (ddd, J=11.4, 4.6, 2.3 Hz, 1H), 3.24-3.15 (m, 1H), 2.80 (td, J=11.7, 2.3 Hz, 1H), 2.57 (dd, J=11.4, 9.5 Hz, 1H), 2.21-2.13 (m, 1H), 1.76-1.63 (m, 1H), 1.56 (s, 9H), 1.48 (s, 9H), 0.91 (s, 9H), 0.14 (s, 3H), 0.11 (s, 3H).

(171D): 3-N-Boc-amino-5-((3R,4R)-4-N-Boc-amino-3-((tert-butyldimethylsilyl)oxy)piperidin-1-yl)-4-chlorobenzonitrile (118 mg, 0.203 mmol) was treated with TFA (25% in 1,2-dichloroethane, 2 mL) at room temperature for 1 h. The reaction mixture was diluted with dichloromethane and washed with saturated sodium bicarbonate/1N aqueous sodium hydroxide (pH 10). The layers were separated and aqueous layer was extracted with dichloromethane two more times. The combined organic layers were dried over magnesium sulfate, filtered and concentrated in vacuo to give (+/−)-3-amino-5-((3R,4R)-4-amino-3-((tert-butyl dimethylsilyl)oxy)piperidin-1-yl)-4-chlorobenzonitrile (77 mg) as a brown oil. The crude product was used without purification.

MS (ESI) m/z 381.2 (M+H).

(171E): (+/−)3-amino-5-((3R,4R)-4-amino-3-((tert-butyldimethylsilyl)oxy)piperidin-1-yl)-4-chlorobenzonitrile (77 mg, 0.203 mmol) was dissolved in dichloromethane (5 mL), triethylamine (0.057 mL, 0.406 mmol) and dimethyl-dicarbonate (40.8 mg, 0.305 mmol) were added at 0 C. The reaction mixture was stirred at room temperature for 1 h. Solvent was evaporated and the crude product was purified by flash chromatography on silica gel using an automated ISCO system (24 g column, eluting with 0-25% ethyl acetate/dichloromethane) to afford (+/−)-methyl((3R,4R)-1-(3-amino-2-chloro-5-cyanophenyl)-3-((tert-butyldimethylsilyl)oxy)piperidin-4-yl)carbamate (76 mg) as a light yellow oil.

MS (ESI) m/z 439.2 (M+H)

1H NMR (500 MHz, chloroform-d) δ 6.77 (d, J=1.9 Hz, 1H), 6.69 (d, J=1.7 Hz, 1H), 4.61 (br. s., 1H), 4.37 (s, 2H), 3.70 (s, 4H), 3.58-3.49 (m, 1H), 3.42 (ddd, J=11.4, 4.6, 2.5 Hz, 1H), 3.26-3.19 (m, 1H), 2.77 (td, J=11.8, 2.5 Hz, 1H), 2.56 (dd, J=11.4, 9.7 Hz, 1H), 2.14 (d, J=11.9 Hz, 1H), 0.89 (s, 10H), 0.10 (d, J=5.3 Hz, 6H).

(171F): The compound was prepared starting from (+/−)-methyl((3R,4R)-1-(3-amino-2-chloro-5-cyanophenyl)-3-((tert-butyldimethylsilyl)oxy)piperidin-4-yl)carbamate (76 mg, 0.173 mmol) and intermediate 6 according to procedure for Example 1G. (+/−)-methyl((3R,4R)-3-((tert-butyldimethylsilyl)oxy)-1-(2-chloro-5-cyano-3-((7-cyano-4-(cyclopropyl(4-methoxybenzyl)amino)imidazo[2,1-f][1,2,4]triazin-2-yl)amino)phenyl)piperidin-4-yl)carbamate (78 mg) was obtained as a white solid.

MS (ESI) m/z 757.5 (M+H).

(171G): The compound was prepared starting from (+/−)-methyl((3R,4R)-3-((tert-butyldimethylsilyl)oxy)-1-(2-chloro-5-cyano-3-((7-cyano-4-(cyclopropyl(4-methoxybenzyl)amino)imidazo[2,1-f][1,2,4]triazin-2-yl)amino)phenyl)piperidin-4-yl)carbamate (78 mg, 0.103 mmol) according to general procedure for tert-butyldimethylsilyl/triisopropylsilyl deprotection. 63 mg of (+/−)-methyl((3R,4R)-1-(2-chloro-5-cyano-3-((7-cyano-4-(cyclopropyl(4-methoxybenzyl)amino)imidazo[2,1-f][1,2,4]triazin-2-yl)amino)phenyl)-3-hydroxypiperidin-4-yl)carbamate was obtained as a white solid.

MS (ESI) m/z 643.2 (M+H).

Example 171

The compound was prepared starting from (+/−)-methyl ((3R,4R)-1-(2-chloro-5-cyano-3-((7-cyano-4-(cyclopropyl (4-methoxybenzyl)amino) imidazo[2,1-f][1,2,4]triazin-2-yl) amino)phenyl)-3-hydroxypiperidin-4-yl)carbamate (63 mg) according to procedure reported for Example 1. (+/−)-methyl((3R,4R)-1-(2-chloro-5-cyano-3-((7-cyano-4-(cyclopropylamino)imidazo[2,1-f][1,2,4]triazin-2-yl)amino)phenyl)-3-hydroxypiperidin-4-yl)carbamate (25 mg) was obtained as a white solid.

MS (ESI) m/z 523.1

$^1$H NMR (500 MHz, chloroform-d) δ 8.81 (s, 1H), 7.87 (s, 1H), 7.58 (s, 1H), 7.05-6.98 (m, 1H), 6.77 (br. s., 1H), 4.82 (br. s., 1H), 3.73-3.82 (m, 4H), 3.66-3.39 (m, 2H), 3.30 (d, J=10.5 Hz, 1H), 3.06 (dd, J=6.8, 3.5 Hz, 1H), 2.89-2.79 (m, 1H), 2.68 (t, J=10.3 Hz, 1H), 2.14 (d, J=10.5 Hz, 1H), 1.83-1.72 (m, 1H), 1.11 (q, J=6.7 Hz, 2H), 0.97-0.88 (m, 2H), 0.85-0.78 (m, 2H).

Example 172

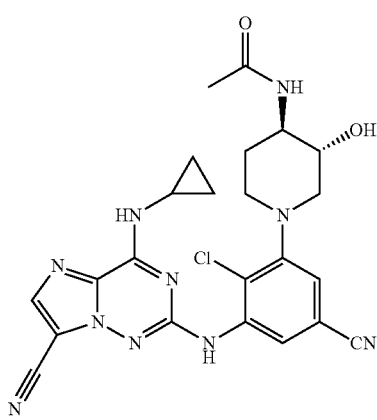 [SMILES: CC(=O)N[C@@H]1CCN(c2cc(C#N)cc(Nc3nc(NC4CC4)c4ncc(C#N)n4n3)c2Cl)C[C@H]1O]

(+/−)-N-((3R,4R)-1-(2-chloro-5-cyano-3-((7-cyano-4-(cyclopropylamino)imidazo[2,1-f][1,2,4]triazin-2-yl)amino)phenyl)-3-hydroxypiperidin-4-yl)acetamide (172A): Acetic anhydride (0.011 mL, 0.119 mmol) was added to a solution of (+/−)-3-amino-5-((3R,4R)-4-amino-3-((tert-butyldimethylsilyl)oxy)piperidin-1-yl)-4-chlorobenzonitrile (Example 7, 41 mg, 0.108 mmol) in dichloromethane (5 mL) at 0° C. The reaction mixture was stirred at room temperature for 1 h. Solvent was evaporated and the crude product was purified by flash chromatography on silica gel using an automated ISCO system (24 g column, eluting with 0.5-5% methanol/dichloromethane). (+/−)-N-((3R,4R)-1-(3-amino-2-chloro-5-cyanophenyl)-3-((tert-butyldimethylsilyl)oxy)piperidin-4-yl)acetamide (44 mg) was obtained as a colorless oil which solidified upon standing.

MS (ESI) m/z 423.2 (M+H).

Example 172

The title compound was prepared starting from 4-(cyclopropyl(4-methoxybenzyl)amino)-2-(methylsulfonyl)imidazo[2,1-f][1,2,4]triazine-7-carbonitrile (Intermediate 1) and (+/−)-N-((3R,4R)-1-(3-amino-2-chloro-5-cyanophenyl)-3-((tert-butyldimethylsilyl)oxy)piperidin-4-yl)acetamide using a method analogous to that used to prepare Example 171.

MS (ESI) m/z 507.4

1H NMR (500 MHz, DMSO-d6) δ 9.33 (d, J=4.2 Hz, 1H), 8.83 (s, 1H), 8.20 (s, 1H), 8.11 (d, J=1.7 Hz, 1H), 7.82 (d, J=7.5 Hz, 1H), 7.32 (d, J=1.9 Hz, 1H), 4.99 (d, J=4.7 Hz, 1H), 3.61-3.50 (m, 2H), 3.61-3.50 (m, 2H), 3.41 (d, J=11.7 Hz, 1H), 3.19 (t, J=16.5 Hz, 2H), 3.24-3.14 (m, 2H), 3.03-2.94 (m, 1H), 2.82-2.73 (m, 1H), 1.90 (d, J=10.0 Hz, 1H), 1.94-1.87 (m, 1H), 1.85 (s, 3H), 1.64-1.45 (m, 2H), 1.37-1.22 (m, 2H), 0.79 (d, J=5.3 Hz, 4H).

Example 173

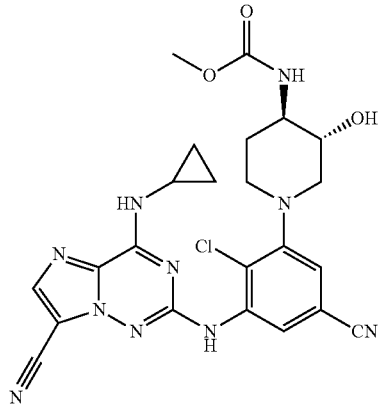 [SMILES: COC(=O)N[C@@H]1CCN(c2cc(C#N)cc(Nc3nc(NC4CC4)c4ncc(C#N)n4n3)c2Cl)C[C@H]1O]

Methyl((3R,4R)-1-(2-chloro-5-cyano-3-((7-cyano-4-(cyclopropylamino)imidazo[2,1-f][1,2,4]triazin-2-yl)amino)phenyl)-3-hydroxypiperidin-4-yl)carbamate (173A): A mixture of tert-butyl(3-bromo-2-chloro-5-cyanophenyl)carbamate (Intermediate 1, 600 mg, 1.809 mmol), (3R,4R)-4-((E)-(4-methoxybenzylidene)amino)piperidin-3-ol (424 mg, 1.809 mmol), Pd$_2$(dba)$_3$ (49.7 mg, 0.054 mmol), 2,2'-bis(diphenylphosphino)-1,1'-binaphthyl (101 mg, 0.163 mmol), and cesium carbonate (1474 mg, 4.52 mmol) in dioxane (20 mL) was evacuated and filled with nitrogen three times and heated at 110° C. overnight. The reaction mixture was diluted with dichloromethane and filtered through Celite. The filtrate was concentrated and the crude product was purified by flash chromatography on silica gel using an automated ISCO system (40 g column, eluting with 0-10% 2N ammonia in methanol/dichloromethane) to give tert-butyl(3-((3R,4R)-4-amino-3-hydroxypiperidin-1-yl)-2-chloro-5-cyanophenyl)carbamate (568 mg) as a brown solid.

MS (ESI) m/z 367.2

$^1$H NMR (500 MHz, chloroform-d) δ 8.30 (d, J=1.4 Hz, 1H), 7.19 (s, 1H), 7.00 (d, J=1.9 Hz, 1H), 3.54 (td, J=9.2, 4.4 Hz, 1H), 3.50-3.44 (m, 1H), 3.29-3.20 (m, 1H), 2.75 (td, J=11.6, 2.4 Hz, 1H), 2.65 (ddd, J=10.8, 8.7, 4.6 Hz, 1H), 2.59 (dd, J=10.8, 9.7 Hz, 1H), 2.23 (br. s., 3H), 2.03-1.95 (m, 1H), 1.72-1.61 (m, 1H).

(173B): Dimethyl dicarbonate (164 mg, 1.227 mmol) was added to a solution of tert-butyl(3-((3R,4R)-4-amino-3-hydroxypiperidin-1-yl)-2-chloro-5-cyanophenyl) carbamate (300 mg, 0.818 mmol) and triethylamine (0.228 mL, 1.636 mmol) in dichloromethane (2 mL) at 0° C. and the resulting solution was stirred at room temperature for 1.5 h. Solvent was evaporated and the crude product was purified by flash chromatography on silica gel using an automated ISCO system (40 g gold column, eluting with 0-30% ethyl acetate/dichloromethane). methyl((3R,4R)-1-(2-chloro-5-cyano-3-(N-Boc-amino)phenyl)-3-hydroxypiperidin-4-yl)carbamate (150 mg) was obtained as a white solid.

MS (ESI) m/z 425.4

¹H NMR (400 MHz, chloroform-d) δ 8.34 (d, J=1.8 Hz, 1H), 7.19 (s, 1H), 7.01 (d, J=2.0 Hz, 1H), 4.81 (br. s., 1H), 3.81-3.69 (m, 4H), 3.65-3.42 (m, 3H), 3.30-3.21 (m, 1H), 2.82 (td, J=11.6, 2.5 Hz, 1H), 2.71-2.60 (m, 1H), 2.13 (d, J=8.8 Hz, 1H), 1.82-1.69 (m, 1H), 1.57 (s, 9H).

(173C): Triisopropylsilyl trifluoromethanesulfonate (0.288 mL, 1.060 mmol) was added to a solution of ((3R, 4R)-1-(2-chloro-5-cyano-3-(N-Boc-amino)phenyl)-3-hydroxypiperidin-4-yl)carbamate (150 mg, 0.353 mmol) and triethylamine (0.196 mL, 1.412 mmol) in dichloromethane (5 mL) and the resulting mixture was stirred at room temperature overnight. The reaction mixture was partitioned between saturated sodium bicarbonate and dichloromethane. The layers were separated and aqueous layer was extracted with dichloromethane two more times. The combined organic layer was dried over magnesium sulfate, filtered and concentrated in vacuo. The crude product was purified by flash chromatography on silica gel using an automated ISCO system (40 g column, eluting with 0-10% ethyl acetate/dichloromethane). methyl((3R,4R)-1-(2-chloro-5-cyano-3-(N-Boc-amino)phenyl)-3-((triisopropylsilyl)oxy)piperidin-4-yl)carbamate (242 mg) was obtained as a brown oil.

MS (ESI) m/z 581.3

(173D): Methyl((3R,4R)-1-(2-chloro-5-cyano-3-(N-Boc-amino)phenyl)-3-((triisopropylsilyl)oxy)piperidin-4-yl)carbamate (242 mg, 0.354 mmol) was treated with TFA (25% in 1,2-dichloroethane, 4 mL, 12.98 mmol) at room temperature for 1 h. The reaction mixture was diluted with dichloromethane and washed with cold saturated sodium bicarbonate/1N aqueous sodium hydroxide (pH 10), the organic layer was dried over magnesium sulfate, filtered and concentrated in vacuo, the crude product was purified by flash chromatography on silica gel using an automated ISCO system (40 g column, eluting with 0-20% ethyl acetate/dichloromethane). Methyl((3R,4R)-1-(3-amino-2-chloro-5-cyanophenyl)-3-((triisopropylsilyl)oxy)piperidin-4-yl)carbamate (135 mg) was obtained as a white solid.

MS (ESI) m/z 481.3

Example 173

The title compound was prepared starting from 4-(cyclopropyl(4-methoxybenzyl)amino)-2-(methylsulfonyl)imidazo[2,1-f][1,2,4]triazine-7-carbonitrile (Intermediate 2) and N-((3R,4R)-1-(3-amino-2-chloro-5-cyanophenyl)-4-((tert-butyldimethylsilyl)oxy)pyrrolidin-3-yl)acetamide using a method analogous to that used to prepare Example 7.

MS (ESI) m/z 523.1 (M+H);

¹H NMR (500 MHz, chloroform-d) δ 8.89-8.78 (m, 1H), 7.89 (s, 1H), 7.59 (s, 1H), 7.03 (d, J=1.7 Hz, 1H), 6.76 (br. s., 1H), 4.83 (br. s., 1H), 3.83-3.69 (m, 4H), 3.67-3.53 (m, 2H), 3.40-3.26 (m, 1H), 3.08 (dd, J=6.9, 3.3 Hz, 1H), 2.89-2.81 (m, 1H), 2.70 (t, J=10.4 Hz, 1H), 2.34-2.11 (m, 1H), 1.95-1.73 (m, 1H), 1.16-1.09 (m, 2H), 0.87-0.80 (m, 2H).

Example 174

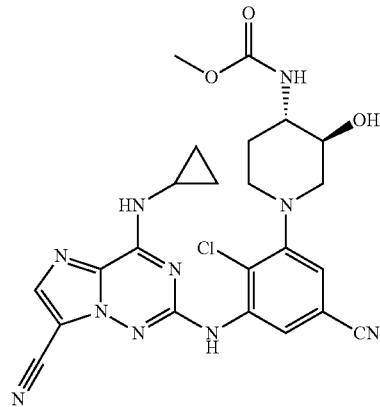 [SMILES: COC(=O)N[C@H]1CCN(c2cc(C#N)cc(Nc3nc(NC4CC4)c4ncc(C#N)n4n3)c2Cl)C[C@@H]1O]

methyl((3S,4S)-1-(2-chloro-5-cyano-3-((7-cyano-4-(cyclopropylamino)imidazo[2,1-f][1,2,4]triazin-2-yl)amino)phenyl)-3-hydroxypiperidin-4-yl)carbamate (174A): (+/−)-methyl((3R,4R)-1-(3-amino-2-chloro-5-cyanophenyl)-3-((tert-butyl dimethylsilyl)oxy)piperidin-4-yl)carbamate (Example 171E, 927 mg, 2.112 mmol) was separated by chiral SFC (Berger SFC MGIII, Column. Lux Cel-4 25×3 cm ID, 5 μm; Flow rate: 85.0 mL/min; Mobile Phase: 85/15 CO₂/methanol; Detector Wavelength: 220 nm). Methyl((3S,4S)-1-(3-amino-2-chloro-5-cyanophenyl)-3-((tert-butyldimethylsilyl)oxy)piperidin-4-yl)carbamate (406 mg) was obtained as a white foaming solid. The enantiomeric purity of each fraction was estimated to be greater than 99.5%.

(174B): methyl((3S,4S)-3-((tert-butyldimethylsilyl)oxy)-1-(2-chloro-5-cyano-3-((7-cyano-4-(cyclopropyl(4-methoxybenzyl)amino)imidazo[2,1-f][1,2,4]triazin-2-yl)amino)phenyl)piperidin-4-yl)carbamate was prepared starting from methyl((3S,4S)-1-(3-amino-2-chloro-5-cyanophenyl)-3-((tert-butyldimethylsilyl)oxy) piperidin-4-yl)carbamate (127 mg, 0.289 mmol) according to general procedure for the coupling of aniline to 4-(cyclopropyl(4-methoxybenzyl)amino)-2-(methylsulfonyl)imidazo[2,1-f][1,2,4]triazine-7-carbonitrile, method described for Example 7. Methyl((3S,4S)-3-((tert-butyldimethylsilyl)oxy)-1-(2-chloro-5-cyano-3-((7-cyano-4-(cyclopropyl(4-methoxybenzyl)amino)imidazo[2,1-f][1,2,4]triazin-2-yl)amino)phenyl)piperidin-4-yl)carbamate (180 mg) was obtained as a white solid.

MS (ESI) m/z 757.5 (M+H)

¹H NMR (500 MHz, chloroform-d) δ 7.94 (s, 1H), 7.21 (d, J=8.6 Hz, 2H), 6.98 (d, J=1.7 Hz, 1H), 6.87 (d, J=8.6 Hz, 2H), 4.55 (d, J=7.2 Hz, 1H), 3.81 (s, 3H), 3.77-3.73 (m, 1H), 3.72 (s, 3H), 3.60-3.51 (m, 1H), 3.44 (ddd, J=11.4, 4.5, 2.1 Hz, 1H), 3.25 (d, J=11.7 Hz, 1H), 2.86 (td, J=11.7, 2.2 Hz, 1H), 2.65 (dd, J=11.4, 9.4 Hz, 1H), 2.22 (dd, J=13.2, 4.3 Hz, 1H), 1.48 (s, 6H), 1.16 (q, J=6.5 Hz, 2H), 0.93 (s, 12H), 0.15 (s, 3H), 0.13 (s, 3H).

Example 174

Methyl((3S,4S)-1-(2-chloro-5-cyano-3-((7-cyano-4-(cyclopropylamino)imidazo[2,1-f][1,2,4]triazin-2-yl)amino)phenyl)-3-hydroxypiperidin-4-yl)carbamate was prepared starting from methyl((3S,4S)-3-((tert-butyldimethylsilyl)oxy)-1-(2-chloro-5-cyano-3-((7-cyano-4-(cyclopropyl(4-methoxybenzyl)amino)imidazo[2,1-f][1,2,4]triazin-2-yl)amino)phenyl)piperidin-4-yl)carbamate using a method analogous to that used to prepare Example 171, MS (ESI) m/z 523.3

¹H NMR (500 MHz, chloroform-d) δ 8.80 (d, J=1.7 Hz, 1H), 7.87 (s, 1H), 7.58 (s, 1H), 7.02 (d, J=1.7 Hz, 1H), 6.76 (br. s., 1H), 4.81 (br. s., 1H), 3.80-3.72 (m, 4H), 3.64-3.42 (m, 3H), 3.30 (d, J=10.0 Hz, 1H), 3.06 (td, J=7.0, 3.5 Hz, 1H), 2.87-2.79 (m, 1H), 2.68 (t, J=10.4 Hz, 1H), 2.14 (d, J=9.4 Hz, 1H), 1.82-1.71 (m, 1H), 1.14-1.08 (m, 2H), 0.85-0.79 (m, 2H).

Example 175

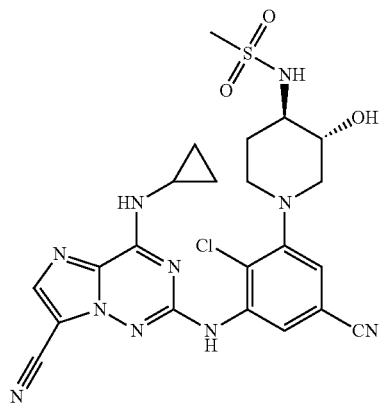 [SMILES: CS(=O)(=O)N[C@@H]1CCN(c2cc(C#N)cc(Nc3nc(NC4CC4)c4ncc(C#N)n4n3)c2Cl)C[C@H]1O]

N-((3R,4R)-1-(2-chloro-5-cyano-3-((7-cyano-4-(cyclopropylamino)imidazo[2,1-f][1,2,4]triazin-2-yl)amino)phenyl)-3-hydroxypiperidin-4-yl)methanesulfonamide (175A): tert-butyl(3-((3R,4R)-4-amino-3-hydroxypiperidin-1-yl)-2-chloro-5-cyano phenyl)carbamate (Example 173A, 326 mg, 0.889 mmol) was treated with TFA (25% in 1,2-dichloroethane, 3 mL) at room temperature for 1 h. Solvent was evaporated and to the residue was added dichloromethane and concentrated again. The crude was dried in vacuo overnight and then dissolved in methanol, 2N ammonia in methanol was added to neutralize TFA and then solvent was evaporated. The crude intermediate 3-amino-5-((3R,4R)-4-amino-3-hydroxypiperidin-1-yl)-4-chlorobenzonitrile was dissolved in THF/Water (10:1) and triethylamine (0.186 mL, 1.333 mmol) and di-tert-butyl dicarbonate (255 mg, 1.17 mmol) was added at 0° C. and the reaction solution was stirred at room temperature overnight. Solvent was evaporated and the crude product was purified by flash chromatography on silica gel using an automated ISCO system (40 g column, eluting with 0-40% ethyl acetate/dichloromethane). tert-butyl((3R,4R)-1-(3-amino-2-chloro-5-cyanophenyl)-3-hydroxypiperidin-4-yl)carbamate (230 mg) was obtained as a light yellow solid.

MS (ESI) m/z 367.3

(175B): Chlorotriisopropylsilane (0.547 mL, 2.194 mmol) was added to a solution of tert-butyl((3R,4R)-1-(3-amino-2-chloro-5-cyanophenyl)-3-hydroxypiperidin-4-yl)carbamate (230 mg, 0.627 mmol) and imidazole (213 mg, 3.13 mmol) in DMF (5 mL) and the resulting solution was stirred at room temperature overnight. LCMS showed half conversion. More imidazole (2 eq, 85 mg) and chlorotriisopropylsilane (0.2 mL) were added and stirring continued for 3 h. There was still 30% SM left. More imidazole (100 mg) and chlorotriisopropylsilane (0.2 mL) were added and the reaction was stirred overnight. The reaction mixture was partitioned between ethyl acetate and water, the layers were separated and the organic layer was washed with water two more times, dried over magnesium sulfate, filtered and concentrated in vacuo, the crude product was purified by flash chromatography on silica gel using an automated ISCO system (40 g column, eluting with 10-30% ethyl acetate/hexanes). tert-butyl((3R,4R)-1-(3-amino-2-chloro-5-cyanophenyl)-3-((triisopropylsilyl)oxy)piperidin-4-yl)carbamate (300 mg) was obtained as a white solid.

MS (ESI) m/z 523.5

(175C): tert-butyl((3R,4R)-1-(2-chloro-5-cyano-3-((7-cyano-4-(cyclopropyl(4-methoxybenzyl)amino)imidazo[2,1-f][1,2,4]triazin-2-yl)amino)phenyl)-3-((triisopropylsilyl)oxy)piperidin-4-yl)carbamate was prepared starting from 4-(cyclopropyl(4-methoxybenzyl)amino)-2-(methylsulfonyl)imidazo[2,1-f][1,2,4]triazine-7-carbonitrile (Intermediate 2) and tert-butyl((3R,4R)-1-(3-amino-2-chloro-5-cyanophenyl)-3-((triisopropylsilyl)oxy)piperidin-4-yl)carbamate using a method analogous to that used to prepare Example 171.

(175D): TFA (1 mL, 3.24 mmol) was added to a solution of tert-butyl((3R,4R)-1-(2-chloro-5-cyano-3-((7-cyano-4-(cyclopropyl(4-methoxybenzyl)amino)imidazo[2,1-f][1,2,4]triazin-2-yl)amino)phenyl)-3-((triisopropylsilyl)oxy)piperidin-4-yl)carbamate (184 mg, 0.219 mmol) and anisole (20 μl, 0.183 mmol) in dichloromethane (1 mL) and the reaction solution was stirred at 30° C. overnight. LCMS showed completion of reaction. The reaction mixture was diluted with dichloromethane and washed with cold saturated sodium bicarbonate/1N aqueous sodium hydroxide (pH 10), the organic layer was dried over magnesium sulfate, filtered and concentrated in vacuo, the crude product was purified by flash chromatography on silica gel using an automated ISCO system (24 g column, eluting with 1-4% methanol/dichloromethane). 2-((3-((3R,4R)-4-amino-3-((triisopropylsilyl)oxy)piperidin-1-yl)-2-chloro-5-cyanophenyl)amino)-4-(cyclopropylamino)imidazo[2,1-f][1,2,4]triazine-7-carbonitrile (126 mg) was obtained as a white solid.

MS (ESI) m/z 621.4

(175E): Methanesulfonyl chloride (7.5 μl, 0.10 mmol) was added to a solution of 2-((3-((3R,4R)-4-amino-3-((triisopropylsilyl)oxy)piperidin-1-yl)-2-chloro-5-cyanophenyl)amino)-4-(cyclopropylamino)imidazo[2,1-f][1,2,4]triazine-7-carbonitrile (25 mg, 0.040 mmol) and triethylamine (17 μl, 0.120 mmol) in dichloromethane (1 mL) and the reaction solution was stirred at room temperature overnight. The crude product was purified by flash chromatography on silica gel using an automated ISCO system (12 g column, eluting with 0-40% ethyl acetate/dichloromethane). N-((3R,4R)-1-(2-chloro-5-cyano-3-((7-cyano-4-(cyclopropylamino)imidazo[2,1-f][1,2,4]triazin-2-yl)amino)phenyl)-3-((triisopropylsilyl)oxy)piperidin-4-yl)methanesulfonamide (28 mg) was obtained as a white solid.

MS (ESI) m/z 699.3

Example 175

TBAF (1M in THF, 0.048 mL, 0.048 mmol) was added to a solution of

N-((3R,4R)-1-(2-chloro-5-cyano-3-((7-cyano-4-(cyclopropylamino)imidazo[2,1-f][1,2,4]triazin-2-yl)amino)phenyl)-3-((triisopropylsilyl)oxy)piperidin-4-yl)methanesulfonamide (28 mg, 0.040 mmol) in THF (2 mL) and the reaction mixture was stirred at room temperature overnight. Solvent was evaporated and the crude product was purified by flash chromatography on silica gel using an automated ISCO system (12 g column, eluting with 0-6% methanol/dichloromethane). N-((3R,4R)-1-(2-chloro-5-cyano-3-((7-cyano-4-(cyclopropylamino)imidazo[2,1-f][1,2,4]triazin-2-yl)amino)phenyl)-3-hydroxypiperidin-4-yl)methanesulfonamide (21 mg) was obtained as a white solid.

MS (ESI) m/z 543.2

$^1$H NMR (500 MHz, DMSO-d$_6$) δ 9.33 (br. s., 1H), 8.84 (br. s., 1H), 8.20 (s, 1H), 8.12 (d, J=1.7 Hz, 1H), 7.31 (d, J=1.7 Hz, 1H), 7.17 (d, J=6.9 Hz, 1H), 5.20 (d, J=5.5 Hz, 1H), 3.51 (tt, J=9.7, 5.0 Hz, 1H), 3.45-3.38 (m, 1H), 3.25-3.17 (m, 2H), 3.06 (br. s., 1H), 3.01-2.95 (m, 4H), 2.83-2.72 (m, 1H), 2.01-1.92 (m, 1H), 1.66 (qd, J=12.2, 4.2 Hz, 1H), 0.79 (d, J=5.3 Hz, 4H).

Example 176

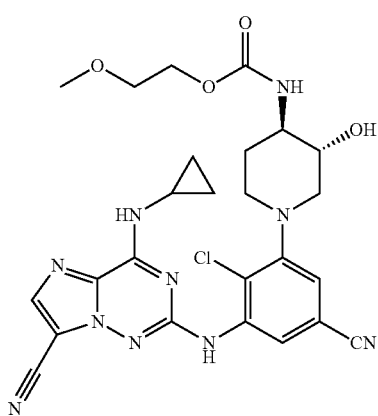 [SMILES: COCCOC(=O)N[C@@H]1CCN(c2cc(C#N)cc(Nc3nc(NC4CC4)c4ncc(C#N)n4n3)c2Cl)C[C@H]1O]

2-methoxyethyl((3R,4R)-1-(2-chloro-5-cyano-3-((7-cyano-4-(cyclopropylamino)imidazo[2,1-f][1,2,4]triazin-2-yl)amino)phenyl)-3-hydroxypiperidin-4-yl)carbamate (176A): 2-methoxyethyl carbonochloridate (5.08 mg, 0.037 mmol) was added to a solution of 2-((3-((3R,4R)-4-amino-3-((triisopropylsilyl)oxy)piperidin-1-yl)-2-chloro-5-cyanophenyl)amino)-4-(cyclopropylamino)imidazo[2,1-f][1,2,4]triazine-7-carbonitrile (Example 174D, 19 mg, 0.031 mmol) and triethylamine (8.53 μl, 0.061 mmol) in dichloromethane (1 mL) and the reaction solution was stirred at room temperature overnight. More 2-methoxyethyl carbonochloridate (5.08 mg, 0.037 mmol) was added and stirring continued over the weekend, still about 30% SM left. More triethylamine (100 μL) and 2-methoxyethyl carbonochloridate (20 μl) was added and stirred for another day. Reaction close to completion. The reaction mixture was diluted with dichloromethane and washed with cold saturated sodium bicarbonate, the organic layer was dried over magnesium sulfate, filtered and concentrated in vacuo, the crude product was purified by flash chromatography on silica gel using an automated ISCO system (24 g column, eluting with 0-40% ethyl acetate/dichloromethane) to give 2-methoxyethyl((3R,4R)-1-(2-chloro-5-cyano-3-((7-cyano-4-(cyclopropylamino) imidazo[2,1-f][1,2,4]triazin-2-yl)amino)phenyl)-3-((triisopropylsilyl)oxy)piperidin-4-yl)carbamate (12 mg).

MS (ESI) m/z 723.4

(176B): The title compound was prepared starting from 2-methoxyethyl((3R,4R)-1-(2-chloro-5-cyano-3-((7-cyano-4-(cyclopropylamino)imidazo[2,1-f][1,2,4]triazin-2-yl)amino)phenyl)-3-((triisopropylsilyl)oxy)piperidin-4-yl)carbamate using a method analogous to that used to prepare Example 175.

MS (ESI) m/z 567.2

$^1$H NMR (500 MHz, DMSO-d$_6$) δ 9.35 (br. s., 1H), 8.87 (br. s., 1H), 8.21 (s, 1H), 8.11 (s, 1H), 7.32 (d, J=2.0 Hz, 1H), 7.21 (d, J=8.4 Hz, 1H), 5.02 (d, J=5.0 Hz, 1H), 4.10-4.04 (m, 2H), 3.54-3.49 (m, 3H), 3.20-3.14 (m, 4H), 2.98 (quin, J=5.6 Hz, 1H), 2.81-2.71 (m, 1H), 1.88 (d, J=10.9 Hz, 1H), 1.60-1.54 (m, 4H), 0.78 (d, J=5.0 Hz, 4H).

Example 177

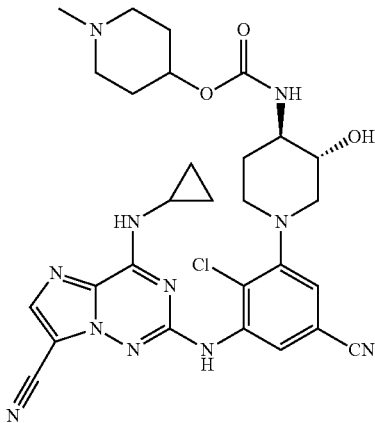

(+/−)-2-(dimethylamino)ethyl((3R,4R)-1-(2-chloro-5-cyano-3-((7-cyano-4-(cyclopropylamino)imidazo[2,1-f][1,2,4]triazin-2-yl)amino)phenyl)-3-hydroxypiperidin-4-yl)carbamate (177A): di-tert-butyl dicarbonate (0.206 g, 0.945 mmol) was added to a solution of (+/−)-3-amino-5-((3R,4R)-4-amino-3-((tert-butyldimethylsilyl)oxy)piperidin-1-yl)-4-chlorobenzonitrile (Example 171D, 0.3 g, 0.787 mmol) and triethylamine (0.220 mL, 1.575 mmol) in dichloromethane (5 mL) at 0° C. and the reaction mixture was stirred at room temperature for 1 h. The reaction mixture was diluted with dichloromethane and washed with saturated sodium bicarbonate. The organic layer was dried over magnesium sulfate, filtered and concentrated in vacuo, the crude product was purified by flash chromatography on silica gel using an automated ISCO system (80 g column, eluting with 5-30% ethyl acetate/dichloromethane). (+/−)-tert-butyl((3R,4R)-1-(3-amino-2-chloro-5-cyanophenyl)-3-((tert-butyldimethylsilyl)oxy) piperidin-4-yl)carbamate (342 mg) was obtained as a colorless oil which was used as such in the next reaction.

(177B): A mixture of 4-(cyclopropyl(4-methoxybenzyl)amino)-2-(methylsulfonyl) imidazo[2,1-f][1,2,4]triazine-7-carbonitrile (Intermediate 2, 185 mg, 0.464 mmol), (+/−)-tert-butyl((3R,4R)-1-(3-amino-2-chloro-5-cyanophenyl)-3-((tert-butyldimethyl silyl)oxy)piperidin-4-yl)carbamate (223 mg, 0.464 mmol) and cesium carbonate (302 mg, 0.927 mmol) in DMF (5 mL) was heated at 50° C. for 4 h. LCMS showed completion of reaction. The reaction mixture was diluted with ethyl acetate and the solid was filtered off. The filtrate was concentrated in vacuo and the crude product was purified by flash chromatography on silica gel using an automated ISCO system (40 g column, eluting with 10-35% ethyl acetate/hexanes). (+/−)-tert-butyl((3R,4R)-3-((tert-butyldimethylsilyl)oxy)-1-(2-chloro-5-cyano-3-((7-cyano-4-(cyclopropyl(4-methoxybenzyl)amino)imidazo[2,1-f][1,2,4]triazin-2-yl)amino)phenyl)piperidin-4-yl)carbamate (270 mg) was obtained as a white solid.

MS (ESI) m/z 799.4

(177C): TFA (25% in 1,2-dichloroethane, 4 mL, 12.98 mmol) was added to a solution of (+/−)-tert-butyl((3R,4R)-3-((tert-butyldimethylsilyl)oxy)-1-(2-chloro-5-cyano-3-((7-cyano-4-(cyclopropyl(4-methoxybenzyl)amino)imidazo[2,1-f][1,2,4]triazin-2-yl)amino)phenyl)piperidin-4-yl)carbamate (270 mg, 0.338 mmol) and anisole (0.148 mL, 1.351 mmol) in 1,2-dichloroethane (2 mL) and the resulting solution was heated at 30° C. overnight. The reaction mixture was diluted with dichloromethane and washed with cold saturated sodium bicarbonate/1N aqueous sodium hydroxide (pH 10), the layers were separated and aqueous layer was extracted with dichloromethane/methanol (4/1) two more times. The combined organic layers were dried over magnesium sulfate, filtered and concentrated in vacuo, the crude product was purified by flash chromatography on silica gel using an automated ISCO system (40 g column, eluting with 1-7% methanol/dichloromethane to afford (+/−)-2-((3-((3R,4R)-4-amino-3-((tert-butyldimethylsilyl)oxy)piperidin-1-yl)-2-chloro-5-cyanophenyl)amino)-4-(cyclopropylamino)imidazo[2,1-f][1,2,4]triazine-7-carbonitrile (119 mg) and then 6-16% 2 N ammonia in methanol/dichloromethane to give (+/−)-2-((3-((3R,4R)-4-amino-3-hydroxypiperidin-1-yl)-2-chloro-5-cyanophenyl)amino)-4-(cyclopropylamino)imidazo[2,1-f][1,2,4]triazine-7-carbonitrile (8 mg).

MS (ESI) m/z 579.4

(177D): A solution of (+/−)-2-((3-((3R,4R)-4-amino-3-((tert-butyldimethylsilyl)oxy)piperidin-1-yl)-2-chloro-5-cyanophenyl)amino)-4-(cyclopropylamino)imidazo[2,1-f][1,2,4]triazine-7-carbonitrile (32 mg, 0.055 mmol) in THF (1 mL) was added to CDI (35.8 mg, 0.221 mmol) in THF (1 mL) at 0° C. and the reaction mixture was stirred at room temperature overnight. In a 1-dram vial charged with 2-(dimethylamino)ethanol (44.6 mg, 0.500 mmol) in THF (1 mL) was added lithium bis(trimethylsilyl)amide (1M in THF, 0.884 mL, 0.884 mmol) at 0° C. and the resulting reaction solution was stirred at room temperature for 10 min before added to the above intermediate. The reaction mixture was stirred at room temperature for 1 h Solvent was evaporated and the residue was partitioned between dichloromethane and saturated sodium bicarbonate. The layers were separated and the organic layer was dried over magnesium sulfate, filtered and concentrated in vacuo, the crude product was purified by flash chromatography on silica gel using an automated ISCO system (24 g column, eluting with 1-8% methanol/dichloromethane). (+/−)-2-(dimethylamino)ethyl ((3R,4R)-3-((tert-butyldimethylsilyl)oxy)-1-(2-chloro-5-cyano-3-((7-cyano-4-(cyclopropylamino)imidazo[2,1-f][1,2,4]triazin-2-yl)amino)phenyl)piperidin-4-yl)carbamate (34 mg) was obtained as a white solid.

MS (ESI) m/z 694.4

Example 177

TBAF (1M in THF, 0.059 mL, 0.059 mmol) was added to a solution of (+/−)-2-(dimethylamino)ethyl((3R,4R)-3-((tert-butyldimethylsilyl)oxy)-1-(2-chloro-5-cyano-3-((7-cyano-4-(cyclopropylamino)imidazo[2,1-f][1,2,4]triazin-2-yl)amino)phenyl)piperidin-4-yl)carbamate (34 mg, 0.049 mmol) in THF (1 mL) and the resulting solution was stirred at room temperature overnight. Solvent was evaporated and the residue was partitioned between dichloromethane and saturated sodium bicarbonate. The layers were separated and aqueous layer was extracted with dichloromethane/methanol (4/1) two more times. The combined organic layers were dried over magnesium sulfate, filtered and concentrated in vacuo, the crude product was purified by flash chromatography on silica gel using an automated ISCO system (24 g gold column, eluting with 2-12% 2 N ammonia in methanol/dichloromethane). (+/−)-2-(dimethylamino)ethyl((3R,4R)-1-(2-chloro-5-cyano-3-((7-cyano-4-(cyclopropylamino)imidazo[2,1-f][1,2,4]triazin-2-yl)amino)phenyl)-3-hydroxypiperidin-4-yl)carbamate (22 mg) was obtained as a white solid.

MS (ESI) m/z 580.2

$^1$H NMR (500 MHz, chloroform-d) δ 8.79 (d, J=1.7 Hz, 1H), 7.87 (s, 1H), 7.59 (s, 1H), 7.07 (d, J=2.2 Hz, 1H), 7.02 (d, J=1.9 Hz, 1H), 5.20 (br. s., 1H), 4.33-4.12 (m, 2H), 3.76 (br. s., 1H), 3.65-3.51 (m, 2H), 3.35-3.27 (m, 1H), 3.07 (tq, J=7.1, 3.5 Hz, 1H), 2.82 (td, J=11.6, 2.1 Hz, 1H), 2.68 (t, J=9.8 Hz, 1H), 2.60 (t, J=5.4 Hz, 2H), 2.32 (s, 6H), 2.17-2.10 (m, 1H), 1.83-1.69 (m, 1H), 1.16-1.07 (m, 2H), 0.86-0.80 (m, 2H).

Example 178

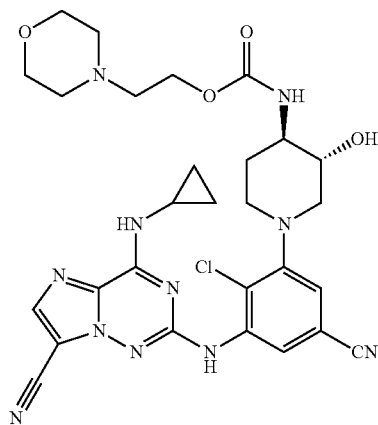 [SMILES: N#Cc1cc(Nc2nc(NC3CC3)c3ncc(C#N)n3n2)c(Cl)c(N2CC[C@@H](NC(=O)OCCN3CCOCC3)[C@H](O)C2)c1]

2-morpholinoethyl((3R,4R)-1-(2-chloro-5-cyano-3-((7-cyano-4-(cyclopropylamino)imidazo[2,1-f][1,2,4]triazin-2-yl)amino)phenyl)-3-hydroxypiperidin-4-yl)carbamate The title compound was prepared from 2-((3-((3R,4R)-4-amino-3-((triisopropylsilyl)oxy)piperidin-1-yl)-2-chloro-5-cyanophenyl)amino)-4-(cyclopropylamino)imidazo[2,1-f][1,2,4]triazine-7-carbonitrile (Example 175D) and 2-morpholinoethanol using a method analogous to that used to prepare Example 177.

MS (ESI) m/z 622.4

$^1$H NMR (500 MHz, chloroform-d) δ 8.81 (d, J=1.7 Hz, 1H), 7.88 (s, 1H), 7.59 (s, 1H), 7.02 (d, J=1.9 Hz, 1H), 6.98 (br. s., 1H), 5.02 (br. s., 1H), 4.27 (br. s., 2H), 3.81-3.71 (m, 6H), 3.63-3.53 (m, 2H), 3.36-3.28 (m, 1H), 3.11-3.04 (m, 1H), 2.84 (td, J=11.7, 2.2 Hz, 1H), 2.67 (t, J=5.5 Hz, 3H), 2.54 (br. s., 4H), 2.19-2.11 (m, 1H), 1.77 (qd, J=11.8, 3.9 Hz, 1H), 1.15-1.09 (m, 2H), 0.86-0.80 (m, 2H).

Example 179

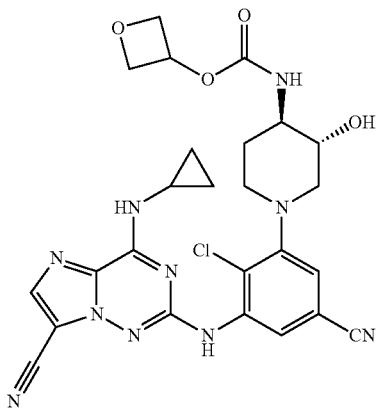 [SMILES: N#Cc1cc(Nc2nc(NC3CC3)c3ncc(C#N)n3n2)c(Cl)c(N2CC[C@@H](NC(=O)OC3COC3)[C@H](O)C2)c1]

(+/−)-oxetan-3-yl((3R,4R)-1-(2-chloro-5-cyano-3-((7-cyano-4-(cyclopropylamino)imidazo[2,1-f][1,2,4]triazin-2-yl)amino)phenyl)-3-hydroxypiperidin-4-yl)carbamate The title compound was prepared from (+/−)-2-((3-((3R,4R)-4-amino-3-((tert-butyldimethylsilyl)oxy)piperidin-1-yl)-2-chloro-5-cyanophenyl)amino)-4-(cyclopropylamino)imidazo[2,1f][1,2,4]triazine-7-carbonitrile (Example 177C) and oxetan-3-ol using a method analogous to that used to prepare Example 177.

MS (ESI) m/z 565.2

$^1$H NMR (500 MHz, chloroform-d) δ 8.82 (d, J=1.7 Hz, 1H), 7.88 (s, 1H), 7.59 (s, 1H), 7.03 (d, J=1.9 Hz, 1H), 6.95 (d, J=2.2 Hz, 1H), 5.53-5.45 (m, 1H), 5.05 (d, J=6.7 Hz, 1H), 4.92 (t, J=6.9 Hz, 2H), 4.74-4.65 (m, 2H), 3.80 (tt, J=9.2, 4.6 Hz, 1H), 3.66-3.51 (m, 2H), 3.37-3.22 (m, 2H), 3.07 (tq, J=7.1, 3.5 Hz, 1H), 2.85 (t, J=10.8 Hz, 1H), 2.70 (t, J=10.1 Hz, 1H), 2.25-2.13 (m, 1H), 1.86-1.75 (m, 1H), 1.15-1.09 (m, 2H), 0.87-0.80 (m, 2H).

Example 180

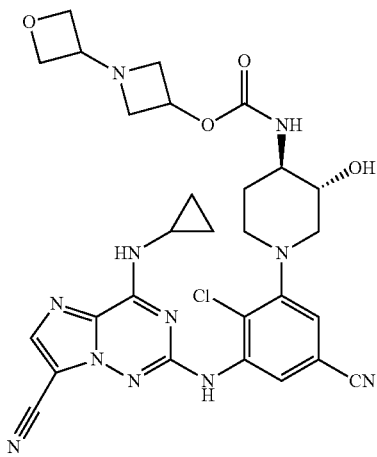 [SMILES: N#Cc1cc(Nc2nc(NC3CC3)c3ncc(C#N)n3n2)c(Cl)c(N2CC[C@@H](NC(=O)OC3CN(C4COC4)C3)[C@H](O)C2)c1]

(+/−)-1-(oxetan-3-yl)azetidin-3-yl((3R,4R)-1-(2-chloro-5-cyano-3-((7-cyano-4-(cyclopropylamino)imidazo[2,1-f][1,2,4]triazin-2-yl)amino)phenyl)-3-hydroxypiperidin-4-yl)carbamate (180A): A mixture of oxetan-3-one (0.5 g, 6.94 mmol), azetidin-3-ol hydrochloride (1.140 g, 10.41 mmol) and 4 A molecular sieves (1.5 g) in dichloromethane (10 mL) was stirred at room temperature for 4 h. sodium triacetoxyborohydride (2.94 g, 13.88 mmol) was added and the reaction mixture was stirred at room temperature overnight. The ppt was filtered through a pad of celite and the filtrate was diluted with ethyl acetate (more ppt appeared) and filtered again. The filtrate was concentrated in vacuo and the crude product was purified by flash chromatography on silica gel using an automated ISCO system (80 g column, eluting with 3-10% 2N ammonia in methanol/dichloromethane). 1-(oxetan-3-yl)azetidin-3-ol was obtained as a colorless oil.

MS (ESI) m/z 130.0

$^1$H NMR (400 MHz, chloroform-d) δ 4.71 (t, J=6.7 Hz, 2H), 4.56-4.48 (m, 3H), 3.78 (tt, J=6.6, 5.3 Hz, 1H), 3.69-3.63 (m, 2H), 3.10-3.04 (m, 2H).

Example 180

The title compound was prepared from (+/−)-2-((3-((3R,4R)-4-amino-3-((tert-butyldimethylsilyl)oxy)piperidin-1-yl)-2-chloro-5-cyanophenyl)amino)-4-(cyclopropylamino)imidazo[2,1-f][1,2,4]triazine-7-carbonitrile (Example 177C) and 1-(oxetan-3-yl)azetidin-3-ol using a method analogous to that used to prepare Example 177.

MS (ESI) m/z 620.1

$^1$H NMR (500 MHz, chloroform-d) δ 8.81 (d, J=1.7 Hz, 1H), 7.88 (s, 1H), 7.59 (s, 1H), 7.03 (d, J=1.7 Hz, 1H), 6.89 (d, J=2.5 Hz, 1H), 5.19-5.12 (m, 1H), 5.03 (d, J=7.2 Hz, 1H), 4.73 (t, J=6.8 Hz, 2H), 4.55 (ddd, J=6.9, 5.2, 2.1 Hz, 2H), 3.88-3.82 (m, 1H), 3.81-3.75 (m, 1H), 3.72 (t, J=7.4 Hz, 2H), 3.64-3.52 (m, 2H), 3.35-3.25 (m, 3H), 3.07 (tq, J=7.1, 3.5 Hz, 1H), 2.89-2.80 (m, 1H), 2.70 (t, J=10.3 Hz, 1H), 2.18 (d, J=10.5 Hz, 1H), 1.83-1.76 (m, 2H), 1.15-1.09 (m, 2H), 0.86-0.81 (m, 2H).

Example 181

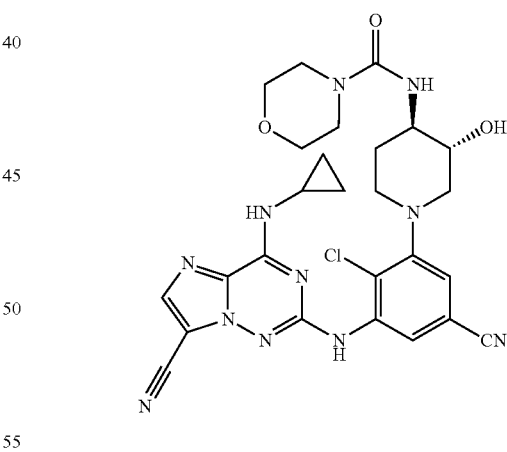

(+/−)-N-((3R,4R)-1-(2-chloro-5-cyano-3-((7-cyano-4-(cyclopropylamino)imidazo[2,1-f][1,2,4]triazin-2-yl)amino)phenyl)-3-hydroxypiperidin-4-yl)morpholine-4-carboxamide (181A): TFA (25% in 1,2-dichloroethane, 3 mL, 9.73 mmol) was added to a solution of (+/−)-tert-butyl((3R,4R)-3-((tert-butyldimethylsilyl)oxy)-1-(2-chloro-5-cyano-3-((7-cyano-4-(cyclopropyl(4-methoxybenzyl)amino)imidazo[2,1-f][1,2,4]triazin-2-yl)amino)phenyl)piperidin-4-yl)carbamate (Example 20B, 180 mg, 0.225 mmol) and anisole (0.098 mL, 0.901 mmol) in dichloromethane (1 mL) and the resulting reaction mixture was stirred at room temperature for 1 h. LCMS showed consumption of starting material and formation of two product (desired product and loss of Boc and PMB by-product). The reaction mixture was diluted with dichloromethane, washed cold saturated sodium bicarbonate/1N aqueous sodium hydroxide (pH 10). The layers were separated and aqueous layer was extracted with dichloromethane two more times. The combined organic layer was dried over magnesium sulfate, filtered and concentrated in vacuo, the crude product was purified by flash chromatography on silica gel using an automated ISCO system (40 g column, eluting with 1-3% methanol/dichloromethane) to give (+/−)-2-((3-((3R,4R)-4-amino-3-((tert-butyldimethylsilyl)oxy)piperidin-1-yl)-2-chloro-5-cyanophenyl)amino)-4-(cyclopropyl(4-methoxybenzyl)amino)imidazo[2,1-f][1,2,4]triazine-7-carbonitrile (114 mg) and (+/−)-2-((3-((3R,4R)-4-amino-3-((tert-butyldimethylsilyl)oxy)piperidin-1-yl)-2-chloro-5-cyanophenyl)amino)-4-(cyclopropylamino)imidazo[2,1-f][1,2,4]triazine-7-carbonitrile (30 mg).

MS (ESI) m/z 699.3 (M+H).

(181B): A solution of (+/−)-2-((3-((3R,4R)-4-amino-3-((tert-butyldimethyl silyl)oxy)piperidin-1-yl)-2-chloro-5-cyanophenyl)amino)-4-(cyclopropyl(4-methoxybenzyl)amino)imidazo[2,1-f][1,2,4]triazine-7-carbonitrile (40 mg, 0.057 mmol) in THF (1 mL) was added to CDI (37.1 mg, 0.229 mmol) in THF (1 mL) at 0° C. and the reaction mixture was stirred at room temperature overnight. Morpholine (39.9 mg, 0.458 mmol) was added and the reaction mixture was stirred at room temperature for 1 h. LCMS showed completion of reaction. Solvent was evaporated and the residue was partitioned between dichloromethane and saturated sodium bicarbonate. The layers were separated and the organic layer was dried over magnesium sulfate, filtered and concentrated in vacuo, the crude product was purified by flash chromatography on silica gel using an automated ISCO system (24 g column, eluting with 2-6% 2 N ammonia in methanol/dichloromethane). (+/−)-N-((3R,4R)-3-((tert-butyldimethylsilyl)oxy)-1-(2-chloro-5-cyano-3-((7-cyano-4-(cyclopropyl(4-methoxybenzyl)amino)imidazo[2,1-f][1,2,4]triazin-2-yl)amino)phenyl)piperidin-4-yl)morpholine-4-carboxamide (34 mg) was obtained as a white solid.

MS (ESI) m/z 812.5 (M+H).

Example 181

(+/−)-N-((3R,4R)-1-(2-chloro-5-cyano-3-((7-cyano-4-(cyclopropylamino)imidazo[2,1-f][1,2,4]triazin-2-yl)amino)phenyl)-3-hydroxypiperidin-4-yl)morpholine-4-carboxamide was prepared from (+/−)-N-((3R,4R)-3-((tert-butyldimethylsilyl)oxy)-1-(2-chloro-5-cyano-3-((7-cyano-4-(cyclopropyl(4-methoxybenzyl)amino)imidazo[2,1-f][1,2,4]triazin-2-yl)amino)phenyl)piperidin-4-yl)morpholine-4-carboxamide using a method analogous to that used to prepare Example 7.

MS (ESI) m/z 578.2

¹H NMR (500 MHz, DMSO-d₆) δ 9.32 (d, J=4.2 Hz, 1H), 8.83 (s, 1H), 8.20 (s, 1H), 8.10 (d, J=1.9 Hz, 1H), 7.32 (d, J=1.9 Hz, 1H), 6.36 (d, J=7.5 Hz, 1H), 3.67-3.60 (m, 1H), 3.59-3.55 (m, 2H), 3.38-3.20 (m, 11H), 3.01-2.95 (m, 1H), 2.81-2.74 (m, 1H), 1.98-1.82 (m, 1H), 1.61 (qd, J=12.2, 4.3 Hz, 1H), 0.81-0.77 (m, 4H).

Example 182

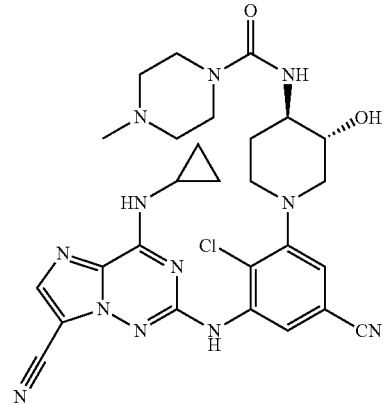 [SMILES: CN1CCN(C(=O)N[C@@H]2CCN(c3cc(C#N)cc(Nc4nc(NC5CC5)c5ncc(C#N)n5n4)c3Cl)C[C@H]2O)CC1]

(+/−)-N-((3R,4R)-1-(2-chloro-5-cyano-3-((7-cyano-4-(cyclopropylamino)imidazo[2,1-f][1,2,4]triazin-2-yl)amino)phenyl)-3-hydroxypiperidin-4-yl)-4-methylpiperazine-1-carboxamide The title compound was prepared from (+/−)-2-((3-((3R,4R)-4-amino-3-hydroxypiperidin-1-yl)-2-chloro-5-cyanophenyl)amino)-4-(cyclopropylamino)imidazo[2,1-f][1,2,4]triazine-7-carbonitrile (byproduct from Example 177), using a method analogous to that used to prepare Example 181.

MS (ESI) m/z 591.2

¹H NMR (500 MHz, chloroform-d) δ 8.80 (d, J=1.7 Hz, 1H), 7.88 (s, 1H), 7.60 (s, 1H), 7.03 (d, J=1.7 Hz, 1H), 6.85 (d, J=2.2 Hz, 1H), 4.55 (d, J=5.3 Hz, 1H), 3.77-3.68 (m, 2H), 3.63-3.56 (m, 1H), 3.47 (q, J=4.5 Hz, 4H), 3.40-3.33 (m, 1H), 3.07 (tq, J=7.0, 3.6 Hz, 1H), 2.83 (td, J=11.8, 2.2 Hz, 1H), 2.65 (dd, J=11.5, 9.3 Hz, 1H), 2.46 (t, J=5.0 Hz, 4H), 2.35 (s, 3H), 2.10-2.04 (m, 1H), 1.86-1.76 (m, 2H), 1.15-1.09 (m, 2H), 0.86-0.81 (m, 2H).

Example 183

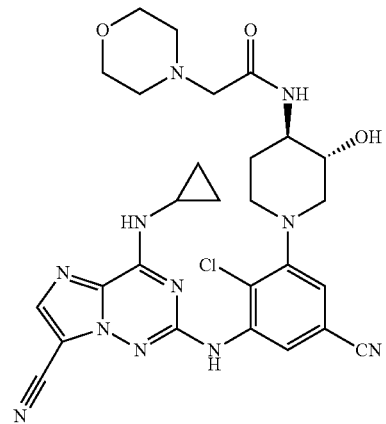 [SMILES: N#Cc1cc(Nc2nc(NC3CC3)c3ncc(C#N)n3n2)c(Cl)c(N2CC[C@@H](NC(=O)CN3CCOCC3)[C@H](O)C2)c1]

(+/−)-N-((3R,4R)-1-(2-chloro-5-cyano-3-((7-cyano-4-(cyclopropylamino)imidazo[2,1-f][1,2,4]triazin-2-yl)amino)phenyl)-3-hydroxypiperidin-4-yl)-2-morpholinoacetamide (183A): A mixture of (+/−)-2-((3-((3R,4R)-4-amino-3-((tert-butyldimethylsilyl)oxy)piperidin-1-yl)-2-chloro-5- cyanophenyl)amino)-4-(cyclopropyl(4-methoxybenzyl) amino)imidazo[2,1-f][1,2,4]triazine-7-carbonitrile (Example 171E, 40 mg, 0.057 mmol), 2-morpholinoacetic acid (9.96 mg, 0.069 mmol) and HATU (26.1 mg, 0.069 mmol) in DMF (1 mL) was stirred at room temperature for 6 h. The reaction mixture was diluted with dichloromethane and was filtered. The filtrate was concentrated in vacuo and the crude product was purified by flash chromatography on silica gel using an automated ISCO system (24 g column, eluting with 5-50% ethyl acetate/hexanes). (+/−)-N-((3R,4R)-3-((tert-butyldimethylsilyl)oxy)-1-(2-chloro-5-cyano-3-((7-cyano-4-(cyclopropyl(4-methoxybenzyl)amino)imidazo[2,1-f][1,2,4]triazin-2-yl)amino)phenyl)piperidin-4-yl)-2-morpholinoacetamide (46 mg) was obtained as a white solid.

MS (ESI) m/z 826.6

(183B): The title compound was prepared from (+/−)-N-((3R,4R)-3-((tert-butyldimethylsilyl)oxy)-1-(2-chloro-5-cyano-3-((7-cyano-4-(cyclopropyl(4-methoxybenzyl)amino)imidazo[2,1-f][1,2,4]triazin-2-yl)amino)phenyl)piperidin-4-yl)-2-morpholinoacetamide using a method analogous to that used to prepare Example 7.

MS (ESI) m/z 592.3

$^1$H NMR (500 MHz, DMSO-$d_6$) δ 9.33 (d, J=4.2 Hz, 1H), 8.83 (s, 1H), 8.20 (s, 1H), 8.12 (d, J=1.9 Hz, 1H), 7.64 (d, J=6.9 Hz, 1H), 7.33 (d, J=1.9 Hz, 1H), 5.00 (d, J=5.5 Hz, 1H), 3.70-3.56 (m, 6H), 3.46-3.38 (m, 1H), 3.23 (d, J=11.1 Hz, 1H), 3.03-2.88 (m, 3H), 2.84-2.74 (m, 1H), 2.59-2.53 (m, 1H), 2.46 (br. s., 3H), 1.95-1.85 (m, 1H), 1.63 (qd, J=12.1, 4.0 Hz, 1H), 0.79 (d, J=5.3 Hz, 4H).

Example 184

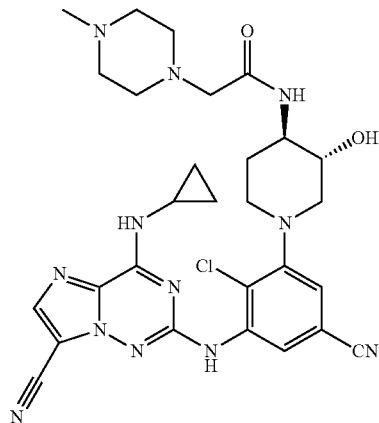 [SMILES: CN1CCN(CC(=O)N[C@@H]2CCN(c3cc(C#N)cc(Nc4nc(NC5CC5)c5ncc(C#N)n5n4)c3Cl)C[C@H]2O)CC1]

(+/−)-N-((3R,4R)-1-(2-chloro-5-cyano-3-((7-cyano-4-(cyclopropylamino)imidazo[2,1-f][1,2,4]triazin-2-yl)amino)phenyl)-3-hydroxypiperidin-4-yl)-2-(4-methylpiperazin-1-yl)acetamide Prepared analogous manner as example 183
MS (ESI) m/z 605.3

$^1$H NMR (500 MHz, DMSO-$d_6$) δ 9.33 (d, J=4.4 Hz, 1H), 8.84 (s, 1H), 8.21 (s, 1H), 8.11 (d, J=1.9 Hz, 1H), 7.63 (br. s., 1H), 7.33 (d, J=1.7 Hz, 1H), 7.15-7.05 (m, 2H), 6.90-6.77 (m, 2H), 5.01 (d, J=5.3 Hz, 1H), 3.83-3.77 (m, 1H), 3.74-3.69 (m, 3H), 3.67-3.55 (m, 2H), 3.42 (d, J=9.7 Hz, 1H), 3.23 (d, J=11.7 Hz, 1H), 3.06-2.94 (m, 3H), 2.84-2.76 (m, 2H), 2.44 (br. s., 2H), 1.91 (d, J=8.9 Hz, 1H), 1.68-1.55 (m, 1H), 0.79 (d, J=5.3 Hz, 4H).

Example 185

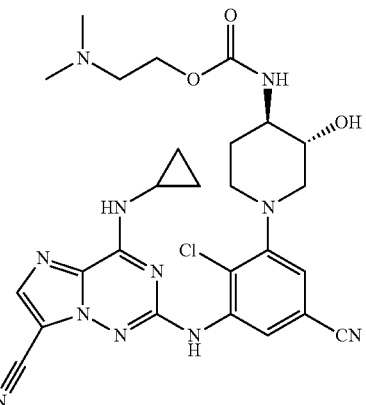

(+/−)-N-((3R,4R)-1-(2-chloro-5-cyano-3-((7-cyano-4-(cyclopropylamino)imidazo[2,1-f][1,2,4]triazin-2-yl)amino)phenyl)-3-hydroxypiperidin-4-yl)-2-(4-methylpiperazin-1-yl)acetamide Prepared analogous manner as example 180
MS (ESI) m/z 581.1

Example 186

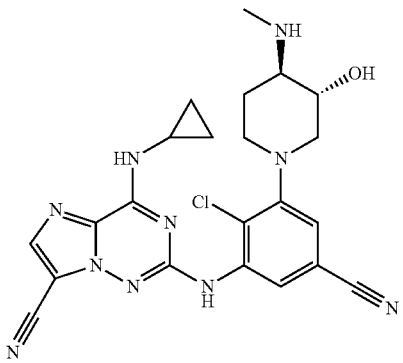 [SMILES: CN[C@@H]1CCN(c2cc(C#N)cc(Nc3nc(NC4CC4)c4ncc(C#N)n4n3)c2Cl)C[C@H]1O]

(+/−)-2-((2-chloro-5-cyano-3-((3R,4R)-3-hydroxy-4-(methylamino)piperidin-1-yl)phenyl)amino)-4-(cyclopropylamino)imidazo[2,1-f][1,2,4]triazine-7-carbonitrile (186A): A mixture of benzyl 7-oxa-3-azabicyclo[4.1.0]heptane-3-carboxylate (0.7 g, 3.00 mmol) and methanamine (3.75 mL, 30.0 mmol) in ethanol (5 mL) was heated in a sealed reaction pressure vessel at 70° C. overnight. The reaction mixture was cooled to room temperature and concentrated to dryness. The residue was dissolved in dichloromethane (5.00 mL), triethylamine (0.502 mL, 3.60 mmol) and di-tert-butyl dicarbonate (0.766 mL, 3.30 mmol) were added and the reaction mixture was stirred at room temperature for 4 h. The reaction mixture was washed with water and brine, dried over magnesium sulfate and concentrated to give a colorless oil. The above oil was dissolved in DMF (5.00 mL), imidazole (0.409 g, 6.00 mmol) and tert-butyldimethylchlorosilane (0.678 g, 4.50 mmol) were added. The mixture was stirred at room temperature overnight. Water was added and the reaction mixture was extracted with ethyl acetate (3×), the organic layer was dried over magnesium sulfate, filtered and concentrated in vacuo, the crude product was purified by flash chromatography on silica gel using an automated ISCO system (80 g gold column, eluting with 5-30% ethyl acetate/hexanes) to give (+/−)-(3R,4R)-benzyl 3-((tert-butoxycarbonyl)(methyl)amino)-4-((tert-butyldimethylsilyl)oxy)piperidine-1-carboxylate (Isomer A, 0.697 g) and (+/−)-(3R,4R)-benzyl 4-((tert-butoxycarbonyl)(methyl)amino)-3-((tert-butyldimethylsilyl)oxy)piperidine-1-carboxylate (Isomer B, 0.556 g). The structures were confirmed by NMR studies ($^1$H-1D, $^{13}$C-1D, COSY, NOESY, dept-$^1$H-$^{13}$C-HSQC, $^1$H-$^{13}$C-HMBC).

Isomer A (+/−)-(3R,4R)-benzyl 3-((tert-butoxycarbonyl)(methyl)amino)-4-((tert-butyldimethylsilyl)oxy)piperidine-1-carboxylate:

MS (ESI) m/z 479.5

$^1$H NMR (500 MHz, methanol-$d_4$) δ 7.39-7.27 (m, 5H), 5.12 (br. s., 2H), 4.82 (s, 2H), 4.09 (dt, J=13.7, 2.0 Hz, 1H), 4.00 (d, J=10.3 Hz, 2H), 3.61 (br. s., 1H), 3.06 (br. s., 1H), 2.82 (br. s., 4H), 2.05-1.92 (m, 1H), 1.51-1.37 (m, 11H), 0.89-0.85 (m, 9H), 0.11-0.06 (m, 6H).

Isomer B (+/−)-(3R,4R)-benzyl 4-((tert-butoxycarbonyl)(methyl)amino)-3-((tert-butyldimethylsilyl)oxy)piperidine-1-carboxylate:

MS (ESI) m/z 501.5

$^1$H NMR (500 MHz, methanol-$d_4$) δ 7.39 (d, J=4.7 Hz, 5H), 5.29-4.96 (m, 2H), 4.84 (s, 2H), 4.27 (br. s., 1H), 4.20-4.11 (m, 1H), 3.94-3.56 (m, 2H), 2.79 (br. s., 4H), 2.72-2.53 (m, 1H), 1.84 (br. s., 1H), 1.65 (br. s., 1H), 1.47 (s, 9H), 0.89 (d, J=2.8 Hz, 9H), 0.26-0.11 (m, 6H).

(186B): (+/−)-tert-butyl((3R,4R)-1-(3-amino-2-chloro-5-cyanophenyl)-3-((tert-butyldimethylsilyl)oxy)piperidin-4-yl)(methyl)carbamate was prepared starting from from (+/−)-(3R,4R)-benzyl 4-((tert-butoxycarbonyl)(methyl)amino)-3-((tert-butyldimethylsilyl)oxy)piperidine-1-carboxylate using a method analogous to that used to prepare Example 171C-D.

MS (ESI) m/z 495.3

Example 186

The title compound was prepared from (+/−)-tert-butyl ((3R,4R)-1-(3-amino-2-chloro-5-cyanophenyl)-3-((tert-butyldimethylsilyl)oxy)piperidin-4-yl)(methyl)carbamate using a method analogous to that used to prepare Example 174.

MS (ESI) m/z 479.3

$^1$H NMR (500 MHz, methanol-$d_4$) δ 8.69 (d, J=1.9 Hz, 1H), 7.87 (s, 1H), 7.01 (d, J=1.9 Hz, 1H), 3.62 (td, J=9.6, 4.7 Hz, 1H), 3.43 (ddd, J=10.8, 4.7, 2.2 Hz, 1H), 3.02 (tt, J=7.2, 3.7 Hz, 1H), 2.71 (td, J=11.9, 2.2 Hz, 1H), 2.57 (t, J=10.4 Hz, 1H), 2.43 (s, 3H), 2.36 (ddd, J=11.3, 9.2, 4.4 Hz, 1H), 2.11-2.05 (m, 1H), 1.54 (qd, J=12.2, 4.2 Hz, 1H), 1.02-0.98 (m, 2H), 0.80-0.74 (m, 2H).

Example 187

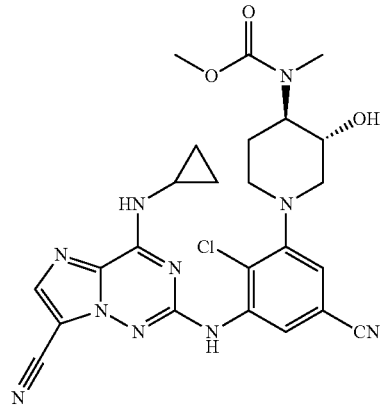 [SMILES: COC(=O)N(C)[C@@H]1CCN(c2cc(C#N)cc(Nc3nc(NC4CC4)c4ncc(C#N)n4n3)c2Cl)C[C@H]1O]

(+/−)-methyl((3R,4R)-1-(2-chloro-5-cyano-3-((7-cyano-4-(cyclopropylamino)imidazo[2,1-f][1,2,4]triazin-2-yl)amino)phenyl)-3-hydroxypiperidin-4-yl)(methyl)carbamate (187A): (+/−)-tert-butyl((3R,4R)-1-(3-amino-2-chloro-5-cyanophenyl)-3-((tert-butyldimethylsilyl)oxy)piperidin-4-yl)(methyl)carbamate (Example 186B, 78 mg, 0.158 mmol) was treated with TFA (25% in 1,2-dichloroethane, 0.012 mL, 0.158 mmol) at rt for 1 h. LCMS showed completion of reaction. The reaction mixture was diluted with dichloromethane and washed with cold saturated sodium bicarbonate/1N aqueous sodium hydroxide (pH 10). The organic layer was dried over magnesium sulfate, filtered and concentrated in vacuo, the crude product was purified by flash chromatography on silica gel using an automated ISCO system (12 g column, eluting with 1-10% 2 N ammonia in methanol/dichloromethane) to give (+/−)-3-amino-5-((3R,4R)-3-((tert-butyldimethylsilyl)oxy)-4-(methylamino)piperidin-1-yl)-4-chlorobenzonitrile (54 mg) was obtained as a colorless oil.

MS (ESI) m/z 495.3.

To a solution of (+/−)-3-amino-5-((3R,4R)-3-((tert-butyldimethylsilyl)oxy)-4-(methylamino)piperidin-1-yl)-4-chlorobenzonitrile (54 mg, 0.137 mmol) and triethylamine (0.022 mL, 0.158 mmol) in dichloromethane (3 mL) at 0° C. was added dimethyl dicarbonate (21.12 mg, 0.158 mmol) in dichloromethane (1 mL) and the reaction solution was stirred at rt for 2 h. Solvent was evaporated and the crude product was purified by flash chromatography on silica gel using an automated ISCO system (24 g column, eluting with 0-25% ethyl acetate/dichloromethane). (+/−)-methyl((3R,4R)-1-(3-amino-2-chloro-5-cyanophenyl)-3-((tert-butyldimethylsilyl)oxy)piperidin-4-yl)(methyl)carbamate (59 mg) was obtained as a light yellow solid.

MS (ESI) m/z 453.2 (M+H).

Example 187

The title compound was prepared from (+/−)-methyl((3R,4R)-1-(3-amino-2-chloro-5-cyanophenyl)-3-((tert-butyldimethylsilyl)oxy)piperidin-4-yl)(methyl)carbamate using a method analogous to that used to prepare Example 171.

MS (ESI) m/z 537.1

¹H NMR (500 MHz, chloroform-d) δ 8.89-8.80 (m, 1H), 7.92-7.86 (m, 1H), 7.61 (s, 1H), 7.04 (dd, J=4.2, 1.7 Hz, 1H), 6.76 (br. s., 1H), 3.76 (br. s., 2H), 3.72-3.62 (m, 1H), 3.47-3.35 (m, 1H), 3.08 (td, J=6.9, 3.3 Hz, 1H), 3.01-2.80 (m, 5H), 2.26-2.01 (m, 1H), 2.01-1.83 (m, 1H), 1.19-1.08 (m, 2H), 0.87-0.80 (m, 2H).

Example 188

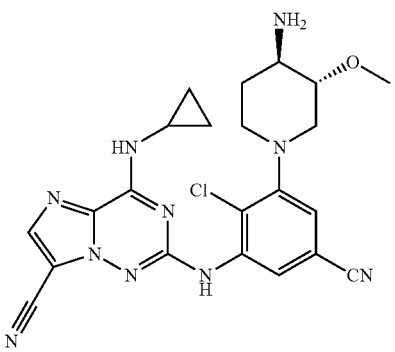 [SMILES: CO[C@@H]1CN(c2cc(C#N)cc(Nc3nc(NC4CC4)c4ncc(C#N)n4n3)c2Cl)CC[C@H]1N]

(+/−)-2-((3-((3R,4R)-4-amino-3-methoxypiperidin-1-yl)-2-chloro-5-cyanophenyl)amino)-4-(cyclopropylamino)imidazo[2,1-f][1,2,4]triazine-7-carbonitrile (188A): TBAF, 1 M in THF (0.774 mL, 0.774 mmol) was added to a solution of (+/−)-3-N-Boc-amino-5-((3R,4R)-4-N-Boc-amino-3-((tert-butyldimethylsilyl)oxy)piperidin-1-yl)-4-chlorobenzonitrile (Example 171C, 300 mg, 0.516 mmol) in THF (2 mL) and the reaction mixture was stirred at room temperature overnight. LCMS showed completion of reaction. Solvent was evaporated and the crude product was purified by flash chromatography on silica gel using an automated ISCO system (40 g column, eluting with 5-60% ethyl acetate/dichloromethane) to give (+/−)-tert-butyl((3R,4R)-1-(3-N-Boc-amino-2-chloro-5-cyanophenyl)-3-hydroxypiperidin-4-yl)carbamate (254 mg) was obtained as a colorless oil.

MS (ESI) m/z 467.2

(188B): Sodium hydride (60% in mineral oil, 15.83 mg, 0.396 mmol) was added to a solution of (+/−)-tert-butyl((3R,4R)-1-(3-N-Boc-amino-2-chloro-5-cyanophenyl)-3-hydroxypiperidin-4-yl)carbamate (154 mg, 0.330 mmol) and iodomethane (61.9 µl, 0.989 mmol) in THF at room temperature and the reaction mixture was stirred for 6 h. The reaction was quenched with addition of water and extracted with ethyl acetate (three times). The combined organic layers were dried over magnesium sulfate, filtered and concentrated in vacuo, the crude product was purified by flash chromatography on silica gel using an automated ISCO system (40 g column, eluting with 0-30% ethyl acetate/dichloromethane). (+/−)-tert-butyl((3R,4R)-1-(3-N-Boc-amino-2-chloro-5-cyanophenyl)-3-methoxypiperidin-4-yl)carbamate (95 mg) was obtained as a colorless oil.

MS (ESI) m/z 481.2

(188C): (+/−)-tert-butyl((3R,4R)-1-(3-N-Boc-amino-2-chloro-5-cyanophenyl)-3-methoxypiperidin-4-yl)carbamate (95 mg, 0.198 mmol) was treated with TFA (25% in 1,2-dichloroethane, 2 mL, 6.49 mmol) at room temperature for 1 h. Solvent was evaporated and the crude was redissolved in dichloromethane and concentrated again.

The crude product was dried under vacuum overnight and neutralized with triethylamine and concentrated. The crude product was used without purification.

MS (ESI) m/z 281.2 (M+H).

(188D): di-tert-butyl dicarbonate (0.028 mL, 0.119 mmol) in dichloromethane (1 mL) was added to a solution of (+/−)-3-amino-5-((3R,4R)-4-amino-3-methoxypiperidin-1-yl)-4-chlorobenzonitrile (0.028 g, 0.099 mmol) and triethylamine (0.028 mL, 0.198 mmol) in dichloromethane (1 mL) at 0° C. and the resulting reaction solution was stirred at room temperature for 2 h Solvent was evaporated and the crude product was purified by flash chromatography on silica gel using an automated ISCO system (24 g column, eluting with 0-30% ethyl acetate/dichloromethane). (+/−)-tert-butyl((3R,4R)-1-(3-amino-2-chloro-5-cyanophenyl)-3-methoxypiperidin-4-yl)carbamate (26 mg) was obtained as a colorless oil.

MS (ESI) m/z 381.1

Example 188

The title compound was prepared from (+/−)-tert-butyl ((3R,4R)-1-(3-amino-2-chloro-5-cyanophenyl)-3-methoxypiperidin-4-yl)carbamate using a method analogous to that used to prepare Example 171.

MS (ESI) m/z 479.1

¹H NMR (500 MHz, methanol-d₄) δ 7.94 (s, 1H), 6.71 (d, J=1.7 Hz, 1H), 6.61 (d, J=1.7 Hz, 1H), 5.00 (td, J=9.6, 4.4 Hz, 1H), 4.00 (ddd, J=11.0, 4.6, 1.9 Hz, 1H), 3.32-3.27 (m, 1H), 3.10-3.03 (m, 2H), 2.95-2.90 (m, 1H), 2.88 (s, 3H), 2.58 (t, J=10.4 Hz, 1H), 2.14-2.08 (m, 1H), 1.80 (qd, J=12.3, 4.3 Hz, 1H), 0.98-0.89 (m, 2H), 0.79-0.71 (m, 2H).

Example 189

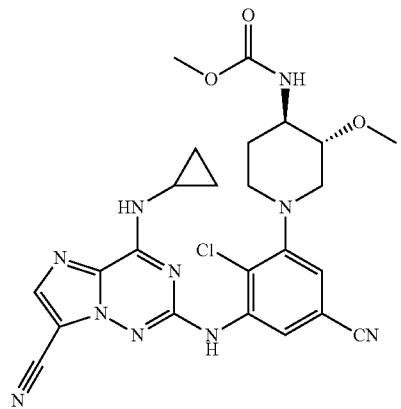 [SMILES: COC(=O)N[C@@H]1CCN(c2cc(C#N)cc(Nc3nc(NC4CC4)c4ncc(C#N)n4n3)c2Cl)C[C@H]1OC]

(+/−)-methyl((3R,4R)-1-(2-chloro-5-cyano-3-((7-cyano-4-(cyclopropylamino)imidazo[2,1-f][1,2,4]triazin-2-yl)amino)phenyl)-3-methoxypiperidin-4-yl)carbamate (189A): Dimethyl dicarbonate (15.93 mg, 0.119 mmol) in dichloromethane (1 mL) was added to a solution of (+/−)-3-amino-5-((3R,4R)-4-amino-3-methoxypiperidin-1-yl)-4-chlorobenzonitrile (Example 41C, 27.8 mg, 0.099 mmol) and triethylamine (0.028 mL, 0.198 mmol) in dichloromethane (1 mL) at 0° C. and the resulting reaction solution was stirred at room temperature for 2 h. Solvent was evaporated and the crude product was purified by flash chromatography on silica gel using an automated ISCO system (24 g column, eluting with 0-50% ethyl acetate/dichloromethane). (+/−)-methyl((3R,4R)-1-(3-amino-2-chloro-5-cyanophenyl)-3-methoxypiperidin-4-yl)carbamate (15 mg) was obtained as a colorless oil.

MS (ESI) m/z 339.0

Example 189

The title compound was prepared (+/−)-methyl((3R,4R)-1-(3-amino-2-chloro-5-cyanophenyl)-3-methoxypiperidin-4-yl)carbamate using a method analogous to that used to prepare Example 171.

MS (ESI) m/z 537.1

$^1$H NMR (500 MHz, methanol-d$_4$) δ 7.94 (s, 1H), 6.72 (d, J=1.7 Hz, 1H), 6.62 (d, J=1.7 Hz, 1H), 5.23 (td, J=9.6, 4.7 Hz, 1H), 3.88 (ddd, J=16.6, 11.5, 4.9 Hz, 2H), 3.64 (br. s., 3H), 3.4-4.269 (m, 1H), 3.07 (tt, J=7.3, 3.7 Hz, 1H), 2.92 (t, J=11.7 Hz, 1H), 2.88 (s, 3H), 2.75 (t, J=10.4 Hz, 1H), 2.26 (d, J=8.3 Hz, 1H), 1.93-1.83 (m, 1H), 0.96-0.91 (m, 2H), 0.77-0.71 (m, 2H).

Example 190

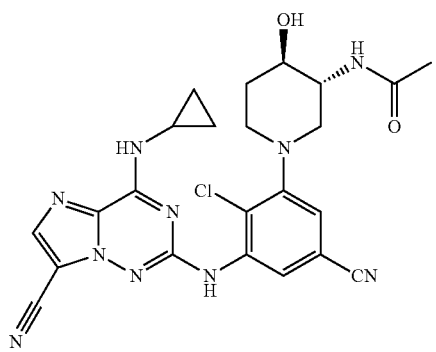 [SMILES: CC(=O)N[C@@H]1CN(c2cc(C#N)cc(Nc3nc(NC4CC4)c4ncc(C#N)n4n3)c2Cl)CC[C@H]1O]

(+/−)-N-((3R,4R)-1-(2-chloro-5-cyano-3-((7-cyano-4-(cyclopropylamino)imidazo[2,1-f][1,2,4]triazin-2-yl)amino)phenyl)-4-hydroxypiperidin-3-yl)acetamide (190A): (+/−)-N-((3R,4R)-1-(3-amino-2-chloro-5-cyanophenyl)-4-((tert-butyldimethyl silyl)oxy)piperidin-3-yl)acetamide was prepared starting from (+/−)-tert-butyl((3R, 4R)-4-hydroxypiperidin-3-yl)carbamate (prepared according to a published literature procedure: Fink, Brian, et al., WO 2005/066176) using a method analogous to that used to prepare Example 7.

MS (ESI) m/z 423.2

(15B): (+/−)-N-((3R,4R)-1-(2-chloro-5-cyano-3-((7-cyano-4-(cyclopropylamino) imidazo[2,1-f][1,2,4]triazin-2-yl)amino)phenyl)-4-hydroxypiperidin-3-yl)acetamide was prepared starting from 4-(cyclopropyl(4-methoxybenzyl)amino)-2-(methylsulfonyl)imidazo[2,1-f][1,2,4]triazine-7-carbonitrile (Intermediate 2) and (+/−)-N-((3R,4R)-1-(3-amino-2-chloro-5-cyanophenyl)-4-((tert-butyldimethylsilyl)oxy) piperidin-3-yl)acetamide using a method analogous to that used to prepare Example 171.

MS (ESI) m/z 507.1

$^1$H NMR (500 MHz, DMSO-d$_6$) δ 9.31 (br. s., 1H), 8.83 (br. s., 1H), 8.20 (s, 1H), 8.09 (s, 1H), 7.77 (d, J=7.5 Hz, 1H), 7.31 (s, 1H), 4.86 (d, J=5.3 Hz, 1H), 3.73 (d, J=4.7 Hz, 1H), 2.97 (d, J=4.7 Hz, 1H), 2.76 (t, J=10.5 Hz, 1H), 2.00 (d, J=9.7 Hz, 1H), 1.85 (s, 3H), 1.63 (d, J=10.0 Hz, 1H), 0.78 (d, J=5.3 Hz, 4H).

Example 191

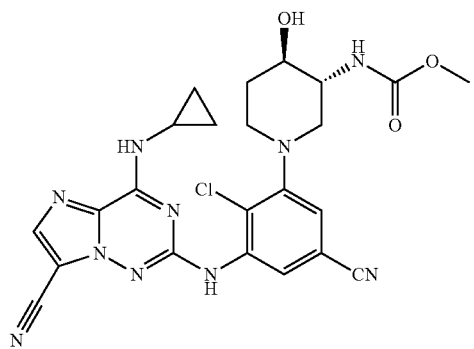 [SMILES: COC(=O)N[C@@H]1CN(c2cc(C#N)cc(Nc3nc(NC4CC4)c4ncc(C#N)n4n3)c2Cl)CC[C@H]1O]

(+/−)-methyl((3R,4R)-1-(2-chloro-5-cyano-3-((7-cyano-4-(cyclopropylamino)imidazo[2,1-f][1,2,4]triazin-2-yl)amino)phenyl)-4-hydroxypiperidin-3-yl)carbamate The title compound was prepared starting from (+/−)-tert-butyl((3R,4R)-4-hydroxypiperidin-3-yl)carbamate (prepared according to a published literature procedure: Fink, Brian, et al., WO 2005/066176) using a method analogous to that used to prepare Example 171.

MS (ESI) m/z 523.2

$^1$H NMR (400 MHz, chloroform-d) δ 8.80 (d, J=1.5 Hz, 1H), 7.86 (s, 1H), 7.59 (s, 1H), 7.02 (d, J=1.8 Hz, 1H), 6.94 (d, J=2.2 Hz, 1H), 5.37 (br. s, 1H), 3.83 (br. s., 2H), 3.72 (s, 3H), 3.51 (d, J=10.3 Hz, 1H), 3.29-3.19 (m, 1H), 3.06 (tq, J=7.0, 3.6 Hz, 1H), 2.95-2.86 (m, 1H), 2.85-2.74 (m, 1H), 2.56 (br. s., 1H), 2.24-2.13 (m, 1H), 1.92-1.81 (m, 1H), 1.14-1.06 (m, 2H), 0.85-0.78 (m, 2H).

Example 192

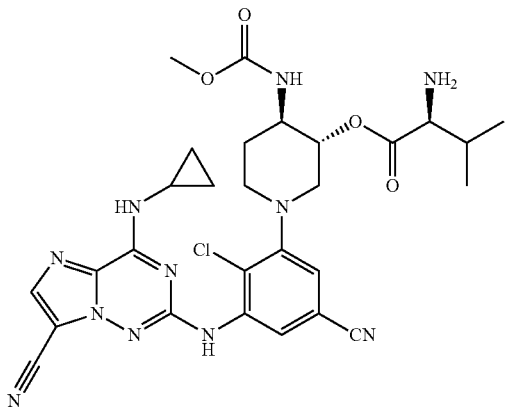 [SMILES: COC(=O)N[C@@H]1CCN(c2cc(C#N)cc(Nc3nc(NC4CC4)c4ncc(C#N)n4n3)c2Cl)C[C@H]1OC(=O)[C@@H](N)C(C)C]

(+/−)-(R)-(3S,4S)-1-(2-chloro-5-cyano-3-((7-cyano-4-(cyclopropylamino)imidazo[2,1-f][1,2,4]triazin-2-yl)amino)phenyl)-4-((methoxycarbonyl)amino)piperidin-3-yl 2-amino-3-methylbutanoate (192A): A mixture of (S)-2-((tert-butoxycarbonyl)amino)-3-methylbutanoic acid (30.4 mg, 0.140 mmol), Tetramethylfluoroformamidinium hexafluorophosphate (37.0 mg, 0.140 mmol) and triethyl amine (0.039 mL, 0.280 mmol) in dichloromethane (1 mL) was stirred at room temperature for 1 h. (+/−)-methyl((3R,4R)-1-(2-chloro-5-cyano-3-((7-cyano-4-(cyclopropyl(4-methoxybenzyl)amino)imidazo[2,1-f][1,2,4]triazin-2-yl)amino)phenyl)-3-hydroxypiperidin-4-yl)carbamate (Example 171, 18 mg, 0.028 mmol) and DMAP (0.342 mg, 2.80 μmol) were added and the reaction solution was stirred at room temperature for 1 h. The reaction mixture was diluted with dichloromethane and washed with saturated sodium bicarbonate. The organic layer was dried over magnesium sulfate, filtered and concentrated in vacuo, the crude product was purified by flash chromatography on silica gel using an automated ISCO system (12 g column, eluting with 5-30% ethyl acetate/ dichloromethane). (+/−)-(R)-(3S,4S)-1-(2-chloro-5-cyano-3-((7-cyano-4-(cyclopropyl(4-methoxybenzyl)amino)imidazo[2,1-f][1,2,4]triazin-2-yl)amino)phenyl)-4-((methoxycarbonyl)amino)piperidin-3-yl 2-((tert-butoxycarbonyl)amino)-3-methylbutanoate (23 mg) was obtained as a colorless oil.

MS (ESI) m/z 842.5 (M+H)

Example 192

TFA (25% in DCE, 2 ml) was added to a solution of (+/−)-(R)-(3S,4S)-1-(2-chloro-5-cyano-3-((7-cyano-4-(cyclopropyl(4-methoxybenzyl)amino)imidazo[2,1-f][1,2,4]triazin-2-yl)amino)phenyl)-4-((methoxycarbonyl)amino)piperidin-3-yl 2-((tert-butoxycarbonyl)amino)-3-methylbutanoate (23 mg, 0.027 mmol) and ANISOLE (0.012 ml, 0.109 mmol) in DCE (1 mL) and the resulting solution was stirred at 35° C. overnight. The reaction mixture was concentrated and purified by prep-HPLC to give the title compound (13 mg) as a white solid.

MS (ESI) m/z 622.2 (M+H)

$^1$H NMR (500 MHz, chloroform-d) δ 8.82 (s, 1H), 7.88 (s, 1H), 7.59 (s, 1H), 7.00 (d, J=1.9 Hz, 1H), 6.86 (d, J=2.2 Hz, 1H), 5.03 (td, J=9.5, 4.3 Hz, 1H), 4.96-4.86 (m, 1H), 3.86 (br. s., 1H), 3.70 (d, J=6.7 Hz, 3H), 3.61-3.51 (m, 1H), 3.40-3.31 (m, 1H), 3.11-3.03 (m, 1H), 2.92-2.76 (m, 2H), 2.33-2.21 (m, 1H), 2.17-2.02 (m, 1H), 1.87-1.77 (m, 1H), 1.15-1.08 (m, 2H), 1.01 (t, J=6.7 Hz, 3H), 0.91 (dd, J=10.0, 6.7 Hz, 3H), 0.86-0.80 (m, 2H)

The compounds listed below were prepared by the similar synthetic procedure used for Examples 192

TABLE 4

| Example No. | Structure | Name | [M + H]+ | HPLC Retention Time (min.)* |
|---|---|---|---|---|
| 193 | 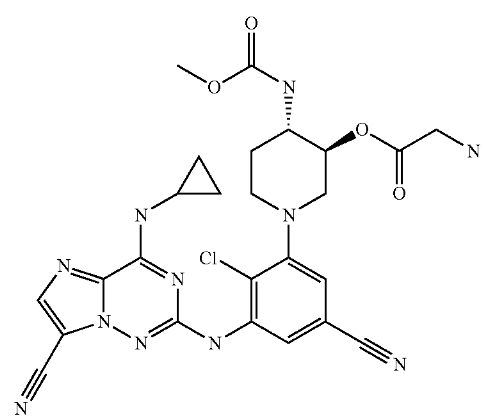 [SMILES: COC(=O)N[C@H]1CCN(c2cc(C#N)cc(Nc3nc(NC4CC4)c4ncc(C#N)n4n3)c2Cl)C[C@@H]1OC(=O)CN] | (3S,4S)-1-(2-chloro-5-cyano-3-((7-cyano-4-(cyclopropylamino)imidazo[2,1-f][1,2,4]triazin-2-yl)amino)phenyl)-4-((methoxycarbonyl)amino)-3-piperidinyl glycinate | 580.01 | 2.57 |
| 194 | Chiral | (3R,4R)-1-(2-chloro-5-cyano-3-((7-cyano-4-(cyclopropylamino)imidazo[2,1-f][1,2,4]triazin-2-yl)amino)phenyl)-4-((methoxycarbonyl)amino)-3-piperidinyl 1-aminocyclopropanecarboxylate | 606.04 | 2.78 |

TABLE 4-continued

| Example No. | Structure | Name | [M + H]+ | HPLC Retention Time (min.)* |
|---|---|---|---|---|
| 195 | Chiral | (3R,4R)-1-(2-chloro-5-cyano-3-((7-cyano-4-(cyclopropylamino)imidazo[2,1-f][1,2,4]triazin-2-yl)amino)phenyl)-4-((methoxycarbonyl)amino)-3-piperidinyl L-alaninate | 594.03 | 2.80 |
| 196 | Chiral | (3R,4R)-1-(2-chloro-5-cyano-3-((7-cyano-4-(cyclopropylamino)imidazo[2,1-f][1,2,4]triazin-2-yl)amino)phenyl)-4-((methoxycarbonyl)amino)-3-piperidinyl 4-morpholinylacetate | 650.10 | 2.73 |
| 197 | Chiral | (3R,4R)-1-(2-chloro-5-cyano-3-((7-cyano-4-(cyclopropylamino)imidazo[2,1-f][1,2,4]triazin-2-yl)amino)phenyl)-4-((methoxycarbonyl)amino)-3-piperidinyl 2-(phosphonooxy)propanoate | 675.00 | 2.72 |

TABLE 4-continued

| Example No. | Structure | Name | [M + H]+ | HPLC Retention Time (min.)* |
|---|---|---|---|---|
| 198 | 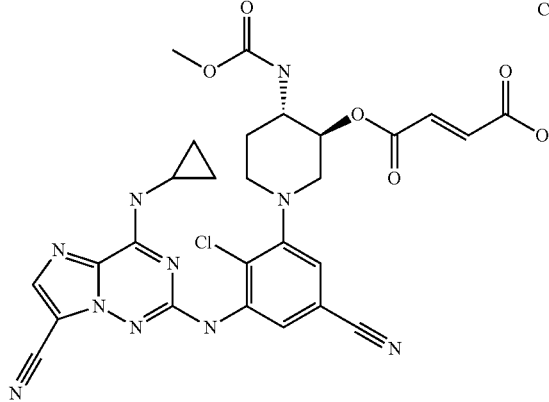 [SMILES: COC(=O)N[C@@H]1CCN(c2cc(C#N)cc(Nc3nc(NC4CC4)c4ncc(C#N)n4n3)c2Cl)C[C@H]1OC(=O)C(C)OP(=O)(O)O] Chiral | (2E)-4-(((3S,4S)-1-(2-chloro-5-cyano-3-((7-cyano-4-(cyclopropylamino) imidazo[2,1-f] [1,2,4]triazin-2-yl)amino)phenyl)-4-((methoxycarbonyl) amino)-3-piperidinyl) oxy)-4-oxo-2-butenoic acid | 621.01 | 3.79 |
| 199 | 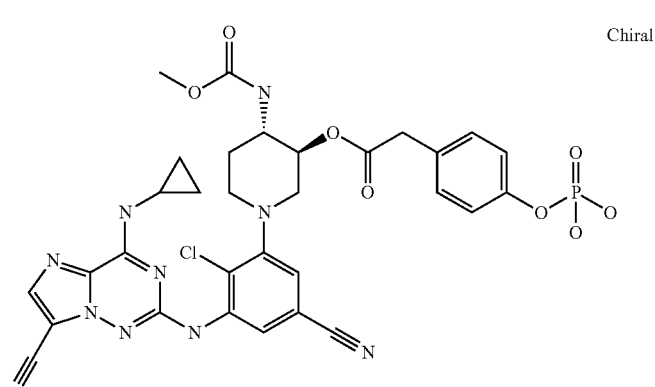 Chiral | (3S,4S)-1-(2-chloro-5-cyano-3-((7-cyano-4-(cyclopropylamino) imidazo[2,1-f][1,2,4] triazin-2-yl)amino) phenyl)-4-((methoxycarbonyl) amino)-3-piperidinyl (4-(phosphonooxy) phenyl)acetate | 737.07 | 3.63 |

* = HPLC conditions
YMC S5 ODS 4.6 × 50 mm, 10-90% aqueous methanol containing 0.2% $H_3PO_4$, 5 min. gradient, monitored at 220 nm Example 200

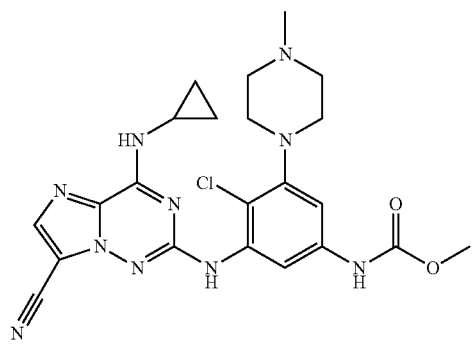 [SMILES: COC(=O)Nc1cc(Nc2nc(NC3CC3)c3ncc(C#N)n3n2)c(Cl)c(N2CCN(C)CC2)c1]

methyl(4-chloro-3-((7-cyano-4-(cyclopropylamino) imidazo[2,1-f][1,2,4]triazin-2-yl)amino)-5-(4-methylpiperazin-1-yl)phenyl)carbamate (200A): Methyl 3-((tert-butoxycarbonyl)amino)-4-chloro-5-(4-methylpiperazin-1-yl)benzoate was prepared starting from methyl 3-bromo-5-((tert-butoxycarbonyl) amino)-4-chlorobenzoate (Intermediate 3) and 1-methylpiperazine according to procedure for example 1A MS (ESI) m/z 384.3

$^1$H NMR (400 MHz, chloroform-d) δ 8.56 (d, J=1.8 Hz, 1H), 7.48 (d, J=2.0 Hz, 1H), 7.15 (s, 1H), 3.93 (s, 3H), 3.10 (t, J=4.2 Hz, 4H), 2.64 (br. s., 4H), 2.39 (s, 3H), 1.57 (s, 9H).

(200B): Lithium hydroxide (2.61 mL, 5.21 mmol) was added to a solution of methyl 3-((tert-butoxycarbonyl) amino)-4-chloro-5-(4-methylpiperazin-1-yl)benzoate (1.0 g, 2.61 mmol) in THF (10 mL) and methanol (2.5 mL). The resulting mixture was stirred at room temperature overnight. The reaction mixture was concentrated and azeotroped with acetonitrile to afford 1.30 g of crude product which was seed as is without further purification.

MS (ESI) m/z 370.1

(200C): To a solution of crude 3-((tert-butoxycarbonyl) amino)-4-chloro-5-(4-methylpiperazin-1-yl)benzoic acid (2.61 mmol) in dioxane (34 mL) were added diphenylphosphoryl azide (2.220 mL, 10.30 mmol) and triethylamine (1.914 mL, 13.74 mmol). The reaction mixture was heated at 80° C. for 3 hours Methanol (5 mL) was added and the reaction was heated for another two hours. The reaction was cooled to room temperature. Solvent was evaporated and the residue was partitioned between dichloromethane and saturated sodium bicarbonate. The layers were separated and aqueous layer was extracted with dichloromethane two more times. The combined organic layers were dried over magnesium sulfate, filtered and concentrated in vacuo, the crude product was purified by flash chromatography on silica gel using an automated ISCO system (80 g column, eluting with 50-100% ethyl acetate/hexanes with 2% triethyl amine) to give tert-butyl methyl(4-chloro-5-(4-methylpiperazin-1-yl)-1,3-phenylene)dicarbamate (630 mg).

MS (ESI) m/z 399.2

$^1$H NMR (400 MHz, chloroform-d) δ 7.79 (d, J=2.4 Hz, 1H), 7.25 (br. s., 1H), 7.16 (s, 1H), 6.66 (s, 1H), 3.79 (s, 3H), 3.09 (br. s., 4H), 2.63 (br. s., 4H), 2.39 (s, 3H), 1.56 (s, 9H).

(200D): methyl(3-amino-4-chloro-5-(4-methylpiperazin-1-yl)phenyl)carbamate was prepared starting from tert-butyl methyl(4-chloro-5-(4-methylpiperazin-1-yl)-1,3-phenylene) dicarbamate using a method analogous to that used to prepare Example 171D.

MS (ESI) m/z 299.1 (M+H).

Example 200

The title compound was prepared from 3-amino-4-chloro-5-(4-(4-methylpiperazin-1-yl)piperidin-1-yl)benzonitrile using a method analogous to that used to prepare Example 171.

MS (ESI) m/z 532.3

$^1$H NMR (500 MHz, DMSO-d$_6$) δ 9.32 (d, J=4.2 Hz, 1H), 8.79 (s, 1H), 8.20 (s, 1H), 8.10 (d, J=1.7 Hz, 1H), 7.29 (d, J=1.9 Hz, 1H), 3.39-3.25 (m, 9H, overlapping with water), 3.03-2.95 (m, 1H), 2.70 (t, J=11.1 Hz, 2H), 2.34 (br. s., 4H), 2.16 (s, 3H), 1.87 (d, J=11.4 Hz, 2H), 1.65-1.53 (m, 2H), 0.80 (d, J=5.5 Hz, 4H).

The compounds listed below were prepared by the similar synthetic procedure used for Examples 200

TABLE 5

| Example No. | Structure | Name | [M + H]$^+$ | HPLC Retention Time (min.)* |
|---|---|---|---|---|
| 201 | 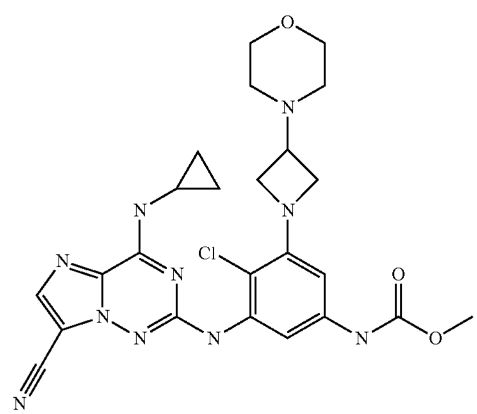 [SMILES: COC(=O)Nc1cc(Nc2nc(NC3CC3)c3ncc(C#N)n3n2)c(Cl)c(N2CC(N3CCOCC3)C2)c1] | methyl (4-chloro-3-((7-cyano-4-(cyclopropylamino)imidazo[2,1-f][1,2,4]triazin-2-yl)amino)-5-(3-(4-morpholinyl)-1-azetidinyl)phenyl)carbamate | 539.00 | 3.57 |
| 202 | Chiral | (+/−) methyl (4-chloro-3-((7-cyano-4-(cyclopropylamino)imidazo[2,1-f][1,2,4]triazin-2-yl)amino)-5-((3S,4R)-3-fluoro-4-((methoxycarbonyl)amino)-1-piperidinyl)phenyl)carbamate | 572.99 | 4.23 |

TABLE 5-continued

| Example No. | Structure | Name | [M + H]+ | HPLC Retention Time (min.)* |
|---|---|---|---|---|
| 203 | 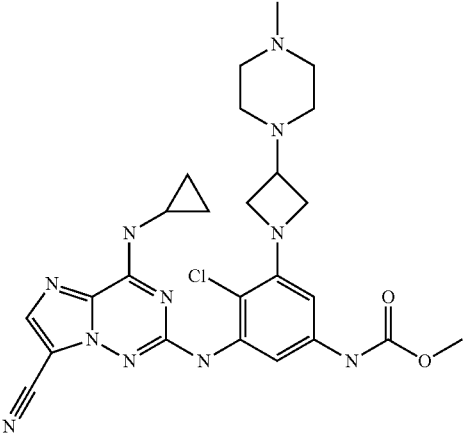 [SMILES: COC(=O)Nc1cc(Nc2nc(NC3CC3)c3ncc(C#N)n3n2)c(Cl)c(N2CC(N3CCN(C)CC3)C2)c1] | methyl (4-chloro-3-((7-cyano-4-(cyclopropylamino)imidazo[2,1-f][1,2,4]triazin-2-yl)amino)-5-(3-(4-methyl-1-piperazinyl)-1-azetidinyl)phenyl)carbamate | 552.04 | 3.80 |
| 204 | 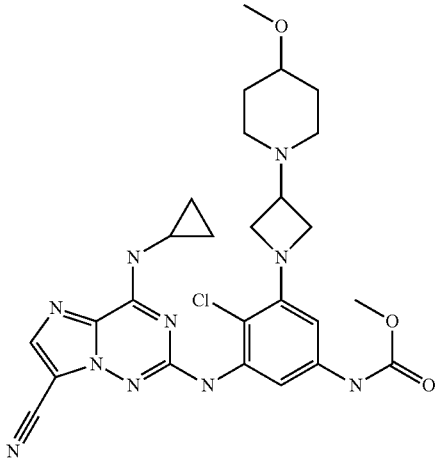 [SMILES: COC(=O)Nc1cc(Nc2nc(NC3CC3)c3ncc(C#N)n3n2)c(Cl)c(N2CC(N3CCC(OC)CC3)C2)c1] | methyl (4-chloro-3-((7-cyano-4-(cyclopropylamino)imidazo[2,1-f][1,2,4]triazin-2-yl)amino)-5-(3-(4-methoxy-1-piperidinyl)-1-azetidinyl)phenyl)carbamate | 567.05 | 4.2 |
| 205 | 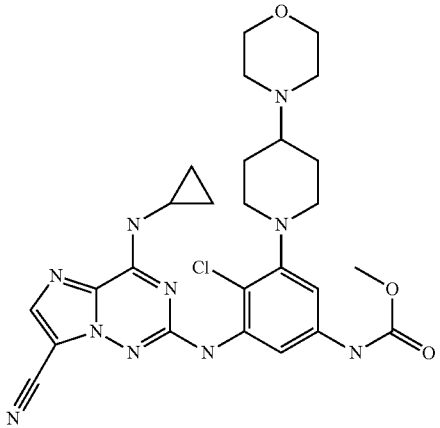 [SMILES: COC(=O)Nc1cc(Nc2nc(NC3CC3)c3ncc(C#N)n3n2)c(Cl)c(N2CCC(N3CCOCC3)CC2)c1] | methyl (4-chloro-3-((7-cyano-4-(cyclopropylamino)imidazo[2,1-f][1,2,4]triazin-2-yl)amino)-5-(4-(4-morpholinyl)-1-piperidinyl)phenyl)carbamate | 567.05 | 4.42 |

TABLE 5-continued

| Example No. | Structure | Name | [M + H]+ | HPLC Retention Time (min.)* |
|---|---|---|---|---|
| 206 | 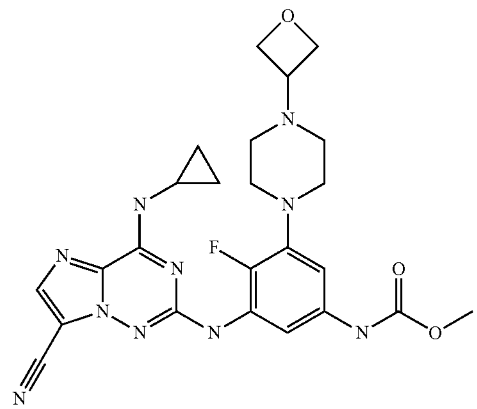 [SMILES: COC(=O)Nc1cc(Nc2nc(NC3CC3)c3ncc(C#N)n3n2)c(F)c(N2CCN(C3COC3)CC2)c1] | methyl 3-(7-cyano-4-(cyclopropylamino)imidazo[2,1-f][1,2,4]triazin-2-yl)amino)-4-fluoro-5-(4-(oxetan-3-yl)piperazin-1-yl)phenylcarbamate | 522.54 | 3.79 c |

* = HPLC conditions
CHROMOLITH ® column 4.6 × 50 mm eluting with 10-90% aqueous methanol over 5 min. containing 0.1% TFA, 4 mL/min, monitoring at 220 nm.

Example 207

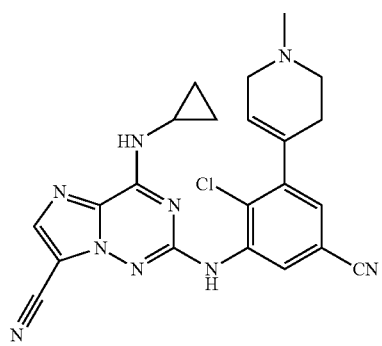 [SMILES: CN1CC=C(c2cc(C#N)cc(Nc3nc(NC4CC4)c4ncc(C#N)n4n3)c2Cl)CC1]

2-(2-chloro-5-cyano-3-(1-methyl-1,2,3,6-tetrahydropyridin-4-yl)phenylamino)-4-(cyclopropylamino)imidazo[1,2-f][1,2,4]triazine-7-carbonitrile (207A): A mixture of 1-methyl-4-(4,4,5,5-tetramethyl-1,3,2-dioxaborolan-2-yl)-1,2,3,6-tetrahydropyridine (300 mg, 1.345 mmol), tert-butyl(3-bromo-2-chloro-5-cyanophenyl)carbamate (Intermediate 1) (372 mg, 1.120 mmol), 1,1'-bis(diphenylphosphino)ferrocenepalladium(II) dichloride (92 mg, 0.112 mmol), and $Cs_2CO_3$ (1095 mg, 3.36 mmol) in DMF (8 ml) in a microwave vial was flushed with N2 and heated at 80° C. for 6 h. This was diluted with EtOAc (200 ml), washed with water (40 ml×4), brine, and dried over $Na_2SO_4$. Removal of the solvent followed by silica gel chromatography eluting with DCM containing 0 to 3% MeOH gave tert-butyl(2-chloro-5-cyano-3-(1-methyl-1,2,3,6-tetrahydropyridin-4-yl)phenyl)carbamate (321 mg) as a solid.

MS (ESI) m/z 348.22

1H NMR (500 MHz, CHLOROFORM-d) δ 8.48 (d, J=1.7 Hz, 1H), 7.20 (s, 1H), 7.14 (d, J=2.0 Hz, 1H), 5.69 (dt, J=3.2, 1.7 Hz, 1H), 3.12 (q, J=2.7 Hz, 2H), 2.68 (t, J=5.6 Hz, 2H), 2.53-2.30 (m, 5H), 1.57-1.51 (m, 9H).

(207B): A solution of tert-butyl(2-chloro-5-cyano-3-(1-methyl-1,2,3,6-tetrahydropyridin-4-yl)phenyl)carbamate (90 mg, 0.207 mmol) in DCM (2 ml) and TFA (1 mL) was stirred at RT for 2 h. Removal of the solvents was followed by preparative HPLC (100×30 mm Luna C18 column, Solvent A=10% Methanol, 90% $H_2O$, 0.1% TFA; solvent B=90% Methanol, 10% $H_2O$, 0.1% TFA, Flow rate 42 ml permin, 0-60% B, over 20 min) The HPLC fractions containing the product were applied onto a cartridge of Phenomenex Strata-X-C 33 um cation mixed-mode polymer. This was washed with methanol and product was eluted with 2 N solution of ammonia in methanol. Removal of the solvents left 3-amino-4-chloro-5-(1-methyl-1,2,3,6-tetrahydropyridin-4-yl)benzonitrile (43 mg) as a solid.

MS (ESI) m/z 248.10 (M+1)

$^1$H NMR (500 MHz, METHANOL-$d_4$) δ 7.02 (d, J=2.0 Hz, 1H), 6.79 (d, J=2.0 Hz, 1H), 5.69 (tt, J=3.3, 1.6 Hz, 1H), 3.14 (q, J=2.7 Hz, 2H), 2.73 (t, J=5.7 Hz, 2H), 2.53-2.46 (m, 2H), 2.42 (s, 3H).

Example 207

A mixture of 4-(cyclopropyl(4-methoxybenzyl)amino)-2-(methylsulfonyl)imidazo[2,1-f][1,2,4]triazine-7-carbonitrile (Intermediate 4, 52.4 mg, 0.131 mmol), 3-amino-4-chloro-5-(1-methyl-1,2,3,6-tetrahydropyridin-4-yl)benzonitrile (31 mg, 0.125 mmol) and $Cs_2CO_3$ (82 mg, 0.250 mmol) in DMF (1 mL) was heated at 70° C. for 2 h. The reaction mixture was diluted with ethyl acetate and washed with water. Removal of the solvent was followed by preparative HPLC (100×30 mm Luna C18 column, Solvent A=10% Methanol, 90% $H_2O$, 0.1% TFA; solvent B=90% Methanol, 10% $H_2O$, 0.1% TFA, Flow rate 42 ml permin, 20-100% B, over 20 min) The HPLC fractions containing the PMB protected product were applied onto a cartridge of Phenomenex Strata-X-C 33 um cation mixed-mode polymer. This was washed with methanol and product was eluted with 2 N solution of ammonia in methanol. Removal of the solvents left 47 mg of material which was dissolved in DCM (2 ml) and treated with anisole (0.027 mL, 0.250 mmol) and TFA (1 mL). After 2 hr, additional TFA (1 mL) was added and the reaction was left stirring at RT overnight.

Removal of the solvents was followed by preparative HPLC (100×30 mm Luna C18 column, Solvent A=10% Methanol, 90% H$_2$O, 0.1% TFA; solvent B=90% Methanol, 10% H$_2$O, 0.1% TFA, Flow rate 42 ml permin, 15-100% B, over 20 min). The fractions containing the product were applied onto a cartridge of Phenomenex Strata-X-C 33 um cation mixed-mode polymer. This was washed with methanol and the product was eluted with 2 N solution of ammonia in methanol. Removal of the solvents left 2-((2-chloro-5-cyano-3-(1-methyl-1,2,3,6-tetrahydropyridin-4-yl)phenyl)amino)-4-(cyclopropylamino)imidazo[2,1-f][1,2,4]triazine-7-carbonitrile (20.2 mg) as a white solid.

MS (ESI) m/z 446.17

1H NMR (500 MHz, CHLOROFORM-d) δ 8.99 (d, J=1.8 Hz, 1H), 7.88 (s, 1H), 7.61 (s, 1H), 7.19 (s, 1H), 6.89 (br. s., 1H), 5.75 (dt, J=3.2, 1.6 Hz, 1H), 3.24 (m., 2H), 3.07 (td, J=7.1, 3.3 Hz, 1H), 2.80 (m, 2H), 2.56 (br. s., 2H), 2.52 (s, 3H), 1.18-1.07 (m, 2H), 0.92-0.75 (m, 2H).

Example 208

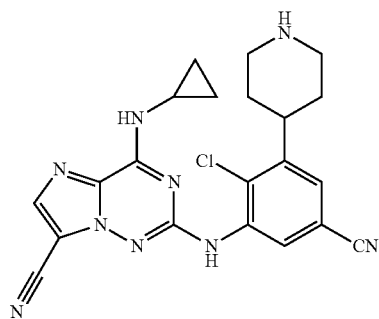 [SMILES: N#Cc1cc(Nc2nc(NC3CC3)c3ncc(C#N)n3n2)c(Cl)c(C2CCNCC2)c1]

2-((2-chloro-5-cyano-3-(piperidin-4-yl)phenyl)amino)-4-(cyclopropylamino)imidazo[2,1-f][1,2,4]triazine-7-carbonitrile (208A): A mixture of tert-butyl(3-bromo-2-chloro-5-cyanophenyl)carbamate (1.0 g, 3.02 mmol), dichloro[1,1'-bis(diphenylphosphino)ferrocene]palladium(II) (0.206 g, 0.302 mmol), and copper(I) iodide (0.115 g, 0.603 mmol) in a dry microwave vial was flushed with nitrogen. N,N-dimethylacetamide (3 mL) was added followed by (1-(tert-butoxycarbonyl)piperidin-4-yl)zinc(II) iodide (9.52 mL, 9.05 mmol, approximately 1 M solution in N,N-dimethylacetamide prepared as described in the Journal of Organic Chemistry, 2004, 69, 5120). The vial was sealed and heated at 80° C. overnight. After cooling to RT, the reaction was partitioned between EtOAc and sat. aq. NH$_4$Cl solution. This was left stirring for 30 min. The aqueous phase was washed with EtOAc and the combined organic phases were washed with brine and dried with sodium sulfate. Removal of the solvents followed by radial silica gel chromatography eluting with hexane containing 5 to 30% EtOAc afforded tert-butyl 4-(3-((tert-butoxycarbonyl)amino)-2-chloro-5-cyanophenyl)piperidine-1-carboxylate (0.376 g) as a white solid.

MS (ESI) m/z 458.21 (M+23)

1H NMR (500 MHz, CHLOROFORM-d) δ 8.48 (d, J=1.7 Hz, 1H), 7.23-7.16 (m, 2H), 4.30 (br. s., 2H), 3.21-3.12 (m, 1H), 2.94-2.76 (m, 2H), 1.90-1.78 (m, 2H), 1.58-1.54 (m, 11H), 1.51 (s, 9H)

(208B): To a solution of tert-butyl 4-(3-((tert-butoxycarbonyl)amino)-2-chloro-5-cyanophenyl)piperidine-1-carboxylate (370 mg, 0.849 mmol) in DCM (24 mL) was added TFA (12 mL). After 2 h, the solvents were removed. The residue was taken in MeOH and applied onto a cartridge of Phenomenex Strata-X-C 33 um cation mixed-mode polymer. This was washed with methanol and product was eluted with 2 N solution of ammonia in methanol. Removal of the solvents left 3-amino-4-chloro-5-(piperidin-4-yl)benzonitrile (196 mg) which was used as such in the next reaction.

MS (ESI) m/z 236.01)

1H NMR (500 MHz, DMSO-d6) δ 6.98 (d, J=2.0 Hz, 1H), 6.87 (d, J=2.0 Hz, 1H), 5.84 (s, 2H), 3.08-2.91 (m, 3H), 2.65-2.54 (m, 2H), 1.63 (d, J=12.8 Hz, 2H), 1.47 (qd, J=12.3, 3.8 Hz, 2H).

(208C): To a suspension of 3-amino-4-chloro-5-(piperidin-4-yl)benzonitrile (168 mg, 0.713 mmol) in DCM (2 ml) was added Et3N (0.099 mL, 0.713 mmol), followed by di-tert-butyl dicarbonate (163 mg, 0.748 mmol). After stirring at RT overnight, the solvents were removed to leave tert-butyl 4-(3-amino-2-chloro-5-cyanophenyl)piperidine-1-carboxylate (257 mg) as a white solid which was used as such.

MS (ESI) m/z 358.12

(208D): A mixture of 4-(cyclopropyl(4-methoxybenzyl)amino)-2-(methylsulfonyl)imidazo[2,1-f][1,2,4]triazine-7-carbonitrile (142 mg, 0.357 mmol), tert-butyl 4-(3-amino-2-chloro-5-cyanophenyl)piperidine-1-carboxylate (100 mg, 0.298 mmol) and Cs$_2$CO$_3$ (194 mg, 0.596 mmol) in DMF (3 mL) was heated at 70° C. for 2 h. This was diluted with EtOAc, washed with water and brine and dried over Na$_2$SO$_4$. The crude mixture containing 2-((2-chloro-5-cyano-3-(piperidin-4-yl)phenyl)amino)-4-(cyclopropyl(4-methoxybenzyl)amino)imidazo[2,1-f][1,2,4]triazine-7-carbonitrile was carried forward to next step.

Example 208

The crude intermediate was dissolved in DCE (1 mL) and anisole (20.70 µL), and TFA (0.5 mL) were added. The resulting mixture was heated at 50° C. for 3 h. Removal of the solvents was followed by preparative HPLC (Waters XBridge C18, 19×200 mm, 5-µm particles; Guard Column: Waters XBridge C18, 19×10 mm, 5-µm particles; Mobile Phase A: water with 20-mM ammonium acetate; Mobile Phase B: 95:5 methanol:water with 20-mM ammonium acetate; Gradient: 40-80% B over 20 minutes, then a 5-minute hold at 100%. B; Flow: 20 mL/min.). Fractions containing the desired product were combined and dried via centrifugal evaporation to afford 2-((2-chloro-5-cyano-3-(4-piperidinyl)phenyl)amino)-4-(cyclopropylamino)imidazo[2,1-f][1,2,4]triazine-7-carbonitrile (164 mg) as a solid.

MS (ESI) m/z 433.91

Example 209

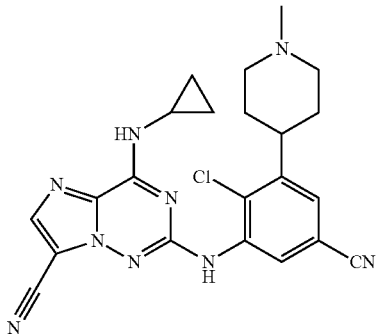 [SMILES: CN1CCC(c2cc(C#N)cc(Nc3nc(NC4CC4)c4ncc(C#N)n4n3)c2Cl)CC1]

2-(2-chloro-5-cyano-3-(1-methylpiperidin-4-yl)phe-
nylamino)-4-(cyclopropylamino)imidazo[1,2-f][1,2,
4]triazine-7-carbonitrile (209A): A mixture of 4-(cyclopropyl(4-methoxybenzyl)
amino)-2-(methylsulfonyl)imidazo[2,1-f][1,2,4]triazine-7-
carbonitrile (142 mg, 0.357 mmol), tert-butyl 4-(3-amino-
2-chloro-5-cyanophenyl)piperidine-1-carboxylate (100 mg,
0.298 mmol) and $Cs_2CO_3$ (194 mg, 0.596 mmol) in DMF (3
mL) was heated at 70° C. for 2 h. This was diluted with
EtOAc, washed with water and brine and dried over
$Na_2SO_4$. After the solvent was removed, the crude Boc
protected intermediate was dissolved in DCE (1 mL). TFA
(0.5 mL) was added and the reaction was stirred at RT for 1
h. The solvents were removed and the residue was taken up
in MeOH and applied onto a cartridge of Phenomenex
Strata-X-C 33 um cation mixed-mode polymer. This was
washed with methanol and product was eluted with 2 N
solution of ammonia in methanol. Removal of the solvents
left 2-((2-chloro-5-cyano-3-(piperidin-4-yl)phenyl)amino)-
4-(cyclopropyl(4-methoxybenzyl)amino)imidazo[2,1-f][1,
2,4]triazine-7-carbonitrile (164 mg) as a solid which was
used as such in the next reaction.
MS (ESI) m/z 554.29 (M+1)

Example 209

Sodium triacetoxyborohydride (24.10 mg, 0.114
mmol) was added to a stirred suspension of 2-((2-chloro-5-cyano-3-(piperidin-
4-yl)phenyl)amino)-4-(cyclopropyl(4-methoxybenzyl)
amino)imidazo[2,1-f][1,2,4]triazine-7-carbonitrile (30.0
mg, 0.038 mmol), formaldehyde 37% in water (8.47 µL,
0.114 mmol) and HOAc (16.27 µL, 0.190 mmol) in DCE
(379 µL) at RT for 30 min. Sat. aq. $NaHCO_3$ solution was
slowly added (gas evolution) and the reaction was left
stirring for 10 min. It was extracted with DCM. The organic
phase was dried with sodium sulfate and the solvents were
removed. The crude intermediate was dissolved in DCE (1
mL) and anisole (20.70 µL, 0.190 mmol), and TFA (0.5 mL)
were added. The resulting mixture was heated at 50° C. for
3 h. Removal of the solvents was followed by preparative
HPLC (Waters XBridge C18, 19×200 mm, 5-µm particles;
Guard Column: Waters XBridge C18, 19×10 mm, 5-µm
particles; Mobile Phase A: water with 20-mM ammonium
acetate; Mobile Phase B: 95:5 methanol:water with 20-mM
ammonium acetate; Gradient: 40-80% B over 20 minutes,
then a 5-minute hold at 100%. B; Flow: 20 mL/min.).
Fractions containing the desired product were combined and
dried via centrifugal evaporation to afford 14.9 mg of
2-((2-chloro-5-cyano-3-(1-methylpiperidin-4-yl)phenyl)
amino)-4-(cyclopropylamino)imidazo[2,1-f][1,2,4]triazine-
7-carbonitrile.
MS (ESI) m/z 448.20
$^1$H NMR (500 MHz, DMSO-$d_6$) δ 9.36 (br. s., 1H), 8.90
(br. s., 1H), 8.36-8.29 (m, 1H), 8.22 (s, 1H), 7.58 (d, J=1.8
Hz, 1H), 3.01-2.87 (m, 4H), 2.22 (s, 3H), 2.00 (td, J=10.8,
4.1 Hz, 2H), 1.81-1.67 (m, 4H), 0.80 (s, 4H).

The compounds listed below were prepared by the similar
synthetic procedure used for Examples 209

TABLE 6

| Example No. | Structure | Name | [M + H]⁺ | HPLC Retention Time (min.)* |
|---|---|---|---|---|
| 210 | 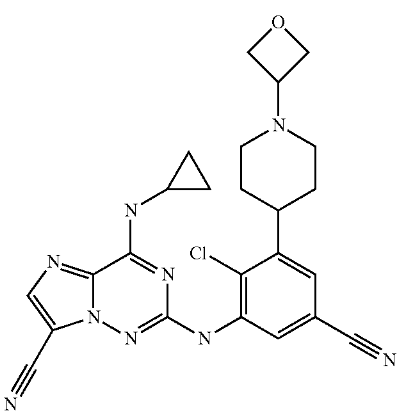 [SMILES: N#Cc1cc(Nc2nc(NC3CC3)c3ncc(C#N)n3n2)c(Cl)c(C2CCN(C3COC3)CC2)c1] | 2-((2-chloro-5-cyano-3-(1-(3-oxetanyl)-4-piperidinyl)phenyl)amino)-4-(cyclopropylamino)imidazo[2,1-f][1,2,4]triazine-7-carbonitrile | 489.97 | 4.37 |

TABLE 6-continued

| Example No. | Structure | Name | [M + H]+ | HPLC Retention Time (min.)* |
|---|---|---|---|---|
| 211 | 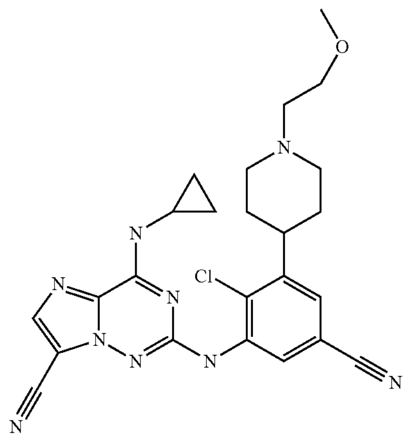 [SMILES: COCCN1CCC(c2cc(C#N)cc(Nc3nc(NC4CC4)c4ncc(C#N)n4n3)c2Cl)CC1] | 2-(2-chloro-5-cyano-3-(1-(2-methoxyethyl)piperidin-4-yl)phenylamino)-4-(cyclopropylamino)imidazo[1,2-f][1,2,4]triazine-7-carbonitrile | 491.98 | 3.28 |
| 212 | 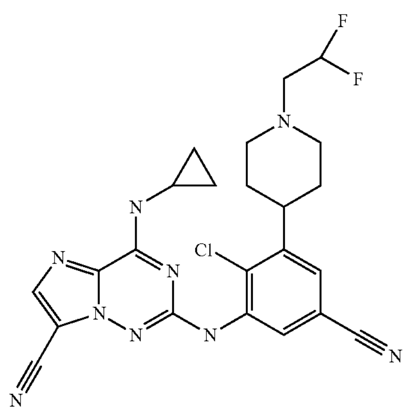 [SMILES: N#Cc1cc(Nc2nc(NC3CC3)c3ncc(C#N)n3n2)c(Cl)c(C2CCN(CC(F)F)CC2)c1] | 2-(2-chloro-5-cyano-3-(1-(2,2-difluoroethyl)piperidin-4-yl)phenylamino)-4-(cyclopropylamino)imidazo[1,2-f][1,2,4]triazine-7-carbonitrile | 497.94 | 3.80 |
| 213 | 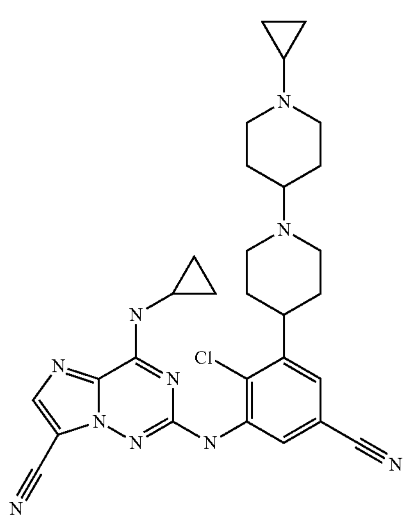 [SMILES: N#Cc1cc(Nc2nc(NC3CC3)c3ncc(C#N)n3n2)c(Cl)c(C2CCN(C3CCN(C4CC4)CC3)CC2)c1] | 2-(2-chloro-5-cyano-3-(1'-cyclopropyl-1,4'-bipiperidin-4-yl)phenylamino)-4-(cyclopropylamino)imidazo[1,2-f][1,2,4]triazine-7-carbonitrile | 557.10 | 4.37 |

TABLE 6-continued

| Example No. | Structure | Name | [M + H]+ | HPLC Retention Time (min.)* |
|---|---|---|---|---|
| 214 | Chiral | 2-((2-chloro-5-cyano-3-(1-((2S)-2-hydroxypropyl)-4-piperidinyl)phenyl)amino)-4-(ethylamino)imidazo[2,1-f][1,2,4]triazine-7-carbonitrile | 479.97 | 3.72 |
| 215 | 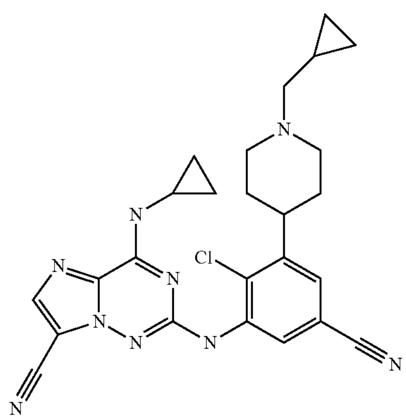 [SMILES: N#Cc1cc(Nc2nc(NC3CC3)c3ncc(C#N)n3n2)c(Cl)c(C2CCN(CC3CC3)CC2)c1] | 2-((2-chloro-5-cyano-3-(1-(cyclopropylmethyl)-4-piperidinyl)phenyl)amino)-4-(cyclopropylamino)imidazo[2,1-f][1,2,4]triazine-7-carbonitrile | 488.00 | 3.89 |
| 216 | Chiral | (S)-2-(2-chloro-5-cyano-3-(1-(2-hydroxypropyl)piperidin-4-yl)phenylamino)-4-(cyclopropylamino)imidazo[1,2-f][1,2,4]triazine-7-carbonitrile | 491.98 | 3.53 |

TABLE 6-continued

| Example No. | Structure | Name | [M + H]+ | HPLC Retention Time (min.)* |
|---|---|---|---|---|
| 217 | Chiral | 2-((3-(1-((3R,4R)-4-amino-3-hydroxycyclohexyl)-4-piperidinyl)-2-chloro-5-cyanophenyl)amino)-4-(cyclopropylamino)imidazo[2,1-f][1,2,4]triazine-7-carbonitrile | 547.06 | 3.91 |
| 218 | Chiral | 2-(3-(1-((3R,4R)-4-amino-3-(tert-butyldimethylsilyloxy)cyclohexyl)piperidin-4-yl)-2-chloro-5-cyanophenylamino)-4-(cyclopropylamino)imidazo[1,2-f][1,2,4]triazine-7-carbonitrile | 661.33 | 4.68 |
| 219 | 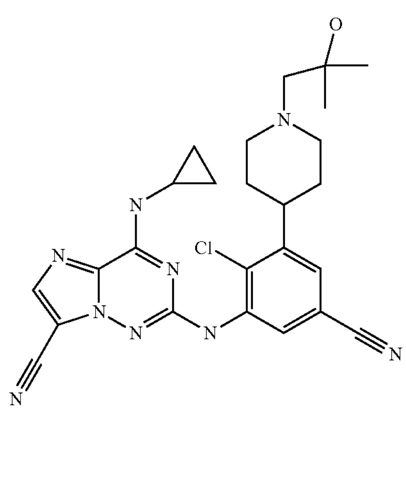 [SMILES: CC(C)(O)CN1CCC(c2cc(C#N)cc(Nc3nc(NC4CC4)c4ncc(C#N)n4n3)c2Cl)CC1] | 2-((2-chloro-5-cyano-3-(1-(2-hydroxy-2-methylpropyl)-4-piperidinyl)phenyl)amino)-4-(cyclopropylamino)imidazo[2,1-f][1,2,4]triazine-7-carbonitrile | 506.01 | 4.14 |

TABLE 6-continued

| Example No. | Structure | Name | [M + H]+ | HPLC Retention Time (min.)* |
|---|---|---|---|---|
| 220 | 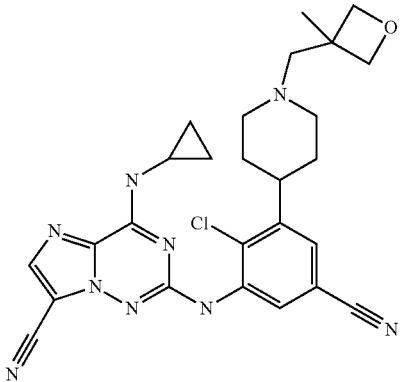 | 2-((2-chloro-5-cyano-3-(1-((3-methyl-3-oxetanyl)methyl)-4-piperidinyl)phenyl)amino)-4-(cyclopropylamino)imidazo[2,1-f][1,2,4]triazine-7-carbonitrile | 518.02 | 3.89 |
| 221 | 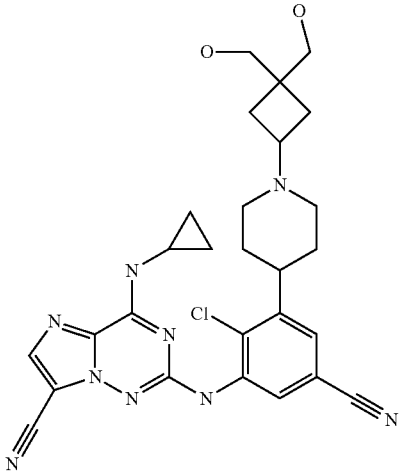 [SMILES: N#Cc1cc(Nc2nc(NC3CC3)c3ncc(C#N)n3n2)c(Cl)c(C2CCN(C3CC(CO)(CO)C3)CC2)c1] | 2-((3-(1-(3,3-bis(hydroxymethyl)cyclobutyl)-4-piperidinyl)-2-chloro-5-cyanophenyl)amino)-4-(cyclopropylamino)imidazo[2,1-f][1,2,4]triazine-7-carbonitrile | 548.05 | 3.22 |
| 222 | 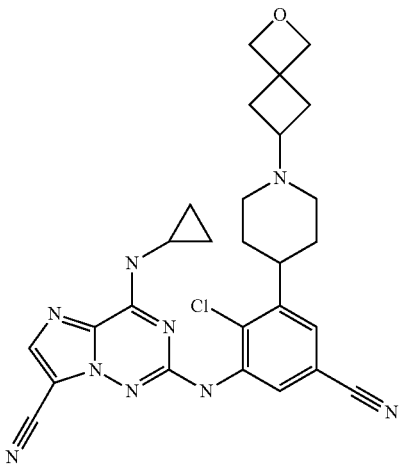 [SMILES: N#Cc1cc(Nc2nc(NC3CC3)c3ncc(C#N)n3n2)c(Cl)c(C2CCN(C3CC4(COC4)C3)CC2)c1] | 2-((2-chloro-5-cyano-3-(1-(2-oxaspiro[3.3]hept-6-yl)-4-piperidinyl)phenyl)amino)-4-(cyclopropylamino)imidazo[2,1-f][1,2,4]triazine-7-carbonitrile | 530.03 | 3.63 |

TABLE 6-continued

| Example No. | Structure | Name | [M + H]+ | HPLC Retention Time (min.)* |
|---|---|---|---|---|
| 223 | 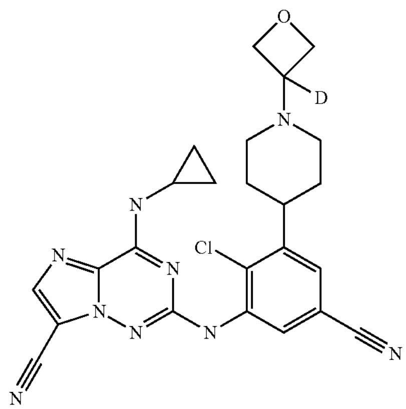 [SMILES: [2H]C1(N2CCC(c3cc(C#N)cc(Nc4nc(NC5CC5)c5ncc(C#N)n5n4)c3Cl)CC2)COC1] | 2-((2-chloro-5-cyano-3-(1-(3-~2~H)-3-oxetanyl-4-piperidinyl)phenyl)amino)-4-(cyclopropylamino)imidazo[2,1-f][1,2,4]triazine-7-carbonitrile | 490.98 | 4.34 |
| 224 | 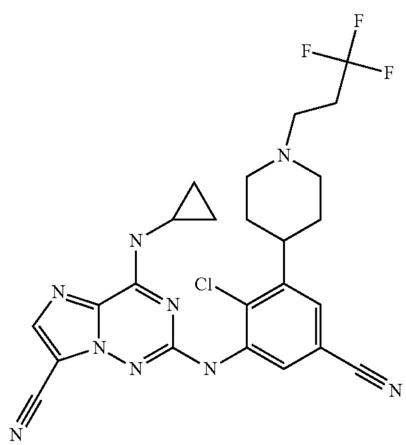 [SMILES: N#Cc1cc(Nc2nc(NC3CC3)c3ncc(C#N)n3n2)c(Cl)c(C2CCN(CCC(F)(F)F)CC2)c1] | 2-((2-chloro-5-cyano-3-(1-(3,3,3-trifluoropropyl)-4-piperidinyl)phenyl)amino)-4-(cyclopropylamino)imidazo[2,1-f][1,2,4]triazine-7-carbonitrile | 529.96 | 4.12 |
| 225 | 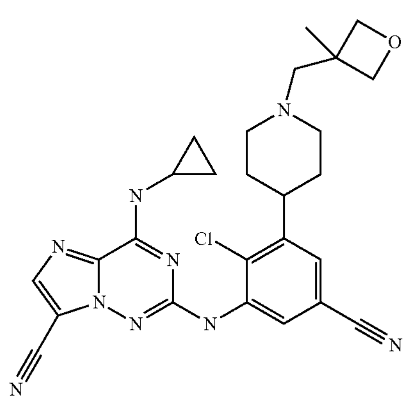 [SMILES: CC1(CN2CCC(c3cc(C#N)cc(Nc4nc(NC5CC5)c5ncc(C#N)n5n4)c3Cl)CC2)COC1] | 2-((2-chloro-5-cyano-3-(1-((3-methyl-3-oxetanyl)methyl)-4-piperidinyl)phenyl)amino)-4-(cyclopropylamino)imidazo[2,1-f][1,2,4]triazine-7-carbonitrile | 518.02 | |

* = HPLC conditions

YMC S5 ODS 4.6×50 mm, 10-90% aqueous methanol containing 0.2% H₃PO₄, 5 min. gradient, monitored at 220 nm Example 226

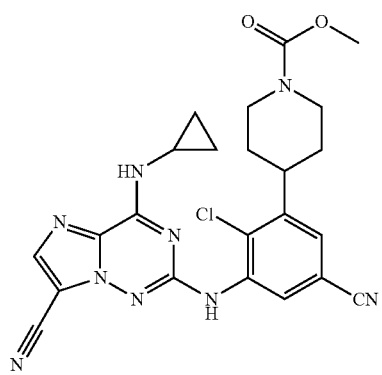 [SMILES: COC(=O)N1CCC(c2cc(C#N)cc(Nc3nc(NC4CC4)c4ncc(C#N)n4n3)c2Cl)CC1]

methyl 4-(2-chloro-5-cyano-3-((7-cyano-4-(cyclopropylamino)imidazo[2,1-f][1,2,4]triazin-2-yl)amino)phenyl)piperidine-1-carboxylate To a solution of 2-((2-chloro-5-cyano-3-(piperidin-4-yl)phenyl)amino)-4-(cyclopropyl(4-methoxybenzyl)amino) imidazo[2,1-f][1,2,4]triazine-7-carbonitrile (Intermediate 208A) (30 mg, 0.054 mmol) in CH₂Cl₂ (2 mL) at 0° C. was added triethylamine (0.015 mL, 0.108 mmol) followed by methyl chloroformate (diluted with CH₂CL₂, 10V %) (0.046 mL, 0.060 mmol) dropwise. The reaction completed within 1 h at 0° C. To the reaction mixture was added anisole (0.023 mL, 0.271 mmol), followed by TFA (0.6 ml), and then heated at 50° C. for 3 h. Removal of the solvent. To the residue was added 2N NH₃ in MeOH (8 ml) and stirred for 10 min, The resulting solid was collected by filtration, rinsed with 2N NH₃ in MeOH (1 ml×2), air dried to give methyl 4-(2-chloro-5-cyano-3-((7-cyano-4-(cyclopropylamino)imidazo[2,1-f][1,2,4]triazin-2-yl)amino)phenyl)piperidine-1-carboxylate (14.5 mg).

MS (ESI) m/z 492.28

1H NMR (500 MHz, CHLOROFORM-d) δ 8.96 (d, J=1.8 Hz, 1H), 7.88 (s, 1H), 7.61 (s, 1H), 7.20 (d, J=1.8 Hz, 1H), 6.86 (br. s., 1H), 4.36 (m., 2H), 3.76 (s, 3H), 3.27 (tt, J=12.1, 3.1 Hz, 1H), 3.07 (td, J=7.0, 3.4 Hz, 1H), 2.96-3.06 (m, 1H), 1.91 (d, J=13.1 Hz, 2H), 1.72-1.54 (m, 3H), 1.16-1.06 (m, 2H), 0.87-0.77 (m, 2H).

The compounds listed below were prepared by the similar synthetic procedure used for Example 226

TABLE 7

| Example No. | Structure | Name | [M + H]⁺ | HPLC Retention Time (min.)* |
| --- | --- | --- | --- | --- |
| 227 | 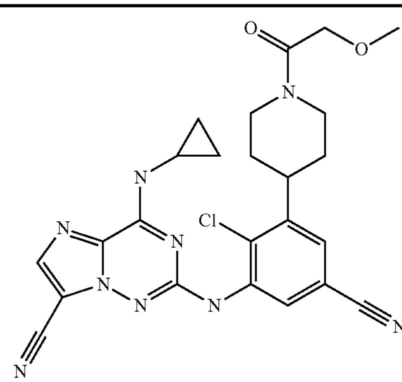 | 2-((2-chloro-5-cyano-3-(1-(methoxyacetyl)-4-piperidinyl)phenyl)amino)-4-(cyclopropylamino)imidazo[2,1-f][1,2,4]triazine-7-carbonitrile | 505.97 | 4.57ᶜ |
| 228 | 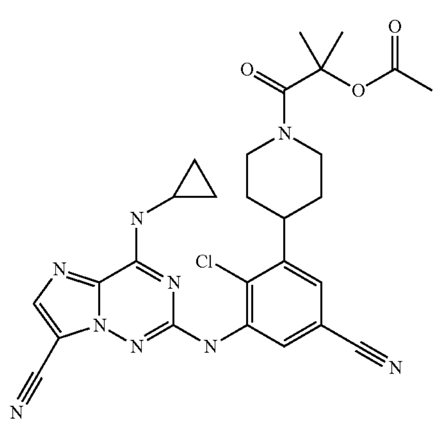 [SMILES: CC(=O)OC(C)(C)C(=O)N1CCC(c2cc(C#N)cc(Nc3nc(NC4CC4)c4ncc(C#N)n4n3)c2Cl)CC1] | 2-(4-(2-chloro-5-cyano-3-((7-cyano-4-(cyclopropylamino)imidazo[2,1-f][1,2,4]triazin-2-yl)amino)phenyl)-1-piperidinyl)-1,1-dimethyl-2-oxoethyl acetate | 562.03 | 4.78 |

TABLE 7-continued

| Example No. | Structure | Name | [M + H]+ | HPLC Retention Time (min.)* |
|---|---|---|---|---|
| 229 | 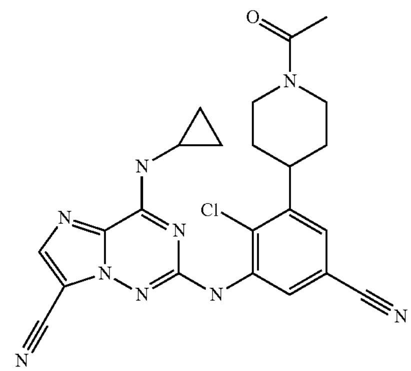 [SMILES: CC(=O)N1CCC(c2cc(C#N)cc(Nc3nc(NC4CC4)c4ncc(C#N)n4n3)c2Cl)CC1] | 2-((3-(1-acetyl-4-piperidinyl)-2-chloro-5-cyanophenyl)amino)-4-(cyclopropylamino)imidazo[2,1-f][1,2,4]triazine-7-carbonitrile | 475.94 | 4.80 |
| 230 | 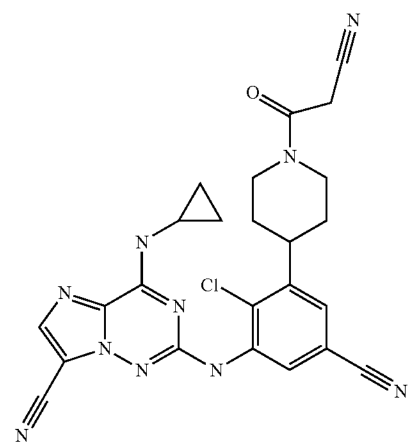 [SMILES: N#CCC(=O)N1CCC(c2cc(C#N)cc(Nc3nc(NC4CC4)c4ncc(C#N)n4n3)c2Cl)CC1] | 2-((2-chloro-5-cyano-3-(1-(cyanoacetyl)-4-piperidinyl)phenyl)amino)-4-(cyclopropylamino)imidazo[2,1-f][1,2,4]triazine-7-carbonitrile | 500.95 | 4.71$^c$ |
| 231 | 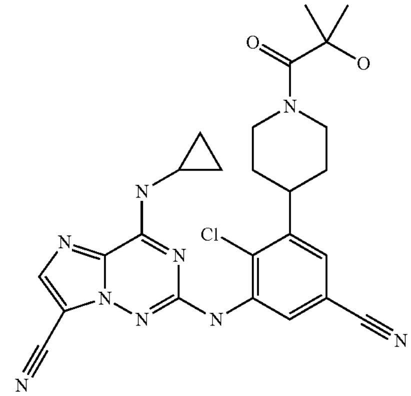 [SMILES: CC(C)(O)C(=O)N1CCC(c2cc(C#N)cc(Nc3nc(NC4CC4)c4ncc(C#N)n4n3)c2Cl)CC1] | 2-((2-chloro-5-cyano-3-(1-(2-hydroxy-2-methylpropanoyl)-4-piperidinyl)phenyl)amino)-4-(cyclopropylamino)imidazo[2,1-f][1,2,4]triazine-7-carbonitrile | 519.99 | 4.72 |

TABLE 7-continued

| Example No. | Structure | Name | [M + H]+ | HPLC Retention Time (min.)* |
|---|---|---|---|---|
| 232 | 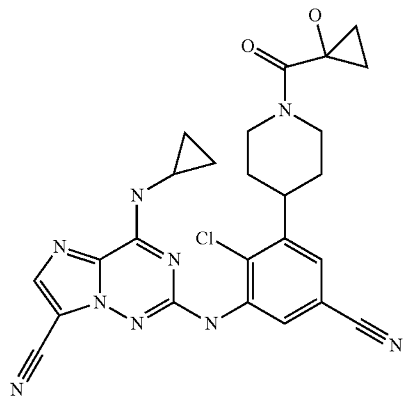 [SMILES: N#Cc1cc(Nc2nc(NC3CC3)c3ncc(C#N)n3n2)c(Cl)c(C2CCN(C(=O)C3(O)CC3)CC2)c1] | 2-((2-chloro-5-cyano-3-(1-((1-hydroxycyclopropyl)carbonyl)-4-piperidinyl)phenyl)amino)-4-(cyclopropylamino)imidazo[2,1-f][1,2,4]triazine-7-carbonitrile | 517.98 | 4.79$^c$ |
| 233 | 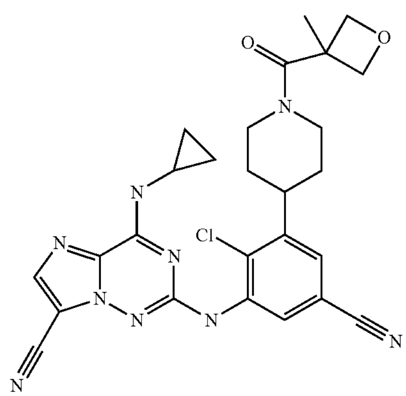 [SMILES: CC1(C(=O)N2CCC(c3cc(C#N)cc(Nc4nc(NC5CC5)c5ncc(C#N)n5n4)c3Cl)CC2)COC1] | 2-((2-chloro-5-cyano-3-(1-((3-methyl-3-oxetanyl)carbonyl)-4-piperidinyl)phenyl)amino)-4-(cyclopropylamino)imidazo[2,1-f][1,2,4]triazine-7-carbonitrile | 532.01 | 4.43 |
| 234 | 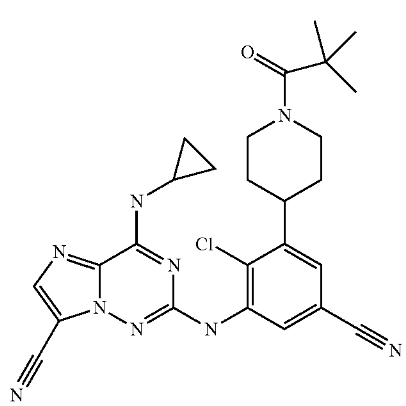 [SMILES: CC(C)(C)C(=O)N1CCC(c2cc(C#N)cc(Nc3nc(NC4CC4)c4ncc(C#N)n4n3)c2Cl)CC1] | 2-((2-chloro-5-cyano-3-(1-(2,2-dimethylpropanoyl)-4-piperidinyl)phenyl)amino)-4-(cyclopropylamino)imidazo[2,1-f][1,2,4]triazine-7-carbonitrile | 518.02 | 4.78 |

TABLE 7-continued

| Example No. | Structure | Name | [M + H]+ | HPLC Retention Time (min.)* |
|---|---|---|---|---|
| 235 | 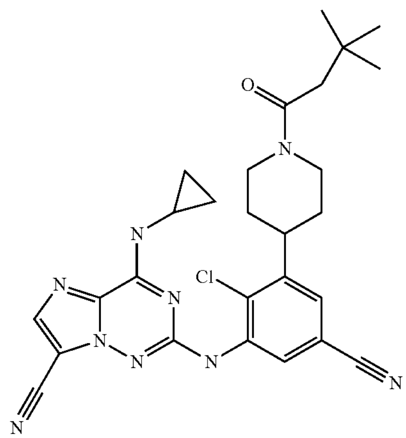 [SMILES: CC(C)(C)CC(=O)N1CCC(c2cc(C#N)cc(Nc3nc(NC4CC4)c4ncc(C#N)n4n3)c2Cl)CC1] | 2-((2-chloro-5-cyano-3-(1-(3,3-dimethylbutanoyl)-4-piperidinyl)phenyl)amino)-4-(cyclopropylamino)imidazo[2,1-f][1,2,4]triazine-7-carbonitrile | 532.05 | 4.54 |
| 236 | 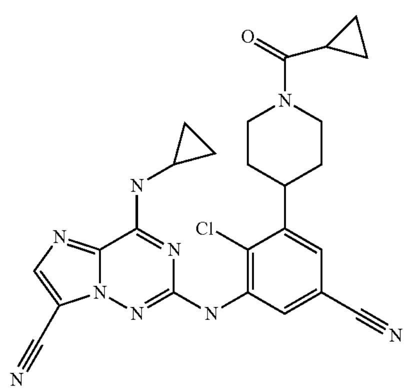 [SMILES: N#Cc1cc(Nc2nc(NC3CC3)c3ncc(C#N)n3n2)c(Cl)c(C2CCN(C(=O)C3CC3)CC2)c1] | 2-((2-chloro-5-cyano-3-(1-(cyclopropylcarbonyl)-4-piperidinyl)phenyl)amino)-4-(cyclopropylamino)imidazo[2,1-f][1,2,4]triazine-7-carbonitrile | 501.98 | 4.82 |
| 237 | 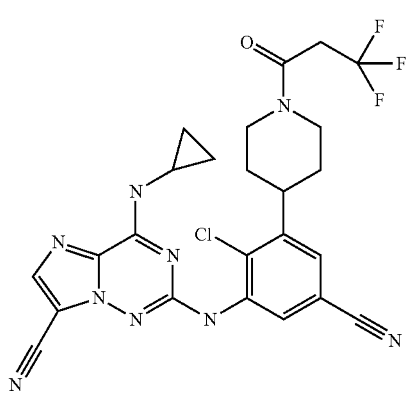 [SMILES: N#Cc1cc(Nc2nc(NC3CC3)c3ncc(C#N)n3n2)c(Cl)c(C2CCN(C(=O)CC(F)(F)F)CC2)c1] | 2-((2-chloro-5-cyano-3-(1-(3,3,3-trifluoropropanoyl)-4-piperidinyl)phenyl)amino)-4-(cyclopropylamino)imidazo[2,1-f][1,2,4]triazine-7-carbonitrile | 543.94 | 4.63 |

TABLE 7-continued

| Example No. | Structure | Name | [M + H]+ | HPLC Retention Time (min.)* |
|---|---|---|---|---|
| 238 | 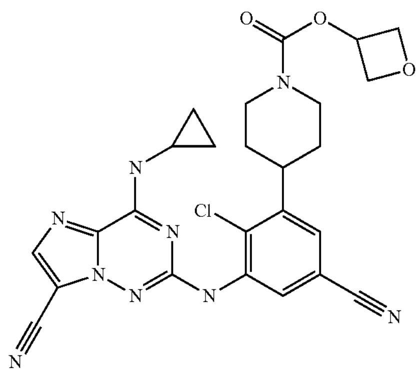 [SMILES: N#Cc1cc(Nc2nc(NC3CC3)c3ncc(C#N)n3n2)c(Cl)c(C2CCN(C(=O)OC3COC3)CC2)c1] | 3-oxetanyl 4-(2-chloro-5-cyano-3-((7-cyano-4-(cyclopropylamino)imidazo[2,1-f][1,2,4]triazin-2-yl)amino)phenyl)-1-piperidinylcarboxylate | 533.98 | 4.67 |
| 239 | 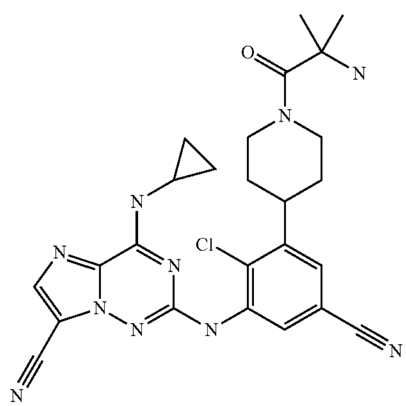 [SMILES: CC(C)(N)C(=O)N1CCC(c2cc(C#N)cc(Nc3nc(NC4CC4)c4ncc(C#N)n4n3)c2Cl)CC1] | 2-((2-chloro-5-cyano-3-(1-(2-methylalanyl)-4-piperidinyl)phenyl)amino)-4-(cyclopropylamino)imidazo[2,1-f][1,2,4]triazine-7-carbonitrile | 519.01 | 4.18 |
| 240 | Chiral | 2-((3-(1-L-alanyl-4-piperidinyl)-2-chloro-5-cyanophenyl)amino)-4-(cyclopropylamino)imidazo[2,1-f][1,2,4]triazine-7-carbonitrile | 504.98 | 4.10 |

TABLE 7-continued

| Example No. | Structure | Name | [M + H]+ | HPLC Retention Time (min.)* |
|---|---|---|---|---|
| 241 | Chiral (structure shown) | 2-((3-(1-D-alanyl-4-piperidinyl)-2-chloro-5-cyanophenyl)amino)-4-(cyclopropylamino)imidazo[2,1-f][1,2,4]triazine-7-carbonitrile | 504.98 | 4.13 |

\* = HPLC conditions
CHROMOLITH ® column 4.6 × 5.0 mm eluting with 10-90% aqueous methanol over 4 min. containing 0.1% TFA, 4 mL/min, monitoring at 220 nm.

Example 242

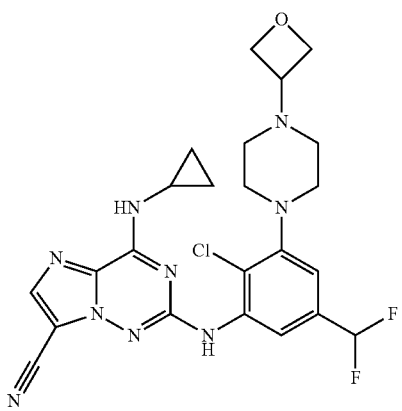 [SMILES: N#Cc1cnc2c(NC3CC3)nc(Nc3cc(C(F)F)cc(N4CCN(C5COC5)CC4)c3Cl)nn12]

2-((2-Chloro-5-(difluoromethyl)-3-(4-(oxetan-3-yl)piperazin-1-yl)phenyl)amino)-4-(cyclopropylamino)imidazo[2,1-f][1,2,4]triazine-7-carbonitrile (242A): Cesium carbonate (672 mg, 2.063 mmol), BINAP (64.2 mg, 0.103 mmol), 1-(oxetan-3-yl)piperazine (176 mg, 1.238 mmol) and Pd$_2$(dba)$_3$ (94 mg, 0.103 mmol) were weighed into a 25 mL round bottom flask at rt. A solution of tert-butyl(3-bromo-2-chloro-5-(difluoromethyl)phenyl)(4-methoxybenzyl)carbamate in toluene (4294 μl, 1.031 mmol) was added and the reaction was degassed 3 times by evacuating the flask under vacuum and then purging with N$_2$. The reaction mixture was heated to 106° C. for 16 h and then cooled to rt. The reaction mixture was diluted with EtOAc, sonicated, filtered through celite and concentrated. The product was purified by column chromatography (40 g SiO2, 30 to 100% EtOAc-hexane gradient elution) to afford 312 mg of tert-butyl(2-chloro-5-(difluoromethyl)-3-(4-(oxetan-3-yl)piperazin-1-yl)phenyl)(4-methoxybenzyl)carbamate.

MS (ESI) m/z 538.4

(242B): Anisole (633 μl, 5.80 mmol) was added to a solution of tert-butyl(2-chloro-5-(difluoromethyl)-3-(4-(oxetan-3-yl)piperazin-1-yl)phenyl)(4-methoxybenzyl)carbamate (312 mg, 0.58 mmol) in DCE (3 mL), followed by the addition 2.8 mL of TFA. The reaction was stirred at 60° C. for 3 h. The residue was partitioned between CH$_2$Cl$_2$ and sat. NaHCO$_3$, and extracted into CH$_2$Cl$_2$ (3×). The solution was dried over Na$_2$SO$_4$ and concentrated. The residue was dissolved in MeOH and loaded onto a 5 g Strata SCX ion exchange cartridge, washing with MeOH. The desired product was eluted with 7 N NH$_3$—CH$_3$OH. After concentration, 163.4 mg of 2-chloro-5-(difluoromethyl)-3-(4-(oxetan-3-yl)piperazin-1-yl)aniline was obtained.

MS (ESI) m/z 318.1 (M$^+$+H).

$^1$H NMR (400 MHz, DMSO-d6) δ ppm 6.70-6.66 (m, 1H), 6.64-6.60 (m, 1H), 6.61-6.38 (m, 1H), 4.72 (quin, J=6.3 Hz, 4H), 4.26 (s, 2H), 3.64 (quin, J=6.4 Hz, 1H), 3.21-3.07 (m, 4H), 2.69-2.47 (m, 4H).

(242C): A mixture of 2-chloro-5-(difluoromethyl)-3-(4-(oxetan-3-yl)piperazin-1-yl)aniline (50 mg, 0.157 mmol), 4-(cyclopropyl(4-methoxybenzyl)amino)-2-(methylsulfonyl)imidazo[2,1-f][1,2,4]triazine-7-carbonitrile (94 mg, 0.236 mmol) and cesium carbonate (103 mg, 0.315 mmol) in DMF (1574 μm) was stirred at 40° C. for 72 h. The reaction mixture was cooled to rt, diluted with H$_2$O and extracted with EtOAc (3×). The combined organics were washed with 10% LiCl solution and concentrated. Column chromatography (12 g SiO$_2$, 0 to 100% EtOAc-hexane gradient elution) afforded 2-((2-chloro-5-(difluoromethyl)-3-(4-(oxetan-3-yl)piperazin-1-yl)phenyl)amino)-4-(cyclopropyl(4-methoxybenzyl)amino)imidazo[2,1-f][1,2,4]triazine-7-carbonitrile (76.7 mg).

MS (ESI) m/z 636.4 (M$^+$+H).

$^1$H NMR (400 MHz, CHLOROFORM-d) δ 8.05 (s, 1H), 7.95 (s, 1H), 7.22 (d, J=8.6 Hz, 2H), 7.00-6.78 (m, 3H), 4.73 (quin, J=6.3 Hz, 4H), 3.82 (s, 3H), 3.65 (quin, J=6.5 Hz, 1H), 3.16 (t, J=4.7 Hz, 4H), 2.99 (s, 1H), 2.92 (s, 1H), 2.59 (d, J=5.3 Hz, 4H), 1.13-1.04 (m, 2H), 0.89 (d, J=4.8 Hz, 2H)

Example 242

2-((2-Chloro-5-(difluoromethyl)-3-(4-(oxetan-3-yl)piperazin-1-yl)phenyl)amino)-4-(cyclopropyl(4-methoxybenzyl)

amino)imidazo[2,1-f][1,2,4]triazine-7-carbonitrile (69 mg, 0.108 mmol) was dissolved in DCE (1 mL) at room temperature. Anisole (59.2 μl, 0.542 mmol) followed by 200 μL of TFA were added and the reaction was stirred at 40° C. overnight and concentrated. The residue was dissolved in MeOH and loaded onto a 1 g/6 mL Strata SCX ion exchange column, washing with CH₃OH. The desired product was eluted with 7 N NH₃—CH₃OH, concentrated under a stream of N2. Column chromatography (12 g SiO2, 0 to 20% CH₃OH—CH₂Cl₂ gradient elution) followed by trituration with ACN afforded 2-((2-chloro-5-(difluoromethyl)-3-(4-(oxetan-3-yl)piperazin-1-yl)phenyl)amino)-4-(cyclopropylamino)imidazo[2,1-f][1,2,4]triazine-7-carbonitrile (14.6 mg).

MS (ESI) m/z 516.3

¹H NMR (400 MHz, DMSO-d₆) δ 9.27 (d, J=4.8 Hz, 1H), 8.67 (s, 1H), 8.20 (s, 1H), 7.99-7.85 (m, 1H), 7.13-7.07 (m, 1H), 7.21-6.84 (m, 1H), 4.63-4.55 (m, 2H), 4.50 (t, J=6.2 Hz, 2H), 3.53 (quin, J=6.4 Hz, 1H), 3.13-2.98 (m, 5H), 2.48 (d, J=1.3 Hz, 4H), 0.84-0.69 (m, 4H).

The compounds listed below were prepared by the similar synthetic procedure used for Example 242

TABLE 8

| Example No. | Structure | Name | [M + H]⁺ | HPLC Retention Time (min.)* |
|---|---|---|---|---|
| 243 | 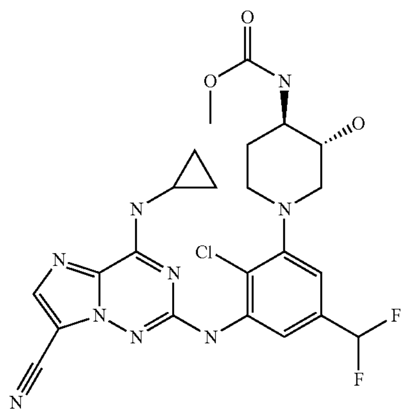 [SMILES: COC(=O)N[C@@H]1CCN(c2cc(C(F)F)cc(Nc3nc(NC4CC4)c4ncc(C#N)n4n3)c2Cl)C[C@H]1O] | methyl (3R,4R)-1-(2-chloro-3-(7-cyano-4-(cyclopropylamino)imidazo[1,2-f][1,2,4]triazin-2-ylamino)-5-(difluoromethyl)phenyl)-3-hydroxypiperidin-4-ylcarbamate | 547.95 | 3.67 |
| 244 | 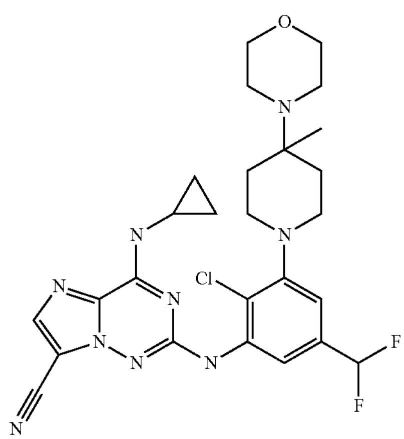 [SMILES: CC1(N2CCOCC2)CCN(c2cc(C(F)F)cc(Nc3nc(NC4CC4)c4ncc(C#N)n4n3)c2Cl)CC1] | 2-((2-chloro-5-(difluoromethyl)-3-(4-methyl-4-(4-morpholinyl)-1-piperidinyl)phenyl)amino)-4-(cyclopropylamino)imidazo[2,1-f][1,2,4]triazine-7-carbonitrile | 558.03 | 3.78 |
| 245 | 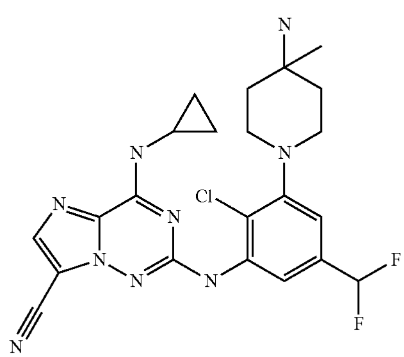 [SMILES: CC1(N)CCN(c2cc(C(F)F)cc(Nc3nc(NC4CC4)c4ncc(C#N)n4n3)c2Cl)CC1] | 2-((3-(4-amino-4-methyl-1-piperidinyl)-2-chloro-5-(difluoromethyl)phenyl)amino)-4-(cyclopropylamino)imidazo[2,1-f][1,2,4]triazine-7-carbonitrile | 487.94 | 2.80 |

TABLE 8-continued

| Example No. | Structure | Name | [M + H]+ | HPLC Retention Time (min.)* |
|---|---|---|---|---|
| 246 | 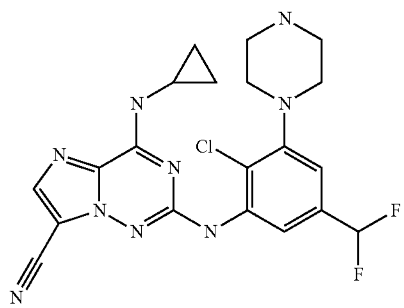 [SMILES: N#Cc1cnc2c(NC3CC3)nc(Nc3cc(C(F)F)cc(N4CCNCC4)c3Cl)nn12] | 2-((2-chloro-5-(difluoromethyl)-3-(1-piperazinyl)phenyl)amino)-4-(cyclopropylamino)imidazo[2,1-f][1,2,4]triazine-7-carbonitrile | 459.89 | 3.75 |
| 247 | 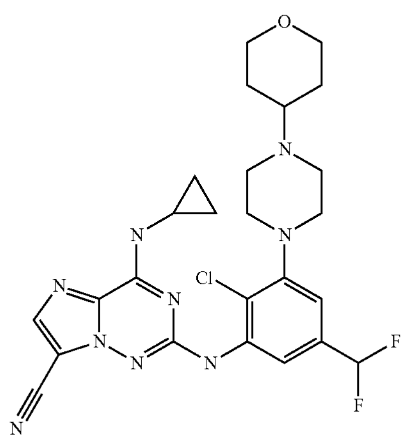 [SMILES: N#Cc1cnc2c(NC3CC3)nc(Nc3cc(C(F)F)cc(N4CCN(C5CCOCC5)CC4)c3Cl)nn12] | 2-((2-chloro-5-(difluoromethyl)-3-(4-(tetrahydro-2H-pyran-4-yl)-1-piperazinyl)phenyl)amino)-4-(cyclopropylamino)imidazo[2,1-f][1,2,4]triazine-7-carbonitrile | 544.01 | 4.72[c] |
| 248 | 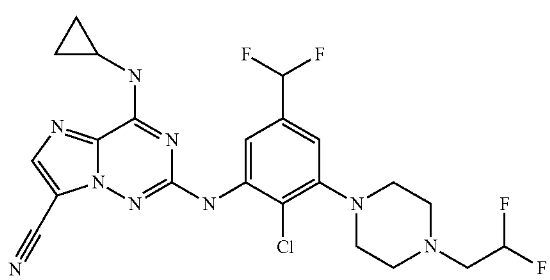 [SMILES: CC(O)CN1CCN(c2cc(C(F)F)cc(Nc3nc(NC4CC4)c4ncc(C#N)n4n3)c2Cl)CC1] | 2-((2-chloro-3-(4-(2,2-difluoroethyl)-1-piperazinyl)-5-(difluoromethyl)phenyl)amino)-4-(cyclopropylamino)imidazo[2,1-f][1,2,4]triazine-7-carbonitrile | 523.92 | 3.96[c] |
| 249 | 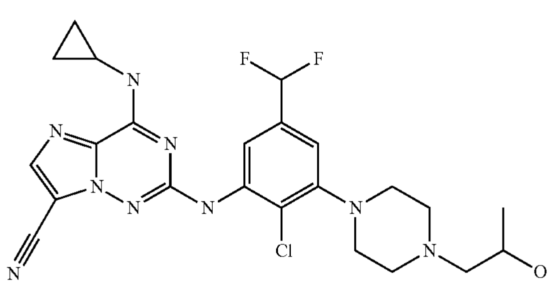 | (+/−) 2-((2-chloro-5-(difluoromethyl)-3-(4-(2-hydroxypropyl)-1-piperazinyl)phenyl)amino)-4-(cyclopropylamino)imidazo[2,1-f][1,2,4]triazine-7-carbonitrile | 517.97 | 3.78 |

TABLE 8-continued

| Example No. | Structure | Name | [M + H]+ | HPLC Retention Time (min.)* |
|---|---|---|---|---|
| 250 | 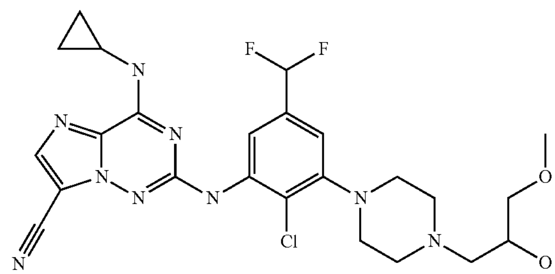 [SMILES: COCC(O)CN1CCN(c2cc(C(F)F)cc(Nc3nc(NC4CC4)c4ncc(C#N)n4n3)c2Cl)CC1] | (+/−) 2-((2-chloro-5-(difluoromethyl)-3-(4-(2-hydroxy-3-methoxypropyl)-1-piperazinyl)phenyl)amino)-4-(cyclopropylamino)imidazo[2,1-f][1,2,4]triazine-7-carbonitrile | 548.00 | 4.21 |
| 251 | Chiral | methyl ((3S,4S)-1-(2-chloro-3-((7-cyano-4-(cyclopropylamino)imidazo[2,1-f][1,2,4]triazin-2-yl)amino)-5-(difluoromethyl)phenyl)-4-methoxy-3-pyrrolidinyl)carbamate | 547.95 | 4.67 |
| 252 | Chiral | methyl ((3S,4R)-1-(2-chloro-3-((7-cyano-4-(cyclopropylamino)imidazo[2,1-f][1,2,4]triazin-2-yl)amino)-5-(difluoromethyl)phenyl)-4-methoxy-3-pyrrolidinyl)carbamate | 547.95 | 4.81 |
| 253 | 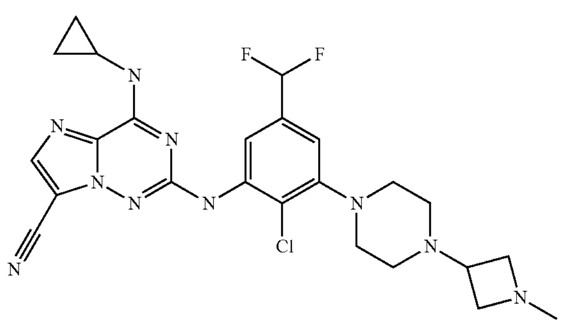 [SMILES: CN1CC(N2CCN(c3cc(C(F)F)cc(Nc4nc(NC5CC5)c5ncc(C#N)n5n4)c3Cl)CC2)C1] | 2-((2-chloro-5-(difluoromethyl)-3-(4-(1-methyl-3-azetidinyl)-1-piperazinyl)phenyl)amino)-4-(cyclopropylamino)imidazo[2,1-f][1,2,4]triazine-7-carbonitrile | 529.00 | 4.01 |
| 254 | 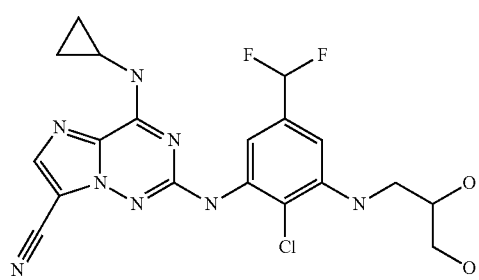 [SMILES: N#Cc1cnc2c(NC3CC3)nc(Nc3cc(C(F)F)cc(NCC(O)CO)c3Cl)nn12] | 2-((2-chloro-5-(difluoromethyl)-3-((2,3-dihydroxypropyl)amino)phenyl)amino)-4-(cyclopropylamino)imidazo[2,1-f][1,2,4]triazine-7-carbonitrile | 464.86 | 3.32 |

TABLE 8-continued

| Example No. | Structure | Name | [M + H]+ | HPLC Retention Time (min.)* |
|---|---|---|---|---|
| 255 | 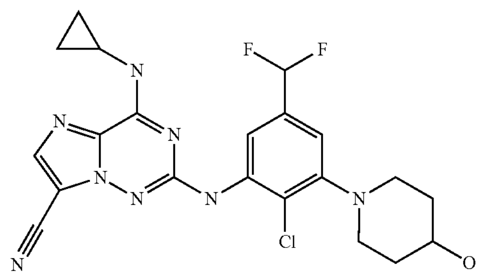 [SMILES: N#Cc1cnc2c(NC3CC3)nc(Nc3cc(C(F)F)cc(N4CCC(O)CC4)c3Cl)nn12] | 2-((2-chloro-5-(difluoromethyl)-3-(4-hydroxy-1-piperidinyl)phenyl)amino)-4-(cyclopropylamino)imidazo[2,1-f][1,2,4]triazine-7-carbonitrile | 474.90 | 4.32 |
| 256 | 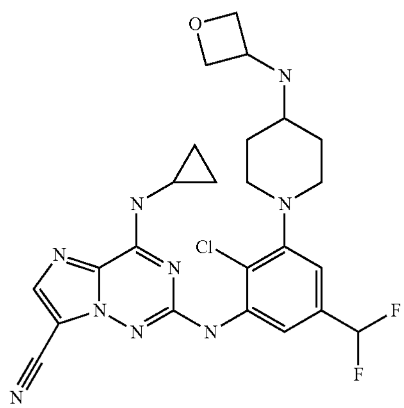 [SMILES: N#Cc1cnc2c(NC3CC3)nc(Nc3cc(C(F)F)cc(N4CCC(NC5COC5)CC4)c3Cl)nn12] | 2-((2-chloro-5-(difluoromethyl)-3-(4-(3-oxetanylamino)-1-piperidinyl)phenyl)amino)-4-(cyclopropylamino)imidazo[2,1-f][1,2,4]triazine-7-carbonitrile | 529.98 | 4.42 |
| 257 | 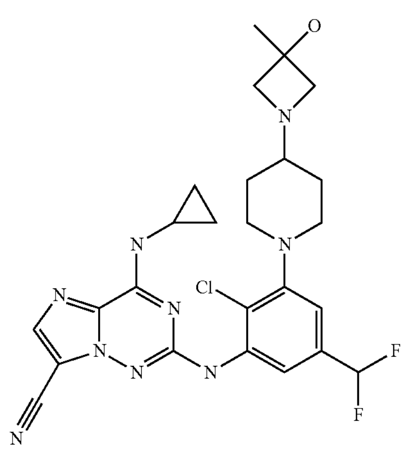 [SMILES: CC1(O)CN(C2CCN(c3cc(C(F)F)cc(Nc4nc(NC5CC5)c5ncc(C#N)n5n4)c3Cl)CC2)C1] | 2-((2-chloro-5-(difluoromethyl)-3-(4-(3-hydroxy-3-methyl-1-azetidinyl)-1-piperidinyl)phenyl)amino)-4-(cyclopropylamino)imidazo[2,1-f][1,2,4]triazine-7-carbonitrile | 544.01 | 4.35 |

TABLE 8-continued

| Example No. | Structure | Name | [M + H]+ | HPLC Retention Time (min.)* |
|---|---|---|---|---|
| 258 | 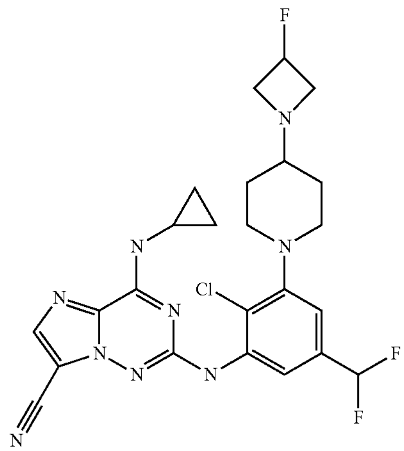 [SMILES: N#Cc1cnc2c(NC3CC3)nc(Nc3cc(C(F)F)cc(N4CCC(N5CC(F)C5)CC4)c3Cl)nn12] | 2-((2-chloro-5-(difluoromethyl)-3-(4-(3-fluoro-1-azetidinyl)-1-piperidinyl)phenyl)amino)-4-(cyclopropylamino)imidazo[2,1-f][1,2,4]triazine-7-carbonitrile | 531.97 | 4.65 |
| 259 | 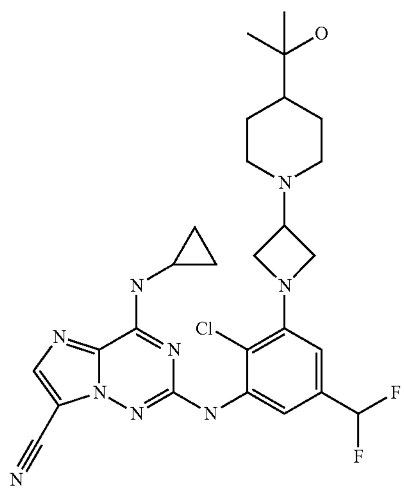 [SMILES: CC(C)(O)C1CCN(C2CN(c3cc(C(F)F)cc(Nc4nc(NC5CC5)c5ncc(C#N)n5n4)c3Cl)C2)CC1] | 2-((2-chloro-5-(difluoromethyl)-3-(3-(4-(1-hydroxy-1-methylethyl)-1-piperidinyl)-1-azetidinyl)phenyl)amino)-4-(cyclopropylamino)imidazo[2,1-f][1,2,4]triazine-7-carbonitrile | 572.06 | 4.83 |
| 260 | 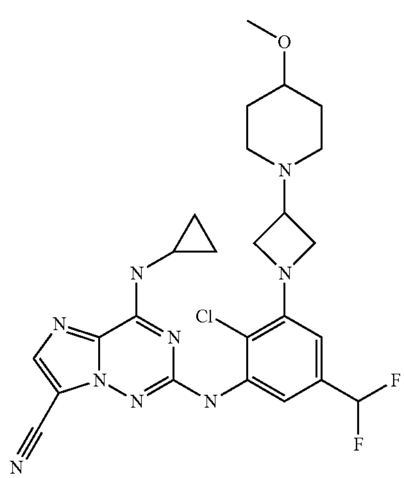 [SMILES: COC1CCN(C2CN(c3cc(C(F)F)cc(Nc4nc(NC5CC5)c5ncc(C#N)n5n4)c3Cl)C2)CC1] | 2-((2-chloro-5-(difluoromethyl)-3-(3-(4-methoxy-1-piperidinyl)-1-azetidinyl)phenyl)amino)-4-(cyclopropylamino)imidazo[2,1-f][1,2,4]triazine-7-carbonitrile | 544.01 | 4.69 |

TABLE 8-continued

| Example No. | Structure | Name | [M + H]+ | HPLC Retention Time (min.)* |
|---|---|---|---|---|
| 261 | 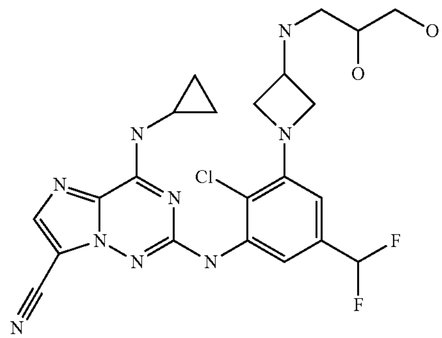 [SMILES: N#Cc1cnc2c(NC3CC3)nc(Nc3cc(C(F)F)cc(N4CC(NCC(O)CO)C4)c3Cl)nn12] | (+/−) 2-((2-chloro-5-(difluoromethyl)-3-(3-((2,3-dihydroxypropyl)amino)-1-azetidinyl)phenyl)amino)-4-(cyclopropylamino)imidazo[2,1-f][1,2,4]triazine-7-carbonitrile | 519.94 | 3.24 |
| 262 | 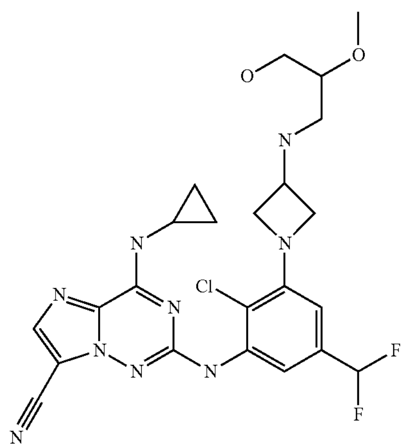 [SMILES: COC(CO)CNC1CN(c2cc(C(F)F)cc(Nc3nc(NC4CC4)c4ncc(C#N)n4n3)c2Cl)C1] | (+/−) 2-((2-chloro-5-(difluoromethyl)-3-(3-((3-hydroxy-2-methoxypropyl)amino)-1-azetidinyl)phenyl)amino)-4-(cyclopropylamino)imidazo[2,1-f][1,2,4]triazine-7-carbonitrile | 533.97 | 4.44 |
| 263 | 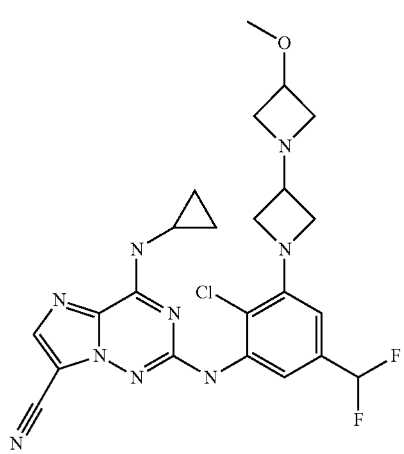 [SMILES: COC1CN(C2CN(c3cc(C(F)F)cc(Nc4nc(NC5CC5)c5ncc(C#N)n5n4)c3Cl)C2)C1] | 2-((2-chloro-5-(difluoromethyl)-3-(3-methoxy-1,3'-biazetidin-1'-yl)phenyl)amino)-4-(cyclopropylamino)imidazo[2,1-f][1,2,4]triazine-7-carbonitrile | 515.95 | 4.19 |

TABLE 8-continued

| Example No. | Structure | Name | [M + H]+ | HPLC Retention Time (min.)* |
|---|---|---|---|---|
| 264 | 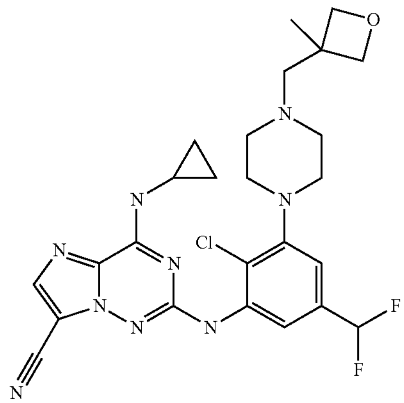 [SMILES: CC1(CN2CCN(c3cc(C(F)F)cc(Nc4nc(NC5CC5)c5ncc(C#N)n5n4)c3Cl)CC2)COC1] | 2-((2-chloro-5-(difluoromethyl)-3-(4-((3-methyl-3-oxetanyl)methyl)-1-piperazinyl)phenyl)amino)-4-(cyclopropylamino)imidazo[2,1-f][1,2,4]triazine-7-carbonitrile | 544.01 | 4.16 |
| 265 | 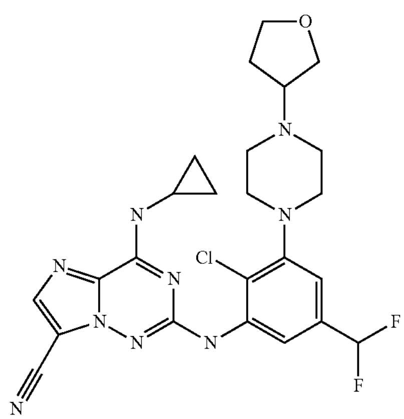 [SMILES: N#Cc1cnc2c(NC3CC3)nc(Nc3cc(C(F)F)cc(N4CCN(C5CCOC5)CC4)c3Cl)nn12] | (+/−) 2-(2-chloro-5-(difluoromethyl)-3-(4-(tetrahydrofuran-3-yl)piperazin-1-yl)phenylamino)-4-(cyclopropylamino)imidazo[1,2-f][1,2,4]triazine-7-carbonitrile | 529.98 | 3.98 |
| 266 | 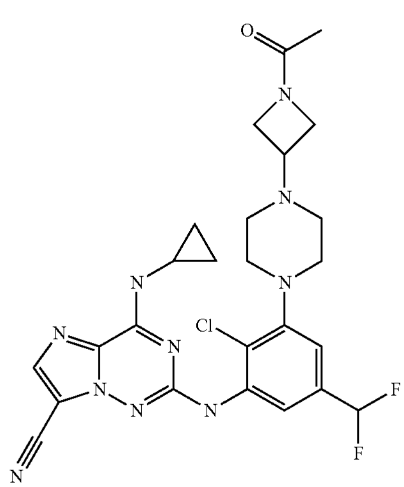 [SMILES: CC(=O)N1CC(N2CCN(c3cc(C(F)F)cc(Nc4nc(NC5CC5)c5ncc(C#N)n5n4)c3Cl)CC2)C1] | 2-((3-(4-(1-acetyl-3-azetidinyl)-1-piperazinyl)-2-chloro-5-(difluoromethyl)phenyl)amino)-4-(cyclopropylamino)imidazo[2,1-f][1,2,4]triazine-7-carbonitrile | 557.01 | 4.01 |

TABLE 8-continued

| Example No. | Structure | Name | [M + H]+ | HPLC Retention Time (min.)* |
|---|---|---|---|---|
| 267 | 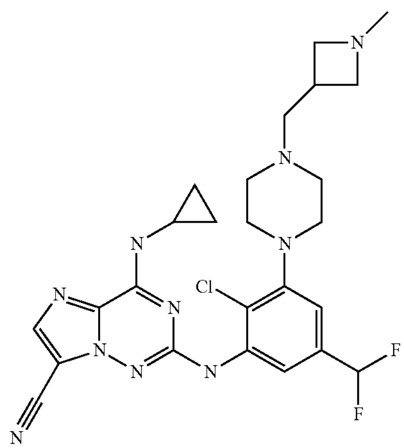 [SMILES: CN1CC(CN2CCN(c3cc(C(F)F)cc(Nc4nc(NC5CC5)c5ncc(C#N)n5n4)c3Cl)CC2)C1] | 2-((2-chloro-5-(difluoromethyl)-3-(4-((1-methyl-3-azetidinyl)methyl)-1-piperazinyl)phenyl)amino)-4-(cyclopropylamino)imidazo[2,1-f][1,2,4]triazine-7-carbonitrile | 543.02 | 3.43 |
| 268 | 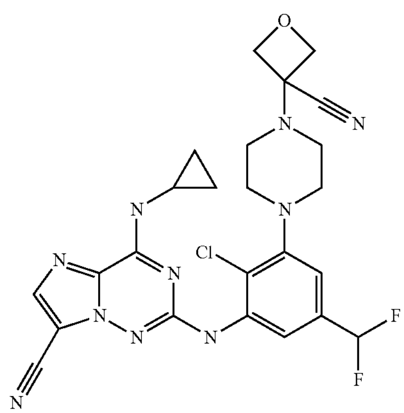 [SMILES: N#Cc1cnc2c(NC3CC3)nc(Nc3cc(C(F)F)cc(N4CCN(C5(C#N)COC5)CC4)c3Cl)nn12] | 2-((2-chloro-3-(4-(3-cyano-3-oxetanyl)-1-piperazinyl)-5-(difluoromethyl)phenyl)amino)-4-(cyclopropylamino)imidazo[2,1-f][1,2,4]triazine-7-carbonitrile | 540.96 | 4.65 |
| 269 | 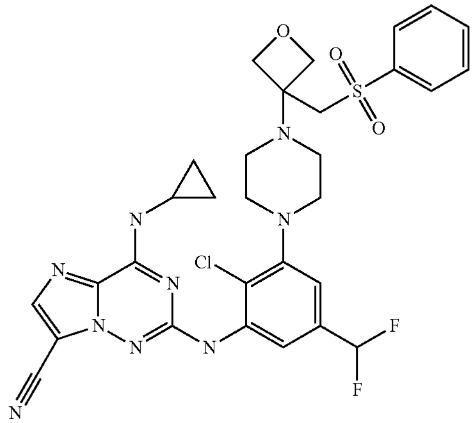 [SMILES: N#Cc1cnc2c(NC3CC3)nc(Nc3cc(C(F)F)cc(N4CCN(C5(CS(=O)(=O)c6ccccc6)COC5)CC4)c3Cl)nn12] | 2-(2-chloro-5-(difluoromethyl)-3-(4-(3-(phenylsulfonylmethyl)oxetan-3-yl)piperazin-1-yl)phenylamino)-4-(cyclopropylamino)imidazo[1,2-f][1,2,4]triazine-7-carbonitrile | 670.14 | 4.82 |

TABLE 8-continued

| Example No. | Structure | Name | [M + H]⁺ | HPLC Retention Time (min.)* |
|---|---|---|---|---|
| 270 | 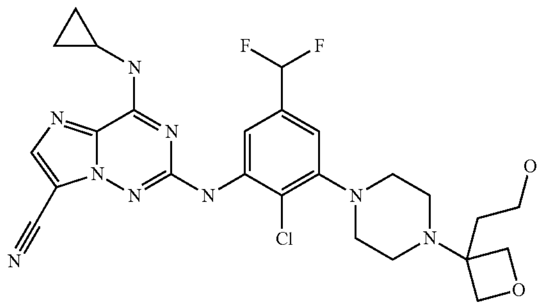 [SMILES: N#Cc1cnc2c(NC3CC3)nc(Nc3cc(C(F)F)cc(N4CCN(C5(CCO)COC5)CC4)c3Cl)nn12] | 2-((2-chloro-5-(difluoromethyl)-3-(4-(3-(2-hydroxyethyl)-3-oxetanyl)-1-piperazinyl)phenyl)amino)-4-(cyclopropylamino)imidazo[2,1-f][1,2,4]triazine-7-carbonitrile | 560.01 | 4.02 |
| 271 | 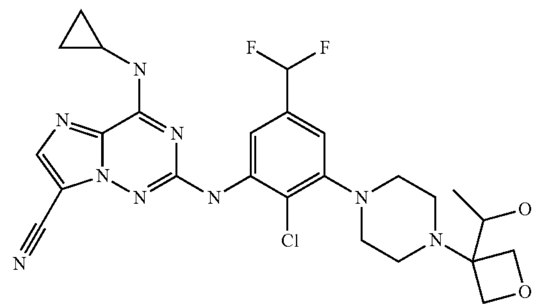 [SMILES: CC(O)C1(N2CCN(c3cc(C(F)F)cc(Nc4nc(NC5CC5)c5ncc(C#N)n5n4)c3Cl)CC2)COC1] | 2-((2-chloro-5-(difluoromethyl)-3-(4-(3-(1-hydroxyethyl)-3-oxetanyl)-1-piperazinyl)phenyl)amino)-4-(cyclopropylamino)imidazo[2,1-f][1,2,4]triazine-7-carbonitrile | 560.01 | 4.11 |
| 272 | 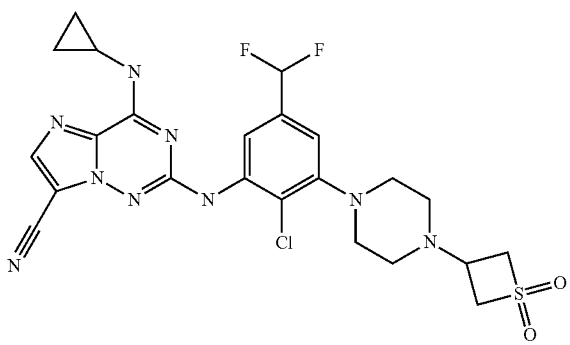 [SMILES: N#Cc1cnc2c(NC3CC3)nc(Nc3cc(C(F)F)cc(N4CCN(C5CS(=O)(=O)C5)CC4)c3Cl)nn12] | 2-((2-chloro-5-(difluoromethyl)-3-(4-(1,1-dioxidothietan-3-yl)piperazin-1-yl)phenyl)amino)-4-(cyclopropylamino)imidazo[2,1-f][1,2,4]triazine-7-carbonitrile | 564.02 | 3.88 |
| 273 | 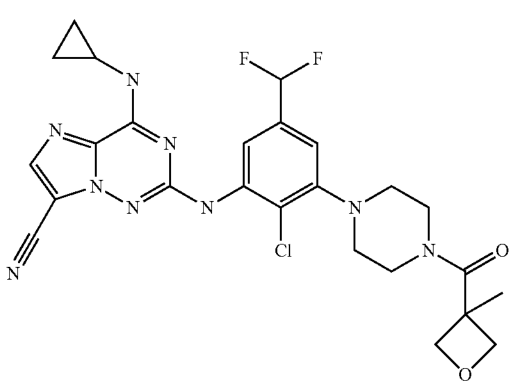 [SMILES: CC1(C(=O)N2CCN(c3cc(C(F)F)cc(Nc4nc(NC5CC5)c5ncc(C#N)n5n4)c3Cl)CC2)COC1] | 2-((2-chloro-5-(difluoromethyl)-3-(4-((3-methyl-3-oxetanyl)carbonyl)-1-piperazinyl)phenyl)amino)-4-(cyclopropylamino)imidazo[2,1-f][1,2,4]triazine-7-carbonitrile | 557.99 | 4.54 |

TABLE 8-continued

| Example No. | Structure | Name | [M + H]+ | HPLC Retention Time (min.)* |
|---|---|---|---|---|
| 274 | 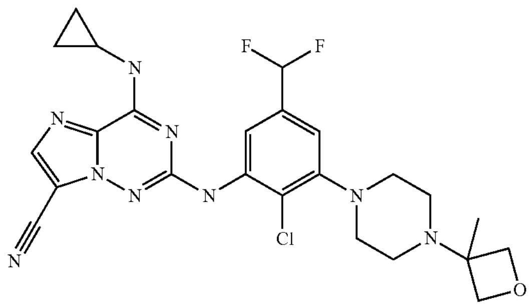 [SMILES: CC1(N2CCN(c3cc(C(F)F)cc(Nc4nc(NC5CC5)c5ncc(C#N)n5n4)c3Cl)CC2)COC1] | 2-((2-chloro-5-(difluoromethyl)-3-(4-(3-methyl-3-oxetanyl)-1-piperazinyl)phenyl)amino)-4-(cyclopropylamino)imidazo[2,1-f][1,2,4]triazine-7-carbonitrile | 529.98 | 4.21 |
| 275 | 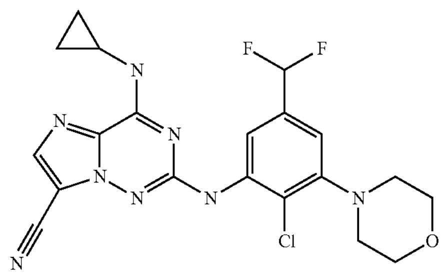 [SMILES: N#Cc1cnc2c(NC3CC3)nc(Nc3cc(C(F)F)cc(N4CCOCC4)c3Cl)nn12] | 2-((2-chloro-5-(difluoromethyl)-3-(4-morpholinyl)phenyl)amino)-4-(cyclopropylamino)imidazo[2,1-f][1,2,4]triazine-7-carbonitrile | 460.87 | 4.72 |
| 276 | 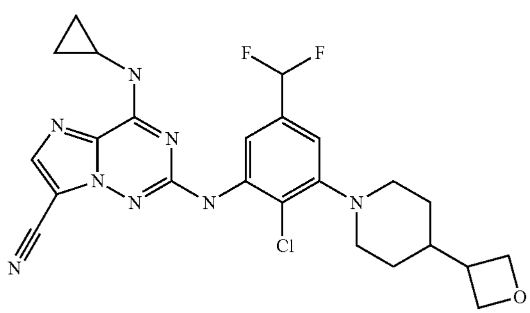 [SMILES: N#Cc1cnc2c(NC3CC3)nc(Nc3cc(C(F)F)cc(N4CCC(C5COC5)CC4)c3Cl)nn12] | 2-((2-chloro-5-(difluoromethyl)-3-(4-(3-oxetanyl)-1-piperidinyl)phenyl)amino)-4-(cyclopropylamino)imidazo[2,1-f][1,2,4]triazine-7-carbonitrile | 514.97 | 4.60 |
| 277 | 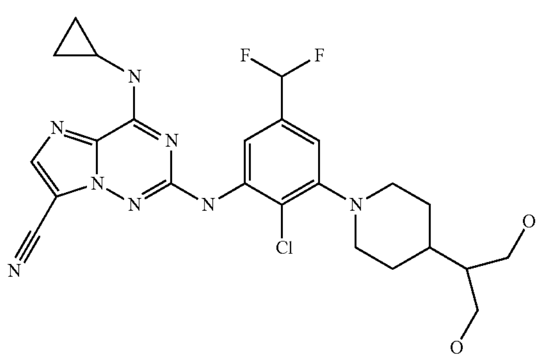 [SMILES: N#Cc1cnc2c(NC3CC3)nc(Nc3cc(C(F)F)cc(N4CCC(C(CO)CO)CC4)c3Cl)nn12] | 2-((2-chloro-5-(difluoromethyl)-3-(4-(2-hydroxy-1-(hydroxymethyl)ethyl)-1-piperidinyl)phenyl)amino)-4-(cyclopropylamino)imidazo[2,1-f][1,2,4]triazine-7-carbonitrile | 532.98 | 3.87 |

TABLE 8-continued

| Example No. | Structure | Name | [M + H]⁺ | HPLC Retention Time (min.)* |
|---|---|---|---|---|
| 278 | 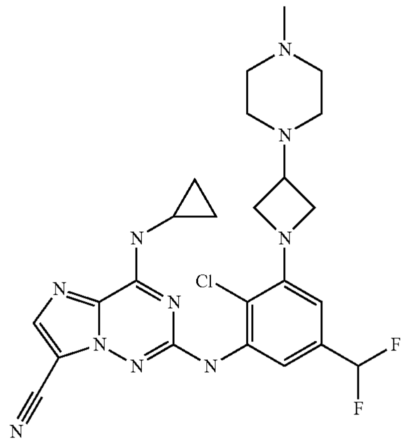 [SMILES: CN1CCN(C2CN(c3cc(C(F)F)cc(Nc4nc(NC5CC5)c5ncc(C#N)n5n4)c3Cl)C2)CC1] | 2-((2-chloro-5-(difluoromethyl)-3-(3-(4-methyl-1-piperazinyl)-1-azetidinyl)phenyl)amino)-4-(cyclopropylamino)imidazo[2,1-f][1,2,4]triazine-7-carbonitrile | 529.00 | 3.72 |
| 279 | 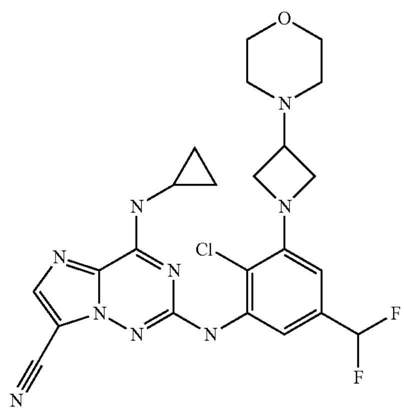 [SMILES: N#Cc1cnc2c(NC3CC3)nc(Nc3cc(C(F)F)cc(N4CC(N5CCOCC5)C4)c3Cl)nn12] | 2-((2-chloro-5-(difluoromethyl)-3-(3-(4-morpholinyl)-1-azetidinyl)phenyl)amino)-4-(cyclopropylamino)imidazo[2,1-f][1,2,4]triazine-7-carbonitrile | 515.95 | 4.21 |
| 280 | 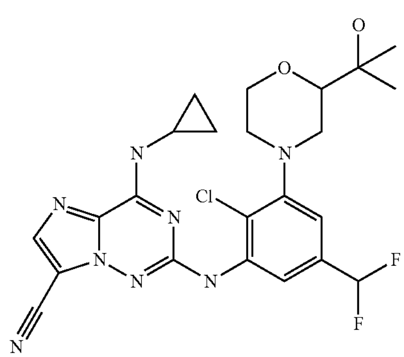 [SMILES: CC(C)(O)C1CN(c2cc(C(F)F)cc(Nc3nc(NC4CC4)c4ncc(C#N)n4n3)c2Cl)CCO1] | (+/−) 2-((2-chloro-5-(difluoromethyl)-3-(2-(1-hydroxy-1-methylethyl)-4-morpholinyl)phenyl)amino)-4-(cyclopropylamino)imidazo[2,1-f][1,2,4]triazine-7-carbonitrile | 518.95 | 4.73 |

YMC S5 ODS 4.6 × 50 mm, 10-90% aqueous methanol containing 0.2% $H_3PO_4$, 5 min gradient, monitored at 220 nm

Example 281

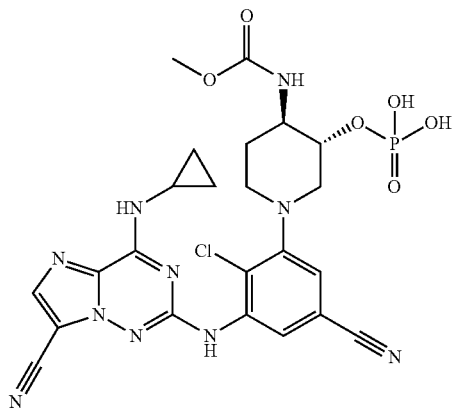 [SMILES: COC(=O)N[C@@H]1CCN(c2cc(C#N)cc(Nc3nc(NC4CC4)c4ncc(C#N)n4n3)c2Cl)C[C@H]1OP(=O)(O)O]

methyl((3R,4R)-1-(2-chloro-5-cyano-3-((7-cyano-4-(cyclopropylamino)imidazo[2,1-f][1,2,4]triazin-2-yl)amino)phenyl)-3-(phosphonooxy)piperidin-4-yl)carbamate (281A): To a solution of methyl((3R,4R)-1-(2-chloro-5-cyano-3-((7-cyano-4-(cyclopropyl(4 methoxybenzyl) amino)imidazo[2,1-f][1,2,4]triazin-2-yl)amino)phenyl)-3-hydroxypiperidin-4-yl)carbamate (Example 173D) (0.010 g, 0.016 mmol) in DCM (1 mL) was added pyridine (0.0063 mL, 0.078 mmol) and cooled to −20° C. POCl3 (0.003 mL, 0.031 mmol) was added to the above reaction and stirred for 20 min. and warmed to room temperature in 30 min. then added water (0.5 mL) and stirred for additional 10 min. After completion of starting material (by LCMS), reaction mixture was concentrated at 30° C. and residue was purified by reverse phase preparative HPLC and fractions were lyophilized to give ((3R,4R)-1-(2-chloro-5-cyano-3-((7-cyano-4-(cyclopropyl(4-methoxybenzyl)amino)imidazo[2,1f][1,2,4]triazin-2-yl)amino)phenyl)-3-(phosphonooxy)piperidin-4-yl)carbamate (0.007 g) as a white solid.

MS (ESI) m/z 723.6

Example 281

To a solution of methyl((3R,4R)-1-(2-chloro-5-cyano-3-((7-cyano-4-(cyclopropyl(4-methoxybenzyl)amino)imidazo[2,1-f][1,2,4]triazin-2-yl)amino)phenyl)-3-(phosphonooxy)piperidin-4 yl)carbamate (0.007 g, 0.009 mmol) in DCE (1 mL) was added anisole (0.006 mL, 0.055 mmol) followed by TFA (25% in DCE) (1.1 mL, 3.57 mmol) and at 35° C. for overnight. After completion of starting material (by LCMS), reaction mixture was concentrated and residue was taken in DCM (5 mL) concentrated under vacuum, the same thing was repeated one more time with 5 mL DCM. The resultant mixture was purified by reverse phase preparative HPLC and collected fractions were lyophilized to give methyl((3R, 4R)-1-(2-chloro-5-cyano-3-((7-cyano-4 (cyclopropylamino) imidazo[2,1-f][1,2,4]triazin-2-yl)amino)phenyl)-3-(phosphonooxy)piperidin-4 yl)carbamate (0.003 g, 4.97 μmol, 51.28% yield) as white solid.

MS (ESI) m/z 723.6
Preparative HPLC: Column: Xteera C18 (250×19×10μ); Solvent A=10 mM Ammonium acetate pH-4.6; Solvent B=Acetonitrile; Time (min)/% B: 0/20, 7/50, 17/50, 18/100; Flow Rate=16 mL/min; Wavelength=220 & 254 nm; Product Retention time=16.10 min.

$^1$H NMR (400 MHz, MeOH-d$_4$) δ ppm 8.64 (s, 1H), 8.00 (s, 1H), 7.22 (s, 1H), 4.58 (br. s, 1H), 4.29-4.19 (m, 1H), 3.86 (dd, J=11.67, 2.64 Hz, 1H), 3.66 (s, 3H), 3.56-3.49 (m, 2H), 3.09-3.05 (m, 1H), 2.86-2.75 (m, 3H), 2.68 (s, 1H), 2.29 (br. s, 1H), 1.74-1.67 (m, 1H), 1.03-0.97 (m, 2H), 0.84-0.79 (m, 2H)

Example 282

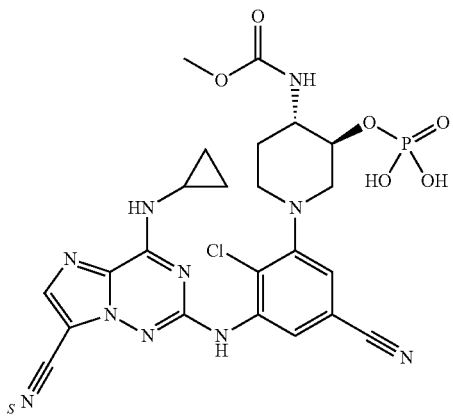

methyl((3S,4S)-1-(2-chloro-5-cyano-3-((7-cyano-4-(cyclopropylamino)imidazo[2,1-f][1,2,4]triazin-2-yl)amino)phenyl)-3-(phosphonooxy)piperidin-4-yl)carbamate Example 282 was prepared in analogous manner as example 281
Preparative HPLC: Column: Xteera C18 (250×19×10μ); Solvent A=10 mM Ammonium acetate pH-4.6 adjusted with AcOH; Solvent B=Acetonitrile; Time (min)/% B: 0/10, 10/70, 15/70, 16/100; Flow Rate=16 mL/min; Wavelength=220 & 254 nm; Product Retention time=10.70 min.
MS (ESI) m/z 601 (M−1)
$^1$H NMR (400 MHz, DMSO-d$_6$) δ ppm 8.87 (br. s, 1H), 8.20 (s, 1H), 8.14 (d, J=2.01 Hz, 1H), 7.82 (d, J=8.28 Hz, 1H), 7.60 (d, J=8.28 Hz, 1H), 7.32 (d, J=1.51 Hz, 1H), 4.03-3.96 (m, 1H), 3.51 (s, 3H), 3.24-3.09 (m, 4H), 3.01-2.94 (m, 1H), 2.76-2.62 (m, 3H), 2.34-2.30 (s, 1H), 1.40-1.31 (m, 1H), 0.80-0.7 (m, 4H)

Example 283

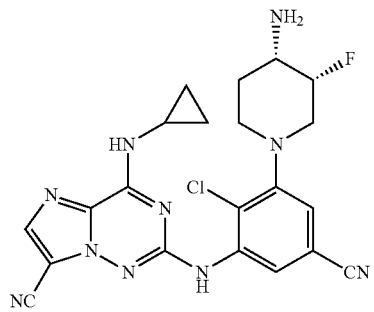 [SMILES: N#Cc1cc(Nc2nc(NC3CC3)c3ncc(C#N)n3n2)c(Cl)c(N2CC[C@H](N)[C@H](F)C2)c1]

2-((3-((3R,4S)-4-amino-3-fluoropiperidin-1-yl)-2-chloro-5-cyanophenyl)amino)-4-(cyclopropylamino) imidazo[2,1-f][1,2,4]triazine-7-carbonitrile, HCl (283A): (3R,4S)-tert-butyl 4-amino-3-fluoropiperidine-1-carboxylate (300 mg, 1.374 mmol) was taken up in DCM (8 mL) and a solution of sodium bicarbonate (346 mg, 4.12 mmol) in water (1 mL) was added. The reaction mixture was cooled to 0° C. and benzyl chloroformate (0.235 mL, 1.649 mmol) was added dropwise. The reaction was stirred at 0° C. for 30 min, then brought to rt and stirred overnight. The reaction mixture was diluted with DCM and water, and the organic layer was collected. The aqueous layer was reextracted with DCM and the organic layers were combined, dried over Na$_2$SO$_4$, filtered, and concentrated. The material was purified by flash column chromatography, eluting with 0-30% EtOAc/Hex. The fractions were combined and concentrated to give (3R,4S)-tert-butyl 4-(((benzyloxy)carbonyl)amino)-3-fluoropiperidine-1-carboxylate (450 mg) as a colorless glass.

MS (ESI) m/z 375 (M+Na)

$^1$H NMR (400 MHz, CHLOROFORM-d) δ 7.39-7.28 (m, 5H), 5.30 (d, J=9.0 Hz, 1H), 5.08 (s, 2H), 4.80-4.47 (m, 1H), 4.51-3.99 (m, 2H), 3.88-3.63 (m, 1H), 3.13-2.58 (m, 2H), 1.70 (dddd, J=9.8, 6.3, 4.0, 3.2 Hz, 2H), 1.44 (s, 9H)

(283B): Benzyl((3R,4S)-3-fluoropiperidin-4-yl)carbamate, HCl was prepared from (3R,4S)-tert-butyl 4-(((benzyloxy) carbonyl)amino)-3-fluoropiperidine-1-carboxylate using the methods described in Example 1B.

MS (ESI) m/z 253

$^1$H NMR (400 MHz, DMSO-d$_6$) δ 7.71 (d, J=7.7 Hz, 1H), 7.42-7.28 (m, 5H), 5.06 (s, 2H), 5.01-4.84 (m, 1H), 3.98-3.73 (m, 1H), 3.56-3.43 (m, 1H), 3.36 (dd, J=13.4, 0.7 Hz, 1H), 3.24 (dd, J=19.1, 13.6 Hz, 2H), 3.04 (td, J=9.6, 6.3 Hz, 1H), 1.98-1.70 (m, 2H)

(283C): Tert-butyl(3-((3R,4S)-4-(((benzyloxy)carbonyl) amino)-3-fluoropiperidin-1-yl)-2-chloro-5-cyanophenyl) carbamate was prepared from benzyl((3R,4S)-3-fluoropiperidin-4-yl)carbamate using the methods described in Example 1C.

MS (ESI) m/z 503

$^1$H NMR (400 MHz, CHLOROFORM-d) δ 8.33 (d, J=1.8 Hz, 1H), 7.44-7.30 (m, 5H), 7.19 (s, 1H), 6.99 (d, J=2.0 Hz, 1H), 5.22-5.08 (m, 3H), 4.94-4.70 (m, 1H), 4.01-3.77 (m, 1H), 3.74-3.57 (m, 1H), 3.43-3.32 (m, 1H), 3.08-2.90 (m, 1H), 2.89-2.78 (m, 1H), 2.13-1.99 (m, 1H), 1.99-1.90 (m, 1H), 1.55 (s, 9H)

(283D): Benzyl((3R,4S)-1-(3-amino-2-chloro-5-cyanophenyl)-3-fluoropiperidin-4-yl)carbamate was prepared from tert-butyl(3-((3R,4S)-4-(((benzyloxy) carbonyl) amino)-3-fluoropiperidin-1-yl)-2-chloro-5-cyanophenyl) carbamate using the methods described in Example 1D.

MS (ESI) m/z 403

$^1$H NMR (400 MHz, DMSO-d$_6$) δ 7.55 (d, J=7.5 Hz, 1H), 7.41-7.29 (m, 5H), 6.84 (d, J=2.0 Hz, 1H), 6.70 (d, J=2.0 Hz, 1H), 5.81 (s, 2H), 5.06 (s, 2H), 4.90-4.67 (m, 1H), 3.83-3.60 (m, 1H), 3.54-3.39 (m, J=11.2 Hz, 1H), 3.13-2.90 (m, 1H), 2.75 (t, J=10.7 Hz, 1H), 2.58-2.53 (m, 1H), 1.98-1.88 (m, 1H), 1.68 (d, J=12.8 Hz, 1H)

Example 283

Benzyl((3R,4S)-1-(3-amino-2-chloro-5-cyanophenyl)-3-fluoropiperidin-4-yl)carbamate (75 mg, 0.186 mmol), 4-(cyclopropyl(4-methoxybenzyl)amino)-2-(methylsulfonyl)imidazo[2,1-f][1,2,4]triazine-7-carbonitrile (96 mg, 0.242 mmol, Intermediate 2), and Cs$_2$CO$_3$ (182 mg, 0.559 mmol) in DMF were heated at 70° C. for 3 h. The reaction mixture was diluted with water and a white solid crashed out. The solid was collected by vacuum filtration, rinsing with water, and dried under vacuum overnight. The material was taken up in DCE (2 mL) and anisole (0.041 mL, 0.372 mmol) was added, followed by TFA (0.574 mL, 7.45 mmol). The reaction was stirred at rt overnight. The reaction was heated at 50° C. for 1 h to deprotect the remaining starting material; a mixture of the Cbz-protected and deprotected product was detected. The solvent was removed in vacuo and the material was dissolved in MeOH. The solution was loaded onto an SCX column (5 g, benzenesulfonic acid sorbent) and rinsed with MeOH, then 7N NH$_3$/MeOH to release the product. The material was purified by flash column chromatography, eluting with 0-70% EtOAc/Hex, then switching to 20% (2N NH$_3$/MeOH)/DCM to recover the Cbz-deprotected product. The SCX column and silica-gel column were flushed with 1:1 DMF/MeOH to obtain additional material, which was purified by preparative HPLC. The fractions were concentrated and azeotroped 3× with toluene. The material from the flash column and preparative HPLC purifications were combined and triturated with MeOH to provide 13 mg of product. The material was dissolved in 1 ml of 1:1 CH$_3$CN/H$_2$O and 1M HCl in water (26 µL, 26 µmol) was added. The material was frozen in a dry ice bath and lyopholized overnight. 2-((3-((3R,4S)-4-amino-3-fluoropiperidin-1-yl)-2-chloro-5-cyanophenyl)amino)-4-(cyclopropylamino)imidazo[2,1-f][1,2,4]triazine-7-carbonitrile, HCl (11.6 mg) was isolated.

MS (ESI) m/z 467

$^1$H NMR (400 MHz, DMSO-d$_6$) δ 9.34 (d, J=5.5 Hz, 1H), 8.88 (s, 1H), 8.20 (s, 1H), 8.11 (d, J=2.0 Hz, 1H), 7.90 (br. s, 2H), 7.34 (d, J=2.0 Hz, 1H), 5.09-4.82 (m, 1H), 3.65 (t, J=14.1 Hz, 1H), 3.57-3.41 (m, J=7.7 Hz, 1H), 3.24-3.07 (m, 2H), 2.97 (tt, J=7.5, 4.8 Hz, 1H), 2.86 (t, J=11.6 Hz, 1H), 2.15-1.77 (m, 2H), 0.85-0.74 (m, 4H)

Example 284

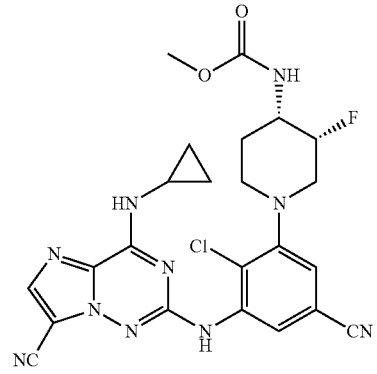 [SMILES: COC(=O)N[C@H]1CCN(c2cc(C#N)cc(Nc3nc(NC4CC4)c4ncc(C#N)n4n3)c2Cl)C[C@H]1F]

methyl((3R,4S)-1-(2-chloro-5-cyano-3-((7-cyano-4-(cyclopropylamino)imidazo[2,1-f][1,2,4]triazin-2-yl) amino)phenyl)-3-fluoropiperidin-4-yl)carbamate, HCl (284A): (3R,4S)-tert-butyl 4-amino-3-fluoropiperidine-1-carboxylate (100 mg, 0.458 mmol) was dissolved in DCM (5 mL) and Et$_3$N (0.128 mL, 0.916 mmol) was added, followed by dropwise addition of dimethyldicarbonate (92 mg, 0.687 mmol). The reaction was stirred at rt for 1 h. The solvent was removed in vacuo and the material purified by flash column chromatography, eluting with 0-4% MeOH/DCM. (3R,4S)-tert-butyl 3-fluoro-4-((methoxycarbonyl)amino)piperidine-1-carboxylate (135 mg) was obtained as a colorless gum.

MS (ESI) m/z 299 (M+Na).

$^1$H NMR (500 MHz, CHLOROFORM-d) δ ppm 4.96 (br. s., 1H), 4.82-4.57 (m, 1H), 4.55-4.06 (m, 2H), 3.90-3.72 (m, 1H), 3.70 (s, 3H), 3.11-2.62 (m, 2H), 1.86-1.69 (m, 2H), 1.47 (s, 9H)

(284B): (3R,4S)-tert-butyl 3-fluoro-4-((methoxycarbonyl)amino)piperidine-1-carboxylate (127 mg, 0.460 mmol) was taken up in DCM (5 mL) and TFA (0.708 mL, 9.19 mmol) was added. The reaction was stirred at rt for 1 h. The solvent was removed in vacuo and the material was dissolved in MeOH. The solution was loaded onto an SCX column (5 g, benzenesulfonic acid sorbent) and the column was rinsed with MeOH, followed by 7N NH$_3$/MeOH to obtain the product. The solvent was removed in vacuo to obtain methyl((3R,4S)-3-fluoropiperidin-4-yl)carbamate (113.5 mg) as a colorless gum. The crude material was taken onto the next step without further purification.

MS (ESI) m/z 177 (M+H).

$^1$H NMR (400 MHz, CHLOROFORM-d) δ ppm 5.10 (d, J=8.4 Hz, 1H), 4.94-4.71 (m, 1H), 4.00-3.80 (m, 1H), 3.71 (s, 3H), 3.59 (t, J=12.4 Hz, 1H), 3.40 (d, J=12.8 Hz, 1H), 3.17-2.98 (m, 1H), 2.91 (ddd, J=12.9, 8.0, 7.0 Hz, 1H), 2.02-1.87 (m, 2H)

(284C): Tert-butyl(3-bromo-2-chloro-5-cyanophenyl)carbamate (90 mg, 0.271 mmol, Intermediate 1), methyl((3R,4S)-3-fluoropiperidin-4-yl)carbamate (62.2 mg, 0.353 mmol), Pd$_2$(dba)$_3$ (24.85 mg, 0.027 mmol), BINAP (16.90 mg, 0.027 mmol), Cs$_2$CO$_3$ (265 mg, 0.814 mmol), and toluene (1 mL) were combined in a 2 dram vial. The vial was evacuated and backfilled with argon, and the reaction was heated at 110° C. overnight. The reaction was cooled to rt and diluted with EtOAc. The solution was filtered through celite, rinsing with EtOAc, and the filtrate was concentrated in vacuo. The material was purified by flash column chromatography 0-30% EtOAc/Hex to obtain 58 mg of the intermediate. The material was taken up in 1 ml DCM and TFA (0.418 mL, 5.43 mmol) was added. The reaction was stirred at rt for 1 h. The solvent was removed in vacuo and the material was taken up in MeOH. The solution was loaded onto an SCX column (2 g, benzenesulfonic acid sorbent) and rinsed with MeOH, then 7N NH$_3$/MeOH solution to obtain the product. Methyl((3R,4S)-1-(3-amino-2-chloro-5-cyanophenyl)-3-fluoropiperidin-4-yl)carbamate(methyl((3R,4S)-1-(3-amino-2-chloro-5-cyanophenyl)-3-fluoropiperidin-4-yl)carbamate (29 mg) was obtained as an orange solid.

MS (ESI) m/z 327 (M+H).

$^1$H NMR (400 MHz, CHLOROFORM-d) δ ppm 6.76 (d, J=1.8 Hz, 1H), 6.68 (d, J=1.8 Hz, 1H), 5.08 (d, J=7.9 Hz, 1H), 4.90-4.67 (m, 1H), 4.35 (br. s., 2H), 4.00-3.78 (m, 1H), 3.77-3.60 (m, 4H), 3.45-3.34 (m, 1H), 3.07-2.88 (m, 1H), 2.87-2.72 (m, 1H), 2.16-1.99 (m, 1H), 1.96-1.84 (m, 1H)

Example 284

4-(cyclopropyl(4-methoxybenzyl)amino)-2-(methylsulfonyl)imidazo[2,1-f][1,2,4]triazine-7-carbonitrile (30 mg, 0.075 mmol, Intermediate 2), methyl((3R,4S)-1-(3-amino-2-chloro-5-cyanophenyl)-3-fluoropiperidin-4-yl)carbamate (29.0 mg, 0.089 mmol), and Cs$_2$CO$_3$ (73.6 mg, 0.226 mmol) in DMF (1 mL) were heated at 80° C. for 4 h. The reaction was diluted with EtOAc and washed 2× with water and once with brine. The organic layer was dried over Na$_2$SO$_4$, filtered, and concentrated in vacuo. The crude material was purified by flash column chromatography, eluting with 0-50% EtOAc/Hex. 43 mg of the intermediate was obtained. The material was taken up in DCE (2 mL) and anisole (0.016 mL, 0.151 mmol) was added, followed by the addition of TFA (0.116 mL, 1.506 mmol). The reaction was stirred at rt overnight. The solvent was removed in vacuo and the material was taken up in MeOH. The solution was loaded onto an SCX column (5 g, benzenesulfonic acid sorbent) and rinsed with MeOH, then 7N NH$_3$/MeOH solution to recover the product. The product was purified by flash column chromatography, eluting with 0-2.5% MeOH/DCM. The material was repurified by preparative HPLC. The fractions were combined and concentrated, then the material was taken up in EtOAc, and washed with sat'd NaHCO$_3$. The organic layer was dried over Na$_2$SO$_4$, filtered, and concentrated to give 6.4 mg of product. The material was converted to the HCl salt by suspending it in 1 ml 1:1 ACN/H$_2$O and adding aq. 1N HCl (12.2 µL, 12.2 µmol). The solution was frozen in a dry ice bath and lyopholized overnight. Methyl ((3R,4S)-1-(2-chloro-5-cyano-3-((7-cyano-4-(cyclopropylamino)imidazo[2,1-f][1,2,4]triazin-2-yl)amino)phenyl)-3-fluoropiperidin-4-yl)carbamate, HCl (6.0 mg) was obtained as an off-white solid.

MS (ESI) m/z 525

$^1$H NMR (400 MHz, DMSO-d$_6$) δ 9.32 (br. s., 1H), 8.84 (br. s., 1H), 8.19 (br. s., 1H), 8.10 (br. s., 1H), 7.43 (br. s., 1H), 7.32 (br. s., 1H), 4.99-4.63 (m, 1H), 3.83-3.65 (m, 1H), 3.64-3.37 (m, 5H), 3.15-3.03 (m, 1H), 3.01-2.78 (m, 2H), 2.15-1.85 (m, 1H), 1.70 (br. s., 1H), 0.78 (br. s., 4H)

The compounds listed below were prepared by the similar synthetic procedure used for Example 284

TABLE 9

| Example No. | Structure | Name | [M + H]$^+$ | HPLC Retention Time (min.)* |
|---|---|---|---|---|
| 285 | Chiral | methyl ((3S,4R)-1-(2-chloro-5-cyano-3-((7-cyano-4-(cyclopropylamino)imidazo[2,1-f][1,2,4]triazin-2-yl)amino)phenyl)-3-fluoro-4-piperidinyl)carbamate | 524.95 | 3.57 |

TABLE 9-continued

| Example No. | Structure | Name | [M + H]+ | HPLC Retention Time (min.)* |
|---|---|---|---|---|
| 286 | 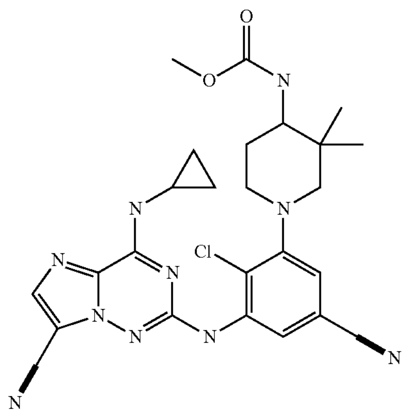 | methyl (1-(2-chloro-5-cyano-3-((7-cyano-4-(cyclopropyl-amino)imidazo[2,1-f][1,2,4]triazin-2-yl)amino)phenyl)-3,3-dimethyl-4-piperidinyl)carbamate | 535.01 | 3.78 |
| 287 | Chiral | methyl ((3R,4R)-1-(2-chloro-5-cyano-3-((7-cyano-4-(cyclopropylamino)imidazo[2,1-f][1,2,4]triazin-2-yl)amino)phenyl)-4-(fluoromethyl)-3-pyrrolidinyl)carbamate | 524.95 | 4.80 |
| 288 | Chiral | methyl ((3S,4S)-1-(2-chloro-5-cyano-3-((7-cyano-4-(cyclopropylamino)imidazo[2,1-f][1,2,4]triazin-2-yl)amino)phenyl)-4-methoxy-3-pyrrolidinyl)carbamate | 522.96 | 4.73 |
| 289 | Chiral | N-((3S,4R)-1-(2-chloro-5-cyano-3-((7-cyano-4-(cyclopropylamino)imidazo[2,1-f][1,2,4]triazin-2-yl)amino)phenyl)-4-methoxy-3-pyrrolidinyl)methanesulfonamide | 543.01 | 4.82 |

TABLE 9-continued

| Example No. | Structure | Name | [M + H]+ | HPLC Retention Time (min.)* |
|---|---|---|---|---|
| 290 | 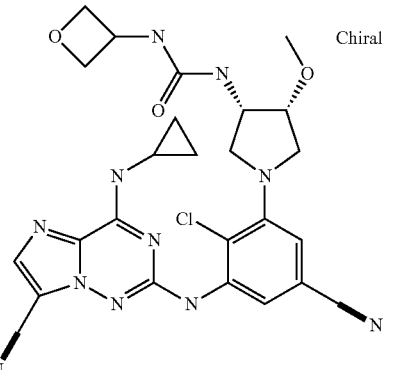 Chiral | 1-((3S,4R)-1-(2-chloro-5-cyano-3-((7-cyano-4-(cyclopropylamino)imidazo[2,1-f][1,2,4]triazin-2-yl)amino)phenyl)-4-methoxy-3-pyrrolidinyl)-3-(3-oxetanyl)urea | 564.01 | 4.79 |
| 291 | 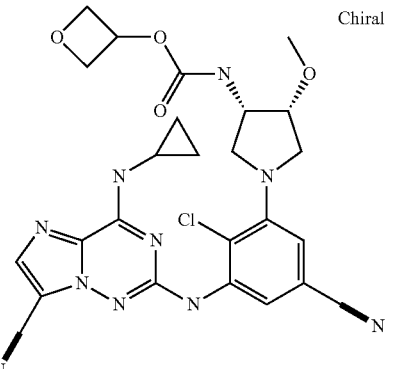 Chiral | 3-oxetanyl ((3S,4R)-1-(2-chloro-5-cyano-3-((7-cyano-4-(cyclopropylamino)imidazo[2,1-f][1,2,4]triazin-2-yl)amino)phenyl)-4-methoxy-3-pyrrolidinyl)carbamate | 564.99 | 4.51 |
| 292 | 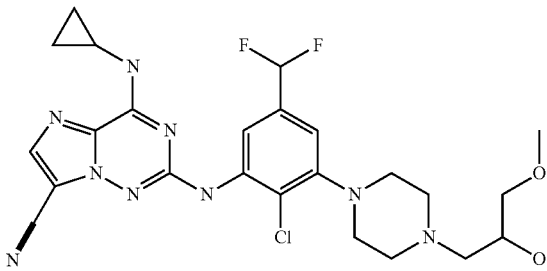 | (+/−) methyl ((3S,4S)-1-(2-chloro-5-cyano-3-((7-cyano-4-(cyclopropylamino)imidazo[2,1-f][1,2,4]triazin-2-yl)amino)phenyl)-4-ethyl-3-pyrrolidinyl)carbamate | 520.98 | 4.69 |
| 293 | 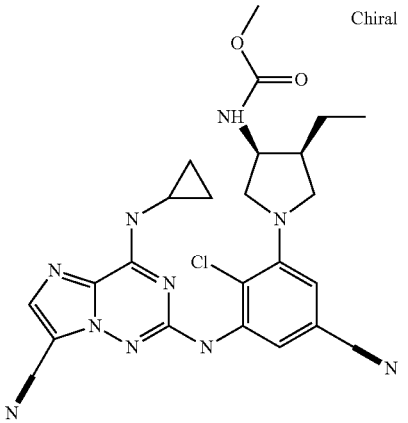 Chiral | methyl ((3S,4S)-1-(2-chloro-5-cyano-3-((7-cyano-4-(cyclopropylamino)imidazo[2,1-f][1,2,4]triazin-2-yl)amino)phenyl)-4-methyl-3-pyrrolidinyl)carbamate | 506.96 | 4.79 |

TABLE 9-continued

| Example No. | Structure | Name | [M + H]+ | HPLC Retention Time (min.)* |
|---|---|---|---|---|
| 294 | 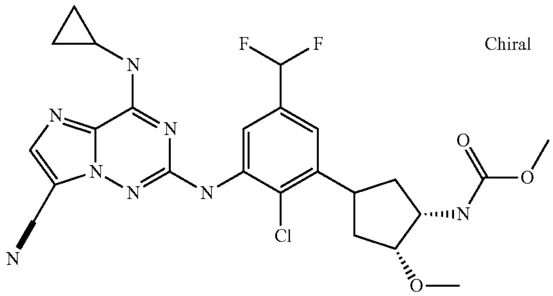 | methyl ((3R,4R)-1-(2-chloro-5-cyano-3-((7-cyano-4-(cyclopropylamino)imidazo[2,1-f][1,2,4]triazin-2-yl)amino)phenyl)-4-methyl-3-pyrrolidinyl)carbamate | 506.96 | 4.82 |
| 295 | 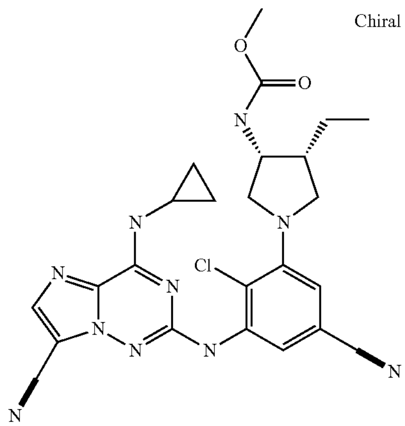 | methyl ((3S,5R)-1-(2-chloro-5-cyano-3-((7-cyano-4-(cyclopropylamino)imidazo[2,1-f][1,2,4]triazin-2-yl)amino)phenyl)-5-hydroxy-3-piperidinyl)carbamate | 522.96 | 4.89 |
| 296 | 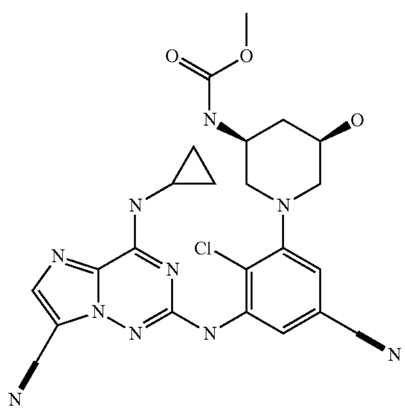 | (+/-) methyl ((3S,4R)-1-(2-chloro-5-cyano-3-((7-cyano-4-(cyclopropylamino)imidazo[2,1-f][1,2,4]triazin-2-yl)amino)phenyl)-3-ethyl-4-piperidinyl)carbamate | 535.01 | 4.32 |
| 297 | 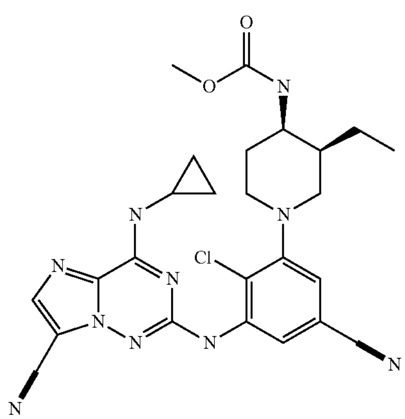 | (+/-) methyl ((3S,4S)-1-(1-(2-chloro-5-cyano-3-((7-cyano-4-(cyclopropylamino)imidazo[2,1-f][1,2,4]triazin-2-yl)amino)phenyl)-3-azetidinyl)-4-methoxy-3-pyrrolidinyl)carbamate | 578.03 | 4.83 |

TABLE 9-continued

| Example No. | Structure | Name | [M + H]+ | HPLC Retention Time (min.)* |
|---|---|---|---|---|
| 298 | 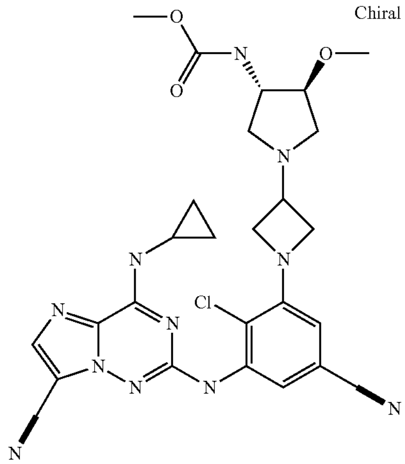 | methyl ((3S,4R)-1-(1-(2-chloro-5-cyano-3-((7-cyano-4-(cyclopropylamino)imidazo[2,1-f][1,2,4]triazin-2-yl)amino)phenyl)-3-azetidinyl)-4-methoxy-3-pyrrolidinyl)carbamate | 578.03 | 4.45 |
| 299 | 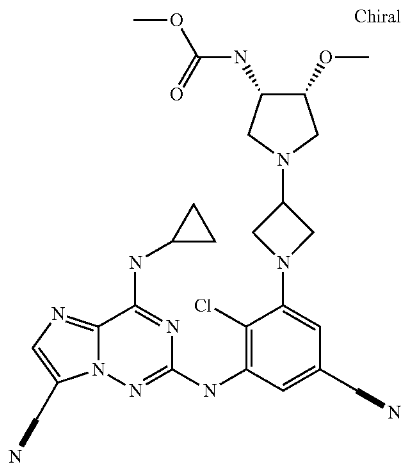 | methyl ((3S,4R)-1-(2-chloro-5-cyano-3-((7-cyano-4-(cyclopropylamino)imidazo[2,1-f][1,2,4]triazin-2-yl)amino)phenyl)-3-fluoro-4-piperidinyl)carbamate | 524.95 | 4.76 |

\* = HPLC conditions
YMC S5 ODS 4.6 × 50 mm, 10-90% aqueous methanol containing 0.2% $H_3PO_4$, 5 min. gradient, monitored at 220 nm

Example 300

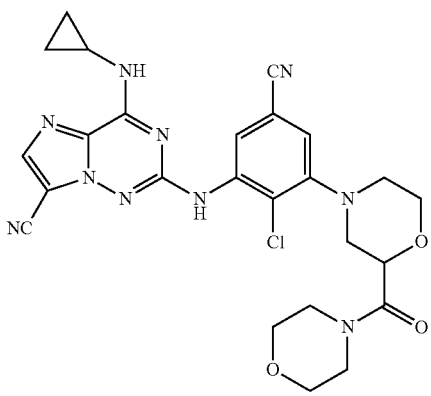 [SMILES: N#Cc1cc(Nc2nc(NC3CC3)c3ncc(C#N)n3n2)c(Cl)c(N2CCOC(C(=O)N3CCOCC3)C2)c1]

(+/−) 2-((2-chloro-5-cyano-3-(2-(morpholine-4-carbonyl)morpholino)phenyl)amino)-4-(cyclopropylamino)imidazo[2,1-f][1,2,4]triazine-7-carbonitrile (300A): To a round bottom flask charged with (+/−)-4-benzylmorpholine-2-carboxylic acid, HCl (0.5 g, 1.940 mmol) in dichloromethane (9.70 ml) was added Hünig's base (1.017 ml, 5.82 mmol), morpholine (0.203 ml, 2.328 mmol) and EDC (0.446 g, 2.328 mmol). The reaction mixture was stirred at rt ON. DMAP (tip), additional morpholine (1.164 ml, 2.328 mmol) and Hünig's base (1.017 ml, 5.82 mmol) were added and stirring continued for 16 h. The reaction mixture was poured into a separatory funnel containing 1:1 saturated aqueous sodium bicarbonate and dichloromethane. The aqueous layer was extracted with dichloromethane (2×). The combined organics were washed with brine, dried over anhydrous sodium sulfate, filtered and concentrated in vacuo. The crude material was purified by column chromatography on the Isco system (24 g, 0-20% (20% MeOH/$CH_2Cl_2$)/$CH_2Cl_2$. (4-Benzylmorpholin-2-yl)(morpholino)methanone (0.17 g) was isolated as an oil.

MS (ESI) m/z 292.2

$^1$H NMR (400 MHz, CHLOROFORM-d) δ 7.35-7.22 (m, 5H), 4.22 (dd, J=10.1, 2.6 Hz, 1H), 3.96-3.89 (m, 1H), 3.75-3.43 (m, 11H), 2.91 (dt, J=12.0, 2.1 Hz, 1H), 2.72-2.66 (m, 1H), 2.41 (dd, J=11.9, 10.1 Hz, 1H), 2.26 (td, J=11.5, 3.4 Hz, 1H)

(300B) To a round bottom flask charged with (4-benzylmorpholin-2-yl)(morpholino)methanone (0.17 g, 0.585 mmol) in DCE (1.952 ml) and cooled to 0° C. was added 1-chloroethyl chloroformate (0.082 ml, 0.761 mmol) dropwise. The reaction mixture was stirred at 0° C. 3 h and rt ON. The reaction mixture was concentrated in vacuo. Methanol (1.952 ml) was added and the reaction mixture was heated at 60° C. 2 h. The reaction mixture was cooled to rt and concentrated in vacuo. The crude residue was triturated with ether leaving a white solid. Morpholin-2-yl(morpholino) methanone, HCl (118 mg) was isolated as a white solid.

$^1$H NMR (400 MHz, METHANOL-$d_4$) δ 4.72 (dd, J=7.0, 3.7 Hz, 1H), 4.02-3.95 (m, 2H), 3.78-3.57 (m, 6H), 3.56-3.45 (m, 2H), 3.39-3.33 (m, 2H), 3.25 (dt, J=13.0, 3.9 Hz, 1H), 3.19-3.08 (m, 1H)

(300C): The compound was prepared starting from morpholin-2-yl(morpholino)methanone, HCl (0.118 g, 0.499 mmol), using procedure for Example 1A. After flash chromatography on silica gel using an automated ISCO system (24 g column, eluting with 0-100% ethyl acetate/dichloromethane), tert-butyl(2-chloro-5-cyano-3-(2-(morpholine-4-carbonyl)morpholino)phenyl)carbamate (90.9 mg) was isolated as a yellow glass.

MS (ESI) m/z 451.3 (M+H)

(300D): To a round bottom flask charged with tert-butyl (2-chloro-5-cyano-3-(2-(morpholine-4-carbonyl)morpholino)phenyl)carbamate (91 mg, 0.202 mmol) was added dichloromethane (1076 µl) and TFA (269 µl). The reaction mixture was stirred at rt 3 h. Excess TFA was removed by concentration in vacuo. The crude residue was free based using a Phenomenex Strata 1 g SCX column. The column was flushed with 3 column volumes methanol and 3 column volumes 3.5 N ammonia/methanol. The ammonia layers were concentrated in vacuo to provide 3-amino-4-chloro-5-(2-(morpholine-4-carbonyl)morpholino)benzonitrile (68 mg, 0.194 mmol, 96%)

MS (ESI) m/z 351.1 (M+H)

$^1$H NMR (400 MHz, CHLOROFORM-d) δ 6.79 (d, J=1.8 Hz, 1H), 6.74 (d, J=1.8 Hz, 1H), 4.44-4.32 (m, 3H), 4.09-4.02 (m, 1H), 3.86 (td, J=11.2, 2.4 Hz, 1H), 3.78-3.65 (m, 6H), 3.59-3.50 (m, 2H), 3.40 (dt, J=12.2, 2.3 Hz, 1H), 3.16 (dd, J=11.7, 1.5 Hz, 1H), 3.03 (dd, J=12.2, 10.0 Hz, 1H), 2.92 (td, J=11.6, 3.1 Hz, 1H)

(300E): A mixture of 4-(cyclopropyl(4-methoxybenzyl) amino)-2-(methylsulfonyl)imidazo[2,1-f][1,2,4]triazine-7-carbonitrile (38.6 mg, 0.097 mmol), 3-amino-4-chloro-5-(2-(morpholine-4-carbonyl)morpholino)benzonitrile (34 mg, 0.097 mmol) and $Cs_2CO_3$ (63.2 mg, 0.194 mmol) in DMF (692 µl) was heated at 50° C. for 4 h. After cooling to rt ON, the reaction mixture was transferred to a separatory funnel containing ethyl acetate and saturated aqueous sodium bicarbonate. The aqueous layer was extracted with ethyl acetate (3×). The combined organics were washed with 10% lithium chloride solution, dried over anhydrous sodium sulfate, filtered and concentrated in vacuo. Material carried forward as is.

MS (ESI) m/z 669.5 (M+H)

Example 300

To a round bottom flask charged with 2-((2-chloro-5-cyano-3-(2-(morpholine-4-carbonyl)morpholino)phenyl) amino)-4-(cyclopropyl(4-methoxybenzyl)amino)imidazo[2,1-f][1,2,4]triazine-7-carbonitrile (64.9 mg, 0.097 mmol) in dichloromethane (485 µl) was added anisole (21.19 µl, 0.194 mmol), followed by TFA (224 µl, 2.91 mmol). The reaction mixture was stirred at rt ON. Additional TFA (224 µl, 2.91 mmol) was added. Stir at rt ON. Additional TFA (224 µl, 2.91 mmol) was added and the reaction mixture was stirred at rt ON. Excess TFA was removed by concentration in vacuo. The crude residue was taken up in methanol and free based using a Phenomenex Strata 1 g SCX column. The column was flushed with 3 column volumes methanol and 3 column volumes 3.5 N ammonia/methanol. The ammonia layers were concentrated in vacuo. The crude material was purified by neutral phase preparatory LC/MS chromatography to provide (+/−)2-((2-chloro-5-cyano-3-(2-(morpholine-4-carbonyl)morpholino)phenyl)amino)-4-(cyclopropylamino)imidazo[2,1-f][1,2,4]triazine-7-carbonitrile (13 mg).

MS (ESI) m/z 549.2 (M+H)

$^1$H NMR (500 MHz, DMSO-$d_6$) δ 9.35 (d, J=4.5 Hz, 1H), 8.93 (s, 1H), 8.20 (s, 1H), 8.13 (d, J=1.5 Hz, 1H), 7.38 (d, J=2.0 Hz, 1H), 4.46 (dd, J=9.9, 2.5 Hz, 1H), 4.05 (s, 2H), 3.97 (d, J=10.4 Hz, 1H), 3.84-3.76 (m, 1H), 3.66-3.50 (m, 6H), 3.16 (d, J=11.4 Hz, 1H), 3.00-2.90 (m, 3H), 0.82-0.73 (m, 4H)

Example 301

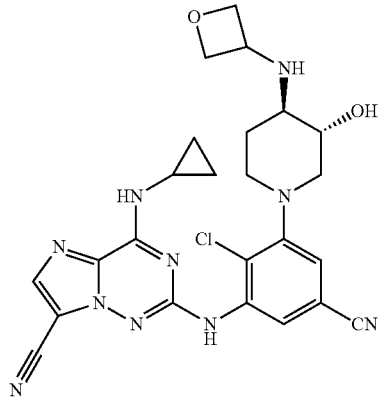 [SMILES: N#Cc1cc(Nc2nc(NC3CC3)c3ncc(C#N)n3n2)c(Cl)c(N2CC[C@@H](NC3COC3)[C@H](O)C2)c1]

(+/−)2-((2-chloro-5-cyano-3-((3R,4R)-3-hydroxy-4-(oxetan-3-ylamino)piperidin-1-yl)phenyl)amino)-4-(cyclopropylamino)imidazo[2,1-f][1,2,4]triazine-7-carbonitrile, HCl (301A): (+/−)2-((3-((3R,4R)-4-amino-3-((tert-butyldimethylsilyl)oxy)piperidin-1-yl)-2-chloro-5-cyanophenyl) amino)-4-(cyclopropylamino)imidazo[2,1-f][1,2,4]triazine-7-carbonitrile (Example 171C)(60 mg, 0.104 mmol) was taken up in MeOH (1 mL) and THF (1 mL) and trimethyl orthoformate (0.859 mL, 7.77 mmol), AcOH (0.024 mL, 0.414 mmol), and oxetan-3-one (0.066 mL, 1.036 mmol) were added. The reaction was stirred at rt for 2 h, then $NaCNBH_4$ (65.1 mg, 1.036 mmol) was added and the reaction was stirred at rt overnight. The reaction mixture was diluted with EtOAc and washed with sat'd $NaHCO_3$, then brine. The organic layer was dried over $Na_2SO_4$, filtered, and concentrated. The material was purified by flash column chromatography, eluting with 0-3% MeOH/DCM. (+/−)-2-((3-((3R,4R)-3-((tert-butyldimethylsilyl)oxy)-4-(oxetan-3-ylamino)piperidin-1-yl)-2-chloro-5-cyanophenyl)amino)-4-(cyclopropylamino) imidazo[2,1-f][1,2,4]triazine-7-carbonitrile (30 mg) was obtained as a white foam.

MS (ESI) m/z 635

$^1$H NMR (400 MHz, CHLOROFORM-d) δ 8.77 (d, J=2.0 Hz, 1H), 7.86 (s, 1H), 7.59 (s, 1H), 6.98 (d, J=2.0 Hz, 1H), 6.90-6.84 (m, 1H), 4.87 (dt, J=12.9, 6.5 Hz, 2H), 4.51-4.39

(m, 2H), 4.21-4.05 (m, 2H), 3.76-3.69 (m, 1H), 3.45-3.36 (m, 1H), 3.30-3.18 (m, 1H), 3.09-3.01 (m, 1H), 2.81-2.69 (m, 1H), 2.59-2.39 (m, 2H), 1.98-1.87 (m, 1H), 1.64-1.53 (m, 1H), 1.15-1.05 (m, 2H), 0.94 (s, 9H), 0.86-0.74 (m, 2H), 0.19 (s, 3H), 0.14 (s, 3H).

Example 301

(+/+2-((3-((3R,4R)-3-((tert-butyldimethylsilyl)oxy)-4-(oxetan-3-ylamino)piperidin-1-yl)-2-chloro-5-cyanophenyl)amino)-4-(cyclopropylamino) imidazo[2,1-f][1,2,4]triazine-7-carbonitrile (30 mg, 0.047 mmol) was taken up in THF (1 mL) and TBAF (0.057 mL, 0.057 mmol) was added. The reaction was stirred at rt for 5 h. The solvent was removed in vacuo and the material was purified by flash column chromatography, eluting with 0-10% MeOH/DCM. The fractions were concentrated and the material was repurified by preparative HPLC to provide 13.4 mg of product. The material was taken up in 1 ml of 1:1 ACN/H$_2$O and 1N HCl (0.026 mL, 0.026 mmol) was added. The solution was frozen in a dry ice bath and lyophilized overnight. (+/−)-2-((2-chloro-5-cyano-3-((3R,4R)-3-hydroxy-4-(oxetan-3-ylamino) piperidin-1-yl)phenyl)amino)-4-(cyclopropylamino)imidazo[2,1-f][1,2,4]triazine-7-carbonitrile, HCl (13.6 mg) was obtained as a white solid.

MS (ESI) m/z 521

$^1$H NMR (500 MHz, DMSO-d$_6$) δ 9.33 (d, J=4.4 Hz, 1H), 8.87 (s, 1H), 8.20 (s, 1H), 8.12 (d, J=1.9 Hz, 1H), 7.33 (d, J=1.9 Hz, 1H), 5.85 (br. s., 1H), 4.76-4.68 (m, 3H), 4.68-4.62 (m, 1H), 4.56 (br. s., 1H), 3.75 (br. s., 1H), 3.50-3.38 (m, 2H), 2.97 (dddd, J=11.6, 7.2, 4.4, 3.4 Hz, 2H), 2.75 (t, J=12.6 Hz, 1H), 2.56 (dd, J=11.4, 10.0 Hz, 1H), 1.97 (d, J=15.5 Hz, 1H), 1.67 (br. s., 1H), 0.81-0.76 (m, 4H).

Example 302

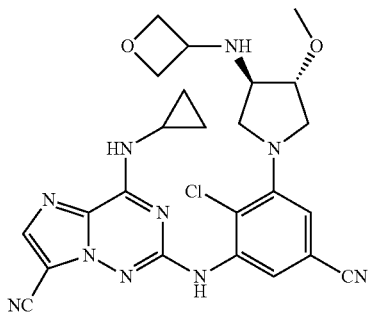 [SMILES: CO[C@@H]1CN(c2cc(C#N)cc(Nc3nc(NC4CC4)c4ncc(C#N)n4n3)c2Cl)C[C@H]1NC1COC1]

2-((2-chloro-5-cyano-3-((3R,4S)-3-methoxy-4-(oxetan-3-ylamino)pyrrolidin-1-yl)phenyl)amino)-4-(cyclopropylamino)imidazo[2,1-f][1,2,4]triazine-7-carbonitrile, HCl Prepared in similar manner as Example 301

MS (ESI) m/z 521

$^1$H NMR (500 MHz, DMSO-d$_6$) δ 9.27 (d, J=1.7 Hz, 1H), 8.73 (br. s., 1H), 8.18 (s, 1H), 7.77 (d, J=1.9 Hz, 1H), 7.00 (d, J=1.9 Hz, 1H), 4.72-4.58 (m, 2H), 4.35 (q, J=6.2 Hz, 2H), 4.03-3.91 (m, 1H), 3.75-3.70 (m, 1H), 3.70-3.59 (m, 1H), 3.38 (dd, J=11.1, 1.9 Hz, 1H), 3.35-3.31 (m, 2H), 3.30 (s, 4H), 3.04-2.96 (m, 1H), 2.45 (br. s., 1H), 0.78 (d, J=5.3 Hz, 4H).

Example 303

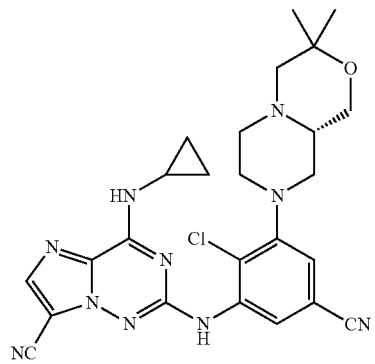 [SMILES: CC1(C)CN2CCN(c3cc(C#N)cc(Nc4nc(NC5CC5)c5ncc(C#N)n5n4)c3Cl)C[C@H]2CO1]

(S)-2-((2-chloro-5-cyano-3-(3,3-dimethylhexahydropyrazino[2,1-c][1,4]oxazin-8(1H)-yl)phenyl)amino)-4-(cyclopropylamino)imidazo[2,1-f][1,2,4]triazine-7-carbonitrile, HCl (303A): To a round bottom flask charged with (S)-tert-butyl 3-(hydroxymethyl)piperazine-1-carboxylate (0.5 g, 2.312 mmol) in DMF (2.167 ml) was added sodium bicarbonate (0.388 g, 4.62 mmol). The reaction mixture was heated at 70° C., at which point a solution of 3-bromo-2-methylpropene (0.350 ml, 3.47 mmol) in DMF (0.722 ml) was added dropwise over 30 min with an addition funnel. After stirring at room temperature for 16 h, the reaction mixture was transferred to a separatory funnel containing water and ether. The aqueous layer was extracted with ether (2×). The combined organics were washed with 10% lithium chloride solution, dried over anhydrous sodium sulfate, filtered and concentrated in vacuo. Material used crude in subsequent chemistry.

$^1$H NMR (400 MHz, CHLOROFORM-d) δ 4.91 (d, J=12.8 Hz, 1H), 3.78 (dd, J=11.3, 5.4 Hz, 1H), 3.69-3.55 (m, 2H), 3.51 (dd, J=11.4, 3.3 Hz, 1H), 3.37 (d, J=13.4 Hz, 2H), 3.23-3.11 (m, 1H), 2.81 (d, J=13.2 Hz, 2H), 2.48 (br. s., 2H), 2.21 (ddd, J=12.2, 8.6, 3.4 Hz, 1H), 1.75 (s, 3H), 1.47 (s, 9H)

(303B): To a round bottom flask charged with (S)-tert-butyl 3-(hydroxymethyl)-4-(2-methylallyl)piperazine-1-carboxylate (0.1 g, 0.370 mmol) in acetonitrile (3.70 ml) was added N-iodosuccinimide (0.125 g, 0.555 mmol) and potassium carbonate (0.077 g, 0.555 mmol). The reaction mixture was stirred at rt ON. The reaction mixture was quenched with 20% sodium thiosulfate solution and stirred 30 min. The mixture was transferred to a separatory funnel and extracted with ethyl acetate (3×). The combined organics were washed with brine, dried over anhydrous sodium sulfate, filtered and concentrated in vacuo. (9aS)-tert-butyl 3-(iodomethyl)-3-methylhexahydropyrazino[2,1-c][1,4]oxazine-8(1H)-carboxylate (0.156 g) was isolated as a yellow oil. Material used crude in subsequent chemistry.

(303C): (9aS)-tert-butyl 3-(iodomethyl)-3-methylhexahydropyrazino[2,1-c][1,4]oxazine-8(1H)-carboxylate (108 mg, 0.273 mmol) was taken up in DCM (3 mL) and TFA (0.42 mL, 5.45 mmol) was added. The reaction was stirred at rt for 1 h. The solvent was removed in vacuo and the material was taken up in MeOH. The solution was loaded onto an SCX column (5 g, benzenesulfonic acid sorbent) and rinsed with MeOH, then 7N NH$_3$/MeOH solution to release the product. The solvent was removed in vacuo give (9aS)-

3-(iodomethyl)-3-methyloctahydropyrazino[2,1-c][1,4]oxazine (79 mg) as an orange oil.

MS (ESI) m/z 297

¹H NMR (400 MHz, MeOD) δ 4.01 (d, J=10.8 Hz, 1H), 3.56-3.51 (m, 1H), 3.50-3.44 (m, 1H), 3.38-3.32 (m, 1H), 2.99-2.83 (m, 3H), 2.83-2.61 (m, 2H), 2.45-2.37 (m, 1H), 2.30 (d, J=11.9 Hz, 1H), 2.20 (tdd, J=8.5, 5.6, 3.7 Hz, 1H), 2.14-2.04 (m, 1H), 1.23 (s, 3H)

(303D): (9aS)-3-(iodomethyl)-3-methyloctahydropyrazino[2,1-c][1,4]oxazine (53 mg, 0.179 mmol) was dissolved in MeOH (5 ml) and Et₃N (0.037 mL, 0.268 mmol) was added. The flask was purged with Ar, and Pd/C (19.05 mg, 0.018 mmol) was added. A balloon with H₂ was attached and the flask was evacuated and filled with H₂ 3×. The reaction was stirred over the weekend. The reaction mixture was filtered through celite, rinsing with MeOH. The solvent was removed in vacuo to give (S)-3,3-dimethyloctahydropyrazino[2,1-c][1,4]oxazine (20 mg) as a yellow solid. The crude material was taken onto the next step.

MS (ESI) m/z 171

¹H NMR (400 MHz, CHLOROFORM-d) δ 5.10-4.90 (m, 1H), 3.58-3.41 (m, 2H), 3.31-3.15 (m, 1H), 3.14-2.94 (m, 2H), 2.77-2.69 (m, 1H), 2.55 (dd, J=12.1, 10.8 Hz, 1H), 2.49-2.29 (m, 3H), 2.14 (d, J=11.4 Hz, 1H), 1.34 (s, 3H), 1.17 (s, 3H)

(303E): (S)-tert-butyl(2-chloro-5-cyano-3-(3,3-dimethylhexahydropyrazino[2,1-c][1,4]oxazin-8(1H)-yl)phenyl)carbamate was prepared from (S)-3,3-dimethyloctahydropyrazino[2,1-c][1,4]oxazine using the method described in Example 1G.

MS (ESI) m/z 421

¹H NMR (400 MHz, CHLOROFORM-d) δ 8.33-8.24 (m, 1H), 7.18 (s, 1H), 6.96 (d, J=1.8 Hz, 1H), 3.91 (br. s, 1H), 3.60-3.46 (m, 2H), 3.29-3.17 (m, 1H), 3.11-3.01 (m, 1H), 2.99-2.85 (m, 1H), 2.80-2.71 (m, 1H), 2.59-2.44 (m, 2H), 2.44-2.30 (m, 1H), 2.15 (d, J=11.2 Hz, 1H), 1.58-1.49 (m, 9H), 1.37 (s, 3H), 1.19 (s, 3H)

(303F): (S)-tert-butyl(2-chloro-5-cyano-3-(3,3-dimethylhexahydropyrazino[2,1-c][1,4]oxazin-8(1H)-yl)phenyl)carbamate (87 mg, 0.207 mmol) was taken up in DCM (2 mL) and cooled to 0° C. 2,6-Lutidine (0.072 mL, 0.620 mmol) was added, followed by dropwise addition of trimethylsilyl trifluoromethanesulfonate (0.112 mL, 0.620 mmol). The reaction was stirred at 0° C. for 30 min, then warmed to rt and stirred for 30 min. The solvent was removed in vacuo and the material was purified by flash column chromatography, eluting with 0-2% (2N NH₃/MeOH)/DCM. (S)-3-amino-4-chloro-5-(3,3-dimethylhexahydropyrazino[2,1-c][1,4]oxazin-8(1H)-yl)benzonitrile (22 mg) was obtained as a yellow glass.

MS (ESI) m/z 321 (M+H)

¹H NMR (400 MHz, CHLOROFORM-d) δ 6.74 (d, J=2.0 Hz, 1H), 6.66 (d, J=1.8 Hz, 1H), 4.34 (s, 2H), 3.60-3.44 (m, 2H), 3.30-3.21 (m, 1H), 3.13-3.06 (m, 1H), 2.94-2.85 (m, 1H), 2.80-2.68 (m, 1H), 2.57-2.34 (m, 4H), 2.15 (d, J=11.2 Hz, 1H), 1.37 (s, 3H), 1.19 (s, 3H)

(303G): (S)-2-((2-chloro-5-cyano-3-(3,3-dimethylhexahydropyrazino[2,1-c][1,4]oxazin-8(1H)-yl)phenyl)amino)-4-(cyclopropyl(4-methoxybenzyl)amino) imidazo[2,1-f][1,2,4]triazine-7-carbonitrile was prepared from (S)-3-amino-4-chloro-5-(3,3-dimethylhexahydropyrazino[2,1-c][1,4]oxazin-8(1H)-yl)benzonitrile using the method described in Example 1.

MS (ESI) m/z 639

¹H NMR (400 MHz, CHLOROFORM-d) δ 8.78 (br. s., 1H), 7.93 (s, 1H), 7.58-7.47 (m, 1H), 7.19 (d, J=8.6 Hz, 2H), 6.96 (d, J=1.8 Hz, 1H), 6.88-6.81 (m, 2H), 5.70 (s, 2H), 3.78 (s, 3H), 3.64-3.44 (m, 2H), 3.32-3.20 (m, 1H), 3.14-3.03 (m, 1H), 3.03-2.86 (m, 2H), 2.85-2.72 (m, 1H), 2.59-2.47 (m, 3H), 2.47-2.34 (m, 1H), 2.18 (d, J=11.2 Hz, 1H), 1.39 (s, 3H), 1.21 (s, 3H), 1.18-1.09 (m, 2H), 0.98-0.85 (m, 2H)

Example 303

(S)-2-((2-chloro-5-cyano-3-(3,3-dimethylhexahydropyrazino[2,1-c][1,4]oxazin-8(1H)-yl)phenyl)amino)-4-(cyclopropylamino)imidazo[2,1-f][1,2,4]triazine-7-carbonitrile, HCl was prepared from (S)-2-((2-chloro-5-cyano-3-(3,3-dimethylhexahydropyrazino[2,1-c][1,4]oxazin-8(1H)-yl)phenyl)amino)-4-(cyclopropyl(4-methoxybenzyl)amino) imidazo[2,1-f][1,2,4]triazine-7-carbonitrile using the method described in Example 1

MS (ESI) m/z 519

¹H NMR (400 MHz, DMSO-d₆) δ 9.41-9.19 (m, 1H), 8.84 (br. s, 1H), 8.19 (s, 1H), 8.09 (d, J=1.8 Hz, 1H), 7.32 (d, J=2.0 Hz, 1H), 3.53-3.36 (m, 2H), 3.27 (d, J=1.8 Hz, 1H), 3.10 (d, J=10.8 Hz, 1H), 3.03-2.93 (m, 1H), 2.93-2.82 (m, 1H), 2.75 (dd, J=8.8, 2.4 Hz, 1H), 2.64-2.53 (m, 2H), 2.37-2.25 (m, 1H), 2.26-2.12 (m, 1H), 1.99 (d, J=11.0 Hz, 1H), 1.29 (s, 3H), 1.10 (s, 3H), 0.78 (d, J=5.7 Hz, 4H)

Example 304

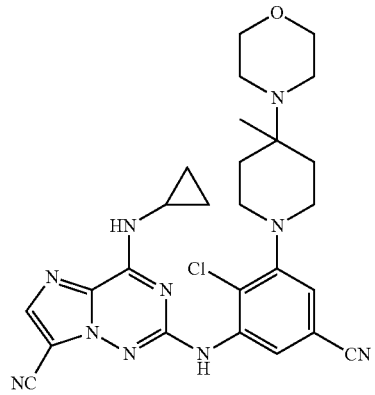 [SMILES: CC1(N2CCOCC2)CCN(c2cc(C#N)cc(Nc3nc(NC4CC4)c4ncc(C#N)n4n3)c2Cl)CC1]

2-((2-chloro-5-cyano-3-(4-methyl-4-morpholinopiperidin-1-yl)phenyl)amino)-4-(cyclopropylamino) imidazo[2,1-f][1,2,4]triazine-7-carbonitrile, HCl Prepared using similar procedure as example 303

MS (ESI) m/z 533

¹H NMR (400 MHz, DMSO-d₆) δ 9.83-9.65 (m, 1H), 9.41-9.28 (m, 1H), 8.88 (s, 1H), 8.20 (s, 1H), 8.11 (d, J=1.8 Hz, 1H), 7.38 (d, J=0.9 Hz, 1H), 4.01 (d, J=11.9 Hz, 2H), 3.80 (t, J=12.0 Hz, 2H), 3.44 (d, J=11.4 Hz, 4H), 3.21-3.06

(m, J=11.9 Hz, 2H), 3.03-2.82 (m, J=16.1, 16.1 Hz, 3H), 2.15-1.86 (m, 4H), 1.41 (s, 3H), 0.78 (d, J=6.2 Hz, 4H)

Example 305

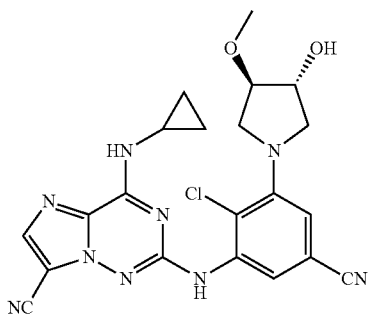 [SMILES: CO[C@@H]1CN(c2cc(C#N)cc(Nc3nc(NC4CC4)c4ncc(C#N)n4n3)c2Cl)C[C@H]1O]

(+/−)-2-((2-chloro-5-cyano-3-((3R,4R)-3-hydroxy-4-methoxypyrrolidin-1-yl)phenyl)amino)-4-(cyclopropylamino)imidazo[2,1-f][1,2,4]triazine-7-carbonitrile, HCl Prepared in similar manner as Example 171 from (+/−)-(3R,4R)-tert-butyl 3-hydroxy-4-methoxypyrrolidine-1-carboxylate.

MS (ESI) m/z 466

$^1$H NMR (400 MHz, DMSO-$d_6$) δ 9.28 (d, J=4.0 Hz, 1H), 8.73 (s, 1H), 8.19 (s, 1H), 7.82 (d, J=2.0 Hz, 1H), 7.06 (d, J=2.0 Hz, 1H), 5.26 (d, J=3.7 Hz, 1H), 4.18 (t, J=4.0 Hz, 1H), 3.82-3.65 (m, 3H), 3.30 (s, 3H), 3.28-3.22 (m, J=9.2 Hz, 1H), 3.13 (dd, J=10.6, 2.2 Hz, 1H), 2.99 (quin, J=5.6 Hz, 1H), 0.78 (d, J=5.3 Hz, 4H)

Example 306

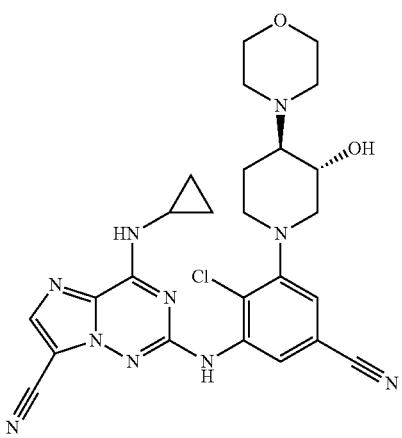 [SMILES: N#Cc1cc(Nc2nc(NC3CC3)c3ncc(C#N)n3n2)c(Cl)c(N2CC[C@@H](N3CCOCC3)[C@H](O)C2)c1]

(+/−)-2-((2-chloro-5-cyano-3-((3R,4R)-3-hydroxy-4-morpholinopiperidin-1-yl)phenyl)amino)-4-(cyclopropylamino)imidazo[2,1-f][1,2,4]triazine-7-carbonitrile (306A): A mixture of benzyl 7-oxa-3-azabicyclo[4.1.0]heptane-3-carboxylate (prepared according to a published literature procedure: Fink, Brian, et al., WO 2005/066176, 700 mg, 3.00 mmol), morpholine (0.581 mL, 6.00 mmol), and lithium perchlorate (639 mg, 6.00 mmol) in acetonitrile (10 mL) was heated at 80° C. for 4 h. Solvent was evaporated and the crude intermediate was dissolved in dichloromethane (10 mL), imidazole (654 mg, 9.60 mmol) and tert-butyldimethylchlorosilane (1357 mg, 9.00 mmol) were added. The reaction mixture was stirred at room temperature overnight. The reaction was diluted with dichloromethane and washed with water and brine, dried over sodium sulfate, filtered, and concentrated. The crude product was purified by flash chromatography on silica gel using an automated ISCO system (220 g gold column, eluting with 5-30% ethyl acetate/hexanes) to give (+/−)-(3R,4R)-benzyl 4-((tert-butyldimethylsilyl)oxy)-3-morpholinopiperidine-1-carboxylate (Isomer A, 0.39 g) as a colorless oil and (+/−)-(3R,4R)-benzyl 3-((tert-butyldimethylsilyl)oxy)-4-morpholinopiperidine-1-carboxylate (Isomer B, 0.43 g) as a colorless oil. The structures were confirmed by NMR studies ($^1$H-1D, $^{13}$C-1D, COSY, NOESY, dept-$^1$H-$^{13}$C-HSQC, $^1$H-$^{13}$C-HMBC).

Isomer A (+/−)-(3R,4R)-benzyl 4-((tert-butyldimethylsilyl)oxy)-3-morpholinopiperidine-1-carboxylate:

MS (ESI) m/z 435.5

$^1$H NMR (400 MHz, chloroform-d) δ 7.42-7.30 (m, 5H), 5.25-5.03 (m, 2H), 3.99 (td, J=5.5, 3.1 Hz, 1H), 3.77-3.44 (m, 8H), 2.77-2.44 (m, 4H), 2.22-2.06 (m, 1H), 2.06-1.96 (m, 1H), 1.44 (br. s., 1H), 0.92 (s, 9H), 0.10 (s, 3H), 0.09 (s, 3H).

Isomer B (+1-)-(3R,4R)-benzyl 3-((tert-butyldimethylsilyl)oxy)-4-morpholinopiperidine-1-carboxylate:

MS (ESI) m/z 435.5

$^1$H NMR (400 MHz, chloroform-d) δ 7.41-7.31 (m, 5H), 5.23-5.06 (m, 2H), 4.20-3.86 (m, 2H), 3.77-3.57 (m, 5H), 2.98 (br. s., 2H), 2.68-2.54 (m, 4H), 2.34 (ddd, J=10.3, 7.9, 3.9 Hz, 1H), 1.85 (br. s., 1H), 1.56-1.43 (m, 1H), 0.91 (s, 9H), 0.12 (br. s., 6H).

(306B): A mixture of (+/−)-(3R,4R)-benzyl 3-((tert-butyldimethylsilyl)oxy)-4-morpholinopiperidine-1-carboxylate (Isomer A, 0.43 g, 0.989 mmol) and Pd/C (0.063 g, 0.030 mmol) in methanol (20 mL) was hydrogenated at 30 psi overnight. The reaction mixture was filtered through a pad of Celite and the filtrate was concentrated in vacuo. (+/−)-4-((3R,4R)-3-((tert-butyldimethylsilyl)oxy)piperidin-4-yl)morpholine (278 mg) was obtained as a colorless oil. The crude was used without purification.

MS (ESI) m/z 301.3

(306C): A mixture of tert-butyl(3-bromo-2-chloro-5-cyanophenyl)carbamate (116 mg, 0.349 mmol), (+/−)-4-((3R,4R)-3-((tert-butyldimethylsilyl)oxy)piperidin-4-yl)morpholine (100 mg, 0.333 mmol), Pd$_2$dba$_3$ (9.14 mg, 9.98 μmol), 2,2'-bis(diphenylphosphino)-1,1'-binaphthyl (18.65 mg, 0.030 mmol), and cesium carbonate (217 mg, 0.666 mmol) in Dioxane (2 mL) was evacuated and filled with nitrogen three times and heated at 110° C. overnight. The reaction mixture was diluted with dichloromethane and filtered through Celite, the filtrate was concentrated and the crude product was purified by flash chromatography on silica gel using an automated ISCO system (24 g column, eluting with 5-25% ethyl acetate/hexanes).

(+/−)-tert-butyl(3-((3R,4R)-3-((tert-butyldimethylsilyl)oxy)-4-morpholinopiperidin-1-yl)-2-chloro-5-cyanophenyl)carbamate (138 mg) was obtained as a white solid MS (ESI) m/z 551.3

(306D): (+/−)-tert-butyl(3-((3R,4R)-3-((tert-butyldimethylsilyl)oxy)-4-morpholinopiperidin-1-yl)-2-chloro-5-cyanophenyl)carbamate (138 mg, 0.250 mmol) was treated with TFA (25% in 1,2-dichloroethane, 3 mL, 9.73 mmol) at room temperature for 1 h. The reaction mixture was diluted with dichloromethane and washed with cold saturated sodium bicarbonate/1N aqueous sodium hydroxide (pH 10). The layers were separated and aqueous layer was extracted with dichloromethane two more times. The combined organic layers were dried over magnesium sulfate, filtered and concentrated in vacuo, the crude product was purified by flash chromatography on silica gel using an automated ISCO system (24 g column, eluting with 5-40% ethyl acetate/hexanes). (+/−)-3-amino-5-((3R,4R)-3-((tert-butyldimethylsilyl)oxy)-4-morpholinopiperidin-1-yl)-4-chlorobenzonitrile (106 mg) was obtained as a yellow/brown solid.

MS (ESI) m/z 451.3

Example 306

The title compound was prepared from (+/−)-3-amino-5-((3R,4R)-3-((tert-butyldimethylsilyl)oxy)-4-morpholinopiperidin-1-yl)-4-chlorobenzonitrile using a method analogous to that used to prepare Example 171.

MS (ESI) m/z 535.3
$^1$H NMR (500 MHz, DMSO-d$_6$) δ 9.33 (d, J=4.4 Hz, 1H), 8.81 (s, 1H), 8.20 (s, 1H), 8.11 (d, J=1.9 Hz, 1H), 7.30 (d, J=1.7 Hz, 1H), 4.57 (d, J=3.9 Hz, 1H), 3.72 (tt, J=9.3, 4.6 Hz, 1H), 3.60 (t, J=4.4 Hz, 4H), 3.47-3.38 (m, 1H), 3.03-2.95 (m, 1H), 2.75-2.57 (m, 5H), 2.40-2.28 (m, 1H), 1.80 (dd, J=12.8, 3.3 Hz, 1H), 1.62 (qd, J=12.3, 4.0 Hz, 1H), 0.79 (d, J=5.3 Hz, 4H).

Example 307

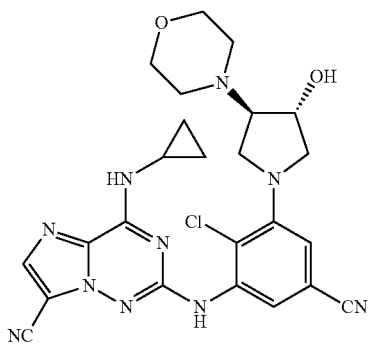 [SMILES: N#Cc1cc(Nc2nc(NC3CC3)c3ncc(C#N)n3n2)c(Cl)c(N2C[C@@H](O)[C@H](N3CCOCC3)C2)c1]

2-((2-chloro-5-cyano-3-((3R,4R)-3-hydroxy-4-(4-morpholinyl)-1-pyrrolidinyl)phenyl)amino)-4-(cyclopropylamino)imidazo[2,1-f][1,2,4]triazine-7-carbonitrile Prepared in similar manner as example 306.

MS (ESI) m/z 521.2 (M+H); 1H NMR (500 MHz, DMSO-d6) δ 9.30 (d, J=4.2 Hz, 1H), 8.77 (br. s., 1H), 8.20 (s, 1H), 7.90 (br. s., 1H), 7.16 (br. s., 1H), 5.21 (br. s., 1H), 4.24 (br. s., 1H), 3.61 (br. s., 4H), 3.54-3.45 (m, 2H), 3.42 (br. s., 1H), 3.04-2.96 (m, 1H), 2.77 (br. s., 1H), 2.65 (br. s., 2H), 1.25 (s, 1H), 0.79 (d, J=5.5 Hz, 4H).

Example 308

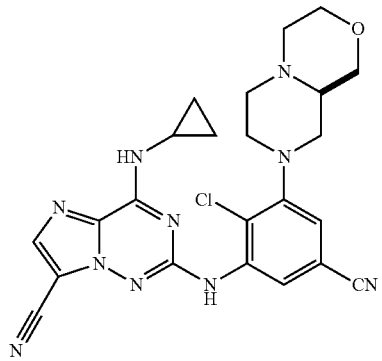 [SMILES: N#Cc1cc(Nc2nc(NC3CC3)c3ncc(C#N)n3n2)c(Cl)c(N2CCN3CCOC[C@H]3C2)c1]

(R)-2-((2-chloro-5-cyano-3-(hexahydropyrazino[2,1-c][1,4]oxazin-8(1H)-yl)phenyl)amino)-4-(cyclopropylamino)imidazo[2,1-f][1,2,4]triazine-7-carbonitrile (308A): (R)-3-amino-4-chloro-5-(hexahydropyrazino[2,1-c][1,4]oxazin-8(1H)-yl)benzonitrile was prepared starting from (R)-octahydropyrazino[2,1-c][1,4]oxazine using a method analogous to that used to prepare Example 171C and 171D.
MS (ESI) m/z 293.0 (M+H).

Example 308

The title compound was prepared from (R)-3-amino-4-chloro-5-(hexahydropyrazino[2,1-c][1,4]oxazin-8(1H)-yl)benzonitrile using a method analogous to that used to prepare Example 171
MS (ESI) m/z 491.2
$^1$H NMR (500 MHz, chloroform-d) δ 8.80 (d, J=1.9 Hz, 1H), 7.88 (s, 1H), 7.61 (s, 1H), 7.01 (d, J=1.7 Hz, 1H), 6.85 (d, J=1.7 Hz, 1H), 3.92 (dd, J=11.2, 2.9 Hz, 1H), 3.80-3.72 (m, 2H), 3.38-3.28 (m, 2H), 3.14-3.09 (m, 1H), 3.07 (td, J=7.1, 3.3 Hz, 1H), 3.01 (td, J=11.4, 2.6 Hz, 1H), 2.90 (dt, J=11.1, 2.4 Hz, 1H), 2.75 (d, J=11.4 Hz, 1H), 2.67-2.56 (m, 2H), 2.56-2.49 (m, 2H), 1.15-1.09 (m, 2H), 0.85-0.81 (m, 2H).

Example 309

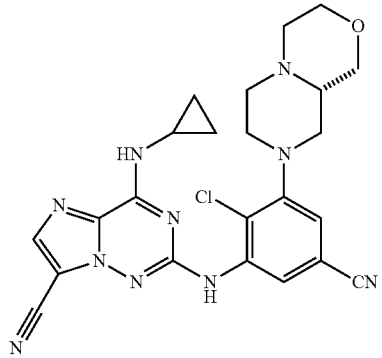 [SMILES: N#Cc1cc(Nc2nc(NC3CC3)c3ncc(C#N)n3n2)c(Cl)c(N2CCN3CCOC[C@@H]3C2)c1]

(S)-2-((2-chloro-5-cyano-3-(hexahydropyrazino[2,1-c][1,4]oxazin-8(1H)-yl)phenyl)amino)-4-(cyclopropylamino)imidazo[2,1-f][1,2,4]triazine-7-carbonitrile The title compound was prepared from (S)-octahydropyrazino[2,1-c][1,4]oxazine using a method analogous to that used to prepare Example 308.

MS (ESI) m/z 491.2

¹H NMR (400 MHz, chloroform-d) δ 8.79 (d, J=1.8 Hz, 1H), 7.90-7.83 (m, 1H), 7.59 (s, 1H), 6.99 (d, J=1.8 Hz, 1H), 6.86 (br. s., 1H), 3.90 (dd, J=11.3, 2.8 Hz, 1H), 3.79-3.69 (m, 2H), 3.38-3.26 (m, 2H), 3.13-3.04 (m, 2H), 2.99 (td, J=11.3, 2.4 Hz, 1H), 2.92-2.84 (m, 1H), 2.73 (d, J=11.7 Hz, 1H), 2.66-2.46 (m, 3H), 1.14-1.06 (m, 2H), 0.85-0.78 (m, 2H).

Example 310

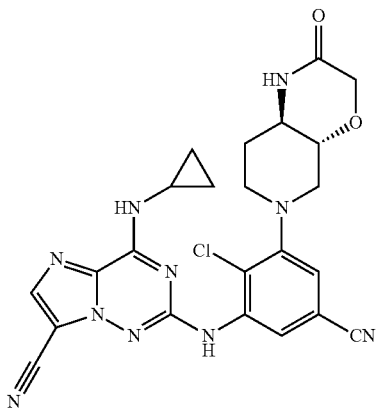 [SMILES: N#Cc1cc(Nc2nc(NC3CC3)c3ncc(C#N)n3n2)c(Cl)c(N2CC[C@H]3NC(=O)CO[C@@H]3C2)c1]

(+/−)-2-((2-chloro-5-cyano-3-((4aR,8aR)-2-oxohexahydro-1H-pyrido[3,4-b][1,4]oxazin-6(7H)-yl)phenyl)amino)-4-(cyclopropylamino)imidazo[2,1-f][1,2,4]triazine-7-carbonitrile, 2HCl (310A): 2-chloroacetyl chloride (7.56 mg, 0.067 mmol) in dichloromethane (0.5 mL) was added to a mixture of (+/−)-2-((3-((3R,4R)-4-amino-3-((tert-butyldimethylsilyl)oxy)piperidin-1-yl)-2-chloro-5-cyanophenyl)amino)-4-(cyclopropyl(4-methoxybenzyl)amino)imidazo[2,1-f][1,2,4]triazine-7-carbonitrile (Example 171D), (39 mg, 0.056 mmol) and triethylamine (0.016 mL, 0.112 mmol) in dichloromethane (1 mL) at 0° C. and the reaction mixture was stirred at for 1 h. LCMS showed completion of reaction. The reaction mixture was diluted with dichloromethane and washed with water. The organic layer was dried over magnesium sulfate, filtered and concentrated in vacuo, the crude product was purified by flash chromatography on silica gel using an automated ISCO system (12 g column, eluting with 5-40% ethyl acetate/dichloromethane to afford (+/−)-N-((3R,4R)-3-((tert-butyldimethylsilyl)oxy)-1-(2-chloro-5-cyano-3-((7-cyano-4-(cyclopropyl(4-methoxybenzyl)amino)imidazo[2,1-f][1,2,4]triazin-2-yl)amino)phenyl)piperidin-4-yl)-2-chloroacetamide (43 mg) as a white solid.

MS (ESI) m/z 775.2 (M+H).

(310B): To (+/−)-N-((3R,4R)-3-((tert-butyldimethylsilyl)oxy)-1-(2-chloro-5-cyano-3-((7-cyano-4-(cyclopropyl(4-methoxybenzyl)amino)imidazo[2,1-f][1,2,4]triazin-2-yl)amino)phenyl)piperidin-4-yl)-2-chloroacetamide (43 mg, 0.055 mmol) in THF (1 mL) was added TBAF (1M in THF, 0.112 mL, 0.112 mmol) and the reaction solution was stirred at room temperature overnight. LCMS showed completion of reaction. Solvent was evaporated and the crude product was purified by flash chromatography on silica gel using an automated ISCO system (24 g column, eluting with 0.5-4% methanol/dichloromethane) to give (+/−)-2-chloro-N-((3R,4R)-1-(2-chloro-5-cyano-3-((7-cyano-4-(cyclopropyl(4-methoxybenzyl)amino)imidazo[2,1-f][1,2,4]triazin-2-yl)amino)phenyl)-3-hydroxypiperidin-4-yl)acetamide (22 mg) as a white solid.

MS (ESI) m/z 661.1 (M+H).

(310C): Sodium hydride (60% in mineral oil, 8.0 mg, 0.200 mmol) was added to a solution of (+/−)-2-2-chloro-N-((3R,4R)-1-(2-chloro-5-cyano-3-((7-cyano-4-(cyclopropyl(4-methoxybenzyl)amino)imidazo[2,1-f][1,2,4]triazin-2-yl)amino)phenyl)-3-hydroxypiperidin-4-yl)acetamide (22 mg, 0.033 mmol) in THF (2 mL) and the reaction mixture was stirred at room temperature for 2 h. Reaction was quenched with water and extracted with dichloromethane (three times). The organic layer was dried over magnesium sulfate, filtered and concentrated in vacuo, the crude product was purified by flash chromatography on silica gel using an automated ISCO system (12 g column, eluting with 20-100% ethyl acetate/hexanes). (+/−)-2-((2-chloro-5-cyano-3-((4aR,8aR)-2-oxohexahydro-1H-pyrido[3,4-b][1,4]oxazin-6(7H)-yl)phenyl)amino)-4-(cyclopropyl(4-methoxybenzyl)amino)imidazo[2,1-f][1,2,4]triazine-7-carbonitrile (15 mg) was obtained as a white solid.

Example 310

TFA (25% in 1,2-dichloroethane, 2 mL, 6.49 mmol) was added to (+/−)-2-((2-chloro-5-cyano-3-((4aR,8aR)-2-oxohexahydro-1H-pyrido[3,4-b][1,4]oxazin-6(7H)-yl)phenyl)amino)-4-(cyclopropyl(4-methoxybenzyl)amino)imidazo[2,1-f][1,2,4]triazine-7-carbonitrile (15 mg, 0.024 mmol) and anisole (10.48 µl, 0.096 mmol) in 1,2-dichloroethane (1 mL) and the reaction mixture was stirred at 40° C. for 5 h. LCMS showed completion of reaction. Solvent was evaporated and the residue was redissolved in dichloromethane and concentrated again. After drying under vacuum overnight, the crude product was washed with hexanes (3×1 mL) and dichloromethane/hexanes (½ mixture, 3×1 mL). The resulting TFA salt was converted to HCl salt.

MS (ESI) m/z 505.1 (M+H);

¹H NMR (500 MHz, mixture of methanol-d₄/chloroform-d) δ 8.76 (d, J=1.7 Hz, 1H), 7.90 (s, 1H), 7.07 (d, J=1.7 Hz, 1H), 4.34-4.24 (m, 2H), 3.65 (td, J=9.4, 4.2 Hz, 1H), 3.55 (ddd, J=10.9, 4.2, 1.8 Hz, 1H), 3.42-3.35 (m, 2H), 3.05 (tt, J=7.3, 3.8 Hz, 1H), 2.84 (td, J=12.0, 2.1 Hz, 1H), 2.76 (t, J=10.4 Hz, 1H), 2.09-2.01 (m, 1H), 1.82 (qd, J=12.2, 4.2 Hz, 1H), 1.07-1.00 (m, 2H), 0.83-0.76 (m, 2H).

Example 311

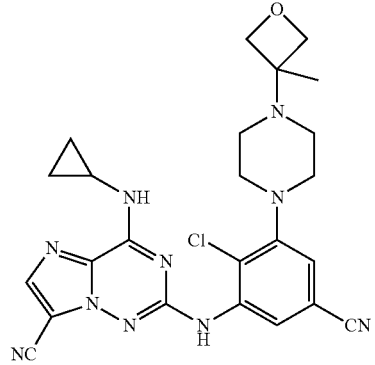 [SMILES: CC1(N2CCN(c3cc(C#N)cc(Nc4nc(NC5CC5)c5ncc(C#N)n5n4)c3Cl)CC2)COC1]

2-((2-chloro-5-cyano-3-(4-(3-methyl-3-oxetanyl)-1-piperazinyl)phenyl)amino)-4-(cyclopropylamino)imidazo[2,1-f][1,2,4]triazine-7-carbonitrile (311A): A clear solution of 3-((phenylsulfonyl)methylene)oxetane (450 mg, 1.284 mmol) in methanol (10 mL) was treated with 1-benzhydrylpiperazine (389 mg, 1.541 mmol) and stirred at 50° C. overnight, more 3-((phenylsulfonyl)methylene)oxetane (100 mg) was added, stirred at 50°

C. o/n, concentrated. The crude was purified by ISCO (40 g), eluted with EA:HX=0-50%, the desired fractions were concentrated to yield 1-benzhydryl-4-(3-((phenylsulfonyl)methyl)oxetan-3-yl)piperazine (670 mg) as a white solid.

MS (ESI) m/z 463.5

$^1$H NMR (400 MHz, CHLOROFORM-d) δ ppm 7.99-7.94 (m, 2H), 7.72-7.60 (m, 1H), 7.59-7.52 (m, 2H), 7.39 (d, J=7.3 Hz, 4H), 7.33-7.26 (m, 4H), 7.22 (d, J=7.3 Hz, 2H), 4.77 (d, J=6.8 Hz, 2H), 4.65 (d, J=7.0 Hz, 2H), 4.22 (s, 1H), 3.67 (s, 2H), 2.58 (t, J=4.6 Hz, 4H), 2.29 (br. s., 4H).

(311B): To a suspension of 1-benzhydryl-4-(3-((phenylsulfonyl)methyl)oxetan-3-yl)piperazine (2.49 g, 5.38 mmol) in MeOH (50 mL), THF (10 mL) was added MAGNESIUM (0.654 g, 26.9 mmol) which was pretreated with 1.0 N HCl and rinsed with MeOH, stirred at rt overnight. The Et$_2$O was added and followed by Na$_2$SO$_4$.10H$_2$O, stirred at rt for 1 hr, filtered. and filtrate was concentrated. The crude was purified by 40 g ISCO silica column, eluted with EA:HX=0-100%, the desired fractions were concentrate to yield 1-benzhydryl-4-(3-methyloxetan-3-yl)piperazine (1.08 g) as a white solid.

MS (ESI) m/z 323.3

$^1$H NMR (400 MHz, CHLOROFORM-d) δ ppm 7.46-7.38 (m, 4H), 7.31-7.24 (m, 4H), 7.22-7.15 (m, 2H), 4.57 (d, J=5.5 Hz, 2H), 4.26 (s, 1H), 4.21 (d, J=5.7 Hz, 2H), 2.57-2.28 (m, 8H), 1.40 (s, 3H)

(311C): A parr shaked bottle charged with 1-benzhydryl-4-(3-methyloxetan-3-yl)piperazine (0.24 g, 0.744 mmol) and MeOH (10 mL) was added Pd(OH)$_2$ (0.045 g, 0.320 mmol), purged with N$_2$, and shaked under H$_2$ (50 psi) overnight. The catalyst was removed by filter through a celite pad, the filtrate was concentrated to yield 153 mg of mixture of 1-(3-methyloxetan-3-yl)piperazine and diphenylmethane ratio (1:1), which was directly carried over to next step.

MS (ESI) m/z 211.1

$^1$H NMR (400 MHz, CHLOROFORM-d) δ ppm 7.35-7.26 (m, 4H), 7.23-7.15 (m, 6H), 4.59 (d, J=5.3 Hz, 2H), 4.22 (d, J=5.7 Hz, 2H), 4.00 (s, 2H), 3.00-2.86 (m, 4H), 2.43-2.27 (m, 4H), 1.45-1.34 (m, 3H)

Example 311

The title compound was prepared using a method analogous to that used to prepare Example 1.

MS (ESI) m/z 505.7

Example 312

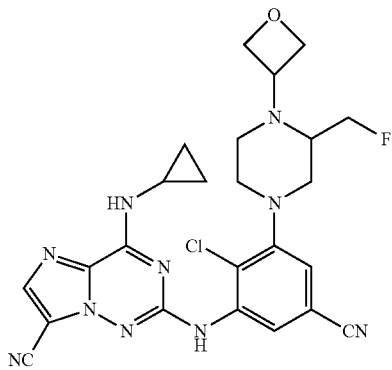 [SMILES: N#Cc1cc(Nc2nc(NC3CC3)c3ncc(C#N)n3n2)c(Cl)c(N2CCN(C3COC3)C(CF)C2)c1]

(+/−)2-((2-chloro-5-cyano-3-(3-(fluoromethyl)-4-(oxetan-3-yl)piperazin-1-yl)phenyl)amino)-4-(cyclopropylamino)imidazo[2,1-f][1,2,4]triazine-7-carbonitrile (312A): (+/−) Tert-butyl 3-(hydroxymethyl)piperazine-1-carboxylate (3.07 g, 14.19 mmol), oxetan-3-one (1.820 mL, 28.4 mmol), AcOH (1.625 mL, 28.4 mmol), and 4A molecular sieves were taken up in DCM (16 mL) and MeOH (16.00 mL), and the reaction was stirred at rt overnight. Sodium cyanoborohydride (4.46 g, 71.0 mmol) was added and the reaction was stirred at rt for 2 h. The reaction mixture was filtered through celite, rinsing with MeOH. The solvent was removed in vacuo and the material was quenched with 2M K$_3$PO$_4$ solution, then extracted 2× with EtOAc. The organic layers were combined, dried over Na$_2$SO$_4$, filtered, and concentrated. The material was purified by flash column chromatography (0-8% MeOH/DCM). (+/−) Tert-butyl 3-(hydroxymethyl)-4-(oxetan-3-yl)piperazine-1-carboxylate (2.40 g) was obtained as a colorless oil.

MS (ESI) m/z 273 (M+H)

$^1$H NMR (400 MHz, CHLOROFORM-d) δ 4.71-4.62 (m, 4H), 4.03 (quin, J=6.8 Hz, 1H), 3.57-3.31 (m, 6H), 2.73 (td, J=10.2, 3.6 Hz, 1H), 2.53 (br. s, 1H), 2.37-2.26 (m, 1H), 1.65 (d, J=0.4 Hz, 1H), 1.47 (s, 9H).

(312B): (+/−) Tert-butyl 3-(hydroxymethyl)-4-(oxetan-3-yl)piperazine-1-carboxylate (1 g, 3.67 mmol) was taken up in DMF (2 mL) and imidazole (0.500 g, 7.34 mmol) and TBS-Cl (0.609 g, 4.04 mmol) were added. The reaction was stirred at rt over the weekend. An additional 0.2 eq. of TBS-Cl and 0.5 eq. of imidazole was added, and the reaction mixture was heated at 40° C. overnight, then at 45° C. for 24 h. The reaction mixture was diluted with EtOAc and washed with water 4×. The organic layer was dried over Na$_2$SO$_4$, filtered, and concentrated. The material was purified by flash column chromatography (0-60% EtOAc/Hex). (+/−) Tert-butyl 3-(((tert-butyldimethylsilyl)oxy)methyl)-4-(oxetan-3-yl)piperazine-1-carboxylate (665 mg) was obtained as a colorless oil.

MS (ESI) m/z 387 (M+H)

$^1$H NMR (400 MHz, CHLOROFORM-d) δ 4.85-4.51 (m, 4H), 3.95 (quin, J=6.8 Hz, 1H), 3.65-3.37 (m, 5H), 3.31 (dd, J=13.1, 6.5 Hz, 1H), 2.75-2.53 (m, 1H), 2.52-2.36 (m, 1H), 2.34-2.17 (m, 1H), 1.46 (s, 9H), 0.96-0.85 (m, 9H), 0.05 (s, 6H)

(312C): Tert-butyl 3-(((tert-butyldimethylsilyl)oxy)methyl)-4-(oxetan-3-yl)piperazine-1-carboxylate (714 mg, 1.847 mmol) was taken up in DCM (8 mL) and TFA (2.85 mL, 36.9 mmol) was added. The reaction was stirred at rt for 30 min. The solvent was removed in vacuo and the material was dissolved in MeOH. The solution was loaded onto an SCX column (3×5 g, benzenesulfonic acid sorbent) and the columns were flushed with MeOH, then 7N NH$_3$/MeOH to release the product. (+/−) 2-(((tert-butyldimethylsilyl)oxy)methyl)-1-(oxetan-3-yl)piperazine (517 mg) was obtained as a yellow oil.

MS (ESI) m/z 287 (M+H)

$^1$H NMR (400 MHz, DMSO-d$_6$) δ 4.68-4.20 (m, 4H), 3.80 (quin, J=6.9 Hz, 1H), 3.57-3.38 (m, 2H), 3.29 (br. s, 2H), 2.81 (dd, J=11.9, 3.3 Hz, 1H), 2.77-2.65 (m, 2H), 2.58 (dd, J=12.1, 6.6 Hz, 1H), 2.28 (dtd, J=6.4, 5.9, 3.2 Hz, 1H), 2.15-2.03 (m, 1H), 0.90-0.82 (m, 9H), 0.03 (s, 6H)

(312D): (+/−) Tert-butyl(3-bromo-2-chloro-5-cyanophenyl)carbamate (545 mg, 1.644 mmol), 2-(((tert-butyldimethylsilyl)oxy)methyl)-1-(oxetan-3-yl)piperazine (518 mg, 1.808 mmol), Pd2(dba)3 (151 mg, 0.164 mmol), BINAP (102 mg, 0.164 mmol), Cs$_2$CO$_3$ (1071 mg, 3.29 mmol), and Toluene (16 mL) were combined in a 2 dram vial. The vial was evacuated and backfilled with Ar 3×, and the reaction was heated at 105° C. for 18 h. The reaction was cooled to rt and diluted with MeOH. The solution was filtered through celite and the filtrate concentrated in vacuo. The crude material was purified by flash column chromatography (0-50% EtOAc/Hex). (+/−) tert-butyl(3-(3-(((tert-butyldimethylsilyl)oxy)methyl)-4-(oxetan-3-yl)piperazin-1-yl)-2-chloro-5-cyanophenyl)carbamate (551 mg) was obtained as an orange glass.

MS (ESI) m/z 537 (M)

$^1$H NMR (400 MHz, CHLOROFORM-d) δ 8.32 (d, J=2.0 Hz, 1H), 7.18 (s, 1H), 6.98 (d, J=1.8 Hz, 1H), 4.80-4.55 (m, 4H), 4.05 (quin, J=6.9 Hz, 1H), 3.79-3.56 (m, 2H), 3.21-3.14 (m, 1H), 3.13-2.97 (m, 2H), 2.97-2.83 (m, 2H), 2.73 (qd, J=6.0, 3.1 Hz, 1H), 2.65-2.47 (m, 1H), 1.55 (s, 9H), 0.88 (s, 9H), 0.03 (d, J=6.8 Hz, 6H)

(312E): (+/−) Tert-butyl(3-(3-(((tert-butyldimethylsilyl)oxy)methyl)-4-(oxetan-3-yl)piperazin-1-yl)-2-chloro-5-cyanophenyl)carbamate (551 mg, 1.026 mmol) was taken up in THF (5 mL) and TBAF (1.539 mL, 1.539 mmol) was added dropwise. The reaction was stirred at rt for 1 h. The reaction mixture was diluted with EtOAc and washed with water, then brine. The organic layer was dried over $Na_2SO_4$, filtered, and concentrated. The material was purified by flash column chromatography (0-100% 20% (2N $NH_3$/MeOH)/DCM). (+/−) Tert-butyl(2-chloro-5-cyano-3-(3-(hydroxymethyl)-4-(oxetan-3-yl)piperazin-1-yl)phenyl)carbamate (416 mg) was obtained as an orange glass.

MS (ESI) m/z 423 (M+H)

$^1$H NMR (400 MHz, CHLOROFORM-d) δ 8.35 (d, J=2.0 Hz, 1H), 7.17 (s, 1H), 7.01 (d, J=1.8 Hz, 1H), 4.83-4.59 (m, 4H), 4.15 (quin, J=6.9 Hz, 1H), 3.88-3.75 (m, 1H), 3.69 (dt, J=11.2, 5.5 Hz, 1H), 3.31-2.89 (m, 5H), 2.78-2.66 (m, 1H), 2.66-2.52 (m, 1H), 2.32 (t, J=5.1 Hz, 1H), 1.55 (s, 9H)

(312F): (+/−) Tert-butyl(2-chloro-5-cyano-3-(3-(hydroxymethyl)-4-(oxetan-3-yl)piperazin-1-yl)phenyl)carbamate (660 mg, 1.561 mmol) was taken up in DCM (10 mL) and cooled to −40° C. Deoxofluor (0.432 mL, 2.341 mmol) was added dropwise, and the reaction was stirred at −40° C. for 30 min, then warmed to rt over 30 min. The reaction continued to stir at rt for 1 h. The reaction mixture was diluted with DCM and washed with 2M $K_3PO_4$ solution, then brine. The organic layer was dried over $Na_2SO_4$, filtered, and concentrated. The mixture was purified by flash column chromatography (0-20% EtOAc/DCM) to give two peaks.

Peak 1-Identified as, (+/−) tert-butyl(2-chloro-5-cyano-3-(6-fluoro-4-(oxetan-3-yl)-1,4-diazepan-1-yl)phenyl)carbamate (107 mg, 0.252 mmol, 16.14% yield) as a yellow gum.

MS (ESI) m/z 425 (M+H)

$^1$H NMR (400 MHz, CHLOROFORM-d) δ 8.31 (d, J=2.0 Hz, 1H), 7.16 (s, 1H), 7.09 (d, J=1.8 Hz, 1H), 5.06-4.82 (m, 1H), 4.77-4.67 (m, 2H), 4.58 (t, J=6.1 Hz, 2H), 3.86 (quin, J=6.4 Hz, 1H), 3.51 (d, J=6.4 Hz, 1H), 3.43-3.38 (m, 1H), 3.32-3.14 (m, 2H), 3.06-2.91 (m, 2H), 2.74 (ddd, J=11.7, 6.4, 3.6 Hz, 1H), 2.60 (ddd, J=12.4, 8.3, 3.5 Hz, 1H), 1.55 (s, 9H)

Peak 2 Identified as (+/−) tert-butyl(2-chloro-5-cyano-3-(3-(fluoromethyl)-4-(oxetan-3-yl)piperazin-1-yl)phenyl)carbamate (315 mg, 0.741 mmol, 47.5% yield) as a white foam.

MS (ESI) m/z 425 (M+H)

$^1$H NMR (500 MHz, CHLOROFORM-d) δ 8.35 (d, J=1.9 Hz, 1H), 7.17 (s, 1H), 6.99 (d, J=1.7 Hz, 1H), 4.83-4.65 (m, 4H), 4.64-4.39 (m, 1H), 4.13-4.02 (m, 1H), 3.53-3.38 (m, 1H), 3.15-2.99 (m, 5H), 2.96 (ddt, J=11.4, 5.5, 2.8 Hz, 1H), 2.68 (ddt, J=8.7, 5.6, 3.0 Hz, 1H), 1.55 (s, 9H)

(312G): (+/−) Tert-butyl(2-chloro-5-cyano-3-(3-(fluoromethyl)-4-(oxetan-3-yl)piperazin-1-yl)phenyl)carbamate (Peak 2) (315 mg, 0.741 mmol) was taken up in DCM (4 mL) and TFA (1.142 mL, 14.83 mmol) was added. The reaction was stirred at rt for 1 h. The solvent was removed in vacuo and the material was taken up in MeOH and loaded onto an SCX column (5 g, benzenesulfonic acid sorbent). The column was rinsed with MeOH, then 7N $NH_3$/MeOH to release the product. The solvent was removed in vacuo to give (+/−)-3-amino-4-chloro-5-(3-(fluoromethyl)-4-(oxetan-3-yl)piperazin-1-yl)benzonitrile (234 mg) as a yellow foam.

MS (ESI) m/z 325 (M+H)

$^1$H NMR (400 MHz, CHLOROFORM-d) δ 6.78 (d, J=2.0 Hz, 1H), 6.70 (d, J=2.0 Hz, 1H), 4.90-4.65 (m, 4H), 4.63-4.44 (m, 1H), 4.32 (br. s., 2H), 4.16-4.05 (m, 1H), 3.76-3.23 (m, 1H), 3.16-3.00 (m, 5H), 2.99-2.89 (m, 1H), 2.72-2.60 (m, 1H)

(312H): (+/−)2-((2-chloro-5-cyano-3-(3-(fluoromethyl)-4-(oxetan-3-yl)piperazin-1-yl)phenyl)amino)-4-(cyclopropyl(4-methoxybenzyl)amino)imidazo[2,1-f][1,2,4]triazine-7-carbonitrile was prepared according to the method described in Example 1G.

MS (ESI) m/z 643 (M)

$^1$H NMR (400 MHz, CHLOROFORM-d) δ 8.82 (br. s., 1H), 7.94 (s, 1H), 7.52 (br. s, 1H), 7.19 (d, J=8.8 Hz, 2H), 6.98 (d, J=1.8 Hz, 1H), 6.85 (d, J=8.6 Hz, 2H), 5.70 (br. s., 2H), 4.88-4.64 (m, J=0.4 Hz, 4H), 4.63-4.39 (m, J=9.5, 5.1 Hz, 1H), 4.18-4.05 (m, 1H), 3.79 (s, 3H), 3.22-2.83 (m, 8H), 2.69 (s, 1H), 1.14 (s, 2H), 1.00-0.84 (m, 2H)

Example 312

(+/−)2-((2-chloro-5-cyano-3-(3-(fluoromethyl)-4-(oxetan-3-yl)piperazin-1-yl)phenyl)amino)-4-(cyclopropyl(4-methoxybenzyl)amino)imidazo[2,1-f][1,2,4]triazine-7-carbonitrile (131 mg, 0.204 mmol) was taken up in DCE (2 mL) and anisole (0.067 mL, 0.611 mmol) was added, followed by TFA (0.314 mL, 4.07 mmol). The reaction was stirred at rt overnight. An additional 40 eq. of TFA was added and the reaction was stirred for 2 h, then an additional 60 eq. of TFA and was added, followed by stirring for 1 h. The solvent was removed in vacuo and the material was dissolved in MeOH. The material was loaded onto an SCX column (5 g, benzenesulfonic acid) and the column was flushed with MeOH, then 1:1 DCM/7N $NH_3$ in MeOH to obtain the product. The solvent was removed in vacuo and the material was dissolved in DMF. A solid precipitated out, which was collected by vacuum filtration and rinsed with MeOH. The solid was suspended in 1 ml of 1:1 $CH_3CN/H_2O$ and lyopholized overnight. (+/−)2-((2-chloro-5-cyano-3-(3-(fluoromethyl)-4-(oxetan-3-yl)piperazin-1-yl)phenyl)amino)-4-(cyclopropylamino)imidazo[2,1-f][1,2,4]triazine-7-carbonitrile was obtained as a beige solid.

MS (ESI) m/z 523 (M+H)

$^1$H NMR (500 MHz, DMSO-$d_6$) δ 9.32 (br. s., 1H), 8.84 (br. s., 1H), 8.19 (s, 1H), 8.13 (d, J=0.8 Hz, 1H), 7.39-7.31 (m, 1H), 4.80-4.37 (m, 5H), 4.05-3.91 (m, 1H), 3.13-3.01 (m, 4H), 3.01-2.78 (m, 4H), 2.55 (s, 1H), 0.78 (d, J=5.5 Hz, 4H)

Example 313

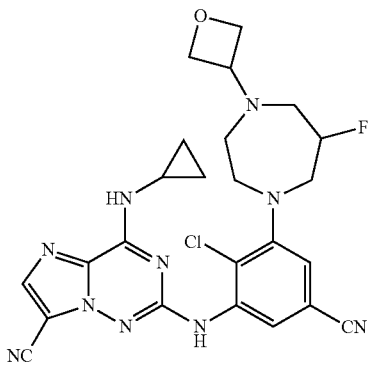 [SMILES: N#Cc1cc(Nc2nc(NC3CC3)c3ncc(C#N)n3n2)c(Cl)c(N2CCN(C3COC3)CC(F)C2)c1]

(+/−)2-((2-chloro-5-cyano-3-(6-fluoro-4-(oxetan-3-yl)-1,4-diazepan-1-yl)phenyl)amino)-4-(cyclopropylamino)imidazo[2,1-f][1,2,4]triazine-7-carbonitrile (313A): (+/−) Tert-butyl(2-chloro-5-cyano-3-(6-fluoro-4-(oxetan-3-yl)-1,4-diazepan-1-yl)phenyl)carbamate (107 mg, 0.252 mmol, Example 312F, Peak 1) was taken up in DCM (1.5 mL) and TFA (0.388 mL, 5.04 mmol) was added. The reaction was stirred at rt for 30 min. The solvent was removed in vacuo and the material taken up in MeOH. The solution was loaded onto an SCX column (5 g, benzenesulfonic acid sorbent) and flushed with MeOH, then 7N $NH_3$/MeOH to obtain the product. The material was purified by flash column chromatography (0-25% EtOAc/DCM). 3-amino-4-chloro-5-(6-fluoro-4-(oxetan-3-yl)-1,4-diazepan-1-yl)benzonitrile (67 mg) was obtained as a yellow glass.

MS (ESI) m/z 325 (M+H)
$^1$H NMR (400 MHz, CHLOROFORM-d) δ 6.77 (d, J=2.0 Hz, 1H), 6.73 (d, J=2.0 Hz, 1H), 5.09-4.81 (m, 1H), 4.74-4.66 (m, 2H), 4.57 (t, J=6.1 Hz, 2H), 4.37 (br. s., 2H), 3.84 (quin, J=6.3 Hz, 1H), 3.64-3.52 (m, 1H), 3.46-3.34 (m, 1H), 3.31-3.15 (m, 2H), 3.03-2.91 (m, 2H), 2.78-2.68 (m, 1H), 2.58 (ddd, J=12.4, 8.3, 3.7 Hz, 1H)

(313B): (+/−)2-((2-chloro-5-cyano-3-(6-fluoro-4-(oxetan-3-yl)phenyl)amino)-4-(cyclopropyl(4-methoxybenzyl)amino)imidazo[2,1-f][1,2,4]triazine-7-carbonitrile was prepared using the method described in Example 312H.

MS (ESI) m/z 643 (M)
$^1$H NMR (400 MHz, CHLOROFORM-d) δ 8.77 (br. s., 1H), 7.93 (s, 1H), 7.51 (d, J=1.1 Hz, 1H), 7.18 (d, J=8.6 Hz, 2H), 7.06 (d, J=1.8 Hz, 1H), 6.84 (d, J=8.8 Hz, 2H), 5.69 (br. s., 2H), 5.09-4.83 (m, 1H), 4.79-4.64 (m, 2H), 4.58 (t, J=6.1 Hz, 2H), 3.86 (dt, J=12.5, 6.3 Hz, 1H), 3.78 (s, 3H), 3.67-3.38 (m, 3H), 3.35-3.16 (m, 2H), 3.06-2.91 (m, 2H), 2.80-2.70 (m, 1H), 2.61 (ddd, J=12.2, 8.0, 3.5 Hz, 1H), 1.23-1.05 (m, 2H), 0.95-0.84 (m, 2H)

Example 313

(+/−)2-((2-chloro-5-cyano-3-(6-fluoro-4-(oxetan-3-yl)-1,4-diazepan-1-yl)phenyl)amino)-4-(cyclopropyl(4-methoxybenzyl)amino)imidazo[2,1-f][1,2,4]triazine-7-carbonitrile (89 mg, 0.138 mmol) was taken up in DCE (1 mL) and anisole (0.076 mL, 0.692 mmol) was added, followed by TFA (0.640 mL, 8.30 mmol). The reaction was stirred at rt overnight. An additional 1 ml of TFA was added, and the reaction was stirred at rt for 4 h. The solvent was removed in vacuo and the material dissolved in MeOH. The material was loaded onto an SCX column (5 g, benzenesulfonic acid sorbent) and the column was flushed with MeOH, then 1:1 DCM/7N $NH_3$/MeOH to obtain the product. The solvent was removed in vacuo and the crude material was purified by preparative HPLC. 2-((2-chloro-5-cyano-3-(6-fluoro-4-(oxetan-3-yl)-1,4-diazepan-1-yl)phenyl)amino)-4-(cyclopropylamino)imidazo[2,1-f][1,2,4]triazine-7-carbonitrile (12 mg, 0.023 mmol, 16.6% yield) was obtained as a yellow solid.

MS (ESI) m/z 523 (M+H)
$^1$H NMR (500 MHz, DMSO-$d_6$) δ 8.19 (s, 1H), 8.12-8.06 (m, 1H), 7.53-7.42 (m, 1H), 5.10-4.85 (m, 1H), 4.58 (t, J=6.6 Hz, 2H), 4.42-4.30 (m, 2H), 3.76 (quin, J=6.1 Hz, 1H), 3.66-3.52 (m, 1H), 3.48-3.35 (m, 1H), 3.31-3.10 (m, 2H), 3.01-2.77 (m, 3H), 2.71-2.63 (m, 1H), 2.57-2.51 (m, 1H), 0.85-0.70 (m, 4H)

Example 314

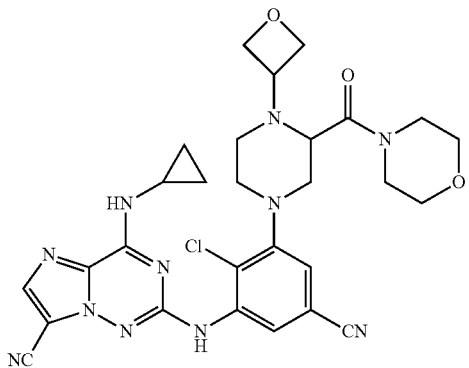 [SMILES: N#Cc1cc(Nc2nc(NC3CC3)c3ncc(C#N)n3n2)c(Cl)c(N2CCN(C3COC3)C(C(=O)N3CCOCC3)C2)c1]

(+/−)2-((2-chloro-5-cyano-3-(3-(morpholine-4-carbonyl)-4-(oxetan-3-yl)piperazin-1-yl)phenyl)amino)-4-(cyclopropylamino)imidazo[2,1-f][1,2,4]triazine-7-carbonitrile (314A): (+/−)1-benzyl 3-methyl piperazine-1,3-dicarboxylate (5 g, 17.97 mmol, contained <20% of 1-benzyl 3-methyl 4-methylpiperazine-1,3-dicarboxylate), oxetan-3-one (2.304 mL, 35.9 mmol), AcOH (2.057 mL, 35.9 mmol), and 4A MS were taken up in DCM (10 mL) and MeOH (10.00 mL), and the reaction was stirred at rt overnight. An additional 1 eq. of oxetanone was added and the reaction was heated at 45° C. for 4 h. The reaction was cooled to rt, then to 0° C. Sodium cyanoborohydride (1.694 g, 26.9 mmol) was added, and the reaction was warmed to rt and stirred overnight. The reaction mixture was diluted with MeOH and filtered through celite. The solvent was removed in vacuo and the material dissolved in EtOAc. The organic layer was washed with 2M $K_3PO_4$ solution, then brine. The organic layer was dried over $Na_2SO_4$, filtered, and concentrated to give 5.9 g of a yellow oil. The material was purified by flash column chromatography, eluting with 0-3% MeOH/DCM. 400 mg of pure (+/−)1-benzyl 3-methyl 4-(oxetan-3-yl)piperazine-1,3-dicarboxylate was obtained as well as 3 g of a 3:1 mixture of 1-benzyl 3-methyl 4-(oxetan-3-yl)piperazine-1,3-dicarboxylate and 1-benzyl 3-methyl 4-methylpiperazine-1,3-dicarboxylate (ratio determined by $^1$H NMR).

MS (ESI) m/z 335 (M+H)

$^1$H NMR (400 MHz, MeOD) δ 7.46-7.23 (m, 5H), 5.28-4.96 (m, 2H), 4.72 (t, J=6.5 Hz, 1H), 4.67-4.51 (m, 3H), 4.43-4.24 (m, 1H), 4.10 (quin, J=7.0 Hz, 1H), 4.00 (dd, J=12.5, 0.4 Hz, 1H), 3.70-3.43 (m, 4H), 3.30-3.18 (m, 1H), 3.17-2.89 (m, 2H), 2.78-2.52 (m, 1H)

(314B): A 3:1 mixture of (+/−)1-benzyl 3-methyl 4-(oxetan-3-yl)piperazine-1,3-dicarboxylate (1.57 g, 4.70 mmol) and 1-benzyl 3-methyl 4-methylpiperazine-1,3-dicarboxylate (458 mg, 1.565 mmol) were taken up in MeOH (20 ml) and the solution was purged with $N_2$. 5% Pd/C (0.999 g, 0.470 mmol) was added, and the solution was again sparged with $N_2$. A balloon with $H_2$ was added, and the flask was evacuated and backfilled with hydrogen 3×. The reaction was hydrogenated at atmospheric pressure overnight. The reaction mixture was filtered through celite, rinsing with MeOH. The solvent was removed in vacuo to give 869 mg of material. A 3:1 mixture of (+/−) methyl 1-(oxetan-3-yl)piperazine-2-carboxylate (688 mg, 3.44 mmol, 73% yield) and (+/−) methyl 1-methylpiperazine-2-carboxylate was obtained (181 mg).

MS (ESI) m/z 201 (M+H)

$^1$H NMR (400 MHz, MeOD) δ 4.74 (t, J=6.6 Hz, 1H), 4.69-4.53 (m, 3H), 4.04 (quin, J=7.0 Hz, 1H), 3.69 (s, 3H), 3.34-3.32 (m, 1H), 3.22-3.14 (m, 1H), 2.95 (dd, J=12.9, 3.9 Hz, 1H), 2.92-2.74 (m, 4H), 2.61-2.54 (m, 1H)

(314C): (+/−) Tert-butyl(3-bromo-2-chloro-5-cyanophenyl)carbamate (1.52 g, 4.58 mmol), a 3:1 mixture of methyl 1-(oxetan-3-yl)piperazine-2-carboxylate (0.688 g, 3.44 mmol) and methyl 1-methylpiperazine-2-carboxylate (0.181 g, 1.144 mmol), $Pd_2(dba)_3$ (0.420 g, 0.458 mmol), BINAP (0.285 g, 0.458 mmol), $Cs_2CO_3$ (2.240 g, 6.88 mmol), and Toluene (40 mL) were combined in a round bottom flask. The flask was evacuated and backfilled with $N_2$ 3×, and the reaction was heated at 105° C. for 18 h. The reaction was cooled to rt and an additional 0.05 eq. each of catalyst and ligand were added. The reaction vial was resealed, evacuated and backfilled with $N_2$ 3×, then heated at 105° C. for 2 h. The reaction was cooled to rt and diluted with EtOAc. The solution was filtered through celite and the filtrate concentrated in vacuo. The crude material was purified by flash column chromatography 0-5% MeOH/DCM, then repurified with 0-20% Acetone/DCM. 292 mg of pure methyl 4-(3-((tert-butoxycarbonyl)amino)-2-chloro-5-cyanophenyl)-1-(oxetan-3-yl)piperazine-2-carboxylate was obtained, along with 592 mg of a 3:1.7 mixture of methyl 4-(3-((tert-butoxycarbonyl)amino)-2-chloro-5-cyanophenyl)-1-(oxetan-3-yl)piperazine-2-carboxylate and methyl 4-(3-((tert-butoxycarbonyl)amino)-2-chloro-5-cyanophenyl)-1-methylpiperazine-2-carboxylate. Estimated yields based on $^1$H NMR: methyl 4-(3-((tert-butoxycarbonyl)amino)-2-chloro-5-cyanophenyl)-1-(oxetan-3-yl)piperazine-2-carboxylate (683 mg, 1.515 mmol, 44.0% yield) and methyl 4-(3-((tert-butoxycarbonyl)amino)-2-chloro-5-cyanophenyl)-1-methylpiperazine-2-carboxylate (201 mg).

MS (ESI) m/z 451 (M+H)

$^1$H NMR (400 MHz, CHLOROFORM-d) δ 8.34 (d, J=1.8 Hz, 1H), 7.16 (s, 1H), 6.99 (d, J=2.0 Hz, 1H), 4.88 (t, J=6.6 Hz, 1H), 4.76-4.59 (m, 3H), 4.23 (quin, J=7.0 Hz, 1H), 3.70 (s, 3H), 3.60-3.51 (m, 2H), 3.43-3.35 (m, 1H), 3.27-3.14 (m, 1H), 3.09 (dd, J=11.1, 3.4 Hz, 1H), 2.98-2.89 (m, 1H), 2.85 (dt, J=11.1, 3.4 Hz, 1H), 1.55 (s, 9H) Analytical data for methyl 4-(3-((tert-butoxycarbonyl)amino)-2-chloro-5-cyanophenyl)-1-methylpiperazine-2-carboxylate MS (ESI) m/z 409 (M+H)

(314D): Methyl 4-(3-((tert-butoxycarbonyl)amino)-2-chloro-5-cyanophenyl)-1-(oxetan-3-yl)piperazine-2-carboxylate (292 mg, 0.648 mmol) was taken up in THF (3 mL) and water (0.3 ml) and lithium hydroxide monohydrate (38.1 mg, 0.907 mmol) was added. The reaction was heated at 40° C. for 2 h, then cooled to rt and stirred overnight. Some starting material was still detected by LCMS, so the reaction was warmed to 40° C. and heated for 2 h. The reaction was cooled to rt and the solvent removed in vacuo. The material was azeotroped 3× with toluene to give 4-(3-((tert-butoxycarbonyl)amino)-2-chloro-5-cyanophenyl)-1-(oxetan-3-yl)piperazine-2-carboxylate, lithium salt (292 mg) as a yellow solid.

MS (ESI) m/z 437 (M+2H)

$^1$H NMR (400 MHz, DMSO-$d_6$) δ 8.81 (br. s., 1H), 7.76 (d, J=1.3 Hz, 1H), 7.05 (br. s, 1H), 4.67 (t, J=6.6 Hz, 1H), 4.52 (t, J=6.6 Hz, 1H), 4.40 (q, J=5.9 Hz, 2H), 4.06-3.92 (m, 1H), 3.13-2.86 (m, 3H), 2.76-2.60 (m, 1H), 2.37-2.25 (m, 1H), 1.44 (s, 9H)

(314E): 4-(3-((tert-butoxycarbonyl)amino)-2-chloro-5-cyanophenyl)-1-(oxetan-3-yl)piperazine-2-carboxylate, lithium salt (200 mg, 0.452 mmol) was azeotroped 3× with toluene and 4A molecular sieves were added. THF (3 mL) was added, followed by DIPEA (0.118 mL, 0.677 mmol), morpholine (0.117 mL, 1.355 mmol), and T3P (0.538 mL, 0.903 mmol). The reaction was stirred at rt for 1 h. The reaction mixture was filtered through a small pad of celite, rinsing with EtOAc. The solvent was removed in vacuo and the material was purified by flash column chromatography (0-4% MeOH/DCM). Tert-butyl(2-chloro-5-cyano-3-(3-(morpholine-4-carbonyl)-4-(oxetan-3-yl)piperazin-1-yl)phenyl)carbamate (112 mg) was obtained as an off-white solid.

MS (ESI) m/z 506 (M+H)

$^1$H NMR (400 MHz, CHLOROFORM-d) δ 8.35 (d, J=2.0 Hz, 1H), 7.15 (s, 1H), 7.00 (d, J=2.0 Hz, 1H), 4.89-4.69 (m, 2H), 4.62-4.52 (m, 2H), 4.05 (quin, J=6.9 Hz, 1H), 3.73-3.59 (m, 9H), 3.32 (d, J=9.7 Hz, 1H), 3.23-3.13 (m, J=7.3 Hz, 3H), 3.07 (q, J=9.2 Hz, 1H), 2.70 (t, J=10.1 Hz, 1H), 1.57-1.55 (m, 9H)

(314F): (+/−) Tert-butyl(2-chloro-5-cyano-3-(3-(morpholine-4-carbonyl)-4-(oxetan-3-yl)piperazin-1-yl)phenyl)carbamate (112 mg, 0.221 mmol) was taken up in DCM (3 mL) and TFA (0.341 mL, 4.43 mmol) was added. The reaction was stirred at rt for 1 h. The solvent was removed in vacuo and the material was azeotroped 2× with DCM and 2× with MeOH, then dried under vacuum. The solid was dissolved in EtOAc, then washed with 2M $K_3PO4$ solution. The organic layer was dried over $Na_2SO_4$, filtered, and concentrated. The material was purified by flash column chromatography (0-5% MeOH/DCM). (+/−)3-amino-4-chloro-5-(3-(morpholine-4-carbonyl)-4-(oxetan-3-yl)piperazin-1-yl)benzonitrile (36 mg) was obtained as a colorless foam.

MS (ESI) m/z 406 (M+H)

$^1$H NMR (400 MHz, CHLOROFORM-d) δ 6.78 (d, J=1.8 Hz, 1H), 6.68 (d, J=1.8 Hz, 1H), 4.87-4.71 (m, 2H), 4.55 (t, J=6.8 Hz, 2H), 4.38 (s, 2H), 4.02 (quin, J=7.2 Hz, 1H), 3.73-3.53 (m, 9H), 3.31-2.94 (m, 5H), 2.76-2.59 (m, 1H)

(314G): (+/−) Tert-butyl(2-chloro-7-cyanoimidazo[2,1-f][1,2,4]triazin-4-yl)(cyclopropyl)carbamate (Intermediate 1) (30 mg, 0.090 mmol), 3-amino-4-chloro-5-(3-(morpholine-4-carbonyl)-4-(oxetan-3-yl)piperazin-1-yl)benzonitrile (36.4 mg, 0.090 mmol), palladium (II) acetate (6.04 mg, 0.027 mmol), dppf (4.97 mg, 8.96 µmol), Xantphos (5.19 mg, 8.96 µmol), and cesium carbonate (52.6 mg, 0.161 mmol) were combined in a 10 ml flask and Dioxane (1 mL)

was added. The flask was evacuated and backfilled with N₂ 3×, then heated at 100° C. for 1 h. The reaction was cooled to rt and filtered through celite, rinsing with EtOAc. The solvent was removed in vacuo and the crude material was purified by flash column (0-5% MeOH/DCM).

(+/−) Tert-butyl(2-((2-chloro-5-cyano-3-(3-(morpholine-4-carbonyl)-4-(oxetan-3-yl)piperazin-1-yl)phenyl)amino)-7-cyanoimidazo[2,1-f][1,2,4]triazin-4-yl)(cyclopropyl)carbamate (45 mg) was obtained as a yellow glass MS (ESI) m/z 704 (M)
$^1$H NMR (400 MHz, CHLOROFORM-d) δ 8.62 (d, J=1.8 Hz, 1H), 8.06 (s, 1H), 7.70 (s, 1H), 7.07 (d, J=1.8 Hz, 1H), 4.79 (dt, J=13.5, 6.9 Hz, 2H), 4.58 (t, J=6.9 Hz, 2H), 4.06 (quin, J=7.2 Hz, 1H), 3.78-3.56 (m, 9H), 3.33 (d, J=11.9 Hz, 1H), 3.27-3.15 (m, 4H), 3.14-3.04 (m, 1H), 2.79-2.67 (m, 1H), 1.51 (s, 9H), 1.14-1.02 (m, 2H), 0.87-0.74 (m, 2H)

Example 314

(+/−) Tert-butyl(2-((2-chloro-5-cyano-3-(3-(morpholine-4-carbonyl)-4-(oxetan-3-yl)piperazin-1-yl)phenyl)amino)-7-cyanoimidazo[2,1-f][1,2,4]triazin-4-yl)(cyclopropyl)carbamate (40 mg, 0.057 mmol) was taken up in DCE (275 μL) and anisole (31.0 μL, 0.284 mmol) was added. The reaction was cooled to 0° C., and TFA (92 μL, 1.193 mmol) was added. The reaction was stirred at 0° C. for 30 min, then warmed to rt and stirred for 1.5 h. The solvent was removed in vacuo and the material was azeotroped 2× with toluene to remove the excess TFA. The crude material was purified by preparative HPLC to provide (+/−)2-((2-chloro-5-cyano-3-(3-(morpholine-4-carbonyl)-4-(oxetan-3-yl)piperazin-1-yl)phenyl)amino)-4-(cyclopropylamino)imidazo[2,1-f][1,2,4]triazine-7-carbonitrile (3.9 mg).

MS (ESI) m/z 604 (M)
$^1$H NMR (500 MHz, DMSO-d₆) δ 9.33 (br. s., 1H), 8.90 (br. s., 1H), 8.19 (s, 1H), 8.09 (s, 1H), 7.34 (s, 1H), 4.66-4.52 (m, J=2.4 Hz, 2H), 4.42 (q, J=6.9 Hz, 2H), 4.17-4.06 (m, 1H), 3.99 (quin, J=7.2 Hz, 1H), 3.73 (s, 1H), 3.55 (br. s, 7H), 3.15-3.09 (m, 1H), 3.08-3.01 (m, 4H), 2.96 (quin, J=5.3 Hz, 1H), 2.59 (s, 1H), 0.77 (d, J=5.5 Hz, 4H)

The compounds listed below were prepared by the similar synthetic procedure used for Example 314

TABLE 10

| Example No. | Structure | Name | [M + H]⁺ | HPLC Retention Time (min.)* |
|---|---|---|---|---|
| 315 | 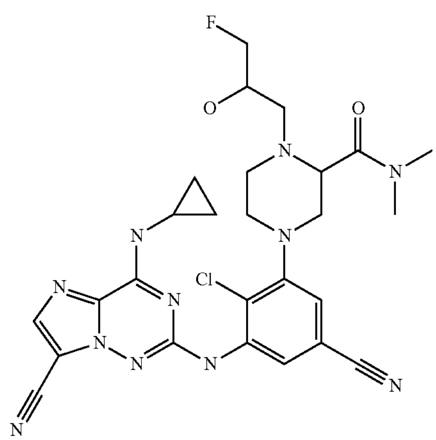 [SMILES: CN(C)C(=O)C1CN(c2cc(C#N)cc(Nc3nc(NC4CC4)c4ncc(C#N)n4n3)c2Cl)CCN1CC(O)CF] | (+/−) 4-(2-chloro-5-cyano-3-((7-cyano-4-(cyclopropylamino)imidazo[2,1-f][1,2,4]triazin-2-yl)amino)phenyl)-1-(3-fluoro-2-hydroxypropyl)-N,N-dimethyl-2-piperazinecarboxamide | 582.04 | 4.23 |
| 316 | 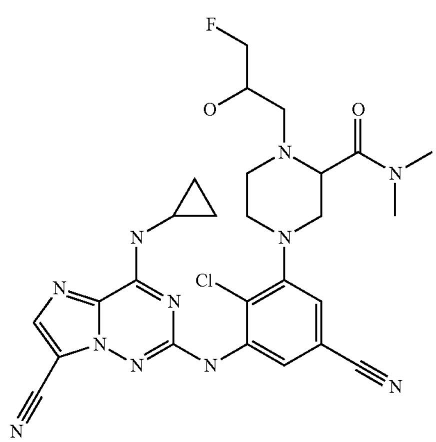 [SMILES: CN(C)C(=O)C1CN(c2cc(C#N)cc(Nc3nc(NC4CC4)c4ncc(C#N)n4n3)c2Cl)CCN1CC(O)CF] | (+/−) 4-(2-chloro-5-cyano-3-((7-cyano-4-(cyclopropylamino)imidazo[2,1-f][1,2,4]triazin-2-yl)amino)phenyl)-1-(3-fluoro-2-hydroxypropyl)-N,N-dimethyl-2-piperazinecarboxamide | 4.30 | 1.78 $^c$ |

TABLE 10-continued

| Example No. | Structure | Name | [M + H]+ | HPLC Retention Time (min.)* |
|---|---|---|---|---|
| 317 | 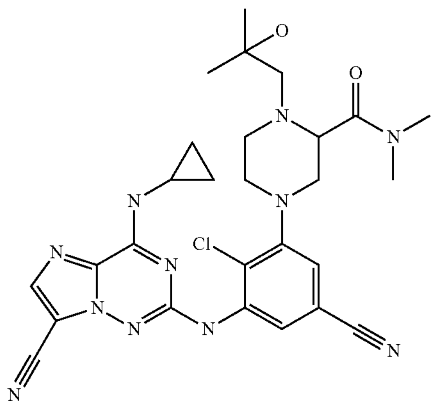 [SMILES: CN(C)C(=O)C1CN(c2cc(C#N)cc(Nc3nc(NC4CC4)c4ncc(C#N)n4n3)c2Cl)CCN1CC(C)(C)O] | 4-(2-chloro-5-cyano-3-((7-cyano-4-(cyclopropylamino)imidazo[2,1-f][1,2,4]triazin-2-yl)amino)phenyl)-1-(2-hydroxy-2-methylpropyl)-N,N-dimethylpiperazine-2-carboxamide | 578.08 | 4.67 |

*a* YMC S5 ODS 4.6 × 50 mm, 10-90% aqueous methanol containing 0.2% $H_3PO_4$, 5 min. gradient, monitored at 220 nm Example 318

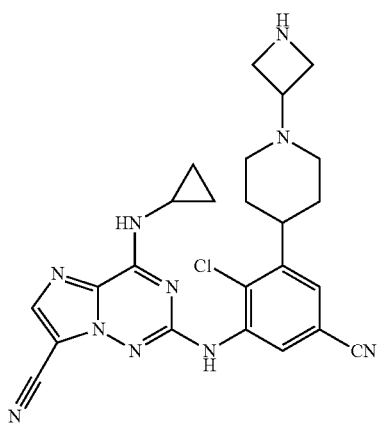 [SMILES: N#Cc1cc(Nc2nc(NC3CC3)c3ncc(C#N)n3n2)c(Cl)c(C2CCN(C3CNC3)CC2)c1]

2-((3-(1-(azetidin-3-yl)piperidin-4-yl)-2-chloro-5-cyanophenyl)amino)-4-(cyclopropylamino)imidazo[2,1-f][1,2,4]triazine-7-carbonitrile To a suspension of 2-((2-chloro-5-cyano-3-(piperidin-4-yl)phenyl)amino)-4-(cyclopropylamino)imidazo[2,1-f][1,2,4]triazine-7-carbonitrile (Example 208) (60 mg, 0.138 mmol) in a mixture solvent of methanol (0.7 ml)/$CH_2CL_2$ (0.7 ml) was added trimethyl orthoformate (0.7 mL, 6.33 mmol), (The suspension converted to a clear solution within 1 min.), tert-butyl 3-oxoazetidine-1-carboxylate (237 mg, 1.383 mmol), and acetic acid (0.032 mL, 0.553 mmol). The mixture was stirred at Rt for 40 min and then sodium cyanoborohydride (87 mg, 1.383 mmol) was added and stirred at RT for overnight. The reaction mixture was partitioned between EtOAc and diluted aq. $NaHCO_3$, The aqueous layer was extracted with EtOAc, the combined organic layer was washed with brine and concentrated. The crude intermediate was purified by prep HPLC (100×30 mm Luna C18 column, Solvent A=10% Methanol, 90% $H_2O$, 0.1% TFA; solvent B=90% Methanol, 10% $H_2O$, 0.1% TFA, Flow rate 42 ml permin, 20-100% B, over 20 min) The HPLC fractions containing the intermediate were applied onto a cartridges of Phenomenex Strata-X-C 33 um cation mixed-mode polymer. This was washed with methanol and product was eluted with 2 N solution of ammonia in methanol/DCM (1:1). Removal of the solvents left 46 mg intermediate as a white solid which was dissolved in DCM (2 ml) and TFA (1 ml) was added. The resulting mixture was stirred at RT for 0.5 hour. Removal of the solvent and the residue was taken in MeOH/DCM and applied onto a cartridges of Phenomenex Strata-X-C 33 um cation mixed-mode polymer. This was washed with methanol and product was eluted with 2 N solution of ammonia in methanol/DCM (1:1). Removal of the solvents left the product (39 mg) as a white solid MS (ESI) m/z 489.28 (M+1)
$^1$H NMR (500 MHz, METHANOL-$d_4$) δ 8.87 (d, J=1.8 Hz, 1H), 7.89 (s, 1H), 7.27 (d, J=2.0 Hz, 1H), 3.72-3.64 (m, 2H), 3.62-3.56 (m, 2H), 3.35-3.26 (m, 1H), 3.11 (tt, J=12.1, 3.5 Hz, 1H), 3.03 (tt, J=7.3, 3.7 Hz, 1H), 2.94 (d, J=11.6 Hz, 2H), 2.09-1.99 (m, 2H), 1.96-1.87 (m, 2H), 1.72 (qd, J=12.5, 3.4 Hz, 2H), 1.06-0.98 (m, 2H), 0.84-0.75 (m, 2H)

Example 319

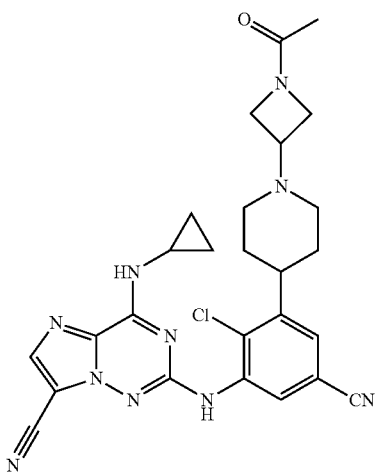 [SMILES: CC(=O)N1CC(N2CCC(c3cc(C#N)cc(Nc4nc(NC5CC5)c5ncc(C#N)n5n4)c3Cl)CC2)C1]

2-((3-(1-(1-acetylazetidin-3-yl)piperidin-4-yl)-2-chloro-5-cyanophenyl)amino)-4-(cyclopropylamino)imidazo[2,1-f][1,2,4]triazine-7-carbonitrile To a suspension of 2-((3-(1-(azetidin-3-yl)piperidin-4-yl)-2-chloro-5-cyanophenyl)amino)-4-(cyclopropylamino)imidazo[2,1-f][1,2,4]triazine-7-carbonitrile (Example 318) (25 mg, 0.051 mmol) and triethylamine (0.014 mL, 0.102 mmol)

in CH₂Cl₂ (1.5 mL) was added dropwise acetyl chloride (4.41 mg, 0.056 mmol, diluted with DCM, 10V % in DCM, 44 uL) at 0° C. The suspension converted to a clear solution in a few min, and continued stirring at 0° C. for 1 h. Removal of the solvent, and the crude material was purified via preparative LC/MS with the following conditions: Column: Waters XBridge C18, 19×200 mm, 5-μm particles; Mobile Phase A: water with 20-mM ammonium acetate; Mobile Phase B: 95:5 acetonitrile:water with 20-mM ammonium acetate; Gradient: 20-60% B over 20 minutes, then a 5-minute hold at 100% B; Flow: 20 mL/min. Fractions containing the desired product were combined and dried via centrifugal evaporation left the titled product (15.6 mg)

MS (ESI) m/z 531.15 (M+1)

1H NMR (500 MHz, DMSO-d6) δ 9.35 (br. s., 1H), 8.91 (br. s., 1H), 8.34 (s, 1H), 8.20 (s, 1H), 7.55 (br. s., 1H), 4.21 (m, 2H), 3.93 (m, 2H), 3.56-3.27 (m, 3H), 3.17 (m, 2H), 2.95 (d, J=4.9 Hz, 1H), 2.90 (s, 1H), 2.74 (s, 1H), 2.00-1.66 (m, 6H), 0.78 (d, J=5.2 Hz, 4H).

Example 320

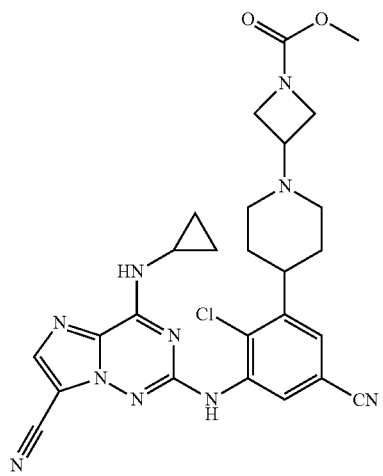 [SMILES: COC(=O)N1CC(N2CCC(c3cc(C#N)cc(Nc4nc(NC5CC5)c5ncc(C#N)n5n4)c3Cl)CC2)C1]

methyl 3-(4-(2-chloro-5-cyano-3-((7-cyano-4-(cyclopropylamino)imidazo[2,1-f][1,2,4]triazin-2-yl)amino)phenyl)piperidin-1-yl)azetidine-1-carboxy The title compound was prepared from 2-((3-(1-(azetidin-3-yl)piperidin-4-yl)-2-chloro-5-cyanophenyl)amino)-4-(cyclopropylamino)imidazo[2,1-f][1,2,4]triazine-7-carbonitrile (Example 318) and methyl chloroformate using a method analogous to that used to prepare Example 319.

HPLC Rt 3.088 min

MS (ESI) m/z 547.17 (M+1)

Example-321

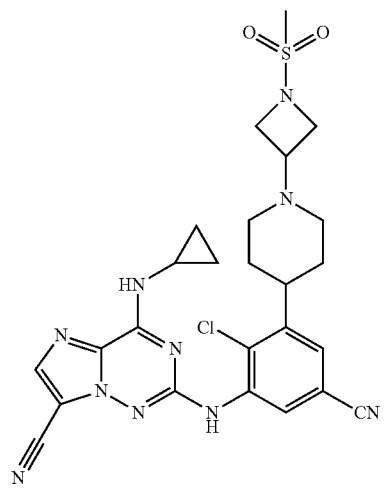 [SMILES: CS(=O)(=O)N1CC(N2CCC(c3cc(C#N)cc(Nc4nc(NC5CC5)c5ncc(C#N)n5n4)c3Cl)CC2)C1]

2-((2-chloro-5-cyano-3-(1-(1-(methylsulfonyl)azetidin-3-yl)piperidin-4-yl)phenyl)amino)-4-(cyclopropylamino)imidazo[2,1-f][1,2,4]triazine-7-carbonitrile The title compound was prepared from 2-((3-(1-(azetidin-3-yl)piperidin-4-yl)-2-chloro-5-cyanophenyl)amino)-4-(cyclopropylamino)imidazo[2,1-f][1,2,4]triazine-7-carbonitrile (Example 318) and methanesulfonyl chloride using a method analogous to that used to prepare Example 319 HPLC Rt 3.020 min MS ESI) m/z 567.27 (M+1)

The compounds listed below were prepared by the similar synthetic procedure used for Example 209

TABLE 11

| Example No. | Structure | Name | [M + H]⁺ | HPLC Retention Time (min.)* |
|---|---|---|---|---|
| 322 | 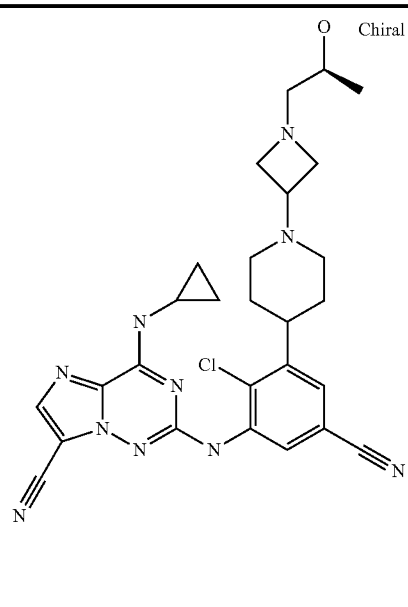 | 2-((2-chloro-5-cyano-3-(1-(1-((2S)-2-hydroxypropyl)-3-azetidinyl)-4-piperidinyl)phenyl)amino)-4-(cyclopropylamino)imidazo[2,1-f][1,2,4]triazine-7-carbonitrile | 547.06 | 3.67 |

TABLE 11-continued

| Example No. | Structure | Name | [M + H]+ | HPLC Retention Time (min.)* |
|---|---|---|---|---|
| 323 | 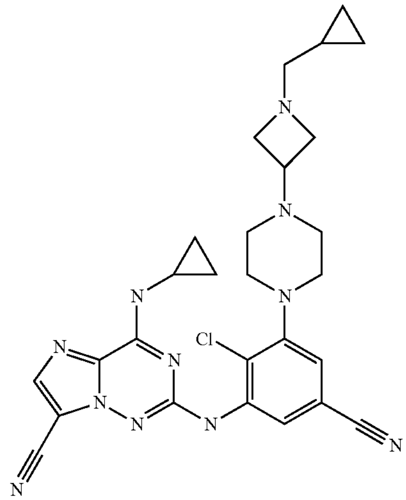 [SMILES: N#Cc1cc(Nc2nc(NC3CC3)c3ncc(C#N)n3n2)c(Cl)c(N2CCN(C3CN(CC4CC4)C3)CC2)c1] | 2-((2-chloro-5-cyano-3-(1-(1-(cyclopropylmethyl)-3-azetidinyl)-4-piperidinyl)phenyl)amino)-4-(cyclopropylamino)imidazo[2,1-f][1,2,4]triazine-7-carbonitrile | 543.08 | 3.78 |
| 324 | 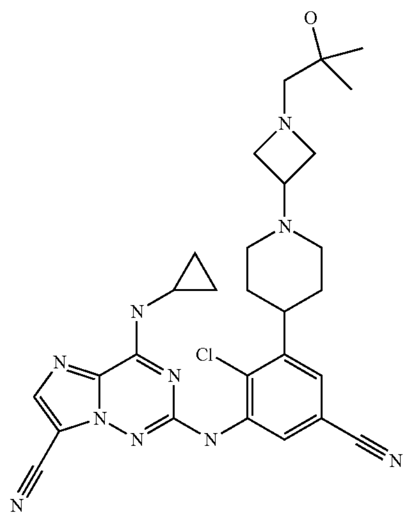 [SMILES: CC(C)(O)CN1CC(N2CCC(c3cc(C#N)cc(Nc4nc(NC5CC5)c5ncc(C#N)n5n4)c3Cl)CC2)C1] | 2-((2-chloro-5-cyano-3-(1-(1-(2-hydroxy-2-methylpropyl)-3-azetidinyl)-4-piperidinyl)phenyl)amino)-4-(cyclopropylamino)imidazo[2,1-f][1,2,4]triazine-7-carbonitrile | 561.09 | 3.80 |
| 325 | 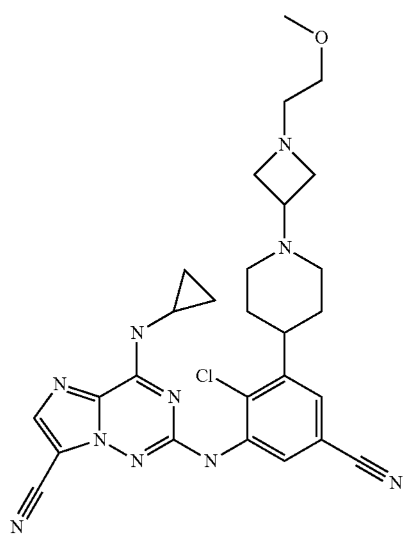 [SMILES: COCCN1CC(N2CCC(c3cc(C#N)cc(Nc4nc(NC5CC5)c5ncc(C#N)n5n4)c3Cl)CC2)C1] | 2-((2-chloro-5-cyano-3-(1-(1-(2-methoxyethyl)-3-azetidinyl)-4-piperidinyl)phenyl)amino)-4-(cyclopropylamino)imidazo[2,1-f][1,2,4]triazine-7-carbonitrile | 547.06 | 3.92 |

CHROMOLITH ® column 4.6 x 50 mm eluting with 10-90% aqueous methanol over 5 min. containing 0.1% TFA, 4 mL/min, monitoring at 220 nm.

Example 326

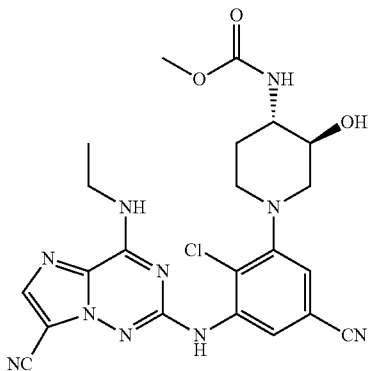 [SMILES: CCNc1nc(Nc2cc(C#N)cc(N3CC[C@H](NC(=O)OC)[C@@H](O)C3)c2Cl)nn2c(C#N)cnc12]

(+/−)methyl((3R,4R)-1-(2-chloro-5-cyano-3-((7-cyano-4-(ethylamino)imidazo[2,1-f][1,2,4]triazin-2-yl)amino)phenyl)-3-hydroxypiperidin-4-yl)carbamate Prepared in analogous manner as Example 171 from Intermediate 2 and example 171E MS (ESI) m/z 511.6 (M+1).

$^1$H NMR (500 MHz, DMSO-d6) δ 9.19 (br. s., 1H), 8.87 (s, 1H), 8.20 (s, 1H), 7.97 (d, J=1.7 Hz, 1H), 7.33 (d, J=1.7 Hz, 1H), 7.09 (d, J=8.0 Hz, 1H), 5.00 (d, J=5.4 Hz, 1H), 3.55 (s, 4H), 3.50-3.36 (m, 3H), 3.31-3.16 (m, 2H), 2.77 (t, J=11.1 Hz, 1H), 2.55 (br. s., 1H), 1.93-1.82 (m, 1H), 1.57 (qd, J=12.2, 4.1 Hz, 1H), 1.19 (t, J=7.2 Hz, 3H)

Example 327

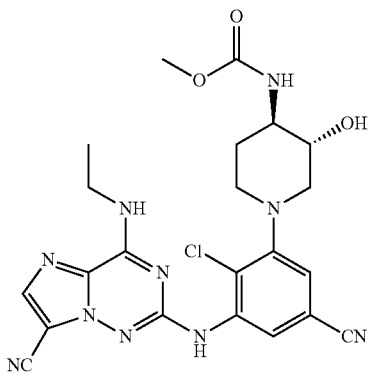 [SMILES: CCNc1nc(Nc2cc(C#N)cc(N3CC[C@@H](NC(=O)OC)[C@H](O)C3)c2Cl)nn2c(C#N)cnc12]

methyl((3R,4R)-1-(2-chloro-5-cyano-3-((7-cyano-4-(ethylamino)imidazo[2,1-f][1,2,4]triazin-2-yl)amino)phenyl)-3-hydroxypiperidin-4-yl)carbamate Prepared in similar way as Example 173 from intermediate 2 in place intermediate 6

MS (ESI): m/z 511.6 (M+1).

1H NMR (500 MHz, DMSO-d6) δ 9.26-9.10 (m, 1H), 8.86 (br. s., 1H), 8.20 (s, 1H), 7.97 (d, J=1.7 Hz, 1H), 7.33 (d, J=1.7 Hz, 1H), 7.09 (d, J=8.2 Hz, 1H), 4.99 (d, J=5.2 Hz, 1H), 3.55 (s, 4H), 3.50-3.36 (m, 3H), 3.31-3.17 (m, 2H), 2.77 (t, J=11.3 Hz, 1H), 2.55 (br. s., 1H), 1.92-1.81 (m, 1H), 1.62-1.49 (m, 1H), 1.19 (t, J=7.2 Hz, 3H)

Example 328

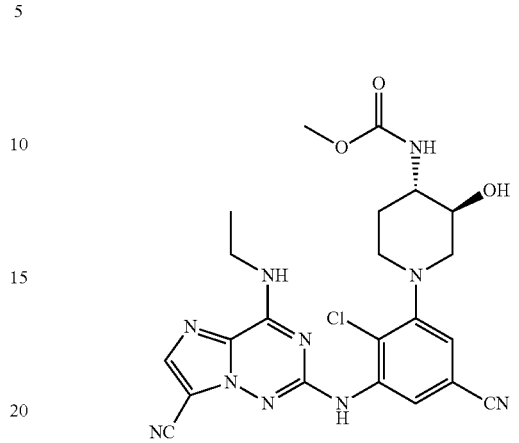

methyl((3S,4S)-1-(2-chloro-5-cyano-3-((7-cyano-4-(ethylamino)imidazo[2,1-f][1,2,4]triazin-2-yl)amino)phenyl)-3-hydroxypiperidin-4-yl)carbamate (328A): 4-(ethyl(4-methoxybenzyl)amino)-2-(methylsulfonyl)imidazo[2,1-f][1,2,4]triazine-7-carbonitrile (Intermediate 7, 70 mg, 0.181 mmol), methyl((3R,4R)-1-(3-amino-2-chloro-5-cyanophenyl)-3-((tert-butyldimethylsilyl)oxy)piperidin-4-yl)carbamate (Example 173D, 80 mg, 0.181 mmol) and Cs2CO3 (177 mg, 0.543 mmol) were mixed with DMF (2 mL) in an sealed microwave vial. The mixture was heated in oil bath at 60° C. for 2 hrs. The mixture was diluted with 50 ml EtOAc, then filtered. The filtrate was washed with water (3×50 ml), then brine; dried over MgSO₄, filtered and concentrated to dryness to give 140 mg of product, which will be used as it is.

(328B): methyl((3R,4R)-3-((tert-butyldimethylsilyl)oxy)-1-(2-chloro-5-cyano-3-((7-cyano-4-(ethyl(4-methoxybenzyl)amino)imidazo[2,1-f][1,2,4]triazin-2-yl)amino)phenyl)piperidin-4-yl)carbamate (140 mg, 0.188 mmol) was dissolved into Tetrahydrofuran (2 mL). TBAF 1M in THF (0.244 mL, 0.244 mmol) was added. The mixture was stirred at r.t. overnight. The mixture was concentrated to dryness, then diluted with EtOAc (50 ml) and washed with sat. NaHCO₃. The water layer was extracted with 20 ml EtOAc. The combined organic layer was washed with brine, dried over MgSO₄, filtered and concentrated to dryness to give 128 mg of product, which was used further without purification.

Example 328 methyl((3R,4R)-1-(2-chloro-5-cyano-3-((7-cyano-4-(ethyl(4-methoxybenzyl)amino)imidazo[2,1-f][1,2,4]triazin-2-yl)amino)phenyl)-3-hydroxypiperidin-4-yl)carbamate (128 mg, 0.183 mmol) was mixed with anisole (0.5 mL, 4.58 mmol) and DCE (2 mL). TFA (0.75 mL, 9.73 mmol) was added. The mixture was stirred at r.t. for 2 hrs. LC/MS showed that there was still large amount of s.m. left. The mixture was heated at 40° C. for 1 hr. The mixture was concentrated to dryness in high-vac. 10 ml 2N NH3/MeOH was added and stirred for 30 mins. The white precipitate was collected by filtration and washed with water and 2 ml cold MeOH and dried under air-suction to give 40 mg desired product methyl((3R,4R)-1-(2-chloro-5-cyano-3-((7-cyano-4-(ethylamino)imidazo[2,1-f][1,2,4]triazin-2-yl)amino)phenyl)-3-hydroxypiperidin-4-yl)carbamate.

MS (ESI) m/z 511.6

$^1$H NMR (500 MHz, DMSO-d6) δ 9.26-9.10 (m, 1H), 8.86 (br. s., 1H), 8.20 (s, 1H), 7.97 (d, J=1.7 Hz, 1H), 7.33 (d, J=1.7 Hz, 1H), 7.09 (d, J=8.2 Hz, 1H), 4.99 (d, J=5.2 Hz, 1H), 3.55 (s, 3H), 3.60-3.36 (m, 4H), 3.31-3.17 (m, 2H), 2.77 (t, J=11.3 Hz, 1H), 2.55 (br. s., 1H), 1.92-1.81 (m, 1H), 1.62-1.49 (m, 1H), 1.19 (t, J=7.2 Hz, 3H)

Alternative Synthesis of Example 328 methyl((3R,4R)-1-(2-chloro-5-cyano-3-((7-cyano-4-(ethylamino)imidazo[2,1-f][1,2,4]triazin-2-yl)amino)phenyl)-3-hydroxypiperidin-4-yl)carbamate (328A1): A 3-liter 3-neck flask was loaded with 4-chlorobenzonitrile (65 g, 472 mmol), equipped with a mechanical stirrer and internal thermometer. The flask was immersed into a (−5° C.) bath and sulfuric acid (700 ml) was added (forms a homogeneous solution). The solution was cooled to an internal temperature of 0° C. NBS (170 g, 945 mmol) was added to this solution. The reaction mixture is a slurry with solid NBS. The reaction mixture was stirred while the ice bath slowly melted. Stirring was continued for 16 hours while the reaction mixture warmed to room temperature. NMR analysis of an aliquot shows mostly mono-bromination. The reaction mixture was heated to 30° C. for 16 hours. The reaction mixture was poured onto 3.5 kg ice in a 6 liter 3-neck flask (that was immersed into an ice-water-bath) with mechanical stirrer and the resulting slurry stirred for 1 hour, then filtered. Solids were washed on the filter funnel with 10% NH4OH 2× (2 L), water 3× (2 L), and dried in a nitrogen stream. 148 g (crude quantitative) 3,5-dibromo-4-chlorobenzamide were obtained and used without further purification.

MS (ESI) m/z 310/312/314/316

$^1$H NMR (500 MHz, DMSO-d$_6$) δ 8.24 (s, 2H), 8.22 (bs, 1H), 7.72 (bs, 1H).

(328B1): Phosphoryl trichloride (90 ml, 966 mmol) was added to a suspension of 3,5-dibromo-4-chlorobenzamide (148 g, crude, ~380 mmol) in acetonitrile (1500 ml) at reflux. The reaction mixture was heated to reflux for additional 90 minutes. The reaction mixture was evaporated to dryness, then partitioned between EtOAc and aq. NaHCO3 solution. The organic layer was washed one more time with aq. NaHCO3 solution, once with brine, then dried over MgSO4, filtered and evaporated to dryness to give 3,5-dibromo-4-chlorobenzonitrile (110 g). The material was used without further purification in the next reaction.

$^1$H NMR (400 MHz, CDCl$_3$) δ 7.89 (s, 2H).

(328C1): A 5-liter 3-neck flask was loaded with 3,5-dibromo-4-chlorobenzonitrile (79 g, 188 mmol), (3R,4R)-4-((E)-(4-methoxybenzylidene)amino)piperidin-3-ol (47 g, 171 mmol), Pd2(dba)3 (5.15 g, 5.63 mmol), BINAP (10.62 g, 17.05 mmol), and Cs2CO3 (222 g, 682 mmol) and flushed with nitrogen. Dioxane (2000 ml) was added. The reaction mixture was heated to 95° C. for 18 hours. LCMS shows significant amount of remaining starting material. Additional Pd2(dba)3 (1.57 g, 1.715 mmol) and BINAP (2.13 g, 3.42 mmol) were added and the temperature increased to 100° C. for 6 hours. The flask was opened under a nitrogen blanket. Pd2(dba)3 (5.15 g, 5.63 mmol), XANTPHOS (9.87 g, 17.05 mmol) and O-t-butyl carbamate (49.9 g, 426 mmol) were added and the flask flushed with nitrogen again. The reaction mixture was heated to 100° C. for 24 hours. Celite was added to the reaction mixture, which was then stirred briefly and filtered through a layer of Celite. Solids were washed with DCM. The filtrate was concentrated to give a brown foam (115 g) that was purified by chromatography on silica (3000 g cartridge). (Loaded as a solution in DCM, eluted with a gradient from 100% DCM to 10% MeOH in DCM (to solvolyzed the imine), then a gradient from 10% to 20% of (2M NH3 in MeOH) in DCM). tert-butyl(3-((3R,4R)-4-amino-3-hydroxypiperidin-1-yl)-2-chloro-5-cyanophenyl)carbamate (27.3 g) was obtained.

MS (ESI) m/z 367/369

(328D1): A solution of tert-butyl(3-((3R,4R)-4-amino-3-hydroxypiperidin-1-yl)-2-chloro-5-cyanophenyl)carbamate (27.3 g, 55.8 mmol, ~75% pure) and DIPEA (48.7 mL, 279 mmol) in MeOH (500 mL) at 0° C. (acetone/ice bath, bath temp ~−10° C.) was treated with Methyl Chlorocarbonate (12.94 ml, 167 mmol) (slow addition, keeping internal temperature <+3° C.). The reaction was stirred for 1 hour at 0° C., then concentrated in vacuo. The residue was partitioned between EtOAc and 0.5 M citric acid. The organic layer was washed with sat. NaHCO3 solution and brine, then dried over MgSO4, filtered and evaporated to dryness. The crude was purified by chromatography on silica (750 g), using gradient elution from 100% hexanes to 50% EtOAc+50% DCM. Product containing fractions were combined and evaporated to a sticky oil to give methyl((3R,4R)-1-((3-N-Boc-amino)-2-chloro-5-cyanophenyl)-3-hydroxypiperidin-4-yl)carbamate (19.7 g).

MS (ESI) m/z 423/425, $^1$H NMR (400 MHz, DMSO-d$_6$) δ 8.90 (s, 1H), 7.71 (d, J=1.7 Hz, 1H), 7.36 (d, J=2.0 Hz, 1H), 7.08 (d, J=7 Hz, 1H), 4.98 (d, J=5.3 Hz, 1H), 3.56 (s, 3H), 3.57-3.49 (m, 2H), 3.45-3.13 (m, 3H), 2.77 (dt, J=1.5, 12.0 Hz, 1H), 1.92-1.84 (m, 1H), 1.62-1.48 (m, 1H), 1.49 (s, 9H).

(328E1): methyl((3R,4R)-1-(3-N-BOC-amino-2-chloro-5-cyanophenyl)-3-hydroxypiperidin-4-yl)carbamate (19.7 g, 34.8 mmol) was dissolved in DCE (100 ml). TFA (25 ml, 324 mmol) was added and the mixture stirred at room temperature for 21 hours under a gentle nitrogen stream. The reaction mixture was evaporated to dryness and dissolved in ammonia (2 molar in MeOH) (200 ml, 400 mmol) and stirred at room temperature for 2 hours. The reaction mixture was evaporated to dryness, then partitioned between aqueous NaHCO3 solution and EtOAc. The organic layer was washed brine, dried over MgSO4, filtered and evaporated to dryness (18.3 g pale brown foam). The crude was purified by column chromatography on silica (1500 g silica, gradient from 100% hexanes to (70% acetone+30% hexanes) over 60 column volumes). Product containing fractions were combined and evaporated to dryness to give a pale brown solidified foam methyl((3R,4R)-1-(3-amino-2-chloro-5-cyanophenyl)-3-hydroxypiperidin-4-yl)carbamate (10.9 g)

MS (ESI) m/z 323/325

$^1$H NMR (400 MHz, DMSO-d$_6$) δ 7.06 (b, 1H), 6.85 (d, J=2.0 Hz, 1H), 6.70 (d, J=1.8 Hz, 1H), 5.82 (b, 2H), 4.93 (d,

J=5.0 Hz, 1H), 3.55 (s, 3H), 3.55-3.45 (m, 1H), 3.35-3.30 (m, 1H), 3.28-3.21 (m, 1H), 3.17-3.11 (m, 1H), 2.67 (dt, J=2, 10 Hz, 1H), 2.43 (t, J=10.6 Hz, 1H), 1.89-1.82 (m, 1H), 1.56 (dq, J=4.0, 12.3 Hz, 1H).

(328F1): A 1 liter round bottom flask was loaded with 2-chloro-4-(ethyl(4-methoxybenzyl)amino)imidazo[2,1-f][1,2,4]triazine-7-carbonitrile (12.05 g, 35.2 mmol, Intermediate 10), methyl((3R,4R)-1-(3-amino-2-chloro-5-cyanophenyl)-3-hydroxypiperidin-4-yl)carbamate (10.9 g, 28.5 mmol), Pd(OAc)2 (377 mg, 1.679 mmol), XANTPHOS (990 mg, 1.711 mmol) and Potassium phosphate (17.1 g, 81 mmol). The vial was evacuated and back-filled with nitrogen 4 times. Toluene (320 mL) was added and the flask was again evacuated and back-filled with nitrogen 4 times, then heated with stirring to 90° C. for 16 hours. LCMS shows product and both starting materials as separate peaks. (~5:1:1 ratio by UV). The flask was opened under nitrogen, additional palladium(II) acetate (190 mg, 0.846 mmol), XANTPHOS (500 mg, 0.864 mmol) and potassium phosphate tribasic (7.5 g, 35.3 mmol) were added and the flask re-sealed, flushed with nitrogen again and heating continued for additional 6 hours. Celite was added to the reaction mixture. The suspension was stirred briefly, then filtered through a layer of Celite. Solids were washed with DCM. The filtrate was concentrated to a brown foam. (23.9 g). Purification by column chromatography on silica (1500 g) using a gradient from 100% CH2Cl2 to (50% EtOAc+50% CH2Cl2) gave methyl((3R,4R)-1-(2-chloro-5-cyano-3-((7-cyano-4-(ethyl(4-methoxybenzyl)amino)imidazo[2,1-f][1,2,4]triazin-2-yl)amino)phenyl)-3-hydroxypiperidin-4-yl)carbamate (11.2 g).

MS (ESI) m/z 629/631

Example 328A

Prepared in identical way as Example 328

Example 329

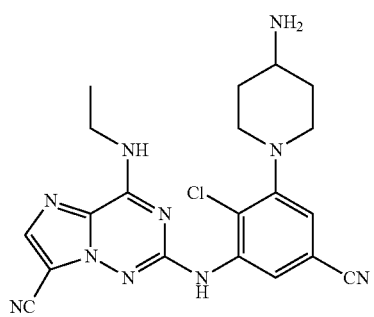 [SMILES: CCNc1nc(Nc2cc(C#N)cc(N3CCC(N)CC3)c2Cl)nn2c(C#N)cnc12]

2-((3-(4-aminopiperidin-1-yl)-2-chloro-5-cyanophenyl)amino)-4-(ethylamino)imidazo[2,1-f][1,2,4]triazine-7-carbonitrile Prepared in similar manner as intermediate 12
MS (ESI) m/z (M+1). 436.91
1H NMR (500 MHz, DMSO-d6) δ 9.19 (t, J=5.8 Hz, 1H), 8.86 (s, 1H), 8.20 (s, 1H), 7.95 (d, J=1.7 Hz, 1H), 7.33 (d, J=1.7 Hz, 1H), 7.23 (d, J=7.6 Hz, 1H), 3.55 (s, 3H), 3.51-3.42 (m, 3H), 3.28 (d, J=12.0 Hz, 2H), 2.78 (t, J=11.2 Hz, 2H), 1.87 (d, J=10.4 Hz, 2H), 1.65-1.54 (m, 2H), 1.19 (t, J=7.2 Hz, 3H)

Example 330

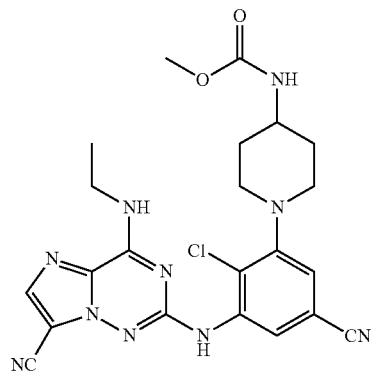 [SMILES: CCNc1nc(Nc2cc(C#N)cc(N3CCC(NC(=O)OC)CC3)c2Cl)nn2c(C#N)cnc12]

methyl(1-(2-chloro-5-cyano-3-((7-cyano-4-(ethylamino)imidazo[2,1-f][1,2,4]triazin-2-yl)amino)phenyl)piperidin-4-yl)carbamate 2-((3-(4-aminopiperidin-1-yl)-2-chloro-5-cyanophenyl)amino)-4-(ethylamino)imidazo[2,1-f][1,2,4]triazine-7-carbonitrile (Example 329) (40 mg, 0.092 mmol) was mixed with N,N-diisopropylethylamine (0.2 ml, 1.145 mmol) in MeOH (1 ml) and THF (1 ml). methyl carbonochloridate (0.05 ml, 0.646 mmol) was added.

The mixture was stirred at r.t. for 1 hr. LC/MS showed product formation. The white precipitate was formed and collected by filtration, washed with cold MeOH (15 ml), then water (5 ml) and dried with air-suction to give 31.7 mg of desired product.

MS (ESI): m/z 495.3
1H NMR (500 MHz, DMSO-d6) δ 9.19 (t, J=5.8 Hz, 1H), 8.86 (s, 1H), 8.20 (s, 1H), 7.95 (d, J=1.7 Hz, 1H), 7.33 (d, J=1.7 Hz, 1H), 7.23 (d, J=7.6 Hz, 1H), 3.55 (s, 3H), 3.51-3.42 (m, 3H), 3.28 (d, J=12.0 Hz, 2H), 2.78 (t, J=11.2 Hz, 2H), 1.87 (d, J=10.4 Hz, 2H), 1.65-1.54 (m, 2H), 1.19 (t, J=7.2 Hz, 3H)

Example 331

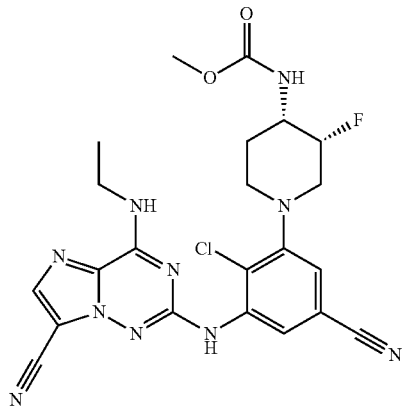 [SMILES: CCNc1nc(Nc2cc(C#N)cc(N3CC[C@H](NC(=O)OC)[C@H](F)C3)c2Cl)nn2c(C#N)cnc12]

methyl((3R,4S)-1-(2-chloro-5-cyano-3-((7-cyano-4-(ethylamino)imidazo[2,1-f][1,2,4]triazin-2-yl)amino)phenyl)-3-fluoro-4-piperidinyl)carbamate The title compound was prepared using procedure similar to Example 284
MS (ESI): m/z 512.94 (M+H)

Example 332

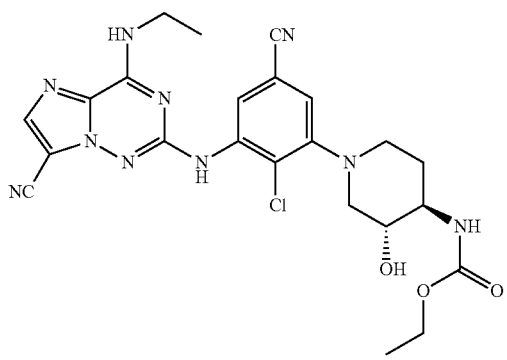 [SMILES: CCNc1nc(Nc2cc(C#N)cc(N3CC[C@@H](NC(=O)OCC)[C@H](O)C3)c2Cl)nn2c(C#N)cnc12]

ethyl((3R,4R)-1-(2-chloro-5-cyano-3-((7-cyano-4-(ethylamino)imidazo[2,1-f][1,2,4]triazin-2-yl)amino)phenyl)-3-hydroxypiperidin-4-yl)carbamate (332A): A solution of tert-butyl(3-((3R,4R)-4-amino-3-hydroxypiperidin-1-yl)-2-chloro-5-cyanophenyl)carbamate (Example 173A) (300 mg, 0.818 mmol) and DIPEA (0.428 mL, 2.453 mmol) in MeOH (15 mL) at 0° C. (ice bath) was treated with ethyl chloroformate (0.078 mL, 0.818 mmol). The reaction was stirred for 1 hour, then the mixture was concentrated in vacuo. To the residue was added EtOAc (50 ml) and the mixture washed with 0.5M citric acid, sat. NaHCO$_3$, water and brine. The solution was dried over Na$_2$SO$_4$ and solvents removed. To the crude material was added. DCE (5 mL) and TFA (2 mL, 26.0 mmol); the reaction stirred 2 h at 25° C. and solvents removed. The material was diluted with DCM and washed with sat. NaHCO$_3$ and water. The organics dried over Na$_2$SO$_4$ and removed solvent. The material was purified on silica gel 25% EtOAc-DCM to afford ethyl((3R,4R)-1-(3-amino-2-chloro-5-cyanophenyl)-3-hydroxypiperidin-4-yl)carbamate (110 mg).

MS (ESI): m/z 325

$^1$H NMR (500 MHz, DMSO-d$_6$) δ ppm 6.99-7.13 (1H, m), 6.83 (1H, d, J=1.83 Hz), 6.62-6.74 (1H, m), 5.78-5.85 (2H, m), 4.82-5.02 (1H, m), 3.54 (3H, s), 3.45-3.52 (1H, m), 3.27 (1H, br. s.), 3.08-3.16 (1H, m), 2.61-2.72 (1H, m), 2.41 (1H, s), 1.69-1.97 (1H, m), 1.34-1.67 (1H, m)

(332B): 2-chloro-4-(ethyl(4-methoxybenzyl)amino)imidazo[2,1-f][1,2,4]triazine-7-carbonitrile (42 mg, 0.123 mmol), ethyl((3R,4R)-1-(3-amino-2-chloro-5-cyanophenyl)-3-hydroxypiperidin-4-yl)carbamate (40 mg, 0.118 mmol), DPPF (4.58 mg, 8.26 umol), Cs$_2$CO$_3$ (65.4 mg, 0.201 mmol), Xantphos (6.83 mg, 0.012 mmol), Palladium (II)Acetate (7.95 mg, 0.035 mmol) and 1,4-dioxane (2 ml) were combined in a microwave vial. The vial was evacuated and backfilled with Nitrogen 3×. The reaction stirred at 100° C. for 3 hr. The reaction mixture cooled to 25° C., diluted with EtOAc and washed with brine and dried (Na$_2$SO$_4$). The solvents were removed and the material purified on silica gel 25% EtOAc in DCM to afford ethyl((3R,4R)-1-(2-chloro-5-cyano-3-((7-cyano-4-(ethyl(4-methoxybenzyl)amino)imidazo[2,1-f][1,2,4]triazin-2-yl)amino)phenyl)-3-hydroxypiperidin-4-yl)carbamate (50 mg).

MS (ESI): m/z 646

Example 332

To ethyl((3R,4R)-1-(2-chloro-5-cyano-3-((7-cyano-4-(ethyl(4-methoxybenzyl)amino)imidazo[2,1-f][1,2,4]triazin-2-yl)amino)phenyl)-3-hydroxypiperidin-4-yl)carbamate (50 mg, 0.068 mmol), in DCE (0.8 mL) was added anisole (0.1 mL, 0.915 mmol) and TFA (0.5 mL, 6.49 mmol); the mixture stirred 2 h at 25° C. and solvent was removed. 2N NH3/MeOH (5 ml) was added and the mixture stirred for 30 min at 25° C. The solution was stored at −20° C. and a white precipitate formed. The material was collected by filtration, washed with 20 ml cold MeOH, 5 ml ether and dried under air-suction for 0.5 h to afford ethyl ((3R,4R)-1-(2-chloro-5-cyano-3-((7-cyano-4-(ethylamino)imidazo[2,1-f][1,2,4]triazin-2-yl)amino)phenyl)-3-hydroxypiperidin-4-yl)carbamate (10 mg).

MS (ESI): m/z 525

$^1$H NMR (500 MHz, DMSO-d$_6$) δ 9.30-9.10 (m, 1H), 8.96-8.75 (m, 1H), 8.20 (s, 1H), 7.96 (d, J=1.8 Hz, 1H), 7.32 (d, J=1.8 Hz, 1H), 7.11-6.91 (m, 1H), 4.97 (d, J=5.5 Hz, 1H), 4.00 (d, J=7.0 Hz, 2H), 3.60-3.49 (m, 1H), 3.49-3.42 (m, 2H), 3.42-3.34 (m, 1H), 3.28 (d, J=8.1 Hz, 1H), 3.24-3.16 (m, 1H), 2.82-2.71 (m, 1H), 2.47 (br. s., 1H), 1.88 (d, J=8.7 Hz, 1H), 1.65-1.48 (m, 1H), 1.18 (td, J=7.1, 4.5 Hz, 6H)

The compounds listed below were prepared by the similar synthetic procedure used for Example 284

TABLE 12

| Example No. | Structure | Name | [M + H]$^+$ | HPLC Retention Time (min.)* |
|---|---|---|---|---|
| 333 | 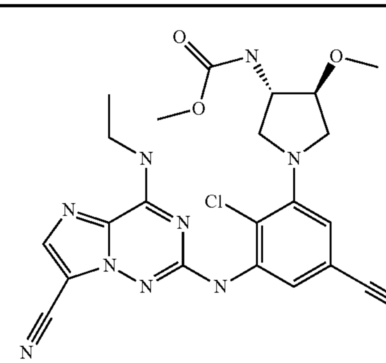 | Chiral methyl ((3S,4S)-1-(2-chloro-5-cyano-3-((7-cyano-4-(ethylamino)imidazo[2,1-f][1,2,4]triazin-2-yl)amino)phenyl)-4-methoxy-3-pyrrolidinyl)carbamate | 510.94 | 3.96 |

TABLE 12-continued

| Example No. | Structure | Name | [M + H]+ | HPLC Retention Time (min.)* |
|---|---|---|---|---|
| 334 | 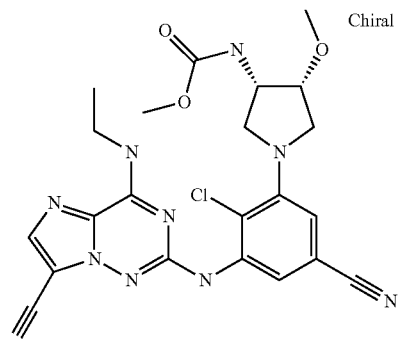 Chiral | methyl ((3S,4R)-1-(2-chloro-5-cyano-3-((7-cyano-4-(ethylamino)imidazo[2,1-f][1,2,4]triazin-2-yl)amino)phenyl)-4-methoxy-3-pyrrolidinyl)carbamate | 510.94 | 3.98 c |
| 335 | 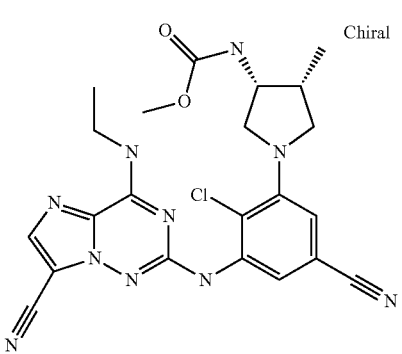 [SMILES: CCNc1nc(Nc2cc(C#N)cc(N3C[C@@H](C)[C@@H](NC(=O)OC)C3)c2Cl)nn2c(C#N)cnc12] Chiral | methyl ((3R,4R)-1-(2-chloro-5-cyano-3-((7-cyano-4-(ethylamino)imidazo[2,1-f][1,2,4]triazin-2-yl)amino)phenyl)-4-methyl-3-pyrrolidinyl)carbamate | 494.95 | 4.32 |
| 336 | 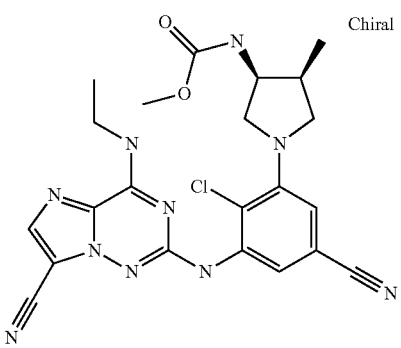 [SMILES: CCNc1nc(Nc2cc(C#N)cc(N3C[C@H](C)[C@H](NC(=O)OC)C3)c2Cl)nn2c(C#N)cnc12] Chiral | methyl ((3S,4S)-1-(2-chloro-5-cyano-3-((7-cyano-4-(ethylamino)imidazo[2,1-f][1,2,4]triazin-2-yl)amino)phenyl)-4-methyl-3-pyrrolidinyl)carbamate | 494.95 | 4.28 | a YMC S5 ODS 4.6 × 50 mm, 10-90% aqueous methanol containing 0.2% $H_3PO_4$, 5 min. gradient, monitored at 220 nm

Example 337

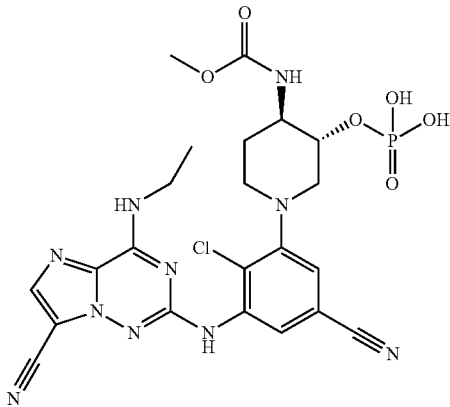 [SMILES: CCNc1nc(Nc2cc(C#N)cc(N3CC[C@@H](NC(=O)OC)[C@H](OP(=O)(O)O)C3)c2Cl)nn2c(C#N)cnc12]

methyl((3R,4R)-1-(2-chloro-5-cyano-3-((7-cyano-4-(ethylamino)imidazo[2,1-f][1,2,4]triazin-2-yl)amino)phenyl)-3-(phosphonooxy)piperidin-4-yl)carbamate To a suspension of methyl((3R,4R)-1-(2-chloro-5-cyano-3-((7-cyano-4-(ethylamino)imidazo[2,1-f][1,2,4]triazin-2-yl)amino)phenyl)-3-hydroxypiperidin-4-yl)carbamate (Example 328) (25 mg, 0.049 mmol) in DCM (2 mL) at 0° C., was added pyridine (0.012 mL, 0.147 mmol) followed by POCl₃ (0.014 mL, 0.147 mmol), DMAP (0.598 mg, 0.0048 mmol). After stirring for 15 min. reaction was warmed to 35° C. and stirring continued for overnight. After confirming the product formation by LC-MS, reaction mixture was hydrolyzed with water (2 mL) and stirred for 10 minutes at room temperature. The reaction was concentrated under vacuum and purified by preparative HPLC and collected fractions lyophilized to yield methyl((3R,4R)-1-(2-chloro-5-cyano-3-((7-cyano-4-(ethylamino)imidazo[2,1-f][1,2,4]triazin-2-yl)amino)phenyl)-3-(phosphonooxy)piperidin-4-yl)carbamate (22 mg) as an off white solid.

Preparative HPLC: Column: Inertsil ODS (19×250) mm×5 u; Solvent A=10 mM Ammonium acetate pH-4.5 with Acetic acid; Solvent B=MeOH; Time (min)/% B: 0/20, 10/70, 15/100; Flow Rate=16 mL/min; Wavelength=220 & 254 nm; Product Retention time=9.37 min.

MS (ESI): m/z 589.0

$^1$H NMR (400 MHz, DMSO-d₆) δ ppm 8.73 (br. S., 1H), 8.19 (s, 1H), 8.02 (s, 1H), 7.32 (s, 1H), 4.03-3.97 (m, 1H), 3.57-3.44 (m, 6H), 3.24-3.21 (m, 2H), 2.78-2.63 (m, 2H), 2.36-2.31 (m, 1H), 1.41-1.32 (m 1H), 1.22 (t, J=6.8 Hz, 3H)

Example 338

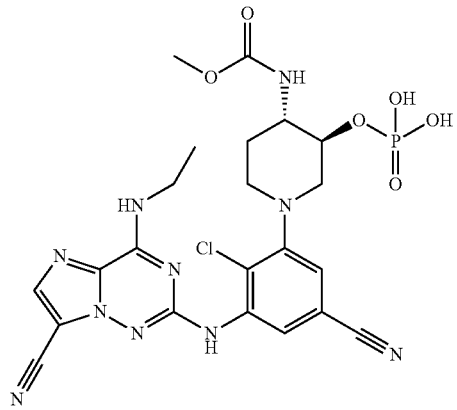 [SMILES: CCNc1nc(Nc2cc(C#N)cc(N3CC[C@H](NC(=O)OC)[C@@H](OP(=O)(O)O)C3)c2Cl)nn2c(C#N)cnc12]

methyl((3S,4S)-1-(2-chloro-5-cyano-3-((7-cyano-4-(ethylamino)imidazo[2,1-f][1,2,4]triazin-2-yl)amino)phenyl)-3-(phosphonooxy)-4-piperidinyl)carbamate Prepared in similar manner as Example 338 from Example 327.

MS (ESI): m/z 589.0

1H NMR (500 MHz, DMSO-d6) δ 9.19 (t, J=5.7 Hz, 1H), 8.85 (s, 1H), 8.20 (s, 1H), 8.02 (d, J=1.7 Hz, 1H), 7.35 (d, J=1.7 Hz, 1H), 7.13 (d, 7.9 Hz, 1H), 4.18 (m, 1H), 3.67 (m, 1H), 3.65 (s, 3H), 3.53-3.43 (m, 3H), 3.24 (m, 1H), 2.81 (m, 2H), 1.96 (m, 1H), 1.68 (dq, J=3.2, 12 Hz, 1H), 1.19 (t, J=7.2 Hz, 3H).

Example 339

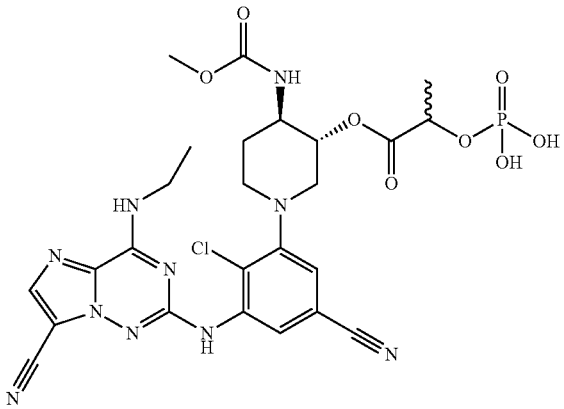 [SMILES: CCNc1nc(Nc2cc(C#N)cc(N3CC[C@@H](NC(=O)OC)[C@H](OC(=O)C(C)OP(=O)(O)O)C3)c2Cl)nn2c(C#N)cnc12]

rac(3R,4R)-1-(2-chloro-5-cyano-3-((7-cyano-4-(ethylamino)imidazo[2,1-f][1,2,4]triazin-2-yl)amino)phenyl)-4-((methoxycarbonyl)amino)piperidin-3-yl 2-(phosphonooxy)propanoate (339A): To a solution of methyl((3R,4R)-1-(2-chloro-5-cyano-3-((7-cyano-4-(ethyl(4-methoxybenzyl)amino)imidazo[2,1-f][1,2,4]triazin-2-yl)amino)phenyl)-3-hydroxypiperidin-4-yl)carbamate (0.040 g, 0.063 mmol), 2-((bis(benzyloxy)phosphoryl)oxy)propanoic acid (0.067 g, 0.19 mmol) in DCM (2 mL) was added DCC (0.039 g, 0.190 mmol) followed DMAP (0.77 mg, 0.006 mmol) and stirred at room temperature for 30 min. After completion of starting material (by LC-MS), reaction mixture was diluted with DCM (50 mL), filtered through celite and filtrate was washed with water and brine solution (5 mL). Combined organic extracts were dried over anhydrous Na₂SO₄, concentrated and purified by flash chromatography on silica gel using an ISCO system (eluted with 1:1 Hexanes and EtOAc) to give diastereomeric mixture of (3R,4R) 1-(2-chloro-5-cyano-3-((7-cyano-4-(ethyl(4-methoxybenzyl)amino)imidazo[2,1-f][1,2,4]triazin-2-yl)amino)phenyl)-4((methoxycarbonyl)amino)piperidin-3-yl-2-((bis(benzyloxy)phosphoryl)oxy)propanoate (0.060 g) as gummy liquid.

MS (ESI) m/z 962.1 (M−1)

Example 339

To a solution of (3R,4R)-1-(2-chloro-5-cyano-3-((7-cyano-4-(ethyl(4-methoxybenzyl)amino)imidazo[2,1-f][1,2,4]triazin-2-yl)amino)phenyl)-4-((methoxycarbonyl)amino)piperidin-3-yl-2-((bis(benzyloxy)phosphoryl)oxy)propanoate (0.060 g, 0.062 mmol) in DCE (3 mL) was added anisole (0.028 mL, 0.258 mmol) followed by TFA (25% in DCE) (4.98 mL, 16.15 mmol) and stirred at 35° C. for overnight. After completion of the starting material (by LC-MS), solvent was removed under vacuum at 30° C. (LC-MS showed PMB cleavage along with anticipated de-benzylation). The crude mixture was purified by reverse phase preparative HPLC to give diastereomeric mixture of (3R,4R)-1-(2-chloro-5-cyano-3-((7-cyano-4-(ethylamino)imidazo[2,1-f][1,2,4]triazin-2-yl)amino)phenyl)-4-((methoxycarbonyl)amino)piperidin-3-yl-2-(phosphonooxy)propanoate (0.014 g) as an off-white solid.

Preparative HPLC: Column: Sunfire C18 (19×150) mm×5 u; Solvent A=10 mM Ammonium acetate pH-4.6 adjusted with AcOH; Solvent B=Acetonitrile; Time (min)/% B: 0/20, 8/70, 12/70; Flow Rate=16 mL/min; Wavelength=220 & 254 nm; Product Retention time=7.066 min.

MS (ESI) m/z 663.0
$^1$H NMR (400 MHz, DMSO-$d_6$) δ ppm 8.98-9.36 (br. m, 1H), 8.25 (s, 1H), 8.03-7.96 (m, 1H), 7.49-7.24 (br. m, 3H), 4.85-4.72 (m, 1H), 4.52-4.42 (m, 1H), 3.68-3.52 (m, 9H), 2.89-2.71 (m, 3H), 2.00-1.93 (m, 1H), 1.82-1.66 (m, 1H) 1.29-1.14 (m, 6H)

Example 340

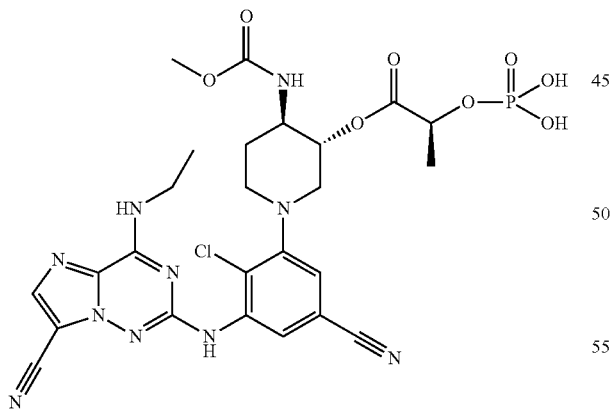

(S)-(3R,4R)-1-(2-chloro-5-cyano-3-((7-cyano-4-(ethylamino)imidazo[2,1-f][1,2,4]triazin-2-yl)amino)phenyl)-4-((methoxycarbonyl)amino)piperidin-3-yl 2-(phosphonooxy)propanoate (340A): To a solution of methyl((3R,4R)-1-(2-chloro-5-cyano-3-((7-cyano-4-(ethyl(4-methoxybenzyl)amino)imidazo[2,1-f][1,2,4]triazin-2-yl)amino)phenyl)-3-hydroxypiperidin-4-yl)carbamate (0.090 g, 0.143 mmol) in DCM (3 mL) was added (S)-2-((bis(benzyloxy)phosphoryl)oxy)propanoic acid (0.150 g, 0.428 mmol) followed by DCC (0.088 g, 0.428 mmol), DMAP (1.74 mg, 0.014 mmol) and stirred at room temperature for overnight. After completion of starting material (by LC-MS), reaction mixture was diluted with DCM (50 mL), filtered through celite and filtrate was washed with water and brine solution (5 mL). Combined organic extracts were dried over anhydrous Na$_2$SO$_4$, concentrated to give (S)-((3R,4R)-1-(2-chloro-5-cyano-3-(7-cyano-4-(ethyl(4-methoxybenzyl)amino)imidazo[1,2-f][1,2,4]triazin-2-ylamino)phenyl)-4-(methoxycarbonylamino)piperidin-3-yl)-2-(bis(benzyloxy)phosphoryloxy) propanoate (0.1 g) as gummy liquid. This was taken for next step without any purification. MS m/z 963.2

Example 340

Prepared using the similar procedure as used for Example 339.

MS (ESI) m/z 663.0
$^1$H NMR (400 MHz, DMSO-$d_6$) δ ppm 9.17 (br. s, 1H), 8.86 (br. s, 1H), 8.18 (s, 1H), 7.95 (s, 1H), 7.39-7.29 (m, 2H), 7.13 (br. s, 1H), 6.57 (br. s, 1H), 4.83-4.78 (m, 1H), 4.57-4.46 (m, 1H), 3.71-3.47 (m, 8H), 2.88-2.72 (m, 2H), 1.95-1.91 (m, 1H), 1.78-1.67 (m, 1H), 1.29 (d, J=6.78 Hz, 3H) 1.22-1.13 (m, 3H)

Example 341

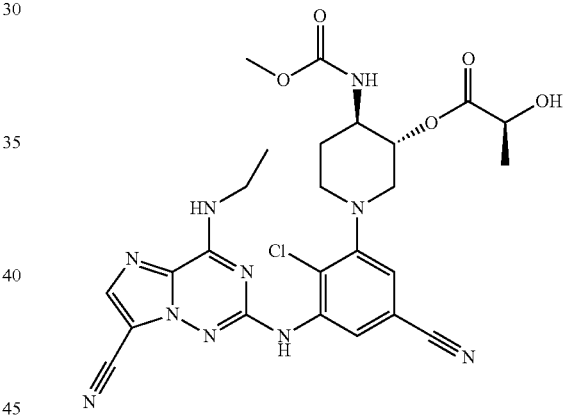

(S)-(3R,4R)-1-(2-chloro-5-cyano-3-((7-cyano-4-(ethylamino)imidazo[2,1-f][1,2,4]triazin-2-yl)amino)phenyl)-4-((methoxycarbonyl)amino)piperidin-3-yl 2-hydroxypropanoate (341A): A mixture of (S)-methyl 2-hydroxypropanoate (1.5 g, 14.41 mmol), 1-(chloromethyl)-4-methoxybenzene (3.38 g, 21.61 mmol), DIPEA (4.03 ml, 23.05 mmol) and sodium iodide (0.150 g, 1.001 mmol) was heated to 150° C. for 2 h. Reaction mixture then was cooled to room temperature diluted with EtOAc (100 mL) and washed with saturated NaHCO3 solution (2×50 mL) and brine. Combined organic extracts were dried over anhydrous Na$_2$SO$_4$ and concentrated. The crude mixture was purified by flash chromatography on silica gel using an ISCO system (eluted with 9:1 Hexanes and EtOAc) to give (S)-methyl 2-((4-methoxybenzyl)oxy)propanoate (2 g) as a gummy liquid.
$^1$H NMR (300 MHz, DMSO-$d_6$) δ ppm 7.25 (d, J=6.9 Hz, 2H), 6.91 (d, J=6.9 Hz, 2H), 4.48 (d, J=10.5 Hz, 1H), 4.34 (d, J=10.5 Hz, 1H), 4.11-4.04 (m, 1H), 3.74 (s, 3H), 3.67 (s, 3H), 1.29 (d, J=6.6 Hz, 3H)

(341B): To a solution of (S)-methyl 2-((4-methoxybenzyl)oxy)propanoate (1 g, 4.46 mmol) in THF (20 mL) and MeOH (6 mL) at 0° C. was added lithium hydroxide (0.225 g, 9.38 mmol) and stirred for 3 h. then warmed to room temperature in 30 min. After completion of starting material (by TLC), reaction mixture was concentrated and the resultant residue was taken EtOAc (100 ml), acidified by 1.5N HCl (up to pH 1) and extracted into EtOAc (2×100 ml). Combined organic extracts were dried over anhydrous $Na_2SO_4$, concentrated to give (S)-2-((4-methoxybenzyl)oxy)propanoic acid (0.6 g) was obtained as a gummy liquid.

$^1$H NMR (400 MHz, DMSO-$d_6$) δ ppm 12.41 (br. s, 1H), 7.27 (d, J=4.8 Hz, 2H), 6.91 (d, J=4.8 Hz, 2H), 4.51 (d, J=11.4 Hz, 1H), 4.32 (d, J=11.4 Hz, 1H), 3.99-3.92 (m, 1H), 3.74 (s, 3H), 1.29 (d, J=4.8 HZ, 3H)

(341C): To a solution of methyl((3R,4R)-1-(2-chloro-5-cyano-3-((7-cyano-4-(ethyl(4-methoxybenzyl)amino)imidazo[2,1-f][1,2,4]triazin-2-yl)amino)phenyl)-3-hydroxypiperidin-4-yl)carbamate (0.050 g, 0.079 mmol) in DCM (2 mL) was added (S)-2-((4-methoxybenzyl)oxy)propanoic acid (0.050 g, 0.238 mmol) followed by DCC (0.049 g, 0.238 mmol), DMAP (0.968 mg, 0.008 mmol) and stirred at room temperature for 1 h. After completion of starting material (by TLC), reaction mixture was diluted with DCM (15 mL), filtered through celite and filtrate was washed with water (10 mL) and brine. Combined organic extracts were dried over anhydrous $Na_2SO_4$, concentrated and purified by flash chromatography on silica gel using an ISCO system (eluted with 4:6 Hexanes and EtOAc) to give (S)-(3R,4R)-1-(2-chloro-5-cyano-3-((7-cyano-4-(ethyl(4-methoxybenzyl)amino)imidazo[2,1-f][1,2,4]triazin-2-yl)amino)phenyl)-4-((methoxycarbonyl)amino)piperidin-3-yl-2-((4-methoxybenzyl)oxy)propanoate (0.050 g) as a gummy solid. The purity of the compound was 57% with major DCU impurity. Product was taken for next step without further purification.

MS (ESI) m/z 823.2

Example 341

To a solution of (S)-(3R,4R)-1-(2-chloro-5-cyano-3-((7-cyano-4-(ethyl(4-methoxybenzyl)amino)imidazo[2,1-f][1,2,4]triazin-2-yl)amino)phenyl)-4-((methoxycarbonyl)amino)piperidin-3-yl 2-((4-methoxybenzyl)oxy)propanoate (0.050 g, 0.061 mmol) in DCE (3 mL) was added anisole (0.027 ml, 0.243 mmol) followed by TFA (25% in DCE) (4.68 mL, 15.18 mmol) and stirred at 35° C. for overnight. The reaction mixture was concentrated at 30° C. and resultant residue was washed with diethylether to give solid and this was purified by reverse phase preparative HPLC and collected fractions were lyophilized to give (S)-(3R,4R)-1-(2-chloro-5-cyano-3-((7-cyano-4-(ethylamino)imidazo[2,1-f][1,2,4]triazin-2-yl)amino)phenyl)-4-((methoxycarbonyl)amino)piperidin-3-yl 2-hydroxypropanoate (0.005 g) as a white solid.

Preparative HPLC: Column: SUNFIRE C-18 (19×150) mm×5 u; Solvent A=10 mM Ammonium acetate pH-4.5 with AcOH; Solvent B=Acetonitrile; Time (min)/% B: 0/30, 12/70, 15/100; Flow Rate=16 mL/min; Wavelength=220 & 254 nm; Product Retention time=8.30 min.

MS (ESI) (ESI) m/z 583.2

$^1$H NMR (400 MHz, DMSO-$d_6$) δ ppm 9.18 (t, J=5.65 Hz, 1H), 8.90 (s, 1H), 8.19 (s, 1H), 7.95 (d, J=1.76 Hz, 1H), 7.38 (d, J=1.76 Hz, 1H), 7.28-7.25 (m, 1H), 5.37 (d, J=5.77 Hz, 1H), 4.83-4.76 (m, 1H), 4.14-4.05 (m, 1H), 3.70-3.59 (m, 1H), 3.53 (s, 3H), 3.49-3.27 (m, 4H), 2.91-2.71 (m, 2H), 1.94 (d, J=9.03 Hz, 1H), 1.80-1.67 (m, 1H), 1.24 (d, J=7.03 Hz, 3H), 1.18 (t, J=7.15 Hz, 3H)

Example 342

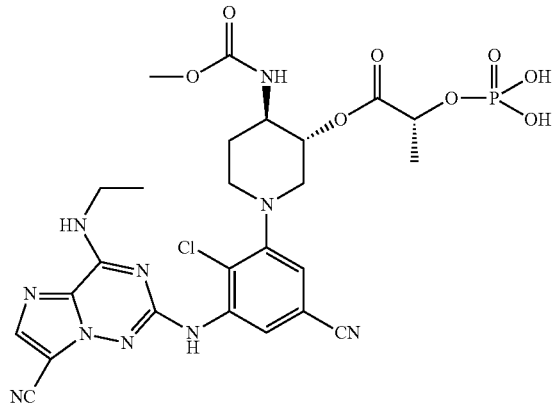 [SMILES: CCNc1nc(Nc2cc(C#N)cc(N3CC[C@@H](NC(=O)OC)[C@H](OC(=O)[C@@H](C)OP(=O)(O)O)C3)c2Cl)nn2c(C#N)cnc12]

(R)-(3R,4R)-1-(2-chloro-5-cyano-3-((7-cyano-4-(ethylamino)imidazo[2,1-f][1,2,4]triazin-2-yl)amino)phenyl)-4-((methoxycarbonyl)amino)piperidin-3-yl 2-(phosphonooxy)propanoate Prepared using method similar to Example 340 and purified using preparative HPLC as below.

Preparative HPLC: Column: Sunfire C-18 (250×19) mm×5 u; Solvent A=10 mm ammonium acetate ph 4.6 adjusted by AcOH; Solvent B=Acetonitrile; Time (min)/% B: 0/10, 10/50, 15/100; Flow Rate=16 mL/min; Wavelength=220 & 254 nm; Product Retention time=11.04 min.

MS (ESI) m/z 663.0 (M+1)

$^1$H NMR (400 MHz, DMSO-$d_6$) δ ppm 9.16 (br. s, 1H), 8.21-8.16 (m, 1H), 8.02-7.96 (m, 1H), 7.37-7.32 (m, 3H), 4.80-4.74 (m, 1H), 4.48-4.44 (m, 1H), 3.63-3.34 (m, 8H), 2.88-2.70 (m, 3H), 1.92-1.89 (m, 1H), 1.79-1.74 (m, 1H), 1.24-1.16 (m, 6H)

Example 343

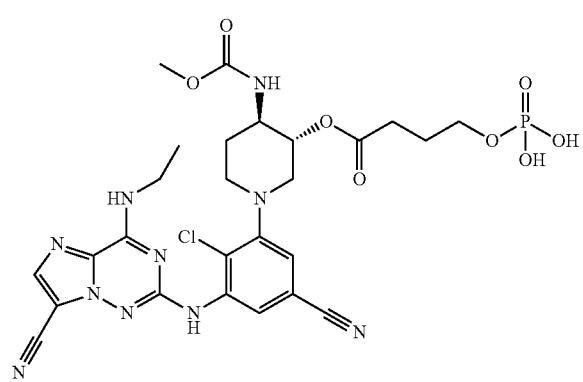 [SMILES: CCNc1nc(Nc2cc(C#N)cc(N3CC[C@@H](NC(=O)OC)[C@H](OC(=O)CCCOP(=O)(O)O)C3)c2Cl)nn2c(C#N)cnc12]

(3R,4R)-1-(2-chloro-5-cyano-3-((7-cyano-4-(ethylamino)imidazo[2,1-f][1,2,4]triazin-2-yl)amino)phenyl)-4-((methoxycarbonyl)amino)piperidin-3-yl 4-(phosphonooxy)butanoate (343A): To a suspension of methyl((3R,4R)-1-(2-chloro-5-cyano-3-((7-cyano-4-(ethyl(4-methoxybenzyl)amino)imidazo[2,1-f][1,2,4]triazin-2-yl)amino)phenyl)-3-hydroxypiperidin-4-yl)carbamate (100 mg, 0.158 mmol) and 4-((di-tert-butoxyphosphoryl)oxy)butanoic acid (141 mg, 0.475 mmol) in DCM (5 mL) at 0° C., was added DCC (98 mg, 0.475 mmol) followed by DMAP (1.936 mg, 0.016 mmol) and stirred at room temperature for overnight. After completion of the starting material (by LC-MS), reaction mixture was diluted with DCM (2 mL) and filtered through celite and filtrate was washed with water and brine. Combined organic extracts were dried over anhydrous $Na_2SO_4$, concentrated. The resultant residue was purified by flash chromatography on silica gel using an ISCO system (eluted with 7:3 Hexanes and EtOAc) to afford (3R,4R)-1-(2-chloro-5-cyano-3-((7-cyano-4 (ethyl(4-methoxybenzyl)amino)imidazo[2,1-f][1,2,4]triazin-2-yl)amino)phenyl)-4-((methoxycarbonyl)amino) piperidin-3-yl 4-((di-tert-butoxyphosphoryl)oxy)butanoate (72 mg) as pale yellow solid.

MS (ESI) m/z 910.2

Example 343

To a solution of (3R,4R)-1-(2-chloro-5-cyano-3-((7-cyano-4-(ethyl(4-methoxybenzyl)amino)imidazo[2,1-f][1,2,4]triazin-2-yl)amino)phenyl)-4-((methoxycarbonyl)amino)piperidin-3-yl 4-((di-tert-butoxyphosphoryl)oxy) butanoate (72 mg, 0.079 mmol) in DCE (2 mL) at 0° C. was added TFA (25% in DCE) (6.10 mL, 19.79 mmol) followed by anisole (0.035 mL, 0.317 mmol) and stirred at 35° c. for overnight. After completion of the starting material (by LC-MS), reaction was concentrated and purified by reverse phase preparative HPLC and collected fractions were lyophilized to give (3R,4R)-1-(2-chloro-5-cyano-3-((7-cyano-4-(ethylamino)imidazo[2,1-f][1,2,4]triazin-2-yl)amino)phenyl)-4-((methoxycarbonyl)amino)piperidin-3-yl 4-(phosphonooxy)butanoate (4 mg) as an off white solid.

Preparative HPLC: Column: Symmetry C-18(250×19) mm, 7 u; Solvent A=10 mM Ammonium acetate; Solvent B=Acetonitrile; Time (min)/% B: 0/10, 10/50; Flow Rate=16 mL/min; Wavelength=220 & 254 nm; Product Retention time=11.75 min.

MS (ESI) m/z 677.0 $^1$H NMR (400 MHz, DMSO-$d_6$) δ ppm 8.18-8.14 (m, 1H), 8.95-8.89 (m, 2H), 7.63-7.59 (m, 1H), 7.39-7.22 (m, 4H), 4.79-4.71 (m, 1H), 3.65-3.42 (m, 10H), 3.28-3.22 (m 1H), 2.85-2.80 (m 1H), 2.64-2.55 (m, 1H), 2.23-2.20 (m, 2H), 1.92-1.89 (m, 1H), 1.71-1.65 (m, 2H), 1.18-1.11 (m, 3H)

Example 344

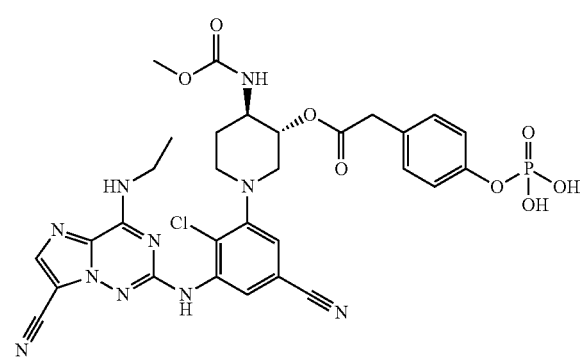 [SMILES: CCNc1nc(Nc2cc(C#N)cc(N3CC[C@@H](NC(=O)OC)[C@H](OC(=O)Cc4ccc(OP(=O)(O)O)cc4)C3)c2Cl)nn2c(C#N)cnc12]

(3R,4R)-1-(2-chloro-5-cyano-3-((7-cyano-4-(ethyl-amino)imidazo[2,1-f][1,2,4]triazin-2-yl)amino)phenyl)-4-((methoxycarbonyl)amino)piperidin-3-yl 2-(4-(phosphonooxy)phenyl)acetate Prepared using methodology similar to the one used for Example 343

MS (ESI) m/z 725
$^1$H NMR (400 MHz, DMSO-$d_6$) δ ppm 8.19 (s, 1H), 7.90 (d, J=1.51 Hz, 1H), 7.36 (d, J=1.51 Hz, 1H), 7.31-7.27 (m, 1H), 7.04 (br. s, 4H), 6.80-6.65 (br., 1H), 4.81-4.76 (m, 1H), 3.65-3.42 (m, 10H), 3.33-3.20 (m, 2H) 2.87 (t, J=10.04 Hz, 1H), 2.73 (t, J=10.67 Hz, 1H), 1.94 (br. m, 1H), 1.78-1.70 (m, 1H), 1.13 (t, J=7.15 Hz, 3H)

Example 345

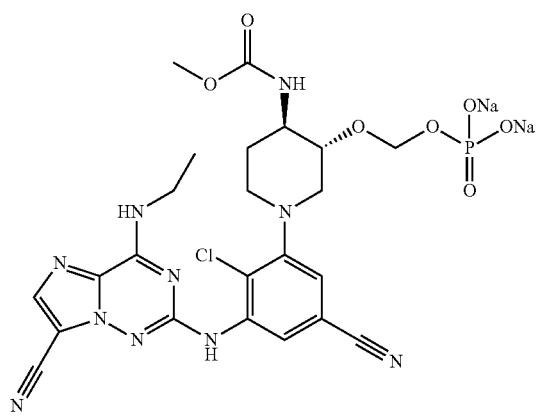

sodium (((3R,4R)-1-(2-chloro-5-cyano-3-((7-cyano-4-(ethylamino)imidazo[2,1-f][1,2,4]triazin-2-yl)amino)phenyl)-4-((methoxycarbonyl)amino)piperidin-3-yl)oxy)methyl phosphate (345A): To a stirred solution of methyl((3R,4R)-1-(2-chloro-5-cyano-3-((7-cyano-4-(ethylamino)imidazo[2,1-f][1,2,4]triazin-2-yl)amino)phenyl)-3-hydroxypiperidin-4-yl) carbamate (Example 328) (25 mg, 0.049 mmol) in acetic anhydride (0.046 ml, 0.489 mmol) at 0° C. was added DMSO (0.052 ml, 0.734 mmol) followed by acetic acid (0.084 ml, 1.468 mmol) and stirring continued for 4 day at room temperature. LCMS showed approx 45% desired compound, with no starting material remaining. Reaction mixture was diluted with ethyl acetate and washed with 10% $Na_2CO_3$ (3 ml) and brine. Combined organic extracts were dried over anhydrous $Na_2SO_4$ and concentrated. Resulted 30 mg crude residue was purified by reverse phase preparative HPLC and collected fractions were lyophilized to give methyl((3R,4R)-1-(2-chloro-5-cyano-3-((7-cyano-4-(ethyl-amino)imidazo[2,1-f][1,2,4]triazin-2-yl)amino)phenyl)-3-((methylthio)methoxy)piperidin-4-yl)carbamate (18 mg) as an off white solid Preparative HPLC: Column: Inertsil ods (250×19) mm, 5 u; Solvent A=10 mM Ammonium acetate pH-4.5 with AcOH; Solvent B=Acetonitrile; Time (min)/% B: 0/30, 10/70, 15/100; Flow Rate=16 mL/min; Wavelength=220 & 254 nm; Product Retention time=18.84 min.

LC-MS (ESI) m/z 571.2
$^1$H NMR (400 MHz, DMSO-$d_6$) δ ppm 9.21-9.15 (m, 1H), 9.87 (s, 1H), 8.20 (s, 1H), 7.99 (s, 1H), 7.37 (s, 1H), 7.20-7.15 (m, 1H), 4.73 (s, 2H), 4.04 (s, 3H), 3.71-3.39 (m, 8H), 3.28-3.19 (m, 1H), 2.80-2.73 (m, 1H), 2.62-2.58 (m, 1H), 1.86-1.82 (m, 1H), 1.72-1.63 (m, 1H), 1.19 (t, J=5.2 Hz, 3H)

Example 345

To a stirred solution of methyl((3R,4R)-1-(2-chloro-5-cyano-3-((7-cyano-4-(ethylamino)imidazo[2,1-f][1,2,4]triazin-2-yl)amino)phenyl)-3-((methylthio)methoxy)piperidin-4-yl)carbamate (18 mg, 0.032 mmol) in THF (2 mL) at 0° C. was added NIS (14.18 mg, 0.063 mmol) followed by crystalline phosphoric acid (15.44 mg, 0.158 mmol) and allowed to warm to room temperature in 1 h. After TLC showed completion of starting material, reaction mixture was diluted with methanol (2 ml) and treated with 1M $Na_2S_2O_3$ until it becomes colorless, then pH adjusted to 10 (approx) by addition of solid $Na_2CO_3$. Resultant precipitate was removed by filtration and submitted for LC-MS, which showed major product. The filtrate was concentrated and lyophilized to give crude off white solid. This was purified by reverse phase preparative HPLC to give pure sodium (((3R,4R)-1-(2-chloro-5-cyano-3-((7-cyano-4-(ethylamino)imidazo[2,1-f][1,2,4]triazin-2-yl)amino)phenyl)-4-((methoxycarbonyl)amino)piperidin-3-yl)oxy)methyl phosphate (9 mg) as an off white solid.

Preparative HPLC: Column: Sunfire C-18 (250×19) mm, 5 u; Solvent A=water; Solvent B=Acetonitrile; Time (min)/% B: 0/10, 10/50, 15/100; Flow Rate=16 mL/min; Wavelength=220 & 254 nm; Product Retention time=5.74 min.

LC-MS (ESI) m/z 619.0 (M−1) (of corresponding acid)
$^1$H NMR (400 MHz, DMSO-$d_6$) δ ppm 8.10 (s, 1H), 8.07 (br. s, 1H), 7.24 (br. s, 1H), 4.87-4.78 (m, 2H), 3.96-3.88 (m, 1H), 3.56-3.47 (m, 8H), 3.28-3.15 (m, 2H), 2.69-2.50 (m, 2H), 2.05 (br. d, J=8.4 Hz, 1H), 1.53-1.48 (m, 1H), 1.20-1.11 (m, 3H)

Example 346

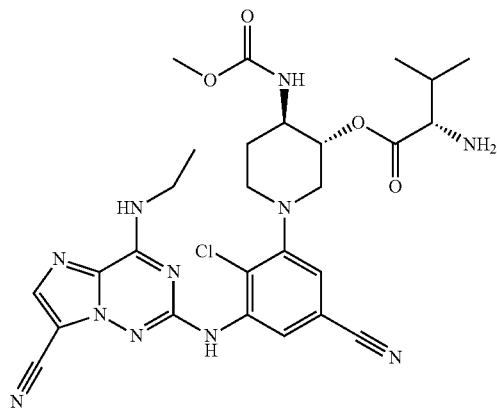 [SMILES: CCNc1nc(Nc2cc(C#N)cc(N3CC[C@@H](NC(=O)OC)[C@H](OC(=O)[C@@H](N)C(C)C)C3)c2Cl)nn2c(C#N)cnc12]

(S)-(3R,4R)-1-(2-chloro-5-cyano-3-((7-cyano-4-(ethylamino)imidazo[2,1-f][1,2,4]triazin-2-yl)amino)phenyl)-4-((methoxycarbonyl)amino)piperidin-3-yl 2-amino-3-methylbutanoate Prepared using methodology similar to the one used for Example 194
MS (ESI) m/z 610.2
$^1$H NMR (400 MHz, DMSO-$d_6$) δ ppm 8.20 (s, 1H), 7.98 (d, J=1.76 Hz, 1H), 7.37 (d, J=1.76 Hz, 1H), 7.27 (d, J=8.53 Hz, 1H), 6.52 (br. s, 1H), 6.29 (br. s, 1H), 4.83-4.79 (m, 1H), 3.74-3.61 (m, 1H), 3.53 (s, 3H), 3.46 (q, J=7.28 Hz, 4H), 3.09 (d, J=5.52 Hz, 1H), 2.94-2.83 (m, 1H) 2.76 (t, J=10.54 Hz, 1H), 1.98-1.69 (m, 4H), 1.26-1.12 (m, 4H), 0.87 (d, J=6.78 Hz, 3H), 0.81 (d, J=6.78 Hz, 3H)

Example 347

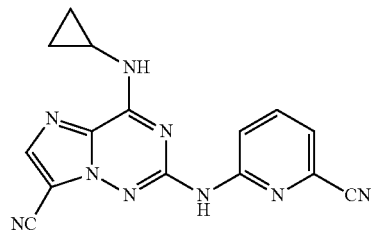 [SMILES: N#Cc1cccc(Nc2nc(NC3CC3)c3ncc(C#N)n3n2)n1]

2-((6-cyanopyridin-2-yl)amino)-4-(cyclopropylamino)imidazo[2,1-f][1,2,4]triazine-7-carbonitrile (347A): To a round bottom flask charged with methyl 6-((tert-butoxycarbonyl)amino)picolinate (1 g, 3.96 mmol) was added ammonia in MeOH (10 ml, 70.0 mmol). The reaction mixture was stirred at rt 3 h. The reaction mixture was concentrated in vacuo, providing a white fluffy solid. Material carried forward as is.
MS (ES−) m/z 236.4 (M−H)
$^1$H NMR (400 MHz, CHLOROFORM-d) δ 8.12 (dd, J=7.9, 1.3 Hz, 1H), 7.90-7.80 (m, 2H), 7.54 (d, J=11.0 Hz, 1H), 7.17 (br. s., 1H), 5.51 (br. s., 1H), 1.55 (s, 9H)

(347B): To a round bottom flask charged with tert-butyl (6-carbamoylpyridin-2-yl)carbamate (0.940 g, 3.96 mmol) in dichloromethane (7.92 ml) was added triethylamine (1.380 ml, 9.90 mmol). The reaction mixture was cooled to 0° C. and trifluoroacetic anhydride (0.671 ml, 4.75 mmol) was added dropwise. The reaction mixture was stirred at 0° C. 90 min. The reaction mixture was quenched with saturated aqueous sodium bicarbonate and transferred to a separatory funnel. The aqueous layer was extracted with dichloromethane (2×). The combined organics were washed with brine, dried over anhydrous sodium sulfate, filtered and concentrated in vacuo. The crude residue was purified by column chromatography on the Isco system (40 g, 0-15% EtOAc/Hex) to provide tert-butyl(6-cyanopyridin-2-yl)carbamate (0.538 g).
MS (ES−) m/z 218.3 (M−H)
$^1$H NMR (400 MHz, CHLOROFORM-d) δ 8.22 (dd, J=8.7, 0.8 Hz, 1H), 7.77 (t, J=7.9 Hz, 1H), 7.36 (dd, J=7.5, 0.9 Hz, 1H), 7.31 (br. s., 1H), 1.54 (s, 9H)

(347C): To a round bottom flask charged with tert-butyl (6-cyanopyridin-2-yl)carbamate (0.5383 g, 2.455 mmol) in dichloromethane (9.82 ml) was added TFA (2.455 ml). The reaction mixture was stirred at rt 4 h. Excess TFA was removed in vacuo. The crude residue was taken up in methanol and free based using 2 parallel Phenomenex 5 g SCX columns. The columns were flushed with three column volumes methanol and three column volumes 3.5 N ammonia/methanol. The ammonia layers were concentrated in vacuo to provide 6-aminopicolinonitrile (0.312 g).
$^1$H NMR (400 MHz, CHLOROFORM-d) δ 7.56-7.47 (m, 1H), 7.06 (dd, J=7.3, 0.7 Hz, 1H), 6.68 (dd, J=8.6, 0.7 Hz, 1H), 4.70 (br. s., 2H)

(347D): The compound was prepared starting from 4-(cyclopropyl(4-methoxybenzyl)amino)-2-(methylsulfonyl)imidazo[2,1-f][1,2,4]triazine-7-carbonitrile (50 mg, 0.125 mmol) and 6-aminopicolinonitrile (17.94 mg, 0.151 mmol) using the procedure for Example 1E, Material was carried forward into the next step as is.
MS (ESI) m/z 438.4 (M+H)

Example 347

To a round bottom flask charged with 2-((6-cyanopyridin-2-yl)amino)-4-(cyclopropyl(4-methoxybenzyl)amino)imidazo[2,1-f][1,2,4]triazine-7-carbonitrile (54.7 mg, 0.125 mmol) in dichloromethane (625 μl) was added anisole (27.3 μl, 0.250 mmol) and TFA (385 μl, 5.00 mmol). The reaction mixture was stirred at rt ON. Additional TFA (1 mL) was added. The reaction mixture was warmed to 50° C. ON. Excess TFA was removed by concentration in vacuo. The crude residue was purified by neutral phase preparatory LC/MS chromatography to provide 2-((6-cyanopyridin-2-yl)amino)-4-(cyclopropylamino)imidazo[2,1-f][1,2,4]triazine-7-carbonitrile (0.7 mg, 2.21 μmol, 2%)

MS (ESI) m/z 318.2 (M+H)

$^1$H NMR (500 MHz, DMSO-d$_6$) δ 10.34 (s, 1H), 9.45 (d, J=4.5 Hz, 1H), 8.51 (d, J=8.4 Hz, 1H), 8.26 (s, 1H), 8.05-7.97 (m, 1H), 7.60 (d, J=7.4 Hz, 1H), 3.16-3.08 (m, 1H), 0.90-0.75 (m, 4H)

Example 348

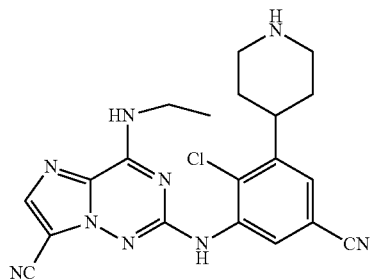 [SMILES: CCNc1nc(Nc2cc(C#N)cc(C3CCNCC3)c2Cl)nn2c(C#N)cnc12]

2-((2-chloro-5-cyano-3-(piperidin-4-yl)phenyl)amino)-4-(ethylamino)imidazo[2,1-f][1,2,4]triazine-7-carbonitrile The title compound was prepared in analogous manner as Example 208

MS (ESI) m/z 422.18 (M+1)

1H NMR (500 MHz, DMSO-d6) δ 9.19 (br. s., 1H), 8.85 (br. s., 1H), 8.20 (s, 1H), 8.17 (br. s., 1H), 7.55 (br. s., 1H), 4.09 (d, J=4.7 Hz, 2H), 3.45 (d, J=7.0 Hz, 2H), 3.05 (d, J=11.7 Hz, 2H), 2.61 (t, J=12.0 Hz, 2H), 1.69 (d, J=12.4 Hz, 2H), 1.56 (d, J=10.1 Hz, 2H), 1.18 (t, J=7.2 Hz, 3H)

Example 349

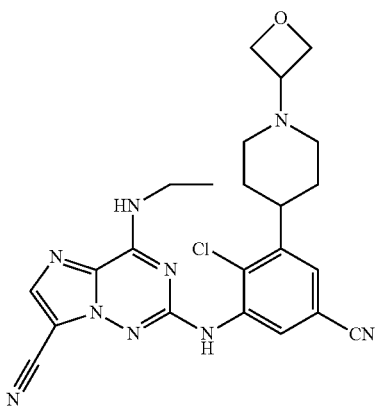 [SMILES: CCNc1nc(Nc2cc(C#N)cc(C3CCN(C4COC4)CC3)c2Cl)nn2c(C#N)cnc12]

2-((2-chloro-5-cyano-3-(1-(oxetan-3-yl)piperidin-4-yl)phenyl)amino)-4-(ethylamino)imidazo[2,1-f][1,2,4]triazine-7-carbonitrile The title compound was prepared similar manner as Example 210.

MS (ESI) m/z 478.26 (M+1)

Following additional examples were prepared in similar was as Example 349

TABLE 13

| Example No. | Structure | Name | [M + H]$^+$ | HPLC Retention Time (min.)* |
|---|---|---|---|---|
| 350 | 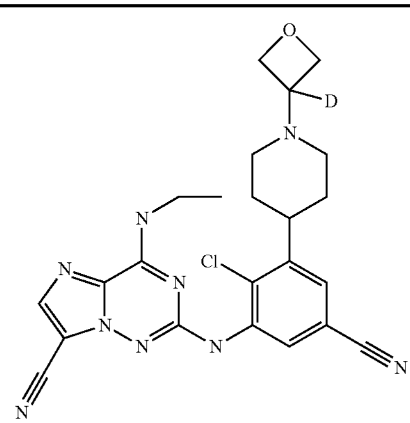 | 2-((2-chloro-5-cyano-3-(1-(3-~2~H)-3-oxetanyl-4-piperidinyl)phenyl)amino)-4-(ethylamino)imidazo[2,1-f][1,2,4]triazine-7-carbonitrile | 478.96 | 2.88 |

TABLE 13-continued

| Example No. | Structure | Name | [M + H]+ | HPLC Retention Time (min.)* |
|---|---|---|---|---|
| 351 | 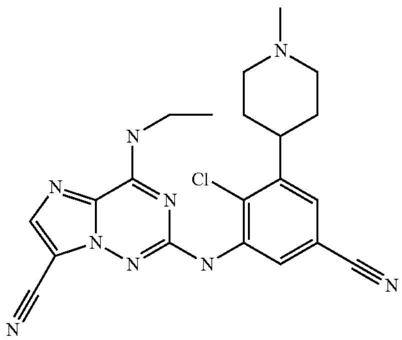 [SMILES: CCNc1nc(Nc2cc(C#N)cc(C3CCN(C)CC3)c2Cl)nn2c(C#N)cnc12] | 2-((2-chloro-5-cyano-3-(1-methyl-4-piperidinyl)phenyl)amino)-4-(ethylamino)imidazo[2,1-f][1,2,4]triazine-7-carbonitrile | 435.92 | 2.67 |
| 352 | 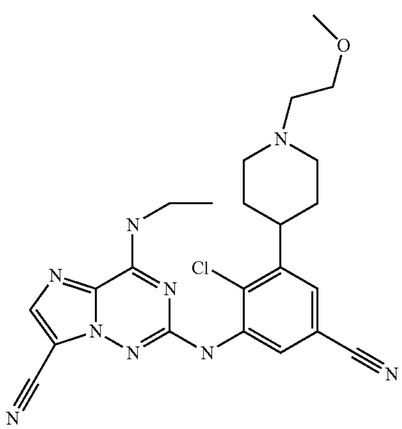 [SMILES: CCNc1nc(Nc2cc(C#N)cc(C3CCN(CCOC)CC3)c2Cl)nn2c(C#N)cnc12] | 2-((2-chloro-5-cyano-3-(1-(2-methoxyethyl)-4-piperidinyl)phenyl)amino)-4-(ethylamino)imidazo[2,1-f][1,2,4]triazine-7-carbonitrile | 479.97 | 2.70 |
| 353 | 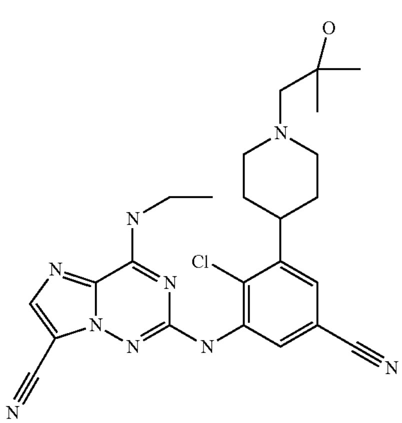 [SMILES: CCNc1nc(Nc2cc(C#N)cc(C3CCN(CC(C)(C)O)CC3)c2Cl)nn2c(C#N)cnc12] | 2-((2-chloro-5-cyano-3-(1-(2-hydroxy-2-methylpropyl)-4-piperidinyl)phenyl)amino)-4-(ethylamino)imidazo[2,1-f][1,2,4]triazine-7-carbonitrile | 494.00 | 2.79 |

TABLE 13-continued

| Example No. | Structure | Name | [M + H]+ | HPLC Retention Time (min.)* |
|---|---|---|---|---|
| 354 | 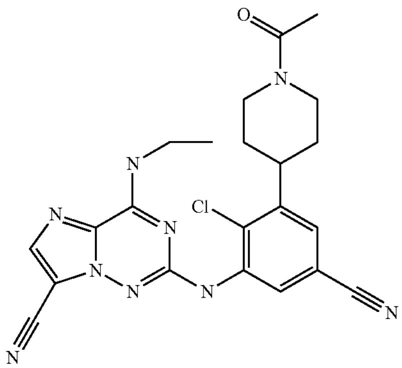 [SMILES: CCNc1nc(Nc2cc(C#N)cc(C3CCN(C(C)=O)CC3)c2Cl)nn2c(C#N)cnc12] | 2-((3-(1-acetyl-4-piperidinyl)-2-chloro-5-cyanophenyl)amino)-4-(ethylamino)imidazo[2,1-f][1,2,4]triazine-7-carbonitrile | 463.93 | 3.81 |
| 355 | 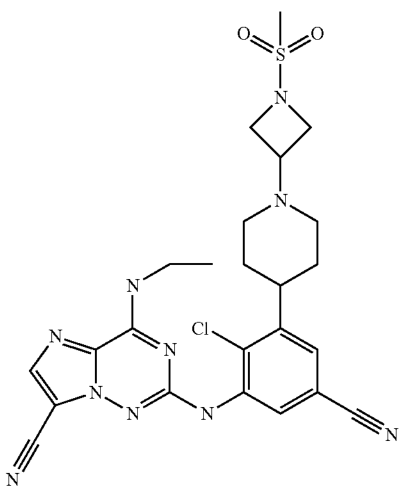 [SMILES: CCNc1nc(Nc2cc(C#N)cc(C3CCN(C4CN(S(C)(=O)=O)C4)CC3)c2Cl)nn2c(C#N)cnc12] | 2-((2-chloro-5-cyano-3-(1-(1-(methylsulfonyl)-3-azetidinyl)-4-piperidinyl)phenyl)amino)-4-(ethylamino)imidazo[2,1-f][1,2,4]triazine-7-carbonitrile | 555.06 | 2.98 |
| 356 | 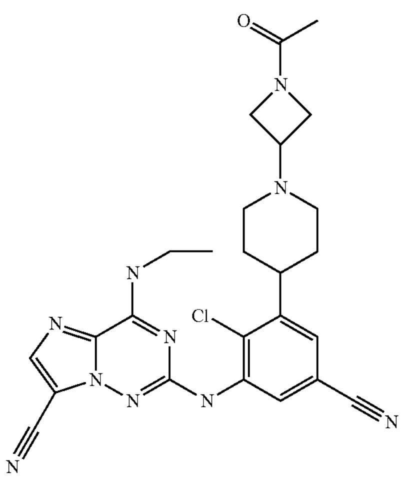 [SMILES: CCNc1nc(Nc2cc(C#N)cc(C3CCN(C4CN(C(C)=O)C4)CC3)c2Cl)nn2c(C#N)cnc12] | 2-((3-(1-(1-acetyl-3-azetidinyl)-4-piperidinyl)-2-chloro-5-cyanophenyl)amino)-4-(ethylamino)imidazo[2,1-f][1,2,4]triazine-7-carbonitrile | 519.01 | 2.95 |

CHROMOLITH ® column 4.6 × 50 mm eluting with 10-90% aqueous methanol over 4 min. containing 0.1% TFA, 4 mL/min, monitoring at 220 nm.

Example 357

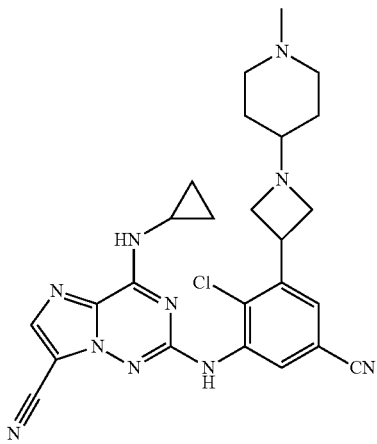

2-((2-chloro-5-cyano-3-(1-(1-methylpiperidin-4-yl)
azetidin-3-yl)phenyl)amino)-4-(cyclopropylamino)
imidazo[2,1-f][1,2,4]triazine-7-carbonitrile (357A): A solution of tert-butyl(3-bromo-2-chloro-5-cyanophenyl)carbamate (Intermediate 1) (3.48 g, 9.45 mmol) in DMF (35 ml) was cooled in an ice bath and NaHMDS (14.17 ml, 14.17 mmol) was added. After 20 min, removal of the cooling bath, stirring at 0° C. to RT for 10 min, then cooled in the ice bath again, and 4-methoxybenzyl chloride (1.929 ml, 14.17 mmol) was added and the reaction was removed from the cooling bath and left stirring at RT for overnight. The reaction was partitioned between EtOAc and sat. aq. $NH_4Cl$. The aqueous phase was extracted with EtOAc and the combined organic phases were washed with brine. After drying with sodium sulfate, the solvents were removed and the residue was purified by flush silica gel column chromatography (160 g column), eluting with hexane containing 2 to 10% EtOAc to give tert-butyl(3-bromo-2-chloro-5-cyanophenyl)(4-methoxybenzyl)carbamate (4.05 g) as a white solid MS (ESI) m/z 475.13

1H NMR (500 MHz, CHLOROFORM-d) δ 7.78 (d, J=1.1 Hz, 1H), 7.10 (d, J=8.7 Hz, 3H), 6.81 (d, J=7.2 Hz, 2H), 5.09 (d, J=14.3 Hz, 1H), 4.23 (d, J=15.0 Hz, 1H), 3.78 (s, 3H), 1.68-1.29 (m, 9H)

(357B): A mixture of tert-butyl(3-bromo-2-chloro-5-cyanophenyl)(4-methoxybenzyl)carbamate (1 g, 1.882 mmol), dichloro[1,1'-bis(diphenylphosphino)ferrocene]palladium (II) (0.129 g, 0.188 mmol), and copper(I) iodide (0.072 g, 0.376 mmol) in N,N-Dimethylacetamide (0.6 mL) in a dry microwave vial was evacuated and backfilled with $N_2$ for 3 times. (1-(tert-butoxycarbonyl)azetidin-3-yl)zinc(II) iodide (5.94 mL, 5.64 mmol, approximately 0.95 M solution in N,N-dimethylacetamide prepared as described in the Journal of Organic Chemistry, 2004, 69, 5120) was then added. The mixture was evacuated and backfilled with $N_2$ one more time and then heated at 80° C. for overnight. After cooling to RT, the reaction was partitioned between EtOAc and sat. aq. $NH_4Cl$ solution. This was left stirring for 30 min. The aqueous phase was extracted with EtOAc and the combined organic phases were washed with brine and dried with sodium sulfate. Removal of the solvents followed by silica gel chromatography eluting with hexane containing 5 to 15% EtOAc to afford tert-butyl 3-(3-((tert-butoxycarbonyl)(4-methoxybenzyl)amino)-2-chloro-5-cyanophenyl)azetidine-1-carboxylate (0.98 g).

(357C): To a solution of tert-butyl 3-(3-((tert-butoxycarbonyl)(4-methoxybenzyl)amino)-2-chloro-5-cyanophenyl)azetidine-1-carboxylate (0.98 g, 1.856 mmol) in DCM (20 ml) was added ansiole (5.70 mL, 5.64 mmol), followed by TFA (10 ml), After 1.5 h, the solvent was removed. The residue was taken in MeOH and applied onto a cartridge of Phenomenex Strata-X-C 33 um cation mixed-mode polymer. This was washed with methanol and product was eluted with 2 N solution of ammonia in methanol. Removal of the solvents left 3-amino-5-(azetidin-3-yl)-4-chlorobenzonitrile (441 mg) which was used as such in the next reaction.

MS (ESI) m/z 208.03 [M+1]

(357D): To a suspension of 3-amino-5-(azetidin-3-yl)-4-chlorobenzonitrile (507 mg, 2.100 mmol) in DCM (50 mL) was added $Et_3N$ (0.293 mL, 2.100 mmol), followed by di-tert-butyl dicarbonate (481 mg, 2.205 mmol). After stirring at RT overnight, the solvent was removed to leave tert-butyl 3-(3-amino-2-chloro-5-cyanophenyl)azetidine-1-carboxylate (786 mg) which was used as such in the next step.

MS (ESI) m/z 330.15 [M+23

1H NMR (500 MHz, DMSO-d6) δ 7.10 (d, J=1.4 Hz, 1H), 7.05 (d, J=1.8 Hz, 1H), 5.92 (s, 2H),
4.20 d, J=17.9 Hz, 2H), 4.05-3.97 (m, 1H), 3.96-3.88 (m, 2H), 1.39 (s, 9H)]

(357E): A mixture of 4-(cyclopropyl(4-methoxybenzyl)amino)-2-(methylsulfonyl)imidazo[2,1-f][1,2,4]triazine-7-carbonitrile (155 mg, 0.390 mmol), tert-butyl 3-(3-amino-2-chloro-5-cyanophenyl)azetidine-1-carboxylate (Intermediate 9) (100 mg, 0.325 mmol) and $Cs_2CO_3$ (212 mg, 0.650 mmol) in DMF (3.5 ml) was heated at 70° C. for 2 h. This was diluted with EtOAc, washed with water and brine, and dried over $Na_2SO_4$, removal of the solvent and purified by radial silica gel chromatography, eluting with DCM containing 0 to 2% MeOH to give the Boc protected intermediate. This was dissolved in DCE (1 ml), TFA (0.5 ml) was added and the mixture was stirred at RT for 1 h. LCMS indicated that Boc-removed, and along with about 14% of both Boc and PMB removed product. Removal of the solvent and the residue was taken in MeOH and applied onto a cartridge of Phenomenex Strata-X-C 33 um cation mixed-mode polymer. This was washed with methanol and product was eluted with a mixture of (1:1) DCM:2 N solution of ammonia in methanol. Removal of the solvents left 107 mg product as a solid which was used in next reaction as such.

MS (ESI) m/z 526.31 [M+1]

Example 357

To a solution of 2-((3-(azetidin-3-yl)-2-chloro-5-cyanophenyl)amino)-4-(cyclopropyl(4-methoxybenzyl)amino) imidazo[2,1-f][1,2,4]triazine-7-carbonitrile (53 mg, 0.084 mmol) in methanol (1.2 ml) was added trimethyl orthoformate (0.6 mL, 5.43 mmol), 1-methylpiperidin-4-one (0.1 ml, 0.866 mmol) and acetic acid (10 µL, 0.175 mmol). The mixture was stirred at RT for 40 min and then sodium cyanoborohydride (42.0 mg, 0.669 mmol) was added. After 4 h, the reaction mixture was partitioned between EtOAc and dilute aq. NaHCO₃ solution. The organic layer was washed with brine, and dried over Na₂SO₄. Removal of the solvent left the crude intermediate. To this was added DCE (1 ml), anisole (0.046 ml, 0.418 mmol), and TFA (0.5 ml). The resulting mixture was heated at 50° C. for 3 h. the solvents were removed and the crude material was purified by prep-HPLC (100×30 mm Luna C18 column, Solvent A=10% Methanol, 90% H2O, 0.1% TFA; solvent B=90% Methanol, 10% H2O, 0.1% TFA, Flow rate 42 ml permin, 20-100% B, over 20 min). The HPLC fractions containing the product were applied onto a cartridge of Phenomenex Strata-X-C 33 um cation mixed-mode polymer. This was washed with methanol and product was eluted with a mixture of 2 N solution of ammonia in methanol and dichloromethane (1:1). Removal of the solvents afforded 2-((2-chloro-5-cyano-3-(1-(1-methylpiperidin-4-yl)azetidin-3-yl)phenyl)amino)-4-(cyclopropylamino)imidazo[2,1-f][1,2,4]triazine-7-carbonitrile (35.2 mg) as a white solid.

MS (ESI) m/z 503.30 [M+1]

1H NMR (500 MHz, CHLOROFORM-d) δ 8.95 (d, J=1.7 Hz, 1H), 7.88 (s, 1H), 7.56 (s, 1H), 7.31-7.28 (m, 1H), 6.93 (br. s., 1H), 4.08-3.97 (m, 1H), 3.92-3.83 (m, 2H), 3.15-3.00 (m, H), 2.82 (d, J=11.6 Hz, 2H), 2.29 (s, 3H), 2.02 (t, J=9.3 Hz, 3H), 1.75 (dd, J=13.0, 2.9 Hz, 2H), 1.49-1.34 (m, 2H), 1.17-1.06 (m, 2H), 0.87-0.77 (m, 2H)

Example 358

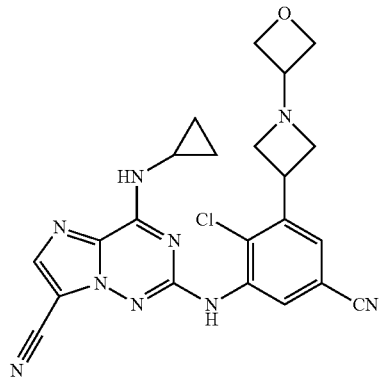 [SMILES: N#Cc1cc(Nc2nc(NC3CC3)c3ncc(C#N)n3n2)c(Cl)c(C2CN(C3COC3)C2)c1]

2-((2-chloro-5-cyano-3-(1-(oxetan-3-yl)azetidin-3-yl)phenyl)amino)-4-(cyclopropylamino)imidazo[2,1-f][1,2,4]triazine-7-carbonitrile The title compound, was prepared from 2-((3-(azetidin-3-yl)-2-chloro-5-cyanophenyl)amino)-4-(cyclopropyl(4-methoxybenzyl)amino)imidazo[2,1-f][1,2,4]triazine-7-carbonitrile (Example 357E) and oxetan-3-one using a method analogous to that used to prepare Example 357.

HPLC Rt 2.746 min

MS: (ESI) m/z 466.22 [M+1]

Example 359

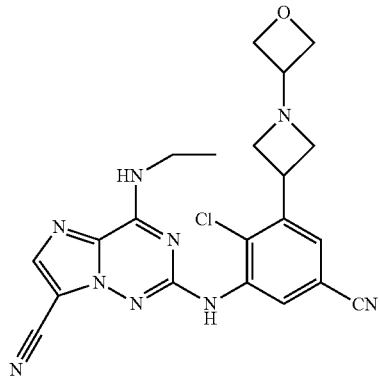 [SMILES: CCNc1nc(Nc2cc(C#N)cc(C3CN(C4COC4)C3)c2Cl)nn2c(C#N)cnc12]

2-((2-chloro-5-cyano-3-(1-(oxetan-3-yl)azetidin-3-yl)phenyl)amino)-4-(ethylamino)imidazo[2,1-f][1,2,4]triazine-7-carbonitrile The title compound, was prepared in analogous manner as Example 358

HPLC Rt 2.873 min

MS (ESI) m/z 450.22

Example 360

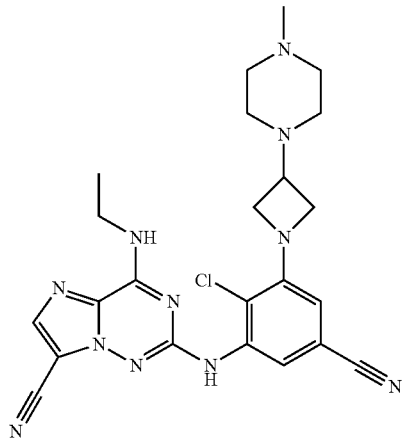 [SMILES: CCNc1nc(Nc2cc(C#N)cc(N3CC(N4CCN(C)CC4)C3)c2Cl)nn2c(C#N)cnc12]

2-((2-chloro-5-cyano-3-(3-(4-methylpiperazin-1-yl)azetidin-1-yl)phenyl)amino)-4-(ethylamino)imidazo[2,1-f][1,2,4]triazine-7-carbonitrile (360A): 3-amino-4-chloro-5-(3-(4-methylpiperazin-1-yl)azetidin-1-yl)benzonitrile (Example 151C) (40 mg, 0.131 mmol), 4-(ethyl(4-methoxybenzyl)amino)-2-(methylsulfonyl)imidazo[2,1-f][1,2,4]triazine-7-carbonitrile (Intermediate 7) (50.5 mg, 0.131 mmol), and Cs2CO3 (128 mg, 0.392 mmol) in DMF were heated at 45° C. for 14 h. LC/MS showed product formation. The mixture was filtered and

Example 360

2-((2-chloro-5-cyano-3-(3-(4-methylpiperazin-1-yl)azetidin-1-yl)phenyl)amino)-4-(ethyl(4-methoxybenzyl)amino)imidazo[2,1-f][1,2,4]triazine-7-carbonitrile (107A) (80 mg, 0.131 mmol) was treated with TFA (0.5 mL, 6.49 mmol) and anisole (0.072 mL, 0.655 mmol) in DCE (1.5 mL). The mixture was stirred at r.t. for 24 hr. The mixture was concentrated to dryness, then purified by prep-HPLC to give 17.6 mg desired product.

MS (ESI): m/z 492.4 (M+1).

1H NMR (400 MHz, DMSO-d6) δ 9.16 (t, J=5.6 Hz, 1H), 8.68 (s, 1H), 8.20 (s, 1H), 7.68 (d, J=1.8 Hz, 1H), 6.80 (d, J=2.0 Hz, 1H), 4.19 (t, J=7.5 Hz, 2H), 3.84 (dd, J=8.0, 5.5 Hz, 2H), 3.55-3.42 (m, 2H), 3.4-3.3 (m, 2H), 3.29-3.12 (m, 1H), 2.35 (d, J=1.8 Hz, 6H), 2.18 (s, 3H), 1.21 (t, J=7.2 Hz, 3H)

Following additional examples were prepared in similar was as Example 360

Example 363

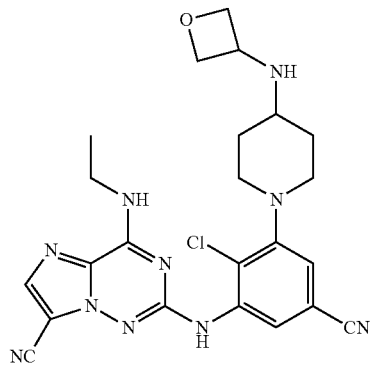

2-((2-chloro-5-cyano-3-(4-(oxetan-3-ylamino)piperidin-1-yl)phenyl)amino)-4-(ethylamino)imidazo[2,1-f][1,2,4]triazine-7-carbonitrile 2-((3-(4-aminopiperidin-1-yl)-2-chloro-5-cyanophenyl)amino)-4-(ethylamino)imidazo[2,1-f][1,2,4]triazine-7-carbonitrile (Example 329) (48 mg, 0.110 mmol) was taken up

TABLE 14

| Example No. | Structure | Name | [M + H]+ | HPLC Retention Time (min.)* |
|---|---|---|---|---|
| 361 | 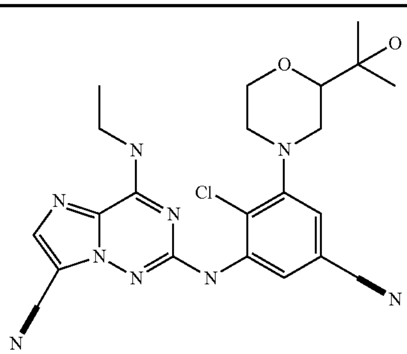 | (+/−) 2-((2-chloro-5-cyano-3-(2-(1-hydroxy-1-methylethyl)-4-morpholinyl)phenyl)amino)-4-(ethylamino)imidazo[2,1-f][1,2,4]triazine-7-carbonitrile | 481.95 | 2.88 |
| 362 | 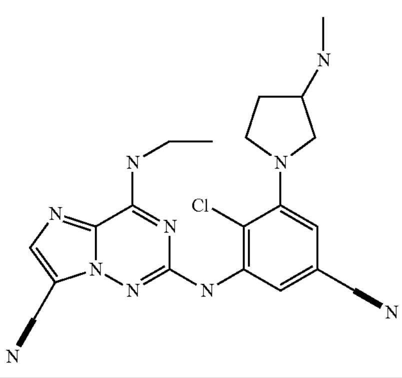 | (+/−) 2-((2-chloro-5-cyano-3-(3-(methylamino)-1-pyrrolidinyl)phenyl)amino)-4-(ethylamino)imidazo[2,1-f][1,2,4]triazine-7-carbonitrile | 436.91 | 2.67 c |

CHROMOLITH ® column 4.6 × 50 mm eluting with 10-90% aqueous methanol over 4 min. containing 0.1% TFA, 4 mL/min, monitoring at 220 nm.

in THF (2 mL) and Methanol (2 mL) and trimethyl orthoformate (0.5 mL, 4.52 mmol), AcOH (0.05 mL, 0.873 mmol) in a round bottom flask. Oxetan-3-one (0.1 mL, 1.560 mmol) were added. The reaction mixture was stirred at rt for 15 mins. sodium cyanoborohydride (50 mg, 0.796 mmol) was added and the reaction was stirred at r.t. for 2 hrs. LC/MS showed about 40% conversion to the desired product. Another batch of oxetan-3-one (0.1 mL, 1.560 mmol), trimethyl orthoformate (0.5 mL, 4.52 mmol), AcOH (0.05 mL, 0.873 mmol) and sodium cyanoborohydride (50 mg, 0.796 mmol) were added to the reaction mixture and let stirred for another 30 mins. LC/MS showed completed conversion to the product. The mixture was concentrated to almost dryness, diluted with EtOAc and washed with NaHCO3, then brine, dried over MgSO4 and concentrated. The crude was then purified by PREP-HPLC to give 21.3 mg of desired product MS (ESI): m/z 493.6 (M+1).

1H NMR (400 MHz, DMSO-d6) δ 9.18 (br. s., 1H), 8.80 (br. s., 1H), 8.20 (br. s., 1H), 7.96 (br. s., 1H), 7.31 (br. s., 1H), 4.66 (br. s., 2H), 4.35 (br.s., 2H), 4.00 (br. s., 1H), 3.48 (br. s., 4H), 2.72 (br. s., 3H), 1.99-1.70 (m, 3H), 1.44 (d, J=8.3 Hz, 2H), 1.21 (br. s., 3H)

Example 364

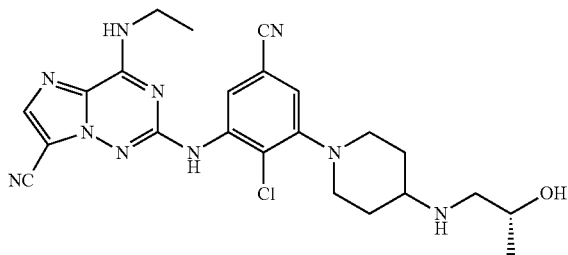 [SMILES: CCNc1nc(Nc2cc(C#N)cc(N3CCC(NC[C@@H](C)O)CC3)c2Cl)nn2c(C#N)cnc12]

(R)-2-((2-chloro-5-cyano-3-(4-((2-hydroxypropyl) amino)piperidin-1-yl)phenyl)amino)-4-(ethylamino) imidazo[2,1-f][1,2,4]triazine-7-carbonitrile 2-((3-(4-aminopiperidin-1-yl)-2-chloro-5-cyanophenyl) amino)-4-(ethylamino)imidazo[2,1-f][1,2,4]triazine-7-carbonitrile (Example 329) (30 mg, 0.069 mmol), was dissolved in MeOH (0.5 mL)/DCM (0.5 mL) in an one dram vial. To this was added triethylamine (0.019 mL, 0.137 mmol), followed by (R)-2-methyloxirane (39.9 mg, 0.687 mmol). The reaction mixture was stirred at 25° C. 16 hr. The crude material was purified via preparative LC/MS with the following conditions:

Column: Waters XBridge C18, 19×200 mm, 5-nm particles;

Guard Column: Waters XBridge C18, 19×10 mm, 5 nm particles; Mobile Phase A: water;

Mobile Phase B: methanol; Buffer: 20-mM ammonium acetate; Gradient: 30-95% B over 19.5 minutes, then a 14.0 minute hold at 95% B; Flow: 20 mL/min. Fractions containing the desired product were combined and dried via centrifugal evaporation to afford (R)-2-((2-chloro-5-cyano-3-(4-((2-hydroxypropyl)amino)piperidin-1-yl)phenyl) amino)-4-(ethylamino)imidazo[2,1-f][1,2,4]triazine-7-carbonitrile (2 mg).

MS (ESI): m/z 495

1H NMR (500 MHz, DMSO-d6) δ 9.25-9.09 (m, 1H), 8.87 (br. s., 1H), 8.19 (s, 1H), 7.96 (s, 1H), 7.34 (s, 1H), 5.46-5.21 (m, 1H), 4.07-3.92 (m, 2H), 3.39-3.31 (m, 2H), 3.26-3.12 (m, 2H), 3.08-2.96 (m, 1H), 2.87-2.68 (m, 3H), 2.24-2.06 (m, 2H), 1.87-1.65 (m, 2H), 1.31-1.07 (m, 7H)

Example 365

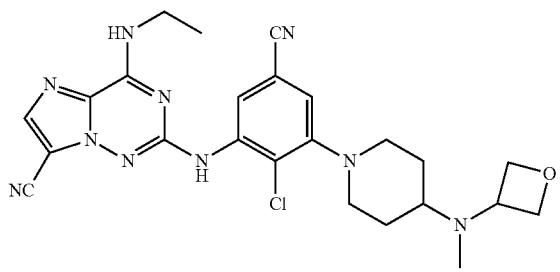 [SMILES: CCNc1nc(Nc2cc(C#N)cc(N3CCC(N(C)C4COC4)CC3)c2Cl)nn2c(C#N)cnc12]

2-((2-chloro-5-cyano-3-(4-(methyl(oxetan-3-yl) amino)piperidin-1-yl)phenyl)amino)-4-(ethylamino) imidazo[2,1-f][1,2,4]triazine-7-carbonitrile 2-((2-chloro-5-cyano-3-(4-(oxetan-3-ylamino)piperidin-1-yl)phenyl)amino)-4-(ethylamino)imidazo[2,1-f][1,2,4]triazine-7-carbonitrile (Example 363) (20 mg, 0.041 mmol) was dissolved in MeOH (0.5 mL)/THF (0.5 mL) in an one dram vial. Trimethyl orthoformate (0.336 ml, 3.04 mmol), acetic acid (9.29 µl, 0.162 mmol), and formaldehyde (3.73 µl, 0.041 mmol) were added. The reaction mixture stirred at 25° C. 5 min and 1M sodium cyanoborohydride in THF (0.406 ml, 0.406 mmol) was added; the reaction stirred at 25° C. 10 min. The crude material was purified via preparative LC/MS with the following conditions: Column: Waters XBridge C18, 19×200 mm, 5-nm particles; Guard Column: Waters XBridge C18, 19×10 mm, 5-nm particles; Mobile Phase A: water with 20-mM ammonium acetate; Mobile Phase B: 95:5 acetonitrile:water with 20-mM ammonium acetate; Gradient: 20-100% B over 20 minutes, then a 5-minute hold at 100% B; Flow: 20 mL/min.

Fractions containing the desired product were combined and dried via centrifugal evaporation to afford 2-((2-chloro-5-cyano-3-(4-(methyl(oxetan-3-yl)amino)piperidin-1-yl) phenyl)amino)-4-(ethylamino)imidazo[2,1-f][1,2,4]triazine-7-carbonitrile (10 mg).

MS (ESI): m/z 507

1H NMR (500 MHz, DMSO-d6) δ 9.17 (br. s., 1H), 8.82 (br. s., 1H), 8.19 (s, 1H), 7.95 (br. s., 1H), 7.29 (br. s., 1H), 4.52 (br. s., 4H), 4.11-3.85 (m, 1H), 3.34 (d, J=10.7 Hz, 4H), 2.79-2.60 (m, 2H), 2.19 (br. s., 3H), 1.68 (br. s., 4H), 1.19 (t, J=6.9 Hz, 4H)

Example 366

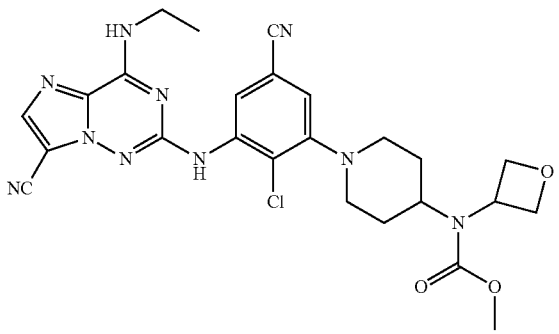 [SMILES: CCNc1nc(Nc2cc(C#N)cc(N3CCC(N(C(=O)OC)C4COC4)CC3)c2Cl)nn2c(C#N)cnc12]

methyl(1-(2-chloro-5-cyano-3-((7-cyano-4-(ethyl-amino)imidazo[2,1-f][1,2,4]triazin-2-yl)amino)phenyl)piperidin-4-yl)(oxetan-3-yl)carbamate 2-((2-chloro-5-cyano-3-(4-(oxetan-3-ylamino)piperidin-1-yl)phenyl)amino)-4-(ethylamino)imidazo[2,1-f][1,2,4]triazine-7-carbonitrile (Example 363) (20 mg, 0.041 mmol) in MeOH (6 mL)/THF (3 mL) at 0° C. (ice bath) was added DIPEA (21.26 µl, 0.122 mmol) and methyl carbonochloride [(60 µl, 0.775 mmol) total 3× (20 µl, 0.258 mmol) portions]. The reaction stirred at 25° C. for 30 min and the mixture was diluted with EtOAc, washed with sat'd NaHCO3 and brine. The organic layer was dried over Na2SO4 and concentrated. The crude material was purified via preparative LC/MS with the following conditions: Column: Waters XBridge C18, 19×200 mm, 5-µm particles; Guard Column: Waters XBridge C18, 19×10 mm, 5-µm particles; Mobile Phase A: water with 20-mM ammonium acetate; Mobile Phase B: 95:5 acetonitrile:water with 20-mM ammonium acetate; Gradient: 40-80% B over 20 minutes, then a 5-minute hold at 100% B; Flow: 20 mL/min. Fractions containing the desired product were combined and dried via centrifugal evaporation to afford methyl(1-(2-chloro-5-cyano-3-((7-cyano-4-(ethylamino)imidazo[2,1-f][1,2,4]triazin-2-yl)amino)phenyl)piperidin-4-yl)(oxetan-3-yl)carbamate (5.8 mg).

MS (ESI): m/z 551
$^1$H NMR (500 MHz, DMSO-d$_6$) δ 9.17 (br. s., 1H), 8.82 (s, 1H), 8.18 (s, 1H), 7.96 (br. s., 1H), 7.31 (br. s., 1H), 4.92-4.70 (m, 3H), 4.62 (br. s., 2H), 3.65 (s, 5H), 3.37-3.27 (m, 2H), 2.85-2.65 (m, 3H), 2.20-1.99 (m, 2H), 1.74-1.57 (m, 2H), 1.27-1.09 (m, 3H)

Example 367

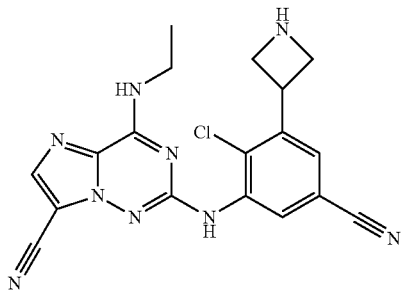 [SMILES: CCNc1nc(Nc2cc(C#N)cc(C3CNC3)c2Cl)nn2c(C#N)cnc12]

2-((3-(azetidin-3-yl)-2-chloro-5-cyanophenyl)amino)-4-(ethylamino)imidazo[2,1-f][1,2,4]triazine-7-carbonitrile A mixture of tert-butyl 3-(3-amino-2-chloro-5-cyanophenyl)azetidine-1-carboxylate (Example 357D)(154 mg, 0.500 mmol), 2-chloro-4-(ethyl(4-methoxybenzyl)amino)imidazo[2,1-f][1,2,4]triazine-7-carbonitrile (Intermediate 10) (172 mg, 0.500 mmol), Cs$_2$CO$_3$ (326 mg, 1.00 mmol), DPPF (27.7 mg, 0.050 mmol), 4,5-bis(diphenylphosphino)-9,9-dimethyxanthene (29 mg, 0.050 mmol), and Pd(OAc)$_2$ (34 mg, 0.150 mmol) in a microwave vial was flushed with nitrogen. Dioxane (5 mL) was added and vial was sealed and heated at 100° C. for 3 hr. After cooling to RT, the reaction was partitioned between EtOAc and water and then filtered through celite. The solvent was removed and radial silica gel chromatography eluting with hexane containing 5 to 40% EtOAc afforded tert-butyl 3-(2-chloro-5-cyano-3-((7-cyano-4-(ethyl(4-methoxybenzyl)amino)-imidazo[2,1-f][1,2,4]triazin-2-yl)amino)phenyl)azetidine-1-carboxylate (207 mg, 67% yield) as a foam. It was dissolved in DCM (0.6 mL) and anisole (30 uL, 0.272 mmol) and TFA (0.4 mL) were added. After 2 hr, the solvent was removed and the residue was applied onto an SCX cartridge using a 1:1 mixture of DCM and MeOH. This was washed with MeOH and eluted with a 1:1 mixture of 1N NH3 in MeOH and DCM to give crude 2-((3-(azetidin-3-yl)-2-chloro-5-cyanophenyl)amino)-4-(ethylamino)imidazo[2,1-f][1,2,4]triazine-7-carbonitrile (70 mg). A sample was purified by preparative HPLC (Column: Waters XBridge C18, 19×200 mm, 5-µm particles; Mobile Phase A: water with 20-mM ammonium acetate; Mobile Phase B: 95:5 methanol:water with 20-mM ammonium acetate; Gradient: 25-65% B over 20 minutes, then a 5-minute hold at 100% B; Flow: 20 mL/min) to give the title compound. This was converted to the momo HCl salt.

MS (ESI) m/z 394.2
$^1$H NMR (500 MHz, DMSO-d6) δ 9.18 (br. s., 1H), 8.20 (s, 2H), 7.67 (s, 1H), 4.11 (quin, J=7.8 Hz, 1H), 3.79 (t, J=8.0 Hz, 2H), 3.66 (t, J=7.6 Hz, 2H), 3.45 (q, J=7.1 Hz, 2H), 1.19 (t, J=7.2 Hz, 3H).

Example 368

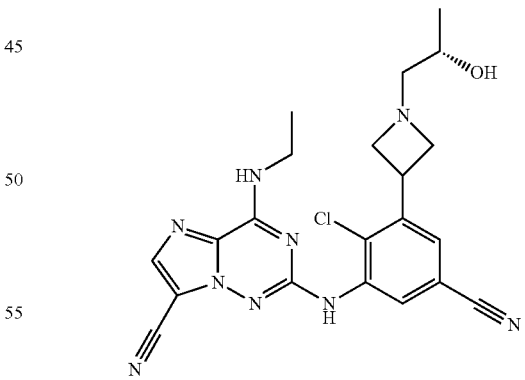

(S)-2-((2-chloro-5-cyano-3-(1-(2-hydroxypropyl)azetidin-3-yl)phenyl)amino)-4-(ethylamino)imidazo[2,1-f][1,2,4]triazine-7-carbonitrile A suspension of 2-((3-(azetidin-3-yl)-2-chloro-5-cyanophenyl)amino)-4-(ethylamino)imidazo[2,14][1,2,4]triazine-7-carbonitrile (Example 367) (16 mg, 0.041 mmol) and

319

(S)-(–)-propylene oxide (0.085 mL, 1.22 mmol) in a mixture of NMP (0.8 mL) and MeOH (0.2 mL) was stirred at 50° C. for 4.5 hr. The solvent was removed and the product was purified by preparative HPLC (Waters XBridge C18, 19×200 mm, 5-µm particles; Mobile Phase A: water with 20-mM ammonium acetate; Mobile Phase B: 95:5 acetonitrile:water with 20-mM ammonium acetate; Gradient: 15-55% B over 20 minutes, then a 5-minute hold at 100% B; Flow: 20 mL/min) to give the title compound (6.1 mg). This was converted to the mono HCl salt.

MS (ESI) m/z 452.4 (M+1).

¹H NMR (500 MHz, DMSO-d6) δ 9.21 (br. s., 1H), 9.00 (s, 1H), 8.29 (s, 1H), 8.20 (s, 1H), 7.74 (br. s., 1H), 5.30 (br. s., 1H), 4.51-4.18 (m, 5H), 3.90 (br. s., 1H), 3.20 (br. s., 1H), 3.05 (d, J=10.1 Hz, 1H), 2.90 (d, J=7.3 Hz, 1H), 1.25-1.17 (m, 3H), 1.10 (d, J=6.1 Hz, 3H).

Example 369

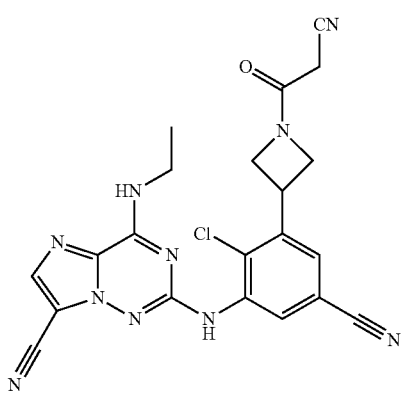 [SMILES: CCNc1nc(Nc2cc(C#N)cc(C3CN(C(=O)CC#N)C3)c2Cl)nn2c(C#N)cnc12]

2-((2-chloro-5-cyano-3-(1-(2-cyanoacetyl)azetidin-3-yl)phenyl)amino)-4-(ethylamino)imidazo[2,1-f][1,2,4]triazine-7-carbonitrile A mixture of 2-((3-(azetidin-3-yl)-2-chloro-5-cyanophenyl)amino)-4-(ethylamino)imidazo[2,1-f][1,2,4]triazine-7-carbonitrile (15 mg, 0.038 mmol), 2-cyanoacetic acid (4.9 mg, 0.057 mmol), 1-(3-dimethylaminopropyl)-3-ethylcarbodiimide hydrochloride (12.4 mg, 0.065 mmol), and HOBT monohydrate (9.9 mg, 0.065 mmol) in NMP (1 mL) was stirred at RT for 4 hr. Preparative HPLC (Waters XBridge C18, 19×200 mm, 5-µm particles; Mobile Phase A: water; Mobile Phase B: methanol; Buffer: 20-mM ammonium acetate; Gradient: 30-95% B over 19.5 minutes, then a 14.0 minute hold at 95% B; Flow: 20 mL/min) afforded the title compound (3.6 mg). This was converted to the mono HCl salt.

MS (ESI) m/z 641.3 (M+1).

¹H NMR (500 MHz, DMSO-d6) δ 9.20 (br. s., 1H), 8.94 (br. s., 1H), 8.27 (s, 1H), 8.20 (s, 1H), 7.80 (s, 1H), 4.62-4.52 (m, 1H), 4.38-4.26 (m, 2H), 4.22 (d, J=7.6 Hz, 1H), 4.11-4.03 (m, 1H), 3.83-3.70 (m, 2H), 1.19 (t, J=6.9 Hz, 3H).

320

Example 370

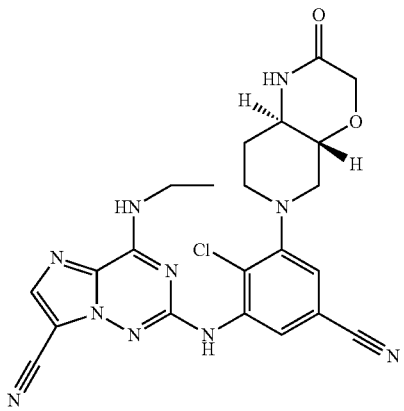 [SMILES: CCNc1nc(Nc2cc(C#N)cc(N3CC[C@H]4NC(=O)CO[C@@H]4C3)c2Cl)nn2c(C#N)cnc12]

(+/–)-2-((2-chloro-5-cyano-3-((4aR,8aR)-2-oxohexahydro-1H-pyrido[3,4-b][1,4]oxazin-6(7H)-yl)phenyl)amino)-4-(ethylamino)imidazo[2,1-f][1,2,4]triazine-7-carbonitrile (370A): (+/–)-3-amino-5-((3R,4R)-4-amino-3-hydroxypiperidin-1-yl)-4-chlorobenzonitrile (prepared from Example 171D) (1.0 g, 3.75 mmol) and potassium acetate (0.736 g, 7.50 mmol) were dissolved in acetone (20 ml)+ water (6 mL). The solution was cooled to 0° C. under nitrogen. Chloroacetic chloride (0.373 ml, 4.69 mmol) was added dropwise and the mixture stirred at 0° C. for 10 minutes, then at room temperature for 60 minutes. The reaction mixture was partitioned between EtOAc and aq. NaHCO3 solution. The organic layer was washed with brine and dried over MgSO4. MgSO4 was removed by filtration and volatiles evaporated in vacuum to afford (+/–)-N-((3R,4R)-1-(3-amino-2-chloro-5-cyanophenyl)-3-hydroxypiperidin-4-yl)-2-chloroacetamide (0.61 g). The material was used without further purification.

MS (ESI) m/z 343

¹H NMR (400 MHz, CHLOROFORM-d) δ 6.78 (d, J=1.8 Hz, 1H), 6.71 (d, J=1.8 Hz, 1H), 6.69 (d, J=6.3 Hz, 1H), 4.38-4.30 (m, 2H), 4.18-4.13 (m, 2H), 4.06 (s, 2H), 3.92-3.75 (m, 2H), 3.60-3.51 (m, 1H), 3.40-3.35 (m, 1H), 3.36-3.27 (m, 1H), 2.87-2.74 (m, 1H), 2.71-2.59 (m, 1H), 2.21-2.09 (m, 1H), 2.06 (s, 1H), 1.92-1.75 (m, 1H), 1.27 (t, J=7.2 Hz, 1H)

(370B): (+/–)-N-((3R,4R)-1-(3-amino-2-chloro-5-cyanophenyl)-3-hydroxypiperidin-4-yl)-2-chloroacetamide (549 mg, 1.600 mmol) was dissolved in anhydrous THF. The solution was cooled to 0° C. sodium hydride (96 mg, 2.399 mmol) and tetrabutylammonium bromide (77 mg, 0.240 mmol) were added (briefly opening the reaction flask to air). The reaction mixture was stirred at 0° C. for 5 minutes, then the ice bath was removed and the mixture stirred at room temperature for 1.5 hours. The reaction was quenched with aq. NH4Cl solution. The reaction mixture was partitioned between water and EtOAc. The organic layer was washed with brine (+small amount of NaHCO3 solution), then dried over MgSO4. The organic layer was filtered and evaporated to dryness to give 0.85 g crude colorless solid, which was purified via silica gel chromatography: gradient from 100% DCM to 100% EtOAc, then isocratic at 100% EtOAc to afford (+/−)-3-amino-4-chloro-5-((4aR,8aR)-2-oxohexahydro-1H-pyrido[3,4-b][1,4]oxazin-6(7H)-yl)benzonitrile (197 mg).

MS (ESI) m/z 307

¹H NMR (500 MHz, CHLOROFORM-d) δ 6.80 (d, J=1.7 Hz, 1H), 6.73 (d, J=1.9 Hz, 1H), 6.08-5.97 (m, 1H), 4.36 (d, J=17.0 Hz, 3H), 3.73-3.62 (m, 1H), 3.62-3.54 (m, 1H), 3.52 (d, J=5.5 Hz, 1H), 3.44-3.32 (m, 2H), 2.82-2.67 (m, 2H), 2.02-1.94 (m, 1H), 1.92-1.81 (m, 1H)

(370C): 2-chloro-4-(ethyl(4-methoxybenzyl)amino)imidazo[2,1-f][1,2,4]triazine-7-carbonitrile (33.5 mg, 0.098 mmol), (Intermediate 10), (+/−)-3-amino-4-chloro-5-((4aR,8aR)-2-oxohexahydro-1H-pyrido[3,4-b][1,4]oxazin-6(7H)-yl)benzonitrile (30 mg, 0.098 mmol), DPPF (3.8 mg, 6.85 μmol), Cs₂CO₃ (65.4 mg, 0.201 mmol), Xantphos (5.66 mg, 9.78 μmol), palladium(II)Acetate (6.83 mg, 0.029 mmol) and 1,4-dioxane (2 ml) were combined in a microwave vial. The vial was evacuated and backfilled with Nitrogen 3×. The reaction stirred at 100° C. for 3 hr. The reaction mixture cooled to 25° C., diluted with EtOAc and washed with brine and dried (Na₂SO₄). The solvents were removed and the material purified on silica gel 5% MeOH in DCM to afford (+/−)-2-((2-chloro-5-cyano-3-((4aR,8aR)-2-oxohexahydro-1H-pyrido[3,4-b][1,4]oxazin-6(7H)-yl)phenyl)amino)-4-(ethyl(4 methoxybenzyl)amino)imidazo[2,1-f][1,2,4]triazine-7-carbonitrile.

MS (ESI) m/z 613

Example 370

(+/−)-2-((2-chloro-5-cyano-3-((4aR,8aR)-2-oxohexahydro-1H-pyrido[3,4-b][1,4]oxazin-6(7H)-yl)phenyl)amino)-4-(ethyl(4-methoxybenzyl)amino)imidazo[2,1-f][1,2,4]triazine-7-carbonitrile was taken up in DCE (0.8 mL), anisole (0.043 mL, 0.391 mmol) and TFA (0.5 mL, 6.49 mmol). The mixture stirred 2 h at 25° C. and solvent was removed. The crude material was purified via preparative LC/MS with the following conditions: Column: Waters XBridge C18, 19×200 mm, 5-μm particles; Guard Column: Waters XBridge C18, 19×10 mm, 5-μm particles; Mobile Phase A: water with 20-mM ammonium acetate; Mobile Phase B: 95:5 acetonitrile:water with 20-mM ammonium acetate; Gradient: 25-65% B over 20 minutes, then a 5-minute hold at 100% B; Flow: 20 mL/min. Fractions containing the desired product were combined and dried via centrifugal evaporation to afford (+/−)-N-((3R,4R)-1-(3-amino-2-chloro-5-cyanophenyl)-3-hydroxypiperidin-4-yl)-2-chloroacetamide (2.2 mg).

MS (ESI) m/z 493

¹H NMR (500 MHz, DMSO-d₆) δ 9.27-9.09 (m, 1H), 8.95-8.75 (m, 1H), 8.34 (s, 1H), 8.18 (s, 1H), 7.98 (s, 1H), 7.39 (s, 1H), 4.14 (s, 2H), 3.33-3.18 (m, 3H), 2.95-2.87 (m, 1H), 2.87-2.79 (m, 1H), 2.79-2.68 (m, 2H), 2.04-1.89 (m, 1H), 1.72-1.60 (m, 1H), 1.60-1.42 (m, 1H), 1.19 (s, 3H)

Example 371

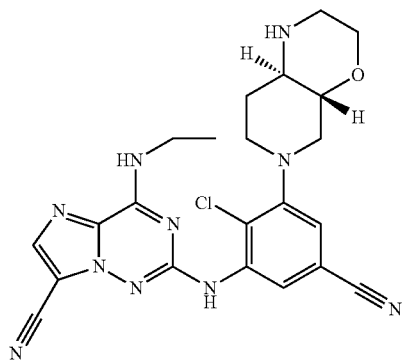 [SMILES: CCNc1nc(Nc2cc(C#N)cc(N3CC[C@H]4NCCO[C@@H]4C3)c2Cl)nn2c(C#N)cnc12]

(+/−)-2-((2-chloro-5-cyano-3-((4aR,8aR)-hexahydro-1H-pyrido[3,4-b][1,4]oxazin-6(7H)-yl)phenyl)amino)-4-(ethylamino)imidazo[2,1-f][1,2,4]triazine-7-carbonitrile (371A): (+/−)-3-amino-4-chloro-5-((4aR,8aR)-2-oxohexahydro-1H-pyrido[3,4-b][1,4]oxazin-6(7H)-yl)benzonitrile (Example 370B) (144 mg, 0.469 mmol) was dissolved in Tetrahydrofuran (10 ml) in a 20 ml scintillation vial. Borane-methyl sulfide complex (2 M in THF) (0.493 ml, 0.986 mmol) was added, the vial was capped and the reaction mixture heated to 90° C. for 3 hours. The reaction mixture was partitioned between EtOAc and aq. NH4Cl solution. The organic layer was washed with brine, then dried over MgSO4, filtered and evaporated to dryness to give (+/−)-3-amino-4-chloro-5-((4aR,8aR)-hexahydro-1H-pyrido[3,4-b][1,4]oxazin-6(7H)-yl)benzonitrile (129.5 mg)

MS (ESI) m/z 293

¹H NMR (400 MHz, METHANOL-d₄) δ 6.84 (d, J=2.0 Hz, 1H), 6.71 (d, J=2.0 Hz, 1H), 3.93-3.83 (m, 1H), 3.77-3.64 (m, 1H), 3.47-3.38 (m, 1H), 3.38-3.34 (m, 1H), 3.29-3.25 (m, 1H), 3.09-2.96 (m, 1H), 2.94-2.86 (m, 1H), 2.83-2.74 (m, 1H), 2.62-2.47 (m, 2H), 1.88-1.78 (m, 1H), 1.76-1.62 (m, 2H)

(371B): To a suspension of (+/−)-3-amino-4-chloro-5-((4aR,8aR)-hexahydro-1H-pyrido[3,4-b][1,4]oxazin-6(7H)-yl)benzonitrile (130 mg, 0.444 mmol) in DCM (5 ml) was added TEA (0.062 mL, 0.444 mmol), and di-tert-butyl dicarbonate (105 mg, 0.481 mmol). The reaction mixture stirred at 25° C. 2 hr. The mixture was diluted with DCM and washed with sat. NaCO₃, brine, and dried over Na₂SO₄. The material was purified on silica gel 0-50% EtOAc in DCM to afford (+/−)-(4aR,8aR)-tert-butyl 6-(3-amino-2-chloro-5-cyanophenyl)octahydro-1H-pyrido[3,4-b][1,4]oxazine-1-carboxylate (100 mg).

MS (ESI) m/z 393

¹H NMR (500 MHz, METHANOL-d₄) δ 6.89-6.82 (m, 1H), 6.75-6.64 (m, 1H), 3.99-3.87 (m, 2H), 3.83-3.75 (m, 1H), 3.74-3.66 (m, 1H), 3.47-3.41 (m, 1H), 3.39-3.35 (m, 1H), 3.31-3.27 (m, 1H), 3.25-3.17 (m, 1H), 2.77-2.69 (m, 1H), 2.66-2.53 (m, 2H), 2.12-2.04 (m, 1H), 1.50 (s, 9H)

(371C): 2-chloro-4-(ethyl(4-methoxybenzyl)amino)imidazo[2,1-f][1,2,4]triazine-7-carbonitrile (Intermediate 10) (85.0 mg, 0.248 mmol), (+/−)-(4aR,8aR)-tert-butyl 6-(3-amino-2-chloro-5-cyanophenyl)octahydro-1H-pyrido[3,4-b][1,4]oxazine-1-carboxylate (97.0 mg, 0.248 mmol), DPPF (9.62 mg, 0.017 mmol), Cs₂CO₃ (137 mg, 0.422 mmol), Xantphos (14.35 mg, 0.025 mmol), Palladium(II)Acetate (16.7 mg, 0.074 mmol) and 1,4-dioxane (2 ml) were combined in a microwave vial. The vial was evacuated and backfilled with Nitrogen (3×). The reaction stirred at 100° C. for 3 hr.

The reaction mixture cooled to 25° C., diluted with EtOAc, washed with brine and dried (Na₂SO₄).

The solvents were removed and the material purified on silica gel 25% EtOAc in DCM to afford (+/−)-(4aR,8aR)-tert-butyl 6-(2-chloro-5-cyano-3-((7-cyano-4-(ethyl(4-methoxybenzyl)amino)imidazo[2,1-f][1,2,4]triazin-2-yl)amino)phenyl)octahydro-1H-pyrido[3,4-b][1,4]oxazine-1-carboxylate (75 mg).

MS (ESI) m/z 702
$^1$H NMR (500 MHz, METHANOL-d$_4$) δ 8.48-8.23 (m, 1H), 8.10-7.98 (m, 1H), 7.32-7.23 (m, 2H), 7.21-7.14 (m, 1H), 6.94-6.85 (m, 2H), 5.71 (s, 1H), 5.51 (s, 3H), 5.00-4.94 (m, 1H), 4.44-4.31 (m, 1H), 3.98-3.88 (m, 2H), 3.79 (s, 2H), 3.76-3.67 (m, 2H), 3.54-3.43 (m, 1H), 3.42-3.34 (m, 2H), 3.29-3.19 (m, 1H), 2.89-2.73 (m, 1H), 2.72-2.58 (m, 2H), 2.03 (s, 1H), 1.50 (s, 9H), 1.26 (t, J=7.2 Hz, 3H) Example 371: (+/−)-(4aR,8aR)-tert-butyl 6-(2-chloro-5-cyano-3-((7-cyano-4-(ethyl(4-methoxybenzyl)amino)imidazo[2,1-f][1,2,4]triazin-2-yl)amino)phenyl)octahydro-1H-pyrido[3,4-b][1,4]oxazine-1-carboxylate (75 mg, 0.104 mmol) was taken up in DCE (2 mL), anisole (0.05 mL, 0.458 mmol) and TFA (0.5 mL, 6.49 mmol). The mixture stirred 2 h at 25° C. and solvents removed. 50 ml 2N NH3/MeOH was added and stirred for 30 mins. The white precipitate was collected by filtration and washed with 20 ml cold MeOH, then ether and dried under air-suction for 2 hrs to give (+/−)-2-((2-chloro-5-cyano-3-((4aR,8aR)-hexahydro-1H-pyrido[3,4-b][1,4]oxazin-6(7H)-yl)phenyl)amino)-4-(ethylamino)imidazo[2,1-f][1,2,4]triazine-7-carbonitrile (38 mg).

MS (ESI) m/z 479
$^1$H NMR (500 MHz, DMSO-d$_6$) δ 9.28-9.10 (m, 1H), 8.91-8.81 (m, 1H), 8.20 (s, 1H), 8.00-7.92 (m, 1H), 7.35 (s, 1H), 3.79-3.71 (m, 1H), 3.55-3.42 (m, 3H), 3.28-3.20 (m, 3H), 3.17 (d, J=5.2 Hz, 1H), 2.88-2.72 (m, 3H), 2.66-2.57 (m, 1H), 2.40-2.34 (m, 1H), 1.80-1.68 (m, 1H), 1.59-1.44 (m, 1H), 1.19 (t, J=7.2 Hz, 3H)

Example 372

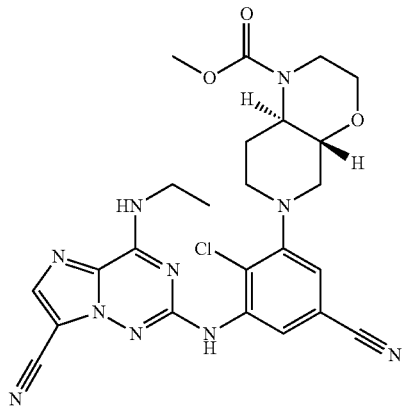 [SMILES: CCNc1nc(Nc2cc(C#N)cc(N3CC[C@@H]4[C@@H](C3)OCCN4C(=O)OC)c2Cl)nn2c(C#N)cnc12]

(+/−)-(4aR,8aR)-methyl 6-(2-chloro-5-cyano-3-((7-cyano-4-(ethylamino)imidazo[2,1-f][1,2,4]triazin-2-yl)amino)phenyl)octahydro-1H-pyrido[3,4-b][1,4]oxazine-1-carboxylate (+/−)-2-((2-chloro-5-cyano-3-((4aR,8aR)-hexahydro-1H-pyrido[3,4-b][1,4]oxazin-6(7H)-yl)phenyl)amino)-4-(ethylamino)imidazo[2,1-f][1,2,4]triazine-7-carbonitrile (Example 371) (10 mg, 0.021 mmol, was taken up in MeOH (1 mL) and DIPEA 20 μL was added. The reaction was stirred at 5° C. (ice bath) and methyl carbonochloridate (1.617 μl, 0.021 mmol) was added; the reaction stirred at 25° C. 1 hr. The solvents removed and the crude material was purified via preparative LC/MS with the following conditions: Column: Waters XBridge C18, 19×200 mm, 5-μm particles; Guard Column: Waters XBridge C18, 19×10 mm, 5-μm particles; Mobile Phase A: water with 20-mM ammonium acetate; Mobile Phase B: 95:5 acetonitrile:water with 20-mM ammonium acetate; Gradient: 40-100% B over 15 minutes, then a 5-minute hold at 100% B; Flow: 20 mL/min. Fractions containing the desired product were combined and dried via centrifugal evaporation to afford (+/−)-(4aR,8aR)-methyl 6-(2-chloro-5-cyano-3-((7-cyano-4-(ethylamino)imidazo[2,1-f][1,2,4]triazin-2-yl)amino)phenyl)octahydro-1H-pyrido[3,4-b][1,4]oxazine-1-carboxylate (7.8 mg).

MS (ESI) m/z 537
$^1$H NMR (500 MHz, DMSO-d$_6$) δ 9.25-9.09 (m, 1H), 8.89-8.75 (m, 1H), 8.28-8.14 (m, 1H), 8.03-7.90 (m, 1H), 7.43-7.27 (m, 1H), 3.94-3.80 (m, 2H), 3.71-3.64 (m, 1H), 3.64-3.55 (m, 4H), 3.23-3.12 (m, 2H), 2.89 (s, 2H), 2.83-2.75 (m, 1H), 2.73 (s, 2H), 2.70-2.56 (m, 2H), 2.09-1.77 (m, 1H), 1.36-1.01 (m, 3H)

Example 373

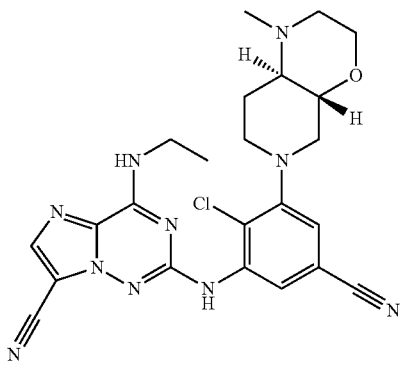 [SMILES: CCNc1nc(Nc2cc(C#N)cc(N3CC[C@@H]4[C@@H](C3)OCCN4C)c2Cl)nn2c(C#N)cnc12]

(+/−)-2-((2-chloro-5-cyano-3-((4aR,8aR)-1-methyl-hexahydro-1H-pyrido[3,4-b][1,4]oxazin-6(7H)-yl)phenyl)amino)-4-(ethylamino)imidazo[2,1-f][1,2,4]triazine-7-carbonitrile (+/−)-2-((2-chloro-5-cyano-3-((4aR,8aR)-hexahydro-1H-pyrido[3,4-b][1,4]oxazin-6(7H)-yl)phenyl)amino)-4-(ethylamino)imidazo[2,1-f][1,2,4]triazine-7-carbonitrile (Example 371) (13 mg, 0.027 mmol) was taken up in MeOH (0.5 mL) and THF (0.5 mL) and trimethyl orthoformate (0.225 mL, 2.036 mmol), AcOH (6.22 μl, 0.109 mmol), and formaldehyde (2.492 μl, 0.027 mmol) were added. The reaction was stirred at 25° C. for 5 min, then NaCNBH4 (0.271 mL, 0.271 mmol) was added and the reaction stirred at 25° C. 1 hr. The reaction mixture was diluted with EtOAc and washed with sat'd NaHCO3, then brine. The organic layer was dried over Na2SO4, and concentrated. The crude material was purified via preparative LC/MS with the following conditions: Column: Waters XBridge C18, 19×200 mm, 5-μm particles; Guard Column: Waters XBridge C18, 19×10 mm, 5-μm particles; Mobile Phase A: water with 20-mM ammonium acetate; Mobile Phase B: 95:5 acetonitrile:water with 20-mM ammonium acetate; Gradient: 50-100% B over 15 minutes, then a 5-minute hold at 100% B; Flow: 20 mL/min. Fractions containing the desired product were combined and dried via centrifugal evaporation to afford (+/−)-2-((2-chloro-5-cyano-3-((4aR,8aR)-1-methyl-hexahydro-1H-pyrido[3,4-b][1,4]oxazin-6(7H)-yl)phenyl)amino)-4-(ethylamino)imidazo[2,1-f][1,2,4]triazine-7-carbonitrile (12.2 mg).

MS (ESI) m/z 493
$^1$H NMR (500 MHz, DMSO-d$_6$) δ 9.26-9.09 (m, 1H), 8.98-8.70 (m, 1H), 8.31-8.13 (m, 1H), 8.04-7.88 (m, 1H), 7.40-7.19 (m, 1H), 3.83-3.73 (m, 1H), 3.70-3.58 (m, 1H), 3.50-3.47 (m, 2H), 3.29-3.23 (m, 3H), 2.86-2.73 (m, 1H), 2.73-2.57 (m, 2H), 2.18 (br. s., 4H), 2.11-2.00 (m, 1H), 1.79-1.66 (m, 1H), 1.47-1.33 (m, 1H), 1.28-1.09 (m, 3H)

Example 374

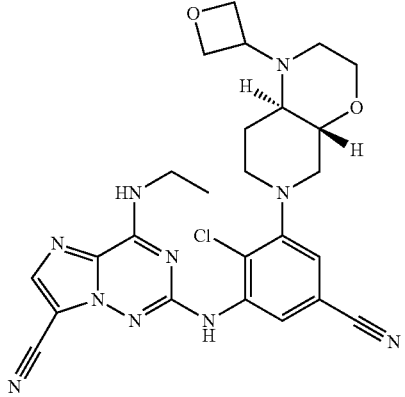 [SMILES: CCNc1nc(Nc2cc(C#N)cc(N3CC[C@@H]4[C@@H](C3)OCCN4C3COC3)c2Cl)nn2c(C#N)cnc12]

(+/−)-2-((2-chloro-5-cyano-3-((4aR,8aR)-1-(oxetan-3-yl)hexahydro-1H-pyrido[3,4-b][1,4]oxazin-6(7H)-yl)phenyl)amino)-4-(ethylamino)imidazo[2,1-f][1,2,4]triazine-7-carbonitrile (+/−)-2-((2-chloro-5-cyano-3-((4aR,8aR)-hexahydro-1H-pyrido[3,4-b][1,4]oxazin-6(7H)-yl)phenyl)amino)-4-(ethylamino)imidazo[2,1-f][1,2,4]triazine-7-carbonitrile (Example 371) (10 mg, 0.021 mmol) was taken up in MeOH (0.5 mL) and THF (0.5 mL) and trimethyl orthoformate (0.173 mL, 1.566 mmol), AcOH (4.78 µl, 0.084 mmol), and oxetan-3-one (0.013 mL, 0.209 mmol) were added. The reaction was stirred at 25° C. for 2 hr, then NaCNBH4 (0.209 mL, 0.209 mmol) was added and the reaction stirred at 25° C. overnight. The reaction mixture was diluted with EtOAc and washed with sat'd NaHCO3, then brine. The organic layer was dried over Na2SO4, filtered, and concentrated. The crude material was purified via preparative LC/MS with the following conditions: Column: Waters XBridge C18, 19×200 mm, 5-nm particles; Guard Column: Waters XBridge C18, 19×10 mm, 5-nm particles; Mobile Phase A: water with 20-mM ammonium acetate; Mobile Phase B: 95:5 acetonitrile:water with 20-mM ammonium acetate; Gradient: 45-85% B over 20 minutes, then a 5-minute hold at 100% B; Flow: 20 mL/min. The material was further purified via preparative LC/MS with the following conditions: Column: Waters XBridge C18, 19×200 mm, 5-nm particles; Guard Column: Waters XBridge C18, 19×10 mm, 5-nm particles; Mobile Phase A: water with 20-mM ammonium acetate; Mobile Phase B: 95:5 acetonitrile:water with 20-mM ammonium acetate; Gradient: 40-80% B over 20 minutes, then a 5-minute hold at 100% B; Flow: 20 mL/min. Fractions containing the desired product were combined and dried via centrifugal evaporation to afford (+/−)-2-((2-chloro-5-cyano-3-((4aR,8aR)-1-(oxetan-3-yl)hexahydro-1H-pyrido[3,4-b][1,4]oxazin-6(7H)-yl)phenyl)amino)-4-(ethylamino)imidazo[2,1-f][1,2,4]triazine-7-carbonitrile (2.4 mg).

MS (ESI) m/z 535

$^1$H NMR (500 MHz, DMSO-$d_6$) δ 9.30-9.07 (m, 1H), 8.95-8.69 (m, 1H), 8.32-8.11 (m, 1H), 8.06-7.85 (m, 1H), 7.44-7.16 (m, 1H), 4.72-4.34 (m, 4H), 3.88-3.75 (m, 2H), 3.74-3.59 (m, 5H), 2.79-2.67 (m, 1H), 2.66-2.55 (m, 2H), 2.16-1.99 (m, 1H), 1.97-1.82 (m, 1H), 1.75-1.63 (m, 1H), 1.57-1.37 (m, 2H), 1.18 (br. s., 3H)

Example 375

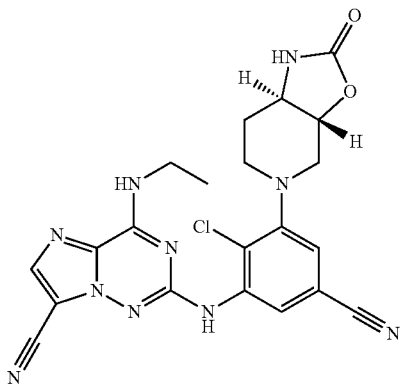 [SMILES: CCNc1nc(Nc2cc(C#N)cc(N3CC[C@H]4NC(=O)O[C@@H]4C3)c2Cl)nn2c(C#N)cnc12]

2-((2-chloro-5-cyano-3-((3aR,7aR)-2-oxohexahydrooxazolo[5,4-c]pyridin-5(2H)-yl)phenyl)amino)-4-(ethylamino)imidazo[2,1-f][1,2,4]triazine-7-carbonitrile (375A): 2-chloro-4-(ethyl(4-methoxybenzyl)amino)imidazo[2,1-f][1,2,4]triazine-7-carbonitrile (Intermediate 10) (350.0 mg, 1.021 mmol), tert-butyl((3R,4R)-1-(3-amino-2-chloro-5-cyanophenyl)-3-hydroxypiperidin-4-yl)carbamate (412.0 mg, 1.123 mmol), DPPF (39.6 mg, 0.071 mmol), Cs$_2$CO$_3$ (566 mg, 1.736 mmol), Xantphos (59.1 mg, 0.102 mmol), Palladium(II)Acetate (68.8 mg, 0.306 mmol) and 1,4-dioxane (11 ml) were combined in a microwave vial. The vial was evacuated and backfilled with Nitrogen 3×. The reaction stirred at 100° C. for 3 hr. The reaction mixture cooled to 25° C., diluted with EtOAc, washed with brine and dried (Na$_2$SO$_4$). The solvents were removed and the material purified on silica gel 25% EtOAc in DCM to afford tert-butyl((3R,4R)-1-(2-chloro-5-cyano-3-((7-cyano-4-(ethylamino)imidazo[2,1-f][1,2,4]triazin-2-yl)amino)phenyl)-3-hydroxypiperidin-4-yl)carbamate (335 mg).

MS (ESI) m/z 673

(375B): tert-butyl((3R,4R)-1-(2-chloro-5-cyano-3-((7-cyano-4-(ethyl(4-methoxybenzyl)amino)imidazo[2,1-f][1,2,4]triazin-2-yl)amino)phenyl)-3-hydroxypiperidin-4-yl)carbamate (335 mg, 0.373 mmol) was mixed with anisole (0.2 mL, 1.831 mmol), DCE (3 mL) and TFA (1 mL, 12.98 mmol). The mixture was stirred at 25° C. for 12 hr. The mixture was concentrated to dryness under high-vac and 50 ml 2N NH3/MeOH was added and the mixture stirred for 30 min. A white precipitate formed and was collected by filtration, washed with 20 ml cold MeOH, 10 ml ether, and dried under air-suction to give 2-((3-((3R,4R)-4-amino-3-hydroxypiperidin-1-yl)-2-chloro-5-cyanophenyl)amino)-4-(ethylamino)imidazo[2,1-f][1,2,4]triazine-7-carbonitrile (200 mg).

MS (ESI) m/z 453

$^1$H NMR (500 MHz, DMSO-$d_6$) δ 9.39-9.03 (br. s, 1H), 9.02-8.77 (br.s, 1H), 8.20 (s, 1H), 8.16-8.08 (m, 1H), 7.95 (d, J=1.8 Hz, 1H), 7.31 (d, J=1.8 Hz, 1H), 5.01 (d, J=4.3 Hz, 1H), 4.18-4.02 (m, 1H), 3.73 (d, J=18.8 Hz, 1H), 3.46 (q, J=7.2 Hz, 1H), 3.30-3.10 (m, 3H), 2.73 (s, 1H), 2.48-2.37 (m, 2H), 1.88-1.73 (m, 1H), 1.50-1.35 (m, 1H), 1.29-1.07 (m, 3H)

Example 375

A solution of 2-((3-((3R,4R)-4-amino-3-hydroxypiperidin-1-yl)-2-chloro-5-cyanophenyl)amino)-4-(ethylamino)imidazo[2,1-f][1,2,4]triazine-7-carbonitrile (30 mg, 0.066 mmol) and DIPEA (0.035 mL, 0.199 mmol) in ethane-1,2-diol 1 mL at 0° C. (ice bath) was treated with 4-nitrophenyl carbonochloridate (18 mg, 0.089 mmol). The reaction was stirred for 0.5 hour and the reaction is complete. The reaction mixture was diluted with THF 1 ml/EtOAc 30 ml, washed 2× brine (5 ml) and dried over Na$_2$SO$_4$. The solvents removed and the crude material was purified via preparative LC/MS with the following conditions: Column: Waters XBridge C18, 19×200 mm, 5-μm particles; Guard Column: Waters XBridge C18, 19×10 mm, 5-μm particles; Mobile Phase A: water with 20-mM ammonium acetate; Mobile Phase B: 95:5 acetonitrile:water with 20-mM ammonium acetate; Gradient: 35-80% B over 25 minutes, then a 5-minute hold at 100% B; Flow: 20 mL/min. Fractions containing the desired product were combined and dried via centrifugal evaporation to afford 2-((2-chloro-5-cyano-3-((3aR,7aR)-2-oxohexahydrooxazolo[5,4-c]pyridin-5(2H)-yl)phenyl)amino)-4-(ethylamino)imidazo[2,1-f][1,2,4]triazine-7-carbonitrile (6.0 mg).

MS (ESI) m/z 479

$^1$H NMR (500 MHz, DMSO-d$_6$) δ 9.09-8.27 (m, 1H), 8.20 (s, 1H), 7.99 (br. s., 1H), 7.83 (br. s., 1H), 7.46 (br. s., 1H), 4.09-3.95 (m, 1H), 3.68-3.58 (m, 1H), 3.46 (br. s., 3H), 3.41-3.38 (m, 1H), 3.39-3.37 (m, 1H), 3.24-3.13 (m, 1H), 3.01-2.84 (m, 1H), 2.08-1.94 (m, 1H), 1.87-1.66 (m, 1H), 1.19 (br. s., 3H)

Example 376

LC/MS with the following conditions: Column: Waters XBridge C18, 19×200 mm, 5-μm particles; Guard Column: Waters XBridge C18, 19×10 mm, 5-μm particles; Mobile Phase A: water with 20-mM ammonium acetate; Mobile Phase B: 95:5 acetonitrile:water with 20-mM ammonium acetate; Gradient: 35-75% B over 20 minutes, then a 5-minute hold at 100% B; Flow: 20 mL/min. Fractions containing the desired product were combined and dried via centrifugal evaporation to afford 2,5,8,11,14,17-hexaoxanonadecan-19-yl((3R,4R)-1-(2-chloro-5-cyano-3-((7-cyano-4-(ethylamino)imidazo[2,1-f][1,2,4]triazin-2-yl)amino)phenyl)-3-hydroxypiperidin-4-yl)carbamate (14.8 mg).

MS (ESI) m/z 775

$^1$H NMR (500 MHz, DMSO-d$_6$) δ 9.13-8.42 (m, 1H), 8.20 (s, 1H), 7.97 (s, 1H), 7.32 (br. s., 1H), 7.20 (br. s., 1H), 5.12-4.85 (m, 1H), 4.06 (br. s., 2H), 3.66-3.39 (m, 28H), 3.24 (s, 5H), 2.84-2.69 (m, 1H), 2.02-1.80 (m, 1H), 1.66-1.44 (m, 1H), 1.19 (t, J=7.2 Hz, 3H)

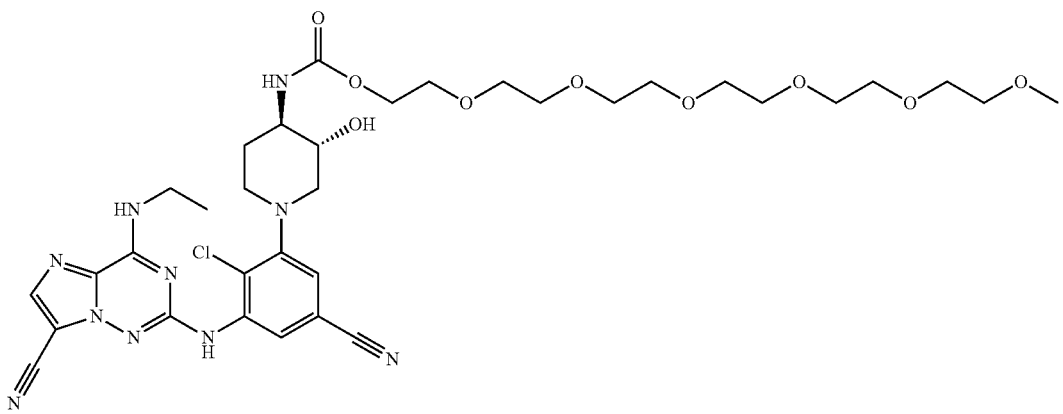 [SMILES: CCNc1nc(Nc2cc(C#N)cc(N3CC[C@@H](NC(=O)OCCOCCOCCOCCOCCOCCOC)[C@H](O)C3)c2Cl)nn2c(C#N)cnc12]

2,5,8,11,14,17-hexaoxanonadecan-19-yl((3R,4R)-1-(2-chloro-5-cyano-3-((7-cyano-4-(ethylamino)imidazo[2,1-f][1,2,4]triazin-2-yl)amino)phenyl)-3-hydroxypiperidin-4-yl)carbamate A solution of 2-((3-((3R,4R)-4-amino-3-hydroxypiperidin-1-yl)-2-chloro-5-cyanophenyl)amino)-4-(ethylamino)imidazo[2,1-f][1,2,4]triazine-7-carbonitrile (Example 375B) (30 mg, 0.066 mmol) and DIPEA (0.035 mL, 0.199 mmol) in MeOH (1.5 mL) was added to 2,5,8,11,14,17-hexaoxanonadecan-19-yl carbonochloridate (121 mg, 0.337 mmol). The reaction was stirred for 0.5 hour and the reaction was complete. The solvents removed and the crude material was purified via preparative LC/MS with the following conditions: Column: Waters XBridge C18, 19×200 mm, 5-μm particles; Guard Column: Waters XBridge C18, 19×10 mm, 5-μm particles; Mobile Phase A: water with 20-mM ammonium acetate; Mobile Phase B: 95:5 acetonitrile:water with 20-mM ammonium acetate; Gradient: 50-90% B over 20 minutes, then a 5-minute hold at 100% B; Flow: 20 mL/min. The material was further purified via preparative Example 377

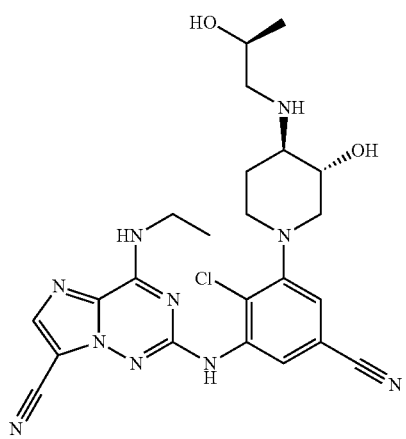 [SMILES: CCNc1nc(Nc2cc(C#N)cc(N3CC[C@@H](NC[C@H](C)O)[C@H](O)C3)c2Cl)nn2c(C#N)cnc12]

2-((2-chloro-5-cyano-3-((3R,4R)-3-hydroxy-4-(((S)-2-hydroxypropyl)amino)piperidin-1-yl)phenyl)amino)-4-(ethylamino)imidazo[2,1-f][1,2,4]triazine-7-carbonitrile To a solution of 2-((3-((3R,4R)-4-amino-3-hydroxypiperidin-1-yl)-2-chloro-5-cyanophenyl)amino)-4-(ethylamino)imidazo[2,1-f][1,2,4]triazine-7-carbonitrile (Example 375B) (50 mg, 0.110 mmol) and DIPEA (0.031 mL, 0.221 mmol) in MeOH (0.5 mL)/DCM (0.5 ml) was added (S)-2-methyloxirane (64.1 mg, 1.104 mmol). The reaction was stirred for 16 hours. The solvents were removed and the crude material was purified via preparative LC/MS with the following conditions: Column: Waters XBridge C18, 19×200 mm, 5-μm particles; Guard Column: Waters XBridge C18, 19×10 mm, 5-μm particles; Mobile Phase A: water with 20-mM ammonium acetate; Mobile Phase B: 95:5 acetonitrile:water with 20-mM ammonium acetate; Gradient: 10-55% B over 25 minutes, then a 8-minute hold at 100% B; Flow: 20 mL/min. Fractions containing the desired product were combined and dried via centrifugal evaporation to afford 2-((2-chloro-5-cyano-3-((3R,4R)-3-hydroxy-4-(((S)-2-hydroxypropyl)amino)piperidin-1-yl)phenyl)amino)-4-(ethylamino)imidazo[2,1-f][1,2,4]triazine-7-carbonitrile (14.5 mg).

MS (ESI) m/z 511

$^1$H NMR (500 MHz, DMSO-d$_6$) δ 9.24-9.15 (m, 1H), 8.86 (s, 1H), 8.20 (s, 1H), 7.99 (d, J=1.8 Hz, 1H), 7.97-7.93 (m, 1H), 7.35 (d, J=1.8 Hz, 1H), 5.84-5.68 (m, 1H), 5.38-5.12 (m, 1H), 3.91 (s, 1H), 3.86-3.71 (m, 1H), 3.46 (d, J=6.1 Hz, 3H), 3.08-2.92 (m, 2H), 2.74 (s, 3H), 2.62-2.54 (m, 1H), 2.23-2.10 (m, 1H), 1.80-1.65 (m, 1H), 1.23-1.16 (m, 3H), 1.14 (d, J=6.4 Hz, 3H)

Example 378

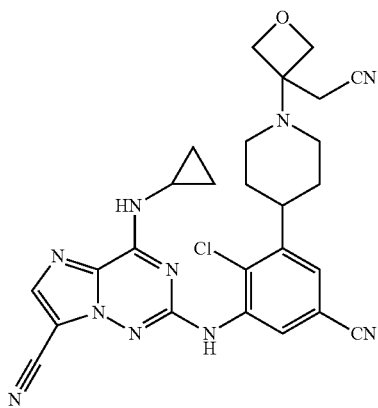 [SMILES: N#CCC1(N2CCC(c3cc(C#N)cc(Nc4nc(NC5CC5)c5ncc(C#N)n5n4)c3Cl)CC2)COC1]

2-((2-chloro-5-cyano-3-(1-(3-(cyanomethyl)oxetan-3-yl)piperidin-4-yl)phenyl)amino)-4-(cyclopropylamino)imidazo[2,1-f][1,2,4]triazine-7-carbonitrile To a solution of 2-((2-chloro-5-cyano-3-(piperidin-4-yl)phenyl)amino)-4-(cyclopropyl(4-methoxybenzyl)amino)imidazo[2,1-f][1,2,4]triazine-7-carbonitrile (Example 208D) (30 mg, 0.054 mmol) in a mixture solvent {CH$_2$Cl$_2$ (1 ml)/MeOH (0.5 mL)} was added Et$_3$N (0.011 ml, 0.081 mmol) followed by 2-(oxetan-3-ylidene)acetonitrile (36.0 mg, 0.379 mmol). The reaction mixture was heated at 50° C. for 2 days. The reaction mixture was partitioned between EtOAc and water. The organic layer was washed with brine, dried over Na$_2$SO$_4$, removal of the solvent and the crude PMB-protected product was purified by silica gel chromatography, eluting with DCM containing 0 to 2% MeOH. The PMB-protected product was dissolved in DCE (2 ml), and added anisole (0.059 ml, 0.541 mmol), followed by TFA (0.5 ml). The resulting mixture was stirred at rt overnight. Removal of the solvent, and the crude material was purified by prep. HPLC (100×30 mm Luna C18 column, Solvent A=10% Methanol, 90% H2O, 0.1% TFA; solvent B=90% Methanol, 10% H2O, 0.1% TFA, Flow rate 42 ml permin, 20-100% B, over 20 min) The HPLC fractions containing the product were applied onto a cartridges of Phenomenex Strata-X-C 33 um cation mixed-mode polymer. This was washed with methanol and product was eluted with large amount of 2 N solution of ammonia in methanol/DCM (1:1). Removal of the solvents left 2-((2-chloro-5-cyano-3-(1-(3-(cyanomethyl)oxetan-3-yl)piperidin-4-yl)phenyl)amino)-4-(cyclopropylamino)imidazo[2,1-f][1,2,4]triazine-7-carbonitrile (10.6 mg) as a solid.

MS (ESI) m/z 529.27 (M+1).

1H NMR (500 MHz, CDCl3/METHANOL-d4) d 8.88 (d, J=2.0 Hz, 1H), 7.86 (s, 1H), 7.25 (d, J=1.8 Hz, 1H), 4.67 (d, J=6.4 Hz, 2H), 4.46 (d, J=6.7 Hz, 2H), 3.16-3.06 (m, 1H), 3.02 (dt, J=7.4, 3.5 Hz, 1H), 2.90 (s, 2H), 2.78 (d, J=11.3 Hz, 2H), 2.50-2.35 (m, 2H), 1.92 (d, J=11.0 Hz, 2H), 1.80-1.67 (m, 2H), 1.07-0.98 (m, 2H), 0.81-0.72 (m, 2H)

Example 379

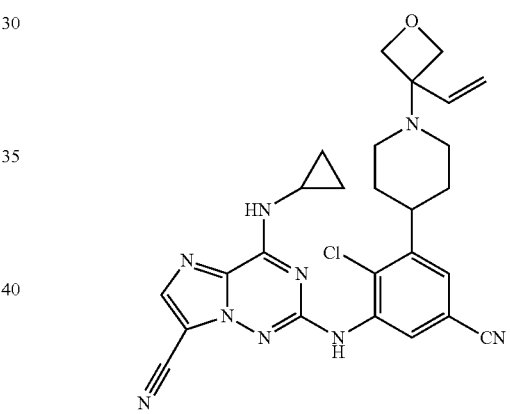

2-((2-chloro-5-cyano-3-(1-(3-vinyloxetan-3-yl)piperidin-4-yl)phenyl)amino)-4-(cyclopropylamino)imidazo[2,1-f][1,2,4]triazine-7-carbonitrile (379A): To a solution of 2-((2-chloro-5-cyano-3-(piperidin-4-yl)phenyl)amino)-4-(cyclopropyl(4-methoxybenzyl)amino)imidazo[2,1-f][1,2,4]triazine-7-carbonitrile (375D) (50 mg, 0.090 mmol) in dry THF (0.3 mL) was added 1,8-Diazabicyclo[5.4.0]undec-7-ene (diluted with THF, 10V %) (0.013 mL, 9.02 μmol) at RT. The mixture was cooled in an ice/NaCl bath (−15° C.). To this was added 2-(oxetan-3-ylidene)acetaldehyde (36 mg, 0.367 mmol), and left stirring at −15° C. to 0° C. for 2.5 h, then the mixture was put in the freezer for 7 days. To the reaction mixture was added MeOH (1 mL), then sodium borohydride (10.30 mg, 0.271 mmol) at RT and stirred for 2 hrs. Diluted with EtOAc, washed with NaHCO3, water, brine, and dried over Na$_2$SO$_4$. Removal of the solvent. The crude material was purified by radial chromatography, eluting with DCM containing 0 to 1% MeOH to give 2-((2-chloro-5-cyano-3-(1-(3-(2-hydroxyethyl)oxetan-3-yl)piperidin-4-yl)phenyl)amino)-4-(cyclopropyl(4-methoxybenzyl)amino)imidazo[2,1-f][1,2,4]triazine-7-carbonitrile (29 mg).

Example 379

2-((2-chloro-5-cyano-3-(1-(3-(2-hydroxyethyl)oxetan-3-yl)piperidin-4-yl)phenyl)amino)-4-(cyclopropyl(4-methoxybenzyl)amino)imidazo[2,1-f][1,2,4]triazine-7-carbonitrile was dissolved in $CH_2Cl_2$ (1.5 mL), flushed with $N_2$, and cooled to −78° C., then added DAST (14.29 mg, 0.089 mmol). The reaction mixture was allowed to warm slowly to RT and stirred for overnight. To the reaction mixture was added anisole (23.97 mg, 0.222 mmol) followed by TFA (0.5 ml), left stirring at rt over weekend. Removal of the solvent. The crude material was purified via preparative LC/MS with the following conditions: Column: Waters XBridge C18, 19×200 mm, 5-μm particles; Mobile Phase A: water with 20-mM ammonium acetate; Mobile Phase B: 95:5 acetonitrile:water with 20-mM ammonium acetate; Gradient: 10-50% B over 20 minutes, then a 5-minute hold at 100% B; Flow: 20 mL/min. Fractions containing the desired product were combined and dried via centrifugal evaporation left the title compound 11(2.9 mg).

MS: (ESI) m/z 516.15 (M+1).

$^1$H NMR (500 MHz, DMSO-$d_6$) δ 9.38 (d, J=7.3 Hz, 1H), 8.92 (br. s., 1H), 8.36 (s, 1H), 8.22 (s, 1H), 7.58 (br. s., 1H), 5.26 (m 1H), 4.63 (m, 2H), 4.27-4.24 (t, J=8.7 Hz, 2H), 3.83-3.63 (m, 2H), 3.04-2.94 (m, 2H), 2.91 (m, 1H), 2.79-2.71 (m, 3H), 2.11-1.92 (m, 4H), 0.80-0.78 (m, 4H)

Example 380

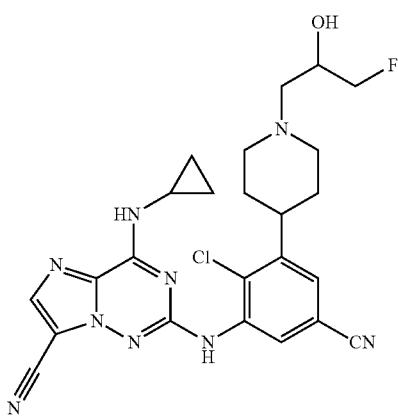 [SMILES: N#Cc1cc(Nc2nc(NC3CC3)c3ncc(C#N)n3n2)c(Cl)c(C2CCN(CC(O)CF)CC2)c1]

(+/−)-2-((2-chloro-5-cyano-3-(1-(3-fluoro-2-hydroxypropyl)-4-piperidinyl)phenyl)amino)-4-(cyclopropylamino)imidazo[2,1-f][1,2,4]triazine-7-carbonitrile Prepared in similar manner as Example 57
MS: (ESI) m/z 510.15

Example 381

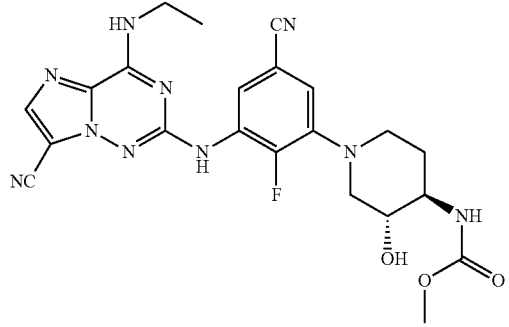 [SMILES: CCNc1nc(Nc2cc(C#N)cc(N3CC[C@@H](NC(=O)OC)[C@H](O)C3)c2F)nn2c(C#N)cnc12]

methyl((3R,4R)-1-(5-cyano-3-((7-cyano-4-(ethylamino)imidazo[2,1-f][1,2,4]triazin-2-yl)amino)-2-fluorophenyl)-3-hydroxypiperidin-4-yl)carbamate (381A): methyl((3R,4R)-1-(3-amino-5-cyano-2-fluorophenyl)-3-hydroxypiperidin-4-yl)carbamate was prepared in similar manner as Example 328E1 from intermediate 17.

(381B): 2-chloro-4-(ethyl(4-methoxybenzyl)amino)imidazo[2,1-f][1,2,4]triazine-7-carbonitrile (Intermediate 7) (50 mg, 0.146 mmol), methyl((3R,4R)-1-(3-amino-5-cyano-2-fluorophenyl)-3-hydroxypiperidin-4-yl)carbamate (46 mg, 0.149 mmol), DPPF (5.66 mg, 10.21 μmol), $Cs_2CO_3$ (81 mg, 0.248 mmol), Xantphos (8.44 mg, 0.015 mmol), Palladium(II)Acetate (9.82 mg, 0.044 mmol) and 1,4-dioxane (2 ml) were combined in a microwave vial. The vial was evacuated and backfilled with Nitrogen 3×. The reaction stirred at 100° C. for 3 hr. The reaction mixture cooled to 25° C., diluted with EtOAc and washed with brine and dried ($Na_2SO_4$). The solvents were removed and the material purified on silica gel 25% EtOAc in DCM to afford methyl ((3R,4R)-1-(5-cyano-3-((7-cyano-4-(ethyl(4-methoxybenzyl)amino)imidazo[2,1-f][1,2,4]triazin-2-yl)amino)-2-fluorophenyl)-3-hydroxypiperidin-4-yl)carbamate (60 mg)
MS: (ESI) m/z 615

Example 381

To methyl((3R,4R)-1-(5-cyano-3-((7-cyano-4-(ethyl(4-methoxybenzyl)amino)imidazo[2,1-f][1,2,4]triazin-2-yl)amino)-2-fluorophenyl)-3-hydroxypiperidin-4-yl)carbamate (60 mg, 0.098 mmol), in DCE (1.5 mL) was added ANISOLE (0.1 mL, 0.915 mmol) and TFA (1.0 mL, 12.98 mmol); the mixture stirred 2 h at 25° C. and solvent was removed. The crude material was purified via preparative LC/MS with the following conditions: Column: Waters XBridge C18, 19×200 mm, 5-μm particles; Guard Column: Waters XBridge C18, 19×10 mm, 5-μm particles; Mobile Phase A: water with 20-mM ammonium acetate; Mobile Phase B: 95:5 acetonitrile:water with 20-mM ammonium acetate; Gradient: 15-100% B over 20 minutes, then a 5-minute hold at 100% B; Flow: 20 mL/min. Fractions containing the desired product were combined and dried via centrifugal evaporation to afford methyl((3R,4R)-1-(5-cyano-3-((7-cyano-4-(ethylamino)imidazo[2,1-f][1,2,4]triazin-2-yl)amino)-2-fluorophenyl)-3-hydroxypiperidin-4-yl)carbamate (3.8 mg).
MS: (ESI) m/z 495

¹H NMR (500 MHz, DMSO-d₆) δ 9.30-9.01 (m, 2H), 8.30-8.06 (m, 1H), 7.93-7.68 (m, 1H), 7.26-7.14 (m, 1H), 7.12-6.97 (m, 1H), 5.18-4.84 (m, 1H), 3.34-3.17 (m, 9H), 2.88-2.70 (m, 1H), 2.63-2.53 (m, 1H), 1.96-1.71 (m, 1H), 1.62-1.41 (m, 1H), 1.19 (br. s., 3H)

Example 382

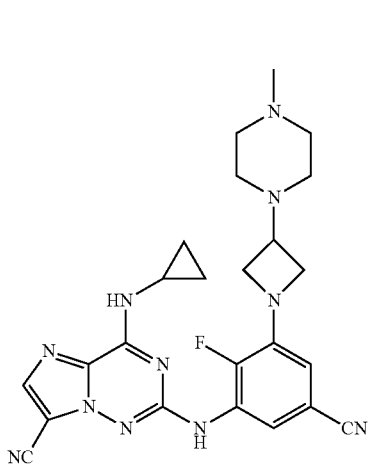 [SMILES: CN1CCN(C2CN(c3cc(C#N)cc(Nc4nc(NC5CC5)c5ncc(C#N)n5n4)c3F)C2)CC1]

2-((5-cyano-2-fluoro-3-(3-(4-methylpiperazin-1-yl)azetidin-1-yl)phenyl)amino)-4-(cyclopropylamino)imidazo[2,1-f][1,2,4]triazine-7-carbonitrile (382A): 3-amino-4-fluoro-5-(3-(4-methylpiperazin-1-yl)azetidin-1-yl)benzonitrile was prepared in analogous manner as Example 151C using intermediate 17

Example 382: 2-chloro-4-(cyclopropyl(4-methoxybenzyl)amino)imidazo[2,1-f][1,2,4]triazine-7-carbonitrile (Intermediate 9) (60 mg, 0.169 mmol), 3-amino-4-fluoro-5-(3-(4-methylpiperazin-1-yl)azetidin-1-yl)benzonitrile (48 mg, 0.166 mmol), DPPF (6.44 mg, 0.012 mmol), Cs₂CO₃ (92 mg, 0.282 mmol), Xantphos (9.60 mg, 0.017 mmol), Palladium(II)Acetate (11.17 mg, 0.050 mmol) and 1,4-dioxane (2 ml) were combined in a microwave vial. The vial was evacuated and backfilled with Nitrogen 3×. The reaction stirred at 100° C. for 3 hr. The reaction mixture was cooled to 25° C., diluted with EtOAc, washed with brine and dried (Na₂SO₄). The solvents were removed and DCE (1 mL)/TFA (0.5 mL) was added. The reaction stirred 3 h and solvents were removed. The crude material was purified via preparative LC/MS with the following conditions: Column: Waters XBridge C18, 19×200 mm, 5-µm particles; Guard Column: Waters XBridge C18, 19×10 mm, 5-µm particles; Mobile Phase A: water with 20-mM ammonium acetate; Mobile Phase B: 95:5 acetonitrile:water with 20-mM ammonium acetate; Gradient: 50-100% B over 20 minutes, then a 5-minute hold at 100% B; Flow: 20 mL/min. Fractions containing the desired product were combined and dried via centrifugal evaporation to afford 2-((5-cyano-2-fluoro-3-(3-(4-methylpiperazin-1-yl)azetidin-1-yl)phenyl)amino)-4-(cyclopropylamino)imidazo[2,1-f][1,2,4]triazine-7-carbonitrile (16.9 mg).

MS: (ESI) m/z 488

¹H NMR (500 MHz, DMSO-d₆) δ 9.54-9.23 (m, 1H), 9.23-9.07 (m, 1H), 8.25-8.07 (m, 1H), 7.82-7.66 (m, 1H), 6.86-6.48 (m, 1H), 4.07 (br. s., 2H), 3.87-3.67 (m, 3H), 3.25-3.15 (m, 3H), 3.10-2.76 (m, 5H), 2.69-2.53 (m, 4H), 0.79 (br. s., 4H)

Example 383

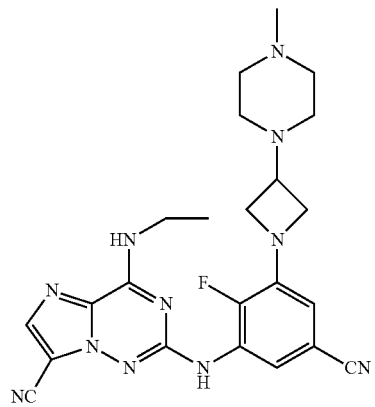 [SMILES: CCNc1nc(Nc2cc(C#N)cc(N3CC(N4CCN(C)CC4)C3)c2F)nn2c(C#N)cnc12]

2-((5-cyano-2-fluoro-3-(3-(4-methylpiperazin-1-yl)azetidin-1-yl)phenyl)amino)-4-(ethylamino)imidazo[2,1-f][1,2,4]triazine-7-carbonitrile Prepared in identical manner as Example 382 from Intermediate 10 MS: (ESI) m/z 476

¹H NMR (500 MHz, DMSO-d₆) δ 9.19-9.14 (m, 1H), 9.14-9.09 (m, 1H), 8.22-8.15 (m, 1H), 8.01-7.90 (m, 1H), 7.66-7.53 (m, 1H), 6.79-6.66 (m, 1H), 4.20-4.02 (m, 2H), 3.88-3.74 (m, 2H), 3.55-3.45 (m, 4H), 2.98-2.83 (m, 4H), 2.73 (s, 5H), 1.28-1.11 (m, 3H)

Example 384

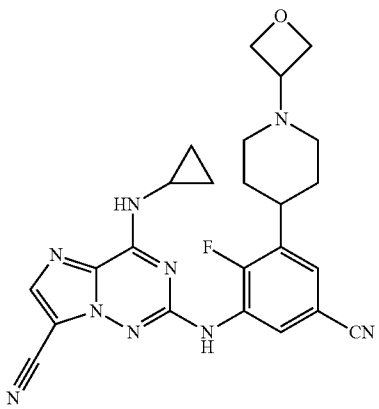 [SMILES: N#Cc1cc(Nc2nc(NC3CC3)c3ncc(C#N)n3n2)c(F)c(C2CCN(C3COC3)CC2)c1]

2-((5-cyano-2-fluoro-3-(1-(oxetan-3-yl)piperidin-4-yl)phenyl)amino)-4-(cyclopropylamino)imidazo[2,1-f][1,2,4]triazine-7-carbonitrile The title compound was prepared using a method analogous to that used to prepare Example 210.

MS (ESI) m/z 474.25 (M+1)

Example 385

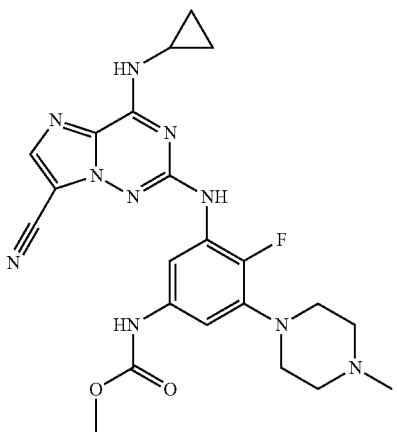 [SMILES: COC(=O)Nc1cc(Nc2nc(NC3CC3)c3ncc(C#N)n3n2)c(F)c(N2CCN(C)CC2)c1]

methyl(3-((7-cyano-4-(cyclopropylamino)imidazo[2,1-f][1,2,4]triazin-2-yl)amino)-4-fluoro-5-(4-methyl-piperazin-1-yl)phenyl)carbamate (BMT-091213, ELN 94895-052)

(385A): 1-fluoro-4-nitrobenzene (5.0 g, 35.4 mmol) was dissolved in sulfuric acid (50 ml, 938 mmol). The solution was warmed to 60° C. with stirring. NBS (14.02 g, 78 mmol) was added in portions during ~30 minutes. The reaction mixture was stirred at 60° C. for 2 hours. The reaction mixture was cooled to room temperature and extracted with toluene (no water added). The organic layer was washed with water, then $NaHCO_3$ solution, then brine, dried over $MgSO_4$, filtered and evaporated to dryness to give 10.4 g crude 1,3-dibromo-2-fluoro-5-nitrobenzene (10.4 g), which solidified after a few hours. The crude product was used "as is" in the next step.

1H NMR (400 MHz, $CD_3CN$) δ ppm 8.48 (d, J=5.5 Hz, 2H)

(385B): A 250 ml round bottom flask was charged with iron powder (325 mesh) (2.6 g, 46.6 mmol), 1,3-dibromo-2-fluoro-5-nitrobenzene (2.0 g, 4.01 mmol) and acetic acid (50 ml). The flask was evacuated and back-filled with nitrogen twice, then stirred at room temperature for 1 hour. The reaction mixture turned into a very thick slurry. Acetic acid (50 ml) was added and the mixture stirred for an additional hour. The reaction mixture was poured into EtOAc. The EtOAc solution was washed with water (2×), $NaHCO_3+Na_2CO_3$ solution until $CO_2$ evolution stopped, then once with brine, then dried over Mg504, filtered and evaporated to dryness to give 1.6 g crude 3,5-dibromo-4-fluoroaniline (1.6 g). The product was used without further purification in the next experiment.

MS (ESI) m/z 309

1H NMR (400 MHz, dmso-d6) δ ppm 6.83 (d, J=5.3 Hz, 2H), 5.46 (br, 2H)

(385C): 3,5-dibromo-4-fluoroaniline (1.6 g, 4.16 mmol) was dissolved in DCM (41.6 ml). Pyridine (0.90 ml, 11.13 mmol) was added and the reaction mixture cooled to 0-5° C. Methyl chloroformate (0.66 ml, 8.52 mmol) was added dropwise via syringe. The reaction mixture was stirred at 0-5° C. for 1 hour. The reaction mixture was diluted with additional 50 ml dichloromethane and washed with 0.5 M citric acid twice, NaHCO3 solution once and brine once, then dried over Mg504, filtered and evaporated to dryness. Chromatography on silica (gradient from 100% hexanes to 100% DCM) gave methyl(3,5-dibromo-4-fluorophenyl)carbamate (1.22 g) as a colorless fluffy solid.

MS (ESI) m/z 324

1H NMR (400 MHz, dmso-d6) δ ppm 9.98 (s, 1H), 7.78 (d, J=5.5 Hz, 2H), 3.71 (s, 3H).

(385D): A stirred solution of methyl(3,5-dibromo-4-fluorophenyl)carbamate (0.82 g, 2.508 mmol) in DMF (20 mL) was treated with sodium bis(trimethylsilyl)amide (3.01 mL, 3.01 mmol), stirred at rt for 30 minutes, then 1-(chloromethyl)-4-methoxybenzene (0.410 mL, 3.01 mmol) was added, stirred at 70° C. for two hours. The reaction mixture was partitioned between NH4Cl solution and EtOAc. The organic layer was washed with NaHCO3 solution (2×), then brine, then dried over Mg504, filtered and evaporated to dryness to give 1.40 g colorless film, which was purified by column chromatography on silica (120 g silica, gradient from 100% hexanes to 20% EtOAC in hexanes) to give methyl(3,5-dibromo-4-fluorophenyl)(4-methoxybenzyl)carbamate (1.01 g)

MS (ESI) m/z 446

1H NMR (400 MHz, dmso-d6) δ ppm 7.63 (d, J=5.8 Hz, 2H), 7.15 (d, J=8.8 Hz, 2H), 6.88 (d, J=8.5 Hz, 2H), 4.82 (s, 2H), 3.73 (s, 3H).

(385E): A round bottom flask was loaded with methyl(3,5-dibromo-4-fluorophenyl)(4-methoxybenzyl)carbamate (350 mg, 0.744 mmol), (S)-BINAP (69.5 mg, 0.112 mmol), Cesium carbonate (969 mg, 2.97 mmol) and $Pd_2dba_3$ (34.1 mg, 0.037 mmol). The flask was evacuated and filled with nitrogen 3 times. Dioxane (10 mL) and 1-methylpiperazine (0.091 mL, 0.818 mmol) were added and the vial evacuated and filled with nitrogen 3 times. The reaction mixture was heated to 90° C. for 20 hours. Benzophenone imine (0.187 mL, 1.116 mmol) was added, the temperature increased to 110° C. and stirring under nitrogen continued for 24 hours. The reaction mixture was cooled to room temperature (immersed into a room temperature water bath). Dioxane (10 ml) and aq. HCl (1.0 molar, 10 ml, 10 mmol) were added and the reaction mixture stirred at room temperature for 2 hours. The reaction mixture was partitioned between EtOAc and aq. NaHCO3 solution. The organic layer was washed with NaHCO3 solution and brine, then dried over MgSO4, filtered and concentrated in vacuum. The crude was purified by column chromatography on silica (80 g cartridge, gradient from 100% EtOAc to 20% MeOH in EtOAc) gave methyl (3-amino-4-fluoro-5-(4-methylpiperazin-1-yl)phenyl)(4-methoxybenzyl)carbamate (207 mg)

MS (ESI) m/z 403

1H NMR (400 MHz, dmso-d6) δ ppm 7.12 (d, J=8.8 Hz, 2H), 6.87 (d, J=8.8 Hz, 2H), 6.15 (dd, J=7.3, 2.3 Hz, 1H), 5.91 (dd, J=7.0, 2.3 Hz, 1H), 4.99 (s, 2H), 4.65 (s, 2H), 3.74 (s, 3H), 3.61 (s, 3H), 2.91-2.85 (m, 4H), 2.45-2.40 (m, 4H), 2.21 (s, 3H).

(385F): methyl(3-amino-4-fluoro-5-(4-methylpiperazin-1-yl)phenyl)(4-methoxybenzyl)carbamate (50 mg, 0.093 mmol), 4-(cyclopropyl(4-methoxybenzyl)amino)-2-(methylsulfonyl)imidazo[2,1-f][1,2,4]triazine-7-carbonitrile (44.6 mg, 0.112 mmol) and $Cs_2CO_3$ (91 mg, 0.280 mmol) in DMF (1 ml) were heated at 45° C. for 14 hours. LCMS showed product formation (m/e+=721, [M+H]+). The mixture was poured onto a Phenomenex Strata XC cation exchange resin (2 g adsorbent). The cartridge was washed with MeOH and $CH_3CN$. The product was eluted with a 1:1 mixture of $CH_3CN$ and a 2 molar solution of $NH_3$ in MeOH. Evaporation to dryness gave crude methyl(3-((7-cyano-4-(cyclopropyl(4-methoxybenzyl)amino)imidazo[2,1-f][1,2,4]triazin-2-yl)amino)-4-fluoro-5-(4-methylpiperazin-1-yl)phenyl)(4-methoxybenzyl)carbamate (69.5 mg). The material was used in the following PMB deprotection reaction without further purification.

MS (ESI) m/z 721

Example 385 methyl(3-((7-cyano-4-(cyclopropyl(4-methoxyben-zyl)amino)imidazo[2,1-f][1,2,4]triazin-2-yl)amino)-4-fluoro-5-(4-methylpiperazin-1-yl)phenyl)(4-methoxybenzyl)carbamate (59.6 mg, 0.062 mmol) [crude product from above] was dissolved in ClCH₂CH₂Cl (10 ml). Anisole (1 ml, 9.15 mmol) and TFA (2 ml, 26.0 mmol) were added and the mixture stirred at room temperature for 1 hour, then heated for 3 hours at 48° C. The reaction mixture was evaporated to a volume of 2 ml. The residue was diluted with MeOH and filtered through a Waters MCX cation exchange cartridge (1 g adsorbent). The cartridge was washed with MeOH+CH₃CN. The product was eluted with a 1:1 mixture of CH₃CN and a 2 molar solution of NH₃ in MeOH. Evaporation to dryness gave a yellow film. The crude material was purified via preparative LC/MS with the following conditions:

Column: Waters XBridge C18, 19×200 mm, 5-μm particles; Guard Column: Waters XBridge C18, 19×10 mm, 5-μm particles; Mobile Phase A: water with 20-mM ammonium acetate; Mobile Phase B: 95:5 acetonitrile:water with 20-mM ammonium acetate; Gradient: 10-100% B over 20 minutes, then a 4-minute hold at 100% B;

Flow: 20 mL/min. Fractions containing the desired product were combined and dried via centrifugal evaporation.

11.6 mg methyl(3-((7-cyano-4-(cyclopropylamino)imidazo[2,1-f][1,2,4]triazin-2-yl)amino)-4-fluoro-5-(4-methylpiperazin-1-yl)phenyl)carbamate was obtained.

MS (ESI) m/z 481

1H NMR (500 MHz, dmso-d6) δ ppm 9.53 (br. s, 1H), 9.11 (br. s, 1H), 8.92 (s, 1H), 8.15 (s, 1H), 7.35 (dd, J=5.6, 2.0 Hz, 1H), 6.94 (br. s., 1H), 3.65 (s, 3H), 3.15-3.09 (m, 1H), 2.99 (br. s., 4H), 2.47 (br. s., 4H), 2.23 (s, 3H), 0.81-0.70 (m, 4H).

Example 386

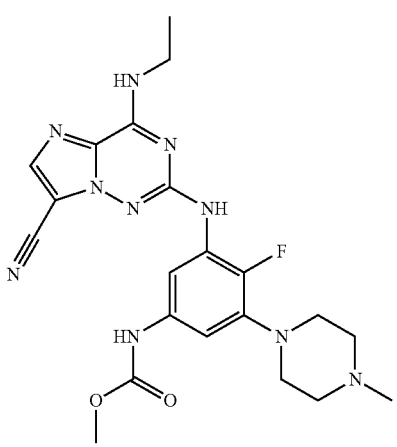 [SMILES: CCNc1nc(Nc2cc(NC(=O)OC)cc(N3CCN(C)CC3)c2F)nn2c(C#N)cnc12]

methyl(3-((7-cyano-4-(ethylamino)imidazo[2,1-f][1,2,4]triazin-2-yl)amino)-4-fluoro-5-(4-methylpiperazin-1-yl)phenyl)carbamate Prepared in analogous manner as Example 385
MS (ESI) m/z 469
1H NMR (500 MHz, dmso-d6) δ ppm) 9.54 (br. s., 1H), 9.00 (t, J=5.8 Hz, 1H), 8.89 (s, 1H), 8.16 (s, 1H), 7.28 (dd, J=5.6, 2.0 Hz, 1H), 6.95 (d, J=4.9 Hz, 1H), 3.66 (s, 3H), 3.49 (quin, J=6.8 Hz, 2H), 3.00 (br. s., 4H), 2.47 (br. s., 4H), 2.23 (s, 3H), 1.17 (t, J=7.2 Hz, 3H)

Example 387

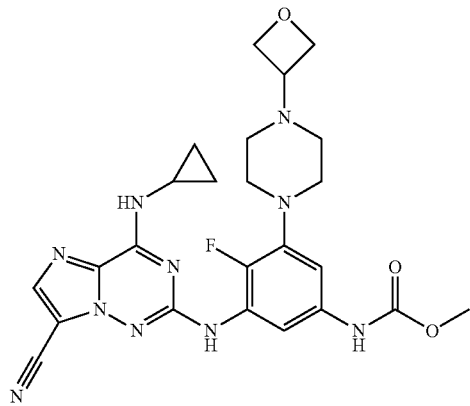 [SMILES: COC(=O)Nc1cc(Nc2nc(NC3CC3)c3ncc(C#N)n3n2)c(F)c(N2CCN(C3COC3)CC2)c1]

methyl(3-((7-cyano-4-(cyclopropylamino)imidazo[2,1-f][1,2,4]triazin-2-yl)amino)-4-fluoro-5-(4-(oxetan-3-yl)piperazin-1-yl)phenyl)carbamate (387A): A round bottom flask was loaded with methyl(3,5-dibromo-4-fluorophenyl)(4-methoxybenzyl)carbamate (Example 385D) (0.42 g, 0.892 mmol), (S)-BINAP (0.083 g, 0.134 mmol), cesium carbonate (1.163 g, 3.57 mmol), tert-butyl piperazine-1-carboxylate (0.188 g, 0.982 mmol) and Pd₂dba₃ (0.041 g, 0.045 mmol). The flask was evacuated and filled with nitrogen 3 times. Dioxane (10 mL) was added and the vial evacuated and filled with nitrogen 3 times. The reaction flask was immersed into a 90° C. oil bath and stirred at 90° C. for 19 hours. Benzophenone imine (0.225 mL, 1.339 mmol) was added, the temperature increased to 110° C. and stirring under nitrogen continued for 24 hours. Dioxane (10 ml) and aq. HCl (1.0 molar, 10 ml, 10 mmol) were added and the reaction mixture stirred at room temperature for 2 hours. The reaction mixture was partitioned between EtOAc and aq. NaHCO₃ solution. The organic layer was washed with NaHCO₃ solution and brine, then dried over MgSO₄, filtered and concentrated in vacuum to give 0.94 g brown oil, which was purified by column chromatography on silica (120 g cartridge, gradient from 100% hexanes to 100% EtOAc) to give tert-butyl 4-(3-amino-2-fluoro-5-((4-methoxybenzyl)(methoxycarbonyl)amino)phenyl)piperazine-1-carboxylate (317 mg).

MS (ESI) m/z 489
1H NMR (400 MHz, dmso-d6) δ ppm 7.12 (d, J=8.8 Hz, 2H), 6.87 (d, J=8.8 Hz, 2H), 6.18 (dd, J=7.0, 2.3 Hz, 1H), 5.94 (dd, J=6.8, 2.3 Hz, 1H), 5.04 (s, 2H), 4.66 (s, 2H), 3.73 (s, 3H), 3.61 (s, 3H), 3.49-3.39 (m, 4H), 2.89-2.77 (m, 4H), 1.44 (s, 9H).

(387B): tert-butyl 4-(3-amino-2-fluoro-5-((4-methoxybenzyl)(methoxycarbonyl)amino)phenyl)piperazine-1-carboxylate (317 mg, 0.474 mmol) was dissolved in ClCH₂CH₂Cl (4 ml). Trifluoroacetic acid (1 ml, 12.98 mmol) was added and the reaction mixture was stirred at room temperature for 2 hours, then evaporated to dryness. 470.1 mg crude methyl(3-amino-4-fluoro-5-(piperazin-1-yl)

phenyl)(4-methoxybenzyl)carbamate, TFA (470.1 mg) were isolated. The material was used for a next step MS (ESI) m/z 389

(387C): methyl(3-amino-4-fluoro-5-(piperazin-1-yl)phenyl)(4-methoxybenzyl)carbamate (470 mg, 0.605 mmol) (crude product from above, contains DCE and TFA) was dissolved in methanol (5 ml)+Tetrahydrofuran (5 ml). oxetan-3-one (0.15 ml, 2.56 mmol), Trimethyl orthoformate (1 ml, 9.05 mmol) and potassium acetate (119 mg, 1.210 mmol) were added and the mixture stirred at room temperature for 15 minutes. pH was checked to be ~4.5. Sodium cyanoborohydride (160 mg, 2.55 mmol) was added and stirring at room temperature continued for 20 hours. The reaction mixture was partitioned between EtOAc and dilute aq. NaHCO$_3$ solution. The organic layer was washed with brine, then dried over MgSO$_4$ and evaporated to dryness to give crude methyl(3-amino-4-fluoro-5-(4-(oxetan-3-yl)piperazin-1-yl)phenyl)(4-methoxybenzyl)carbamate (248.4 mg) which was used without further purification.

MS (ESI) m/z 445

(387D): 4-(cyclopropyl(4-methoxybenzyl)amino)-2-(methylsulfonyl)imidazo[2,1-f][1,2,4]triazine-7-carbonitrile (Intermediate 3) (58.4 mg, 0.146 mmol), methyl(3-amino-4-fluoro-5-(4-(oxetan-3-yl)piperazin-1-yl)phenyl)(4-methoxybenzyl)carbamate (62 mg, 0.098 mmol) and Cs$_2$CO$_3$ (95 mg, 0.293 mmol) in DMF (1 ml) were heated at 70° C. for 80 minutes. Additional 4-(cyclopropyl(4-methoxybenzyl)amino)-2-(methylsulfonyl)imidazo[2,1-f][1,2,4]triazine-7-carbonitrile (58.4 mg, 0.146 mmol) and Cs$_2$CO$_3$ (95 mg, 0.293 mmol) were added and the mixture stirred at 45° C. for 16 hours. The mixture was partitioned between EtOAc and dilute aq. NH$_4$Cl solution. The organic layer was washed twice with dilute NaHCO$_3$ solution, once with brine, then dried over MgSO$_4$, filtered and evaporated to dryness to give methyl(3-((7-cyano-4-(cyclopropyl(4-methoxybenzyl)amino)imidazo[2,1-f][1,2,4]triazin-2-yl)amino)-4-fluoro-5-(4-(oxetan-3-yl)piperazin-1-yl)phenyl)(4-methoxybenzyl)carbamate (134.4 mg). The material was used in the following reaction without further purification.

MS (ESI) m/z 763 consistent with [M+H]+.

Example 387 methyl(3-((7-cyano-4-(cyclopropyl(4-methoxybenzyl)amino)imidazo[2,1-f][1,2,4]triazin-2-yl)amino)-4-fluoro-5-(4-(oxetan-3-yl)piperazin-1-yl)phenyl)(4-methoxybenzyl)carbamate (74.8 mg, 0.098 mmol) was dissolved in ClCH$_2$CH$_2$Cl (5 ml). Anisole (1 ml, 9.15 mmol) and TFA (2 ml, 26.0 mmol) were added and the mixture stirred at 55° C. for 3 hours. The reaction mixture was concentrated in vacuum and purified via preparative LC/MS with the following conditions:
Column: Waters XBridge C18, 19×200 mm, 5-µm particles; Guard Column: Waters XBridge C18, 19×10 mm, 5-µm particles; Mobile Phase A: water with 20-mM ammonium acetate; Mobile Phase B: 95:5 acetonitrile:water with 20-mM ammonium acetate; Gradient: 30-70% B over 12 minutes, then a 5-minute hold at 100% B; Flow: 20 mL/min.

Fractions containing the desired product were combined and dried via centrifugal evaporation to give methyl(3-((7-cyano-4-(cyclopropylamino)imidazo[2,1-f][1,2,4]triazin-2-yl)amino)-4-fluoro-5-(4-(oxetan-3-yl)piperazin-1-yl)phenyl)carbamate (8.8 mg) were obtained.

MS (ESI) m/z 523

1H NMR (500 MHz, dmso-d6) δ ppm 9.53 (br. s., 1H), 9.09 (br. s., 1H), 8.89 (s, 1H), 8.13 (s, 1H), 7.38-7.35 (m, 1H), 6.94-6.90 (m, 1H), 4.56 (t, J=6.0 Hz, 2H), 4.47 (t, J=6.0 Hz, 2H), 3.64 (s, 3H), 3.56-3.53 (m, 1H), 3.09 (br. s., 1H), 3.02 (br. s., 4H), 2.42 (br. s., 4H), 0.78-0.70 (m, 4H).

Example 388

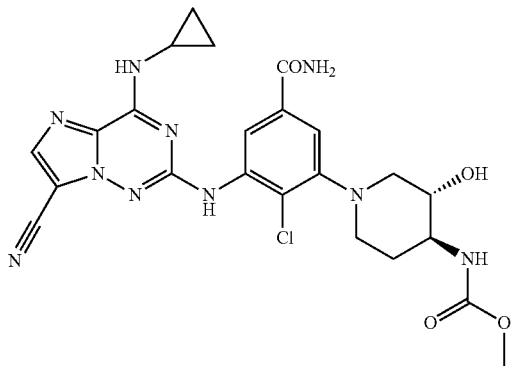 [SMILES: COC(=O)N[C@H]1CCN(c2cc(C(N)=O)cc(Nc3nc(NC4CC4)c4ncc(C#N)n4n3)c2Cl)C[C@@H]1O]

methyl((3S,4S)-1-(5-carbamoyl-2-chloro-3-((7-cyano-4-(cyclopropylamino)imidazo[2,1-f][1,2,4]triazin-2-yl)amino)phenyl)-3-hydroxypiperidin-4-yl)carbamate (BMT-096196, ELN 94895-070)

(388A): methyl((3S,4S)-1-(3-amino-2-chloro-5-cyanophenyl)-3-((tert-butyldimethylsilyl)oxy)piperidin-4-yl)carbamate (Example 174A) (91 mg, 0.207 mmol) was dissolved in tetrahydrofuran (10 ml). DMAP (13.3 mg, 0.109 mmol) was added, followed by BO$_{C2}$O (0.8 ml, 3.45 mmol) and DIPEA (0.30 ml, 1.72 mmol). The reaction mixture was stirred at room temperature for 2 days. The reaction mixture was partitioned between 0.5 M aq. citric acid and EtOAc. The organic layer was washed with NaHC$_{O3}$ solution, then brine, dried over MgS$_{O4}$, filtered and evaporated to give 483.5 mg crude di-tert-butyl(3-((3S,4S)-3-((tert-butyldimethylsilyl)oxy)-4-((methoxycarbonyl)amino)piperidin-1-yl)-2-chloro-5-cyanophenyl)imino dicarbonate (483.5 mg). The crude was used "as is" in the next reaction.

MS (ESI) m/z 639

(388B): di-tert-butyl(3-((3S,4S)-3-((tert-butyldimethylsilyl)oxy)-4-((methoxycarbonyl)amino)piperidin-1-yl)-2-chloro-5-cyanophenyl)imidodicarbonate (128 mg, 0.20 mmol) was dissolved in DMSO (10 mL). K$_2$CO$_3$ (400 mg, 2.89 mmol) was added, followed by H$_2$O$_2$ (0.6 ml, 5.87 mmol). The reaction mixture was stirred at room temperature. Dioxane (10 mL) and Methanol (10 mL) were added and the reaction mixture was refluxed for 15 minutes (reference Boger, Dale L et al. Journal of the American Chemical Society (2007), 129(49), 15391-15397). The reaction mixture was partitioned between EtOAc and aq. Na$_2$S$_2$O$_3$ solution (+NH$_4$Cl solution). The organic layer was washed with NaHCO$_3$ solution (+small amount of Na$_2$S$_2$O$_3$) twice, then with brine once, then dried over MgSO$_4$. 125 mg (colorless solid) crude product methyl((3S,4S)-1-(3-(N—BOC-amino)-5-carbamoyl-2-chlorophenyl)-3-((tert-butyldimethylsilyl)oxy)piperidin-4-yl)carbamate were obtained.

MS (ESI) m/z 557

(388C): methyl((3S,4S)-1-(3-(N—BOC-amino)-5-carbamoyl-2-chlorophenyl)-3-((tert-butyldimethylsilyl)oxy)piperidin-4-yl)carbamate (125 mg, 0.168 mmol) was dissolved in ClCH$_2$CH$_2$Cl (10 ml). Trifluoroacetic acid (3 ml, 38.9 mmol) was added and the reaction mixture was stirred at room temperature for 2 hours, then evaporated to dryness. The crude was purified by column chromatography on silica (40 g cartridge, gradient from 100% DCM to 100% EtOAc, then hold at 100% EtOAc) to give methyl((3S,4S)-1-(3-amino-5-carbamoyl-2-chlorophenyl)-3-((tert-butyldimethylsilyl)oxy)piperidin-4-yl)carbamate (67 mg).

MS (ESI) m/z 457/

1H NMR (400 MHz, dmso-d6) δ ppm 7.82 (br. s., 1H), 7.20 (br. s., 1H), 7.06-6.98 (m, 2H), 6.82 (d, J=1.8 Hz, 1H), 5.43 (br. s., 2H), 3.73-3.62 (m, 1H), 3.53 (s, 3H), 3.12 (d, J=12.5 Hz, 1H), 2.75 (t, J=11.0 Hz, 1H), 2.40 (t, J=10.7 Hz, 1H), 1.85-1.62 (m, 2H), 0.87-0.82 (m, 9H), 0.08 (s, 3H), 0.07 (s, 3H).

Example 388 methyl((3S,4S)-1-(3-amino-5-carbamoyl-2-chlorophenyl)-3-((tert-butyldimethylsilyl)oxy)piperidin-4-yl)carbamate (65 mg, 0.114 mmol), 4-(cyclopropyl(4-methoxybenzyl)amino)-2-(methylsulfonyl)imidazo[2,1-f][1,2,4]triazine-7-carbonitrile (Intermediate 3) (47.6 mg, 0.119 mmol), and Cs$_2$CO$_3$ (320 mg, 0.982 mmol) in DMF (1 ml) were heated at 80° C. for 4 hours. The reaction mixture was partitioned between EtOAc and aq. NH$_4$Cl solution. The organic layer was washed with dilute NaHCO$_3$ solution, then brine, then dried over MgSO$_4$, filtered and evaporated to dryness. 89.1 mg crude. The crude was dissolved in ClCH$_2$CH$_2$Cl (5 ml). Anisole (1 ml, 9.15 mmol) and trifluoroacetic acid (2 ml, 26.0 mmol) were added and the mixture stirred for 2 hours at 70° C. The reaction mixture was evaporated to dryness, dissolved in Acetonitrile (10 ml)+Water (1 ml) and trifluoroacetic acid (1 ml, 13.0 mmol) and stirred overnight at room temperature. The reaction mixture was evaporated to dryness, dissolved in dmso and purified via preparative LC/MS with the following conditions:

Column: Waters XBridge C18, 19×200 mm, 5-μm particles; Guard Column: Waters XBridge C18, 19×10 mm, 5-μm particles; Mobile Phase A: water with 20-mM ammonium acetate; Mobile Phase B: 95:5 methanol:water with 20-mM ammonium acetate; Gradient: 25-65% B over 20 minutes, then a 5-minute hold at 100% B; Flow: 20 mL/min.

Fractions containing the desired product were combined and dried via centrifugal evaporation.

methyl((3S,4S)-1-(5-carbamoyl-2-chloro-3-((7-cyano-4-(cyclopropylamino)imidazo[2,1-f][1,2,4]triazin-2-yl)amino)phenyl)-3-hydroxypiperidin-4-yl)carbamate (7.7 mg) was obtained.

MS (ESI) m/z 541

1H NMR (500 MHz, dmso-d6) δ ppm 9.20 (br. s., 1H), 8.77 (s, 1H), 8.18 (s, 1H), 8.02 (d, J=1.9 Hz, 1H), 7.98 (br. s., 1H), 7.42-7.37 (m, 2H), 7.10 (d, J=8.4 Hz, 1H), 4.99 (br. s., 1H), 3.55 (s, 3H), 3.58-3.51 (m, 2H), 3.43-3.37 (m, 1H), 3.24 (d, J=10.4 Hz, 1H), 3.04-2.98 (m, 1H), 2.73-2.66 (m, 1H), 2.57-2.53 (m, 1H), 1.92-1.85 (m, 1H), 1.59 (qd, J=12.2, 4.2 Hz, 1H), 0.76-0.71 (m, 4H).

Example 389

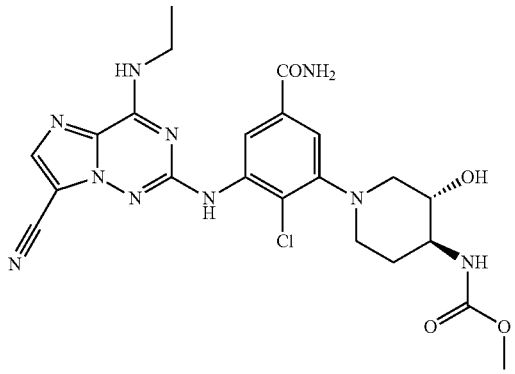 [SMILES: CCNc1nc(Nc2cc(C(N)=O)cc(N3CC[C@H](NC(=O)OC)[C@@H](O)C3)c2Cl)nn2c(C#N)cnc12]

(+/−)-methyl((3R,4R)-1-(5-carbamoyl-2-chloro-3-((7-cyano-4-(ethylamino)imidazo[2,1-f][1,2,4]triazin-2-yl)amino)phenyl)-3-hydroxypiperidin-4-yl)carbamate Prepared in analogous manner as Example 388.
MS (ESI) m/z 529
1H NMR (500 MHz, DMSO-d6) δ ppm 9.05 (t, J=5.6 Hz, 1H), 8.77 (s, 1H), 8.16 (s, 1H), 8.00 (br. s., 1H), 7.93 (d, J=1.5 Hz, 1H), 7.40 (m, 2H), 7.09 (d, J=8.2 Hz, 1H), 5.00 (d, J=4.3 Hz, 1H), 3.54 (s, 3H), 3.57-3.47 (m, 2H), 3.34-3.19 (m, 2H), 2.76-2.64 (m, 1H), 1.93-1.83 (m, 1H), 1.64-1.52 (m, 1H), 1.15 (t, J=7.2 Hz, 3H) The two missing proton signals are most likely hidden under the very large water and dmso signals.

Example 390

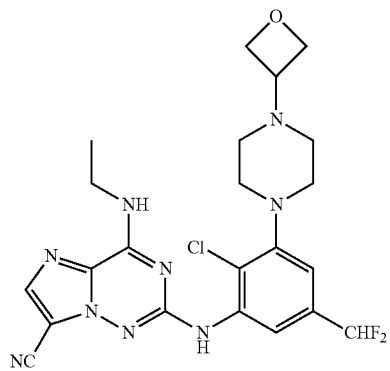 [SMILES: CCNc1nc(Nc2cc(C(F)F)cc(N3CCN(C4COC4)CC3)c2Cl)nn2c(C#N)cnc12]

2-((2-chloro-5-(difluoromethyl)-3-(4-(oxetan-3-yl)piperazin-1-yl)phenyl)amino)-4-(ethylamino)imidazo[2,1-f][1,2,4]triazine-7-carbonitrile Prepared in analogous manner as Example 247
MS (ESI) m/z 504.4
1H NMR (500 MHz, DMSO-d6) δ 9.14 (br. s., 1H), 8.69 (s, 1H), 8.19 (s, 1H), 7.81 (s, 1H), 7.15-6.87 (m, 2H), 4.57 (t, J=6.5 Hz, 2H), 4.49 (t, J=6.1 Hz, 2H), 3.56-3.41 (m, 3H), 3.06 (br. s., 4H), 2.47 (br. s., 3H), 1.18 (t, J=7.2 Hz, 3H)

Example 391

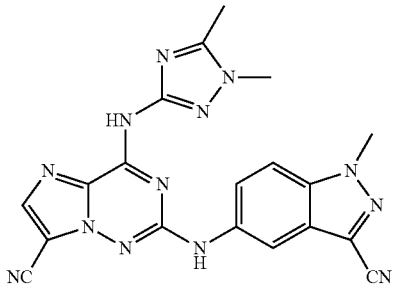 [SMILES: Cc1nc(Nc2nc(Nc3ccc4c(c3)c(C#N)nn4C)nn3c(C#N)cnc23)nn1C]

2-((3-cyano-1-methyl-1H-indazol-5-yl)amino)-4-((1,5-dimethyl-1H-1,2,4-triazol-3-yl)amino)imidazo[2,1-f][1,2,4]triazine-7-carbonitrile, HCl (391A): 1,5-dimethyl-1H-1,2,4-triazol-3-amine (170 mg, 1.517 mmol) was taken up in 6 ml of anhydrous THF and cooled to 0° C. Sodium tert-butoxide (243 mg, 2.53 mmol) was added and the reaction was stirred at 0° C. for 5 min. Next, a solution of 2,4-bis(methylthio)imidazo[2,1-f][1,2,4]triazine-7-carbonitrile (Intermediate (300 mg, 1.264 mmol) in 8 ml of THF was added, and the reaction was brought to rt. The reaction was stirred at rt for 1 h. The solvent was removed in vacuo and the material was dissolved in EtOAc. The organic layer was washed once with water, and the aqueous layer was reextracted with EtOAc. The organic layers were combined, washed with brine, dried over $Na_2SO_4$, filtered and concentrated to give 4-((1,5-dimethyl-1H-1,2,4-triazol-3-yl)amino)-2-(methylthio)imidazo[2,1-f][1,2,4]triazine-7-carbonitrile (157 mg) as a yellow solid. The crude material was taken onto the next step without further purification.

MS (ESI) m/z 302

$^1$H NMR (400 MHz, CHLOROFORM-d) δ 9.48 (br. s, 1H), 8.00 (s, 1H), 3.85 (s, 3H), 2.63 (s, 3H), 2.48 (s, 3H)

(391B): 4-((1,5-dimethyl-1H-1,2,4-triazol-3-yl)amino)-2-(methylthio)imidazo[2,1-f][1,2,4]triazine-7-carbonitrile (157 mg, 0.521 mmol) was taken up in DMF (6 mL) under argon and NaH (22.92 mg, 0.573 mmol) was added. The reaction mixture was stirred at rt for 30 min, then alpha-chloro-4-methoxytoluene (0.074 mL, 0.547 mmol) was added. The reaction mixture was heated at 80° C. for 3 h. The reaction was quenched with sat'd $NaHCO_3$ solution and extracted 3× with EtOAc. The organic layers were combined, dried over $Na_2SO_4$, filtered, and concentrated to give 4-((1,5-dimethyl-1H-1,2,4-triazol-3-yl)(4-methoxybenzyl)amino)-2-(methylthio)imidazo[2,1-f][1,2,4]triazine-7-carbonitrile (185 mg) as a red solid.

MS (ESI) m/z 422

$^1$H NMR (400 MHz, CHLOROFORM-d) δ ppm 7.73 (s, 1H), 7.39 (d, J=8.8 Hz, 2H), 6.83 (d, J=8.8 Hz, 2H), 5.28 (s, 2H), 3.81 (s, 3H), 3.78 (s, 3H), 2.56 (s, 3H), 2.48 (s, 3H)

(391C): 4-((1,5-dimethyl-1H-1,2,4-triazol-3-yl)(4-methoxybenzyl)amino)-2-(methylthio)imidazo[2,1-f][1,2,4]triazine-7-carbonitrile (185 mg, 0.439 mmol) was taken up in DCM (5 mL) and mCPBA (246 mg, 1.097 mmol) was added. The reaction was stirred at rt for 2 h. The reaction mixture was diluted with DCM and quenched with sat'd $NaHCO_3$. The organic layer was collected, dried over $Na_2SO_4$, filtered, and concentrated. The material was purified by flash column chromatography eluting with 0-3% MeOH/DCM. 4-((1,5-dimethyl-1H-1,2,4-triazol-3-yl)(4-methoxybenzyl)amino)-2-(methylsulfonyl)imidazo[2,1-f][1,2,4]triazine-7-carbonitrile (132 mg) was obtained as a yellow solid.

MS (ESI) m/z 454

$^1$H NMR (400 MHz, CHLOROFORM-d) δ ppm 7.92 (s, 1H), 7.46 (d, J=8.6 Hz, 2H), 6.83 (d, J=8.8 Hz, 2H), 5.35 (br. s., 2H), 3.84 (s, 3H), 3.77 (s, 3H), 3.34 (s, 3H), 2.52 (s, 3H)

(391D): 5-nitro-1H-indazole (2 g, 12.26 mmol) was taken up in DMF (40 mL) and NIS (5.52 g, 24.52 mmol) was added. The reaction was stirred at rt for 72 h. The reaction mixture was diluted with EtOAc and washed with sat'd sodium bisulfite solution, water, and then 2× with brine. The organic layer was dried over $Na_2SO_4$, filtered and concentrated to give 3-iodo-5-nitro-1H-indazole (3.4 g) as a yellow solid.

MS (ESI) m/z 290 (M+H).

$^1$H NMR (400 MHz, DMSO-$d_6$) δ ppm 14.11 (br. s., 1H), 8.37-8.31 (m, 1H), 8.25 (dd, J=9.2, 2.2 Hz, 1H), 7.76 (d, J=9.2 Hz, 1H)

(391E): 3-iodo-5-nitro-1H-indazole (6.9 g, 23.87 mmol) was taken up in NMP (90 mL) and copper (I) cyanide (4.28 g, 47.7 mmol) was added. The reaction was heated at 160° C. for 1 h, then cooled to rt. The reaction mixture was diluted with EtOAc and filtered through celite, rinsing with EtOAc. The filtrate was washed 2× with water and 2× with brine. The organic layer was dried over $Na_2SO_4$, filtered, and concentrated. The crude material was purified by flash column chromatography eluting with 0%-50% EtOAc/Hex. 0.91 g of 5-nitro-1H-indazole-3-carbonitrile was obtained.

$^1$H NMR (400 MHz, MeOD) δ ppm 8.91-8.78 (m, 1H), 8.43 (dd, J=9.2, 2.2 Hz, 1H), 7.91 (dd, J=9.2, 0.7 Hz, 1H)

(391F): 5-nitro-1H-indazole-3-carbonitrile (150 mg, 0.797 mmol) was taken up in DMA (4 mL) and $K_2CO_3$ (331 mg, 2.392 mmol) was added, followed by dropwise addition of MeI (0.060 mL, 0.957 mmol). The reaction was stirred at rt overnight. The reaction mixture was quenched with a saturated solution of $NaHCO_3$ and $Na_2S_2O_3$, then diluted with EtOAc. The organic layer was washed with sat'd $NaHCO_3$, then brine, and dried over $Na_2SO_4$, filtered, and concentrated. The material was purified by flash column chromatography eluting with 0%-50% EtOAc/Hex. 1-methyl-5-nitro-1H-indazole-3-carbonitrile (134 mg) was obtained as a yellow solid.

MS (ESI) m/z 203 (M+H).

$^1$H NMR (400 MHz, DMSO-$d_6$) δ ppm 8.85 (dd, J=2.0, 0.7 Hz, 1H), 8.39 (dd, J=9.4, 2.1 Hz, 1H), 8.14 (dd, J=9.2, 0.7 Hz, 1H), 4.28 (s, 3H)

(391G): 1-methyl-5-nitro-1H-indazole-3-carbonitrile (134 mg, 0.663 mmol) was taken up in EtOH (6 mL) and Water (6 mL). Iron powder (259 mg, 4.64 mmol) and ammonium chloride (319 mg, 5.97 mmol) were added, and the reaction mixture was brought to reflux and heated for 15 min. The reaction was cooled to rt and filtered through celite, washing with EtOH, then EtOAc. The solvent was removed in vacuo, and the reaction mixture taken up in EtOAc. The organic layer was washed with sat'd $NaHCO_3$ solution, then brine, dried over $Na_2SO_4$, filtered, and concentrated. The material was purified by flash column chromatography eluting with 0%-80% EtOAc/Hex. 1-methyl-5-nitro-1H-indazole-3-carbonitrile (48.5 mg) was obtained as a yellow solid.

MS (ESI) m/z 173 (M+H).

$^1$H NMR (400 MHz, DMSO-$d_6$) δ ppm 7.56 (d, J=9.0 Hz, 1H), 6.96 (dd, J=9.0, 2.0 Hz, 1H), 6.71 (dd, J=2.0, 0.7 Hz, 1H), 5.36 (s, 2H), 4.06 (s, 3H)

Example 391

5-amino-1-methyl-1H-indazole-3-carbonitrile (24.68 mg, 0.143 mmol) was taken up in 1 ml DMF (2 mL) and NaH (11.47 mg, 0.287 mmol) was added portionwise under argon. The reaction was stirred at rt for 10 min. Next, a solution of 4-((1,5-dimethyl-1H-1,2,4-triazol-3-yl)(4-methoxybenzyl)amino)-2-(methylsulfonyl)imidazo[2,1-f][1,2,4]triazine-7-carbonitrile (65 mg, 0.143 mmol) in 1 ml DMF was added. The reaction was stirred at rt for 2.5 h. The reaction mixture was diluted with EtOAc and washed with water 2×, then brine 2×. The material was dried over $Na_2SO_4$, filtered, and concentrated. The aqueous layer was filtered to collect additional material. This was combined with the compound obtained from the organic layer. The intermediate was taken up in DCM (2 mL) and anisole (0.031 mL, 0.287 mmol) and TFA (0.110 mL, 1.433 mmol) were added. The reaction stirred at rt overnight, then heated at 35° C. for 2 h to obtain complete conversion to the product. The solvent was removed in vacuo and the material taken up in MeOH, then filtered through an SCX column (5 g, benzenesulfonic acid sorbent). The column was rinsed with 7N $NH_3$/MeOH solution to recover the product. The product was purified by flash column chromatography (0-6% MeOH/DCM; 12 g ISCO gold column) The material was taken up in a small amount of DCM/MeOH and hexanes was added to precipitate the compound. The product was collected by filtration to yield 5 mg of product. The material was taken up in 1 ml of 1:1 $ACN/H_2O$ and 1N aq. HCl (0.143 mL, 0.143 mmol) was added dropwise. The solution was lyopholized overnight to yield 2-((3-cyano-1-methyl-1H-indazol-5-yl)amino)-4-((1,5-dimethyl-1H-1,2,4-triazol-3-yl)amino)imidazo[2,1-f][1,2,4]triazine-7-carbonitrile, HCl (4.7 mg) as a brown solid.

MS (ESI) m/z 426

$^1$H NMR (500 MHz, DMSO-$d_6$) δ ppm 10.08 (br. s., 1H), 8.31 (s, 1H), 7.90 (d, J=9.2 Hz, 1H), 7.84-7.74 (m, 1H), 4.16 (s, 3H), 3.82 (s, 3H), 2.53 (d, J=2.8 Hz, 3H)

Example 392

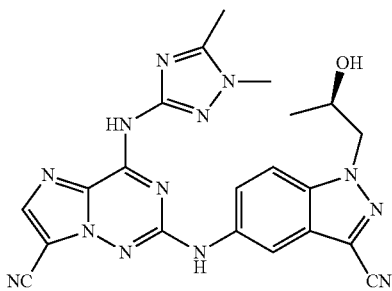 [SMILES: Cc1nc(Nc2nc(Nc3ccc4c(c3)c(C#N)nn4C[C@@H](C)O)nn3c(C#N)cnc23)nn1C]

(R)-2-((3-cyano-1-(2-hydroxypropyl)-1H-indazol-5-yl)amino)-4-((1,5-dimethyl-1H-1,2,4-triazol-3-yl)amino)imidazo[2,1-f][1,2,4]triazine-7-carbonitrile, HCl (392A): 5-nitro-1H-indazole-3-carbonitrile (600 mg, 3.19 mmol, Example 391E) was taken up in DMF (3 ml), and $K_2CO_3$ (580 mg, 4.20 mmol) and (R)-2-methyloxirane (1.85 ml, 26.4 mmol) were added. The reaction mixture was heated at 85° C. for 1 h. The reaction mixture was partitioned between half-saturated aq. $NH_4Cl$ solution and EtOAc. The organic layer was washed with half-saturated aq. $NaHCO_3$ solution, then brine, dried over $MgSO_4$, filtered and evaporated to dryness. The crude material was purified by flash column chromatography eluting with 0-50% EtOAc/DCM. (R)-1-(2-hydroxypropyl)-5-nitro-1H-indazole-3-carbonitrile (760 mg) was obtained as a colorless film.

MS (ESI) m/z 247

$^1$H NMR (400 MHz, DMSO-$d_6$) δ ppm 8.84 (d, J=2.0 Hz, 1H), 8.37 (dd, J=9.4, 2.1 Hz, 1H), 8.15 (d, J=9.5 Hz, 1H), 5.00 (d, J=5.3 Hz, 1H), 4.55 (dtd, J=14.1, 12.7, 5.8 Hz, 2H), 4.16-4.06 (m, 1H), 1.16 (d, J=6.5 Hz, 3H)

(392B): A solution of (R)-1-(2-hydroxypropyl)-5-nitro-1H-indazole-3-carbonitrile (0.76 g, 2.93 mmol) in EtOH (10 ml) was added to a suspension of iron (powder) (1.310 g, 23.46 mmol) and ammonium chloride (1.569 g, 29.3 mmol) in water (10 ml). The reaction mixture was heated in a microwave reactor at 80° C. for 15 min. The reaction vial was cooled to rt and the reaction mixture was filtered through celite, rinsing with EtOH, water, EtOH again, and then EtOAc. The filtrates were combined and diluted with EtOAc. The organic layer was washed with saturated aq. $NaHCO_3$ solution, water, then brine, then dried over $MgSO_4$, filtered, and evaporated to dryness. (R)-5-amino-1-(2-hydroxypropyl)-1H-indazole-3-carbonitrile (470 mg) was obtained as a pale yellow solid.

MS (ESI) m/z 217 (M+H).

$^1$H NMR (400 MHz, DMSO-$d_6$) δ ppm 7.58 (d, J=9.0 Hz, 1H), 6.92 (dd, J=9.0, 2.0 Hz, 1H), 6.70 (d, J=2.0 Hz, 1H), 5.35 (s, 2H), 4.94 (d, J=5.0 Hz, 1H), 4.30 (dd, J=5.9, 2.9 Hz, 2H), 4.15-3.97 (m, 1H), 1.08 (d, J=6.3 Hz, 3H)

(392C): (R)-5-amino-1-(2-hydroxypropyl)-1H-indazole-3-carbonitrile (180 mg, 0.832 mmol) was taken up in DCM (6 mL) and imidazole (227 mg, 3.33 mmol) and DMAP (10.17 mg, 0.083 mmol) were added, followed by TBS-Cl (439 mg, 2.91 mmol). The reaction was stirred at rt overnight. The reaction mixture was quenched with sat'd $NH_4Cl$ solution and diluted with DCM. The organic layer was collected and washed with brine, dried over $Na_2SO_4$, filtered, and concentrated. The crude material was purified by flash column chromatography eluting with 0-40% EtOAc/Hex. (R)-5-amino-1-(2-((tert-butyldimethylsilyl)oxy)propyl)-1H-indazole-3-carbonitrile (230.5 mg) was obtained as an orange solid.

MS (ESI) m/z 331 (M+H).

$^1$H NMR (400 MHz, DMSO-$d_6$) δ ppm 7.57 (d, J=9.0 Hz, 1H), 6.93 (dd, J=9.0, 2.0 Hz, 1H), 6.70 (d, J=1.5 Hz, 1H), 4.53-4.29 (m, 2H), 4.29-4.19 (m, 1H), 1.20 (d, J=5.9 Hz, 3H), 0.72-0.52 (m, 9H), —0.19 (s, 3H), —0.56 (s, 3H)

Example 392

(R)-5-amino-1-(2-((tert-butyldimethylsilyl)oxy)propyl)-1H-indazole-3-carbonitrile (38.0 mg, 0.115 mmol), 4-((1,5-dimethyl-1H-1,2,4-triazol-3-yl)(4-methoxybenzyl)amino)-2-(methylsulfonyl)imidazo[2,1-f][1,2,4]triazine-7-carbonitrile (43.5 mg, 0.096 mmol, Example 55C), $Cs_2CO_3$ (94 mg, 0.288 mmol), and DMSO (1 mL) were heated in a sealed vial at 80° C. under an argon atmosphere for 8 h. The reaction mixture was diluted with EtOAc and washed once with water and 2× with brine. The organic layer was dried over $Na_2SO_4$, filtered, and concentrated. The crude material was purified by flash column chromatography eluting with 0-2% MeOH/DCM. 11 mg of the intermediate was obtained. The compound was dissolved in DCE (1 ml) and anisole (0.021 mL, 0.192 mmol) and TFA (0.148 mL, 1.919 mmol) were added. The reaction was heated at 40° C. for 3 h, then an additional 0.5 ml of TFA was added and the reaction was stirred at rt for 72 h. The solvent was removed in vacuo and the material dissolved in MeOH. The solution was loaded onto an SCX column (5 g, benzenesulfonic acid sorbent), which was rinsed with MeOH, then a 7N solution of ammonia in methanol to recover the product. The solvent was removed in vacuo and the product purified by flash column chromatography eluting with 0-5% MeOH/DCM. The product was repurified by preparative HPLC and the product converted to the free base by dissolving in EtOAc and extraction with sat'd aq. NaHCO₃ solution to provide 2.2 mg of the final product. The material was taken up in 1 ml of 1:1 ACN/H₂O and 1N HCl in water (4.7 μL, 4.7 μmol) was added. The solution was frozen in a dry ice bath and lyopholized overnight to give (R)-2-((3-cyano-1-(2-hydroxypropyl)-1H-indazol-5-yl)amino)-4-((1,5-dimethyl-1H-1,2,4-triazol-3-yl)amino)imidazo[2,1-f][1,2,4]triazine-7-carbonitrile, HCl (1.0 mg) as an off-white solid.

MS (ESI) m/z 470

¹H NMR (400 MHz, DMSO-d₆) δ ppm 9.75 (s, 1H), 8.30 (s, 1H), 8.25 (s, 1H), 7.83 (q, J=9.2 Hz, 2H), 7.02 (br. s., 1H), 4.42 (t, J=5.3 Hz, 2H), 4.11 (dt, J=11.9, 5.8 Hz, 1H), 3.80 (s, 3H), 2.44 (s, 3H), 1.15-1.07 (m, 3H)

Example 393

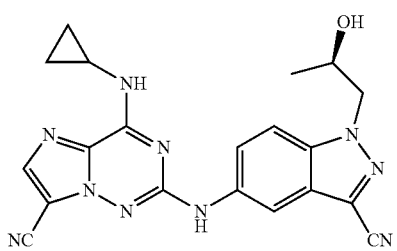 [SMILES: C[C@@H](O)Cn1nc(C#N)c2cc(Nc3nc(NC4CC4)c4ncc(C#N)n4n3)ccc21]

(R)-2-((3-cyano-1-(2-hydroxypropyl)-1H-indazol-5-yl)amino)-4-(cyclopropylamino)imidazo[2,1-f][1,2,4]triazine-7-carbonitrile, HCl (R)-5-amino-1-(2-((tert-butyldimethylsilyl)oxy)propyl)-1H-indazole-3-carbonitrile (49.8 mg, 0.151 mmol, Example 392C), 4-(cyclopropyl(4-methoxybenzyl)amino)-2-(methylsulfonyl)imidazo[2,1-f][1,2,4]triazine-7-carbonitrile (Intermediate 2) (50 mg, 0.125 mmol), Cs₂CO₃ (123 mg, 0.376 mmol), and DMSO (2 mL) were heated in a sealed vial at 80° C. for 8 h. The reaction mixture was diluted with EtOAc and washed once with water and 2× with brine. The organic layer was dried over Na₂SO₄, filtered, and concentrated. The intermediate was taken up in DCE (2 mL) and anisole (0.027 mL, 0.251 mmol) and TFA (0.483 mL, 6.27 mmol) were added. The reaction was stirred at rt overnight. The solvent was removed in vacuo and the material taken was up in MeOH. The solution was loaded onto an SCX column (5 g, benzenesulfonic acid sorbent) and rinsed with MeOH, then 7N NH₃/MeOH to obtain the product. The product was purified by flash column chromatography, eluting with 0-30% EtOAc/DCM. The material was then triturated with MeOH to give 9.5 mg of an off-white solid. The compound was suspended in 1 ml of a 1:1 mixture of CH₃CN/H₂O and aq. 1N HCl (23 μL, 23 μmol) was added. The solution was frozen in a dry ice bath and lyopholized overnight. (R)-2-((3-cyano-1-(2-hydroxypropyl)-1H-indazol-5-yl)amino)-4-(cyclopropylamino)imidazo[2,1-f][1,2,4]triazine-7-carbonitrile, HCl (9.5 mg) was obtained as an off-white solid.

MS (ESI) m/z 415

¹H NMR (400 MHz, DMSO-d₆) δ ppm 9.76 (br. s., 1H), 9.32 (br. s., 1H), 8.61 (s, 1H), 8.21 (s, 1H), 7.85 (d, J=9.2 Hz, 1H), 7.77-7.69 (m, 1H), 4.98 (br. s., 1H), 4.43 (t, J=5.5 Hz, 1H), 4.19-3.99 (m, J=11.8, 11.8 Hz, 1H), 3.21-3.09 (m, 1H), 1.14 (d, J=6.2 Hz, 3H), 0.98-0.73 (m, J=4.8 Hz, 4H)

Example 394

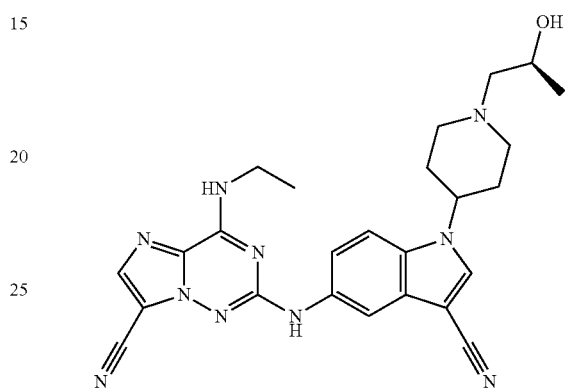

(S)-2-((3-cyano-1-(1-(2-hydroxypropyl)piperidin-4-yl)-1H-indol-5-yl)amino)-4-(ethylamino)imidazo[2,1-f][1,2,4]triazine-7-carbonitrile (394A): To a solution of 5-nitro-1H-indole-3-carbonitrile (2.0 g, 10.69 mmol), tert-butyl 4-hydroxypiperidine-1-carboxylate (4.30 g, 21.37 mmol) and triphenylphosphine (5.61 g, 21.37 mmol) in 90 ml THF was slowly added DEAD (3.38 mL, 21.37 mmol) in 50 ml of THF over 3 hrs. The mixture was stirred 32 hrs at 25° C. The mixture was concentrated and purified on silica: 100% DCM 500 ml, then (5-60% EtOAc in Hexanes) to give tert-butyl 4-(3-cyano-5-nitro-1H-indol-1-yl)piperidine-1-carboxylate (1.3 g).

¹H NMR (500 MHz, DMSO-d₆) δ 8.80 (s, 1H), 8.59-8.43 (m, 1H), 8.31-8.18 (m, 1H), 8.13-8.04 (m, 1H), 4.93-4.80 (m, 1H), 4.23-4.03 (m, 2H), 3.06-2.85 (m, 2H), 2.09-1.96 (m, 2H), 1.94-1.80 (m, 2H), 1.45-1.36 (m, 9H) tert-butyl 4-(3-cyano-5-nitro-1H-indol-1-yl)piperidine-1-carboxylate (1.02 g, 2.75 mmol), Iron (0.923 g, 16.52 mmol), and ammonium chloride (1.031 g, 19.28 mmol) were suspended in a mixture of Ethanol (10 mL)/Water (10 mL). The reaction mixture was heated in oil bath at 85° C. for 20 min. The reaction mixture was filtered through Celite, then washed with water, MeOH and EtOAc. The combined filtrates were concentrated to almost dryness, then mixed with aq. NaHCO3 and EtOAc. The organic layer was washed with brine, dried over MgSO4, filtered and evaporated to dryness to give tert-butyl 4-(5-amino-3-cyano-1H-indol-1-yl)piperidine-1-carboxylate (200 mg).

¹H NMR (500 MHz, DMSO-d₆) 8.16 (s, 1H), 7.44 (d, J=8.8 Hz, 1H), 6.73 (d, J=1.4 Hz, 1H), 6.69 (s, 1H), 4.97 (br. s., 2H), 4.61-4.45 (m, 1H), 4.24-3.94 (m, 2H), 3.07-2.82 (m, 2H), 2.04-1.89 (m, 2H), 1.88-1.71 (m, 2H), 1.44 (s, 9H)

(394B): A mixture of 2-chloro-4-(ethyl(4-methoxybenzyl)amino)imidazo[2,1-f][1,2,4]triazine-7-carbonitrile (Intermediate 10) (200 mg, 0.583 mmol), tert-butyl 4-(5-amino-3-cyano-1H-indol-1-yl)piperidine-1-carboxylate (199 mg, 0.583 mmol), Pd(OAc)2 (13.10 mg, 0.058 mmol), Brettphos (62.6 mg, 0.117 mmol) and K2CO3 (242 mg, 1.750 mmol) was suspended in Dioxane (4 mL) in a 5 ml microwave vial. The vial was sealed, flushed with nitrogen 4 times, and then heated in microwave at 115° C. for 2 hr. The mixture was diluted with CH3CN and CH2Cl2, filtered through celite and concentrated. The crude was carried forward in the next reaction.

MS (ESI) m/z 647 tert-butyl 4-(3-cyano-5-((7-cyano-4-(ethyl(4-methoxybenzyl)amino)imidazo[2,1-f][1,2,4]triazin-2-yl)amino)-1H-indol-1-yl)piperidine-1-carboxylate (500 mg, 0.503 mmol) was mixed with ANISOLE (0.5 mL, 4.58 mmol) and DCE (5 mL). TFA (1 mL, 12.98 mmol) was added. The mixture was stirred at 25° C. for 24 hrs. LC/MS showed product formation. The mixture was concentrated to dryness, diluted with MeOH and applied onto a cartridge of Phenomenex Strata-X-C 33 um cation mixed-mode polymer. This was washed with methanol and product was eluted with 2 N solution of ammonia in methanol. Removal of the solvents left 2-((3-cyano-1-(piperidin-4-yl)-1H-indol-5-yl)amino)-4-(ethylamino)imidazo[2,1-f][1,2,4]triazine-7-carbonitrile (80 mg) as solid.

MS (ESI) m/z 427

Example 394

2-((3-cyano-1-(piperidin-4-yl)-1H-indol-5-yl)amino)-4-(ethylamino)imidazo[2,1-f][1,2,4]triazine-7-carbonitrile (25 mg, 0.044 mmol) was dissolved in MeOH (0.5 mL)/DCM (0.5 mL) in an one dram vial. To this was added TEA (0.012 mL, 0.088 mmol) and (S)-2-methyloxirane (25.5 mg, 0.440 mmol). The reaction mixture was stirred at 25° C. 16 hr. The solvents were removed and the crude material was purified via preparative LC/MS with the following conditions:

Column: Waters XBridge C18, 19×200 mm, 5-µm particles; Guard Column: Waters XBridge C18, 19×10 mm, 5-µm particles; Mobile Phase A: water with 20-mM ammonium acetate; Mobile Phase B: 95:5 acetonitrile:water with 20-mM ammonium acetate; Gradient: 20-60% B over 20 minutes, then a 5-minute hold at 100% B; Flow: 20 mL/min.

Fractions containing the desired product were combined and dried via centrifugal evaporation to afford (S)-2-((3-cyano-1-(1-(2-hydroxypropyl)piperidin-4-yl)-1H-indol-5-yl)amino)-4-(ethylamino)imidazo[2,1-f][1,2,4]triazine-7-carbonitrile (10.9 mg).

MS (ESI) m/z 485

$^1$H NMR (500 MHz, DMSO-$d_6$) δ 10.17-9.96 (m, 1H), 9.55-9.37 (m, 1H), 9.19-8.97 (m, 1H), 8.18 (s, 1H), 7.86-7.78 (m, 1H), 7.69-7.60 (m, 1H), 5.59-5.34 (m, 1H), 4.88-4.67 (m, 1H), 4.30-4.16 (m, 1H), 3.81-3.68 (m, 1H), 3.67-3.54 (m, 2H), 3.31-3.11 (m, 3H), 3.08-2.97 (m, 1H), 2.90 (s, 2H), 2.74 (s, 2H), 2.30-2.16 (m, 2H), 1.28 (t, J=7.2 Hz, 3H), 1.21-1.09 (m, 3H)

Example 395

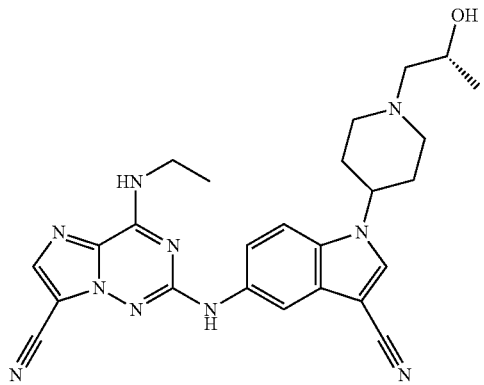 [SMILES: CCNc1nc(Nc2ccc3c(c2)c(C#N)cn3C2CCN(C[C@@H](C)O)CC2)nn2c(C#N)cnc12]

(R)-2-((3-cyano-1-(1-(2-hydroxypropyl)piperidin-4-yl)-1H-indol-5-yl)amino)-4-(ethylamino)imidazo[2,1-f][1,2,4]triazine-7-carbonitrile Prepared in analogous manner as Example 394

MS (ESI) m/z 485

$^1$H NMR (500 MHz, DMSO-$d_6$) δ 10.16-9.95 (m, 1H), 9.48 (s, 1H), 9.16-9.00 (m, 1H), 8.28-8.13 (m, 2H), 7.99-7.93 (m, 1H), 7.87-7.75 (m, 1H), 7.69-7.56 (m, 1H), 5.60-5.42 (m, 1H), 4.85-4.72 (m, 1H), 4.28-4.10 (m, 1H), 3.84-3.68 (m, 1H), 3.65-3.55 (m, 2H), 3.28-3.11 (m, 2H), 3.08-2.97 (m, 1H), 2.90 (s, 2H), 2.74 (s, 2H), 2.30-2.14 (m, 2H), 1.28 (s, 3H), 1.21-1.09 (m, 3H)

Example 396

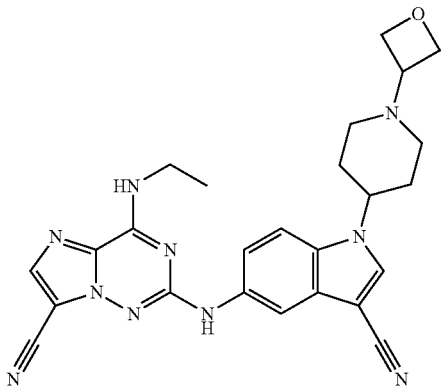 [SMILES: CCNc1nc(Nc2ccc3c(c2)c(C#N)cn3C2CCN(C3COC3)CC2)nn2c(C#N)cnc12]

2-((3-cyano-1-(1-(oxetan-3-yl)piperidin-4-yl)-1H-indol-5-yl)amino)-4-(ethylamino)imidazo[2,1-f][1,2,4]triazine-7-carbonitrile 2-((3-cyano-1-(piperidin-4-yl)-1H-indol-5-yl)amino)-4-(ethylamino)imidazo[2,1-f][1,2,4]triazine-7-carbonitrile (25 mg, 0.059 mmol) in Methanol (2 ml)/Tetrahydrofuran (2 ml) was added oxetan-3-one (0.052 ml, 0.879 mmol), acetic acid (6.71 µl, 0.117 mmol) and trimethyl orthoformate (0.350 ml, 3.17 mmol). The mixture was stirred at 25° C. for 15 min. Sodium cyanoborohydride (29 mg, 0.461 mmol) was added and the reaction stirred at room temperature 12 hr. The solvents were removed and the crude material was purified via preparative LC/MS with the following conditions:

Column: Waters XBridge C18, 19×200 mm, 5-μm particles; Guard Column: Waters XBridge C18, 19×10 mm, 5-μm particles; Mobile Phase A: water with 20-mM ammonium acetate; Mobile Phase B: 95:5 acetonitrile:water with 20-mM ammonium acetate; Gradient: 30-80% B over 20 minutes, then a 5-minute hold at 100% B; Flow: 20 mL/min.

Fractions containing the desired product were combined and dried via centrifugal evaporation to afford 2-((3-cyano-1-(1-(oxetan-3-yl)piperidin-4-yl)-1H-indol-5-yl)amino)-4-(ethylamino)imidazo[2,1-f][1,2,4]triazine-7-carbonitrile (13.6 mg).

MS (ESI) m/z 483

$^1$H NMR (500 MHz, DMSO-$d_6$) δ 12.16-11.86 (m, 1H), 9.49 (s, 1H), 9.21-8.96 (m, 1H), 8.33-8.21 (m, 2H), 8.18 (s, 1H), 7.99-7.91 (m, 1H), 7.88-7.75 (m, 1H), 7.66-7.52 (m, 1H), 5.01-4.63 (m, 5H), 4.54-4.37 (m, 1H), 3.68-3.48 (m, 3H), 3.20-2.99 (m, 2H), 2.90 (s, 3H), 2.74 (s, 3H), 2.37-2.17 (m, 2H), 1.28 (s, 3H)

Example 397

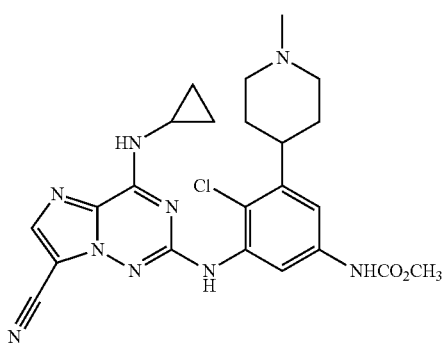

Methyl-4-chloro-3-(7-cyano-4-(cyclopropylamino)imidazo[1,2-f][1,2,4]triazin-2-ylamino)-5-(1-methyl-piperidin-4-yl)phenylcarbamate (397A): A mixture of methyl(3-bromo-4-chloro-5-nitrophenyl)carbamate (229 mg, 0.740 mmol), 1-methyl-4-(4,4,5,5-tetramethyl-1,3,2-dioxaborolan-2-yl)-1,2,3,6-tetrahydropyridine (150 mg, 0.672 mmol), tetrakis(triphenylphosphine) palladium (O) (78 mg, 0.067 mmol) and K3PO4 (527 mg, 2.487 mmol) in a microwave vial was flushed with nitrogen. A nitrogen sparged mixture of dioxane (5602 μL) and water (1120 μL) was added and the vial was sealed and heated at 80° C. overnight. The reaction was partitioned between EtOAc and water. The aqueous phase was extracted with EtOAc and the combined organic phases were washed with brine and dried with sodium sulfate. After removal of the solvents, the crude material was applied onto a cartridge of Phenomenex Strata-X-C 33 um cation mixed-mode polymer. This was washed with methanol and the product was eluted with 2 N solution of ammonia in methanol. Removal of the solvent left methyl(4-chloro-3-(1-methyl-1,2,3,6-tetrahydropyridin-4-yl)-5-nitrophenyl)carbamate (213 mg) as a solid which was used as such.

MS (ESI) m/z 326.07

1H NMR (500 MHz, CHLOROFORM-d) δ 8.43 (s, 1H), 7.94 (br. s., 1H), 5.68 (dt, J=3.1, 1.6 Hz, 1H), 3.76 (s, 3H), 3.11 (q, J=2.7 Hz, 2H), 3.04 (br. s., 1H), 2.69 (t, J=5.6 Hz, 2H), 2.51-2.4 (m, 2H), 2.40 (s, 3H)

(397B): A mixture of methyl(4-chloro-3-(1-methyl-1,2,3,6-tetrahydropyridin-4-yl)-5-nitrophenyl)carbamate (213 mg, 0.654 mmol) and platinum (IV) oxide (240 mg, 0.654 mmol) in a mixture of MeOH (50 mL) and ethyl acetate (3 mL) was hydrogenated (balloon of H2). The reaction completed within 1 h. The catalyst was removed by filtration through a celite pad and the pad was rinsed with MeOH. The solvent was removed and radial silica gel chromatography, eluting with DCM containing 0 to 3% MeOH gave methyl (3-amino-4-chloro-5-(1-methylpiperidin-4-yl)phenyl)carbamate (131 mg) as a white solid.

MS (ESI) m/z 298.10 (M+1)

1H NMR (400 MHz, METHANOL-d4) d 7.04 (d, J=1.8 Hz, 1H), 6.64 (d, J=2.5 Hz, 1H), 3.73 (s, 3H), 3.09-2.91 (m, 3H), 2.35 (s, 3H), 2.26-2.13 (m, 2H), 1.91-1.80 (m, 2H), 1.72 (dd, J=12.8, 3.3 Hz, 2H)

(397C): A mixture of 4-(cyclopropyl(4-methoxybenzyl)amino)-2-(methylsulfonyl)imidazo[2,1-f][1,2,4]triazine-7-carbonitrile (Intermediate 2) (77 mg, 0.193 mmol), methyl (3-amino-4-chloro-5-(1-methylpiperidin-4-yl)phenyl)carbamate (48 mg, 0.161 mmol) and Cs2CO3 (158 mg, 0.484 mmol) in DMF (1.2 mL) was heated at 70° C. for 3 h. It was diluted with EtOAc and washed with water. Removal of the solvent was followed by preparative HPLC (100×30 mm Luna C18 column, Solvent A=10% Methanol, 90% H2O, 0.1% TFA; solvent B=90% Methanol, 10% H2O, 0.1% TFA, Flow rate 42 ml permin, 20-100% B, over 20 min). The solvent was removed from the fractions containing the intermediate on a speed vac. The intermediate was dissolved in DCE (3 mL) and anisole (0.088 mL, 0.806 mmol) and TFA (1.5 mL) were added. This was heated at 50° C. for 3 h. Removal of the solvents was followed by preparative HPLC (100×30 mm Luna C18 column, Solvent A=10% Methanol, 90% H2O, 0.1% TFA; solvent B=90% Methanol, 10% H2O, 0.1% TFA, Flow rate 42 ml permin, 20-100% B, over 20 min). The HPLC fractions containing the product were applied onto a cartridge of Phenomenex Strata-X-C 33 um cation mixed-mode polymer. This was washed with methanol and product was eluted with 2 N solution of ammonia in methanol. Removal of the solvents left methyl(4-chloro-3-((7-cyano-4-(cyclopropylamino)imidazo[2,1-f][1,2,4]triazin-2-yl)amino)-5-(1-methylpiperidin-4-yl)phenyl)carbamate (7 mg) as a solid.

MS (ESI) m/z 496.20

$^1$H NMR (500 MHz, CHLOROFORM-d) δ 8.52 (s, 1H), 7.84 (s, 1H), 7.52 (s, 1H), 7.21 (br. s., 1H), 6.79 (s, 1H), 6.63 (br. s., 1H), 3.79 (s, 3H), 3.51 (s, 3H), 3.25-3.03 (m, 3H), 2.32 (d, J=8.2 Hz, 2H), 2.03-1.86 (m, 5H), 1.06-0.95 (m, 2H), 0.82-0.71 (m, 2H).

Example 398

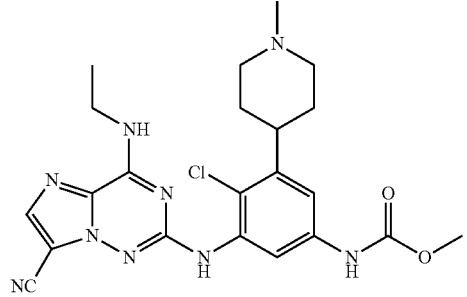 [SMILES: CCNc1nc(Nc2cc(NC(=O)OC)cc(C3CCN(C)CC3)c2Cl)nn2c(C#N)cnc12]

methyl(4-chloro-3-((7-cyano-4-(ethylamino)imidazo[2,1-f][1,2,4]triazin-2-yl)amino)-5-(1-methylpiperidin-4-yl)phenyl)carbamate Prepared in analogous manner as Example 397

MS (ESI) m/z 484.3

1H NMR (500 MHz, DMSO-d6) δ 9.73 (s, 1H), 9.04 (t, J=5.6 Hz, 1H), 8.66 (s, 1H), 8.17 (s, 1H), 7.77 (d, J=2.1 Hz,

1H), 7.28 (d, J=1.8 Hz, 1H), 3.67 (s, 3H), 3.48-3.43 (m, 2H), 2.96-2.81 (m, 3H), 2.21 (s, 3H), 2.05-1.94 (m, 2H), 1.75 (d, J=12.5 Hz, 2H), 1.59 (qd, J=12.3, 3.8 Hz, 2H), 1.15 (t, J=7.2 Hz, 3H)

Example 399

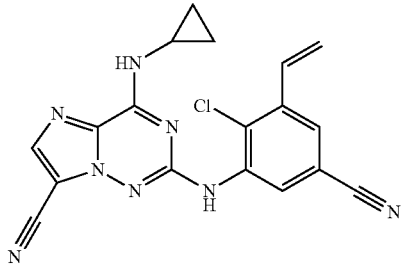 [SMILES: C=Cc1cc(C#N)cc(Nc2nc(NC3CC3)c3ncc(C#N)n3n2)c1Cl]

2-((2-chloro-5-cyano-3-vinylphenyl)amino)-4-(cyclopropylamino)imidazo[2,1-f][1,2,4]triazine-7-carbonitrile (399A): A mixture of tert-butyl(3-bromo-2-chloro-5-cyanophenyl)carbamate (Intermediate 1) (200 mg, 0.603 mmol), potassium vinyltrifluoroborate (121 mg, 0.905 mmol), and [1,1'-bis(diphenylphosphino)ferrocene dichloropalladium(II) (44 mg, 0.060 mmol) in a microwave vial was flushed with nitrogen. EtOH (3 mL) and TEA (126 µL, 0.905 mmol) were added and the mixture was degassed and flushed with nitrogen. This was sealed and heated at 80° C. for 18 hr. It was diluted with water and extracted with a mixture of EtOAc: hexane=3:1. The organic phase was washed with brine and dried with sodium sulfate. Removal of the solvents followed by silica gel radial chromatography eluting with hexane containing 0 to 20% EtOAc afforded tert-butyl(2-chloro-5-cyano-3-vinylphenyl)carbamate (122 mg) as a white solid.

$^1$H NMR (500 MHz, CHLOROFORM-d) δ 8.51 (d, J=1.5 Hz, 1H), 7.50 (d, J=1.8 Hz, 1H), 7.20 (br. s., 1H), 7.04 (dd, J=17.4, 11.0 Hz, 1H), 5.81 (d, J=17.4 Hz, 1H), 5.54 (d, J=11.3 Hz, 1H), 1.58-1.54 (m, 9H).

(399B): A solution of tert-butyl(2-chloro-5-cyano-3-vinylphenyl)carbamate (122 mg, 0.438 mmol) in a mixture of TFA (1.9 mL) and DCM (1.9 mL) was stirred at RT for 1 hr. The solvents were removed and the residue was dissolved in DCM. This was washed with saturated aq. NaHCO$_3$ solution. The organic phase was separated and dried with sodium sulfate. Removal of the solvent left 3-amino-4-chloro-5-vinylbenzonitrile (76 mg) as a white solid.

MS (ESI) m/z 179.0 (M+1)

$^1$H NMR (500 MHz, CHLOROFORM-d) δ 7.23 (d, J=1.8 Hz, 1H), 7.04 (dd, J=17.4, 11.0 Hz, 1H), 6.93 (d, J=1.8 Hz, 1H), 5.78 (dd, J=17.5, 0.7 Hz, 1H), 5.50 (dd, J=11.0, 0.6 Hz, 1H), 4.35 (br. s., 2H).

(399C): A mixture of 3-amino-4-chloro-5-vinylbenzonitrile (75 mg, 0.42 mmol), 2-chloro-4-(cyclopropyl(4-methoxybenzyl)amino)imidazo[2,1-f][1,2,4]triazine-7-carbonitrile (Intermediate 9) (149 mg, 0.420 mmol), Cs$_2$CO$_3$ (274 mg, 0.840 mmol), DPPF (23 mg, 0.042 mmol), 4,5-bis(diphenylphosphino)-9,9-dimethyxanthene (24 mg, 0.042 mmol), and Pd(OAc)$_2$ (28 mg, 0.13 mmol) in a microwave vial was flushed with nitrogen. Dioxane (3.5 mL) was added and the vial was sealed and heated at 100° C. for 4 hr. The reaction was diluted with EtOAc and filtered through celite. The solvent was removed from the filtrate and radial silica gel chromatography eluting with hexane containing 5 to 40% EtOAc afforded 2-((2-chloro-5-cyano-3-vinylphenyl)amino)-4-(cyclopropyl(4-methoxybenzyl)amino)imidazo[2,1-f][1,2,4]triazine-7-carbonitrile (106 mg, 51% yield) as an oil. This was dissolved in DCM (3 mL) and anisole (0.582 mL, 5.33 mmol) and TFA (3 mL) were added. After stirring at RT overnight, the solvent was removed and the yellow solid was dissolved in DCM. This was was washed with a saturated aq. NaHCO$_3$ solution and the organic phase was separated. The aqueous phase contained some suspended yellow solid and was exacted 2× with DCM. The combined organic phases were dried with sodium sulfate and the solvent was removed. The residue was suspended in a mixture of EtOAc:hexane=1:1 and filtration gave the title compound (59 mg) as a light yellow solid.

MS (ESI) m/z 377.2

$^1$H NMR (500 MHz, DMSO-d6) δ 9.36 (d, J=4.1 Hz, 1H), 8.93 (s, 1H), 8.37 (d, J=2.0 Hz, 1H), 8.23-8.18 (m, 1H), 7.94 (d, J=2.0 Hz, 1H), 7.06 (dd, J=17.4, 11.1 Hz, 1H), 6.08 (d, J=17.5 Hz, 1H), 5.60 (d, J=11.6 Hz, 1H), 2.99-2.90 (m, 1H), 0.84-0.72 (m, 4H) 9.36 (d, J=4.1 Hz, 1H), 8.93 (s, 1H), 8.37 (d, J=2.0 Hz, 1H), 8.23-8.18 (m, 1H), 7.94 (d, J=2.0 Hz, 1H), 7.06 (dd, J=17.4, 11.1 Hz, 1H), 6.08 (d, J=17.5 Hz, 1H), 5.60 (d, J=11.6 Hz, 1H), 2.99-2.90 (m, 1H), 0.84-0.72 (m, 4H).

Example 400

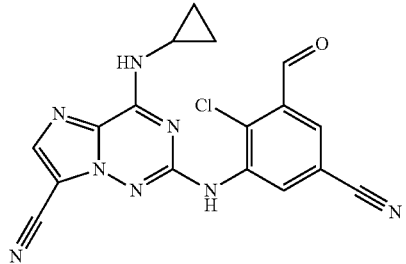 [SMILES: N#Cc1cc(C=O)c(Cl)c(Nc2nc(NC3CC3)c3ncc(C#N)n3n2)c1]

2-((2-chloro-5-cyano-3-formylphenyl)amino)-4-(cyclopropylamino)imidazo[2,1-f][1,2,4]triazine-7-carbonitrile (400): A suspension of 2-((2-chloro-5-cyano-3-vinylphenyl)amino)-4-(cyclopropylamino)imidazo[2,1-f][1,2,4]triazine-7-carbonitrile (210 mg, 0.557 mmol) in acetone (50 mL) was heated to give a cloudy solution. After cooling to RT, water (5 mL), osmium tetroxide (0.350 mL, 2.5 wt % in t-BuOH, 0.028 mmol) and sodium periodate (262 mg, 1.23 mmol) were added. This was stirred overnight. Additional water (20 mL) was added and the reaction was left stirring for 1 day. Most of the acetone was removed and the suspended solid was collected by filtration, washed with water, and air dried to leave 2-((2-chloro-5-cyano-3-formylphenyl)amino)-4-(cyclopropylamino)imidazo[2,1-f][1,2,4]triazine-7-carbonitrile (188 mg) as a light yellow solid.

MS (ESI) m/z 379.0 (M+1)

$^1$H NMR (500 MHz, DMSO-d6) δ 10.34 (s, 1H), 9.41 (d, J=3.5 Hz, 1H), 9.27 (s, 1H), 8.71 (d, J=1.5 Hz, 1H), 8.23 (s, 1H), 7.96 (d, J=1.5 Hz, 1H), 2.92 (d, J=4.1 Hz, 1H), 0.82-0.75 (m, 4H).

Example 401

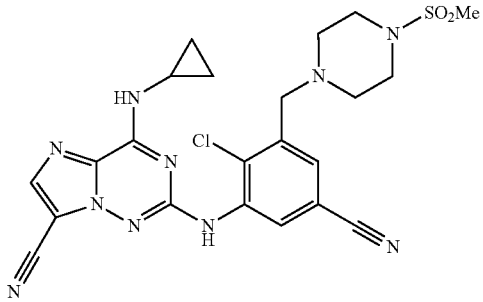 [SMILES: CS(=O)(=O)N1CCN(Cc2cc(C#N)cc(Nc3nc(NC4CC4)c4ncc(C#N)n4n3)c2Cl)CC1]

2-((2-chloro-5-cyano-3-((4-(methylsulfonyl)piperazin-1-yl)methyl)phenyl)amino)-4-(cyclopropylamino)imidazo[2,1-f][1,2,4]triazine-7-carbonitrile A solution of 2-((2-chloro-5-cyano-3-formylphenyl)amino)-4-(cyclopropylamino)imidazo[2,1-f][1,2,4]triazine-7-carbonitrile (Example 400) (18 mg, 0.048 mmol), 1-(methylsulfonyl)piperazine (9.5 mg, 0.058 mmol), trimethylorthoformate (0.027 mL, 0.242 mmol), and acetic acid (3 µL, 0.05 mmol) in a mixture of MeOH (0.5 mL) and DCM (0.5 mL) was stirred at RT for 15 min. A solution of sodium cyanoborohydride (0.097 mL, 1M in THF mL, 0.097 mmol) was added and the reaction was left stirring at RT overnight. Additional sodium cyanoborohydride (0.097 mL, 1M in THF mL, 0.097 mmol) was added and the reaction was left stirring for 1 day. A saturated aq. solution of NaHCO₃ solution was added and, after 15 min, this was extracted with a mixture of 5% MeOH in DCM (5×). The combined organic extracts were dried with sodium sulfate and the solvent was removed. Silica gel radial chromatography of the residue eluting with DCM containing 0 to 2% MeOH afforded the title compound (7.9 mg) as a foam.

MS (ESI) m/z 527.2 (M+1)
$^1$H NMR (400 MHz, CHLOROFORM-d) δ 9.00 (d, J=1.8 Hz, 1H), 7.88 (s, 1H), 7.58 (s, 1H), 7.50 (d, J=2.0 Hz, 1H), 6.79 (br. s., 1H), 3.72 (s, 2H), 3.34-3.28 (m, 4H), 3.07 (tq, J=7.1, 3.5 Hz, 1H), 2.83 (s, 3H), 2.73-2.64 (m, 4H), 1.16-1.07 (m, 2H), 0.87-0.78 (m, 2H).

Example 402

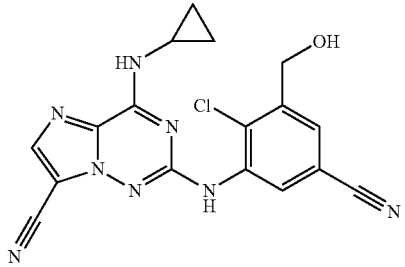 [SMILES: N#Cc1cc(CO)c(Cl)c(Nc2nc(NC3CC3)c3ncc(C#N)n3n2)c1]

2 2-((2-chloro-5-cyano-3-(hydroxymethyl)phenyl)amino)-4-(cyclopropylamino)imidazo[2,1-f][1,2,4]triazine-7-carbonitrile The title compound (7.3 mg, 38% yield) was obtained as a side product in Example 403.

MS (ESI) m/z 381.2 (M+1).
$^1$H NMR (400 MHz, METHANOL-d4/CHLOROFORM-d) δ 8.90 (d, J=2.0 Hz, 1H), 7.85 (s, 1H), 7.57-7.51 (m, 1H), 4.73 (s, 2H), 3.01 (dt, J=7.2, 3.5 Hz, 1H), 1.06-0.98 (m, 2H), 0.81-0.73 (m, 2H).

Example 403

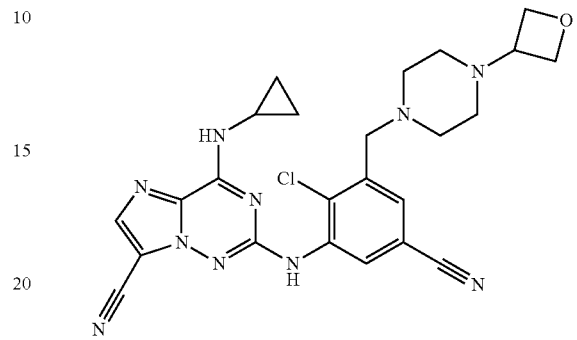

2-((2-chloro-5-cyano-3-((4-(oxetan-3-yl)piperazin-1-yl)methyl)phenyl)amino)-4-(cyclopropylamino)imidazo[2,1-f][1,2,4]triazine-7-carbonitrile HCl salt (401A): A nitrogen sparged mixture of THF (2.2 mL) and water (0.22 mL) was added to a nitrogen flushed mixture of potassium (4-Boc-piperazin-1-yl)methyl trifluoroborate (200 mg, 0.653 mmol), tert-butyl(3-bromo-2-chloro-5-cyanophenyl)carbamate (Intermediate 1) (197 mg, 0.594 mmol), 2-dicyclohexylphosphino-2'-4'-6'-trisisopropylbiphenyl (34.0 mg, 0.071 mmol), Pd(OAc)₂ (8.0 mg, 0.036 mmol), and Cs₂CO₃ (580 mg, 1.78 mmol) in a microwave vial. This was sealed and heated at 80° C. for 17 hr. The reaction was extracted 3× with EtOAc and the combined organic extracts were washed with brine and dried with sodium sulfate. Removal of the solvent followed by silica gel radial chromatography eluting with hexane containing 10 to 50% EtOAc afforded tert-butyl 4-(3-((tert-butoxycarbonyl)amino)-2-chloro-5-cyanobenzyl)piperazine-1-carboxylate (59 mg) as a film.

MS (ESI) m/z 451.1
$^1$H NMR (500 MHz, CHLOROFORM-d) δ 8.50 (d, J=1.5 Hz, 1H), 7.50 (d, J=2.0 Hz, 1H), 7.18 (s, 1H), 3.61 (s, 2H), 3.50-3.43 (m, 4H), 2.46 (br. s., 4H), 1.58-1.54 (m, 9H), 1.48 (s, 9H).

(401B): TFA (1.0 mL) was added to a solution of tert-butyl 4-(3-((tert-butoxycarbonyl)amino)-2-chloro-5-cyanobenzyl)piperazine-1-carboxylate (59 mg, 0.13 mmol) in DCM (1.0 mL) at RT. After 1 hr, the solvent was removed and the residue was dissolved in MeOH and applied onto an SCX column. This was washed with MeOH and the product was eluted with 2N NH₃ in MeOH to give 3-amino-4-chloro-5-(piperazin-1-ylmethyl)benzonitrile (22 mg) as an oil.

MS (ESI) m/z 251.0
$^1$H NMR (500 MHz, CHLOROFORM-d) δ 7.26-7.21 (m, 1H), 6.94-6.89 (m, 1H), 4.33 (br. s., 2H), 3.56 (s, 2H), 2.95-2.90 (m, 4H), 2.50 (br. s., 4H).

(401C): A solution of 3-amino-4-chloro-5-(piperazin-1-ylmethyl)benzonitrile (22 mg, 0.088 mmol), Boc₂O (24 mg, 0.097 mmol), and TEA (0.013 mL, 0.097 mmol) in DCM (0.5 mL) was stirred at RT overnight. The solvents were removed and radial silica gel chromatography eluting with hexane containing 0 to 30% EtOAc afforded tert-butyl 4-(3-amino-2-chloro-5-cyanobenzyl)piperazine-1-carboxylate (28 mg) as film.

MS (ESI) m/z 351.1

¹H NMR (500 MHz, CHLOROFORM-d) δ 7.20 (d, J=1.8 Hz, 1H), 6.94 (d, J=2.0 Hz, 1H), 4.35 (s, 2H), 3.59 (s, 2H), 3.49-3.44 (m, 4H), 2.46 (br. s., 4H), 1.48 (s, 9H).

(402D): A mixture of tert-butyl 4-(3-amino-2-chloro-5-cyanobenzyl)piperazine-1-carboxylate (28 mg, 0.079 mmol), 2-chloro-4-(cyclopropyl(4-methoxybenzyl)amino) imidazo[2,1-f][1,2,4]triazine-7-carbonitrile (Intermediate 9) (28 mg, 0.079 mmol), Cs₂CO₃ (51.4 mg, 0.158 mmol), DPPF (4.4 mg, 7.9 μmol), 4,5-bis(diphenylphosphino)-9,9-dimethyxanthene (4.6 mg, 7.9 μmol), and in a microwave vial was flushed with nitrogen. Dioxane (0.7 mL) was added and the vial was sealed and heated at 100° C. for 3 hr. The reaction was diluted with EtOAc and filtered through celite. The solvent was removed and radial silica gel chromatography with hexane containing 5 to 40% EtOAc afforded tert-butyl 4-(2-chloro-5-cyano-3-((7-cyano-4-(cyclopropyl (4-methoxybenzyl)amino)imidazo[2,1-f][1,2,4]triazin-2-yl) amino)benzyl)piperazine-1-carboxylate (22 mg) as an oil.

MS (ESI) m/z 669.3 (M+1).

¹H NMR (400 MHz, CHLOROFORM-d) δ 9.10-8.58 (m, 1H), 7.95 (s, 1H), 7.48 (d, J=1.8 Hz, 2H), 7.19 (d, J=8.3 Hz, 2H), 6.85 (d, J=8.8 Hz, 2H), 5.78-5.58 (m, 1H), 3.82-3.77 (m, 3H), 3.71 (s, 2H), 3.65 (s, 2H), 3.52-3.44 (m, 4H), 3.04-2.83 (m, 1H), 2.48 (t, J=4.4 Hz, 4H), 1.50-1.46 (m, 9H), 1.20-1.07 (m, 2H), 0.92 (dd, J=4.1, 1.1 Hz, 2H).

Example 402

A solution of tert-butyl 4-(2-chloro-5-cyano-3-((7-cyano-4-(cyclopropyl(4-methoxybenzyl)amino)imidazo[2,1-f][1,2,4]triazin-2-yl)amino)benzyl)piperazine-1-carboxylate (22 mg, 0.033 mmol) and anisole (0.090 mL, 0.822 mmol) in DCM (0.5 mL) and TFA (0.5 mL) was left stirring at RT overnight. The solvent was removed and the residue was dissolved in MeOH and applied onto a SCX column. This was washed with MeOH and then eluted with 2 N NH₃ in MeOH with DCM to give crude 2-((2-chloro-5-cyano-3-(piperazin-1-ylmethyl)phenyl)amino)-4-(cyclopropylamino)imidazo[2,1-f][1,2,4]triazine-7-carbonitrile (15 mg). This was dissolved in a mixture of DCM (0.25 mL) and MeOH (0.25 mL) and oxetan-3-one (48 mg, 0.67 mmol), trimethylorthoformate (0.19 mL, 1.7 mmol), and acetic acid (0.019 mL, 0.33 mmol) were added. After stirring for 15 min, sodium cyanoborohydride (1M in THF, 0.33 mL, 0.33 mmol) was added and the reaction was left stirring for 3 hrs. The reaction was partitioned between EtOAc and sat. aq. NaHCO₃ solution. After stirring for 15 min, the aqueous phase was separated and washed with EtOAc. The combined organic phases were washed with brine, dried with sodium sulfate, and the solvent removed. Preparative HPLC (Column: Waters XBridge C18, 19×200 mm, 5-μm particles; Mobile Phase A: water with 20-mM ammonium acetate; Mobile Phase B: 95:5 acetonitrile:water with 20-mM ammonium acetate; Gradient: 20-100% B over 16 minutes, then a 5-minute hold at 100% B; Flow: 20 mL/min) afforded the title compound (5.9 mg, 39%). It was converted to the mono HCl salt.

MS (ESI) m/z 505.4

¹H NMR (500 MHz, DMSO-d6) δ 8.92 (br. s., 1H), 8.38 (s, 1H), 8.22 (s, 1H), 7.69-7.56 (m, 1H), 4.56 (br. s., 4H), 3.66 (br. s., 2H), 3.58-3.39 (m, 2H), 3.32-3.25 (m, 1H), 2.99-2.93 (m, 1H), 2.66-2.54 (m, 2H), 2.50-2.10 (m, 4H), 0.79 (d, J=5.5 Hz, 4H).

Example 404

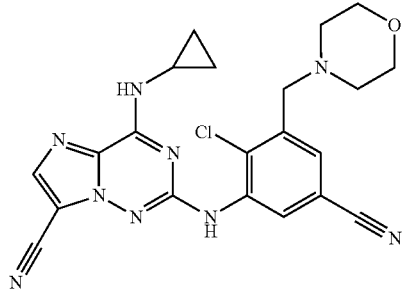 [SMILES: N#Cc1cc(CN2CCOCC2)c(Cl)c(Nc2nc(NC3CC3)c3ncc(C#N)n3n2)c1]

2-((2-chloro-5-cyano-3-(morpholinomethyl)phenyl) amino)-4-(cyclopropylamino)imidazo[2,1-f][1,2,4] triazine-7-carbonitrile (403A): A nitrogen sparged mixture of THF (1.6 mL) and water (0.16 mL) was added to a nitrogen flushed mixture of 4-((difluoroboryl)methyl)morpholin-4-ium fluoride (0.112 g, 0.663 mmol), tert-butyl(3-bromo-2-chloro-5-cyanophenyl)carbamate (Intermediate 1) (0.20 g, 0.603 mmol), 2-dicyclohexylphosphino-2'-4'-6'-trisisopropylbiphenyl (0.069 g, 0.15 mmol), Pd(OAc)₂ (0.016 g, 0.072 mmol), and Cs₂CO₃ (0.590 g, 1.809 mmol) in a microwave vial. This was sealed and heated at 80° C. for 22 hr. The reaction was extracted 3× with EtOAc and the combined organic extracts were washed with brine and dried with sodium sulfate. Removal of the solvent followed by silica gel radial chromatography eluting with hexane containing 10 to 30% EtOAc afforded tert-butyl(2-chloro-5-cyano-3-(morpholinomethyl)phenyl)carbamate (46 mg) as a film.

MS (ESI) m/z 352.2

¹H NMR (400 MHz, CHLOROFORM-d) δ 8.50 (d, J=1.8 Hz, 1H), 7.51 (d, J=2.0 Hz, 1H), 7.18 (s, 1H), 3.77-3.71 (m, 4H), 3.60 (s, 2H), 2.55-2.49 (m, 4H), 1.56-1.54 (m, 9H).

(403B): A solution of tert-butyl(2-chloro-5-cyano-3-(morpholinomethyl)phenyl)carbamate (45 mg, 0.128 mmol) in a mixture of DCM (2 mL) and TFA (2 mL) was left stirring at RT for 1 hr. The solvent was removed and the residue was dissolved in MeOH and applied onto an SCX column. This was washed with MeOH and the product was eluted with 2N NH₃ in MeOH. The solvent was removed to leave 3-amino-4-chloro-5-(morpholinomethyl)benzonitrile (32 mg, 100% yield).

MS (ESI) m/z 252.0

¹H NMR (400 MHz, CHLOROFORM-d) δ 7.21 (d, J=2.0 Hz, 1H), 6.93 (d, J=2.0 Hz, 1H), 4.34 (br. s., 2H), 3.77-3.72 (m, 4H), 3.57 (s, 2H), 2.55-2.49 (m, 4H).

Example 403

A mixture of 3-amino-4-chloro-5-(morpholinomethyl) benzonitrile (32 mg, 0.13 mmol), 2-chloro-4-(cyclopropyl (4-methoxybenzyl)amino)imidazo[2,1-f][1,2,4]triazine-7-carbonitrile (Intermediate 9) (47 mg, 0.13 mmol), Cs₂CO₃ (85 mg, 0.262 mmol), DPPF (7.3 mg, 0.013 mmol), 4,5-bis (diphenylphosphino)-9,9-dimethyxanthene (7.6 mg, 0.013 mmol) in a microwave vial was flushed with nitrogen. Dioxane (1 mL) was added and the vial was sealed and heated at 100° C. for 4 hr. The reaction was diluted with EtOAc and filtered through celite. The solvent was removed and radial silica gel chromatography eluting with hexane containing 5 to 40% EtOAc afforded 2-((2-chloro-5-cyano-3-(morpholinomethyl)phenyl)amino)-4-(cyclopropyl(4-methoxybenzyl)amino)imidazo[2,1-f][1,2,4]triazine-7-carbonitrile (33 mg, 44% yield) as an oil. This was dissolved in DCM (1.5 mL) and anisole (0.158 mL, 1.447 mmol) and TFA (0.9 mL) were added. After stirring at RT overnight, the solvent was removed and the residue was dissolved in MeOH and applied onto a SCX column. This was washed with MeOH and then eluted with 2 N $NH_3$ in MeOH with DCM. Silica gel radial chromatography eluting with DCM containing 1% MeOH gave the title compound (19 mg, 68% yield) as a white solid.

MS (ESI) m/z 450.2

$^1$H NMR (400 MHz, CHLOROFORM-d) δ 8.98 (d, J=2.0 Hz, 1H), 7.87 (s, 1H), 7.59 (s, 1H), 7.53 (d, J=2.0 Hz, 1H), 6.87 (br. s., 1H), 3.80-3.73 (m, 4H), 3.66 (s, 2H), 3.06 (td, J=7.0, 3.5 Hz, 1H), 2.60-2.52 (m, 4H), 1.16-1.07 (m, 2H), 0.87-0.77 (m, 2H).

Example 405

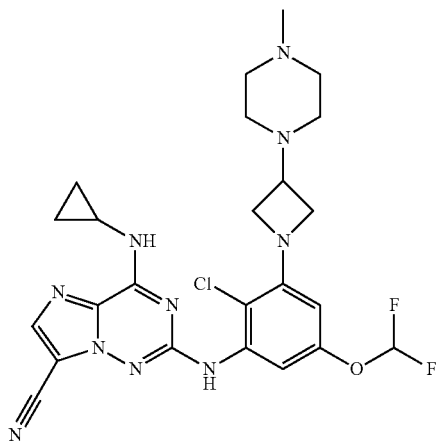 [SMILES: CN1CCN(C2CN(c3cc(OC(F)F)cc(Nc4nc(NC5CC5)c5ncc(C#N)n5n4)c3Cl)C2)CC1]

2-((2-chloro-5-(difluoromethoxy)-3-(3-(4-methylpiperazin-1-yl)azetidin-1-yl)phenyl)amino)-4-(cyclopropylamino)imidazo[2,1-f][1,2,4]triazine-7-carbonitrile (405A): 1,3-Dibromo-2-chloro-5-(difluoromethoxy)benzene (4.38 g, 13.02 mmol), tert-butyl carbamate (1.220 g, 10.42 mmol), palladium(ii) acetate (0.146 g, 0.651 mmol), XANTPHOS (0.942 g, 1.628 mmol) and cesium carbonate (16.97 g, 52.1 mmol) were suspended in dioxane (87 ml) at room temperature. The reaction mixture was degassed through evacuating under vacuum and backfilling with N2 (Repeated 3×) and heated to 105° C. for 2 h. After cooling to room temperature, the reaction mixture was diluted with EtOAc, filtered through celite and concentrated. Column chromatography (120 g $SiO_2$, 0 to 20% EtOAc-hexane gradient elution) afforded the desired product (2.79 g).

MS (ESI) m/z 372.1

$^1$H NMR (400 MHz, CHLOROFORM-d) δ 8.13 (d, J=2.6 Hz, 1H), 7.18 (d, J=2.2 Hz, 1H), 7.14 (d, J=2.9 Hz, 1H), 6.78-6.28 (m, 1H), 1.57 (s, 9H).

(405B): tert-Butyl(3-bromo-2-chloro-5-(difluoromethoxy)phenyl)carbamate (2.78 g, 7.46 mmol) was dissolved in DMF (37.3 ml) at room temperature. NaHMDS (8.95 ml, 8.95 mmol) was added dropwise and the reaction mixture was stirred for 30 min before the addition of 4-methoxybenzyl chloride (1.321 ml, 9.70 mmol). The reaction was allowed to stir overnight. EtOAc (250 mL) was added and the organic layer was washed with 10% LiCl solution (2×, dried over $Na_2SO_4$ and concentrated. Column chromatography (120 g SiO2, 0 to 10% EtOAc-hexane gradient elution) afforded the desired product as a clear oil (2.68 g)

MS (ESI) m/z 435.9

(405C): 1-(Azetidin-3-yl)-4-methylpiperazine (95 mg, 0.609 mmol), tert-butyl(3-bromo-2-chloro-5-(difluoromethoxy)phenyl)(4-methoxybenzyl)carbamate (300 mg, 0.609 mmol), cesium carbonate (397 mg, 1.218 mmol), Pd2(dba)3 (27.9 mg, 0.030 mmol) and BINAP (56.9 mg, 0.091 mmol) were suspended in toluene (6088 µl) at room temperature. The reaction was degassed under vacuum and backfilled with $N_2$ (4 times), and then heated to 105° C. for 4 h. After cooling to room temperature, the reaction mixture was diluted with EtOAc, filtered through celite and concentrated. Column chromatography (24 g SiO2, 0 to 10% CH3OH—CH2Cl2 gradient elution) afforded the desired product (213.1 mg).

MS (ESI) m/z 567.5

$^1$H NMR (400 MHz, CHLOROFORM-d) δ 7.22-7.07 (m, 2H), 6.82 (d, J=8.6 Hz, 2H), 6.38-5.93 (m, 3H), 5.10 (d, J=15.0 Hz, 1H), 4.40-4.09 (m, 3H), 3.97-3.70 (m, 5H), 3.26 (t, J=6.5 Hz, 1H), 2.69-2.42 (m, 8H), 2.34 (s, 3H), 1.59-1.27 (m, 9H)

(405D): tert-butyl(2-chloro-5-(difluoromethoxy)-3-(3-(4-methylpiperazin-1-yl)azetidin-1-yl)phenyl)(4-methoxybenzyl)carbamate (210 mg, 0.370 mmol) was dissolved in $CH_2Cl_2$ (3000 µl). anisole (405 µl, 3.70 mmol) was added, followed by TFA (1000 µL) and the reaction mixture was stirred at rt overnight. After concentrated, the residue was dissolved in MeOH and loaded on top of a 5 g Phenomenex Cation exchange cartridge, washing with MeOH. The desired product was eluted from the column using 7 N $NH_3$—$CH_3OH$. Concentrated and drying afforded the desired product as a light amber oil (129.2 mg).

MS (ESI) m/z 347.2

(405E): 2-Chloro-4-(cyclopropyl(4-methoxybenzyl)amino)imidazo[2,1-f][1,2,4]triazine-7-carbonitrile (Intermediate 9) (120 mg, 0.338 mmol), 2-chloro-5-(difluoromethoxy)-3-(3-(4-methylpiperazin-1-yl)azetidin-1-yl) aniline (129 mg, 0.372 mmol), palladium(ii) acetate (22.78 mg, 0.101 mmol), XANTPHOS (19.57 mg, 0.034 mmol), DPPF (18.75 mg, 0.034 mmol) and CESIUM CARBONATE (220 mg, 0.676 mmol) were suspended in Dioxane (3382 µl) at rt. The reaction vessel was evacuated and purged with $N_2$ (4 times) and then heated to 105° C. for 4 h. After cooling to room temperature, the reaction mixture was diluted with EtOAc, filtered through celite and concentrated. Column chromatography (40 g SiO2, 0 to 10% CH3OH—CH2Cl2 gradient elution) afforded the expected product (139.8 mg).

MS (ESI) m/z 665.5

Example 405

2-((2-Chloro-5-(difluoromethoxy)-3-(3-(4-methylpiperazin-1-yl)azetidin-1-yl)phenyl)amino)-4-(cyclopropyl(4-methoxybenzyl)amino)imidazo[2,1-f][1,2,4]triazine-7-carbonitrile (140 mg, 0.210 mmol) was dissolved in DCE (2105 µl) at rt. Anisole (115 µL) was added, followed by TFA (400 µL) and the reaction was heated to 50° C. for 2 h. After concentration, the crude compound was treated with 7 N NH₃—CH₃OH and sonicated. The tan precipitate was collected by filtration and further triturated with ACN to afford the expected product as a cream solid (32.3 mg).

MS (ESI) m/z 545.4 (M+1).

¹H NMR (400 MHz, DMSO-d₆) δ 9.27 (br. s., 1H), 8.40-8.28 (m, 1H), 8.20 (d, J=0.9 Hz, 1H), 7.54-7.40 (m, 1H), 7.39-6.97 (m, 1H), 6.17 (d, J=2.6 Hz, 1H), 4.16 (t, J=7.5 Hz, 2H), 3.86-3.75 (m, 2H), 3.24-3.15 (m, 1H), 3.15-3.03 (m, 1H), 2.46-2.28 (m, 8H), 2.20 (d, J=1.3 Hz, 3H), 0.79 (d, J=5.7 Hz, 4H).

Example 406

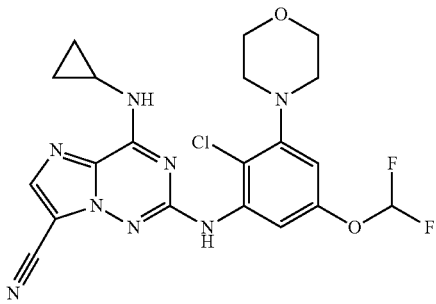 [SMILES: N#Cc1cnc2c(NC3CC3)nc(Nc3cc(OC(F)F)cc(N4CCOCC4)c3Cl)nn12]

2-(2-chloro-5-(difluoromethoxy)-3-morpholinophenylamino)-4-(cyclopropylamino)imidazo[1,2-f][1,2,4]triazine-7-carbonitrile Prepared in analogous manner as Example 405
MS (ESI) m/z 477.87

Example 407

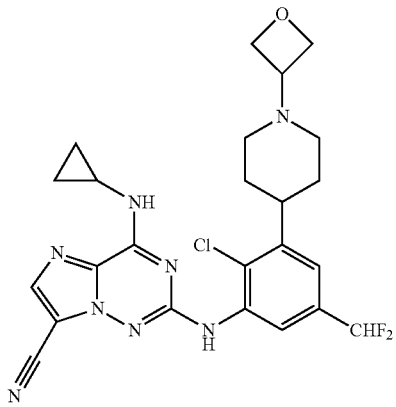 [SMILES: N#Cc1cnc2c(NC3CC3)nc(Nc3cc(C(F)F)cc(C4CCN(C5COC5)CC4)c3Cl)nn12]

2-((2-chloro-5-(difluoromethyl)-3-(1-(3-oxetanyl)-4-piperidinyl)phenyl)amino)-4-(cyclopropylamino)imidazo[2,1-f][1,2,4]triazine-7-carbonitrile Prepared in analogous manner as Example 242.
MS (ESI) m/z 514.97

Example 408

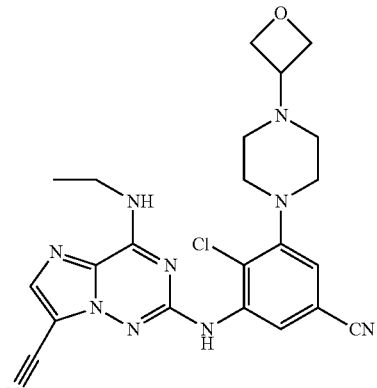

2-((2-chloro-5-cyano-3-(4-(3-oxetanyl)-1-piperazinyl)phenyl)amino)-4-(ethylamino)imidazo[2,1-f][1,2,4]triazine-7-carbonitrile Prepared using the procedure similar to Example 242.
MS (ESI) m/z 478.95

Example 409

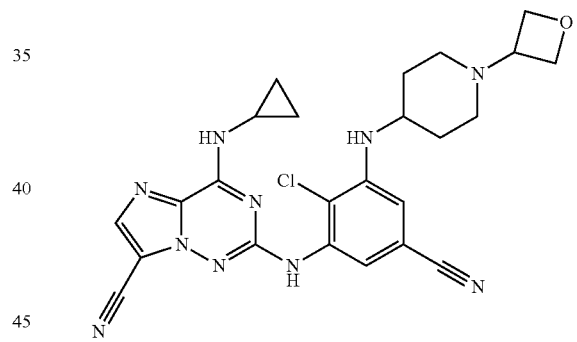

2-((2-chloro-5-cyano-3-((1-(oxetan-3-yl)piperidin-4-yl)amino)phenyl)amino)-4-(cyclopropylamino)imidazo[2,1-f][1,2,4]triazine-7-carbonitrile.HCl (409A): A mixture of tert-butyl(3-bromo-2-chloro-5-cyanophenyl)(4-methoxybenzyl)carbamate (Example 357A) (300 mg, 0.624 mmol), tert-butyl 4-aminopiperidine-1-carboxylate (162 mg, 0.811 mmol), Pd₂(dba)₃ (28.6 mg, 0.031 mmol), 4,5-bis(diphenylphosphino)-9,9-dimethyxanthene (36.1 mg, 0.062 mmol), and Cs₂CO₃ (610 mg, 1.872 mmol) in a dried microwave vial was flushed with nitrogen. Dioxane (6 mL) was added and the vial was sealed and heated at 95° C. overnight. The reaction was diluted with EtOAc and filtered through celite. Removed solvent from the filtrate followed by radial silica gel chromatography eluting with hexane containing 0 to 40% EtOAc to give tert-butyl 4-((3-((tert-butoxycarbonyl)(4-methoxybenzyl)amino)-2-chloro-5-cyanophenyl)amino)piperidine-1-carboxylate (211 mg, 56% yield) as a foam. This was dissolved in DCM (3 mL)

and anisole (0.202 ml, 1.847 mmol) and TFA (2 ml) were added. After 4 hr, the solvents were removed and the residue was taken up in MeOH and applied onto an SCX column. This was washed with MeOH, and then eluted with 2N NH$_3$ in MeOH. Removal of the solvents followed by silica gel radial chromatography with DCM containing 0 to 12% 2 N NH$_3$ in MeOH gave 3-amino-4-chloro-5-(piperidin-4-ylamino)benzonitrile (84 mg).

$^1$H NMR (500 MHz, CHLOROFORM-d) δ 6.40 (d, J=1.8 Hz, 1H), 6.33 (d, J=1.7 Hz, 1H), 4.36 (d, J=7.8 Hz, 1H), 4.20 (br. s., 2H), 3.43-3.33 (m, 1H), 3.15 (dt, J=12.9, 3.5 Hz, 2H), 2.80-2.71 (m, 2H), 2.10-2.02 (m, 2H), 1.47-1.37 (m, 2H).

(409B): A solution of 3-amino-4-chloro-5-(piperidin-4-ylamino)benzonitrile (54.8 mg, 0.219 mmol), Boc$_2$O (53 mg, 0.240 mmol), and TEA (33.5 μL, 0.240 mmol) in DCM (0.5 mL) was stirred at RT for 1 hr. The solvent was removed and radial silica gel chromatography eluting with hexane containing 0 to 30% EtOAc afforded tert-butyl 4-((3-amino-2-chloro-5-cyanophenyl)amino)piperidine-1-carboxylate (57.6 mg).

$^1$H NMR (400 MHz, CHLOROFORM-d) δ 6.43 (d, J=1.8 Hz, 1H), 6.34 (d, J=1.8 Hz, 1H), 4.34 (d, J=7.8 Hz, 1H), 4.21 (s, 2H), 4.12-4.01 (m, 2H), 3.52-3.37 (m, 1H), 3.06-2.90 (m, 2H), 2.06-1.98 (m, 2H), 1.49 (s, 9H), 1.47-1.37 (m, 2H).

(409C): A mixture of tert-butyl 4-((3-amino-2-chloro-5-cyanophenyl)amino)piperidine-1-carboxylate (57 mg, 0.16 mmol), 2-chloro-4-(cyclopropyl(4-methoxybenzyl)amino)imidazo[2,1-f][1,2,4]triazine-7-carbonitrile (Intermediate 9) (58 mg, 0.16 mmol), Cs$_2$CO$_3$ (106 mg, 0.325 mmol), dppf (9 mg, 0.016 mmol), 4,5-bis(diphenylphosphino)-9,9-dimethylxanthene (9 mg, 0.016 mmol), and Pd(OAc)$_2$ (11 mg, 0.049 mmol) in a microwave vial was flushed with nitrogen. Dioxane (3 mL) was added and the vial was sealed and heated at 100° C. for 3 hr. The reaction was diluted with EtOAc and filtered through celite. The solvent was removed from the filtrate and radial silica gel chromatography with DCM containing 0 to 10% EtOAc afforded tert-butyl 4-((2-chloro-5-cyano-3-((7-cyano-4-(cyclopropyl(4-methoxybenzyl)amino)imidazo[2,1-f][1,2,4]triazin-2-yl)amino)phenyl)amino)piperidine-1-carboxylate (74 mg, 68% yield) as a white solid. This was dissolved in DCM (1 mL) and anisole (0.238 mL, 2.18 mmol) and TFA (1 mL) were added. After stirring at RT overnight, the solvent were removed and the residue was applied onto a SCX column. This was washed with MeOH and the crude product was eluted with 2 N NH$_3$ in MeOH. Removal solvents followed by silica gel radial chromatography eluting with DCM containing 0 to 5% 2N NH$_3$ in MeOH) afforded 2-((2-chloro-5-cyano-3-(piperidin-4-ylamino)phenyl)amino)-4-(-(cyclopropylamino)imidazo[2,1-f][1,2,4]triazine-7-carbonitrile (38 mg, 0.085 mmol, 78% yield) as a white solid. This was suspended in a mixture of MeOH (0.5 mL) and DCM (0.5 mL). Oxetan-3-one (117 mg, 1.62 mmol), triethylorthoformate (0.448 mL, 4.05 mmol), and acetic acid (0.046 mL, 0.811 mmol) were added with stirring. After 15 min. sodium cyanoborohydride (1 M in THF, 0.811 mL, 0.811 mmol) was added and the reaction was left stirring for 4 hrs. It was partitioned between EtOAc and sat. aq. NaHCO$_3$ solution. After stirring for 15 min, the aqueous phase was separated and washed with EtOAc. The combined organic phases were washed with brine and dried with sodium sulfate. Preparative HPLC (Column: Waters XBridge C18, 19×200 mm, 5-nm particles; Mobile Phase A: water with 20-mM ammonium acetate; Mobile Phase B: 95:5 acetonitrile:water with 20-mM ammonium acetate; Gradient: 20-100% B over 25 minutes, then a 5-minute hold at 100% B; Flow: 20 mL/mins) to give the title compound (7.3 mg). This was converted to the mono HCl salt.

MS (ESI) m/z 505.2

$^1$H NMR (500 MHz, DMSO-d6) δ 9.32 (br. s., 1H), 8.65 (br. s., 1H), 8.20 (s, 1H), 7.95 (s, 1H), 7.73 (br. s., 1H), 7.03 (br. s., 1H), 5.78 (br. s., 1H), 4.89 (br. s., 2H), 4.68 (br. s., 2H), 4.37 (br. s., 1H), 3.70 (br. s., 1H), 2.98 (br. s., 2H), 2.08 (br. s., 2H), 1.91 (br. s., 3H), 0.78 (br. s., 4H).

Example 410

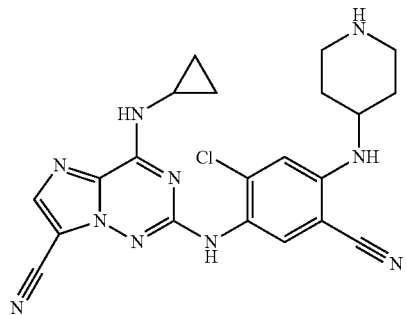 [SMILES: N#Cc1cc(Nc2nc(NC3CC3)c3ncc(C#N)n3n2)c(Cl)cc1NC1CCNCC1]

2-((2-chloro-5-cyano-4-(piperidin-4-ylamino)phenyl)amino)-4-(cyclopropylamino)imidazo[2,1-f][1,2,4]triazine-7-carbonitrile (410A): Sodium bis(trimethylsilyl)amide (1M in THF, 37.0 mL, 37.0 mmol) was added to a solution of 5-amino-2-bromo-4-chlorobenzonitrile (3.43 g, 14.8 mmol) in dry THF (75 ml) at 0° C. After stirring for 15 min at 0° C., a solution of di-tert-butyl dicarbonate (3.56 g, 16.3 mmol) in THF (10 ml) was added. The reaction was allowed to warm to RT overnight. Aqueous 0.1 N HCl was slowly added to bring the pH to 10. The reaction was extracted twice with EtOAc and the combined organic phases were washed with brine, dried over Na$_2$SO$_4$. The solvent was removed and column chromatography with hexane/EtOAc as eluent afforded tert-butyl(4-bromo-2-chloro-5-cyanophenyl)carbamate (2.76 gm) as a white solid.

$^1$H NMR (500 MHz, CHLOROFORM-d) δ 8.65 (s, 1H), 7.69 (s, 1H), 7.06 (br. s., 1H), 1.57 (s, 9H).

(410B): A mixture of tert-butyl(4-bromo-2-chloro-5-cyanophenyl)carbamate (150 mg, 0.452 mmol), tert-butyl 4-aminopiperidine-1-carboxylate (118 mg, 0.588 mmol), Pd$_2$(dba)$_3$ (20.7 mg, 0.023 mmol), 4,5-bis(diphenylphosphino)-9,9-dimethyxanthene (26 mg, 0.045 mmol), and Cs$_2$CO$_3$ (442 mg, 1.36 mmol) in a dried microwave vial was flushed with nitrogen. Dioxane (4 mL) was added and the vial was sealed and heated at 95° C. overnight. The reaction was diluted with EtOAc and filtered through celite. The solvent was removed from the filtrate and radial silica gel chromatography of eluting with hexane/EtOAc afforded tert-butyl 4-((4-((tert-butoxycarbonyl)amino)-5-chloro-2-cyanophenyl)amino)piperidine-1-carboxylate (168 mg). This was dissolved in DCM (4 mL) and TFA (4 mL) was added. After 1 hr, the solvent was removed and the residue was dissolve in MeOH and applied onto an SCX column. After washing with MeOH, the product was eluted with 2 N NH$_3$ in MeOH. Removal of the solvents left tert-butyl 4-((4-((tert-butoxycarbonyl)amino)-5-chloro-2-cyanophenyl)amino)piperidine-1-carboxylate (89 mg) as an oil. A portion of this (49.6 mg, 0.198 mmol) was dissolved in DCM (1 mL) and Boc$_2$O (0.051 ml, 0.218 mmol) and TEA (0.030 ml, 0.218 mmol) were added. After stirred at rt for 1 hr, the solvent was removed and radial silica gel chromatography with hexane containing 0 to 30% EtOAc afforded tert-butyl 4-((4-amino-5-chloro-2-cyanophenyl)amino)piperidine-1-carboxylate (67 mg) as a yellow oil that solidified.

$^1$H NMR (500 MHz, CHLOROFORM-d) δ 6.85 (s, 1H), 6.67 (s, 1H), 4.09-3.98 (m, 2H), 3.38 (s, 1H), 2.93 (br. s., 2H), 2.03-1.96 (m, 2H), 1.47 (s, 9H), 1.43-1.34 (m, 2H).

Example 410

A mixture of cyanophenyl)amino)piperidine-1-carboxylate (67 mg, 0.191 mmol), 2-chloro-4-(cyclopropyl(4-methoxybenzyl)amino)imidazo[2,1-f][1,2,4]triazine-7-carbonitrile (Intermediate 9) (57 mg, 0.161 mmol), Cs$_2$CO$_3$ (124 mg, 0.382 mmol), dppf (10.6 mg, 0.019 mmol), 4,5-bis(diphenylphosphino)-9,9-dimethyxanthene (11.1 mg, 0.019 mmol), and Pd(OAc)$_2$ (12.9 mg, 0.057 mmol) in a microwave vial was flushed with nitrogen. Dioxane (4 mL) was added and the vial was sealed and heated at 100° C. for 3 hr. The reaction was diluted with EtOAc and filtered through celite. The solvent was removed and radial silica gel chromatography with DCM containing 0 to 10% EtOAc afforded tert-butyl 4-((5-chloro-2-cyano-4-((7-cyano-4-(cyclopropyl(4-methoxybenzyl)amino)imidazo[2,1-f][1,2,4]triazin-2-yl)amino)phenyl)amino)piperidine-1-carboxylate (94 mg, 74% yield) as a film. This was dissolved in DCM (1.5 mL) and anisole (0.152 mL, 1.39 mmol) and TFA (1 mL) were added and left stirring at RT overnight. The solvents were removed and the residue was applied onto a SCX column. This was washed with MeOH and the crude product was eluted with 2 N NH3 in MeOH mixed with DCM. Removal of the solvent left 62 mg of impure 2-((2-chloro-5-cyano-4-(piperidin-4-ylamino)phenyl)amino)-4-(cyclopropylamino)imidazo[2,1-f][1,2,4]triazine-7-carbonitrile. A sample was purified by preparative HPLC (Column: Waters XBridge C18, 19×200 mm, 5-µm particles; Mobile Phase A: water with 20-mM ammonium acetate; Mobile Phase B: 95:5 acetonitrile:water with 20-mM ammonium acetate; Gradient: 10-50% B over 20 minutes, then a 5-minute hold at 100% B; Flow: 20 mL/min) to give the pure title compound.

MS (ESI) m/z 449.3

$^1$H NMR (400 MHz, DMSO-d6) δ 9.18 (d, J=4.5 Hz, 1H), 8.70 (s, 1H), 8.16 (s, 1H), 7.81 (s, 1H), 7.35 (s, 1H), 7.22 (s, 1H), 7.10 (s, 1H), 6.24 (d, J=8.0 Hz, 1H), 3.74 (d, J=7.5 Hz, 1H), 3.33 (d, J=11.8 Hz, 3H), 3.10-2.92 (m, 3H), 2.03 (d, J=12.5 Hz, 2H), 1.83-1.68 (m, 2H), 0.78-0.74 (m, 4H).

Example 411

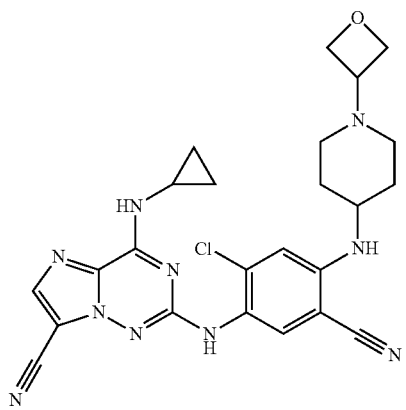 [SMILES: N#Cc1cc(Nc2nc(NC3CC3)c3ncc(C#N)n3n2)c(Cl)cc1NC1CCN(C2COC2)CC1]

2-((2-chloro-5-cyano-4-((1-(oxetan-3-yl)piperidin-4-yl)amino)phenyl)amino)-4-(cyclopropylamino)imidazo[2,1-f][1,2,4]triazine-7-carbonitrile A suspension of 2-((2-chloro-5-cyano-4-(piperidin-4-ylamino)phenyl)amino)-4-(cyclopropylamino)imidazo[2,1-f][1,2,4]triazine-7-carbonitrile (Example 410) (36 mg, 0.080 mmol), oxetan-3-one (116 mg, 1.604 mmol), trimethylorthoformate (0.443 mL, 4.01 mmol), and acetic acid (0.046 mL, 0.802 mmol) in a mixture of MeOH (0.5 mL) and DCM (0.5 mL) was stirred at RT for 15 min. Sodium cyanoborohydride (1M in THF, 0.802 mL, 0.802 mmol) was added and the reaction was left stirring for 9 hrs. It was partitioned between EtOAc and sat. aq. NaHCO$_3$ solution. After stirring for 15 min, the aqueous phase was separated and washed with EtOAc (3×) and then a mixture of 10% MeOH in DCM (4×). The combined organic phases were dried with sodium sulfate and the solvent removed. Preparative HPLC (Column: Waters XBridge C18, 19×200 mm, 5-µm particles; Mobile Phase A: water with 20-mM ammonium acetate; Mobile Phase B: 95:5 acetonitrile:water with 20-mM ammonium acetate; Gradient: 10-100% B over 30 minutes, then a 5-minute hold at 100% B; Flow: 20 mL/min) afforded the title compound (13 mg).

MS (ESI) m/z 505.3

$^1$H NMR (500 MHz, DMSO-d6) δ 9.15 (d, J=4.0 Hz, 1H), 8.66 (s, 1H), 8.14 (s, 1H), 7.95 (s, 1H), 7.80 (br. s., 1H), 7.06 (br. s., 1H), 4.86 (br. s., 2H), 4.67 (br. s., 2H), 4.36 (br. s., 1H), 3.70 (br. s., 1H), 3.31-3.25 (m, 1H), 3.30-3.17 (m, 2H), 2.94 (d, J=4.3 Hz, 3H), 2.15-1.79 (m, 5H), 0.75 (br. s., 4H).

Example 412

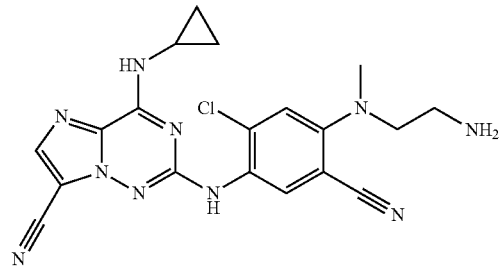 [SMILES: CN(CCN)c1cc(Cl)c(Nc2nc(NC3CC3)c3ncc(C#N)n3n2)cc1C#N]

2-((4-((2-aminoethyl)(methyl)amino)-2-chloro-5-cyanophenyl)amino)-4-(cyclopropylamino)imidazo[2,1-f][1,2,4]triazine-7-carbonitrile (412A): A solution of tert-butyl(4-bromo-2-chloro-5-cyanophenyl)carbamate (1.0 g, 3.02 mmol) in DMF (10 mL) was cooled in an icebath and NaHMDS (1 M solution in THF, 4.52 ml, 4.52 mmol) was added. After 20 min, 4-methoxybenzyl chloride (0.616 ml, 4.52 mmol) was added and the reaction was removed from the bath and left stirring at RT overnight. The reaction was partitioned between EtOAc and sat. aq. NH$_4$Cl solution. The aqueous phase was extracted with EtOAc and the combined organic extracts were washed with brine. After drying with sodium sulfate, the solvents were removed and silica gel chromatography with hexane containing 0 to 30% EtOAc afforded tert-butyl (4-bromo-2-chloro-5-cyanophenyl)(4-methoxybenzyl)carbamate (1.04 g) as a white solid.

$^1$H NMR (500 MHz, CHLOROFORM-d) δ 7.75 (br. s., 1H), 7.11 (d, J=8.5 Hz, 3H), 6.84 (d, J=7.9 Hz, 2H), 5.04 (d, J=14.6 Hz, 1H), 4.29 (d, J=14.6 Hz, 1H), 3.82 (s, 3H), 1.56-1.31 (m, 9H).

(412B): A mixture of tert-butyl(4-bromo-2-chloro-5-cyanophenyl)(4-methoxybenzyl)carbamate (363 mg, 0.803 mmol), tert-butyl(2-(methylamino)ethyl)carbamate (182 mg, 1.05 mmol), Pd$_2$(dba)$_3$ (51.5 mg, 0.056 mmol), BINAP (105 mg, 0.169 mmol), and Cs$_2$CO$_3$ (524 mg, 1.61 mmol) in a dry microwave vial was flushed with nitrogen. Toluene (5 mL) was added and the vial was sealed and heated at 100° C. overnight. The reaction was diluted with EtOAc and filtered through celite. The solvent was removed from the filtrate and silica gel radial chromatography eluting with hexane containing 5 to 30% EtOAc afforded tert-butyl(4-((2-((tert-butoxycarbonyl)amino)ethyl)(methyl)amino)-2-chloro-5-cyanophenyl)(4-methoxybenzyl)carbamate (397 mg) as an oil.

$^1$H NMR (500 MHz, CHLOROFORM-d) δ 7.17-6.89 (m, 4H), 6.82 (d, J=7.6 Hz, 2H), 5.04 (d, J=14.5 Hz, 1H), 4.85 (br. s., 1H), 4.17 (d, J=14.6 Hz, 1H), 3.81 (s, 3H), 3.58-3.33 (m, 4H), 3.02 (br. s., 3H), 1.61-1.32 (m, 18H).

(412C): TFA (4 mL) was added to a solution of tert-butyl (4-((2-((tert-butoxycarbonyl)amino)ethyl)(methyl)amino)-2-chloro-5-cyanophenyl)(4-methoxybenzyl)carbamate (397 mg, 0.728 mmol) and anisole (1.59 ml, 14.8 mmol) in DCM (5 ml) at RT for 3 hr. The solvents were removed and the residue was taken up in MeOH, applied onto an SCX column. This was washed with MeOH and then eluted with 2N NH$_3$ in MeOH. Removal of the solvents left 5-amino-2-((2-aminoethyl)(methyl)amino)-4-chlorobenzonitrile as an oil.

MS (ESI) m/z 225.1

$^1$H NMR (500 MHz, CHLOROFORM-d) δ 7.04 (s, 1H), 6.95 (s, 1H), 4.05 (br. s., 2H), 3.11 (t, J=6.3 Hz, 2H), 2.89 (t, J=6.3 Hz, 2H), 2.80 (s, 3H), 1.52 (br. s., 2H).

(412D): A solution of 5-amino-2-((2-aminoethyl)(methyl)amino)-4-chlorobenzonitrile (153 mg, 0.681 mmol), Boc$_2$O (163 mg, 0.749 mmol), and TEA (104 μL, 0.749 mmol) in DCM (1 mL) was stirred at RT for 2 hr. The solvent was removed and radial silica gel chromatography with hexane containing 0 to 30% EtOAc afforded tert-butyl(2-((4-amino-5-chloro-2-cyanophenyl)(methyl)amino)ethyl)carbamate (207 mg) as an oil.

$^1$H NMR (500 MHz, CHLOROFORM-d) δ 7.03 (s, 1H), 6.96 (s, 1H), 4.96 (br. s., 1H), 4.04 (s, 2H), 3.35 (q, J=6.0 Hz, 2H), 3.22-3.16 (m, 2H), 2.82 (s, 3H), 1.44 (s, 9H).

(412E): A mixture of tert-butyl(2-((4-amino-5-chloro-2-cyanophenyl)(methyl)amino)ethyl)carbamate (207 mg, 0.637 mmol), 2-chloro-4-(cyclopropyl(4-methoxybenzyl)amino)imidazo[2,1-f][1,2,4]triazine-7-carbonitrile (Intermediate 9) (226 mg, 0.637 mmol), Cs$_2$CO$_3$ (415 mg, 1.28 mmol), dppf (35.3 mg, 0.064 mmol), 4,5-bis(diphenylphosphino)-9,9-dimethyxanthene (36.9 mg, 0.064 mmol), and Pd(OAc)$_2$ (42.9 mg, 0.191 mmol) in a microwave vial was flushed with nitrogen. Dioxane (9 mL) was added and the vial was sealed and heated at 100° C. for 4 hr. The reaction was diluted with EtOAc and filtered through celite. The solvent was removed and radial silica gel chromatography with hexane containing 5 to 40% EtOAc afforded tert-butyl (2-((5-chloro-2-cyano-4-((7-cyano-4-(cyclopropyl(4-methoxybenzyl)amino)imidazo[2,1-f][1,2,4]triazin-2-yl)amino)phenyl)(methyl)amino)ethyl)carbamate (283 mg) as an oil.

MS (ESI) m/z 643.3

$^1$H NMR (500 MHz, CHLOROFORM-d) δ 8.79 (br. s., 1H), 7.95-7.88 (m, 1H), 7.19 (d, J=8.5 Hz, 2H), 7.16-6.98 (m, 2H), 6.85 (d, J=8.7 Hz, 2H), 5.85-5.53 (m, 1H), 4.88 (br. s., 1H), 3.79 (s, 3H), 3.41 (d, J=2.9 Hz, 4H), 2.97 (s, 3H), 2.94-2.81 (m, 1H), 1.52-1.38 (m, 9H), 1.13 (d, J=4.0 Hz, 2H), 0.93-0.82 (m, 2H).

Example 412

A solution of tert-butyl(2-((5-chloro-2-cyano-4-((7-cyano-4-(cyclopropyl(4-methoxybenzyl)amino)imidazo[2,1-f][1,2,4]triazin-2-yl)amino)phenyl)(methyl)amino)ethyl) carbamate (283 mg, 0.440 mmol) and anisole (0.481 mL, 4.40 mmol) in DCM (3 mL) and TFA (3 mL) was left stirring at RT overnight. The solvents were removed and the residue was dissolved in MeOH and applied onto a SCX column. This was washed with MeOH and then eluted with 2 N NH$_3$ in MeOH mixed with DCM. Removal of the solvents followed by silical gel radial chromatography eluting with DCM containing 0 to 5% 2N NH$_3$ in MeOH afforded the title compound (146 mg, 71% yield) as an oil that solidified.

MS (ESI) 423.1

$^1$H NMR (500 MHz, CHLOROFORM-d) δ 8.79 (s, 1H), 7.84 (s, 1H), 7.18 (s, 1H), 7.07 (s, 1H), 6.95 (br. s., 1H), 3.37 (t, J=6.5 Hz, 2H), 3.08-3.00 (m, 3H), 2.98 (s, 3H), 1.60-1.30 (m, 2H), 1.12-1.07 (m, 2H), 0.83-0.77 (m, 2H).

Example 413

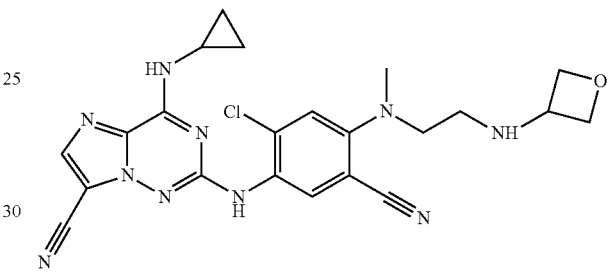

2-((2-chloro-5-cyano-4-(methyl(2-(oxetan-3-ylamino)ethyl)amino)phenyl)amino)-4-(cyclopropylamino)imidazo[2,1-f][1,2,4]triazine-7-carbonitrile A solution of 2-((4-((2-aminoethyl)(methyl)amino)-2-chloro-5-cyanophenyl)amino)-4-(cyclopropylamino)imidazo[2,1-f][1,2,4]triazine-7-carbonitrile (Example 412) (63 mg, 0.149 mmol), oxetan-3-one (215 mg, 2.98 mmol), trimethylorthoformate (0.823 mL, 7.45 mmol), and acetic acid (0.085 mL, 1.490 mmol) in a mixture of MeOH (0.5 mL) and DCM (0.5 mL) was stirred at RT for 15 min. Added sodium cyanoborohydride (1M in THF, 1.49 mL, 1.49 mmol) and left the reaction stirring for 3 hrs. The reaction was partitioned between EtOAc and sat. aq. NaHCO$_3$ solution. After stirring for 15 min, the aqueous phase was separated and washed with EtOAc. The combined organic phases were washed with brine, dried with sodium sulfate, and the solvent removed. Preparative HPLC (Column: Waters XBridge C18, 19×200 mm, 5-μm particles; Mobile Phase A: water with 20-mM ammonium acetate; Mobile Phase B: 95:5 acetonitrile:water with 20-mM ammonium acetate; Gradient: 20-60% B over 20 minutes, then a 5-minute hold at 100% B; Flow: 20 mL/min) afforded the title compound (10 mg, 15% yield).

MS (ESI) m/z 379.2

$^1$H NMR (500 MHz, DMSO-d6) δ 9.22 (br. s., 1H), 8.75 (br. s., 1H), 8.17 (s, 1H), 8.02 (s, 1H), 7.19 (s, 1H), 4.61 (t, J=6.6 Hz, 2H), 4.29 (t, J=6.3 Hz, 2H), 3.88 (quin, J=6.4 Hz, 1H), 3.41-3.37 (m, 2H), 3.00-2.93 (m, 4H), 2.72 (t, J=7.0 Hz, 2H), 0.78 (d, J=5.5 Hz, 4H).

Example 414

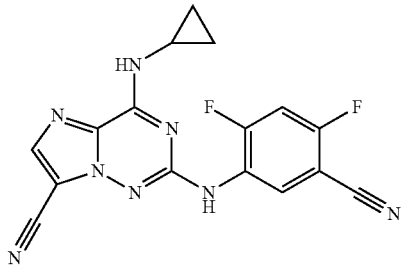 [SMILES: N#Cc1cc(Nc2nc(NC3CC3)c3ncc(C#N)n3n2)c(F)cc1F]

2-((5-cyano-2,4-difluorophenyl)amino)-4-(cyclopropylamino)imidazo[2,1-f][1,2,4]triazine-7-carbonitrile (414A): A suspension of 2,4-difluoro-5-nitrobenzonitrile (1.0 g, 5.43 mmol) and Pd/C 10% (0.1 g, 0.94 mmol) in MeOH (20 mL) was hydrogenated (balloon) for 5 hr. This was filtered and the solvent was removed. Flash chromatography on silica gel eluting with hexane containing 20% EtOAc gave 5-amino-2,4-difluorobenzonitrile (0.59 g) as a light yellow solid.
MS (ESI) 155.0
$^1$H NMR (500 MHz, CHLOROFORM-d) δ 6.98 (dd, J=9.1, 6.0 Hz, 1H), 6.93 (dd, J=10.5, 8.5 Hz, 1H), 3.84 (br. s., 2H).

(414B): A mixture of 5-amino-2,4-difluorobenzonitrile (300 mg, 1.947 mmol), 2-chloro-4-(cyclopropyl(4-methoxybenzyl)amino)imidazo[2,1-f][1,2,4]triazine-7-carbonitrile (Intermediate 9) (691 mg, 1.947 mmol), $Cs_2CO_3$ (1268 mg, 3.89 mmol), DPPF (108 mg, 0.195 mmol), 4,5-bis(diphenylphosphino)-9,9-dimethyxanthene (113 mg, 0.195 mmol), and $Pd(OAc)_2$ (131 mg, 0.584 mmol) in a microwave vial was flushed with nitrogen. Dioxane (16 mL) was added and the vial was sealed and heated at 100° C. for 4 hr. The reaction was diluted with EtOAc and filtered through celite. The solvent was removed and radial silica gel chromatography eluting with hexane containing 5 to 40% EtOAc afforded 2-((5-cyano-2,4-difluorophenyl)amino)-4-(cyclopropyl(4-methoxybenzyl)amino)imidazo[2,1-f][1,2,4]triazine-7-carbonitrile (799 mg) as a foam.

Example 414

A portion of 2-((5-cyano-2,4-difluorophenyl)amino)-4-(cyclopropyl(4-methoxybenzyl)amino)imidazo[2,1-f][1,2,4]triazine-7-carbonitrile (61 mg, 0.129 mmol) was dissolved in DCM (1.5 mL) and anisole (0.141 mL, 1.291 mmol) and TFA (1 mL) was added. After stirring at RT overnight, the solvents were removed. Preparative HPLC (Column: Waters XBridge C18, 19×200 mm, 5-µm particles; Mobile Phase A: water with 20-mM ammonium acetate; Mobile Phase B: 95:5 acetonitrile:water with 20-mM ammonium acetate; Gradient: 30-100% B over 20 minutes, then a 5-minute hold at 100% B; Flow: 20 mL/min) afforded the title compound (36 mg). This was converted to the mono HCl salt.
MS (ESI) m/z 353.1
$^1$H NMR (500 MHz, DMSO-d6) δ 9.36 (br. s., 2H), 8.47 (t, J=7.6 Hz, 1H), 8.20 (s, 1H), 7.74 (t, J=10.1 Hz, 1H), 2.96 (d, J=4.6 Hz, 1H), 0.88-0.49 (m, 4H).

Example 415

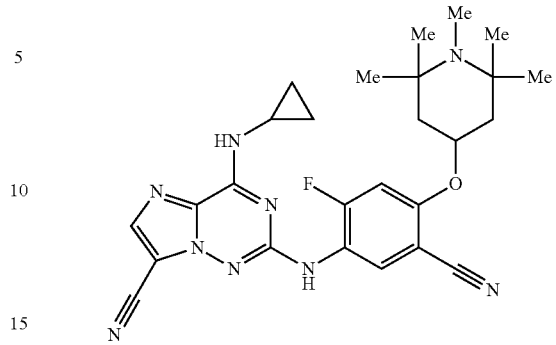

2-((5-cyano-2-fluoro-4-((1,2,2,6,6-pentamethylpiperidin-4-yl)oxy)phenyl)amino)-4-(cyclopropylamino)imidazo[2,1-f][1,2,4]triazine-7-carbonitrile (415A): Added DMAP (10.3 mg, 0.085 mmol) to a solution of 2-((5-cyano-2,4-difluorophenyl)amino)-4-(cyclopropyl(4-methoxybenzyl)amino)imidazo[2,1-f][1,2,4]triazine-7-carbonitrile (Example 414B) (200 mg, 0.423 mmol), TEA (0.089 mL, 0.635 mmol) and $Boc_2O$ (148 mg, 0.677 mmol) in THF (1 mL) at RT. After 15 min, the reaction was diluted with EtOAc, washed with water followed by brine. After drying with sodium sulfate, the solvent was removed and silica gel radial chromatography eluting with hexane containing 10 to 30% EtOAc afforded tert-butyl(5-cyano-2,4-difluorophenyl)(7-cyano-4-(cyclopropyl(4-methoxybenzyl)amino)imidazo[2,1-f][1,2,4]triazin-2-yl)carbamate (203 mg) as a foam.
MS (ESI) m/z 573.2
$^1$H NMR (500 MHz, CHLOROFORM-d) δ 8.09-7.94 (m, 1H), 7.74-7.41 (m, 1H), 7.23-6.62 (m, 4H), 5.71-5.49 (m, 1H), 4.72 (br. s., 1H), 3.81 (d, J=11.3 Hz, 2H), 3.90-3.72 (m, 3H), 3.68-2.43 (m, 1H), 1.57-1.53 (m, 9H), 0.88 (br. s., 4H).

Example 415

NaH (60% in mineral oil, 13.4 mg, 0.335 mmol) was added to a solution of 1,2,2,6,6-pentamethylpiperidin-4-ol (53.8 mg, 0.314 mmol) in dry DMF (1 mL) at RT. After stirring for 30 min, added solid tert-butyl(5-cyano-2,4-difluorophenyl)(7-cyano-4-(cyclopropyl(4-methoxybenzyl) amino)imidazo[2,1-f][1,2,4]triazin-2-yl)carbamate (60 mg, 0.11 mmol). After 0.5 hr. sat. aq. $NH_4Cl$ solution was added and the reaction was extracted with DCM. The organic phase was washed with water and dried with sodium sulfate. After removal of the solvent, the crude tert-butyl(5-cyano-2-fluoro-4-((1,2,2,6,6-pentamethylpiperidin-4-yl)oxy)phenyl)(7-cyano-4-(cyclopropyl(4-methoxybenzyl)amino)imidazo[2,1-f][1,2,4]triazin-2-yl)carbamate (76 mg) was dissolved in DCM (1.5 mL) and anisole (0.287 mL, 2.62 mmol) and TFA (1.5 mL) were added. After stirring at RT overnight, the solvent was removed and the residue was dissolved in MeOH and applied onto a SCX column. The column was washed with MeOH and the crude product was eluted with 2 N $NH_3$ in MeOH mixed with DCM. Removal of the solvents followed by silica gel radial chromatography eluting with DCM containing 0 to 6% MeOH afforded the title compound (16.8 mg) as a film.
MS (ESI) m/z 504.2
$^1$H NMR (500 MHz, CHLOROFORM-d) δ 8.77 (d, J=9.0 Hz, 1H), 7.85 (s, 1H), 6.94 (d, J=2.6 Hz, 1H), 6.80 (d, J=12.5 Hz, 2H), 4.55 (tt, J=11.0, 4.0 Hz, 1H), 3.02 (dd, J=7.0, 3.7 Hz, 1H), 2.31 (s, 3H), 2.02 (d, J=3.8 Hz, 2H), 1.74 (t, J=11.6 Hz, 2H), 1.24 (s, 5H), 1.27-1.22 (m, 6H), 1.15 (s, 6H), 1.12-1.08 (m, 2H), 0.83-0.78 (m, 2H).

Example 416

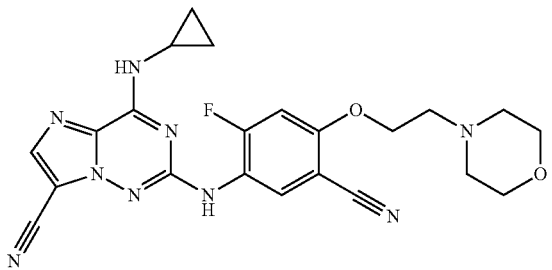 [SMILES: N#Cc1cc(Nc2nc(NC3CC3)c3ncc(C#N)n3n2)c(F)cc1OCCN1CCOCC1]

2-((5-cyano-2-fluoro-4-(2-morpholinoethoxy)phenyl)amino)-4-(cyclopropylamino)imidazo[2,1-f][1,2,4]triazine-7-carbonitrile The title compound was obtained as the major product from the reaction between tert-butyl(5-cyano-2,4-difluorophenyl)(7-cyano-4-(cyclopropyl(4-methoxybenzyl)amino)-imidazo[2,1-f][1,2,4]triazin-2-yl)carbamate (Example 414B) and 2-morpholinoethanol according to the procedure described in Example 415.

MS (ESI) m/z 464.2

$^1$H NMR (500 MHz, DMSO-d6) δ 9.32-9.26 (m, 1H), 9.22-9.14 (m, 1H), 8.29-8.22 (m, 1H), 8.21-8.16 (m, 1H), 7.48-7.39 (m, 1H), 4.60 (br. s., 2H), 3.99 (br. s., 2H), 3.80 (br. s., 2H), 3.69-3.49 (m, 4H), 3.31-3.22 (m, 2H), 2.96 (d, J=4.3 Hz, 1H), 0.82-0.76 (m, 4H).

Example 417

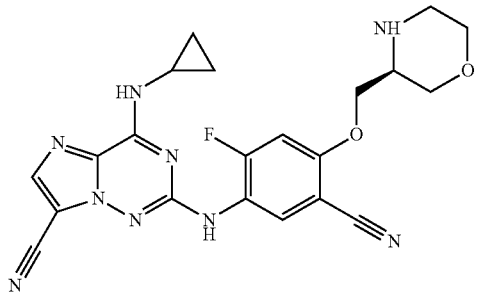 [SMILES: N#Cc1cc(Nc2nc(NC3CC3)c3ncc(C#N)n3n2)c(F)cc1OC[C@@H]1COCCN1]

(S)-2-((5-cyano-2-fluoro-4-(morpholin-3-ylmethoxy)phenyl)amino)-4-(cyclopropylamino)imidazo[2,1-f][1,2,4]triazine-7-carbonitrile The title compound was similarly obtained as the major product from the reaction between tert-butyl(5-cyano-2,4-difluorophenyl)(7-cyano-4-(cyclopropyl(4-methoxybenzyl)amino)-imidazo[2,1-f][1,2,4]triazin-2-yl)carbamate (Example 414B) and (R)-tert-butyl 3-(hydroxymethyl)morpholine-4-carboxylate according to the procedure described in Example 416 followed by removal of the Boc protecting group with TFA.

MS (ESI) m/z 450.4 (M+1).

$^1$H NMR (500 MHz, DMSO-d6) δ 9.31-9.27 (m, 1H), 9.20-9.17 (m, 1H), 8.28-8.23 (m, 1H), 8.21-8.17 (m, 1H), 7.51-7.44 (m, 1H), 4.41 (d, J=5.2 Hz, 2H), 4.09 (d, J=11.3 Hz, 1H), 3.94 (d, J=12.5 Hz, 1H), 3.75-3.66 (m, 2H), 3.29 (br. s., 2H), 3.22-3.12 (m, 1H), 2.96 (d, J=4.6 Hz, 1H), 0.79 (br. s., 4H).

Example 418

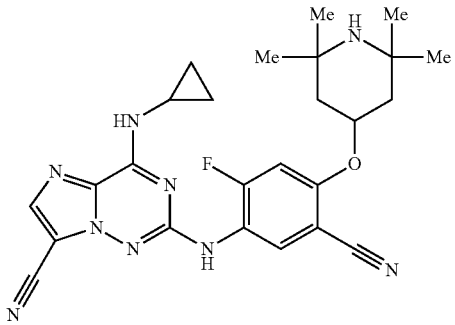 [SMILES: CC1(C)CC(Oc2cc(F)c(Nc3nc(NC4CC4)c4ncc(C#N)n4n3)cc2C#N)CC(C)(C)N1]

2-((5-cyano-2-fluoro-4-((2,2,6,6-tetramethylpiperidin-4-yl)oxy)phenyl)amino)-4-(cyclopropylamino)imidazo[2,1-f][1,2,4]triazine-7-carbonitrile The title compound was similarly obtained as the major product from the reaction between tert-butyl(5-cyano-2,4-difluorophenyl)(7-cyano-4-(cyclopropyl(4-methoxybenzyl)amino)-imidazo[2,1-f][1,2,4]triazin-2-yl)carbamate (Example 414B) and 2,2,6,6-tetramethylpiperidin-4-ol according to the procedure described in Example 416.

MS (ESI) m/z 464.2

$^1$H NMR (500 MHz, DMSO-d6) δ 9.31-9.28 (m, 1H), 9.20-9.16 (m, 1H), 8.28-8.23 (m, 1H), 8.20-8.17 (m, 1H), 7.56-7.49 (m, 1H), 5.19-5.09 (m, 1H), 2.97 (d, J=5.2 Hz, 1H), 2.20 (d, J=10.4 Hz, 2H), 1.79-1.70 (m, 2H), 1.51 (s, 6H), 1.49 (s, 6H), 0.79 (d, J=5.5 Hz, 4H).

Example 419

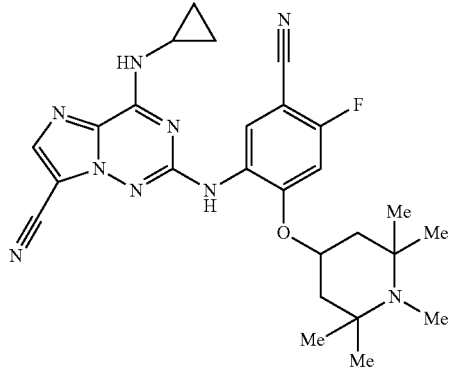 [SMILES: CN1C(C)(C)CC(Oc2cc(F)c(C#N)cc2Nc2nc(NC3CC3)c3ncc(C#N)n3n2)CC1(C)C]

2-((5-cyano-4-fluoro-2-((1,2,2,6,6-pentamethylpiperidin-4-yl)oxy)phenyl)amino)-4-(cyclopropylamino)imidazo[2,1-f][1,2,4]triazine-7-carbonitrile NaH (60% in mineral oil, 18 mg, 0.45 mmol) added to a solution of 1,2,2,6,6-pentamethylpiperidin-4-ol (73 mg, 0.43 mmol) in dry DMF (1 mL) at RT. This was left stirring for 30 min and then solid 2-((5-cyano-2,4-difluorophenyl)amino)-4-(cyclopropylamino)imidazo[2,1-f][1,2,4]triazine-7-carbonitrile (Example 414) (50 mg, 0.14 mmol) was added. The reaction was left stirring at RT for ¾ hr and then heated at 55° C. for 7 hr. It was quenched with sat. aq. NH$_4$Cl solution (0.5 mL) and diluted with DCM. After washing with water (3×), the organic phase was dried with sodium sulfate. The solvent was removed and radial silica gel chromatography with DCM containing 0 to 3% MeOH and then 1 to 4% 2N NH₃ in MeOH afforded the title compound (37 mg) as a glass.

MS (ESI) m/z 504.2
¹H NMR (500 MHz, CHLOROFORM-d) δ 8.91 (d, J=7.0 Hz, 1H), 7.86 (s, 1H), 7.37 (s, 1H), 6.80-6.70 (m, 2H), 4.73-4.64 (m, 1H), 3.07 (tq, J=7.0, 3.6 Hz, 1H), 2.32 (s, 3H), 2.09 (dd, J=12.4, 4.0 Hz, 2H), 1.81-1.75 (m, 2H), 1.27 (s, 6H), 1.18 (s, 6H), 1.14-1.09 (m, 2H), 0.85-0.78 (m, 2H).

Example 420

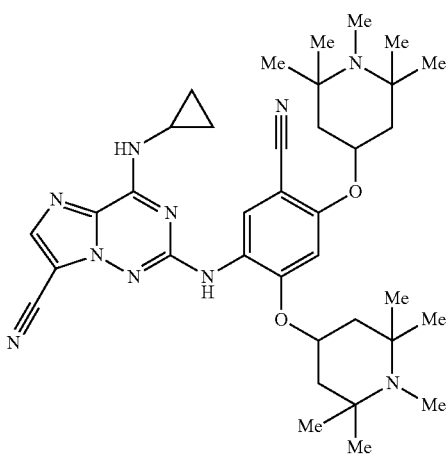 [SMILES: CN1C(C)(C)CC(Oc2cc(OC3CC(C)(C)N(C)C(C)(C)C3)c(Nc3nc(NC4CC4)c4ncc(C#N)n4n3)cc2C#N)CC1(C)C]

2-((5-cyano-2,4-bis((1,2,2,6,6-pentamethylpiperidin-4-yl)oxy)phenyl)amino)-4-(cyclopropylamino)imidazo[2,1-f][1,2,4]triazine-7-carbonitrile The title compound was obtained as minor product (10 mg) during the preparation of Example 419.

MS (ESI) m/z 555.5
¹H NMR (500 MHz, DMSO-d6) δ 9.24 (br. s., 1H), 8.29 (br. s., 1H), 8.17 (br. s., 2H), 7.00 (br. s., 1H), 5.10 (br. s., 2H), 3.02 (br. s., 1H), 2.73 (br. s., 4H), 2.45-1.75 (m, 10H), 1.34 (br. s., 24H), 0.80 (d, J=12.5 Hz, 4H).

Example 421

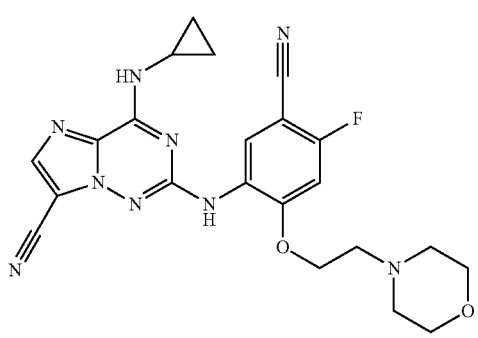 [SMILES: N#Cc1cc(Nc2nc(NC3CC3)c3ncc(C#N)n3n2)c(OCCN2CCOCC2)cc1F]

2-((5-cyano-4-fluoro-2-(2-morpholinoethoxyl)phenyl)amino)-4-(cyclopropylamino)imidazo[2,1-f][1,2,4]triazine-7-carbonitrile The title compound was obtained as the major product (34% yield) from the reaction between 2-((5-cyano-2,4-difluorophenyl)amino)-4-(cyclopropylamino)imidazo[2,1-f][1,2,4]triazine-7-carbonitrile (Example 414) and 2-morpholinoethanol according to the procedure described in Example 419.

MS (ESI) m/z 464.4
¹H NMR (500 MHz, DMSO-d6) δ 9.36 (d, J=3.4 Hz, 1H), 8.68 (br. s., 1H), 8.51 (d, J=7.0 Hz, 1H), 8.21 (s, 1H), 7.41 (d, J=11.0 Hz, 1H), 4.59 (br. s., 2H), 4.02-3.77 (m, 4H), 3.71-3.46 (m, 4H), 3.19 (br. s., 2H), 3.02 (d, J=3.1 Hz, 1H), 0.86-0.76 (m, 4H).

Example 422

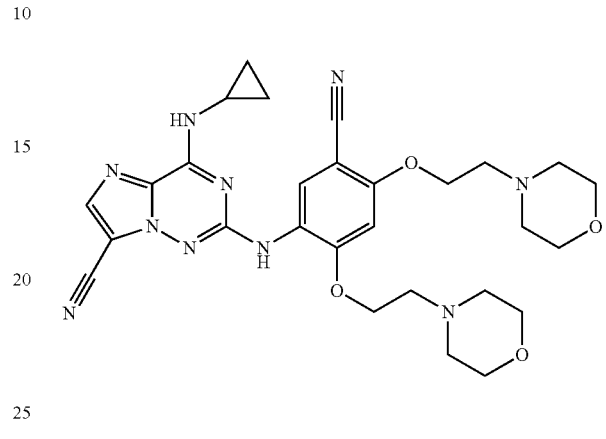

2-((5-cyano-2,4-bis(2-morpholinoethoxy)phenyl)amino)-4-(cyclopropylamino)imidazo[2,1-f][1,2,4]triazine-7-carbonitrile The title compound was obtained as the minor product (33% yield) from the reaction between 2-((5-cyano-2,4-difluorophenyl)amino)-4-(cyclopropylamino)imidazo[2,1-f][1,2,4]triazine-7-carbonitrile (Example 414) and 2-morpholinoethanol according to the procedure described in Example 419.

MS (ESI) m/z 575.5.2
¹H NMR (500 MHz, DMSO-d6) δ 9.26 (br. s., 1H), 8.36 (br. s., 1H), 8.27 (br. s., 1H), 8.18 (s, 1H), 4.45 (br. s., 4H), 3.92-3.54 (m, 9H), 3.93-3.52 (m, 10H), 3.28-2.53 (m, 11H), 0.78 (br. s., 4H).)

Example 423

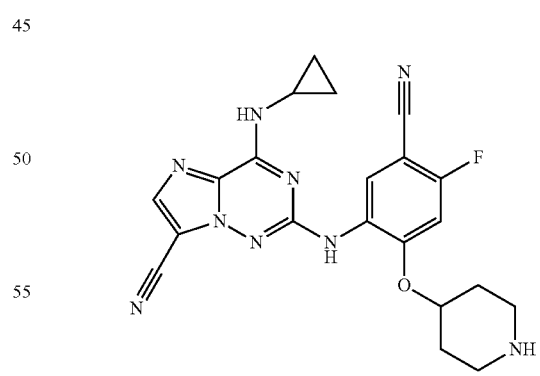

2-((5-cyano-4-fluoro-2-(piperidin-4-yloxy)phenyl)amino)-4-(cyclopropylamino)imidazo[2,1-f][1,2,4]triazine-7-carbonitrile The title compound was obtained as the major product from the reaction between 2-((5-cyano-2,4-difluorophenyl)amino)-4-(cyclopropylamino)imidazo[2,1-f][1,2,4]triazine- 7-carbonitrile (Example 414) and tert-butyl 4-hydroxypiperidine-1-carboxylate according to the procedure described in Example 419 and the subsequent removal of the Boc protecting group with TFA.

MS (ESI) m/z 434.1 (M+1).

$^1$H NMR (500 MHz, METHANOL-d4) δ 8.81 (d, J=7.2 Hz, 1H), 7.96 (s, 1H), 7.12 (d, J=10.8 Hz, 1H), 4.76-4.68 (m, 1H), 3.19-3.10 (m, 2H), 3.05 (dt, J=7.3, 3.5 Hz, 1H), 2.80 (ddd, J=13.0, 9.8, 3.0 Hz, 2H), 2.19-2.07 (m, 2H), 1.87-1.75 (m, 2H), 1.04-0.94 (m, 2H), 0.85-0.75 (m, 2H).

Example 424

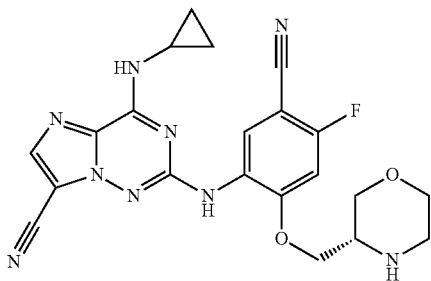 [SMILES: N#Cc1cc(Nc2nc(NC3CC3)c3ncc(C#N)n3n2)c(OC[C@@H]2COCCN2)cc1F]

(S)-2-((5-cyano-4-fluoro-2-(morpholin-3-ylmethoxy)phenyl)amino)-4-(cyclopropylamino)imidazo[2,1-f][1,2,4]triazine-7-carbonitrile The title compound was obtained as the major product from the reaction between 2-((5-cyano-2,4-difluorophenyl)amino)-4-(cyclopropylamino)imidazo[2,1-f][1,2,4]triazine-7-carbonitrile (Example 414) and (R)-tert-butyl 3-(hydroxymethyl)morpholine-4-carboxylate according to the procedure described in Example 423.

MS (ESI) m/z 450.3

Example 425

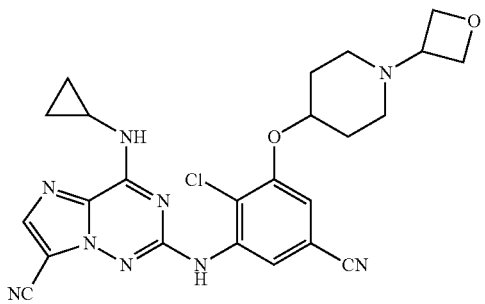 [SMILES: N#Cc1cc(Nc2nc(NC3CC3)c3ncc(C#N)n3n2)c(Cl)c(OC2CCN(C3COC3)CC2)c1]

2-((2-chloro-5-cyano-3-((1-(oxetan-3-yl)piperidin-4-yl)oxy)phenyl)amino)-4-(cyclopropylamino)imidazo[2,1-f][1,2,4]triazine-7-carbonitrile (425A): Sodium triacetoxyborohydride (3.18 g, 15.00 mmol) and acetic acid (0.859 mL, 15.00 mmol) were added to a solution of piperidin-4-ol (1.011 g, 10 mmol) and oxetan-3-one (0.721 g, 10.00 mmol) in DCE (35 mL) and the reaction mixture was stirred at room temperature overnight. Celite was added to the sticky reaction mixture and the reaction mixture was filtered, the filtrate was concentrated in vacuo to give a brown oil. The solid was purified by flash chromatography on silica gel using an automated ISCO system (120 g column, eluting with 0-8% 2 N ammonia in methanol/dichloromethane). 1-(oxetan-3-yl)piperidin-4-ol (0.80 g) was obtained as a white solid.

(425B): A mixture of 3,4-dihydroxy-5-nitrobenzaldehyde (5 g, 27.3 mmol), hydroxylamine hydrochloride (2.467 g, 35.5 mmol), toxic acid (0.779 g, 4.10 mmol) and magnesium sulfate (26.3 g, 218 mmol) in toluene (25 ml) was heated at reflux for 6 hours. The reaction mixture was cooled to room temperature, the reaction mixture was partitioned between ethyl acetate and water. The layers were separated and aqueous layer was extracted with ethyl acetate two more times. The combined organic layers were washed with water and brine, dried over magnesium sulfate, filtered and concentrated in vacuo to a small volume and a brown precipitate formed. the precipitate was collected by filtration and after drying under vacuum to give 4.1 g of 4-chloro-3-hydroxy-5-nitrobenzonitrile.

$^1$H NMR (500 MHz, DMSO-d$_6$) δ 11.19 (s, 1H), 10.45 (br. s., 2H), 8.07 (s, 1H), 7.53 (d, J=1.9 Hz, 1H), 7.39 (d, J=1.9 Hz, 1H)

(425C): DIAD (0.368 mL, 1.781 mmol) was added to a solution of 4-chloro-3-hydroxy-5-nitrobenzonitrile (265 mg, 1.336 mmol), 1-(oxetan-3-yl)piperidin-4-ol (200 mg, 1.272 mmol) and triphenylphosphine resin (3 mmol/g loading, 890 mg, 2.672 mmol) in THF (5 mL) and the reaction mixture was stirred at room temperature overnight. The reaction mixture was filtered and the filtrate was concentrated. The crude containing 4-chloro-3-nitro-5-(1-(oxetan-3-yl)piperidin-4-yloxy)benzonitrile was carried forward without purification.

(425D): A mixture of 4-chloro-3-nitro-5-((1-(oxetan-3-yl)piperidin-4-yl)oxy)benzonitrile (430 mg, 1.272 mmol) and Pd/C (271 mg, 0.127 mmol) in methanol (20 mL) was hydrogenated at 20 psi for 1.5 h. The reaction mixture was filtered through a pad of celite and the filtrate was concentrated in vacuo. The crude product was purified by flash chromatography on silica gel using an automated ISCO system (40 g gold column, eluting with 1-5% 2 N ammonia in methanol/dichloromethane). 3-amino-4-chloro-5-((1-(oxetan-3-yl)piperidin-4-yl)oxy)benzonitrile (50 mg) was obtained as a foaming solid.

MS (ESI) m/z 308.3

(425E): A mixture of 2-chloro-4-(cyclopropyl(4-methoxybenzyl)amino)imidazo[2,1-f][1,2,4]triazine-7-carbonitrile (Intermediate 9) (57.6 mg, 0.162 mmol), 3-amino-4-chloro-5-((1-(oxetan-3-yl)piperidin-4-yl)oxy)benzonitrile (50 mg, 0.162 mmol), palladium(II) acetate (9.67 mg, 0.043 mmol), xantphos (9.40 mg, 0.016 mmol), DPPF (9.01 mg, 0.016 mmol) and cesium carbonate (138 mg, 0.422 mmol) in dioxane (1 ml) was evacuated and back filled with nitrogen three time and was heated at 60° C. for 2 h. The reaction mixture was filtered through a pad of celite, the filtrate was concentrated and the crude product was purified by flash chromatography on silica gel using an automated ISCO system (24 g gold column, eluting with 0-6% 2 N ammonia in methanol/dichloromethane). Compound from ISCO was suspended in methanol (1 ml) and the white precipitate was collected by filtration. 2-((2-chloro-5-cyano-3-((1-(oxetan-3-yl)piperidin-4-yl)oxy)phenyl)amino)-4-(cyclopropyl(4-methoxybenzyl)amino)imidazo[2,1-f][1,2,4]triazine-7-carbonitrile (50 mg) was obtained as a white solid.

MS (ESI) m/z 626.4 (M+H)

¹H NMR (500 MHz, mixture of methanol-d4/chloroform-d) δ 7.99 (s, 1H), 7.57 (s, 1H), 7.20 (d, J=8.3 Hz, 2H), 6.97 (d, J=1.7 Hz, 1H), 6.85 (d, J=8.6 Hz, 2H), 4.76-4.70 (m, 2H), 4.64 (t, J=6.2 Hz, 2H), 3.77 (s, 3H), 3.57 (quin, J=6.5 Hz, 1H), 2.57 (t, J=8.5 Hz, 2H), 2.36 (br. s., 2H), 2.09-2.00 (m, 2H), 1.99-1.91 (m, 2H), 1.10 (d, J=6.4 Hz, 2H), 0.94-0.89 (m, 2H)

Example 425

TFA (25% in DCE, 2 ml, 6.49 mmol) was added to a solution of 2-((2-chloro-5-cyano-3-((1-(oxetan-3-yl)piperidin-4-yl)oxy)phenyl)amino)-4-(cyclopropyl(4-methoxybenzyl)amino)imidazo[2,1-f][1,2,4]triazine-7-carbonitrile (50 mg, 0.080 mmol) and anisole (0.035 ml, 0.319 mmol) in DCE (1 mL) and the reaction mixture was heated at 45° C. for 3 hours. Solvent was evaporated in vacuo and the residue was dried under vacuum overnight. The residue was washed with hexane (2×2 ml), dissolved in acetonitrile (2 ml) and 2N ammonia in methanol was added to give a suspension. Solvent was evaporated until a very small amount and the precipitate was collected by filtration. 2-((2-chloro-5-cyano-3-((1-(oxetan-3-yl)piperidin-4-yl)oxy)phenyl)amino)-4-(cyclopropylamino)imidazo[2,1-f][1,2,4]triazine-7-carbonitrile (27 mg) was obtained as a white solid.

MS (ESI) m/z 506.4

¹H NMR (500 MHz, mixture of methanol-d4/chloroform-d) δ 8.67 (d, J=1.4 Hz, 1H), 7.92 (s, 1H), 6.99 (d, J=1.7 Hz, 1H), 4.76-4.69 (m, 2H), 4.65 (t, J=6.2 Hz, 2H), 3.58 (quin, J=6.5 Hz, 1H), 3.05 (tt, J=7.2, 3.7 Hz, 1H), 2.58 (t, J=8.3 Hz, 2H), 2.37 (d, J=4.4 Hz, 2H), 2.11-2.01 (m, 2H), 2.01-1.92 (m, 2H), 1.06-0.98 (m, 2H), 0.84-0.77 (m, 2H)

Example 426

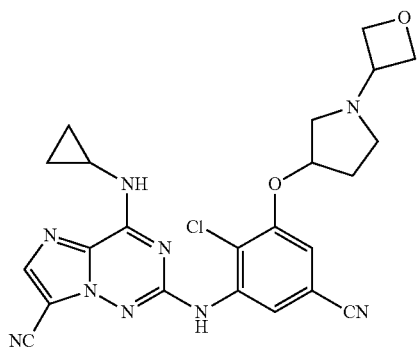 [SMILES: N#Cc1cc(Nc2nc(NC3CC3)c3ncc(C#N)n3n2)c(Cl)c(OC2CCN(C3COC3)C2)c1]

(+/−)-2-((2-chloro-5-cyano-3-((1-(oxetan-3-yl)pyrrolidin-3-yl)oxy)phenyl)amino)-4-(cyclopropylamino)imidazo[2,1-f][1,2,4]triazine-7-carbonitrile (426A): DIAD (0.309 mL, 1.495 mmol) was added to a solution of 4-chloro-3-hydroxy-5-nitrobenzonitrile (Example 425B) (223 mg, 1.122 mmol), (+/−)-tert-butyl 3-hydroxypyrrolidine-1-carboxylate (200 mg, 1.068 mmol) and triphenylphosphine resin (3 mmol/g loading, 560 mg, 2.136 mmol) in THF (5 mL) and the reaction mixture was stirred at room temperature overnight. The reaction mixture was filtered and the filtrate was concentrated, the crude product was purified by flash chromatography on silica gel using an automated ISCO system (40 g column, eluting with 0-20% ethyl acetate/dichloromethane). (+/−)-tert-butyl 3-(2-chloro-5-cyano-3-nitrophenoxy)pyrrolidine-1-carboxylate (272 mg) was obtained as a yellow solid.

MS (ESI) m/z 389.9

(426B): A mixture of (+/−)-tert-butyl 3-(2-chloro-5-cyano-3-nitrophenoxy)pyrrolidine-1-carboxylate (278 mg, 0.756 mmol) and Pd/C (80 mg, 0.038 mmol) in Methanol (20 mL) was hydrogenated at 20 psi for 2 h. The reaction mixture was filtered through a pad of celite and the filtrate was concentrated. The crude product was purified by flash chromatography on silica gel using an automated ISCO system (40 g column, eluting with 5-60% ethyl acetate/hexanes) to give (+/−) tert-butyl 3-(3-amino-2-chloro-5-cyanophenoxy)pyrrolidine-1-carboxylate (48 mg).

MS (ESI) m/z 360.0

¹H NMR (500 MHz, chloroform-d) δ 6.72 (br. s., 1H), 6.52 (d, J=1.1 Hz, 1H), 4.91 (br. s., 1H), 4.44 (br. s., 2H), 3.68-3.50 (m, 4H), 2.21 (br. s., 2H), 1.49 (s, 9H)

(426C): A mixture of 2-chloro-4-(cyclopropyl(4-methoxybenzyl)amino)imidazo[2,1-f][1,2,4]triazine-7-carbonitrile (Intermediate 9) (50 mg, 0.141 mmol), (+/−)-tert-butyl 3-(3-amino-2-chloro-5-cyanophenoxy)pyrrolidine-1-carboxylate (47.6 mg, 0.141 mmol), palladium(II) acetate (8.38 mg, 0.037 mmol), xantphos (8.15 mg, 0.014 mmol), DPPF (7.81 mg, 0.014 mmol) and cesium carbonate (119 mg, 0.366 mmol) in dioxane (1 ml) was evacuated and back filled with nitrogen three time and was heated at 70° C. for 3 h. The reaction mixture was filtered through a pad of celite, the filtrate was concentrated, the crude product was purified by flash chromatography on silica gel using an automated ISCO system (40 g gold column, eluting with 0-40% ethyl acetate/dichloromethane). (+/−)-tert-butyl 3-(2-chloro-5-cyano-3-((7-cyano-4-(cyclopropyl(4-methoxybenzyl)amino)imidazo[2,1-f][1,2,4]triazin-2-yl)amino)phenoxy)pyrrolidine-1-carboxylate (60 mg) was obtained as a colorless oil which was carried as such to the next reaction.

MS (ESI) m/z 656.0

(426D): (+/−)-tert-butyl 3-(2-chloro-5-cyano-3-((7-cyano-4-(cyclopropyl(4-methoxybenzyl)amino)imidazo[2,1-f][1,2,4]triazin-2-yl)amino)phenoxy)pyrrolidine-1-carboxylate (60 mg, 0.091 mmol) was treated with TFA (25% in DCE, 2 ml, 6.49 mmol) at room temperature for 1 h. The reaction mixture was diluted with dichloromethane and washed with saturated sodium bicarbonate/1N sodium hydroxide (pH 10). The aqueous layer was extracted with dichloromethane/methanol (4/1) two more times. The combined organic layers were dried over magnesium sulfate, filtered and concentrated in vacuo, the crude product (36 mg) was used in next reaction without purification.

MS (ESI) m/z 556.1

(426E): A mixture of (+/−)-2-((2-chloro-5-cyano-3-(pyrrolidin-3-yloxy)phenyl)amino)-4-(cyclopropyl(4-methoxybenzyl)amino)imidazo[2,1-f][1,2,4]triazine-7-carbonitrile (36 mg, 0.065 mmol), oxetan-3-one (8.30 µl, 0.129 mmol), acetic acid (7.41 µl, 0.129 mmol) and molecular sieves (30 mg) in dichloromethane (1 mL)/Methanol (1 mL) was stirred at room temperature overnight. sodium cyanoborohydride (12.21 mg, 0.194 mmol) was added and the reaction mixture was stirred for 1 h. The reaction mixture was filtered through a plug of celite and the filtrate was concentrated. The crude product (38 mg) was used without purification.

MS (ESI) m/z 612.0

Example 426

TFA (25% in DCE, 2 ml, 26.0 mmol) was added to a solution of (+/−)-2-((2-chloro-5-cyano-3-((1-(oxetan-3-yl)pyrrolidin-3-yl)oxy)phenyl)amino)-4-(cyclopropyl(4-methoxybenzyl)amino)imidazo[2,1-f][1,2,4]triazine-7-carbonitrile (38 mg, 0.062 mmol) and anisole (0.027 ml, 0.248 mmol) in DCE (1 mL) and the reaction mixture was heated at 60° C. for 2 hours. Solvent was evaporated in vacuo and the residue was dried under vacuum overnight. The crude was triturated with hexane 3×1 ml, dissolved in acetonitrile and neutralized with 2N ammonia in methanol. Solvent was evaporated to give a solid which was purified by flash chromatography on silica gel using an automated ISCO system (24 g gold column, eluting with 1-4% 2 N ammonia in methanol/dichloromethane). (+/−)-2-((2-chloro-5-cyano-3-((1-(oxetan-3-yl)pyrrolidin-3-yl)oxy)phenyl)amino)-4-(cyclopropylamino)imidazo[2,1-f][1,2,4]triazine-7-carbonitrile (22 mg) was obtained as a white solid.

MS (ESI) m/z 492.0 (M+H)

$^1$H NMR (500 MHz, mixture of methanol-d4/chloroform-d) δ 8.69 (d, J=1.7 Hz, 1H), 7.92 (s, 1H), 6.89 (d, J=1.7 Hz, 1H), 5.05-4.96 (m, 1H), 4.77 (td, J=6.7, 1.7 Hz, 2H), 4.67 (dt, J=12.6, 6.2 Hz, 2H), 3.88-3.80 (m, 1H), 3.11 (dd, J=11.1, 6.1 Hz, 1H), 3.05 (tt, J=7.2, 3.7 Hz, 1H), 2.88-2.80 (m, 2H), 2.70 (ddd, J=9.2, 7.5, 5.3 Hz, 1H), 2.39 (dq, J=14.1, 7.2 Hz, 1H), 2.16-2.07 (m, 1H), 1.06-1.00 (m, 2H), 0.83-0.78 (m, 2H)

Example 427

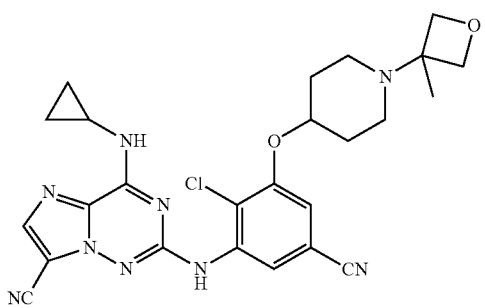 [SMILES: CC1(N2CCC(Oc3cc(C#N)cc(Nc4nc(NC5CC5)c5ncc(C#N)n5n4)c3Cl)CC2)COC1]

2-((2-chloro-5-cyano-3-((1-(3-methyloxetan-3-yl)piperidin-4-yl)oxy)phenyl)amino)-4-(cyclopropylamino)imidazo[2,1-f][1,2,4]triazine-7-carbonitrile (427A): A solution of piperidin-4-ol (100 mg, 0.989 mmol) and 3-((phenylsulfonyl)methylene)oxetane (prepared according to a published literature procedure: Wuitschik et al. J. Med. Chem. 53(8) 3227-3246, 2010, 416 mg, 1.977 mmol) in methanol (5 mL) was heated at 50° C. for 20 h. Solvent was evaporated in vacuo and the crude product was purified by flash chromatography on silica gel using an automated ISCO system (40 g column, eluting with 0-8% 2 N ammonia in methanol/dichloromethane). 1-(3-((phenylsulfonyl)methyl)oxetan-3-yl)piperidin-4-ol (300 mg) was obtained as a colorless oil.

MS (ESI) m/z 312.0

$^1$H NMR (500 MHz, CHLOROFORM-d) δ 7.95 (dd, J=8.5, 1.2 Hz, 2H), 7.69-7.63 (m, 1H), 7.60-7.55 (m, 2H), 4.67 (s, 4H), 3.72-3.62 (m, 1H), 3.57 (s, 2H), 2.71-2.61 (m, 2H), 2.39-2.30 (m, 2H), 1.95 (s, 1H), 1.84-1.73 (m, 2H), 1.49-1.38 (m, 2H)

(427B): 1-(3-((phenylsulfonyl)methyl)oxetan-3-yl)piperidin-4-ol (300 mg, 0.963 mmol, 97% yield) was dissolved in methanol (5 mL) and magnesium (pre-treated with 1N HCl and rinsed with methanol, 120 mg, 4.94 mmol) was added. The reaction mixture was sonicated for 1 min and stirred overnight. The reaction mixture was diluted with ethyl acetate and celite was added. The mixture was filtered and the filtrate was concentrated and purified by flash chromatography on silica gel using an automated ISCO system (24 g column, eluting with 2-12% 2 N ammonia in methanol/dichloromethane). 1-(3-methyloxetan-3-yl)piperidin-4-ol (78 mg) as a white solid.

MS (ESI) m/z 172.1

$^1$H NMR (500 MHz, chloroform-d) δ 4.55 (d, J=5.3 Hz, 2H), 4.20 (d, J=5.8 Hz, 2H), 3.66 (br. s., 1H), 2.56-2.44 (m, 3H), 2.33 (br. s., 1H), 2.17-2.09 (m, 2H), 1.94-1.84 (m, 2H), 1.58 (dtd, J=12.8, 9.2, 3.6 Hz, 2H), 1.34 (s, 3H)

(427C): DIAD (0.132 mL, 0.638 mmol) was added to a solution of 4-chloro-3-hydroxy-5-nitrobenzonitrile (95 mg, 0.478 mmol), 1-(3-methyloxetan-3-yl)piperidin-4-ol (78 mg, 0.456 mmol) and triphenylphosphine resin (3 mmol/g loading, 560 mg, 2.136 mmol) in THF (2 mL) and the reaction mixture was stirred at room temperature overnight. The reaction mixture was filtered and the filtrate was concentrated, the crude product was purified by flash chromatography on silica gel using an automated ISCO system (24 g column, eluting with 1-6% 2 N ammonia in methanol/dichloromethane). 4-chloro-3-((1-(3-methyloxetan-3-yl)piperidin-4-yl)oxy)-5-nitrobenzonitrile (106 mg) was obtained as a yellow solid.

MS (ESI) m/z 352.0

(427D): Ammonium chloride (584 mg, 10.92 mmol) and zinc (356 mg, 5.46 mmol) were added to a solution of 4-chloro-3-((1-(3-methyloxetan-3-yl)piperidin-4-yl)oxy)-5-nitrobenzonitrile (96 mg, 0.273 mmol) in methanol (10 mL) and the reaction mixture was stirred at room temperature for 2 hours. The reaction mixture was filtered through celite and the filtrate was concentrated, the crude was purified by flash chromatography on silica gel using an automated ISCO system (loaded onto a 24 g dry column, 24 g column, eluting with 0-6% 2 N ammonia in methanol/dichloromethane). 3-amino-4-chloro-5-((1-(3-methyloxetan-3-yl)piperidin-4-yl)oxy)benzonitrile (87 mg) was obtained as a foaming solid.

MS (ESI) m/z 322.0

(427E): A mixture of 2-chloro-4-(cyclopropyl(4-methoxybenzyl)amino)imidazo[2,1-f][1,2,4]triazine-7-carbonitrile (Intermediate 9) (47.4 mg, 0.134 mmol), 3-amino-4-chloro-5-((1-(3-methyloxetan-3-yl)piperidin-4-yl)oxy)benzonitrile (43 mg, 0.134 mmol), palladium(II) acetate (7.95 mg, 0.035 mmol), xantphos (7.73 mg, 0.013 mmol), DPPF (7.41 mg, 0.013 mmol) and cesium carbonate (113 mg, 0.347 mmol) in dioxane (2 ml) was evacuated and back filled with nitrogen three time and was heated at 80° C. for 6 h. The reaction mixture was filtered through a pad of celite, the filtrate was concentrated and the crude was purified by prep-HPLC. 2-((2-chloro-5-cyano-3-((1-(3-methyloxetan-3-yl)piperidin-4-yl)oxy)phenyl)amino)-4-(cyclopropyl(4-methoxybenzyl)amino)imidazo[2,1-f][1,2,4]triazine-7-carbonitrile (35 mg) was obtained.

MS (ESI) m/z 640.1

$^1$H NMR (500 MHz, Methanol-d4) δ 7.98 (s, 1H), 7.20 (d, J=8.3 Hz, 2H), 7.10 (d, J=1.7 Hz, 1H), 6.84 (d, J=8.6 Hz, 2H), 5.04 (d, J=7.5 Hz, 2H), 4.43 (d, J=7.5 Hz, 2H), 3.77 (s, 3H), 3.24-3.12 (m, 2H), 2.45-2.33 (m, 2H), 2.27 (d, J=13.6 Hz, 2H), 1.80 (s, 3H), 1.09 (d, J=6.4 Hz, 2H), 0.96-0.88 (m, 2H)

Example 427

TFA (25% in DCE, 2 ml, 6.49 mmol) was added to a solution of 2-((2-chloro-5-cyano-3-((1-(3-methyloxetan-3-yl)piperidin-4-yl)oxy)phenyl)amino)-4-(cyclopropyl(4-methoxybenzyl)amino)imidazo[2,1-f][1,2,4]triazine-7-carbonitrile (35 mg, 0.055 mmol) and anisole (0.024 ml, 0.219 mmol) and the reaction mixture was heated at 35° C. overnight. Solvent was evaporated and the residue was dried under vacuum. The crude was washed with hexane (3×1 ml), dissolved in acetonitrile and neutralized with 2N ammonia in methanol, after concentration, the crude product was purified by flash chromatography on silica gel using an automated ISCO system (24 g gole column, eluting with 0-4% 2 N ammonia in methanol/dichloromethane). 2-((2-chloro-5-cyano-3-((1-(3-methyloxetan-3-yl)piperidin-4-yl)oxy)phenyl)amino)-4-(cyclopropylamino)imidazo[2,1-f][1,2,4]triazine-7-carbonitrile, HCl (21 mg) was obtained as a white solid.

MS (ESI) m/z 520.1

¹H NMR (500 MHz, mixture of methanol-d4/chloroform-d) δ 8.67 (d, J=1.7 Hz, 1H), 7.93 (s, 1H), 6.99 (d, J=1.7 Hz, 1H), 4.63 (d, J=5.8 Hz, 2H), 4.28 (d, J=5.8 Hz, 2H), 3.05 (tt, J=7.3, 3.8 Hz, 1H), 2.70-2.60 (m, 2H), 2.34 (ddd, J=11.0, 6.7, 3.7 Hz, 2H), 2.10-2.01 (m, 2H), 1.96 (td, J=6.5, 3.1 Hz, 2H), 1.44 (s, 3H), 1.07-0.99 (m, 2H), 0.83-0.77 (m, 2H)

Example 428

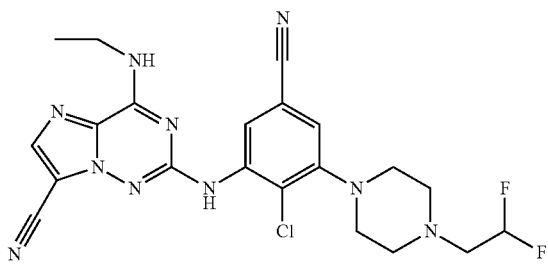 [SMILES: CCNc1nc(Nc2cc(C#N)cc(N3CCN(CC(F)F)CC3)c2Cl)nn2c(C#N)cnc12]

2-((2-chloro-5-cyano-3-(4-(2,2-difluoroethyl)-1-piperazinyl)phenyl)amino)-4-(ethylamino)imidazo[2,1-f][1,2,4]triazine-7-carbonitrile Prepared in analogous manner as Example 52
MS (ESI) m/z 486.92
1H NMR (400 MHz, DMSO-d6) δ 9.42-9.26 (m, 1H), 8.90 (s, 1H), 8.32-8.02 (m, 2H), 7.49 (d, J=1.5 Hz, 1H), 3.62-3.19 (m, 8H), 3.09-2.86 (m, 1H), 0.78 (d, J=5.7 Hz, 4H).

Example 429

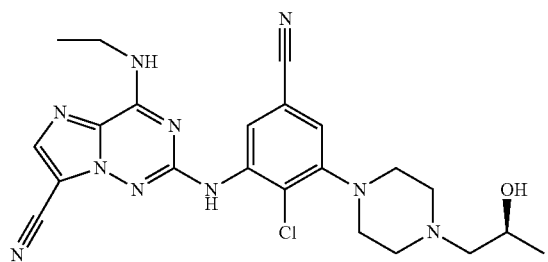 [SMILES: CCNc1nc(Nc2cc(C#N)cc(N3CCN(C[C@H](C)O)CC3)c2Cl)nn2c(C#N)cnc12]

2-((2-chloro-5-cyano-3-(4-((2R)-2-hydroxypropyl)-1-piperazinyl)phenyl)amino)-4-(ethylamino)imidazo[2,1-f][1,2,4]triazine-7-carbonitrile Prepared in analogous manner as Example 57
MS (ESI) m/z 480.96

1H NMR (400 MHz, DMSO-d6) δ 9.42-9.26 (m, 1H), 8.90 (s, 1H), 8.32-8.02 (m, 2H), 7.49 (d, J=1.5 Hz, 1H), 3.62-3.19 (m, 8H), 3.09-2.86 (m, 1H), 0.78 (d, J=5.7 Hz, 4H).

Example 430

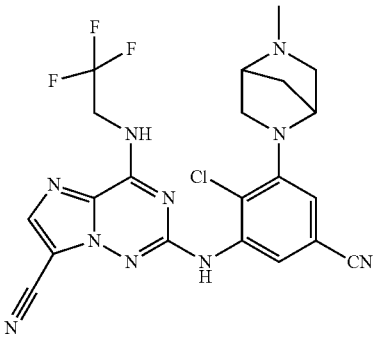 [SMILES: CN1CC2CC1CN2c1cc(C#N)cc(Nc2nc(NCC(F)(F)F)c3ncc(C#N)n3n2)c1Cl]

(+/−)-2-((2-chloro-5-cyano-3-((1R,4R)-5-methyl-2,5-diazabicyclo[2.2.1]heptan-2-yl)phenyl)amino)-4-((2,2,2-trifluoroethyl)amino)imidazo[2,1-f][1,2,4]triazine-7-carbonitrile (430A): (+/−)-3-amino-4-chloro-5-((1R,4R)-5-methyl-2,5-diazabicyclo[2.2.1]heptan-2-yl)benzonitrile was prepared starting from tert-butyl(3-bromo-2-chloro-5-cyanophenyl)carbamate (Intermediate 1) and (+/−)-(1R,4R)-2-methyl-2,5-diazabicyclo[2.2.1]heptane dihydrobromide using a method analogous to that used to prepare Example 1.

MS (ESI) m/z 263.2

1H NMR (400 MHz, DMSO-d6) δ 6.67 (d, J=1.8 Hz, 1H), 6.59 (d, J=1.5 Hz, 1H), 4.39 (br. s., 1H), 4.09 (br. s., 1H), 3.84-3.71 (m, 1H), 3.42 (d, J=10.8 Hz, 2H), 3.10 (d, J=10.3 Hz, 1H), 2.73 (br. s., 3H), 2.16 (br. s., 1H), 2.00 (d, J=11.0 Hz, 1H).

Example 430

The compound was prepared from 4-((4-methoxybenzyl)(2,2,2-trifluoroethyl)amino)-2-(methylsulfonyl)imidazo[2,1-f][1,2,4]triazine-7-carbonitrile (Intermediate 2) and (+/−)-3-amino-4-chloro-5-((1R,4R)-5-methyl-2,5-diazabicyclo[2.2.1]heptan-2-yl)benzonitrile using a method analogous to that used to prepare Example 1.

MS (ESI) m/z 503.1

¹H NMR (500 MHz, DMSO-d₆) δ 9.67 (br. s., 1H), 9.00 (s, 1H), 8.26 (s, 1H), 7.56 (d, J=1.7 Hz, 1H), 7.10 (d, J=1.7 Hz, 1H), 4.33-4.21 (m, 3H), 3.67 (dd, J=9.4, 2.5 Hz, 1H), 3.40 (s, 1H), 2.84 (dd, J=9.8, 2.1 Hz, 1H), 2.71 (d, J=9.7 Hz, 1H), 2.28 (s, 3H), 1.86 (d, J=9.2 Hz, 1H), 1.73 (d, J=9.4 Hz, 1H).

Example 431

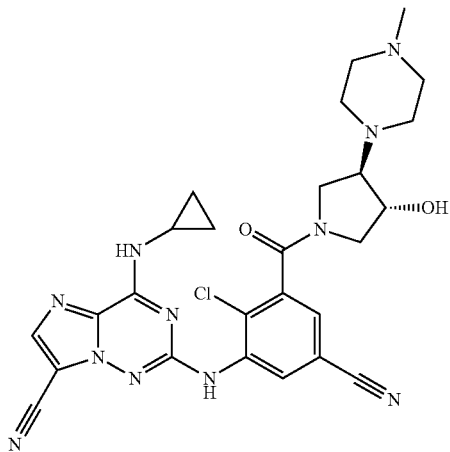 [SMILES: CN1CCN([C@@H]2CN(C(=O)c3cc(C#N)cc(Nc4nc(NC5CC5)c5ncc(C#N)n5n4)c3Cl)C[C@H]2O)CC1]

(+/−)-methyl((3R,4R)-1-(2-chloro-5-cyano-3-((7-cyano-4-(cyclopropylamino)imidazo[2,1-f][1,2,4]triazin-2-yl)amino)phenyl)-3-hydroxypiperidin-4-yl)(methyl)carbamate (431A): A steel autoclave charged with tert-butyl(3-bromo-2-chloro-5-cyanophenyl)carbamate (Intermediate 1, 500 mg, 1.508 mmol), palladium(II) acetate (1.693 mg, 7.54 μmol), DPPF (62.7 mg, 0.113 mmol), triethylamine (0.631 mL, 4.52 mmol) and ethanol (40 mL) was evacuated and filled with nitrogen three times to remove the air from the reaction vessel and then filled with carbon monoxide to 80 psi and heated at 100° C. for 5 h. The reaction mixture was cooled to room temperature and concentrated in vacuo, the crude product was purified by flash chromatography on silica gel using an automated ISCO system (80 g column, eluting with 5-20% ethyl acetate/hexanes). ethyl 3-((tert-butoxycarbonyl)amino)-2-chloro-5-cyanobenzoate (222 mg) was obtained as a colorless oil.

$^1$H NMR (500 MHz, chloroform-d) δ 8.72 (d, J=1.7 Hz, 1H), 7.71 (d, J=1.9 Hz, 1H), 7.35 (s, 1H), 4.42 (q, J=7.1 Hz, 2H), 1.55 (s, 9H), 1.41 (t, J=7.1 Hz, 3H).

(431B): 1N NaOH (1.367 mL, 1.367 mmol) was added to a solution of ethyl 3-((tert-butoxycarbonyl)amino)-2-chloro-5-cyanobenzoate (222 mg, 0.684 mmol) in methanol (1 mL) and the reaction mixture was stirred at room temperature for 2 h. 1N HCl was added to neutralize the reaction mixture to pH 5 and the reaction mixture was then concentrated in vacuo and lyophilized to give a crude white solid (309 mg, 65% pure). The crude was used in next step without purification.

MS (ESI) m/z 319.2

(431C): HATU (150 mg, 0.394 mmol) was added to a solution of crude 3-((tert-butoxycarbonyl)amino)-2-chloro-5-cyanobenzoic acid (Example 431B) (150 mg, 0.329 mmol), (+/−)-4-(4-methylpiperazin-1-yl)pyrrolidin-3-ol, 3 HCl (97 mg, 0.329 mmol) and diisopropyl ethylamine (0.230 mL, 1.314 mmol) in DMF (1 mL) and the resulting reaction mixture was stirred at room temperature overnight.

The reaction mixture was diluted with ethyl acetate and washed with saturated sodium bicarbonate. The organic layer was dried over magnesium sulfate, filtered and concentrated in vacuo, the crude product was purified by flash chromatography on silica gel using an automated ISCO system (24 g column, eluting with 2-12% 2N ammonia in methanol/dichloromethane) to give (+/−)-tert-butyl(2-chloro-5-cyano-3-(3-hydroxy-4-(4-methylpiperazin-1-yl)pyrrolidine-1-carbonyl)phenyl)carbamate (119 mg).

MS (ESI) m/z 464.4.

(431D): tert-Butyldimethylsilyl trifluoromethanesulfonate (0.240 mL, 1.026 mmol) was added to a solution of (+/−)-tert-butyl(2-chloro-5-cyano-3-(3-hydroxy-4-(4-methylpiperazin-1-yl)pyrrolidine-1-carbonyl)phenyl)carbamate (119 mg, 0.256 mmol) and imidazole (69.8 mg, 1.026 mmol) in DMF (3 mL) and the reaction solution was stirred at room temperature over the weekend. The reaction mixture was diluted with ethyl acetate and washed with saturated sodium bicarbonate. The organic layer was dried over magnesium sulfate, filtered and concentrated in vacuo, the crude product was purified by flash chromatography on silica gel using an automated ISCO system (40 g column, eluting with 1-6% methanol/dichloromethane). (+/−)-tert-butyl(3-(3-((tert-butyldimethylsilyl)oxy)-4-(4-methylpiperazin-1-yl)pyrrolidine-1-carbonyl)-2-chloro-5-cyanophenyl)carbamate (120 mg) was obtained as a colorless oil.

MS (ESI) m/z 578.4

(431E): (+/−)-tert-butyl(3-(3-((tert-butyldimethylsilyl)oxy)-4-(4-methylpiperazin-1-yl)pyrrolidine-1-carbonyl)-2-chloro-5-cyanophenyl)carbamate (120 mg, 0.208 mmol) was treated with TFA (25% in 1,2-dichloroethane, 2 mL, 6.49 mmol) at room temperature for 1 h. The reaction mixture was diluted with dichloromethane and washed with cold saturated sodium bicarbonate/1N aqueous sodium hydroxide (pH 10). The organic layer was dried over magnesium sulfate, filtered and concentrated in vacuo, the crude product was purified by flash chromatography on silica gel using an automated ISCO system (40 g column, eluting with 1-7.5% methanol/dichloromethane). (+/−)-3-amino-5-(3-((tert-butyldimethylsilyl)oxy)-4-(4-methylpiperazin-1-yl)pyrrolidine-1-carbonyl)-4-chlorobenzonitrile (86 mg) was obtained as a brown oil.

MS (ESI) m/z 478.4

Example 431

The title compound was prepared (+/−)-3-amino-5-(3-((tert-butyldimethylsilyl)oxy)-4-(4-methylpiperazin-1-yl)pyrrolidine-1-carbonyl)-4-chlorobenzonitrile using a method analogous to that used to prepare Example 1.

MS (ESI) m/z 562.3.1

$^1$H NMR (400 MHz, chloroform-d) δ 9.10 (d, J=1.5 Hz, 0.5H), 8.99 (d, J=1.5 Hz, 0.5H), 7.87 (d, J=4.0 Hz, 1H), 7.58 (d, J=6.2 Hz, 1H), 7.25 (dd, J=8.58, 1.54 Hz, 1H), 7.02 (br. s., 1H), 4.50 (q, J=5.7 Hz, 0.5H), 4.40 (q, J=5.9 Hz, 0.5H), 4.05 (dd, J=13.0, 6.6 Hz, 0.5H), 3.98 (dd, J=12.8, 7.5 Hz, 0.5H), 3.73-3.45 (m, 2H), 3.28-3.12 (m, 1H), 2.98 (q, J=6.6 Hz, 1H), 2.85-2.58 (m, 4H), 2.57-2.37 (m, 5H), 2.31 (s, 1.5H), 2.27 (s, 1.5H), 1.14-1.06 (m, 2H), 0.85-0.79 (m, 2H).

Example 432

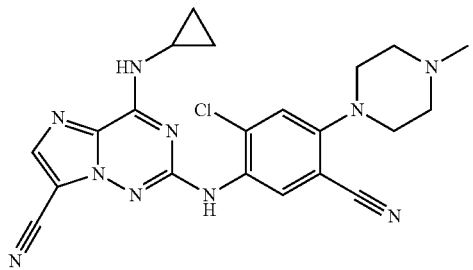 [SMILES: CN1CCN(c2cc(Cl)c(Nc3nc(NC4CC4)c4ncc(C#N)n4n3)cc2C#N)CC1]

2-((2-chloro-5-cyano-4-(4-methyl-1-piperazinyl)phenyl)amino)-4-(cyclopropylamino)imidazo[2,1-f][1,2,4]triazine-7-carbonitrile Prepared in similar manner as Example 410.
MS (ESI) m/z 448.92

Example 433

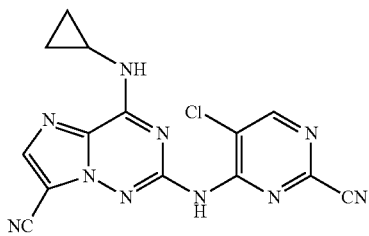 [SMILES: N#Cc1ncc(Cl)c(Nc2nc(NC3CC3)c3ncc(C#N)n3n2)n1]

2-((5-Chloro-2-cyanopyrimidin-4-yl)amino)-4-(cyclopropylamino)imidazo[2,1-f][1,2,4]triazine-7-carbonitrile (433A): 2-Bromo-4-(cyclopropyl(4-methoxybenzyl)amino)imidazo[2,1-f][1,2,4]triazine-7-carbonitrile (Intermediate 9) (168 mg, 0.421 mmol), 4-amino-5-chloropyrimidine-2-carbonitrile (65 mg, 0.421 mmol) Pd2(dba)3 (77 mg, 0.084 mmol), xantphos (48.7 mg, 0.084 mmol) and cesium carbonate (274 mg, 0.841 mmol) were suspended in dioxane (4206 µl) at rt. The reaction was degassed using the vacuum/purge method (4 times) to put the reaction under $N_2$. The reaction was heated to 70° C. for 4 h before cooling to room temperature, diluting with EtOAc, filtered through celite and concentrated. The crude product was purified by column chromatography (40 g SiO2, 0 to 100% EtOAc-hexane gradient elution) to afford 30 mg of 2-((5-Chloro-2-cyanopyrimidin-4-yl)amino)-4-(cyclopropyl(4-methoxybenzyl)amino)imidazo[2,1-f][1,2,4]triazine-7-carbonitrile
MS (ESI) m/z 473.2 (M+1).

Example 433

2-((5-Chloro-2-cyanopyrimidin-4-yl)amino)-4-(cyclopropyl(4-methoxybenzyl)amino)imidazo[2,1-f][1,2,4]triazine-7-carbonitrile was dissolved in DCE. Anisole (50 µL) was added followed by TFA (200 µL) and the reaction was stirred at 50° C. overnight. The reaction was concentrated and dried under vacuum.

The crude product was purified by preparative LC/MS with the following conditions:
Column: Waters XBridge C18, 19×250 mm, 5-nm particles; Mobile Phase A: 5:95 acetonitrile:water with 10-mM ammonium acetate;
Mobile Phase B: 95:5 acetonitrile:water with 10-mM ammonium acetate; Gradient: 0-100% B over 15 minutes, then a 5-minute hold at 100% B; Flow: 20 mL/min. Fractions concentrated and dried via centrifugal evaporation to afford 3.6 mg of 2-((5-Chloro-2-cyanopyrimidin-4-yl)amino)-4-(cyclopropylamino)imidazo[2,1-f][1,2,4]triazine-7-carbonitrile.
MS (ESI) m/z 353.1 (M+1).
$^1$H NMR (500 MHz, DMSO-$d_6$) δ 10.77 (s, 1H)., 9.59 (br. s., 1H), 8.83 (br. s., 1H), 8.36 (s, 1H), 3.08-2.98 (m, 1H), 0.84-0.70 (m, 4H).

What is claimed is:
1. A compound according to Formula (I):

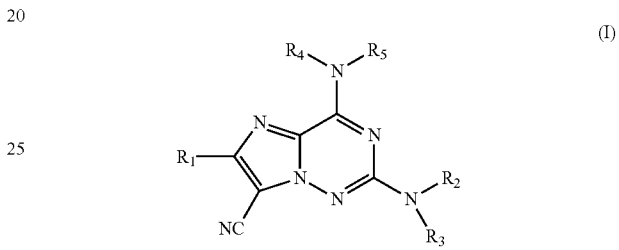

or a pharmaceutically acceptable salt thereof, wherein
$R_1$ is selected from the group consisting of H, F, Cl, Br, CN, and $C_{1-6}$alkyl;
$R_2$ is heteroaryl substituted with 1-5 $R_6$;
$R_3$ is selected from the group consisting of hydrogen and $C_{1-6}$alkyl substituted with 1-5 $R_e$;
$R_4$ is selected from the group consisting of H, $C_{1-6}$alkyl substituted with 1-5 $R_e$, —(CH$_2$)$_r$OR$_b$, —(CH$_2$)$_r$S(O)$_p$R$_c$, —(CH$_2$)$_r$C(=O)R$_d$, —(CH$_2$)$_r$NR$_a$R$_a$, —(CH$_2$)$_r$C(=O)NR$_a$R$_a$, —(CH$_2$)$_r$NR$_a$C(=O)R$_d$, —(CH$_2$)$_r$NR$_a$C(=O)OR$_b$, —(CH$_2$)$_r$OC(=O)NR$_a$R$_a$, —(CH$_2$)$_r$NR$_a$C(=O)NR$_a$R$_a$, —(CH$_2$)$_r$C(=O)OR$_b$, —(CH$_2$)$_r$S(O)$_2$NR$_a$R$_a$, —(CH$_2$)$_r$NR$_a$S(O)$_2$NR$_a$R$_a$, —(CH$_2$)$_r$NR$_a$S(O)$_2$R$_c$, —(CH$_2$)$_r$—$C_{3-10}$carbocyclyl substituted with 1-5 $R_e$, —(CH$_2$)$_r$-heterocyclyl substituted with 1-5 $R_e$;
$R_5$ is selected from the group consisting of H and $C_{1-6}$alkyl substituted with 1-5 $R_e$;
$R_6$, at each occurrence, is independently selected from the group consisting of H, F, Cl, Br, CN, $NO_2$, —OR$_b$, —C(=O)NR$_7$R$_7$, —NR$_a$C(=O)R$_b$, —NR$_a$C(=O)OR$_b$, $C_{1-6}$ alkyl substituted with 1-5 $R_e$, $C_{3-6}$carbocyclyl substituted with 1-5 $R_8$, and heterocyclyl substituted with 1-5 $R_8$;
$R_7$, at each occurrence, is independently selected from the group consisting of H, $C_{1-6}$ alkyl substituted with 1-5 $R_e$, —(CH$_2$)$_r$—$C_{3-10}$carbocyclyl substituted with 1-5 $R_e$, and —(CH$_2$)$_r$-heterocyclyl substituted with 1-5 $R_e$; or $R_7$ and $R_7$ together with the nitrogen atom to which they are both attached form a heterocyclic ring substituted with 1-5 $R_8$;
$R_8$, at each occurrence, is independently selected from the group consisting of H, F, Cl, Br, $C_{1-6}$ alkyl substituted with 1-5 $R_e$, $C_{2-6}$ alkenyl substituted with 1-5 $R_e$, =O, —(CR$_g$R$_g$)$_r$OR$_b$, —(CR$_g$R$_g$)$_r$S(O)$_p$R$_c$, —(CR$_g$R$_g$)$_r$C(=O)(CR$_g$R$_g$)$_r$R$_d$, —(CR$_g$R$_g$)$_r$NR$_a$R$_a$, —(CR$_g$R$_g$)$_r$C(=O)NR$_a$R$_a$, —(CR$_g$R$_g$)$_r$NR$_a$C(=O)R$_d$, —(CR$_g$R$_g$)$_r$NR$_a$C(=O)OR$_b$, —(CR$_g$R$_g$)$_r$OC(=O)R$_d$, —(CR$_g$R$_g$)$_r$OC(=O)(CR$_g$R$_g$)$_r$NR$_a$R$_a$, —(CR$_g$R$_g$)$_r$NR$_a$C(=O)

$NR_aR_a$, $-(CR_gR_g)_rC(=O)(CH_2)_rOR_b$, $-(CR_gR_g)_rC(=O)(CR_gR_g)_rOC(=O)R_b$, $-(CR_gR_g)_rS(O)_2NR_aR_a$, $-(CR_gR_g)_rNR_aS(O)_2NR_aR_a$, $-(CR_gR_g)_rNR_aS(O)_2R_c$, $-OPO_3H_2$, $-(CR_gR_g)_rNR_aC(=O)O(CR_gR_g)_rO(CR_gR_g)_rO(CR_gR_g)_rO(CR_gR_g)_rO(CR_gR_g)_rO(CR_gR_g)_rOC_{1-4}$alkyl, $-(CR_gR_g)_r-C_{3-10}$carbocyclyl substituted with 1-5 $R_e$ and $-(CR_gR_g)_r$-heterocyclyl substituted with 1-5 $R_e$;

$R_a$, at each occurrence, is independently selected from the group consisting of H, CN, $C_{1-6}$ alkyl substituted with 1-5 $R_e$, $C_{2-6}$ alkenyl substituted with 1-5 $R_e$, $C_{2-6}$ alkynyl substituted with 1-5 $R_e$, $-(CH_2)_r-C_{3-10}$carbocyclyl substituted with 1-5 $R_e$, and $-(CH_2)_r$-heterocyclyl substituted with 1-5 $R_e$; or $R_a$ and $R_a$ together with the nitrogen atom to which they are both attached form a heterocyclic ring substituted with 1-5 $R_e$;

$R_b$, at each occurrence, is independently selected from the group consisting of H, $C_{1-6}$ alkyl substituted with 1-5 $R_e$, $C_{2-6}$ alkenyl substituted with 1-5 $R_e$, $C_{2-6}$ alkynyl substituted with 1-5 $R_e$, $-(CH_2)_r-C_{3-10}$carbocyclyl substituted with 1-5 $R_e$, and $-(CH_2)_r$-heterocyclyl substituted with 1-5 $R_e$;

$R_c$, at each occurrence, is independently selected from the group consisting of $C_{1-6}$ alkyl substituted with 1-5 $R_e$, $C_{2-6}$alkenyl substituted with 1-5 $R_e$, $C_{2-6}$alkynyl substituted with 1-5 $R_e$, $C_{3-6}$carbocyclyl, and heterocyclyl;

$R_d$, at each occurrence, is independently selected from the group consisting of H, OH, $C_{1-6}$ alkyl substituted with 1-5 $R_e$, $C_{2-6}$alkenyl substituted with 1-5 $R_e$, $C_{2-6}$alkynyl substituted with 1-5 $R_e$, $-(CH_2)_r-C_{3-10}$carbocyclyl substituted with 1-5 $R_e$, and $-(CH_2)_r$-heterocyclyl substituted with 1-5 $R_e$;

$R_e$, at each occurrence, is independently selected from the group consisting of H, $C_{1-6}$alkyl substituted with 1-5 $R_f$, $C_{2-6}$alkenyl, $C_{2-6}$alkynyl, $-(CH_2)_r-C_{3-6}$cycloalkyl, $-(CH_2)_r$-heterocyclyl, F, Cl, Br, $-(CH_2)_rCN$, $NO_2$, $=O$, $-OPO_3H_2$, $-OSi(C_{1-4}alkyl)_3$, $-(CH_2)_rOC_{1-5}$ alkyl, $-(CH_2)_rOH$, $-(CH_2)_rS(O)_2C_{1-5}$ alkyl, $-(CH_2)_rS(O)_2$-phenyl, $-(CH_2)_rNHS(O)_2C_{1-5}$ alkyl, $-S(O)_2NH_2$, SH, $-(CH_2)_rNR_fR_f$, $-(CH_2)_rNHC(=O)OR_f$, $-(CH_2)_rNHC(=O)R_f$, $-(CH_2)_rC(=O)R_f$, and $-(CH_2)_rC(=O)OR_f$;

$R_f$, at each occurrence, is independently selected from the group consisting of H, $C_{1-5}$alkyl, OH, $OC_{1-5}$alkyl, C3-6 cycloalkyl, and phenyl, heterocyclyl substituted with alkyl and CN, or $R_f$ and $R_f$ together with the nitrogen atom to which they are both attached form a heterocyclic ring optionally substituted with $C_{1-4}$alkyl;

$R_g$, at each occurrence, is independently selected from the group consisting of H and $C_{1-5}$alkyl;

p, at each occurrence, is independently selected from the group consisting of zero, 1, and 2; and r, at each occurrence, is independently selected from the group consisting of zero, 1, 2, 3, and 4.

2. The compound according to claim 1 of Formula (II):

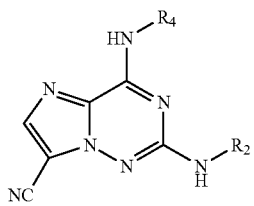

(II)

wherein $R_2$ is heteroaryl substituted with 1-4 $R_6$, wherein said heteroaryl comprises carbon atoms and 1-4 heteroatoms selected from the group consisting of N, $NR_{6a}$, O, and $S(O)_p$;

$R_4$ is selected from the group consisting of H, $C_{1-4}$alkyl substituted with 1-4 $R_e$, $C_{3-6}$cycloalkyl substituted with 1-4 $R_e$, aryl substituted with 1-4 $R_e$, and heterocyclyl substituted with 1-4 $R_e$;

$R_6$, at each occurrence, is independently selected from the group consisting of H, F, Cl, Br, CN, $-NR_7R_7$, $-C(=O)NR_7R_7$, $-NR_aC(=O)OR_b$, $C_{1-4}$alkyl substituted with 1-3 $R_e$, $C_{3-6}$carbocyclyl substituted with 1-3 $R_8$, and heterocyclyl substituted with 1-3 $R_8$;

$R_{6a}$ is selected from the group consisting of H and $C_{1-4}$alkyl substituted with 1-3 $R_e$;

$R_7$ and $R_7$ together with the nitrogen atom to which they are both attached form a heterocyclic ring comprising carbon atoms and 1-4 heteroatoms selected from the group consisting of N, $NR_{8a}$, O, and $S(O)_p$ and substituted with 1-5 $R_8$;

$R_8$, at each occurrence, is independently selected from the group consisting of H, F, Cl, Br, $C_{1-4}$alkyl substituted with 1-4 $R_e$, $=O$, $-OR_b$, $-S(O)_pR_c$, $-C(=O)R_d$, $-NR_aR_a$, $-C(=O)NR_aR_a$, $-NR_aC(=O)R_d$, $-NR_aC(=O)OR_b$, $-OC(=O)R_d$, $-OC(=O)(CH_2)_rNR_aR_a$, $NR_aC(=O)NR_aR_a$, $-C(=O)OR_b$, $S(O)_2NR_aR_a$, $-NR_aS(O)_2NR_aR_a$, $-NR_aS(O)_2R_c$, and heterocyclyl substituted with 1-4 $R_e$;

$R_{8a}$ is selected from the group consisting of H, $C_{1-4}$alkyl, $S(O)_pR_c$, and heterocyclyl substituted with 1-4 $R_e$;

p, at each occurrence, is independently selected from the group consisting of zero, 1, and 2.

3. The compound according to claim 2, wherein $R_2$ is 4- to 7-membered monocyclic or 7- to 12-membered bicyclic heteroaryl comprising carbon atoms and 1-4 heteroatoms selected from the group consisting of N, $NR_{6a}$, and substituted with 1-4 $R_6$;

$R_4$ is selected from the group consisting of $C_{1-4}$alkyl substituted with 1-3 $R_e$, $C_{3-6}$cycloalkyl substituted with 1-4 $R_e$, phenyl substituted with 1-3 $R_e$, and 5- to 6-membered heteroaryl comprising carbon atoms and 1-4 heteroatoms selected from the group consisting of N, NH, $NC_{1-4}$alkyl, O, and $S(O)_p$ and substituted with 1-3 $R_e$;

$R_6$, at each occurrence, is independently selected from the group consisting of H, F, Cl, Br, CN, $-NR_7R_7$, $-C(=O)NR_7R_7$, $-NHC(=O)OR_b$, $C_{1-4}$alkyl substituted with 1-3 $R_e$ and 5- to 6-membered heterocyclyl substituted with 1-3 $R_8$;

$R_7$ and $R_7$ together with the nitrogen atom to which they are both attached form a heterocyclic ring comprising carbon atoms and 1-4 heteroatoms selected from the group consisting of N, $NR_{8a}$, O, and $S(O)_p$ and substituted with 1-4 $R_8$; and $R_{8a}$ is selected from the group consisting of H and $C_{1-4}$alkyl, $S(O)_pR_c$, and heterocyclyl substituted with 1-4 $R_e$.

4. The compound according to claim 3, wherein $R_2$ is selected from the group consisting of

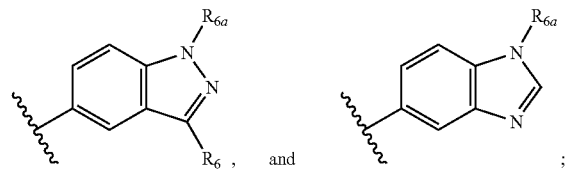

$R_{6a}$ is selected from the group consisting of H and $C_{1-4}$alkyl substituted with 1-2 $R_e$;

$R_6$, at each occurrence, is independently selected from the group consisting of H, F, Cl, Br, CN, —NR$_7$R$_7$, —C(=O)NR$_7$R$_7$, —NR$_a$C(=O)R$_b$, —NR$_a$C(=O)OR$_b$, C$_{1-4}$alkyl substituted with 1-3 R$_e$, and heterocyclyl substituted with 1-3 R$_8$;

R$_7$ and R$_7$ together with the nitrogen atom to which they are both attached form a heterocyclic ring comprising carbon atoms and 1-4 heteroatoms selected from the group consisting of N, NR$_{8a}$, O, and S(O)$_p$ and substituted with 1-4 R$_8$; and R$_e$, at each occurrence, is independently selected from the group consisting of C$_{1-6}$alkyl and OH.

5. The compound according to claim 4 of Formula (III) or (IV):

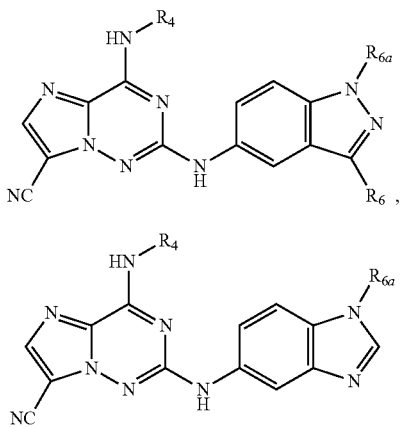

(III)

(IV)

wherein
R$_4$ is selected from the group consisting of C$_{1-4}$alkyl substituted with 1-3 R$_e$, C$_{3-6}$cycloalkyl substituted with 1-3 R$_e$, and 5- to 6-membered heteroaryl comprising carbon atoms and 1-4 heteroatoms selected from the group consisting of N, NH, NC$_{1-4}$alkyl, O, and S(O)$_p$ and substituted with 1-3 R$_e$;

R$_{6a}$ is selected from the group consisting of H and C$_{1-4}$alkyl optionally substituted with OH; and R$_6$ is selected from the group consisting of H, F, Cl, Br, CN, and C$_{1-4}$alkyl substituted with 1-2 R$_e$.

6. The compound according to claim 2, wherein R$_2$ is selected from the group consisting of

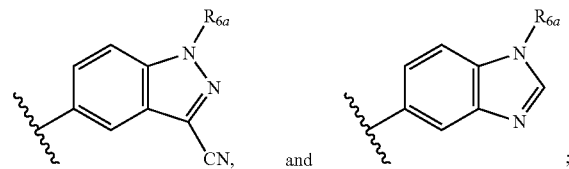

R$_4$ is selected from the group consisting of CH$_2$CH$_3$, CH$_2$CF$_3$, CH$_2$CH$_2$CH$_2$OCH$_3$,

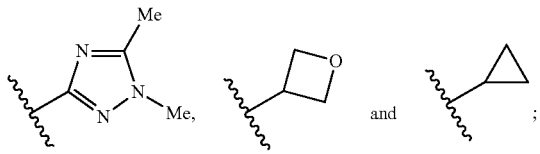

and
R$_{6a}$ is selected from the group consisting of H and CH$_3$, CH$_2$CH$_3$, and CH$_2$CHOHCH$_3$.

7. A pharmaceutical composition comprising one or more compounds according to claim 1 in combination with a pharmaceutically acceptable carrier.

* * * * *